(12) United States Patent
Wilt et al.

(10) Patent No.: US 11,724,011 B2
(45) Date of Patent: Aug. 15, 2023

(54) BLOOD TREATMENT SYSTEMS AND METHODS

(71) Applicant: DEKA Products Limited Partnership, Manchester, NH (US)

(72) Inventors: Michael J. Wilt, Windham, NH (US); Todd A. Ballantyne, Amherst, NH (US); Jason A. Demers, Manchester, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 0 days.

(21) Appl. No.: 17/974,364

(22) Filed: Oct. 26, 2022

(65) Prior Publication Data

US 2023/0124240 A1    Apr. 20, 2023

Related U.S. Application Data

(60) Continuation of application No. 16/901,926, filed on Jun. 15, 2020, now Pat. No. 11,529,444, which is a (Continued)

(51) Int. Cl.
*A61M 1/16*    (2006.01)
*A61M 1/14*    (2006.01)
(Continued)

(52) U.S. Cl.
CPC .......... *A61M 1/1601* (2014.02); *A61M 1/14* (2013.01); *A61M 1/16* (2013.01); *A61M 1/1621* (2014.02);
(Continued)

(58) Field of Classification Search
CPC ........ A61M 1/14; A61M 1/16; A61M 1/1601; A61M 1/1621; A61M 1/1696;
(Continued)

(56) References Cited

U.S. PATENT DOCUMENTS 2,339,876 A    1/1944    Phillips
3,083,943 A    4/1963    Stewart et al.
(Continued)

FOREIGN PATENT DOCUMENTS

CA    1119971 A    3/1982
CA    1323312 C    10/1993
(Continued)

OTHER PUBLICATIONS

Bengtsson P O et al., Proceedings of the 1999 International Conference on Software Engineering (IEEE Cat. No. 99CB37002) ACM New York, NY, USA (1999), pp. 516-525.*
(Continued)

*Primary Examiner* — John Kim

(57) ABSTRACT

Dialysis systems comprising actuators that cooperate to perform dialysis functions and sensors that cooperate to monitor dialysis functions are disclosed. According to one aspect, such a hemodialysis system comprises a user interface model layer, a therapy layer, below the user interface model layer, and a machine layer below the therapy layer. The user interface model layer is configured to manage the state of a graphical user interface and receive inputs from a graphical user interface. The therapy layer is configured to run state machines that generate therapy commands based at least in part on the inputs from the graphical user interface. The machine layer is configured to provide commands for the actuators based on the therapy commands.

7 Claims, 159 Drawing Sheets

Related U.S. Application Data continuation of application No. 15/469,065, filed on Mar. 24, 2017, now Pat. No. 10,682,450, which is a continuation of application No. 14/313,809, filed on Jun. 24, 2014, now Pat. No. 9,603,985, which is a continuation of application No. 13/855,620, filed on Apr. 2, 2013, now abandoned, which is a division of application No. 12/549,285, filed on Aug. 27, 2009, now Pat. No. 8,409,441, which is a continuation-in-part of application No. 12/199,452, filed on Aug. 27, 2008, now Pat. No. 8,357,298, which is a continuation-in-part of application No. 12/072,908, filed on Feb. 27, 2008, now Pat. No. 8,246,826.

(60) Provisional application No. 61/092,239, filed on Aug. 27, 2008, provisional application No. 60/903,582, filed on Feb. 27, 2007, provisional application No. 60/904,024, filed on Feb. 27, 2007.

(51) Int. Cl.
| | |
|---|---|
| *A61M 5/172* | (2006.01) |
| *G06F 9/00* | (2006.01) |
| *G06F 11/30* | (2006.01) |
| *G16H 40/60* | (2018.01) |
| *G16H 40/63* | (2018.01) |
| *A61M 1/26* | (2006.01) |

(52) U.S. Cl.
CPC ............ *A61M 1/267* (2014.02); *A61M 5/172* (2013.01); *G06F 9/00* (2013.01); *G06F 11/30* (2013.01); *G06F 11/3089* (2013.01); *G16H 40/60* (2018.01); *G16H 40/63* (2018.01); *A61M 1/1696* (2013.01); *A61M 2205/18* (2013.01); *A61M 2205/3317* (2013.01); *A61M 2205/3331* (2013.01); *A61M 2205/3334* (2013.01); *A61M 2205/3379* (2013.01); *A61M 2205/502* (2013.01)

(58) Field of Classification Search
CPC .. A61M 1/267; A61M 5/172; A61M 2205/18; A61M 2205/3317; A61M 2205/3331; A61M 2205/3334; A61M 2205/3379; A61M 2205/502; G06F 9/00; G06F 11/30; G06F 11/3089; G16H 40/60; G16H 40/63
See application file for complete search history.

(56) References Cited

U.S. PATENT DOCUMENTS

| | | |
|---|---|---|
| 3,711,770 A | 1/1973 | Wilson |
| 3,882,861 A | 5/1975 | Kettering et al. |
| 3,946,731 A | 3/1976 | Lichtenstein |
| 4,155,852 A | 5/1979 | Fischel et al. |
| 4,222,127 A | 9/1980 | Donachy et al. |
| 4,267,040 A | 5/1981 | Schal |
| 4,381,545 A | 4/1983 | Biddle, III et al. |
| 4,441,357 A | 4/1984 | Kahn et al. |
| 4,661,246 A | 4/1987 | Ash |
| 4,668,400 A | 5/1987 | Veech |
| 4,695,385 A | 9/1987 | Boag |
| 4,797,655 A | 1/1989 | Orndal et al. |
| 4,828,543 A | 5/1989 | Weiss et al. |
| 4,844,072 A | 7/1989 | French et al. |
| 4,950,235 A | 8/1990 | Slate et al. |
| 4,969,363 A | 11/1990 | Mochizuki |
| 4,971,700 A | 11/1990 | Tsuji et al. |
| 4,997,570 A | 3/1991 | Polaschegg |
| 5,024,756 A | 6/1991 | Sternby |
| 5,098,262 A | 3/1992 | Wecker et al. |
| 5,100,554 A | 3/1992 | Polaschegg |
| 5,247,434 A | 9/1993 | Peterson et al. |
| 5,324,422 A | 6/1994 | Colleran et al. |
| 5,350,357 A | 9/1994 | Kamen et al. |
| 5,351,686 A | 10/1994 | Steuer et al. |
| 5,378,231 A | 1/1995 | Johnson et al. |
| 5,427,509 A | 6/1995 | Chapman et al. |
| 5,431,626 A | 7/1995 | Bryant et al. |
| 5,431,627 A | 7/1995 | Pastrone et al. |
| 5,431,811 A | 7/1995 | Tusini et al. |
| 5,438,510 A | 8/1995 | Bryant et al. |
| 5,472,614 A | 12/1995 | Rossi |
| 5,486,286 A | 1/1996 | Peterson et al. |
| 5,487,827 A | 1/1996 | Peterson et al. |
| 5,496,273 A | 3/1996 | Pastrone et al. |
| 5,580,460 A | 12/1996 | Polaschegg |
| 5,586,438 A | 12/1996 | Fahy |
| 5,609,572 A | 3/1997 | Lang |
| 5,609,770 A | 3/1997 | Zimmerman et al. |
| 5,628,908 A | 5/1997 | Kamen et al. |
| 5,714,060 A | 2/1998 | Kenley et al. |
| 5,744,027 A | 4/1998 | Connell et al. |
| 5,769,811 A | 6/1998 | Stacey et al. |
| 5,788,851 A | 8/1998 | Kenley et al. |
| 5,795,317 A | 8/1998 | Brierton et al. |
| 5,808,181 A | 9/1998 | Wamsiedler et al. |
| 5,827,223 A | 10/1998 | Butterfield |
| 5,846,419 A | 12/1998 | Nederlof |
| 5,863,421 A | 1/1999 | Peter, Jr. et al. |
| 5,906,978 A | 5/1999 | Ash |
| 5,925,011 A | 7/1999 | Faict et al. |
| 6,041,801 A | 3/2000 | Gray et al. |
| 6,044,691 A | 4/2000 | Kenley et al. |
| 6,070,761 A | 6/2000 | Bloom et al. |
| 6,077,055 A | 6/2000 | Vilks |
| 6,146,523 A | 11/2000 | Kenley et al. |
| 6,223,130 B1 | 4/2001 | Gray et al. |
| 6,228,047 B1 | 5/2001 | Dadson |
| 6,234,989 B1 | 5/2001 | Brierton et al. |
| 6,261,065 B1 | 7/2001 | Nayak et al. |
| 6,277,272 B1 | 8/2001 | Nikaido et al. |
| 6,284,131 B1 | 9/2001 | Hogard et al. |
| 6,295,918 B1 | 10/2001 | Simmons et al. |
| 6,327,895 B1 | 12/2001 | Jeppsson et al. |
| 6,406,426 B1 | 6/2002 | Reuss et al. |
| 6,468,241 B1 | 10/2002 | Gelfand et al. |
| 6,497,676 B1 | 12/2002 | Childers et al. |
| 6,503,062 B1 | 1/2003 | Gray et al. |
| 6,579,253 B1 | 6/2003 | Burbank et al. |
| 6,602,424 B1 | 8/2003 | Kramer et al. |
| 6,614,008 B2 | 9/2003 | Tidrick |
| 6,638,478 B1 | 10/2003 | Treu et al. |
| 6,649,063 B2 | 11/2003 | Brugger et al. |
| 6,663,353 B2 | 12/2003 | Lipscomb et al. |
| 6,673,314 B1 | 1/2004 | Burbank et al. |
| 6,692,457 B2 | 2/2004 | Flaherty |
| 6,723,062 B1 | 4/2004 | Westberg et al. |
| 6,811,707 B2 | 11/2004 | Rovatti et al. |
| 6,814,547 B2 | 11/2004 | Childers et al. |
| 6,821,441 B2 | 11/2004 | Pedrini et al. |
| 6,852,090 B2 | 2/2005 | Burbank et al. |
| 6,868,309 B1 | 3/2005 | Begelman |
| 6,877,419 B2 | 4/2005 | Ohrle et al. |
| 6,929,751 B2 | 8/2005 | Bowman, Jr. et al. |
| 6,939,471 B2 | 9/2005 | Gross et al. |
| 6,949,079 B1 | 9/2005 | Westberg et al. |
| 7,029,245 B2 | 4/2006 | Maianti et al. |
| 7,041,076 B1 | 5/2006 | Westberg et al. |
| 7,083,719 B2 | 8/2006 | Bowman, Jr. et al. |
| 7,147,616 B2 | 12/2006 | Pedrazzi et al. |
| 7,153,286 B2 | 12/2006 | Busby et al. |
| 7,175,606 B2 | 2/2007 | Bowman, Jr. et al. |
| 7,238,164 B2 | 7/2007 | Childers et al. |
| 7,300,413 B2 | 11/2007 | Burbank et al. |
| 7,303,540 B2 | 12/2007 | O'Mahony et al. |
| 7,318,292 B2 | 1/2008 | Helbling et al. |
| 7,327,273 B2 | 2/2008 | Hung et al. |
| 7,461,968 B2 | 12/2008 | Demers et al. |
| 7,465,285 B2 | 12/2008 | Hutchinson et al. |

(56) References Cited

U.S. PATENT DOCUMENTS

| | | | |
|---|---|---|---|
| 7,473,238 B2 | 1/2009 | Brugger et al. |
| 7,500,962 B2 | 3/2009 | Childers et al. |
| 7,524,417 B2 | 4/2009 | Sunohara et al. |
| 7,544,179 B2 | 6/2009 | Distler et al. |
| 7,544,301 B2 | 6/2009 | Shah et al. |
| 7,560,686 B2 | 7/2009 | Bisch et al. |
| 7,563,240 B2 | 7/2009 | Gross et al. |
| 7,575,564 B2 | 8/2009 | Childers |
| 7,615,028 B2 | 11/2009 | O'Mahony |
| 7,632,078 B2 | 12/2009 | Demers et al. |
| 7,648,627 B2 | 1/2010 | Beden et al. |
| 7,699,806 B2 | 4/2010 | Ware et al. |
| 7,744,553 B2 | 6/2010 | Kelly et al. |
| 7,758,532 B2 | 7/2010 | Mori et al. |
| 7,776,006 B2 | 8/2010 | Childers et al. |
| 7,780,619 B2 | 8/2010 | Brugger et al. |
| 7,794,141 B2 | 9/2010 | Perry et al. |
| 7,909,795 B2 | 3/2011 | Childers et al. |
| 7,922,899 B2 | 4/2011 | Vasta et al. |
| 7,935,250 B2 | 5/2011 | Castellano et al. |
| 7,967,022 B2 | 6/2011 | Grant et al. |
| 8,029,454 B2 | 10/2011 | Kelly et al. |
| 8,038,639 B2 | 10/2011 | Lo et al. |
| 8,042,563 B2 | 10/2011 | Wilt et al. |
| 8,105,265 B2 | 1/2012 | Demers et al. |
| 8,113,244 B2 | 2/2012 | Kamen et al. |
| 8,246,826 B2 | 8/2012 | Wilt et al. |
| 8,273,049 B2 | 9/2012 | Demers et al. |
| 8,287,480 B2 | 10/2012 | Sasaki et al. |
| 8,292,594 B2 | 10/2012 | Tracey et al. |
| 8,317,492 B2 | 11/2012 | Demers et al. |
| 8,357,298 B2 | 1/2013 | Demers et al. |
| 8,393,690 B2 | 3/2013 | Grant et al. |
| 8,409,441 B2 | 4/2013 | Wilt |
| 8,425,471 B2 | 4/2013 | Grant et al. |
| 8,459,292 B2 | 6/2013 | Wilt et al. |
| 8,469,331 B2 | 6/2013 | Burbank et al. |
| 8,491,184 B2 | 7/2013 | Kamen et al. |
| 8,499,780 B2 | 8/2013 | Wilt et al. |
| 8,512,553 B2 | 8/2013 | Cicchello et al. |
| 8,545,698 B2 | 10/2013 | Wilt et al. |
| 8,562,834 B2 | 10/2013 | Kamen et al. |
| 8,597,229 B2 | 12/2013 | Pan |
| 8,597,505 B2 | 12/2013 | Fulkerson et al. |
| 8,612,055 B2 | 12/2013 | Ali et al. |
| 8,721,879 B2 | 5/2014 | van der Merwe et al. |
| 8,721,884 B2 | 5/2014 | Wilt et al. |
| 8,764,702 B2 | 7/2014 | Childers et al. |
| 8,771,508 B2 | 7/2014 | Grant et al. |
| 8,821,475 B2 | 9/2014 | Distler et al. |
| 8,858,787 B2 | 10/2014 | Muller et al. |
| 8,863,772 B2 | 10/2014 | Dale et al. |
| 8,870,549 B2 | 10/2014 | Tracey et al. |
| 8,882,700 B2 | 11/2014 | Chapman et al. |
| 8,888,470 B2 | 11/2014 | Demers et al. |
| 8,906,240 B2 | 12/2014 | Crnkovich et al. |
| 8,926,294 B2 | 1/2015 | Demers et al. |
| 8,968,232 B2 | 3/2015 | Kamen et al. |
| 8,985,133 B2 | 3/2015 | Grant et al. |
| 8,986,252 B2 | 3/2015 | Cummings et al. |
| 8,992,075 B2 | 3/2015 | Kamen et al. |
| 8,992,189 B2 | 3/2015 | Wilt et al. |
| 9,028,691 B2 | 5/2015 | Grant et al. |
| 9,089,653 B2 | 7/2015 | O'Mahony |
| 9,115,708 B2 | 8/2015 | van der Merwe et al. |
| 9,272,082 B2 | 3/2016 | Demers et al. |
| 9,302,037 B2 | 4/2016 | Wilt et al. |
| 9,302,039 B2 | 4/2016 | Kelly et al. |
| 9,364,655 B2 | 6/2016 | Grant et al. |
| 9,514,283 B2 | 12/2016 | Childers et al. |
| 9,517,295 B2 | 12/2016 | Wilt et al. |
| 9,535,021 B2 | 1/2017 | Kamen et al. |
| 9,539,379 B2 | 1/2017 | Grant et al. |
| 9,550,018 B2 | 1/2017 | Demers et al. |
| 9,555,179 B2 | 1/2017 | Wilt et al. |
| 9,561,317 B2 | 2/2017 | Distler et al. |
| 9,561,318 B2 | 2/2017 | Distler et al. |
| 9,597,442 B2 | 3/2017 | Wilt |
| 9,603,985 B2 | 3/2017 | Wilt et al. |
| 9,649,418 B2 | 5/2017 | Demers et al. |
| 9,677,554 B2 | 6/2017 | Wilt et al. |
| 9,700,660 B2 | 7/2017 | Demers et al. |
| 9,700,711 B2 | 7/2017 | Grant et al. |
| 9,713,667 B2 | 7/2017 | Distler et al. |
| 9,717,834 B2 | 8/2017 | Wilt et al. |
| 9,719,964 B2 | 8/2017 | Blumberg, Jr. |
| 9,724,012 B2 | 8/2017 | Chetham |
| 9,724,458 B2 | 8/2017 | Grant et al. |
| 9,750,865 B2 | 9/2017 | Vasta et al. |
| 9,770,546 B2 | 9/2017 | Vasta |
| 9,795,728 B2 | 10/2017 | Grant et al. |
| 9,907,897 B2 | 3/2018 | Burbank et al. |
| 9,907,972 B2 | 3/2018 | Kameli |
| 9,951,768 B2 | 4/2018 | Grant et al. |
| 9,987,407 B2 | 6/2018 | Grant et al. |
| 9,999,717 B2 | 6/2018 | van der Merwe et al. |
| 10,060,867 B2 | 8/2018 | Kamen et al. |
| 10,077,766 B2 | 9/2018 | Demers et al. |
| 10,098,998 B2 | 10/2018 | Wilt |
| 10,201,647 B2 | 2/2019 | Norris et al. |
| 10,201,650 B2 | 2/2019 | Wilt et al. |
| 10,302,075 B2 | 5/2019 | Tracey et al. |
| 10,415,559 B2 | 9/2019 | Demers et al. |
| 10,441,697 B2 | 10/2019 | Kamen et al. |
| 10,443,591 B2 | 10/2019 | Wilt et al. |
| 10,449,280 B2 | 10/2019 | Wilt et al. |
| 10,463,774 B2 | 11/2019 | Ballantyne et al. |
| 10,500,327 B2 | 12/2019 | Grant et al. |
| 10,537,671 B2 | 1/2020 | Wilt et al. |
| 10,576,194 B2 | 3/2020 | Distler et al. |
| 10,682,450 B2 | 6/2020 | Wilt et al. |
| 10,697,913 B2 | 6/2020 | Kamen et al. |
| 10,780,210 B2 | 9/2020 | Grant et al. |
| 10,780,213 B2 | 9/2020 | Grant et al. |
| 10,799,628 B2 | 10/2020 | Wilt et al. |
| 10,850,089 B2 | 12/2020 | Grant et al. |
| 10,851,769 B2 | 12/2020 | Demers et al. |
| 10,871,157 B2 | 12/2020 | Tracey et al. |
| 11,033,671 B2 | 6/2021 | van der Merwe et al. |
| 11,052,181 B2 | 7/2021 | Wilt et al. |
| 11,103,625 B2 | 8/2021 | Wilt |
| 11,110,212 B2 | 9/2021 | Grant et al. |
| 11,154,646 B2 | 10/2021 | Wilt et al. |
| 11,197,951 B2 | 12/2021 | Wilt et al. |
| 11,253,636 B2 | 2/2022 | McGill et al. |
| 11,311,656 B2 | 4/2022 | Kamen et al. |
| 11,364,329 B2 | 6/2022 | Demers et al. |
| 11,371,498 B2 | 6/2022 | Grant et al. |
| 11,419,965 B2 | 8/2022 | Demers et al. |
| 11,529,444 B2 | 12/2022 | Wilt et al. |
| 11,568,043 B2 | 1/2023 | Ballantyne et al. |
| 11,598,329 B2 | 3/2023 | Grant et al. |
| 2002/0056672 A1* | 5/2002 | Lyle ............... G16Z 99/00 210/94 |
| 2002/0103453 A1 | 8/2002 | Burbank et al. |
| 2003/0004492 A1 | 1/2003 | Munis et al. |
| 2003/0220607 A1 | 11/2003 | Busby et al. |
| 2003/0220627 A1 | 11/2003 | Distler et al. |
| 2004/0087895 A1 | 5/2004 | Cho et al. |
| 2004/0194210 A1 | 10/2004 | Foster et al. |
| 2004/0243049 A1 | 12/2004 | Brugger et al. |
| 2004/0254513 A1 | 12/2004 | Shang et al. |
| 2005/0045540 A1 | 3/2005 | Connell et al. |
| 2005/0095141 A1 | 5/2005 | Lanigan et al. |
| 2005/0145010 A1 | 7/2005 | Vanderveen et al. |
| 2005/0209563 A1 | 9/2005 | Hopping et al. |
| 2005/0234385 A1 | 10/2005 | Vandlik et al. |
| 2006/0084906 A1 | 4/2006 | Burbank et al. |
| 2006/0144396 A1 | 7/2006 | DeVries et al. |
| 2007/0023334 A1 | 2/2007 | Hallstadius et al. |
| 2007/0135758 A1 | 6/2007 | Childers et al. |
| 2008/0033346 A1 | 2/2008 | Childers et al. |
| 2008/0058697 A1 | 3/2008 | Kamen et al. |
| 2008/0097283 A1 | 4/2008 | Plahey |

(56) References Cited

U.S. PATENT DOCUMENTS

| | | |
|---|---|---|
| 2008/0114330 A1 | 5/2008 | Distler et al. |
| 2008/0125693 A1 | 5/2008 | Gavin et al. |
| 2008/0132828 A1 | 6/2008 | Howard |
| 2008/0161751 A1 | 7/2008 | Plahey et al. |
| 2008/0175719 A1 | 7/2008 | Tracey et al. |
| 2008/0203023 A1 | 8/2008 | Burbank et al. |
| 2008/0253911 A1 | 10/2008 | Demers et al. |
| 2008/0286076 A1 | 11/2008 | Elliott et al. |
| 2009/0009290 A1 | 1/2009 | Kneip et al. |
| 2009/0024070 A1 | 1/2009 | Gelfand et al. |
| 2009/0043253 A1 | 2/2009 | Podaima |
| 2009/0107335 A1 | 4/2009 | Wilt et al. |
| 2009/0222119 A1 | 9/2009 | Plahey et al. |
| 2009/0306573 A1 | 12/2009 | Gagner et al. |
| 2010/0056975 A1 | 3/2010 | Dale et al. |
| 2010/0114027 A1 | 5/2010 | Jacobson et al. |
| 2010/0191180 A1 | 7/2010 | Childers et al. |
| 2010/0191181 A1 | 7/2010 | Childers et al. |
| 2010/0312162 A1 | 12/2010 | Masaoka et al. |
| 2011/0005992 A1 | 1/2011 | Kelly et al. |
| 2011/0105877 A1 | 5/2011 | Wilt et al. |
| 2013/0104120 A1 | 4/2013 | Arrizza et al. |
| 2013/0193041 A1 | 8/2013 | Rohde |
| 2013/0304020 A1 | 11/2013 | Wilt et al. |
| 2014/0112828 A1 | 4/2014 | Grant et al. |
| 2014/0199193 A1 | 7/2014 | Wilt et al. |
| 2014/0231319 A1 | 8/2014 | Oide et al. |
| 2014/0288488 A1 | 9/2014 | Distler et al. |
| 2014/0288489 A1 | 9/2014 | Distler et al. |
| 2014/0288490 A1 | 9/2014 | Distler et al. |
| 2014/0309611 A1 | 10/2014 | Wilt et al. |
| 2015/0196699 A9 | 7/2015 | Wilt et al. |
| 2016/0030657 A1 | 2/2016 | Kelly et al. |
| 2016/0030658 A1 | 2/2016 | van der Merwe et al. |
| 2016/0058933 A1 | 3/2016 | Ballantyne et al. |
| 2016/0082173 A1 | 3/2016 | Coll et al. |
| 2016/0101227 A1 | 4/2016 | Norris et al. |
| 2016/0101278 A1 | 4/2016 | Norris et al. |
| 2016/0144093 A1 | 5/2016 | Demers et al. |
| 2016/0175506 A1 | 6/2016 | Wilt et al. |
| 2018/0372084 A1 | 12/2018 | Grant et al. |
| 2019/0321535 A1 | 10/2019 | Beavers et al. |
| 2020/0139031 A1 | 5/2020 | Wilt et al. |
| 2020/0171226 A1 | 6/2020 | Wilt et al. |
| 2020/0215252 A1 | 7/2020 | Distler et al. |
| 2020/0376185 A1 | 12/2020 | Wilt et al. |
| 2020/0400595 A1 | 12/2020 | Kamen et al. |
| 2021/0228793 A1 | 7/2021 | Scarpaci et al. |
| 2021/0285435 A1 | 9/2021 | Tracey et al. |
| 2021/0290928 A1 | 9/2021 | Grant et al. |
| 2021/0316058 A1 | 10/2021 | van der Merwe et al. |
| 2021/0332813 A1 | 10/2021 | Wilt et al. |
| 2021/0361841 A1 | 11/2021 | van der Merwe et al. |
| 2022/0096718 A1 | 3/2022 | Grant et al. |
| 2022/0133968 A1 | 5/2022 | Wilt et al. |
| 2022/0152286 A1 | 5/2022 | Wilt et al. |
| 2022/0241479 A1 | 8/2022 | Kamen et al. |

FOREIGN PATENT DOCUMENTS

| | | |
|---|---|---|
| CA | 2336478 A1 | 2/2000 |
| CA | 2341993 A1 | 3/2000 |
| CA | 2704411 A1 | 5/2009 |
| EP | 0 406 562 A2 | 1/1991 |
| EP | 1 195 171 A2 | 4/2002 |
| EP | 1 356 836 A2 | 10/2003 |
| EP | 1 666 078 A2 | 6/2006 |
| GB | 2110564 A | 6/1983 |
| GB | 2181311 A | 4/1987 |
| JP | S59-115049 A | 7/1984 |
| JP | H06-154314 A | 6/1994 |
| JP | H06-75504 U | 10/1994 |
| JP | H11-128343 A | 5/1999 |
| JP | 2001-112863 A | 4/2001 |
| JP | 2003-180825 A | 7/2003 |
| JP | 2003-246246 A | 9/2003 |
| JP | 2006-198141 A | 8/2006 |
| JP | 2006-343254 A | 12/2006 |
| WO | 84/02473 A1 | 7/1984 |
| WO | 93/11829 A1 | 6/1993 |
| WO | 96/25214 A1 | 8/1996 |
| WO | 97/10013 A1 | 3/1997 |
| WO | 97/11771 A1 | 4/1997 |
| WO | 01/18396 A1 | 3/2001 |
| WO | 01/037895 A2 | 5/2001 |
| WO | 03/099353 A2 | 12/2003 |
| WO | 2004/041081 A1 | 5/2004 |
| WO | 2005/044435 A2 | 5/2005 |
| WO | 2007/062197 A1 | 5/2007 |
| WO | 2007/113936 A1 | 10/2007 |
| WO | 2007/120812 A2 | 10/2007 |
| WO | 2009/006498 A2 | 1/2009 |
| WO | 2009/051669 A1 | 4/2009 |
| WO | 2010/043905 A1 | 4/2010 |
| WO | 2015/183976 A2 | 12/2015 |
| WO | 2015/183981 A2 | 12/2015 |

OTHER PUBLICATIONS

Invitation to Pay Additional Fees dated Dec. 8, 2009 for Application PCT/US2009/004877.

International Search Report and Written Opinion dated Feb. 12, 2010 for Application PCT/US2009/004877.

International Preliminary Report on Patentability for Application No. PCT/US2009/004877 dated Mar. 10, 2011.

Office Action for MX Application No. MX/a/2016/004974 filed Aug. 27, 2009, which Office Action is dated Oct. 20, 2016, and claims as pending for MX Application No. MX/a/2016/004974 as of Oct. 20, 2016.

[No. Author Listed] Homechoice Patient At-Home Guide, Jun. 1998. 84 pages.

[No. Author Listed], 2008K Hemodialysis Machine Operator's Manual. Fresenius Medical Care. 2018. https://laz2qm2bxvodlae4oellp3es-wpengine.netdna-ssl.com/wp-content/uploads/2018/09/490136_Rev_K.pdf. 240 pages.

[No. Author Listed], Patient At-Home Guide, HomeChoice Automated PD System. Version 2.0 (published May 1997); Baxter Healthcare Corporation. Copyright 1994. 61 pages.

Bengtsson et al., Haemo dialysis software architecture design experiences. Proceeedings of the 1999 International Conference on Software Engineering. IEEE Cat. No. 99CB37002. New York, NY. 1999:516-25.

Choppy et al., Architectural patterns for problem frames—relating software requirements and architectures. IEEE Proceedings: Software, IEE. Stevenage, GB. Aug. 5, 2005;52(4):198-208.

Gentilini et al., Automatic controllers capable of regulating mutliple patient outputs for higher-quality anesthesia treatment. IEEE Engineering in Medicine and Biology Magazine. IEEE Service Centers. Piscataway, NJ. Jan. 1, 2001;20(1):39-53.

Harel, Statecharts: A Visual Formalism for Complex Systems. Sci Comput Program. Jun. 1987;8(3):231-74.

Krasner et al., A cookbook for using the model-view-controller user interface paradigm in smalltalk-80. JOOP. Aug. 1, 1988;1(3):26-49.

Mineshima et al., Efficacy of internal filtration enhanced hemodialysis. Artificial Organs. 1999;28(1):127-33. Abstract only.

* cited by examiner

1100

900

1100

1300

900

1000

1100

900

BLOOD TREATMENT SYSTEMS AND METHODS

RELATED APPLICATIONS

This application is a continuation of U.S. patent application Ser. No. 16/901,926, filed Jun. 15, 2020, now U.S. Pat. No. 11,529,444, which is a continuation of U.S. patent application Ser. No. 15/469,065, filed Mar. 24, 2017, now U.S. Pat. No. 10,682,450, which is a continuation of U.S. patent application Ser. No. 14/313,809, entitled "Blood Treatment Systems and Methods," filed Jun. 24, 2014, now U.S. Pat. No. 9,603,985, which is a continuation of U.S. patent application Ser. No. 13/855,620, entitled "Blood Treatment Systems and Methods," filed on Apr. 2, 2013, now abandoned, which is a divisional of U.S. patent application Ser. No. 12/549,285, entitled "Blood Treatment Systems and Methods," filed on Aug. 27, 2009, now U.S. Pat. No. 8,409,441, which claims the benefit, under 35 U.S.C. § 119(e), of U.S. Provisional Application Ser. No. 61/092,239, entitled "Control System and Methods for Hemodialysis Device," filed on Aug. 27, 2008, which is hereby incorporated herein by reference in its entirety.

U.S. patent application Ser. No. 12/549,285 also claims priority, as a continuation-in-part, to U.S. patent application Ser. No. 12/199,452, filed Aug. 27, 2008, entitled "Hemodialysis Systems and Methods," now U.S. Pat. No. 8,357,298, which in turn is a continuation-in-part of U.S. patent application Ser. No. 12/072,908, filed Feb. 27, 2008, entitled "Hemodialysis Systems and Methods," now U.S. Pat. No. 8,246,826, which claims the benefit of each of U.S. Provisional Patent Application Ser. No. 60/903,582, filed Feb. 27, 2007, entitled "Hemodialysis System and Methods," and U.S. Provisional Patent Application Ser. No. 60/904,024, filed Feb. 27, 2007, entitled "Hemodialysis System and Methods." Each of the foregoing applications is hereby incorporated herein by reference in its entirety.

FIELD OF INVENTION

The present invention generally relates to hemodialysis and similar dialysis systems, e.g., systems able to treat blood or other bodily fluids extracorporeally. In certain aspects, the systems include a variety of systems and methods that would make hemodialysis more efficient, easier, and/or more affordable.

BACKGROUND

Many factors make hemodialysis inefficient, difficult, and expensive. These factors include the complexity of hemodialysis, the safety concerns related to hemodialysis, and the very large amount of dialysate needed for hemodialysis. Moreover, hemodialysis is typically performed in a dialysis center requiring skilled technicians. Therefore any increase in the ease and efficiency of the dialysis process could have an impact on treatment cost or patient outcome.

FIG. 1 is a schematic representation of a hemodialysis system. The system 5 includes two flow paths, a blood flow path 10 and a dialysate flow path 20. Blood is drawn from a patient. A blood flow pump 13 causes the blood to flow around blood flow path 10, drawing the blood from the patient, causing the blood to pass through the dialyzer 14, and returning the blood to the patient. Optionally, the blood may pass through other components, such as a filter and/or an air trap 19, before returning to the patient. In addition, in some cases, anticoagulant may be supplied from an anticoagulant supply 11 via an anticoagulant valve 12.

A dialysate pump 15 draws dialysate from a dialysate supply 16 and causes the dialysate to pass through the dialyzer 14, after which the dialysate can pass through a waste valve 18 and/or return to the dialysate feed via dialysate pump 15. A dialysate valve 17 controls the flow of dialysate from the dialysate supply 16. The dialyzer is a type of filter having a semi-permeable membrane, and is constructed such that the blood from the blood flow circuit flows through tiny tubes and the dialysate solution circulates around the outside of the tubes. Therapy is achieved by the passing of waste molecules (e.g., urea, creatinine, etc.) and water from the blood through the walls of the tubes and into the dialysate solution. At the end of treatment, the dialysate solution is discarded.

SUMMARY OF THE INVENTION

The present invention generally relates to hemodialysis and similar extracorporeal blood treatment systems. The subject matter of the present invention involves, in some cases, interrelated products, alternative solutions to a particular problem, and/or a plurality of different uses of one or more systems and/or articles. Although the various systems and methods described herein are described in relation to hemodialysis, it should be understood that the various systems and method described herein are applicable to other dialysis systems and/or in any extracorporeal system able to treat blood or other bodily fluids, such as hemofiltration, hemodiafiltration, etc.

In one aspect, the system includes four fluid paths: blood; inner dialysate; outer dialysate and dialysate mixing. In some embodiments, these four paths are combined in a single cassette. In other embodiments, these four paths are each in a respective cassette. In still other embodiments, two or more fluid paths are included on one cassette.

In one embodiment, there is provided a hemodialysis system having at least two fluid paths integrated into: 1) a blood flow pump cassette, 2) an inner dialysate cassette; 3) an outer dialysate cassette; and 4) a mixing cassette. The cassettes may be fluidly connected one to another. In some embodiments, one or more aspects of these cassettes can be combined into a single cassette.

Also provided, in another embodiment, is a hemodialysis system including a blood flow path through which untreated blood is drawn from a patient and is passed through a dialyzer and through which treated blood is returned to the patient. The blood flow path may include at least one blood flow pump located in a removable cassette. The hemodialysis system also can include a first receiving structure for receiving the blood flow path's cassette, a dialysate flow path through which dialysate flows from a dialysate supply through the dialyzer, a second receiving structure for receiving the dialysate flow path's cassette, and a control fluid path for providing a control fluid from an actuator mechanism to the cassettes for actuating each of the blood flow pump and the dialysate pump. In some instances, the dialysate flow path can include at least one dialysate pump located in a removable cassette.

In yet another embodiment, a hemodialysis system is disclosed. The hemodialysis system, in this embodiment, includes a blood flow path through which untreated blood is drawn from a patient and is passed through a dialyzer and through which treated blood is returned to the patient. The blood flow path may include at least one blood valve. The hemodialysis system may also include a control fluid path for providing a control fluid from an actuator mechanism to the blood valve for actuating the blood valve, a dialysate mixing system fluidly connected to the dialyzer (which may include at least one dialyzer valve), and a heating means or a heater for heating the dialysate.

A hemodialysis system is disclosed in yet another embodiment that includes a blood flow path through which untreated blood is drawn from a patient and passed through a dialyzer and through which treated blood is returned to the patient. The blood flow path can include at least one blood flow pump. The hemodialysis system also can include a dialysate flow path through which dialysate flows from a dialysate supply through the dialyzer. The dialysate flow path may include at least one pneumatic pump.

In one aspect, the invention is directed to a hemodialysis system. In one set of embodiments, the hemodialysis system includes a blood flow path, a first cassette defining an inner dialysate fluid path, a dialyzer in fluid communication with the blood flow path and the inner dialysate fluid path, a second cassette defining an outer dialysate fluid path, and a filter fluidly connecting the first cassette to the second cassette.

In another set of embodiments, the hemodialysis system, includes a blood flow path, an inner dialysate fluid path, a dialyzer in fluid communication with the blood flow path and the inner dialysate fluid path, an outer dialysate fluid path, a filter fluidly connecting the inner dialysate fluid path and the outer dialysate fluid path, a first dialysate pump for pumping dialysate through the inner dialysate fluid path, and a second dialysate pump for pumping dialysate through the outer dialysate fluid path, where the second dialysate pump and the first dialysate pump are operably connected such that flow through the inner dialysate fluid path is substantially equal to flow through the outer dialysate fluid path.

The hemodialysis system, in yet another set of embodiments, includes a blood flow path through which blood is drawn from a patient and passed through a dialyzer, and a dialysate flow path through which dialysate flows from a dialysate supply through the dialyzer. In some cases, the dialysate flow path comprises a balancing cassette which controls the amount of dialysate passing through the dialyzer, a mixing cassette which forms dialysate from water, and a directing cassette which passes water from a water supply to the mixing cassette and passes dialysate from the mixing cassette to the balancing cassette.

In still another set of embodiments, the hemodialysis system includes a cassette system, comprising a directing cassette, a mixing cassette and a balancing cassette. In some cases, the directing cassette is able to direct water from a water supply to the mixing cassette and direct dialysate from the mixing cassette to a balancing cassette, the mixing cassette is able to mix water from the directing cassette with dialysate from a dialysate supply precursor to produce a precursor, and the balancing cassette is able to control the amount of dialysate passing through a dialyzer.

In one set of embodiments, the hemodialysis system includes a blood flow path through which blood is drawn from a patient and passed through a dialyzer, the blood flow path including a blood flow pump, a dialysate flow path through which dialysate flows from a dialysate supply through the dialyzer, where the dialysate flow path includes a dialysate pump, and a control fluid path through which a control fluid actuates the blood flow pump and the dialysate pump.

The hemodialysis system, in another set of embodiments, comprises a blood flow path through which blood is drawn from a patient and passed through a dialyzer; and a dialysate flow path through which dialysate flows from a dialysate supply through the dialyzer. In some cases, the dialysate flow path includes at least one pneumatic pump.

The hemodialysis system, in still another set of embodiments, includes a first pump comprising a pumping chamber and an actuation chamber, a second pump comprising a pumping chamber and an actuation chamber, a control fluid in fluidic communication with each of the actuation chambers of the first and second pumps, and a controller able to pressurize the control fluid to control operation of the first and second pumps.

In yet another set of embodiments, the hemodialysis system includes a first valve comprising a valving chamber and an actuation chamber, a second valve comprising a valving chamber and an actuation chamber, a control fluid in fluidic communication with each of the actuation chambers of the first and second valves, and a controller able to pressurize the control fluid to control operation of the first and second valves.

In one set of embodiments, the hemodialysis system includes a blood flow path through which blood is drawn from a patient and passed through a dialyzer, a cassette containing at least a portion of the blood flow path, and a spike integrally formed with the cassette, the spike able to receive a vial of fluid, the integrally formed spike in fluidic communication with the blood flow path within the cassette.

The hemodialysis system, in another set of embodiments, includes a blood flow path through which untreated blood is drawn from a patient and passed through a dialyzer, a dialysate flow path through which dialysate flows from a dialysate supply through the dialyzer, the dialyzer permitting dialysate to pass from the dialysate flow path to the blood flow path, and a gas supply in fluidic communication with the dialysate flow path so that, when activated, gas from the gas supply causes the dialysate to pass through the dialyzer and urge blood in the blood flow path back to the patient.

In yet another set of embodiments, the hemodialysis system includes a blood flow path through which untreated blood is drawn from a patient and passed through a dialyzer, a dialysate flow path through which dialysate flows from a dialysate supply through the dialyzer, the dialyzer permitting dialysate to pass from the dialysate flow path to the blood flow path, a fluid supply, a chamber in fluid communication with the fluid supply and the dialysate fluid path, the chamber having a diaphragm separating fluid of the fluid supply from dialysate of the dialysate flow path, and a pressurizing device for pressurizing the fluid supply to urge the diaphragm against the dialysate in the chamber, so as to cause the dialysate to pass through the dialyzer and urge blood in the blood flow path back to the patient.

The hemodialysis system, in still another set of embodiments, includes a blood flow path through which untreated blood is drawn from a patient and passed through a dialyzer, a dialysate flow path through which dialysate flows from a dialysate supply through the dialyzer, the dialysate flow path and the blood flow path being in fluidic communication, and a pressure device able to urge dialysate in the dialysate flow path to flow into the blood flow path.

In one set of embodiments, the hemodialysis system includes a first housing containing a positive-displacement pump actuated by a control fluid, a fluid conduit fluidly connecting the positive-displacement pump with a control fluid pump, and a second housing containing the control fluid pump, where the second housing is detachable from the first housing.

In another set of embodiments, the hemodialysis system includes a housing comprising a first compartment and a second compartment separated by an insulating wall, the first compartment being sterilizable at a temperature of at least about 80° C., the second compartment containing electronic components that, when the first compartment is heated to a temperature of at least about 80° C., are not heated to a temperature of more than 60° C.

The hemodialysis system, in yet another set of embodiments, includes a blood flow path through which untreated blood is drawn from a patient and passed through a dialyzer, the blood flow path including at least one blood valve; a control fluid path for providing a control fluid from an actuator mechanism to the blood valve for actuating the blood valve; a dialysate mixing system fluidly connected to the dialyzer, including at least one dialyzer valve; and a heater for heating the dialysate.

Another aspect of the present invention is directed to a valving system. In one set of embodiments, the valving system includes a valve housing containing a plurality of valves, at least two of which valves each comprises a valving chamber and an actuation chamber, each of the at least two valves being actuatable by a control fluid in the actuation chamber; a control housing having a plurality of fluid-interface ports for providing fluid communication with a control fluid from a base unit; and a plurality of tubes extending between the valve housing and the control housing, each tube providing fluid communication between one of the fluid-interface ports and at least one of the actuation chambers, such that the base unit can actuate a valve by pressurizing control fluid in the fluid interface port.

In one set of embodiments, the invention is directed to a valve including a first plate; a second plate, the second plate having an indentation on a side facing the first plate, the indentation having a groove defined therein, the groove being open in a direction facing the first plate; a third plate, wherein the second plate is located between the first and third plate; and a diaphragm located in the indentation between the first plate and the second plate, the diaphragm having a rim, the rim being held in the groove. The second plate may include a valve seat arranged so that the diaphragm may be urged by pneumatic pressure to seal the valve seat closed, the groove surrounding the valve seat. In some cases, a valve inlet and a valve outlet are defined between the second and third plates. In one embodiment, a passage for providing pneumatic pressure is defined between the first and second plates.

Yet another aspect of the present invention is directed to a pumping system. The pumping system, in one set of embodiments, includes a pump housing containing a plurality of pumps, at least two of which pumps each includes a pumping chamber and an actuation chamber, each of the at least two pumps being actuatable by a control fluid in the actuation chamber; a control housing having a plurality of fluid-interface ports for providing fluid communication with a control fluid from a base unit; and a plurality of tubes extending between the pump housing and the control housing, each tube providing fluid communication between one of the fluid-interface ports and at least one of the actuation chambers, such that the base unit can actuate a pump by pressurizing control fluid in the fluid interface port.

The invention is generally directed to a pumping cassette in another aspect. In one set of embodiments, the pumping cassette includes at least one fluid inlet, at least one fluid outlet, a flow path connecting the at least one fluid inlet and the at least one fluid outlet, and a spike for attaching a vial to said cassette. The spike may be in fluidic communication with the flow path in some cases.

In one aspect, the invention is generally directed to a pumping cassette for balancing flow to and from a target. In one set of embodiments, the pumping cassette includes a cassette inlet, a supply line to the target, a return line from the target, a cassette outlet, a pumping mechanism for causing fluid to flow from the cassette inlet to the supply line and from the return line to the cassette outlet, and a balancing chamber. In some cases, the pumping mechanism includes a pod pump comprising a rigid curved wall defining a pumping volume and having an inlet and an outlet, a pump diaphragm mounted within the pumping volume; and an actuation port for connecting the pod pump to a pneumatic actuation system so that the diaphragm can be actuated to urge fluid into and out of the pumping volume, wherein the pump diaphragm separates the fluid from a gas in fluid communication with the pneumatic actuation system. In certain instances, the balancing chamber includes a rigid curved wall defining a balance volume; and a balance diaphragm mounted within the balance volume, where the balance diaphragm separates the balance volume into a supply side and a return side, each of the supply side and the return side having an inlet and an outlet. In some cases, fluid from the cassette inlet flows to the supply side inlet, fluid from the supply side outlet flows to the supply line, fluid from the return line flows to the return side inlet, and fluid from the return side outlet flows to the cassette outlet.

In another set of embodiments, the pumping system includes a system inlet, a supply line to the target, a return line from the target, a system outlet, a pumping mechanism for causing fluid to flow from the system inlet to the supply line and from the return line to the system outlet, and a balancing chamber.

In one embodiment, the pumping mechanism includes a pod pump comprising a rigid spheroid wall defining a pumping volume and having an inlet and an outlet, a pump diaphragm mounted within and to the spheroid wall, and a port for connecting the pod pump to a pneumatic actuation system so that the diaphragm can be actuated to urge fluid into and out of the pumping volume. In some cases, the pump diaphragm separates the fluid from a gas in fluid communication with the pneumatic actuation system;

In certain instances, the balancing chamber includes a rigid spheroid wall defining a balance volume, and a balance diaphragm mounted within and to the spheroid wall. In one embodiment, the balance diaphragm separates the balance volume into a supply side and a return side, each of the supply side and the return side having an inlet and an outlet. In some cases, fluid from the system inlet flows to the supply side inlet, fluid from the supply side outlet flows to the supply line, fluid from the return line flows to the return side inlet, and fluid from the return side outlet flows to the system outlet. The pumping mechanism may also include valving mechanisms located at each of the inlets and outlets of the supply side and the return side. The valving mechanisms may be pneumatically actuated.

Yet another aspect of the invention is directed to a cassette. In one set of embodiments, the cassette includes a first flow path connecting a first inlet to a first outlet, a second flow path connecting a second inlet to a second outlet, a pump able to pump fluid through at least a portion of the second flow path, and at least two balancing chambers, each balancing chamber comprising a rigid vessel containing a diaphragm dividing the rigid vessel into a first compartment and a second compartment, the first compartment of each balancing chamber being in fluidic communication with the first flow path and the second compartment being in fluidic communication with the second flow path.

In another set of embodiments, the cassette includes a first flow path connecting a first inlet to a first outlet; a second flow path connecting a second inlet to a second outlet; a control fluid path; at least two pumps, each pump comprising a rigid vessel containing a diaphragm dividing the rigid vessel into a first compartment and a second compartment, the first compartment of each pump being in fluidic communication with the control fluid path and the second compartment being in fluidic communication with the second flow path; and a balancing chamber able to balance flow between the first flow path and the second flow path.

The cassette, in still another set of embodiments, includes a first flow path connecting a first inlet to a first outlet, a second flow path connecting a second inlet to a second outlet, and a rigid vessel containing a diaphragm dividing the rigid vessel into a first compartment and a second compartment. In some cases, the first compartment are in fluidic communication with the first fluid path and the second compartment being in fluidic communication with the second flow path.

Still another aspect of the invention is generally directed at a pump. The pump includes, in one set of embodiments, a first rigid component; a second rigid component, the second rigid component having on a side facing the first plate a groove defined therein, the groove being open in a direction facing the first rigid component; and a diaphragm having a rim, the rim being held in the groove by a friction fit in the groove but without contact by the first rigid component against the rim. In some cases, the first and second rigid components define, at least partially, a pod-pump chamber divided by the diaphragm into separate chambers, and further define, at least partially, flow paths into the pod-pump chamber, wherein the groove surrounds the pod-pump chamber.

In another set of embodiments, the pump includes a substantially spherical vessel containing a flexible diaphragm dividing the rigid vessel into a first compartment and a second compartment, the first compartment and the second compartment not in fluidic communication with each other, whereby movement of the diaphragm due to fluid entering the first compartment causes pumping of fluid within the second compartment to occur.

In another set of embodiments, the pump is a reciprocating positive-displacement pump. In one embodiment, the pump includes a rigid chamber wall; a flexible diaphragm attached to the rigid chamber wall, so that the flexible diaphragm and rigid chamber wall define a pumping chamber; an inlet for directing flow through the rigid chamber wall into the pumping chamber; an outlet for directing flow through the rigid chamber wall out of the pumping chamber; a rigid limit wall for limiting movement of the diaphragm and limiting the maximum volume of the pumping chamber, the flexible diaphragm and the rigid limit wall forming an actuation chamber; a pneumatic actuation system that intermittently provides a control pressure to the actuation chamber. In some cases, the pneumatic actuation system includes an actuation-chamber pressure transducer for measuring the pressure of the actuation chamber, a gas reservoir having a first pressure, a variable valve mechanism for variably restricting gas flowing between the actuation chamber and the gas reservoir, and a controller that receives pressure information from the actuation-chamber pressure transducer and controls the variable valve so as to create the control pressure in the actuation chamber, the control pressure being less than the first pressure.

Still another aspect of the invention is directed to a method. The method, in one set of embodiments, includes acts of providing a first pump comprising a pumping chamber and an actuation chamber, and a second pump comprising a pumping chamber and an actuation chamber, urging a common fluid into the actuation chambers of each of the first and second pumps, and pressurizing the common fluid to pump fluids through each of the first and second pumps.

In another set of embodiments, the method includes acts of providing a first valve comprising a valving chamber and an actuation chamber, and a second valve comprising a valving chamber and an actuation chamber, urging a common fluid into the actuation chambers of each of the first and second valves, and pressurizing the common fluid to at least partially inhibit fluid flow through each of the first and second valves.

In yet another set of embodiments, the method is a method for measuring the clearance of a dialyzer, the dialyzer being located in a blood flow path, through which untreated blood can be drawn from a patient and passed through the dialyzer, and in a dialysate flow path, through which dialysate can flow from a dialysate supply through the dialyzer, the blood flow path being separated from the dialysate flow path by membranes in the dialyzer. In one embodiment, the method includes acts of urging a liquid through the dialysate flow path to the dialyzer, so as to keep the membranes wet and prevent the flow of a gas through the membranes, urging a gas through the blood flow path to the dialyzer so as to fill the blood flow path in the dialyzer with the gas, measuring the volume of gas in the dialyzer, and calculating the clearance of the dialyzer based on the volume of gas measured in the dialyzer.

The method, in still another set of embodiments, is a method for measuring the clearance of a dialyzer. In one embodiment, the method includes acts of applying a pressure differential across the dialyzer, measuring the flow rate of the dialyzer, and determining the clearance of the dialyzer based on the pressure differential and the flow rate.

In yet another set of embodiments, the method is a method for measuring the clearance of a dialyzer. In one embodiment, the method includes acts of passing water through the dialyzer, measuring the amount of ions collected by the water after passing through the dialyzer, and determining the clearance of the dialyzer based on the amount of ions collected by the water after passing through the dialyzer. In another set of embodiments, the method includes acts of passing water through the dialyzer, measuring the conductivity of the water, and determining the clearance of the dialyzer based on changes in the conductivity of the water.

In one set of embodiments, the method is a method for introducing a fluid into blood. The method includes, in one embodiment, acts of providing a cassette including an integrally formed spike for receiving a vial of fluid, and a valving mechanism for controlling flow of the fluid from the vial into the cassette, attaching a vial containing the fluid to the spike, pumping blood through the cassette, and introducing the fluid from the vial into the blood.

In one set of embodiments, the method includes acts of providing a hemodialysis system comprising a blood flow path through which untreated blood is drawn from a patient and passed through a dialyzer, and a dialysate flow path through which dialysate flows from a dialysate supply through the dialyzer, putting the blood flow path and the dialysate flow path into fluidic communication, and urging dialysate through the dialysate flow path to cause blood in the blood flow path to pass into the patient.

The method, in another set of embodiments, includes acts of providing a hemodialysis system comprising a blood flow path through which untreated blood is drawn from a patient and passed through a dialyzer, and a dialysate flow path through which dialysate flows from a dialysate supply through the dialyzer, putting the blood flow path and the dialysate flow path into fluidic communication, and urging a gas into the dialysate flow path to cause flow of blood in the blood flow path.

The method is a method of performing hemodialysis, in still another set of embodiments. In one embodiment, the method includes acts of providing a blood flow path, through which untreated blood can be drawn from a patient and passed through a dialyzer; providing a dialysate flow path, through which dialysate can flow from a dialysate supply through the dialyzer; providing ingredients for preparing a total volume of dialysate; providing water for mixing with the dialysate ingredients; mixing a volume of water with a portion of the ingredients so as to prepare a first partial volume of dialysate, the first partial volume being less than the total volume; pumping the partial volume of dialysate through the dialysate flow path and through the dialyzer; pumping blood through the blood flow path and through the dialyzer, while the first partial volume of dialysate is being pumped to the dialyzer; and mixing a volume of water with a portion of the ingredients so as to prepare a second partial volume of dialysate and storing the second partial volume of dialysate within a vessel while the blood and the first partial volume of dialysate are pumped through the dialyzer.

In another embodiment, the method includes acts of passing blood from a patient and dialysate through a dialyzer contained within a hemodialysis system at a first rate, and forming dialysate within the hemodialysis system at a second rate that is substantially different from the first rate, wherein excess dialysate is stored within a vessel contained within the hemodialysis system.

Another aspect of the invention is directed to a hemodialysis system comprising a dialysis unit and a user interface unit. The dialysis unit comprises an automation computer and dialysis equipment. The user interface unit comprises a user interface computer and a user interface, the user interface being adapted to display information and receive inputs. The automation computer is configured to receive requests for safety-critical information from the user interface computer and to access the safety-critical information on behalf of the user interface computer. The user interface computer is configured to display information related to a dialysis process via the user interface using the safety-critical information.

A further aspect of the invention is directed to a method of managing a user interface in a hemodialysis system. The method comprises receiving an input related to a dialysis process at a user interface associated with a user interface computer and, in response to the input, transmitting a request for safety-critical information from the user interface computer to an automation computer associated with dialysis equipment. The method further comprises accessing the safety-critical information on behalf of the user interface computer and, using the safety-critical information, displaying information related to the dialysis process via the user interface.

Still another aspect of the invention is directed to a computer storage media encoded with instructions that, when executed, perform a method. The method comprising acts of receiving, from a user interface associated with a user interface computer, an input related to a dialysis process and, in response to the input, transmitting a request for safety-critical information from the user interface computer to an automation computer associated with dialysis equipment. The method further comprises accessing the safety-critical information on behalf of the user interface computer, transmitting the safety-critical information to the user interface computer, accessing screen design information stored within the user interface computer and, using the safety-critical information and the screen design information, causing the user interface to display information related to the dialysis process.

In another aspect, the present invention is directed to a method of making one or more of the embodiments described herein, for example, a hemodialysis system. In another aspect, the present invention is directed to a method of using one or more of the embodiments described herein, for example, a hemodialysis system.

In yet another aspect, the invention relates to a control architecture for such a hemodialysis system comprising a user interface model layer, a therapy layer, below the user interface model layer, and a machine layer below the therapy layer. The user interface model layer is configured to manage the state of a graphical user interface and receive inputs from a graphical user interface. The therapy layer is configured to run state machines that generate therapy commands based at least in part on the inputs from the graphical user interface. The machine layer is configured to provide commands for the actuators based on the therapy commands.

A further aspect of the invention is directed to a method for disinfecting fluid pathways in a dialysis system. The method comprises storing, on at least one storage medium, disinfection parameters including a disinfection temperature and a disinfection time. The method further comprises circulating a fluid in the fluid pathways, monitoring a temperature of the fluid at each of a plurality of temperature sensors, and determining that disinfection of the fluid pathways is complete when the temperature of the fluid at each of the plurality of temperature sensors remains at or above the disinfection temperature for at least the disinfection time.

Another aspect of the invention is directed to at least one computer-readable medium encoded with instructions that, when executed on at least one processing unit, perform a method for disinfecting fluid pathways in a dialysis system. The method comprises electronically receiving disinfection parameters including a disinfection temperature and a disinfection time. The method further comprises controlling a plurality of actuators to circulate a fluid in the fluid pathways, monitoring a temperature of the fluid at each of a plurality of temperature sensors, and determining whether the temperature of the fluid at each of the plurality of temperature sensors remains at or above the disinfection temperature for at least the disinfection time.

A further aspect of the invention is directed to a method for controlling the administration of an anticoagulant in a dialysis system. The method comprises storing, on at least one storage medium, an anticoagulant protocol comprising a maximum amount of anticoagulant, automatically administering the anticoagulant according to the anticoagulant protocol, and prohibiting the administration of additional anticoagulant after determining that the maximum amount of anticoagulant has been administered.

Another aspect of the invention is directed to at least one computer-readable medium encoded with instructions that, when executed on at least one processing unit, perform a method for controlling the administration of an anticoagulant in a dialysis system. The method comprises electronically receiving an anticoagulant protocol comprising a maximum amount of anticoagulant, controlling a plurality of actuators to administer the anticoagulant according to the anticoagulant protocol, and prohibiting the administration of additional anticoagulant after determining that the maximum amount of anticoagulant has been administered.

A further aspect of the invention is directed to a method for determining a fluid level in a dialysate tank of a dialysis system. The method comprises tracking a first number of strokes delivering fluid to the dialysate tank, tracking a second number of strokes withdrawing fluid from the dialysate tank, and determining a fluid level in the dialysate tank based, at least in part, on the first number of strokes, the second number of strokes, and a per-stroke volume.

A further aspect of the invention is directed to a method for determining a fluid level in a dialysate tank of a dialysis system. The method comprises charging a reference chamber of a known volume to a predetermined pressure and venting the reference chamber to the dialysate tank. The method further comprises, after venting the reference chamber to the dialysate tank, determining a pressure in the dialysate tank. In addition, the method comprises determining a fluid level in the dialysate tank based, at least in part, on the determined pressure in the dialysate tank.

Another aspect of the invention is directed to a method for returning blood to a patient in the event of a power failure condition in a dialysis system that uses compressed air to actuate pumps and/or valves during a dialysis process, wherein the dialysis system comprises a dialyzer having a membrane that separates a blood flow path from a dialysate flow path. The method comprises identifying a power failure condition in a dialysis system. The method further comprises, in response to the identification of a power failure condition, releasing compressed air from a reservoir associated with the dialysis system. In addition, the method comprises using the released compressed air, increasing a pressure in the dialysate flow path to cause blood in the blood flow path to return to the patient.

A further aspect of the invention is directed to a method for returning extracorporeal blood to a patient, in an extracorporeal treatment system, using a source of compressed gas in the event of a power failure. The extracorporeal treatment system comprises a filter having a semi-permeable membrane that separates a blood flow path from an electrolyte solution flow path. The compressed gas is in valved communication with an electrolyte solution container, and the electrolyte solution container is in valved communication with the electrolyte solution flow path. The method comprises, in response to a termination of electrical power to one or more electrically actuated valves that control a distribution of compressed gas or a distribution of electrolyte solution flow in the extracorporeal treatment system, causing one or more first electrically actuated valves to open a first fluid pathway between the compressed gas and the electrolyte solution container, causing one or more second electrically actuated valves to open a second fluid pathway between said electrolyte solution container and said filter, causing one or more third electrically actuated valves to close an alternate fluid pathway in said electrolyte solution flow path if said alternate fluid pathway diverts electrolyte solution away from said filter; and using the compressed gas to increase pressure in the electrolyte solution flow path to cause blood in the blood flow path to return to the patient.

Another aspect of the invention is directed to a method for returning extracorporeal blood to a patient, in an extracorporeal treatment system, using a source of compressed gas in the event of a power failure. The extracorporeal treatment system comprises a filter having a semi-permeable membrane that separates a blood flow path from an electrolyte solution flow path. The compressed gas is in valved communication with an electrolyte solution container, and the electrolyte solution container is in valved communication with the electrolyte solution flow path. The method comprises, in response to a termination of electrical power to one or more electrically actuated valves that control a distribution of compressed gas or a distribution of electrolyte solution flow in the extracorporeal treatment system: causing one or more electrically actuated valves to open a fluid pathway between the compressed gas and the electrolyte solution container, and, using the compressed gas, causing flow of an electrolyte solution from the electrolyte solution container through the filter to cause blood in the blood flow path to return to the patient.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

Figure 76A:
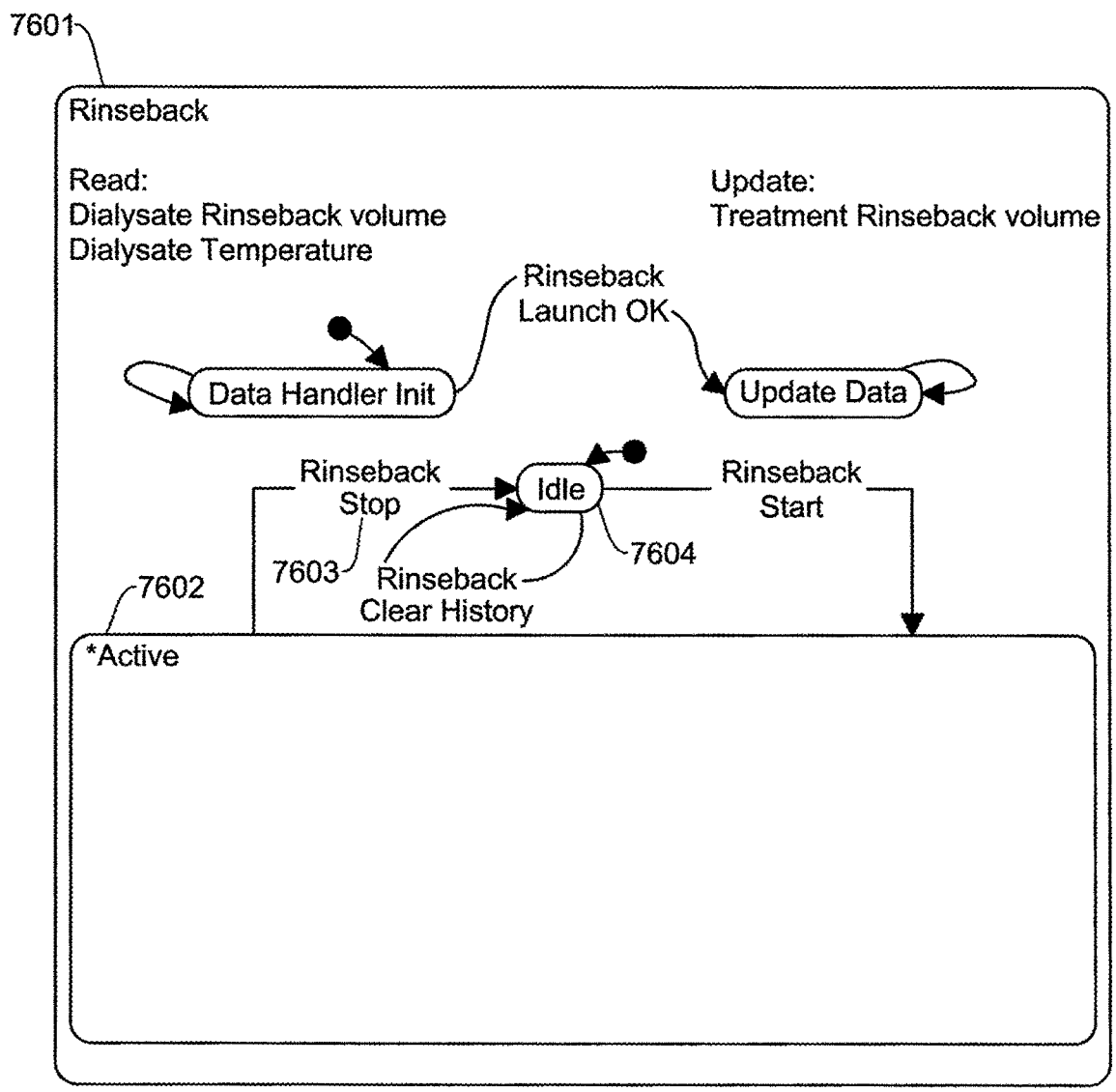
Figure 76B:
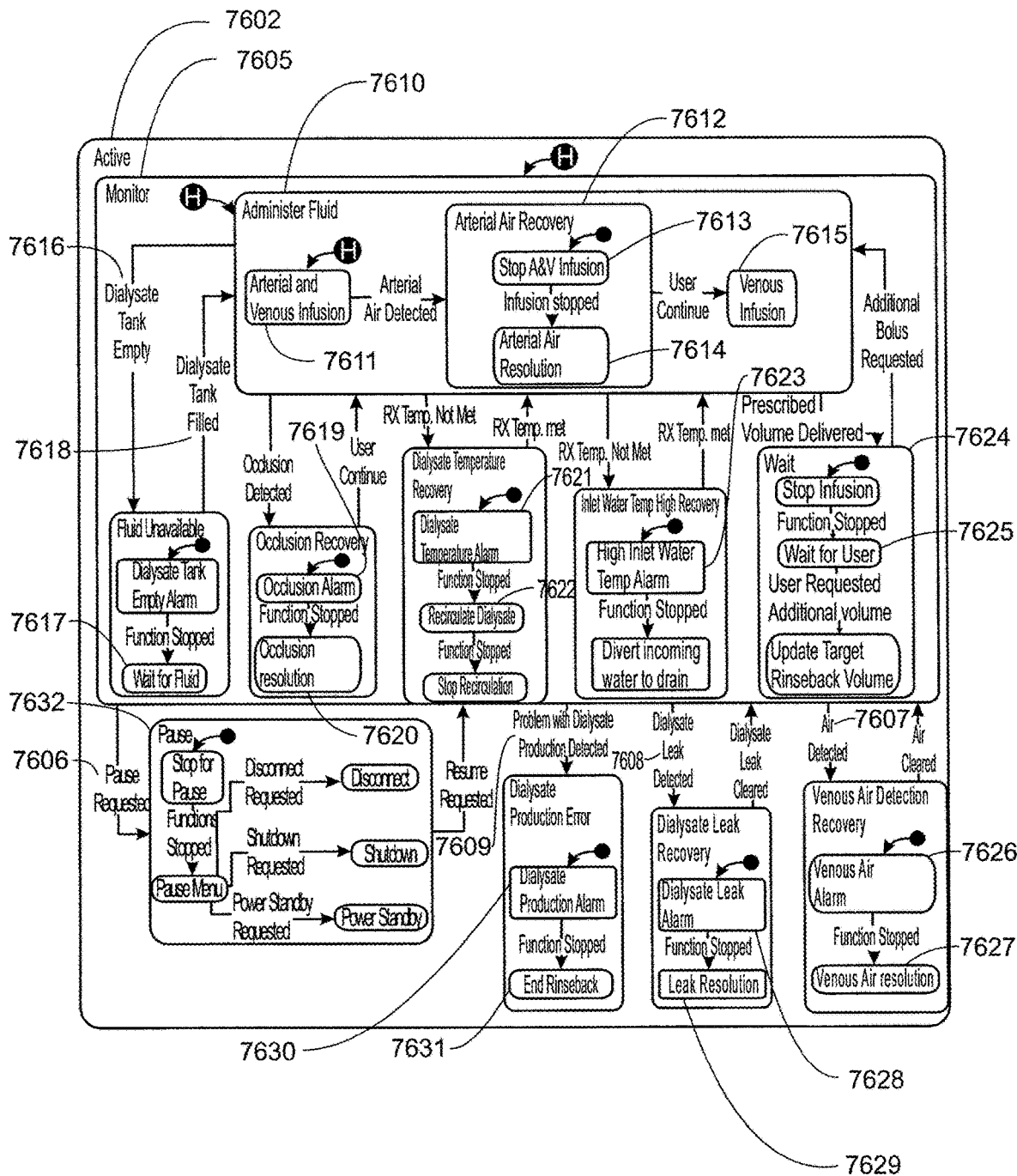
Figure 77:
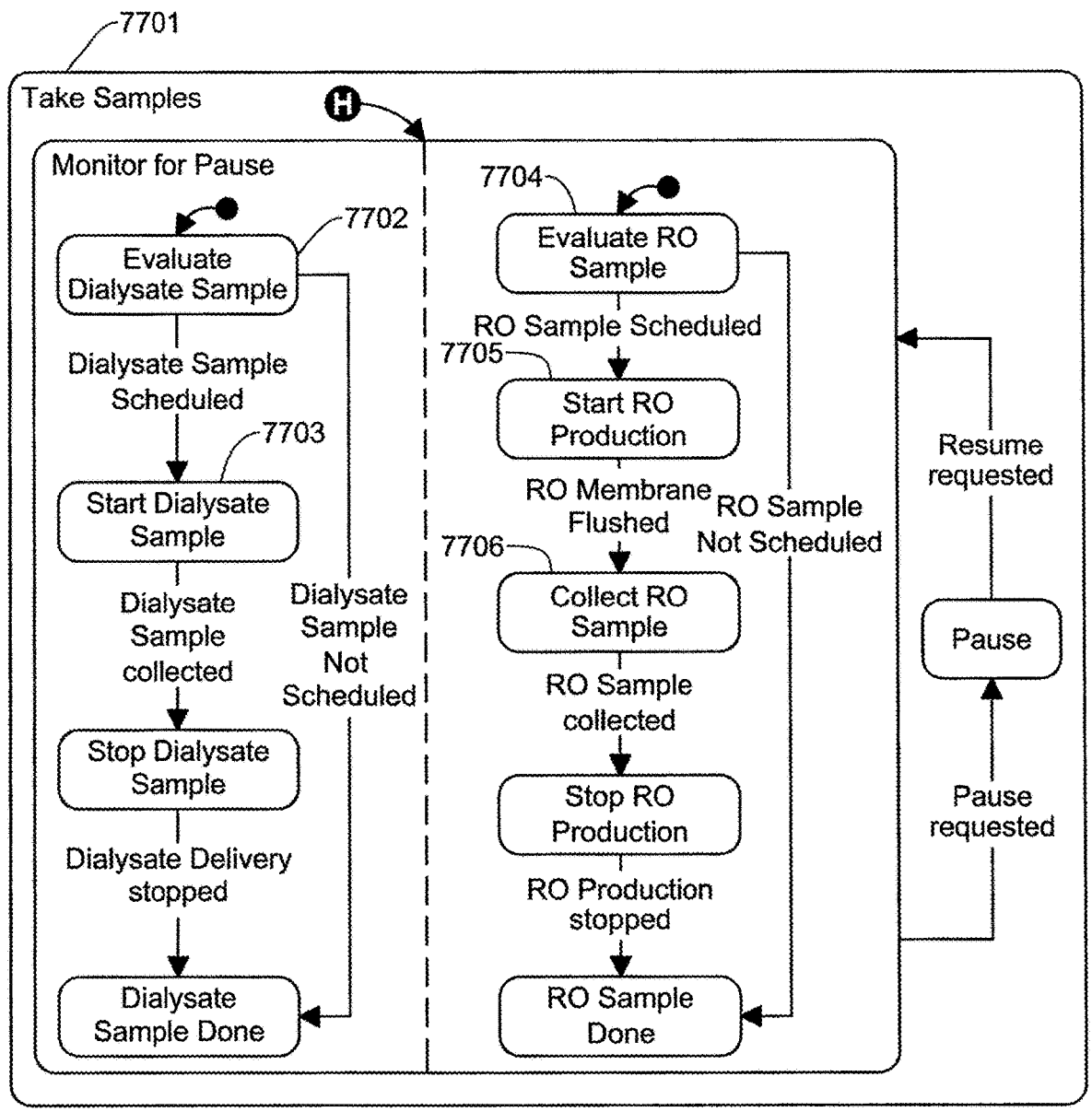
Figure 78A:
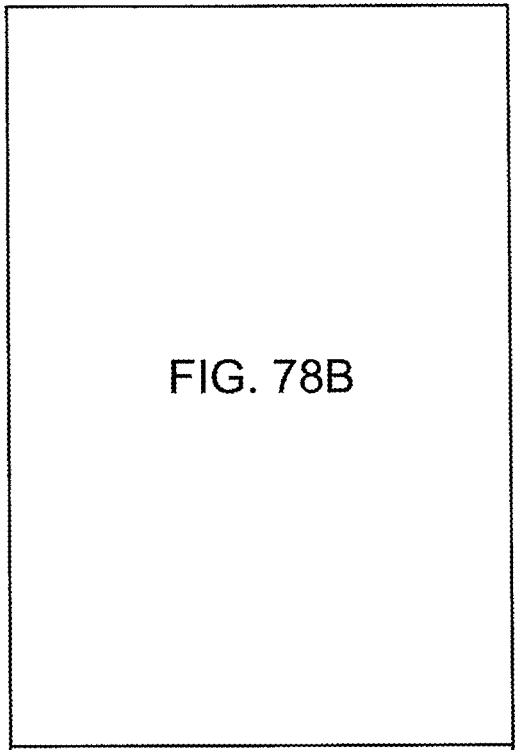
Figure 78A:
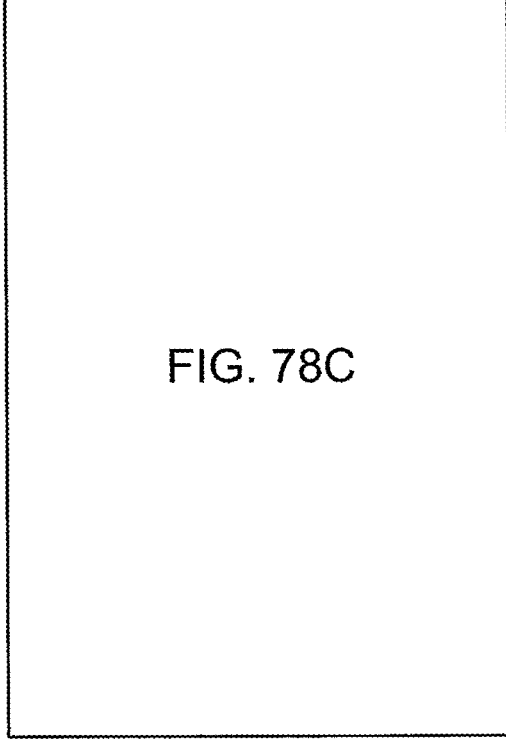
Figure 78B:
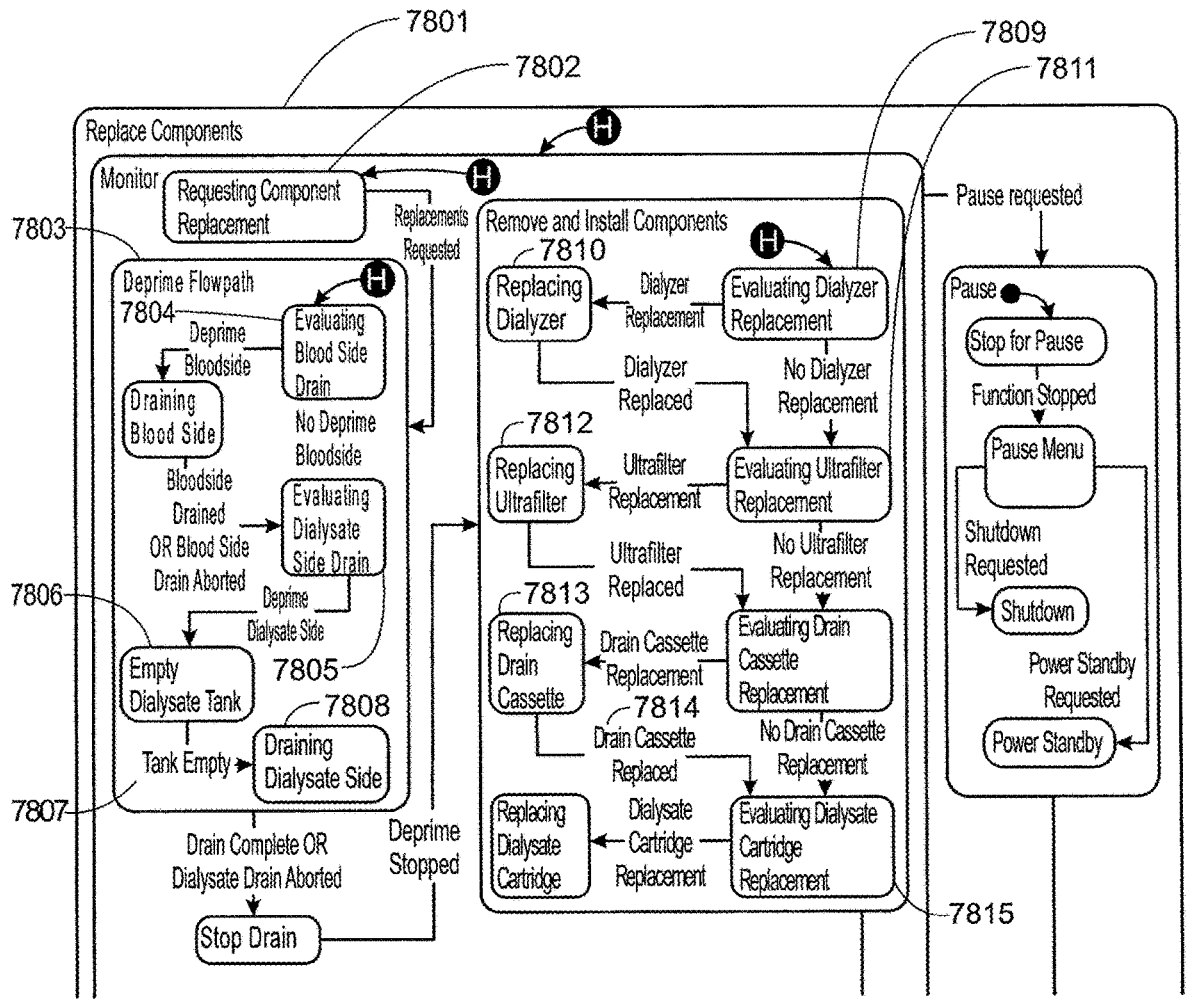
Figure 78C:
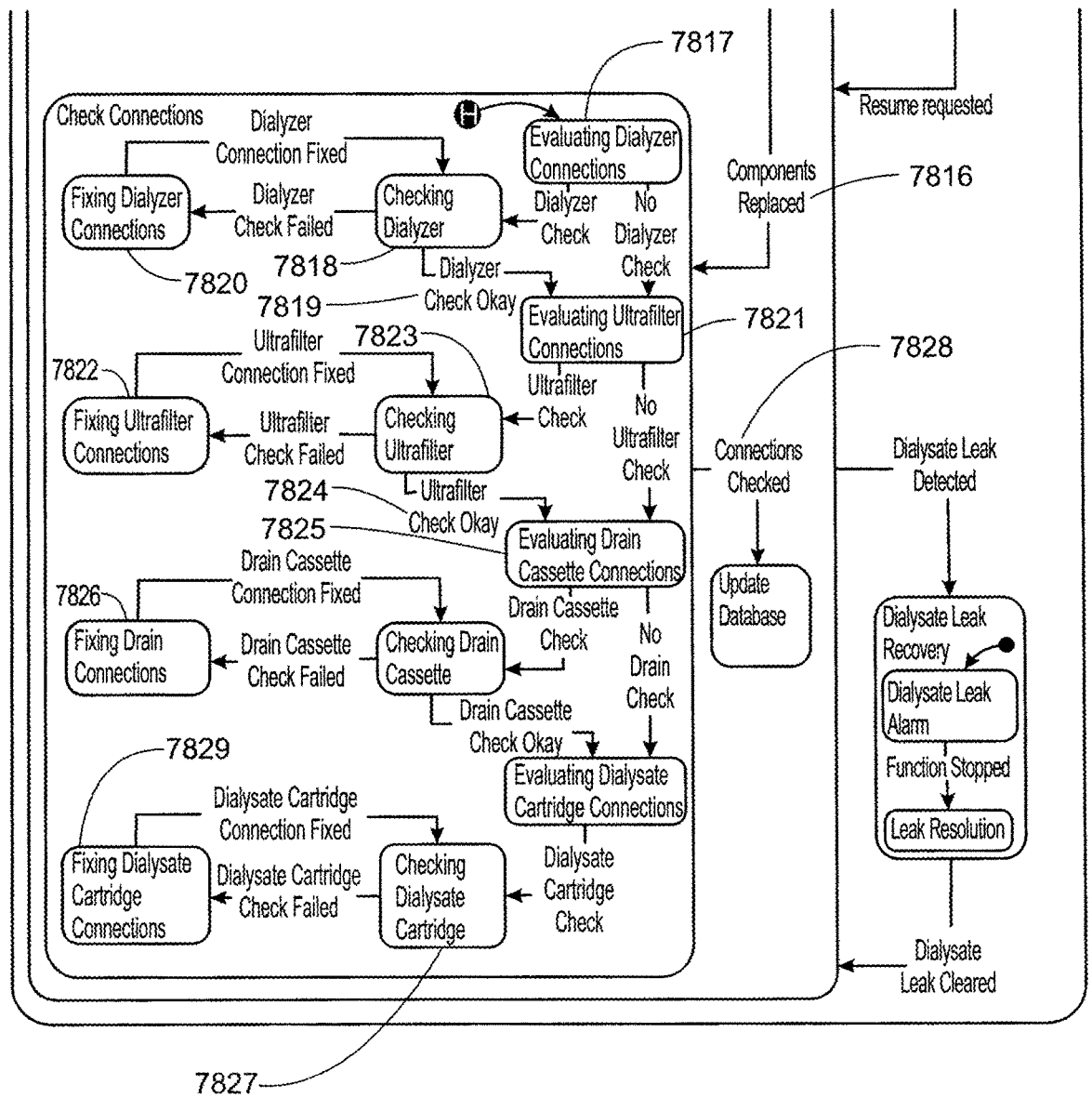
Figure 79A:
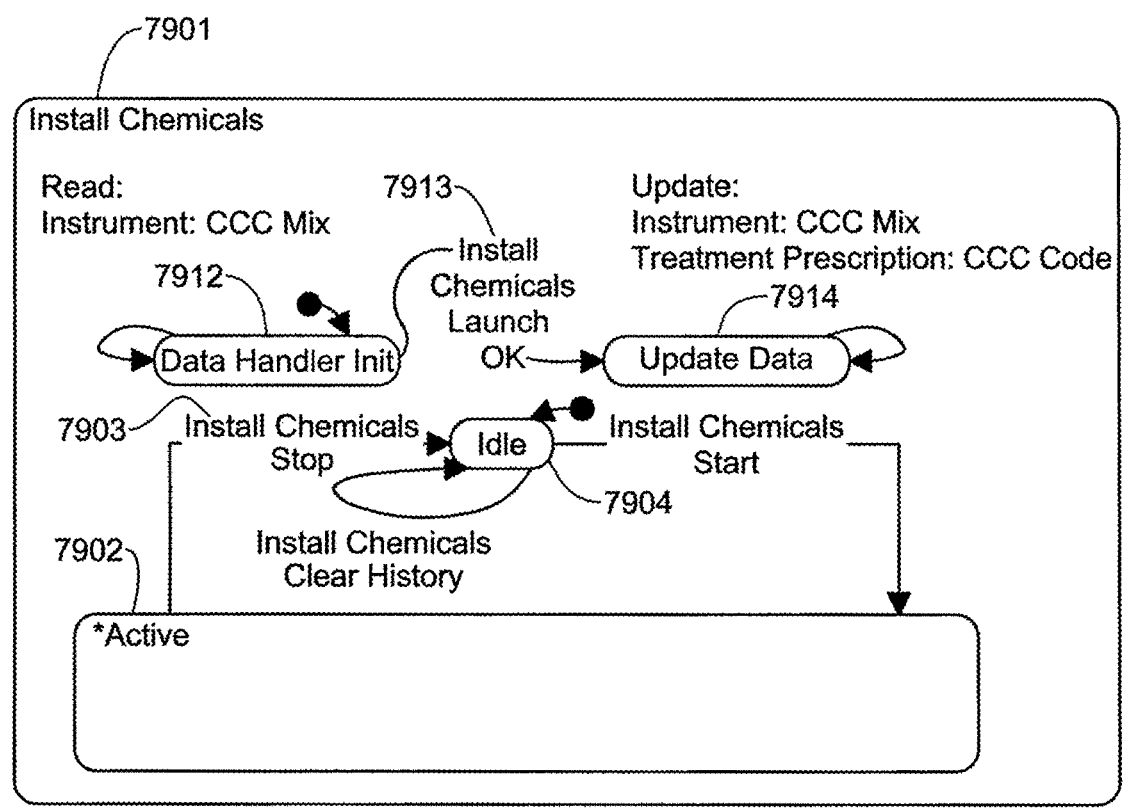
Figure 79B:
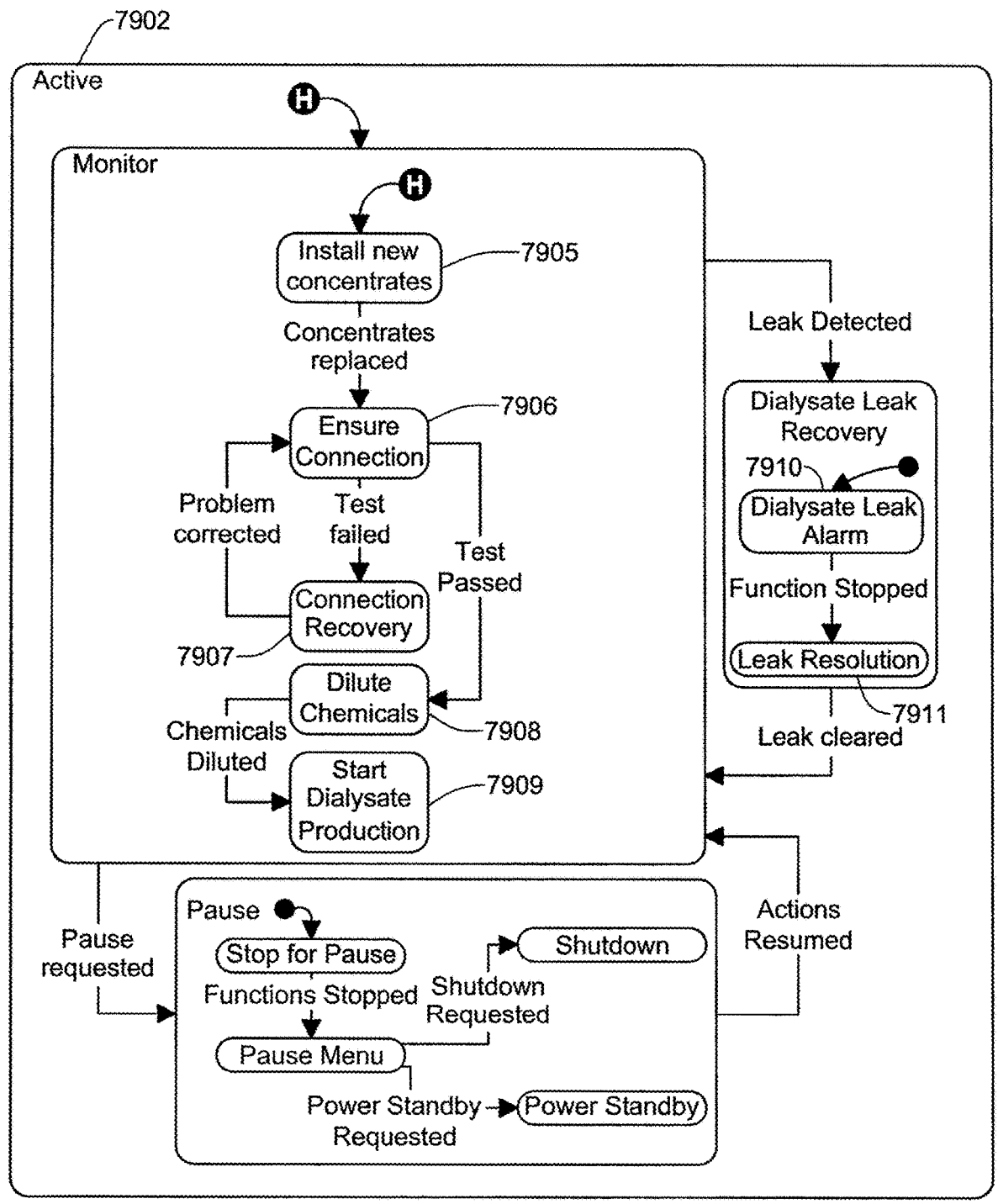
Figure 80:
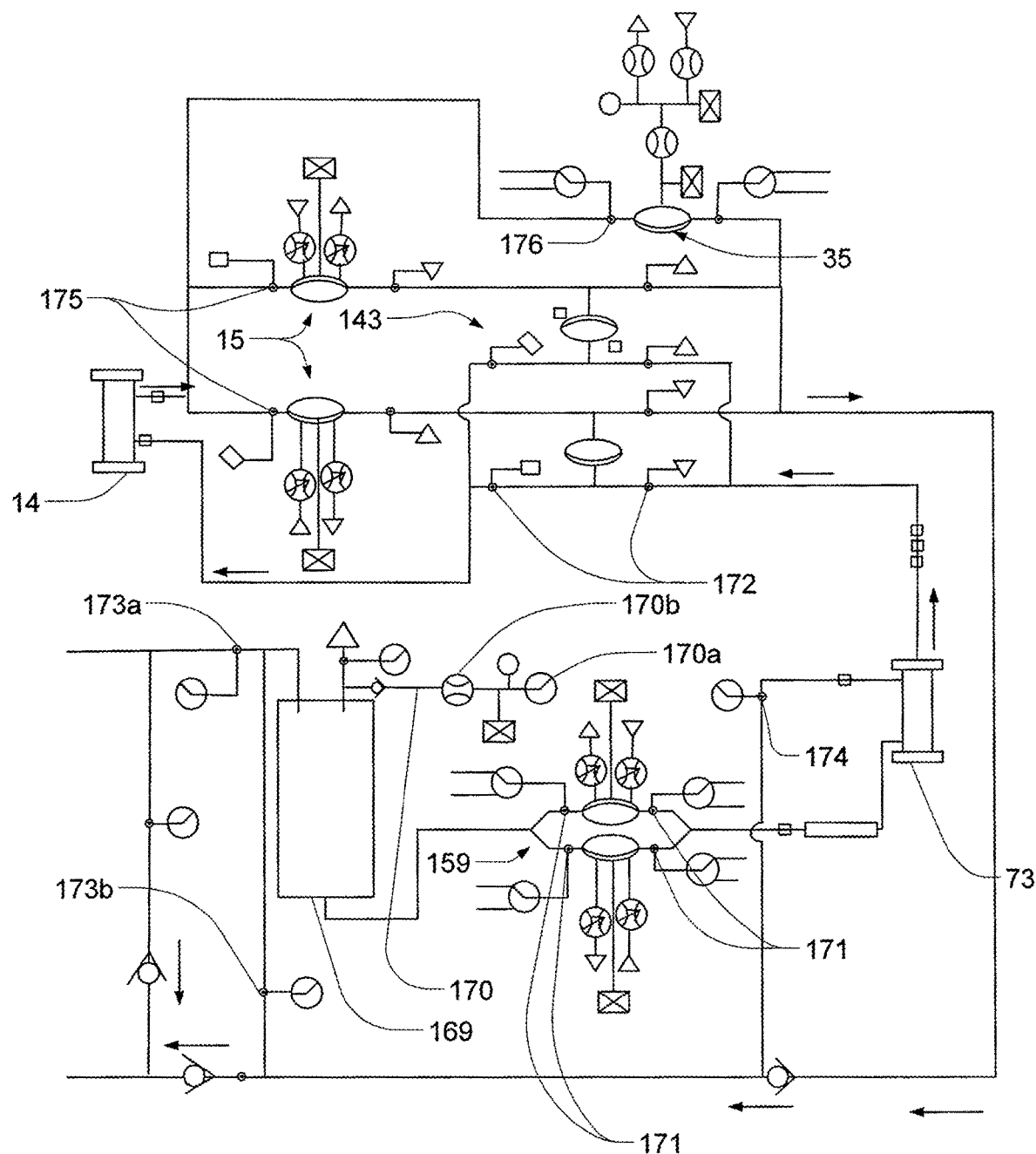

FIGS. 75a-e are schematic views showing shows an exemplary implementation of the Solution Infusion application;

FIGS. 76a-b are schematic views showing shows an exemplary implementation of the Rinseback application;

FIG. 77 is a schematic view showing shows an exemplary implementation of the Take Samples application;

FIG. 78A is a template showing how the partial diagrams of FIGS. 78B and 78C should be joined for viewing of the complete Replace Components application protocol;

FIG. 78B and FIG. 78C are schematic views each showing a portion of an exemplary implementation of the Replace Components application;

FIGS. 79a-b are schematic views showing shows an exemplary implementation of the Install Chemicals application; and FIG. 80 shows, in the context of the hemodialysis system, a pathway between a pressurized air tank and a dialysate tank.

DETAILED DESCRIPTION

The present invention generally relates to hemodialysis and similar extracorporeal blood treatment systems, including a variety of systems and methods that would make hemodialysis more efficient, easier, and/or more affordable.

One aspect of the invention is generally directed to new fluid circuits for fluid flow. In one set of embodiments, a hemodialysis system may include a blood flow path and a dialysate flow path, where the dialysate flow path includes one or more of a balancing circuit, a mixing circuit, and/or a directing circuit. Preparation of dialysate by the mixing circuit, in some instances, may be decoupled from patient dialysis. In some cases, the circuits are defined, at least partially, within one or more cassettes, optionally interconnected with conduits, pumps, or the like. In one embodiment, the fluid circuits and/or the various fluid flow paths may be at least partially isolated, spatially and/or thermally, from electrical components of the hemodialysis system. In some cases, a gas supply may be provided in fluid communication with the dialysate flow path and/or the dialyzer that, when activated, is able to urge dialysate to pass through the dialyzer and urge blood in the blood flow path back to the patient. Such a system may be useful, for example, in certain emergency situations (e.g., a power failure) where it is desirable to return as much blood to the patient as possible. The hemodialysis system may also include, in another aspect of the invention, one or more fluid handling devices, such as pumps, valves, mixers, or the like, which can be actuated using a control fluid, such as air. In some cases, the control fluid may be delivered to the fluid handling devices using an external pump or other device, which may be detachable in certain instances. In one embodiment, one or more of the fluid handling devices may be generally rigid (e.g., having a spheroid shape), optionally with a diaphragm contained within the device, dividing it into first and second compartments.

Various aspects of the present invention are generally directed to new systems for hemodialysis and the like, such as hemofiltration systems, hemodiafiltration systems, plasmapheresis systems, etc. Accordingly, although the various systems and methods described herein are described in relation to hemodialysis, it should be understood that the various systems and method described herein are applicable to other dialysis systems and/or in any extracorporeal system able to treat blood or other bodily fluids, such as plasma.

As discussed above, a hemodialysis system typically includes a blood flow path and a dialysate flow path. It should be noted that within such flow paths, the flow of fluid is not necessarily linear, and there may be any number of "branches" within the flow path that a fluid can flow from an inlet of the flow path to an outlet of the flow path. Examples of such branching are discussed in detail below. In the blood flow path, blood is drawn from a patient, and is passed through a dialyzer, before being returned to the patient. The blood is treated by the dialyzer, and waste molecules (e.g., urea, creatinine, etc.) and water are passed from the blood, through a semi-permeable membrane in the dialyzer, into a dialysate solution that passes through the dialyzer by the dialysate flow path. In various embodiments, blood may be drawn from the patient from two lines (e.g., an arterial line and a venous line, i.e., "dual needle" flow), or in some cases, blood may be drawn from the patient and returned through the same needle (e.g., the two lines may both be present within the same needle, i.e., "single needle" flow). In still other embodiments, a "Y" site or "T" site is used, where blood is drawn from the patient and returned to the patient through one patient connection having two branches (one being the fluid path for the drawn blood, the second the fluid path for the return blood). In an embodiment, a "Y" or "T" connection can be made with a single-lumen needle or catheter. In another embodiment, a "dual needle" flow effect can be obtained with the use of a single catheter or needle having dual lumens. The patient may be any subject in need of hemodialysis or similar treatments, although typically the patient is a human. However, hemodialysis may be performed on non-human subjects, such as dogs, cats, monkeys, and the like.

In the dialysate flow path, fresh dialysate is prepared and is passed through the dialyzer to treat the blood from the blood flow path. The dialysate may also be equalized for blood treatment within the dialyzer (i.e., the pressure between the dialysate and the blood are equalized), i.e., the pressure of dialysate through the dialyzer is closely matched to the pressure of blood through the dialyzer, often exactly, or in some embodiments, at least within about 1% or about 2% of the pressure of the blood. In some cases, it may be desirable to maintain a greater pressure difference (either positive or negative) between the blood flow path and dialysate flow path. After passing through the dialyzer, the used dialysate, containing waste molecules (as discussed below), is discarded in some fashion. In some cases, the dialysate is heated prior to treatment of the blood within the dialyzer using an appropriate heater, such as an electrical resistive heater. The dialysate may also be filtered to remove contaminants, infectious organisms, debris, and the like, for instance, using an ultrafilter. The ultrafilter may have a mesh or pore size chosen to prevent species such as these from passing therethrough. For instance, the mesh or pore size may be less than about 0.3 micrometers, less than about 0.2 micrometers, less than about 0.1 micrometers, or less than about 0.05 micrometers, etc. The dialysate is used to draw waste molecules (e.g., urea, creatinine, ions such as potassium, phosphate, etc.) and water from the blood into the dialysate through osmosis or convective transport, and dialysate solutions are well-known to those of ordinary skill in the art.

The dialysate typically contains various ions such as sodium chloride, bicarbonate, potassium and calcium that are similar in concentration to that of normal blood. In some cases, the bicarbonate, may be at a concentration somewhat higher than found in normal blood. Typically, the dialysate is prepared by mixing water from a water supply with one or more ingredients: an "acid" (which may contain various species such as acetic acid, dextrose, NaCl, CaCl, KCl, MgCl, etc.), sodium bicarbonate ($NaHCO_3$), and/or sodium chloride (NaCl). The preparation of dialysate, including using the appropriate concentrations of salts, osmolarity, pH, and the like, is well-known to those of ordinary skill in the art. As discussed in detail below, the dialysate need not be prepared at the same rate that the dialysate is used to treat the blood. For instance, the dialysate can be made concurrently or prior to dialysis, and stored within a dialysate storage vessel or the like.

Within the dialyzer, the dialysate and the blood typically do not come into physical contact with each other, and are separated by a semi-permeable membrane. Typically, the semipermeable membrane is formed from a polymer such as cellulose, polyarylethersulfone, polyamide, polyvinylpyrrolidone, polycarbonate, polyacrylonitrile, or the like, which allows the transport of ions or small molecules (e.g., urea, water, etc.), but does not allow bulk transport or convection during treatment of the blood. In some cases, even larger molecules, such as beta-2-microglobulin, may pass through the membrane. In other cases, convective transfer of fluid, ions and small molecules can occur, for example, when there is a hydrostatic pressure difference across the semi-permeable membrane.

The dialysate and the blood do not come into contact with each other in the dialyzer, and are usually separated by the membrane. Often, the dialyzer is constructed according to a "shell-and-tube" design comprising a plurality of individual tubes or fibers (through which blood flows), formed from the semipermeable membrane, surrounded by a larger "shell" through which the dialysate flows (or vice versa in some cases). Flow of the dialysate and the blood through the dialyzer can be countercurrent, or concurrent in some instances. Dialyzers are well-known to those of ordinary skill in the art, and are obtainable from a number of different commercial sources.

In one aspect, the dialysate flow path can be divided into one or more circuits, such as a balancing circuit, a mixing circuit, and/or a directing circuit. It should be noted that a circuit, in reference to fluid flow, is not necessarily fluidically isolated, i.e., fluid may flow into a fluid circuit and out of a fluid circuit. Similarly, a fluid may pass from one fluid circuit to another fluid circuit when the fluid circuits are in fluid communication or are fluidly connected to each other. It should be noted that, as used herein, "Fluid" means anything having fluidic properties, including but not limited to, gases such as air, and liquids such as water, aqueous solution, blood, dialysate, etc.

A fluid circuit is typically a well-defined module that receives a certain number of fluid inputs and in some cases performs one or more tasks on the fluid inputs, before directing the fluids to appropriate outputs. In certain embodiments of the invention, as discussed below, the fluid circuit is defined as a cassette. As a specific example, a dialysate flow path may include a balancing circuit, a directing circuit, and a mixing circuit. As another example, a blood flow path may include a blood flow circuit. Within the balancing circuit, dialysate is introduced into the balancing circuit and pumps operate on the dialysate such that the pressure of dialysate passing through the dialyzer balances the pressure of blood passing through the dialysate, as previously discussed. Similarly, within the directing circuit, fresh dialysate is passed from the mixing circuit to the balancing circuit, while used dialysate is passed from the balancing circuit to a drain. Within the mixing circuit, ingredients and water are mixed together to form fresh dialysate. The blood flow circuit is used to draw blood from the patient, pass the blood through a dialyzer, and return the blood to the patient. These circuits will be discussed in detail below.

Figure 1:
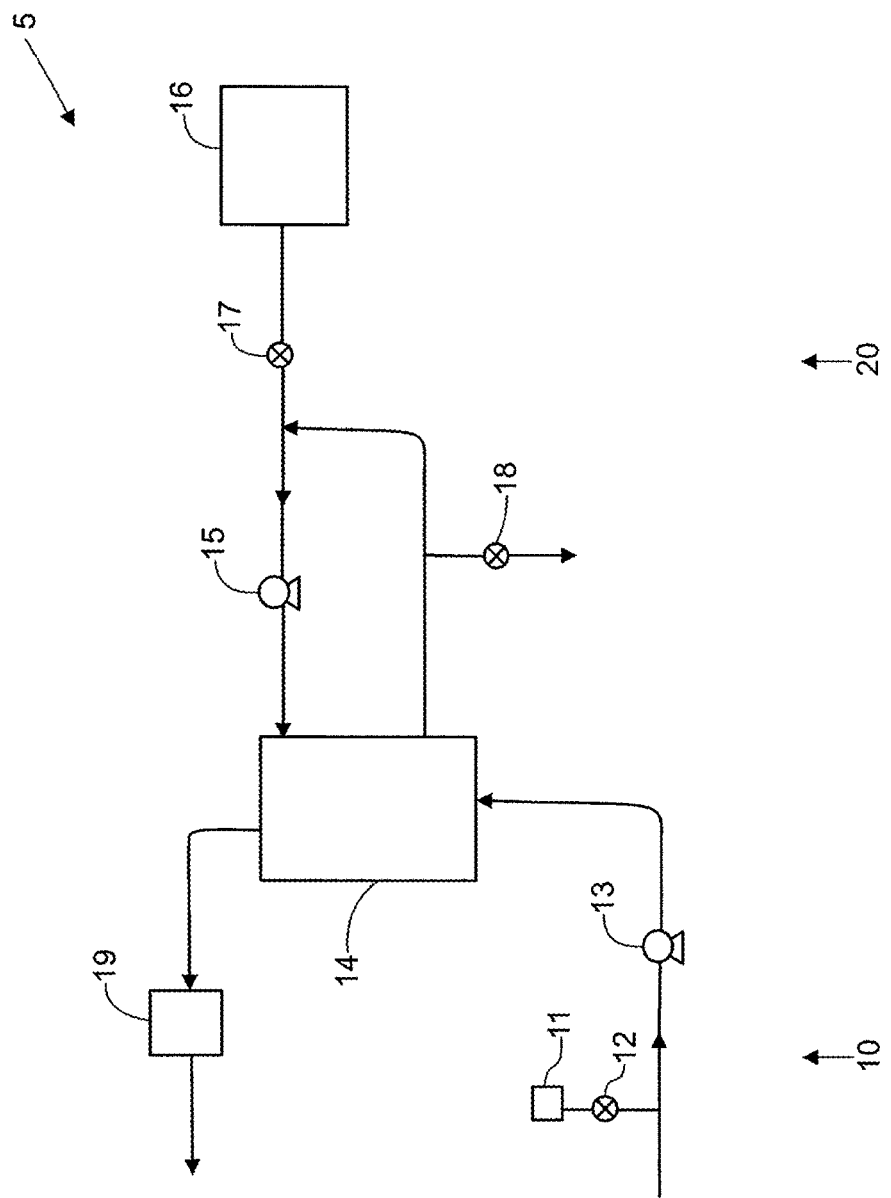
FIG. 1 is a schematic representation of a hemodialysis system.
Figure 2A:
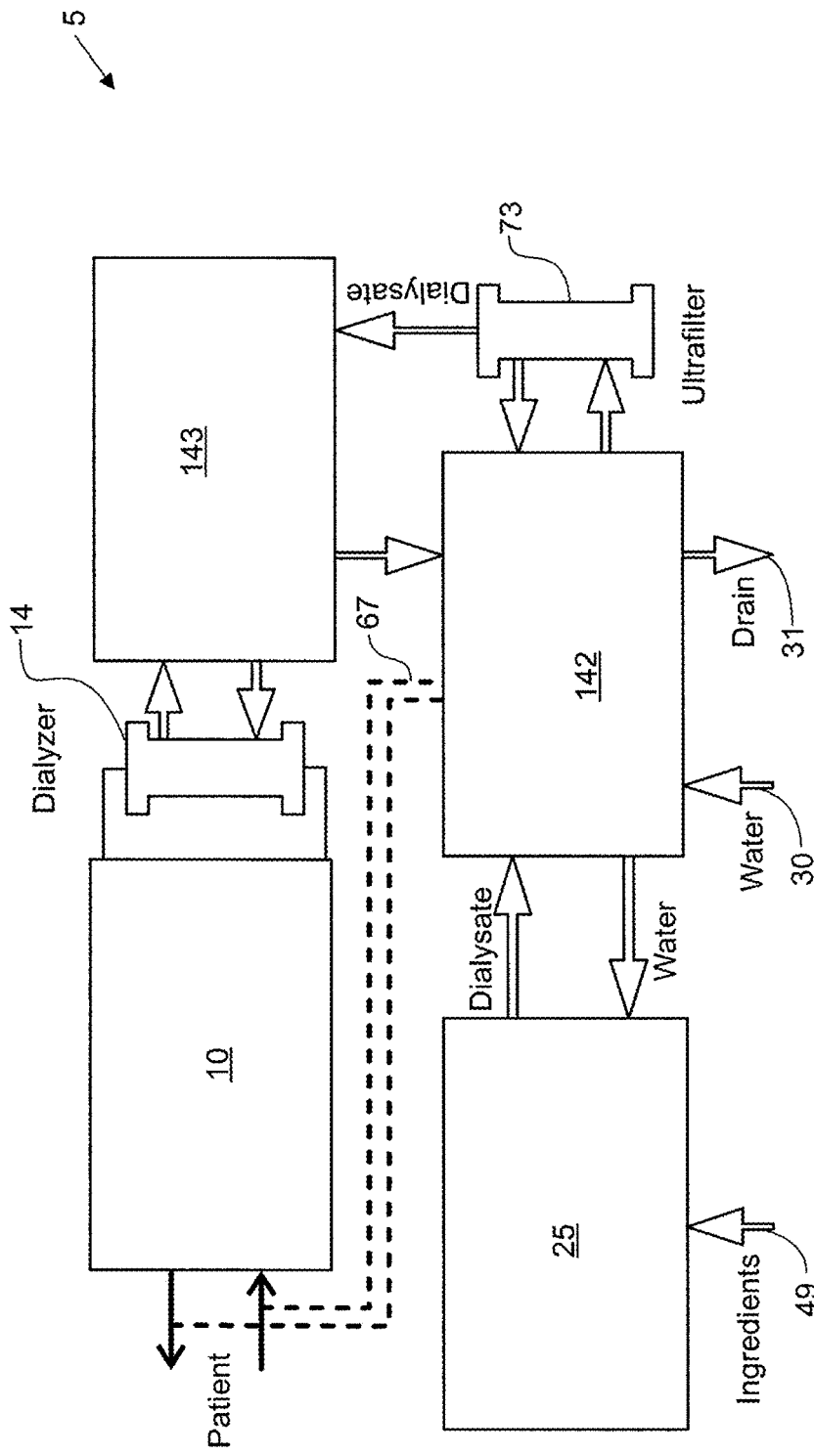
FIGS. 2A-2B are high-level schematics of various embodiments of a dialysis system.

An example of a hemodialysis system having such fluid circuits is illustrated schematically in FIG. 2A as a high-level overview. FIG. 2A illustrates a dialysis system 5 that includes a blood flow circuit 10, through which blood passes from a patient to a dialyzer 14, and through which treated blood returns to the patient. The hemodialysis system in this example also includes a balancing circuit 143 (part of an internal or inner dialysate circuit), which takes dialysate after it passes through an ultrafilter 73 and passes the dialysate through dialyzer 14, with used dialysate returning to balancing circuit 143 from dialyzer 14. A directing circuit 142 (part of an external or outer dialysate circuit) handles fresh dialysate before it passes through ultrafilter 73. A mixing circuit 25 prepares dialysate, for instance, on an as-needed basis, during and/or in advance of dialysis, etc., using various ingredients 49 and water. The directing circuit 142 can also receive water from a water supply 30 and pass it to mixing circuit 25 for preparation of the dialysate, and the directing circuit 142 can also receive used dialysate from balancing circuit 143 and pass it out of system 5 as waste via drain 31. Also shown, in dotted lines, are conduits 67 that can be connected between blood flow circuit 10, and directing circuit 142, e.g., for disinfection of the hemodialysis system. In one set of embodiments, one or more of these circuits (e.g., the blood flow circuit, the balancing circuit, the directing circuit, and/or the mixing circuit) may include a cassette incorporating the valves and pumps needed for controlling flow through that portion. Examples of such systems are discussed in detail below.

Figure 2B:
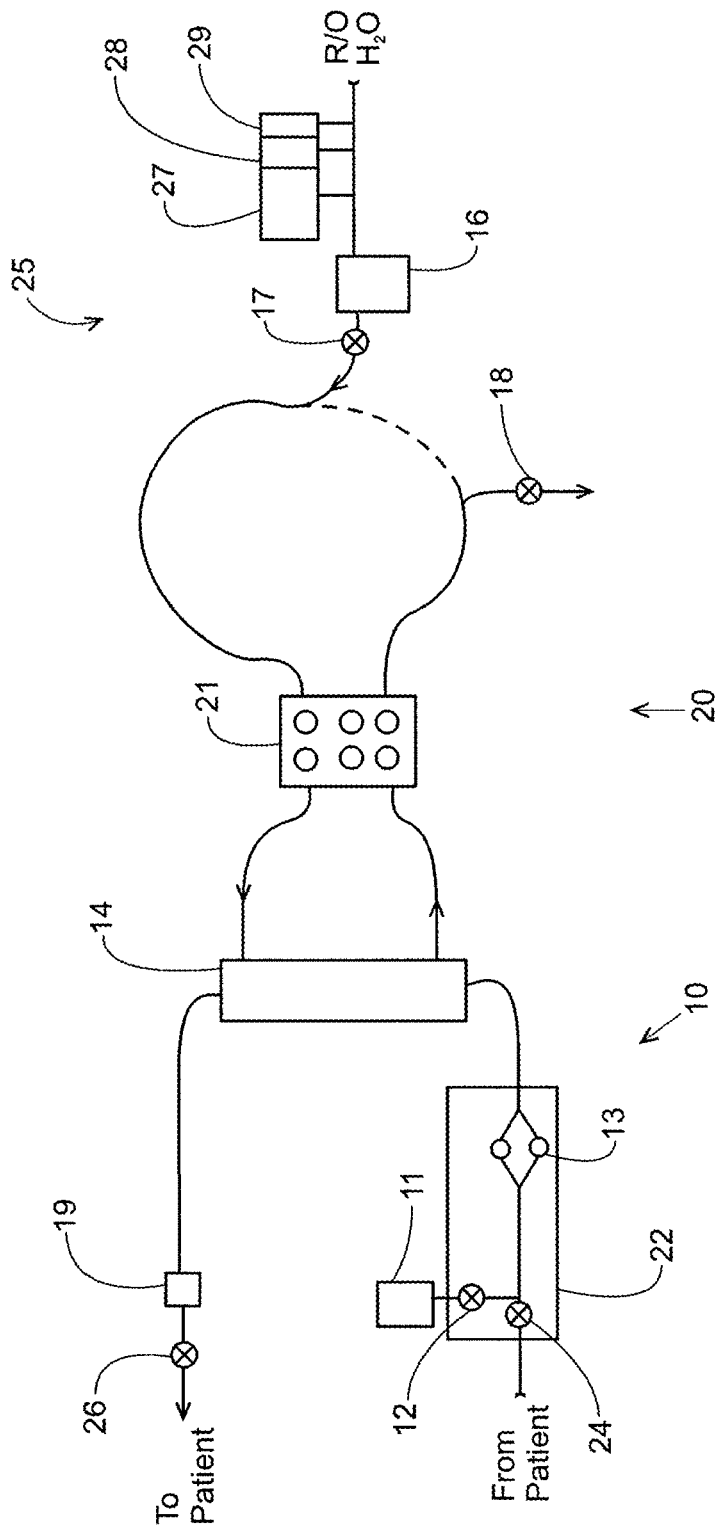

FIG. 2B is a schematic representation of a hemodialysis system according to one embodiment of the invention. In this schematic, a blood flow cassette 22 is used to control flow through the blood flow circuit 10, and a dialysate cassette 21 is used to control flow through the dialysate circuit. The blood flow cassette includes at least one inlet valve 24 (in other embodiments, more than one inlet valve is included) to control the flow of blood through cassette 22 as well as an anticoagulant valve or pump 12 to control the flow of anticoagulant into the blood, and a blood flow pump 13, which may include a pair of pod pumps in some cases. These pod pumps may be of the type (or variations of the type) as described in U.S. Provisional Patent Application Ser. No. 60/792,073, filed Apr. 14, 2006, entitled "Extracorporeal Thermal Therapy Systems and Methods"; or in U.S. patent application Ser. No. 11/787,212, filed Apr. 13, 2007, entitled "Fluid Pumping Systems, Devices and Methods," each of which is incorporated herein in its entirety. All the pumps and valves in this example system may be controlled by a control system, e.g., an electronic and digital control system, although other control systems are possible in other embodiments.

Providing two pod pumps may allow for a more continuous flow of blood through the blood flow circuit 10; however, a single pod pump, such as a single pod pump may be used in other embodiments. The pod pumps may include active inlet and outlet valves (instead of passive check valves at their inlets and outlets) so that flow in the blood flow circuit 10 may be reversed under some conditions. For instance, by reversing flow in the blood flow circuit, the hemodialysis system can check whether the outlet of the blood flow circuit is properly connected to the patient so that the treated blood is correctly returned to the patient. If, for example, the patient connection point has been disconnected, e.g., by falling out, reversing the blood flow pump would draw air rather than blood. This air can be detected by standard air detectors incorporated into the system.

In another embodiment, blood outlet valve 26 and air trap/filter 19, which are located downstream of the dialyzer, may be incorporated into blood flow cassette 22. The pod pumps and all the valves (including the valves associated with the pod pumps' inlets and outlets) in the blood flow cassette 22 may be actuated pneumatically. Sources of positive and negative gas pressure in one embodiment, are provided by a base unit holding cassette or other device holding the cassette. However, in other embodiments, the positive and negative gas pressure may be provided by an external device fluidly connected to the cassettes, or any device build into the system The pump chamber may be actuated in the manner described in U.S. Provisional Patent Application Ser. No. 60/792,073, filed Apr. 14, 2006, entitled "Extracorporeal Thermal Therapy Systems and Methods"; or in U.S. patent application Ser. No. 11/787,212, filed Apr. 13, 2007, entitled "Fluid Pumping Systems, Devices and Methods," referred to hereinabove. For instance, the pumps may be controlled and the end of stroke detected in the manner described below. The blood flow cassette 22 may also contain an integrally formed spike for receiving a vial of anticoagulant.

The anticoagulant pump, in one embodiment, includes three fluid valves (which may be controlled with a control fluid) and a single pumping compartment (although there may be more than one pumping compartment in other embodiments. The valves may connect the compartment to a filtered air vent, to a vial of anticoagulant (or other anticoagulant supply, such as a bag or a bottle, etc.), or to the blood flow path. The anticoagulant pump can be operated by sequencing the opening and closing of the fluid valves and controlling the pressure in the pump compartment, e.g., via the control fluid. When the anticoagulant is removed from the vial it may be replaced with an equal volume of air, e.g., to keep pressure within the vial relatively constant. This replacement of anticoagulant volume with air may be accomplished, for example, by (i) opening the valve from the filtered air vent to the pump compartment, (ii) drawing air into the compartment by connecting the negative pressure source to the chamber, (iii) closing the air vent valve, (iv) opening the valve connecting the compartment to the vial, and (v) pushing air into the vial by connecting the positive pressure source to the compartment. The anticoagulant can be pumped from the vial into the blood flow path with a similar sequence, using the valves to the vial and the blood path rather than the valves to the air vent and the vial.

Figure 3A:
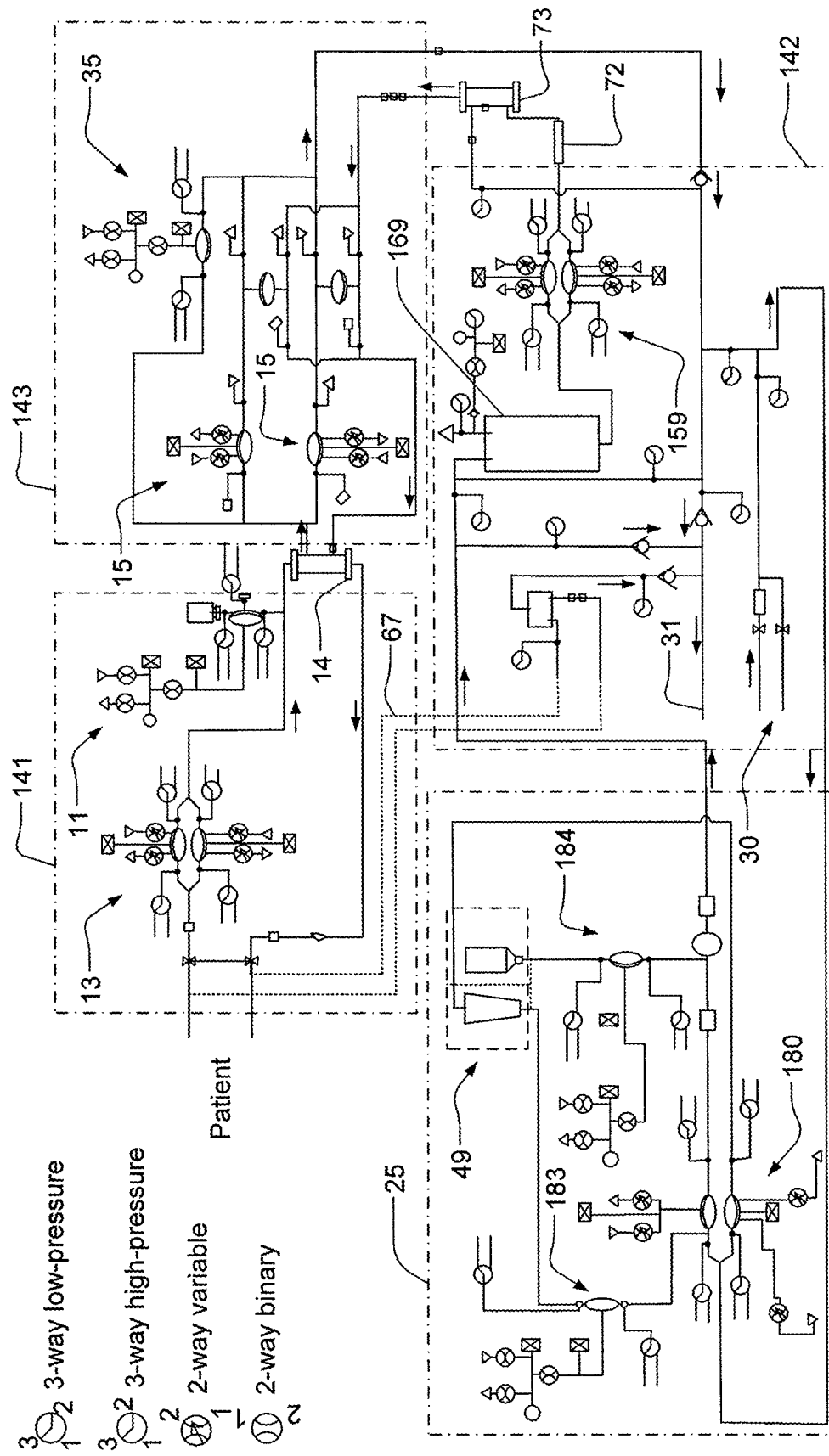
FIGS. 3A-3B are schematics showing an example of a fluid schematic for a dialysis system.

FIG. 3A is a schematic diagram showing a specific embodiment of the general overview shown in FIG. 2A. FIG. 3A shows, in detail, how a blood flow circuit 141, a balancing circuit 143, a directing circuit 142, and a mixing circuit 25 can be implemented on cassettes and made to interrelate with each other and to a dialyzer 14, an ultrafilter 73, and/or a heater 72, in accordance with one embodiment of the invention. It should be understood, of course, that FIG. 3A is only one possible embodiment of the general hemodialysis system of FIG. 2A, and in other embodiments, other fluid circuits, modules, flow paths, layouts, etc. are possible. Examples of such systems are discussed in more detail below, and also can be found in the following, each of which is incorporated herein by reference: U.S. Provisional Patent Application Ser. No. 60/903,582, filed Feb. 27, 2007, entitled "Hemodialysis System and Methods"; U.S. Provisional Patent Application Ser. No. 60/904,024, filed Feb. 27, 2007, entitled "Hemodialysis System and Methods"; U.S. patent application Ser. No. 11/871,680, filed Oct. 12, 2007, entitled "Pumping Cassette"; U.S. patent application Ser. No. 11/871,712, filed Oct. 12, 2007, entitled "Pumping Cassette"; U.S. patent application Ser. No. 11/871,787, filed Oct. 12, 2007, entitled "Pumping Cassette"; U.S. patent application Ser. No. 11/871,793, filed Oct. 12, 2007, entitled "Pumping Cassette"; or U.S. patent application Ser. No. 11/871,803, filed Oct. 12, 2007, entitled "Cassette System Integrated Apparatus."

The components in FIG. 3A will be discussed in detail below. Briefly, blood flow circuit 141 includes an anticoagulant supply 11 and a blood flow pump 13 which pumps blood from a patient to a dialyzer 14. The anticoagulant supply 11, although shown in the path of blood flowing towards the dialyzer, in other embodiments, may be instead located in the path of blood flowing towards the patient, or in another suitable location, such as upstream or downstream of blood flow pump 13. The anticoagulant supply 11 may be placed in any location downstream from blood flow pump 13. Balancing circuit 143 includes two dialysate pumps 15, which also pump dialysate into dialyzer 14, and a bypass pump 35. Directing circuit 142 includes a dialysate pump 159, which pumps dialysate from dialysate tank 169 through heater 72 and/or ultrafilter 73 to the balancing circuit. Directing circuit 142 also takes waste fluid from balancing circuit 143 and directs it to a drain 31. In some cases, the blood flow circuit 141 can be connected via conduits 67 to directing circuit 142, e.g., for disinfection, as discussed below. Dialysate flows into dialysate tank 169 from a dialysate supply. In one embodiment, as is shown in FIG. 3A, the dialysate is produced in mixing circuit 25. Water from water supply 30 flows through directing circuit 142 into mixing circuit 25. Dialysate ingredients 49 (e.g., bicarbonate and acid) are also added into mixing circuit 25, and a series of mixing pumps 180, 183, 184 are used to produce the dialysate, which is then sent to directing circuit 142.

In this example system, one of the fluid circuits is a blood flow circuit, e.g., blood flow circuit 141 in FIG. 3A. In the blood flow circuit, blood from a patient is pumped through a dialyzer and then is returned to the patient. In some cases, blood flow circuit is implemented on a cassette, as discussed below, although it need not be. The flow of blood through the blood flow circuit, in some cases, is balanced with the flow of dialysate flowing through the dialysate flow path, especially through the dialyzer and the balancing circuit.

Figure 4A:
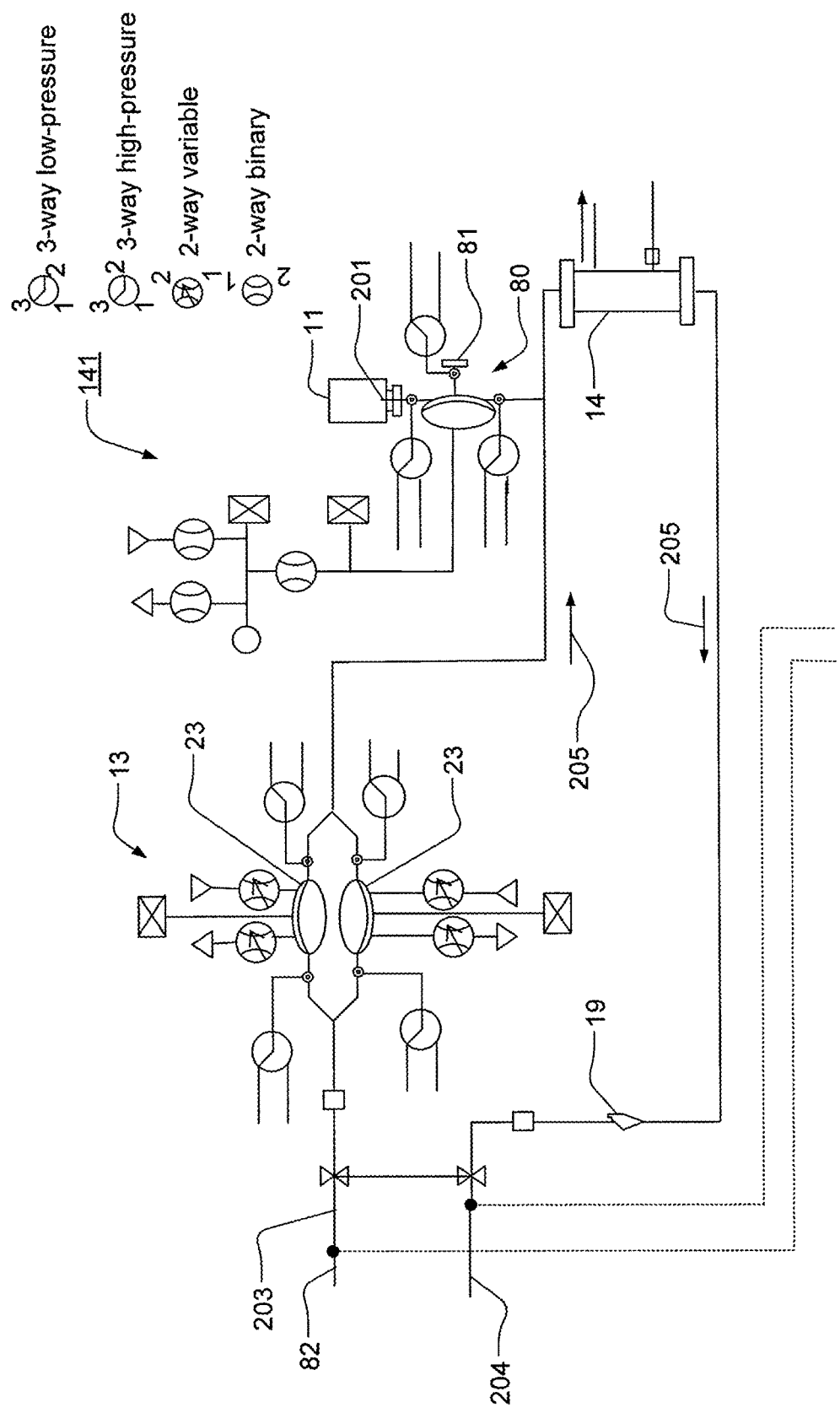
FIGS. 4A-4B are schematic representations of various embodiments of a blood flow circuit that may be used in a hemodialysis system.
Figure 4B:
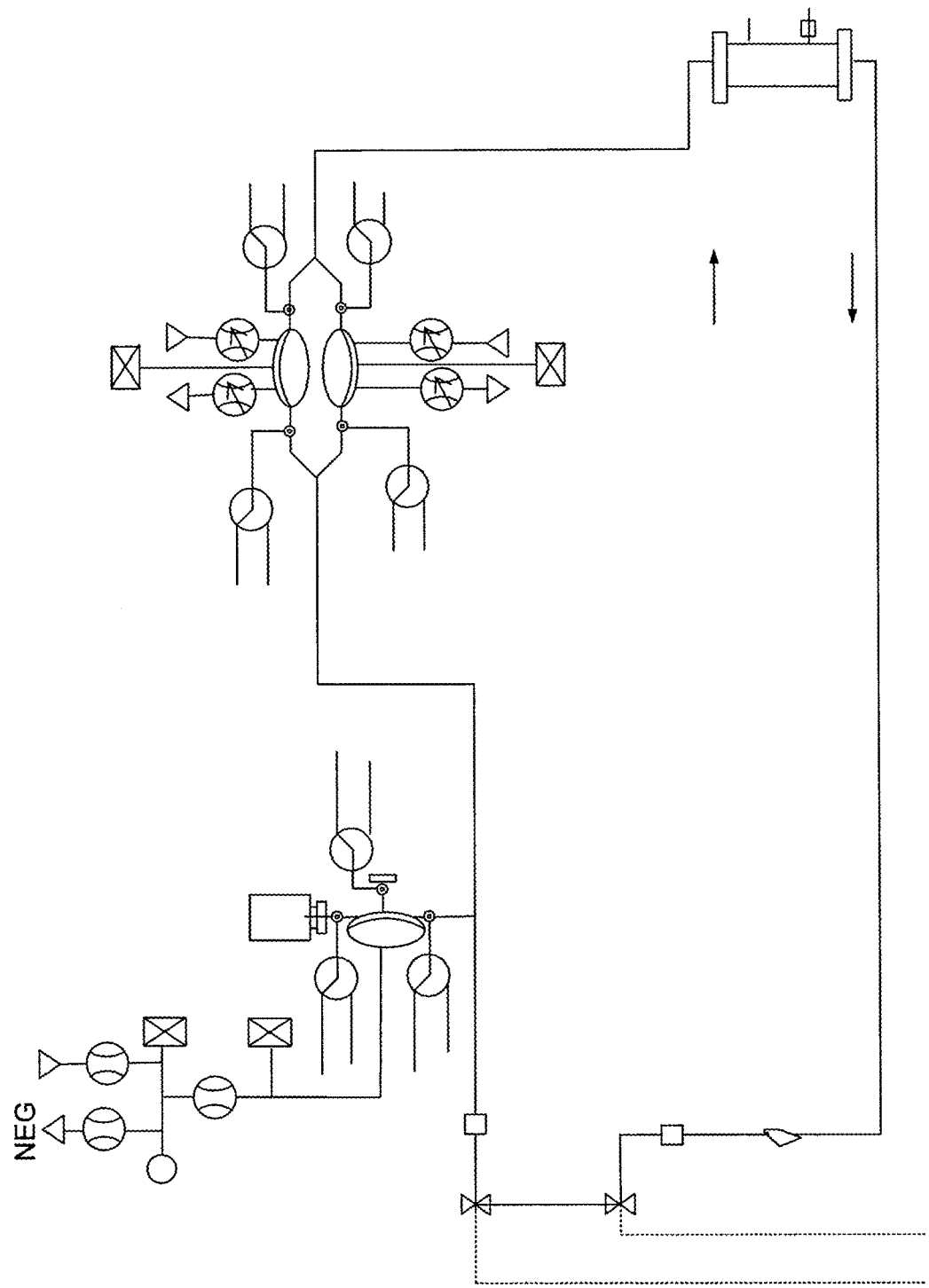

One example of a blood flow circuit is shown in FIG. 4A. Generally, blood flows from a patient through arterial line 203 via blood flow pump 13 to dialyzer 14 (the direction of flow during normal dialysis is indicated by arrows 205; in some modes of operation, however, the flow may be in different directions, as discussed below). Optionally, an anticoagulant may be introduced into the blood via anticoagulant pump 80 from an anticoagulant supply. As shown in FIG. 4A, the anticoagulant can enter the blood flow path after the blood has passed through blood flow pump 13; however, the anticoagulant may be added in any suitable location along the blood flow path in other embodiments. For example, in FIG. 4B, the anticoagulant enters the blood flow path before the blood has passed through blood flow pump 13. This may be useful, for example, if a blood pump cassette of the type shown in FIGS. 30C-33D is used, and blood flow is directed to cause blood to enter at the top of the cassette, and exit at the bottom of the cassette. The blood pump chambers can thus additionally serve to trap air that may be present in the blood before it is pumped to the dialyzer. In other embodiments, anticoagulant supply 11 may be located anywhere downstream from the blood flow pump. After passing through dialyzer 14 and undergoing dialysis, the blood returns to the patient through venous line 204, optionally passing through air trap and/or a blood sample port 19.

As is shown in FIG. 4A, blood flow cassette 141 also includes one or more blood flow pumps 13 for moving blood through the blood flow cassette. The pumps may be, for instance, pumps that are actuated by a control fluid, such as is discussed below. For instance, in one embodiment, pump 13 may comprise two (or more) pod pumps, e.g., pod pumps 23 in FIG. 4A. Each pod pump, in this particular example, may include a rigid chamber with a flexible diaphragm or membrane dividing each chamber into a fluid compartment and control compartment. There are four entry/exit valves on these compartments, two on the fluid compartment and two on the control compartment. The valves on the control compartment of the chambers may be two-way proportional valves, one connected to a first control fluid source (e.g., a high pressure air source), and the other connected to a second control fluid source (e.g., a low pressure air source) or a vacuum sink. The fluid valves on the compartments can be opened and closed to direct fluid flow when the pod pumps are pumping. Non-limiting examples of pod pumps are described in U.S. Provisional Patent Application Ser. No. 60/792,073, filed Apr. 14, 2006, entitled "Extracorporeal Thermal Therapy Systems and Methods"; or in U.S. patent application Ser. No. 11/787,212, filed Apr. 13, 2007, entitled "Fluid Pumping Systems, Devices and Methods," each incorporated herein by reference. Further details of the pod pumps are discussed below. If more than one pod pump is present, the pod pumps may be operated in any suitable fashion, e.g., synchronously, asynchronously, in-phase, out-of-phase, etc.

For instance, in some embodiments, the two-pump pumps can be cycled out of phase to affect the pumping cycle, e.g., one pump chamber fills while the second pump chamber empties. A phase relationship anywhere between 0° (the pod pumps act in the same direction, filling and emptying in unison) and 180° (the pod pumps act in opposite directions, in which one pod pump fills as the other empties) can be selected in order to impart any desired pumping cycle.

Figure 8A:
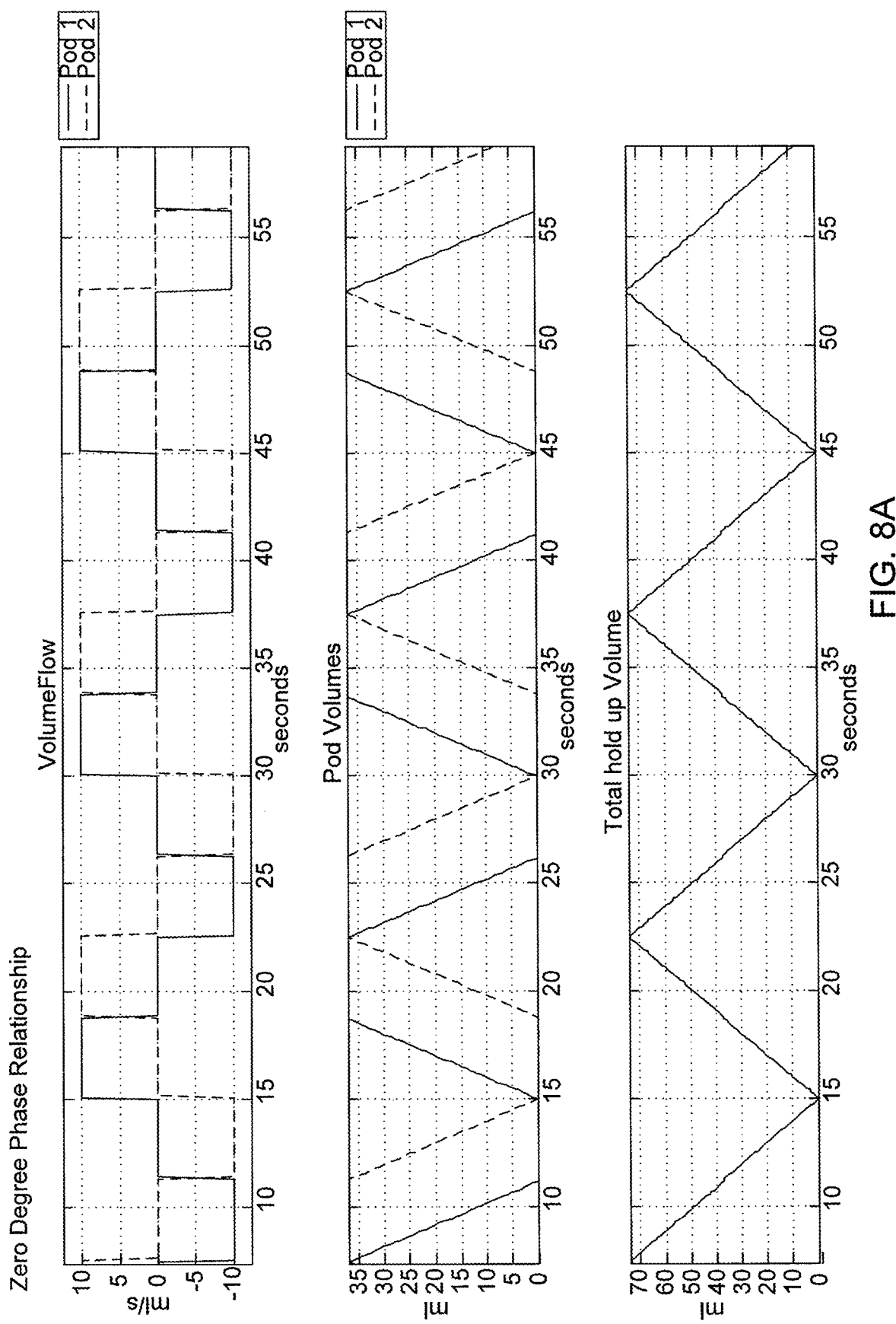
FIGS. 8A-8C are graphical representations of phase relationships.
Figure 8B:
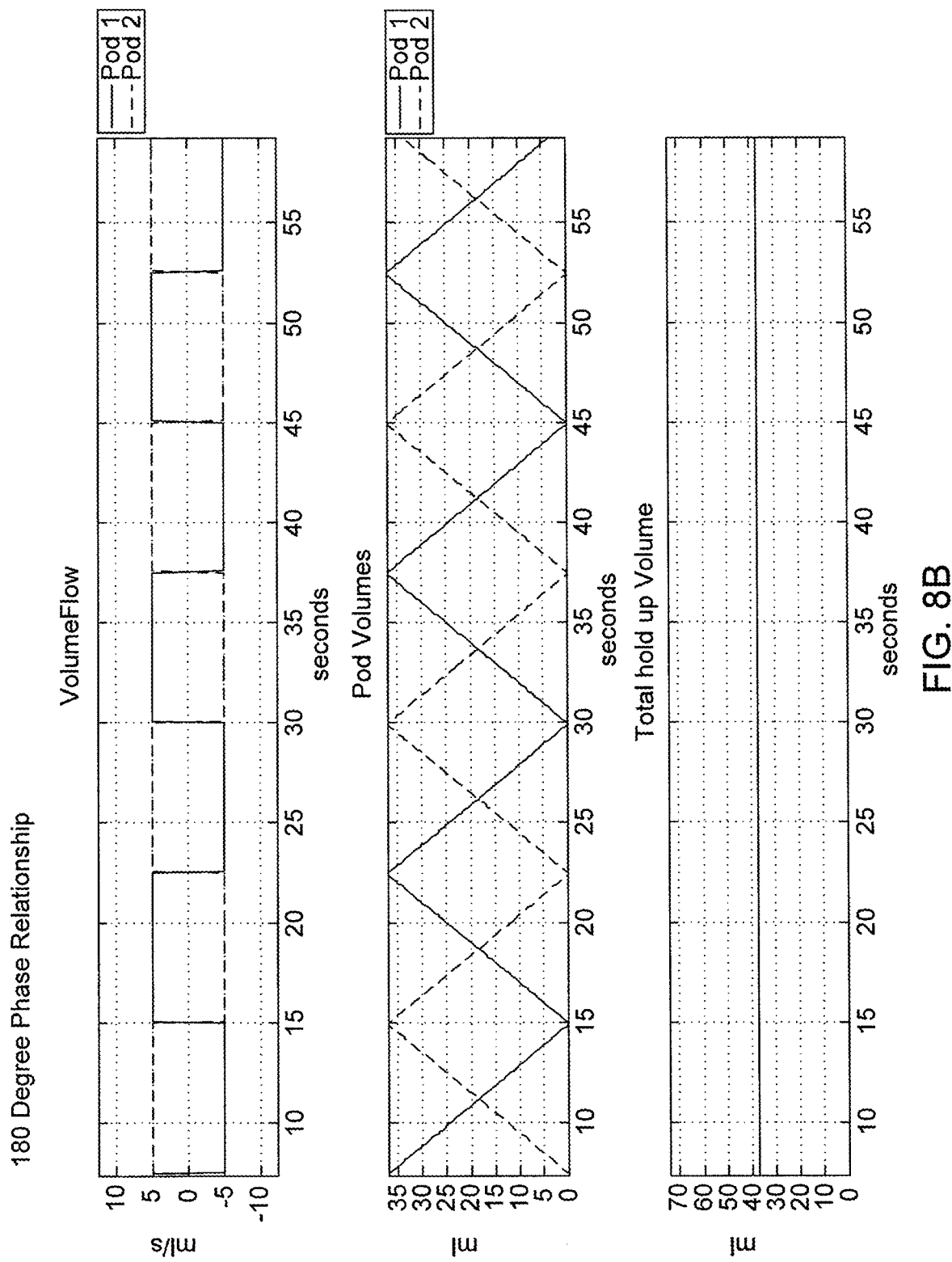
Figure 8C:
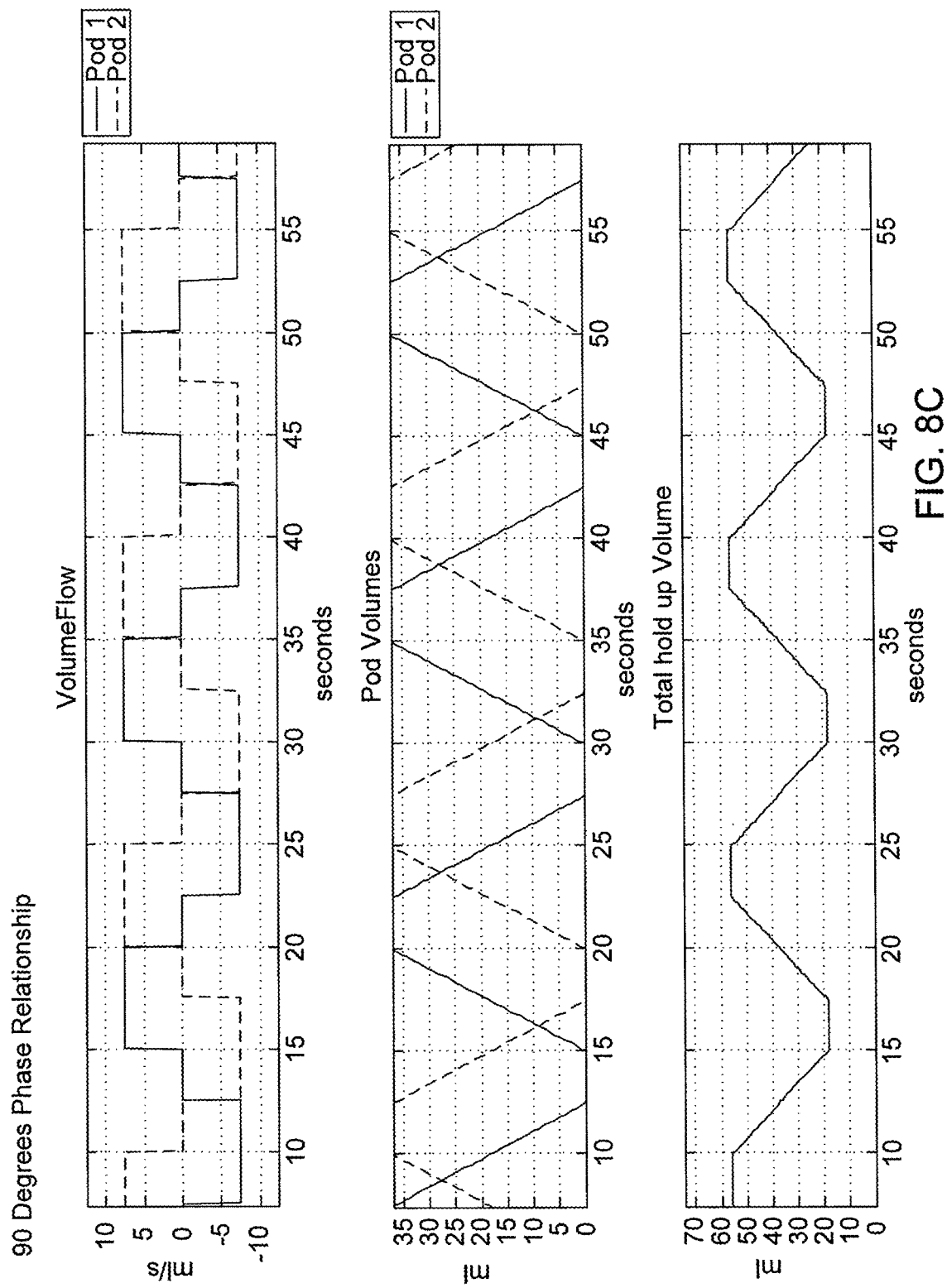

A phase relationship of 180° may yield continuous flow into and out of the pod pump cassette. This is useful, for instance, when continuous flow is desired, e.g., for use with dual needle flow or a "Y" or "T" connection. Setting a phase relationship of 0°, however, may be useful in some cases for single needle flow, in situations in which a "Y" or "T" connection is made with a single needle or single lumen catheter, or in other cases. In a 0° relationship, the pod pumps will first fill from the needle, then deliver blood through the blood flow path and back to the patient using the same needle. In addition, running at phases between 0° and 180° can be used in some cases, to achieve a push/pull relationship (hemodiafiltration or continuous back flush) across the dialyzer. FIGS. 8A-8C are graphical representations of examples of such phase relationships. In these figures, the volume or flow of each pod pump, the volumes of each pod pumps, and the total hold up volume of both pod pumps is shown as a function of time. These times and flow rates are arbitrarily chosen, and are presented here to illustrate the relationships between the pod pumps at different phasings. For instance, at a 180° phase relationship (FIG. 8B), the total hold up volume remains substantially constant.

Figure 14:
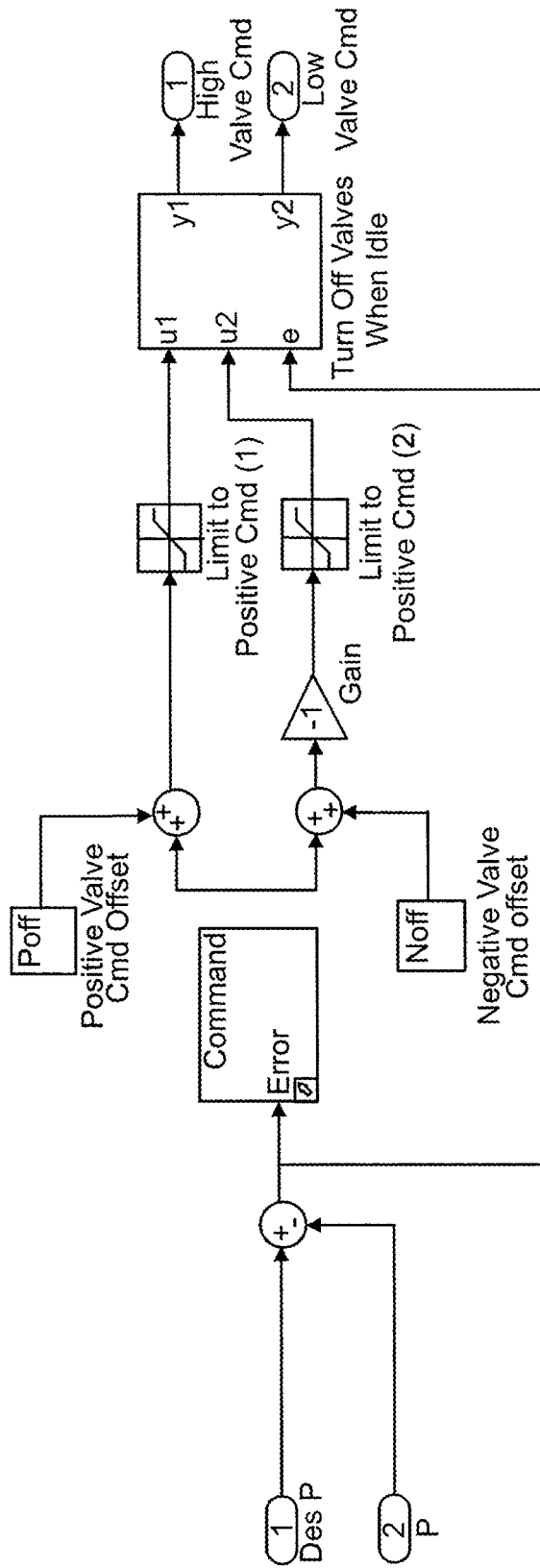
FIG. 14 is a diagram of one embodiment of a control algorithm.

In some cases, an anticoagulant (e.g., heparin, or any other anticoagulant known to those of ordinary skill in the art) may be mixed with the blood within blood flow cassette 141 as is shown in FIG. 14. For instance, the anticoagulant may be contained within a vial 11 (or other anticoagulant supply, such as a tube or a bag), and blood flow cassette 141 may be able to receive the anticoagulant vial with an integrally formed spike 201 (which, in one embodiment, is a needle) that can pierce the seal of the vial. The spike may be formed from plastic, stainless steel, or another suitable material, and may be a sterilizable material in some cases, e.g., the material may be able to withstand sufficiently high temperatures and/or radiation so as to sterilize the material. As an example, as is shown in FIG. 4A, spike 201 may be integrally formed with a blood flow cassette 141, and a vial 11 can be placed onto the spike, piercing the seal of the vial, such that anticoagulant can flow into blood flow cassette to be mixed with the blood in the blood flow path, or in some cases, mixed with dialysate as discussed below.

A third pump 80, which can act as a metering chamber in some cases, in blood flow cassette 141 can be used to control the flow of anticoagulant into the blood within the cassette. Third pump 80 may be of the same or of a different design than pump 13. For instance, third pump 80 may be a pod pump and/or third pump 80 may be actuated by a control fluid, such as air. For example, third pump 80 may be a membrane-based metering pump. For instance, as is shown in FIG. 4A, third pump 80 may include a rigid chamber with a flexible diaphragm dividing the chamber into a fluid compartment and a control compartment. Valves on the control compartment of the chamber may be connected to a first control fluid source (e.g., a high pressure air source), and the other compartment connected to a second control fluid source (e.g., a low pressure air source) or a vacuum sink. Valves on the fluid compartment of the chamber can be opened and closed in response to the control compartment, thus controlling the flow of anticoagulant into the blood. Further details of such a pod pump are discussed below. In one set of embodiments, air may also be introduced into the blood flow path through a filter 81, as discussed below.

Fluid Management System ("FMS") measurements may be used to measure the volume of fluid pumped through a pump chamber during a stroke of the membrane, or to detect air in the pumping chamber. FMS methods are described in U.S. Pat. Nos. 4,808,161; 4,826,482; 4,976,162; 5,088,515; and 5,350,357, which are hereby incorporated herein by reference in their entireties. In some cases, the volume of liquid delivered by an anticoagulant pump, a dialysate pump, or other membrane-based pump is determined using an FMS algorithm in which changes in chamber pressures are used to calculate a volume measurement at the end of a fill stroke and at the end of a delivery stroke. The difference between the computed volumes at the end of a fill and delivery stroke is the actual stroke volume. This actual stroke volume can be compared to an expected stroke volume for the particular sized chamber. If the actual and expected volumes are significantly different, the stroke has not properly completed and an error message can be generated.

If stroke volumes are collected with a scale, the calculation can be worked backwards to determine a calibration value for the reference chamber. FMS systems can vent to atmosphere for the FMS measurement. Alternatively, the system can vent to a high pressure positive source and a low pressure negative source for the FMS measurement. Doing so provides the following advantages, amongst others: (1) if the high pressure source is a pressure reservoir with a controlled pressure, there is an opportunity to do a cross check on the pressure sensors of the reservoir and chamber to ensure they are similar when the chamber is being vented to the reservoir. This can be used to detect a broken pressure sensor or a failed valve; (2) by using higher/lower pressures to vent, there are larger pressure differences for the FMS measurements so better resolution can be obtained.

Blood flow circuit 141 may also include an air trap 19 incorporated into blood flow circuit 141 in some cases. Air trap 19 may be used to remove air bubbles that may be present within the blood flow path. In some cases, air trap 19 is able to separate any air that may be present from the blood due to gravity. In some cases, air trap 19 may also include a port for sampling blood. Air traps are known to those of ordinary skill in the art.

Figure 4C:
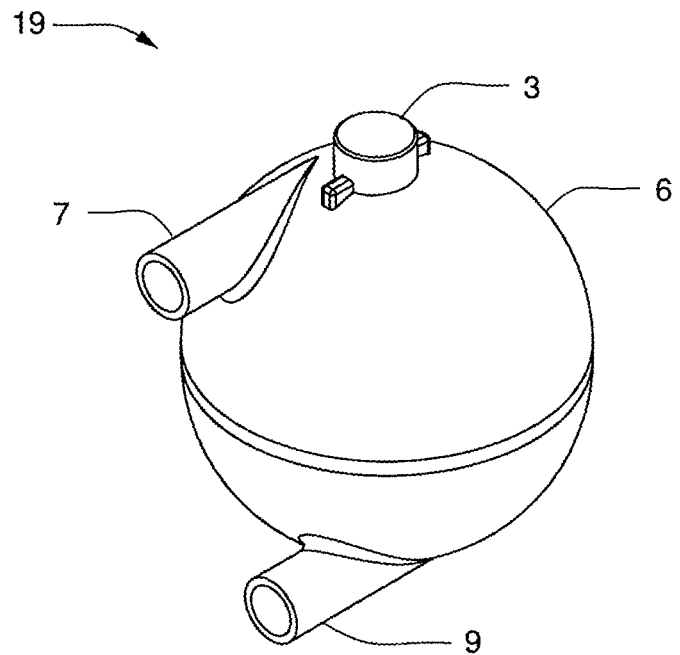
FIGS. 4C and 4D are perspective and side views, respectively, of the air trap shown in FIG. 4A.
Figure 4D:
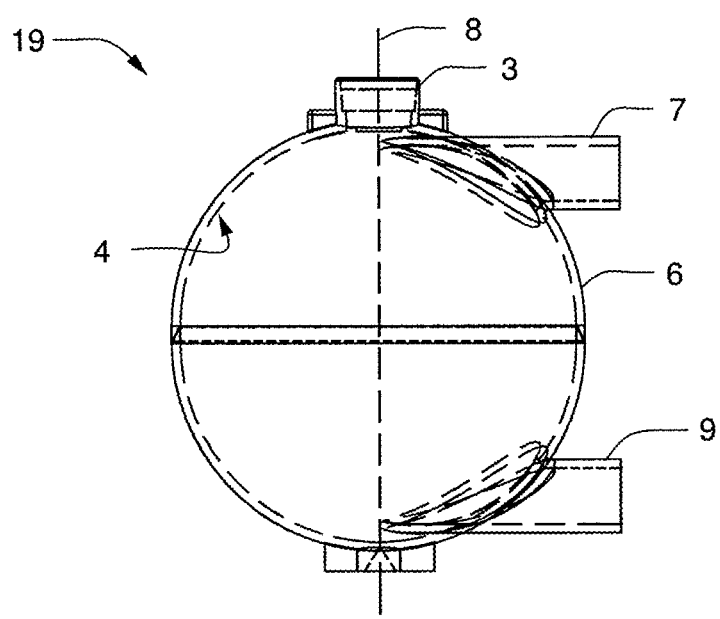

In accordance with another aspect of the invention, the air trap 19 is placed in the blood flow path after the blood exits the dialyzer and before it is returned to the patient. As shown in FIGS. 4C and 4D, air trap 19 may have a spherical or spheroid-shape container 6, and have its inlet port 7 located near the top and offset from the vertical axis of the container, and an outlet 9 at a bottom of the container. The curved shape of the inside wall 4 of the trap can thus direct the blood to circulate along the inside wall as the blood gravitates to the bottom of the container, facilitating the removal of air bubbles from the blood. Air present in the blood exiting the outlet 9 of the dialyzer 14 will enter at the top of the air trap 19 and remain at the top of the container as blood flows out the outlet at the bottom and to the venous blood line 204. By locating the inlet port 7 near the top of trap 19, it is also possible to circulate blood through the trap with minimal or no air present within the container (as a "run-full" air trap). The ability to avoid an air-blood interface for routine circulation of blood in the trap can be advantageous. Placing the inlet port 7 at or near the top of the container also allows most or all of the air present in the trap to be removed from the trap by reversing the flow of fluid through the blood tubing (i.e. from the bottom to the top of the trap 19, exiting through the inlet port of the trap 19). In an embodiment, a self-sealing port 3, such as a self-sealing stopper with a split septum or membrane, or another arrangement, is located at the top of the trap, allowing the withdrawal of air from the container (e.g., by syringe). The blood-side surface of the self-sealing membrane can be situated nearly flush with the top of the interior of the trap, in order to facilitate cleaning of the self-sealing port during disinfection. The self-sealing port 3 can also serve as a blood sampling site, and/or to allow the introduction of liquids, drugs or other compounds into the blood circuit. A sealed rubber-type stopper can be used if access with a needle is contemplated. Using a self-sealing stopper with split septum permits sampling and fluid delivery using a needleless system.

Additional fluid connections 82 may allow blood flow circuit 10 to also be connected to the patient, and/or to a fluid source for priming or disinfecting the system, including blood flow circuit 10. Generally, during disinfection, arterial line 203 and venous line 204 are connected directly to directing circuit 142 via conduits 67, such that a disinfecting fluid (e.g., heated water and in some embodiments, a combination heated water and one or more chemical agent) may be flowed through dialyzer 14 and blood flow circuit 141 back to directing circuit 142 for recirculation, this disinfection is similar to those shown in U.S. Pat. No. 5,651,898 to Kenley, et al., which is incorporated herein by reference. This is also discussed in more detail below.

The pressure within arterial line 203, to draw blood from the patient, may be kept to a pressure below atmospheric pressure in some cases. If a pod pump is used, the pressure within blood flow pump 13 may be inherently limited to the pressures available from the positive and negative pressure reservoirs used to operate the pump. In the event that a pressure reservoir or valve fails, the pump chamber pressure will approach the reservoir pressure. This will increase the fluid pressure to match the reservoir pressure until the diaphragm within the pod pump "bottoms" (i.e., is no longer is able to move, due to contact with a surface), and the fluid pressure will not exceed a safe limit and will equilibrate with a natural body fluid pressure. This failure naturally stops operation of the pod pump without any special intervention.

A specific non-limiting example of a blood flow cassette is shown in FIGS. 30-33. Referring now to FIGS. 30A and 30B, the outer side of the top plate 900 of an exemplary embodiment of the cassette is shown. The top plate 900 includes one half of the pod pumps 820, 828. This half is the liquid half where the source fluid will flow through. The two fluid paths 818, 812 are shown. These fluid paths lead to their respective pod pumps 820, 828.

The pod pumps 820, 828 include a raised flow path 908, 910. The raised flow path 908, 910 allows for the fluid to continue to flow through the pod pumps 820, 828 after the diaphragm (not shown) reaches the end of stroke. Thus, the raised flow path 908, 910 minimizes the diaphragm causing air or fluid to be trapped in the pod pump 820, 828 or the diaphragm blocking the inlet or outlet of the pod pump 820, 828, which would inhibit continuous flow. The raised flow path 908, 910 is shown in one exemplary embodiment having particular dimensions, and in some cases, the dimensions are equivalent to the fluid flow paths 818, 812. However, in alternate embodiments, the raised flow path 908, 910 is narrower, or in still other embodiments, the raised flow path 908, 910 can be any dimensions as the purpose is to control fluid flow so as to achieve a desired flow rate or behavior of the fluid. In some embodiments, the raised flow path 908, 910 and the fluid flow paths 818, 812 have different dimensions. Thus, the dimensions shown and described here with respect to the raised flow path, the pod pumps, the valves or any other aspect are mere exemplary and alternate embodiments. Other embodiments are readily apparent.

In one exemplary embodiment of this cassette, the top plate includes a spike 902 as well as a container perch 904. The spike 902 is hollow in this example, and is fluidly connected to the flow path. In some embodiments, a needle is attached into the spike. In other embodiments, a needle is connected to the container attachment.

Figure 30A:
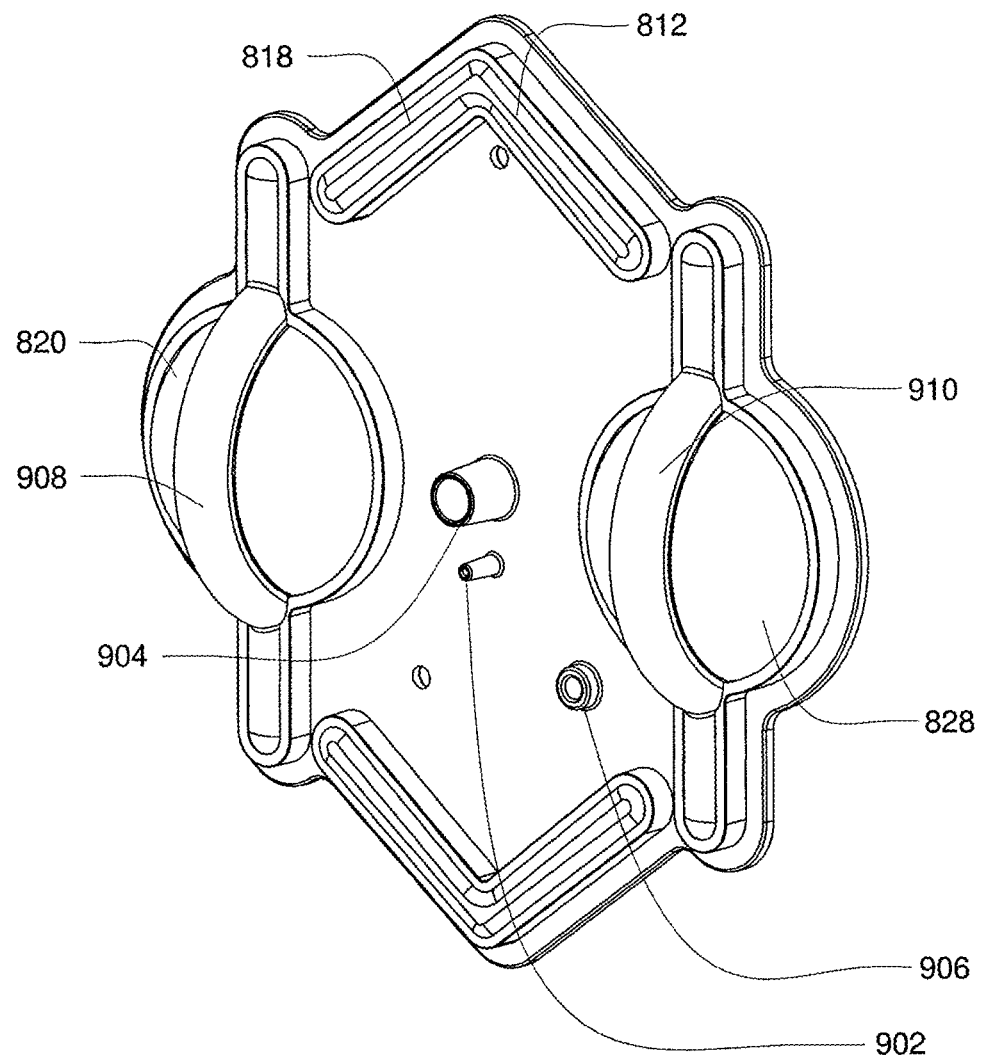
FIGS. 30A and 30B are isometric and top views of an outer top plate of an exemplary embodiment of the cassette.
Figure 30B:
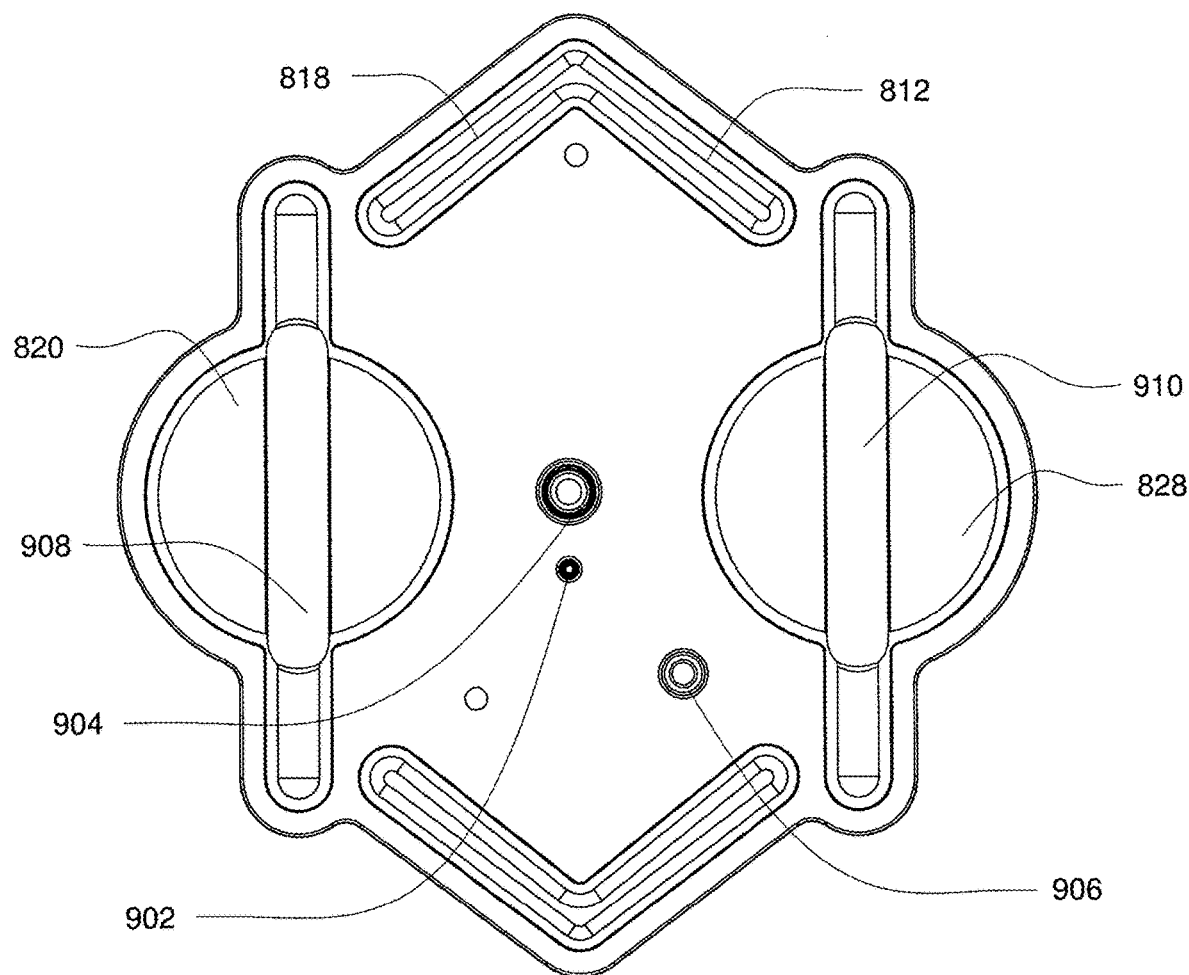
Figure 30C:
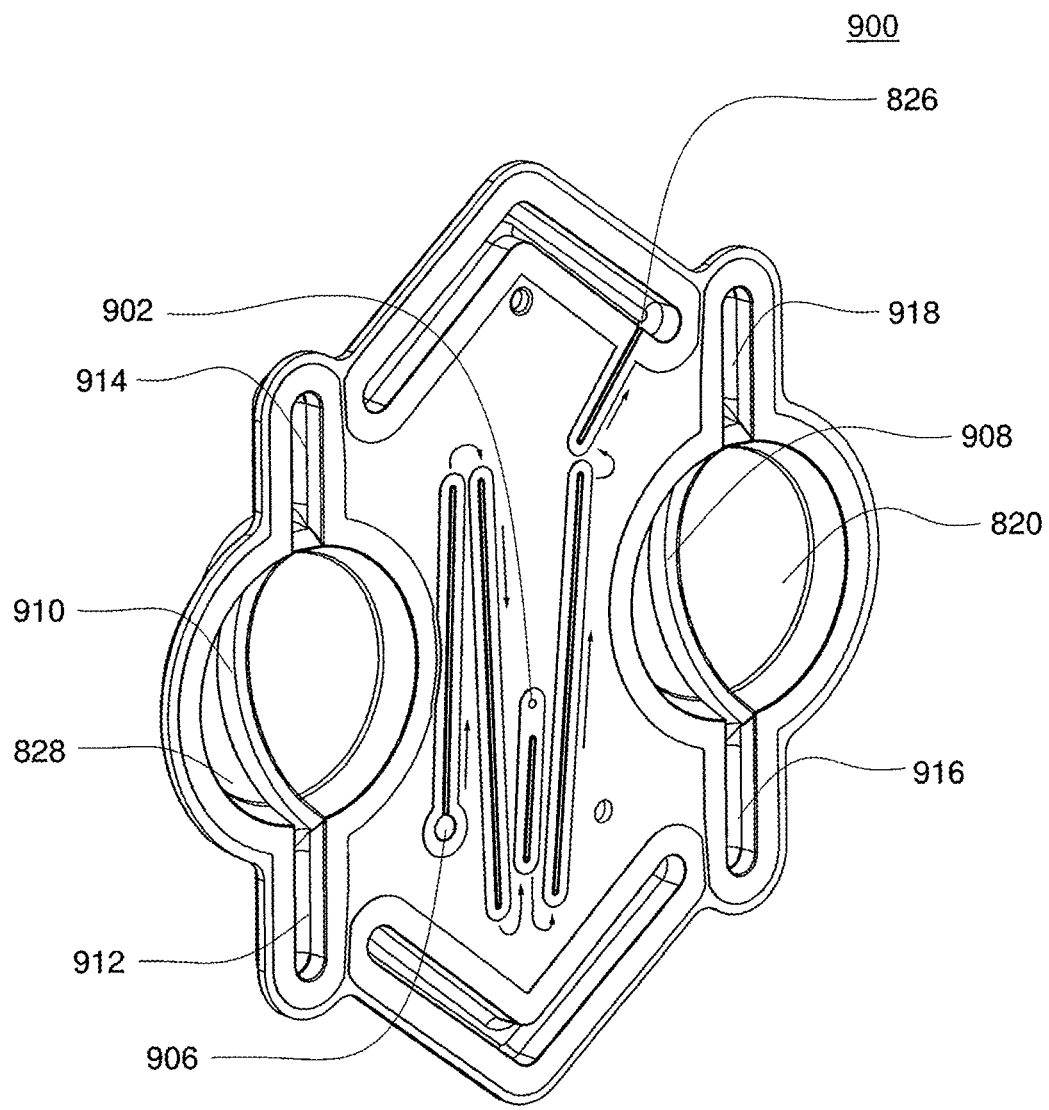
FIGS. 30C and 30D are isometric and top views of an inner top plate of an exemplary embodiment of the cassette.
Figure 30D:
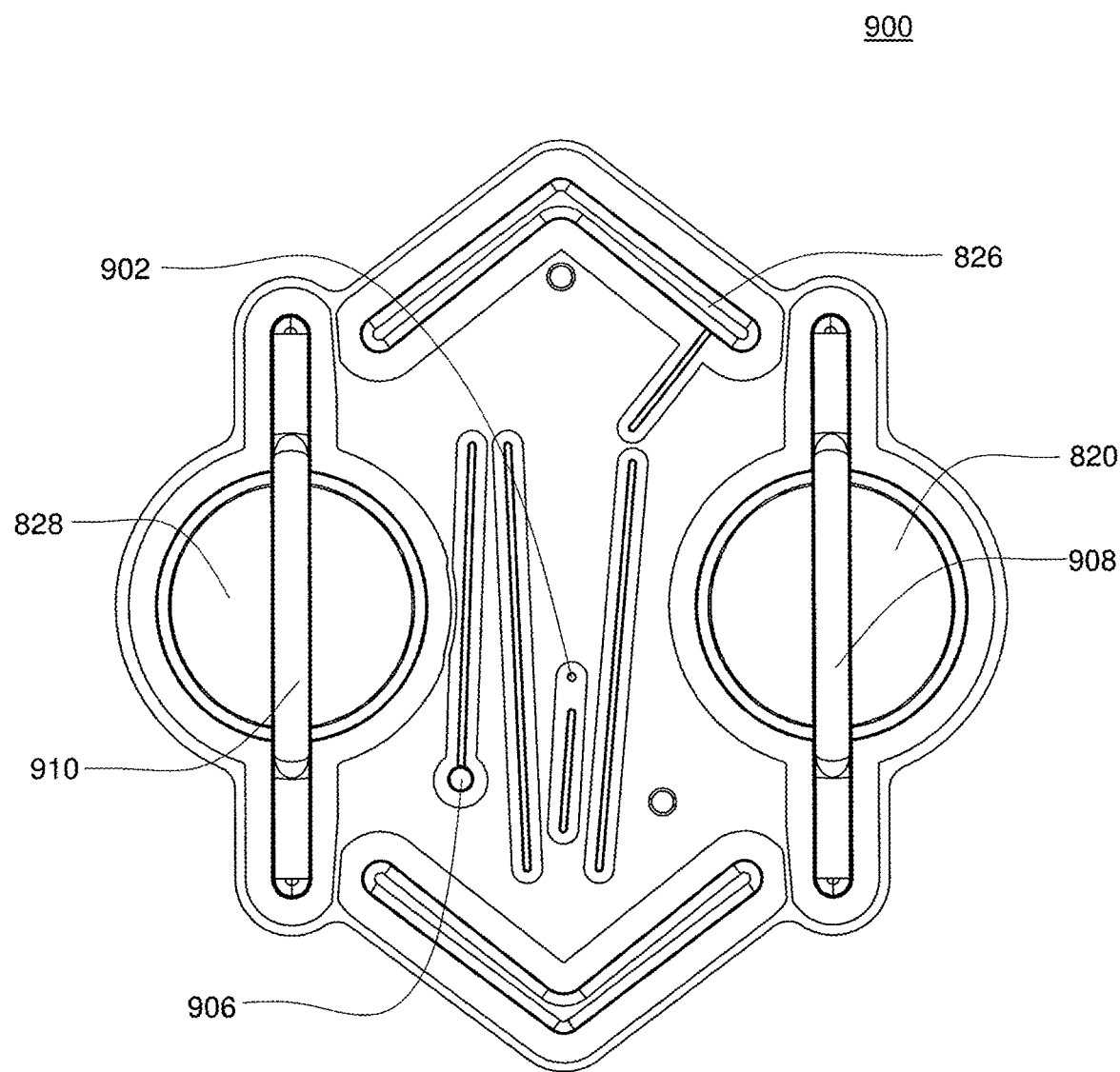
Figure 30E:
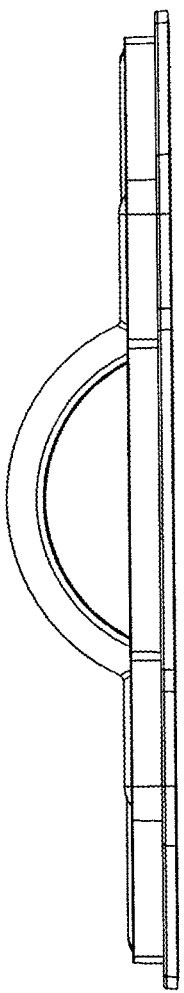
FIG. 30E is a side view of the top plate of an exemplary embodiment of an cassette.

Referring now to FIGS. 30C and 30D, the inside of the top plate 900 is shown. The raised flow paths 908, 910 connects to the inlet flow paths 912, 916 and outlet flow paths 914, 918 of the pod pumps 820, 828. The raised flow paths are described in more detail above.

The metering pump (not shown) includes connection to an air vent 906 as well as connection to the spike's hollow path 902. In one exemplary embodiment, the air vent 906 includes an air filter (not shown). The air filter may be a particle air filter in some cases. In some embodiments, the filter is a somicron hydrophobic air filter. In various embodiments, the size of the filter may vary, in some instances the size will depend on desired outcome. The metering pump works by taking air in through the air vent 906, pumping the air to the container of second fluid (not shown) through the spike's hollow path 902 and then pumping a volume of second fluid out of the container (not shown) through the spike's hollow path 902 and into the fluid line at point 826. This fluid flow path for the metering pump is shown with arrows on FIG. 30C.

Figure 31A:
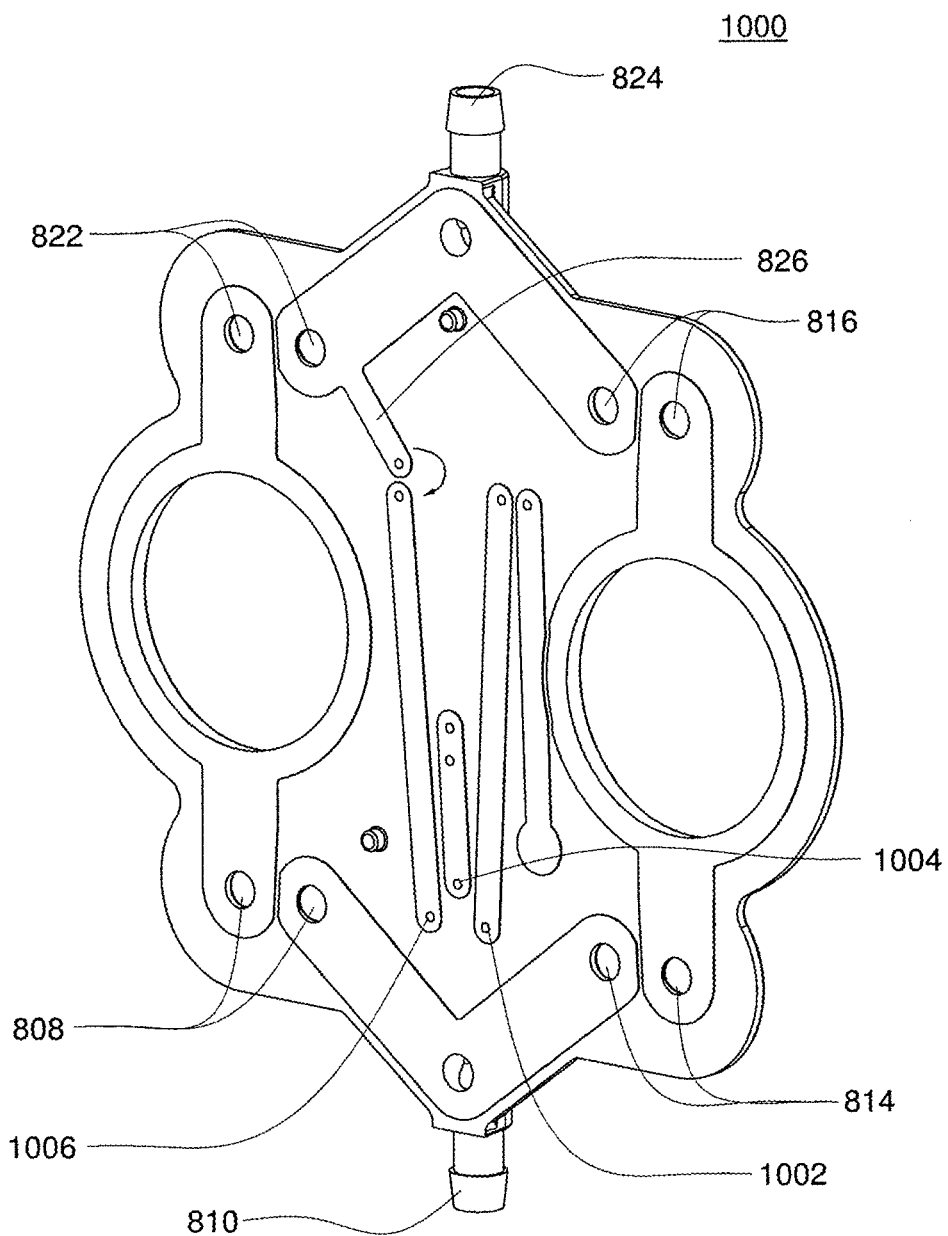
FIGS. 31A and 31B are isometric and top views of the liquid side of a midplate according to an exemplary embodiment of the cassette.
Figure 31B:
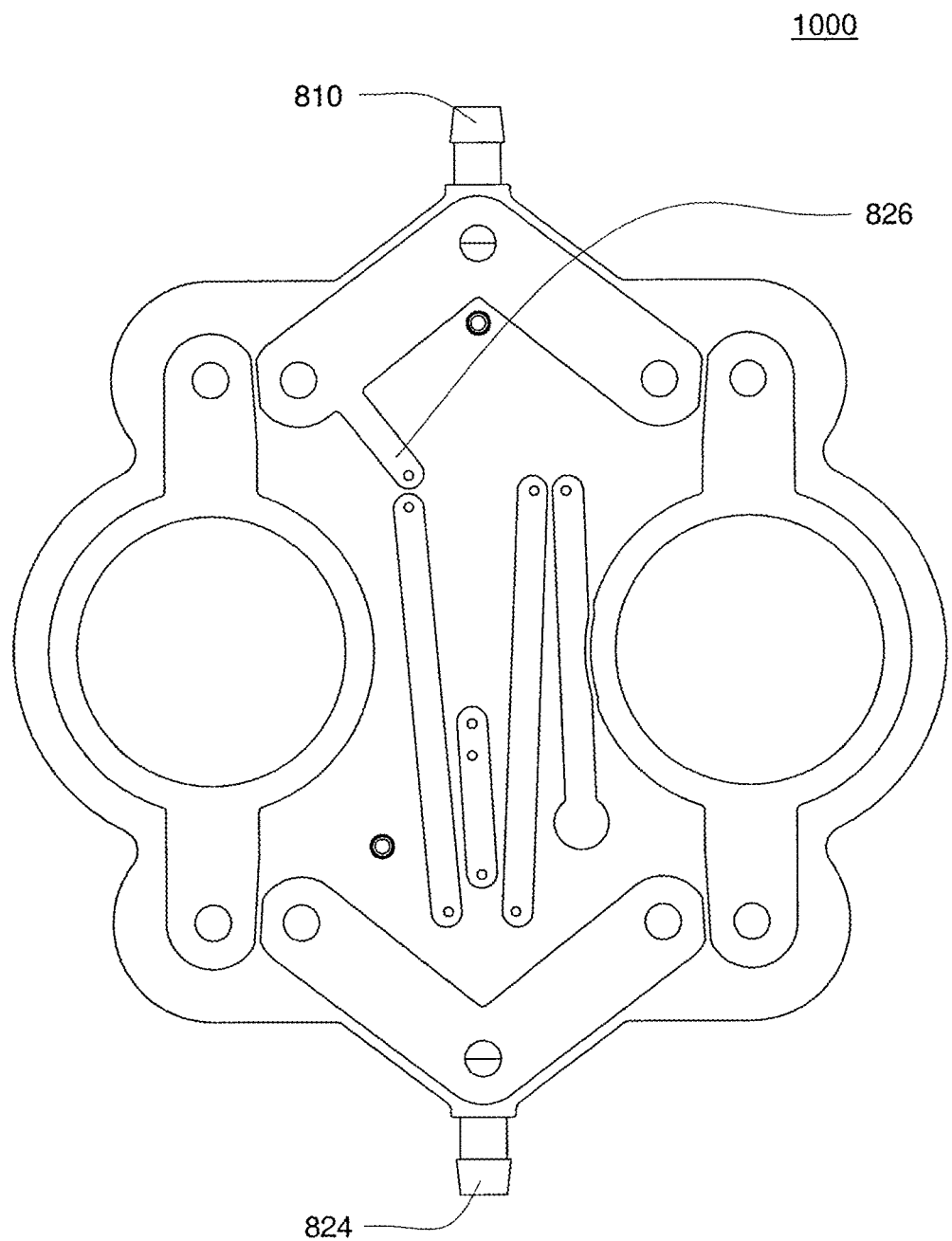

Referring now to FIGS. 31A and 31B, the liquid side of the midplate 1000 is shown. The areas complementary to the fluid paths on the inner top plate are shown. These areas are slightly raised tracks that present a surface finish that is conducive to laser welding, which is the mode of manufacture in one embodiment. The fluid inlet 810 and fluid outlet 824 are also shown in this view.

Figure 31C:
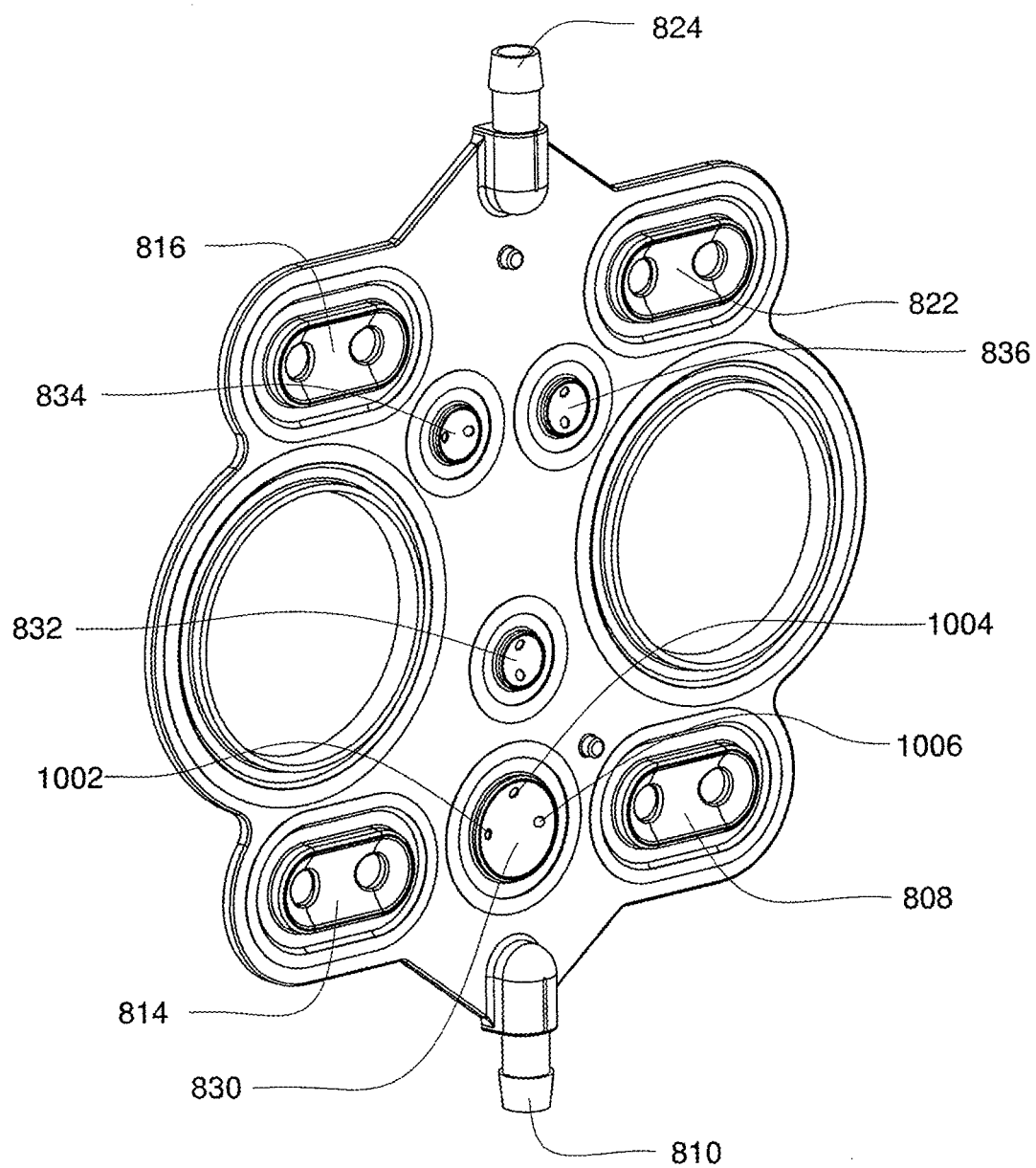
FIGS. 31C and 31D are isometric and top views of the air side of a midplate according to an exemplary embodiment of the cassette.
Figure 31D:
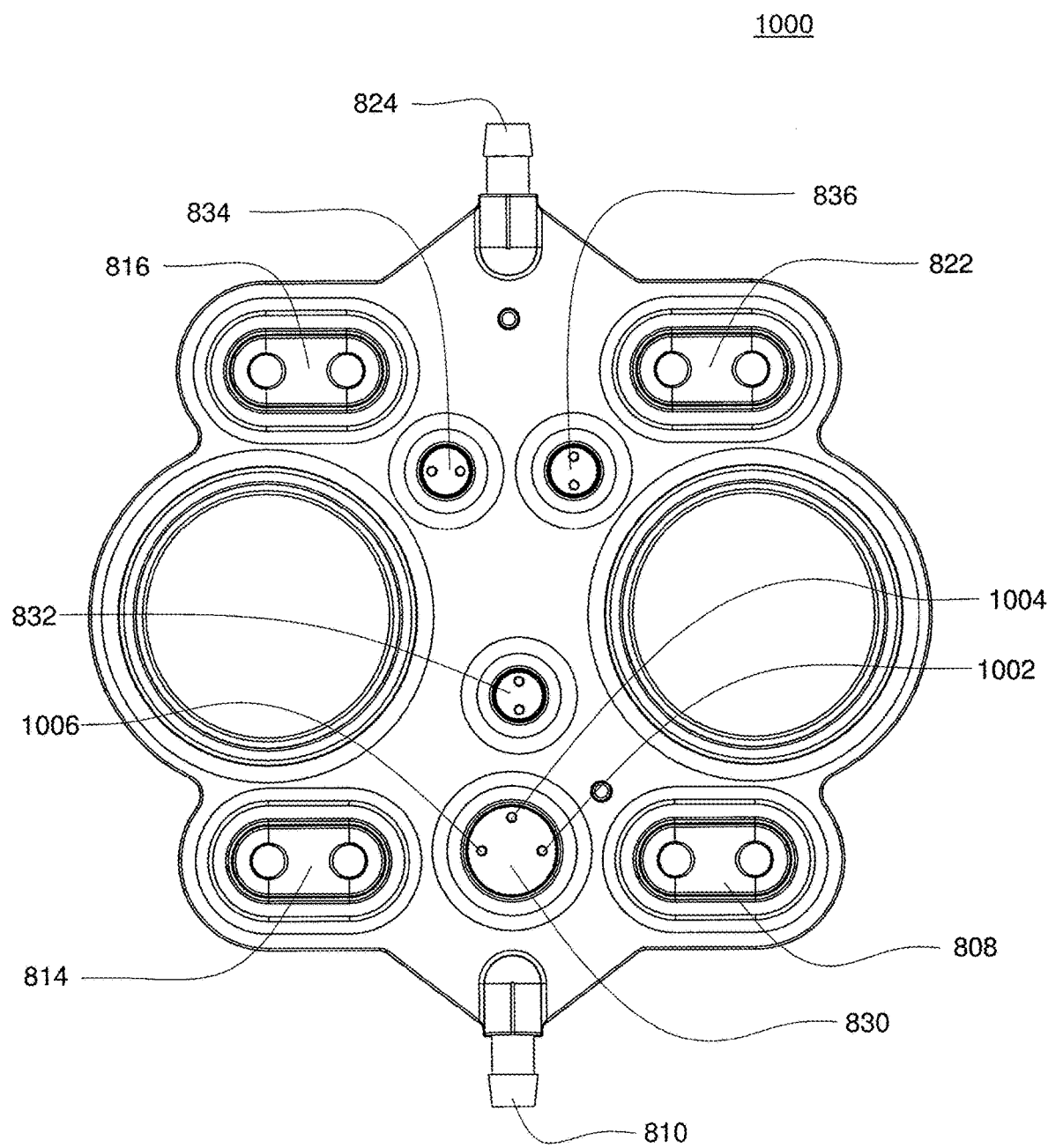

Referring next to FIGS. 31C and 31D, the air side of the midplate 1000 is shown according to one embodiment. The air side of the valve holes 808, 814, 816, 822 correspond to the holes in the fluid side of the midplate (shown in FIG. 31A). As seen in FIGS. 33C and 33D, diaphragms 1220 complete valves 808, 814, 816, 822 while diaphragms 1226 complete pod pumps 820, 828. The metering pump 830 is completed by diaphragm 1224. The valves 808, 814, 816, 822, 832, 834, 836 are actuated pneumatically, and as the diaphragm is pulled away from the holes, liquid is drawn in, and as the diaphragm is pushed toward the holes, liquid is pushed through. The fluid flow is directed by the opening and closing of the valves 808, 814, 816, 822, 832, 834, 836.

Referring to FIGS. 31A and 31C, the metering pump includes three holes, 1002, 1004, 1006. One hole 1002 pulls air into the metering pump, the second hole 1004 pushes air to the spike/source container and also, draws liquid from the source container, and the third hole 1006 pushes the second fluid from the metering pump 830 to the fluid line to point 826.

Valves 832, 834, 836 actuate the second fluid metering pump. Valve 832 is the second fluid/spike valve, valve 834 is the air valve and valve 836 is the valve that controls the flow of fluid to the fluid line to area 826.

Figure 32A:
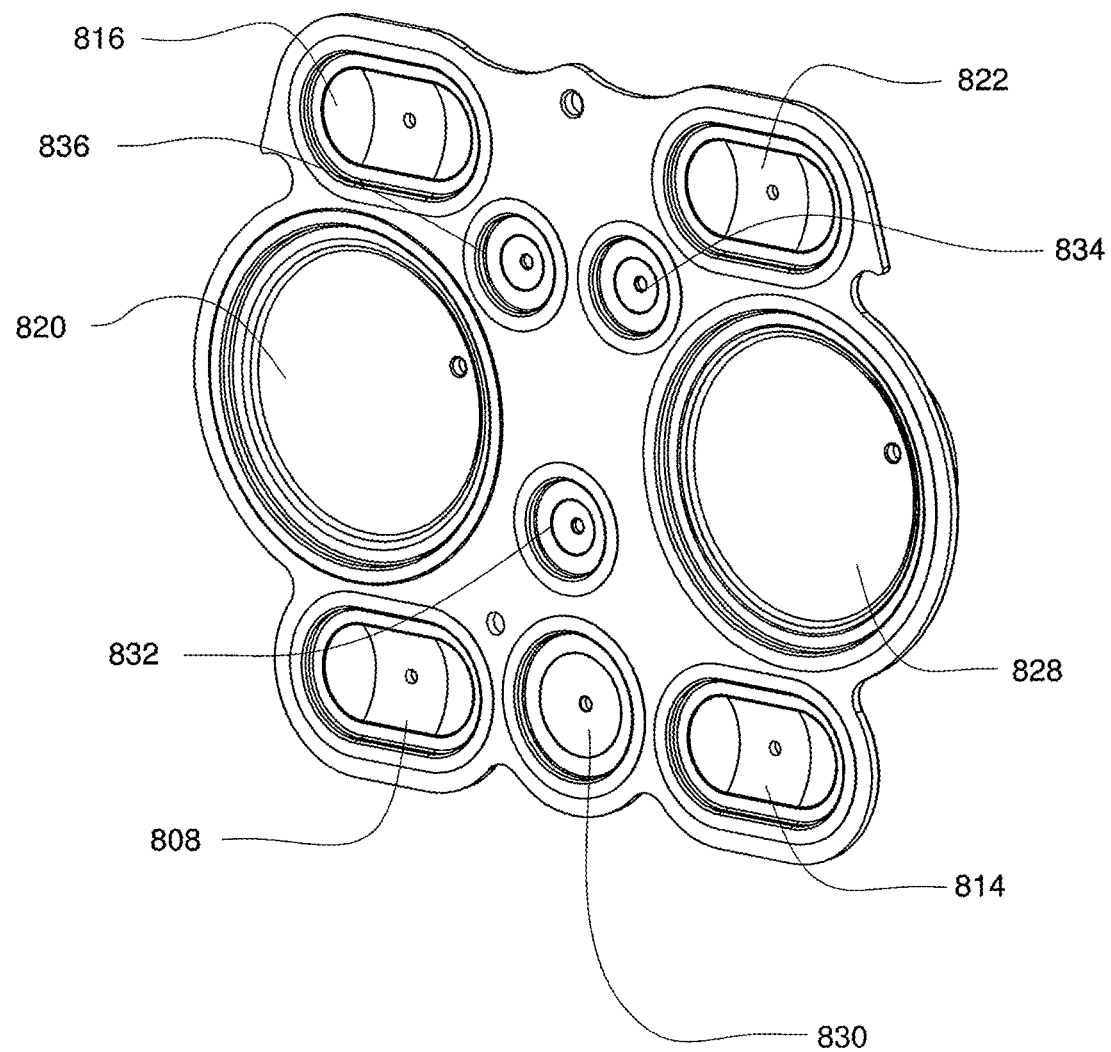
FIGS. 32A and 32B are isometric and top views of the inner side of a bottom plate according to an exemplary embodiment of the cassette.
Figure 32B:
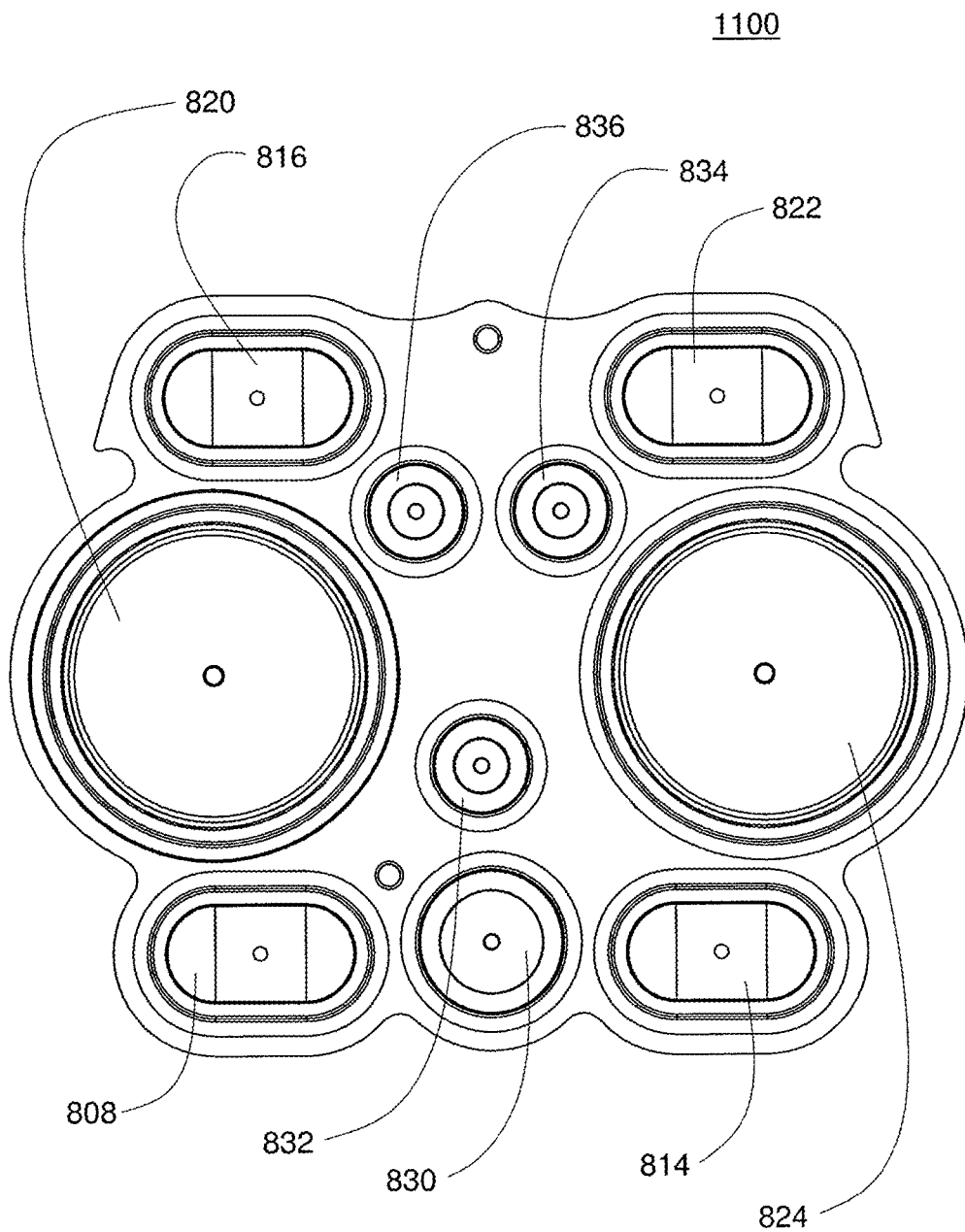
Figure 32C:
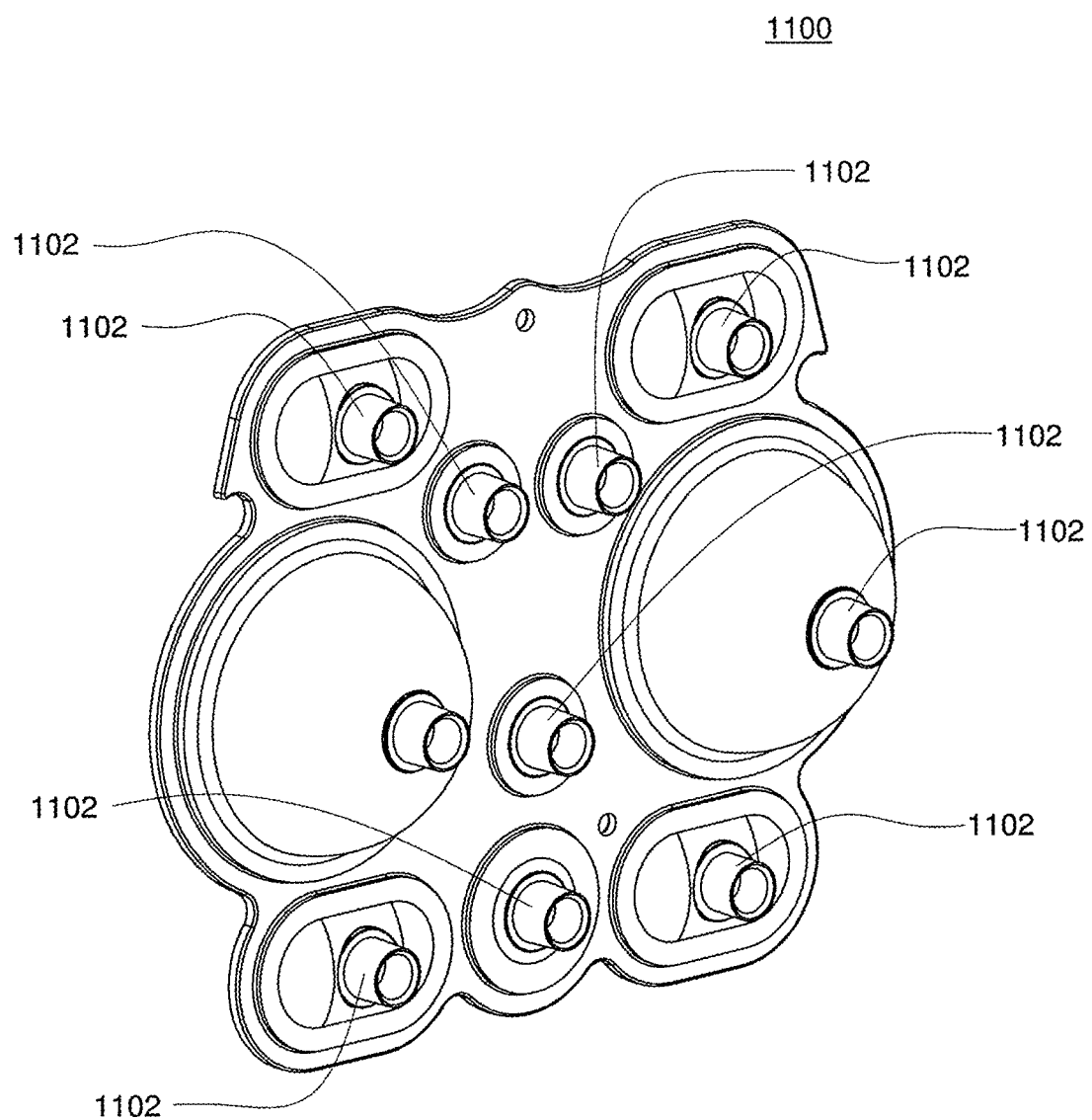
FIGS. 32C and 32D are isometric and top views of the outer side of a bottom plate according to an exemplary embodiment of the cassette.
Figure 32D:
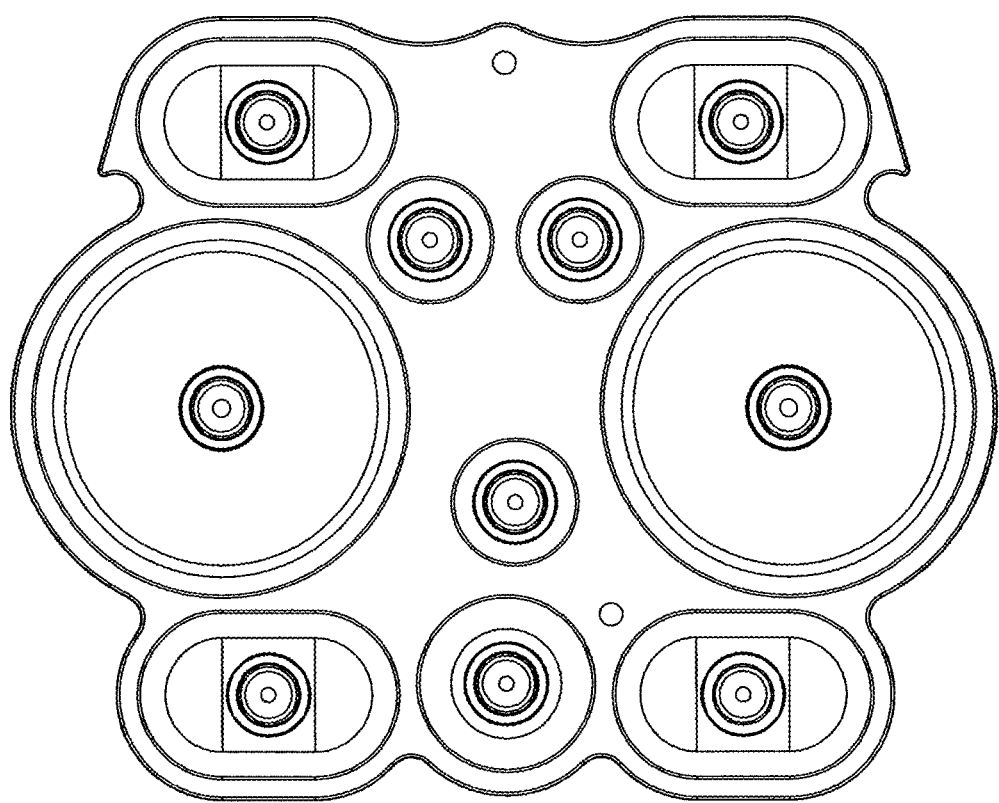
Figure 32E:
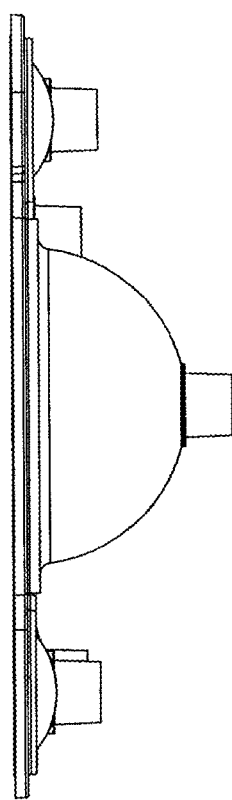
FIG. 32E is a side view of a bottom plate according to an exemplary embodiment of the cassette.

Referring next to FIGS. 32A and 32B, the inner view of the bottom plate 1100 is shown. The inside view of the pod pumps 820, 828, the metering pump 830 and the valves 808, 814, 816, 822, 832, 834, 836 actuation/air chamber is shown. The pod pumps 820, 828, metering pump 830 and the valves 808, 814, 816, 822, 832, 834, 836 are actuated by a pneumatic air source. Referring now to FIGS. 32C and 32D, the outer side of the bottom plate 1100 is shown. The source of air is attached to this side of the cassette. In one embodiment, tubes connect to the features on the valves and pumps 1102. In some embodiments, the valves are ganged, and more than one valve is actuated by the same air line.

Figure 33A:
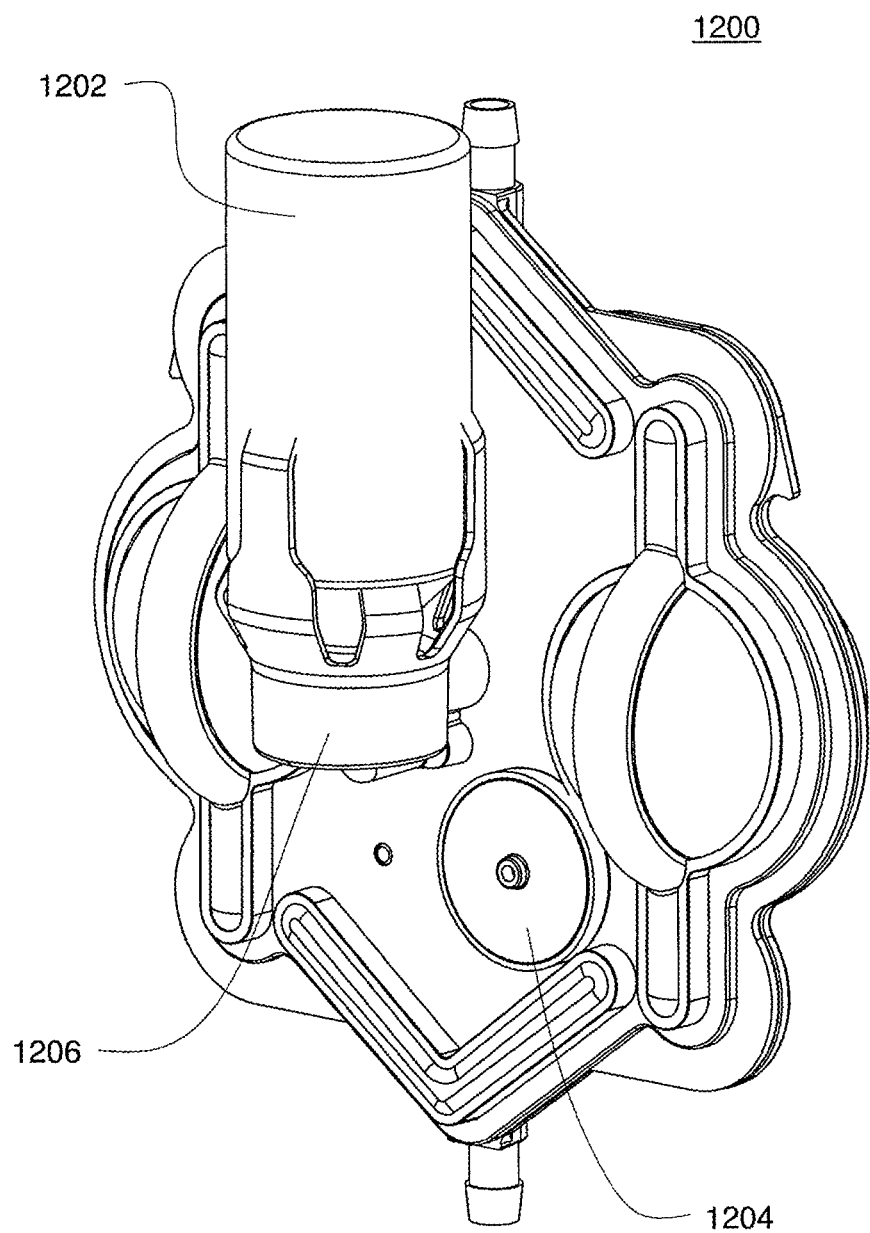
FIG. 33A is a top view of an assembled exemplary embodiment of a cassette with a vial attached.
Figure 33B:
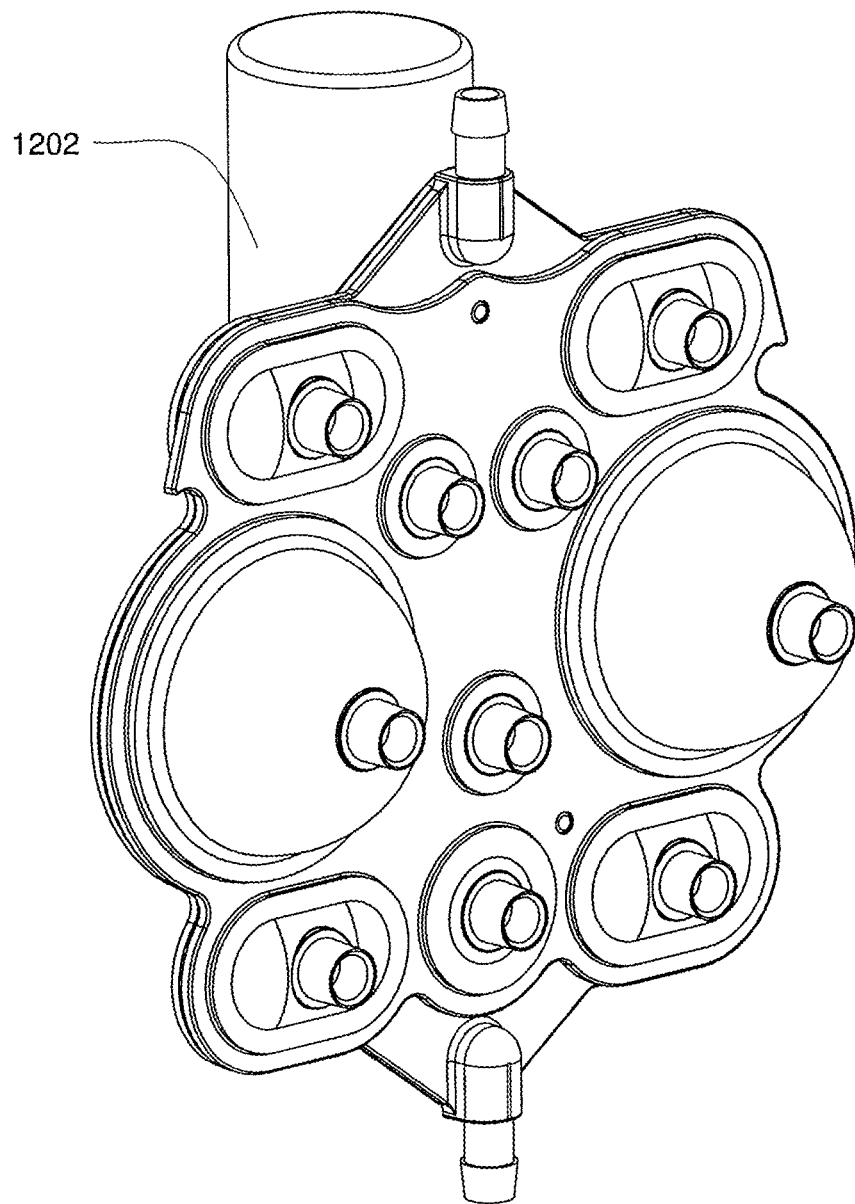
FIG. 33B is a bottom view of an assembled exemplary embodiment of a cassette with a vial attached.
Figure 33C:
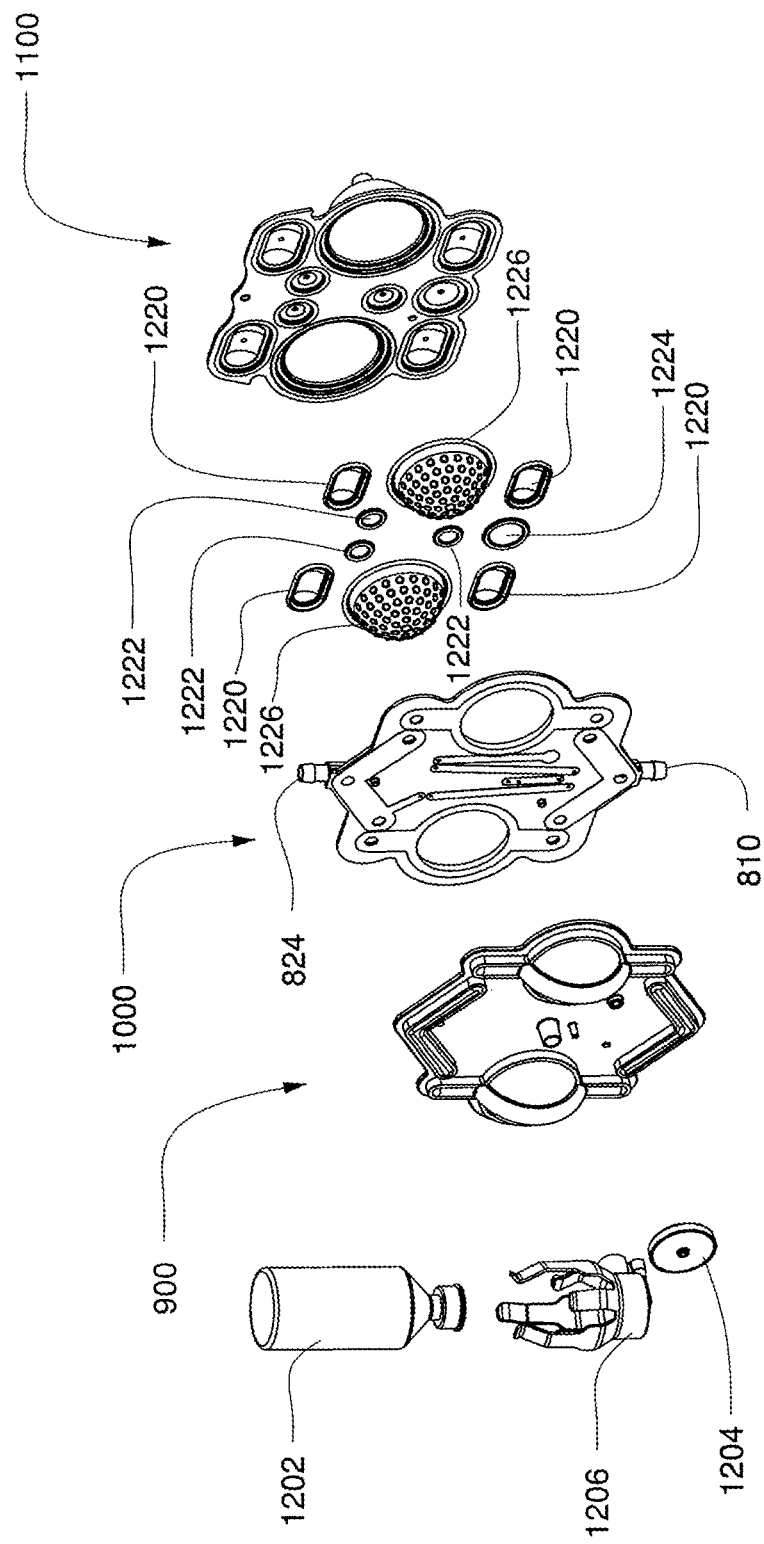
FIG. 33C is an exploded view of an assembled exemplary embodiment of a cassette with a vial.
Figure 33D:
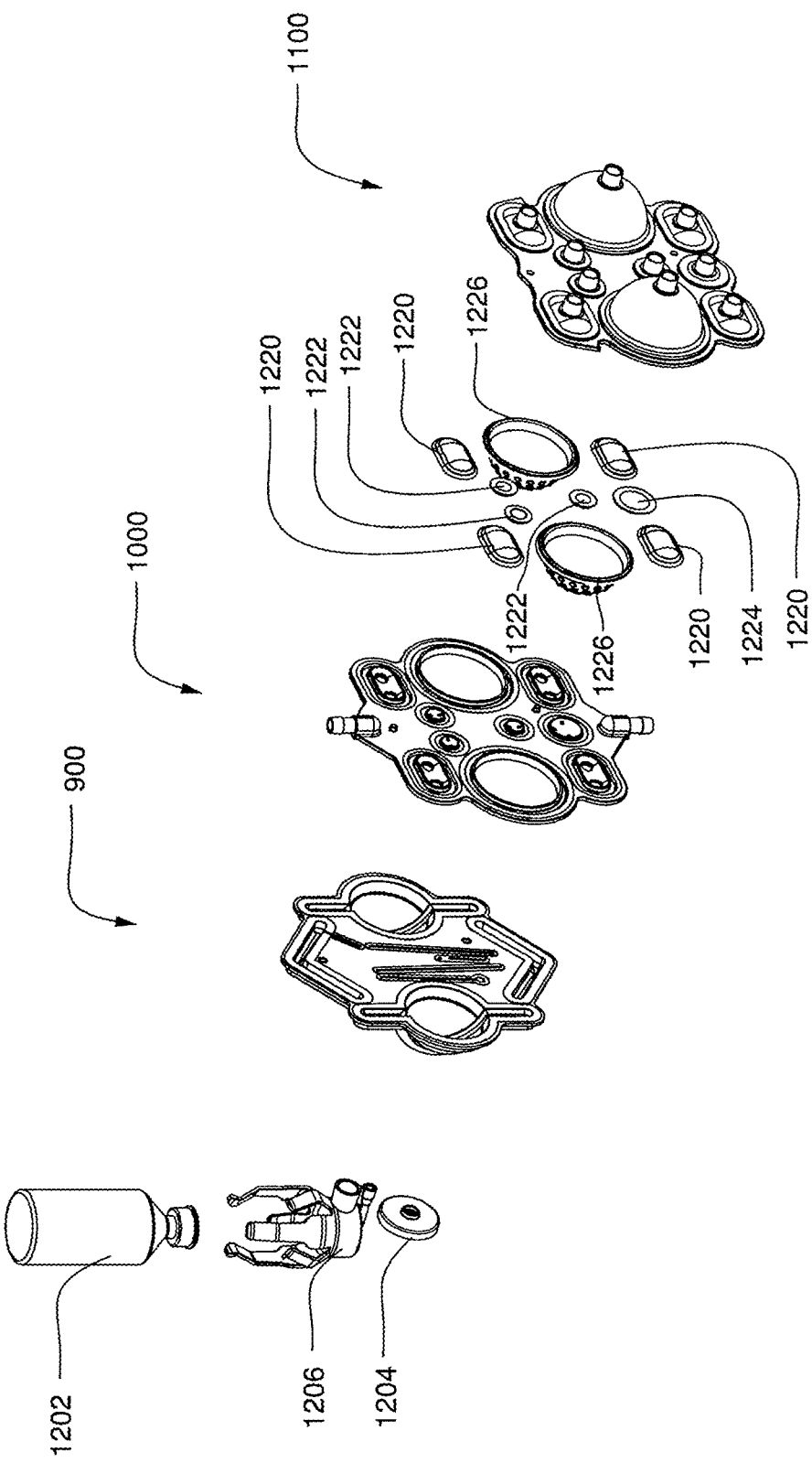
FIG. 33D is an exploded view of an assembled exemplary embodiment of a cassette with a vial.
Figure 34A:
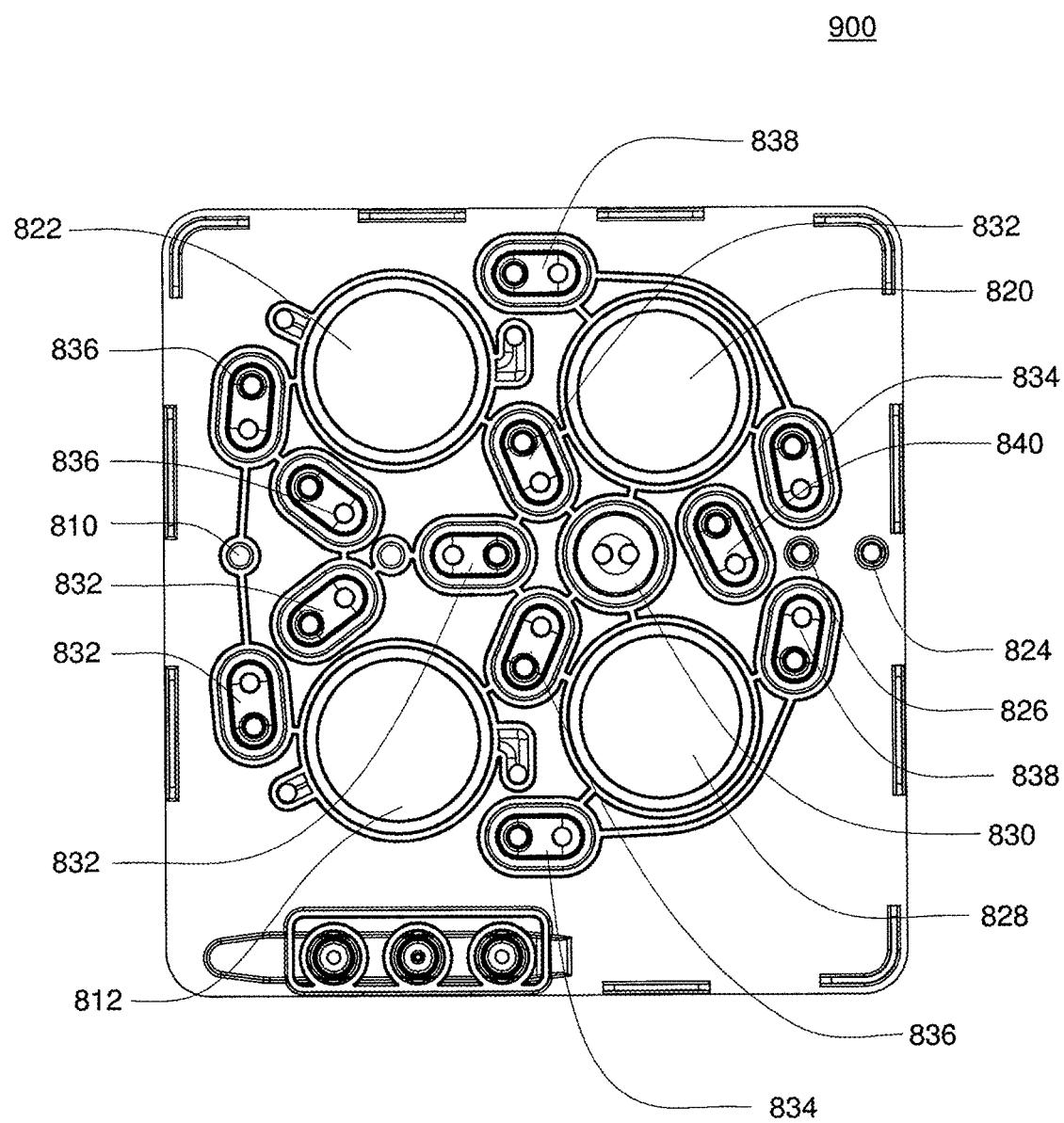
FIG. 34A is an isometric bottom view of an exemplary embodiment of the midplate of an exemplary embodiment of the cassette.
Figure 34B:
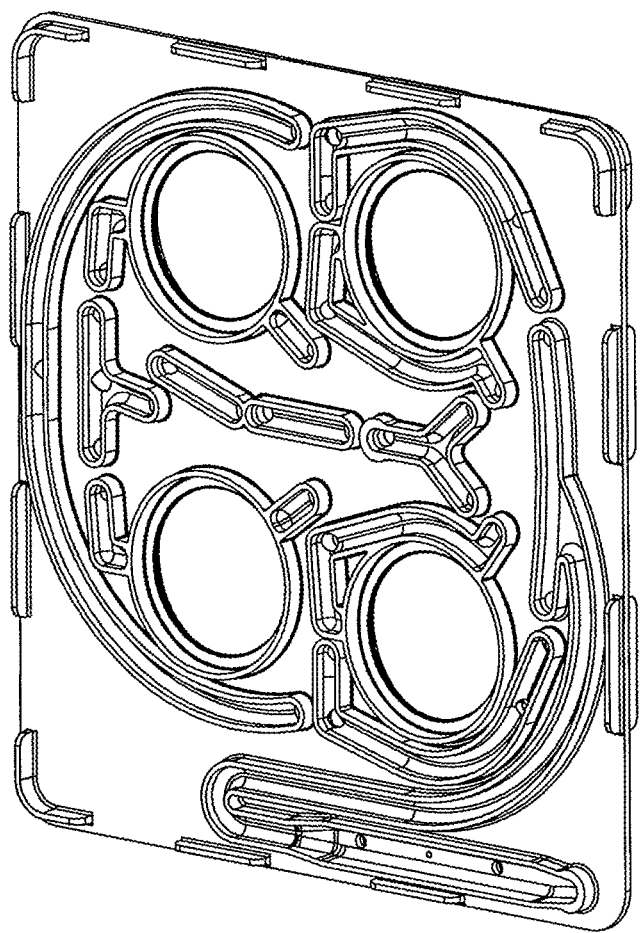
FIG. 34B is an isometric top view of the midplate of an exemplary embodiment of a cassette.
Figure 34C:
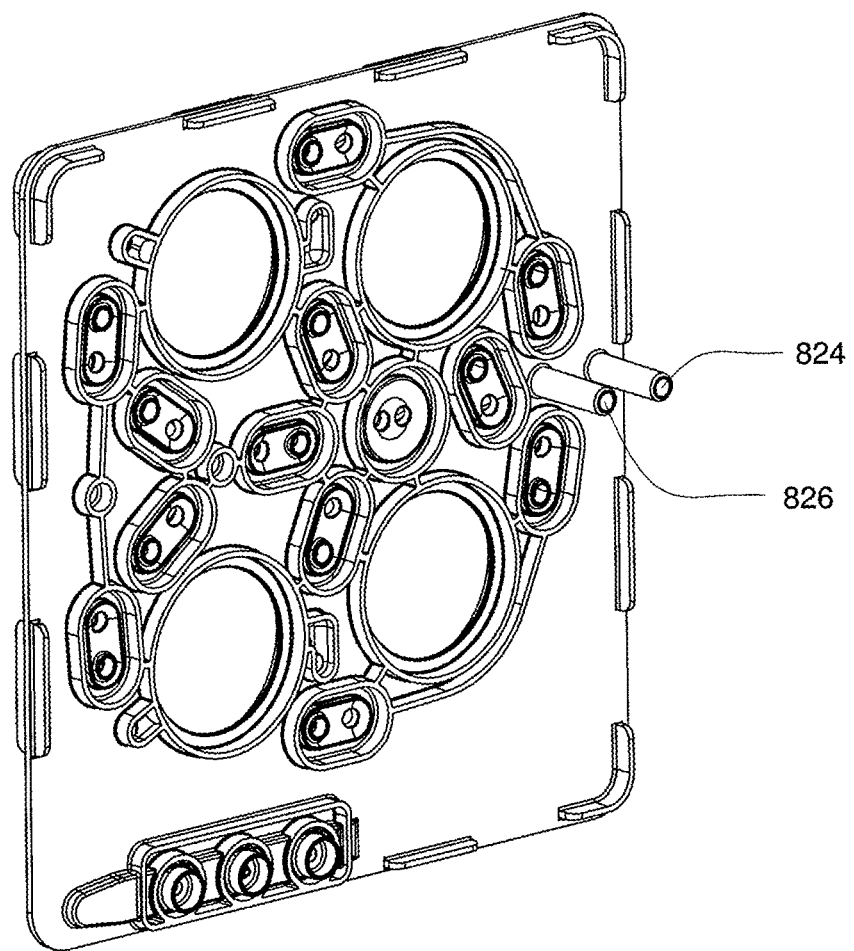
FIG. 34C is an isometric bottom view of an exemplary embodiment of the midplate of a cassette.
Figure 34D:
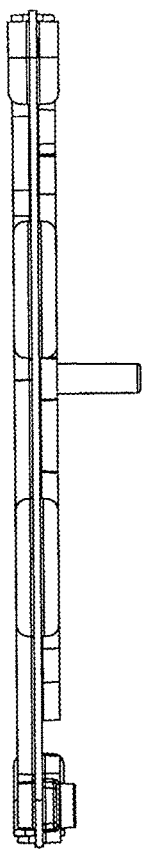
FIG. 34D is a side view of an exemplary embodiment of the midplate of a cassette.

Referring now to FIGS. 33A and 33B, an assembled cassette 1200 with a container (or other source) of a second fluid 1202 is shown, which, in this embodiment, may be an anticoagulant as described above, attached is shown. The container 1202 contains the source of the second fluid and is attached to a hollow spike (not shown) by a container attachment 1206. The spike may be situated within the container attachment 1206, directed upward to penetrate the top of the container 1202, which is held in an inverted position by the container attachment 1206. The spike is in fluid communication with a fluid channel similar to the hollow path 902 depicted in FIGS. 30C and 30D. The air filter 1204 is shown attached to the air vent (not shown, shown in FIG. 30A as 906). Although not visible in FIG. 33A, the container perch (shown in FIG. 30A as 904) is under the container attachment 1206.

In some cases, the metering pump is an FMS pump, associated with a reference chamber and capable of being monitored with a pressure transducer to determine the volume of fluid that it delivers. The FMS algorithm uses changes in pressures to calculate a volume measurement at the end of a fill stroke and at the end of a delivery stroke. The difference between the computed volumes at the end of a fill and delivery stroke is the actual stroke volume. This actual stroke volume can be compared to an expected stroke volume for the particular sized chamber. If the actual and expected volumes are significantly different, the stroke has not properly completed and an error message can be generated. FMS systems can vent to atmosphere for the FMS measurement. Alternatively, the system can vent to a high pressure positive source and a low pressure negative source for the FMS measurement. In one set of embodiments, the metering pump (e.g., the anticoagulant pump) is primed. Priming the pump removes air from the metering pump and the flow path, and ensures that the pressure in the fluid container (e.g., the anticoagulant vial) is acceptable.

The metering pump can be designed such that air in the pump chamber flows up into the vial. The test is performed by closing all of the metering pump fluid valves, measuring the external volume, charging the pump's FMS chamber with vacuum, opening valves to draw from the vial into the pumping chamber, measuring the external volume (again), charging the FMS chamber with pressure, opening the valves to push fluid back into the vial, and then measuring the external volume (again). Changes in external volume resulting from fluid flow should correspond to the known volume of the pumping chamber. If the pumping chamber cannot fill from the vial, then the pressure in the vial is too low and air must be pumped in. Conversely, if the pumping chamber cannot empty into the vial, then the pressure in the vial is too high and some of the anticoagulant must be pumped out of the vial. Anticoagulant pumped out of the vial during these tests can be discarded, e.g., through the drain.

During routine delivery of heparin or other medication to the blood path, the pressure in the vial can be measured periodically. If the vial pressure is approaching a predefined threshold value below atmospheric pressure, for example, the metering pump can first introduce air into the vial via the metering pump air vent, normalizing the pressure in the vial and helping to ensure the withdrawal of a reasonably precise amount of medication from the vial. If the vial pressure approaches a predefined threshold value above atmospheric pressure, the metering pump can forego instilling any further air into the vial before the next withdrawal of medication from the vial.

An exploded view of the assembled cassette 1200 shown in FIGS. 33A and 12B is shown in FIGS. 33C and 33D. In these views, an exemplary embodiment of the pod pump diaphragms 1226 is shown. The gasket of the diaphragm provides a seal between the liquid chamber (in the top plate 900) and the air/actuation chamber (in the bottom plate 1100). The dimpled texture on the dome of diaphragms 1226 provide, amongst other features, additional space for air and liquid to escape the chamber at the end of stroke.

A system of the present invention may also include a balancing circuit, e.g., balancing circuit 143 as shown in FIG. 3A. In some cases, blood flow circuit is implemented on a cassette, although it need not be. Within the balancing circuit, the flow of dialysate that passes in and out of the dialyzer may be balanced in some cases such that essentially the same amount of dialysate comes out of the dialyzer as goes into it (however, this balance can be altered in certain cases, due to the use of a bypass pump, as discussed below).

In addition, in some cases, the flow of dialysate may also be balanced through the dialyzer such that the pressure of dialysate within the dialyzer generally equals the pressure of blood through the blood flow circuit. The flow of blood through the blood flow circuit 141 and dialyzer in some cases is synchronized with the flow of dialysate in the dialysate flow path through the dialyzer. Because of the potential of fluid transfer across the semi-permeable membrane of the dialyzer, and because the pumps of the balancing circuit run at positive pressures, the balancing circuit pumps can be timed to synchronize delivery strokes to the dialyzer with the delivery strokes of the blood pumps, using pressure and control data from the blood flow pumps.

Figure 5:
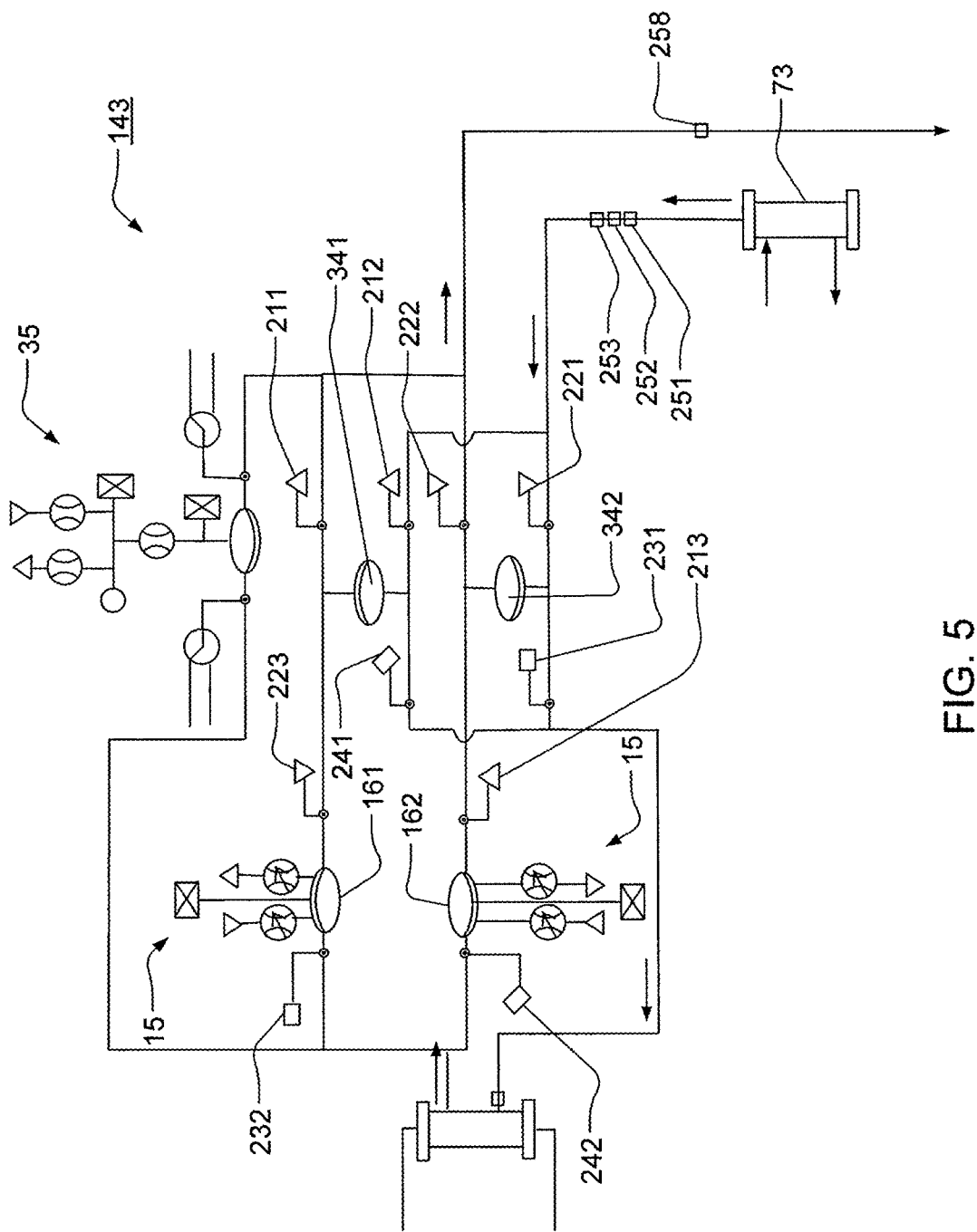
FIG. 5 is a schematic representation of one embodiment of a balancing circuit that may be used in a hemodialysis system.

A non-limiting example of a balancing circuit is shown in FIG. 5. In balancing circuit 143, dialysate flows from optional ultrafilter 73 into one or more dialysate pumps 15 (e.g., two as shown in FIG. 5). The dialysate pumps 15 in this figure include two pod pumps 161, 162, two balancing chambers 341, 342, and pump 35 for bypassing the balancing chambers. The balancing chambers may be constructed such that they are formed from a rigid chamber with a flexible diaphragm dividing the chamber into two separate fluid compartments, so that entry of fluid into one compartment can be used to force fluid out of the other compartment and vice versa. Non-limiting examples of pumps that can be used as pod pumps and/or balancing chambers are described in U.S. Provisional Patent Application Ser. No. 60/792,073, filed Apr. 14, 2006, entitled "Extracorporeal Thermal Therapy Systems and Methods"; or in U.S. patent application Ser. No. 11/787,212, filed Apr. 13, 2007, entitled "Fluid Pumping Systems, Devices and Methods," each incorporated herein by reference. Additional examples of pod pumps are discussed in detail below. As can be seen in the schematic of FIG. 5, many of the valves can be "ganged" or synchronized together in sets, so that all the valves in a set can be opened or closed at the same time.

Figure 18A:
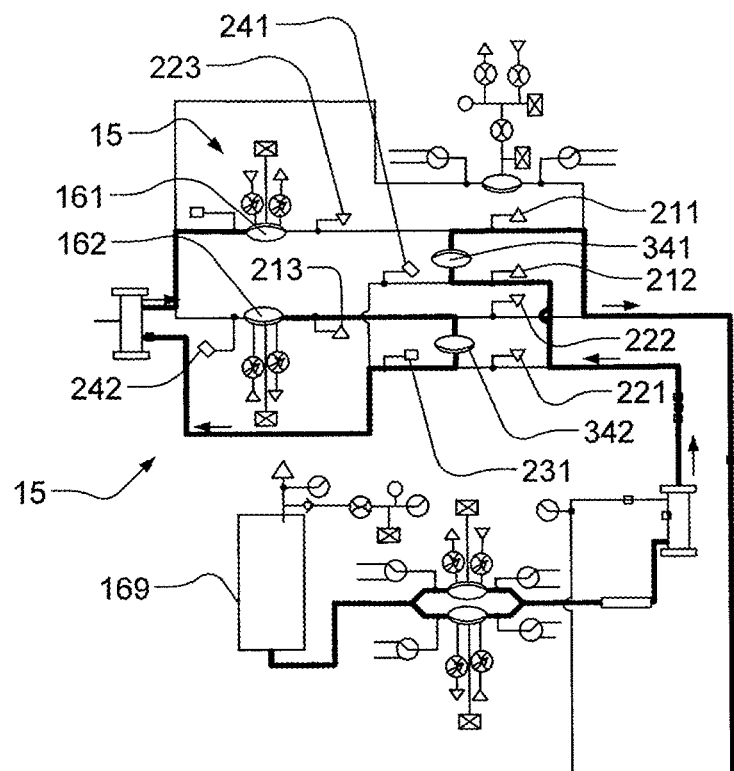
FIGS. 18A-18B illustrate the fluid flow of dialysate from a dialysate tank, through the dialyzer and out to drain in one embodiment of the invention.

More specifically, in one embodiment, balancing of flow works as follows. FIG. 5 includes a first synchronized, controlled together set of valves 211, 212, 213, 241, 242, where valves 211, 212, 213 are ganged and valves 241 and 242 are ganged, as well as a second synchronized, controlled together set of valves 221, 222, 223, 231, 232, where valves 221, 222, 223 are ganged, and valves 231 and 232 are ganged. At a first point of time, the first ganged set of valves 211, 212, 213, 241, 242 is opened while the second ganged set of valves 221, 222, 223, 231, 232 is closed. Fresh dialysate flows into balancing chamber 341 while used dialysate flows from dialyzer 14 into pod pump 161. Fresh dialysate does not flow into balancing chamber 342 since valve 221 is closed. As fresh dialysate flows into balancing chamber 341, used dialysate within balancing chamber 341 is forced out and exits balancing circuit 143 (the used dialysate cannot enter pod pump 161 since valve 223 is closed). Simultaneously, pod pump 162 forces used dialysate present within the pod pump into balancing chamber 342 (through valve 213, which is open; valves 242 and 222 are closed, ensuring that the used dialysate flows into balancing chamber 342). This causes fresh dialysate contained within balancing chamber 342 to exit the balancing circuit 143 into dialyzer 14. Also, pod pump 161 draws in used dialysate from dialyzer 14 into pod pump 161. This is also illustrated in FIG. 18A.

Figure 18B:
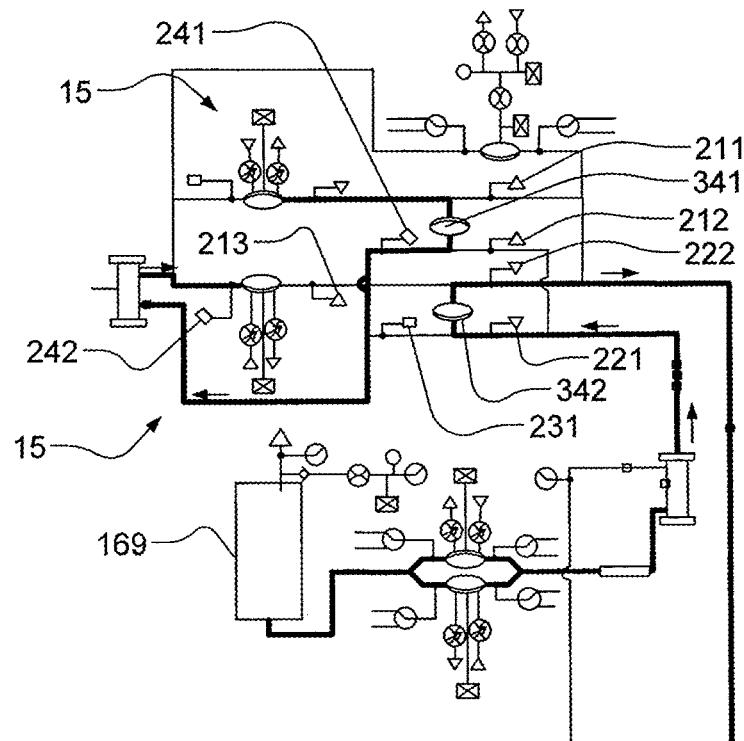

Once pod pump 161 and balancing chamber 341 have filled with dialysate, the first set of valves 211, 212, 213, 241, 242 is closed and the second set of valves 221, 222, 223, 231, 232 is opened. Fresh dialysate flows into balancing chamber 342 instead of balancing chamber 341, as valve 212 is closed while valve 221 is now open. As fresh dialysate flows into balancing chamber 342, used dialysate within the chamber is forced out and exits balancing circuit, since valve 213 is now closed. Also, pod pump 162 now draws used dialysate from the dialyzer into the pod pump, while used dialysate is prevented from flowing into pod pump 161 as valve 232 is now closed and valve 222 is now open. Pod pump 161 forces used dialysate contained within the pod pump (from the previous step) into balancing chamber 341, since valves 232 and 211 are closed and valve 223 is open. This causes fresh dialysate contained within balancing chamber 341 to be directed into the dialyzer (since valve 241 is now open while valve 212 is now closed). At the end of this step, pod pump 162 and balancing chamber 342 have filled with dialysate. This puts the state of the system back into the configuration at the beginning of this description, and the cycle is thus able to repeat, ensuring a constant flow of dialysate to and from the dialyzer. This is also illustrated in FIG. 18B. In an embodiment, the fluid (e.g. pneumatic) pressures on the control side of the balancing chamber valves are monitored to ensure they are functioning properly.

As a specific example, a vacuum (e.g., 4 p.s.i. of vacuum) can be applied to the port for the first ganged set of valves, causing those valves to open, while positive pressure (e.g., 20 p.s.i. of air pressure, 1 p.s.i. is 6.89475 kilopascals) is applied to the second ganged set of valves, causing those valves to close (or vice versa). The pod pumps each urge dialysate into one of the volumes in one of the balancing chambers 341, 342. By forcing dialysate into a volume of a balancing chamber, an equal amount of dialysate is squeezed by the diaphragm out of the other volume in the balancing chamber. In each balancing chamber, one volume is occupied by fresh dialysate heading towards the dialyzer and the other volume is occupied by used dialysate heading from the dialyzer. Thus, the volumes of dialysate entering and leaving the dialyzer are kept substantially equal.

It should be noted that any valve associated with a balancing chamber may be opened and closed under any suitable pressure. However, it may be advantageous to apply a lower or more controlled pressure to initiate and effect valve closure than the pressure ultimately used to keep the valve closed ("holding pressure"). Applying the equivalent of the holding pressure to effectuate valve closure may lead to transient pressure elevations in the fluid line sufficient to cause an already closed downstream valve to leak, adversely affecting the balancing of dialysate flow into and out of the dialyzer. Causing the dialysate pump and balancing chamber inlet and/or outlet valves to close under a lower or more controlled pressure may improve the balancing of dialysate flow into and out of the dialyzer. In an embodiment, this can be achieved, for example, by employing pulse width modulation ("PWM") to the pressure being applied in the fluid control lines of the valves. Without being limited to the following theories, the use of moderate or controlled pressure to 'slow-close' the valves may be effective for example, because: (1) it is possible that in some cases, the pressure in a balancing chamber can transiently exceed the holding pressure in the closed balancing chamber outlet valve (caused, for example by applying excessive pressure to close the balancing chamber inlet valve against the mass of fluid behind the valve diaphragm). The transient elevation of pressure in the fluid line can overcome the holding pressure of the closed outlet valve, resulting in a leak of fluid and an imbalance of fluid delivery between the two sides of the balancing chamber. (2) Also, the presence of air or gas between the balancing chamber and a balancing chamber valve, coupled with a rapid valve closure, could cause excess fluid to be pushed through the balancing chamber without being balanced by fluid from the opposite side of the balancing chamber.

As the diaphragms approach a wall in the balancing chambers (so that one volume in a balancing chamber approaches a minimum and the other volume approaches a maximum), positive pressure is applied to the port for the first ganged set of valves, causing those valves to close, while a vacuum is applied to the second gangd set of valves, causing those valves to open. The pod pumps then each urge dialysate into one of the volumes in the other of the balancing chambers 341, 342. Again, by forcing dialysate into a volume of a balancing chamber, an equal amount of dialysate is squeezed by the diaphragm out of the other volume in the balancing chamber. Since, in each balancing chamber, one volume is occupied by fresh dialysate heading towards the dialyzer and the other volume is occupied by used dialysate heading from the dialyzer, the volumes of dialysate entering and leaving the dialyzer are kept equal.

Also shown within FIG. 5 is bypass pump 35, which can direct the flow of dialysate from dialyzer 14 through balancing circuit 143 without passing through either of pod pumps 161 or 162. In this figure, bypass pump 35 is a pod pump, similar to those described above, with a rigid chamber and a flexible diaphragm dividing each chamber into a fluid compartment and a control compartment. This pump may be the same or different from the other pod pumps, metering pumps and/or balancing chambers described above. For example, this pump may be a pump as was described in U.S. Provisional Patent Application Ser. No. 60/792,073, filed Apr. 14, 2006, entitled "Extracorporeal Thermal Therapy Systems and Methods"; or in U.S. patent application Ser. No. 11/787,212, filed Apr. 13, 2007, entitled "Fluid Pumping Systems, Devices and Methods," each incorporated herein by reference. Pod pumps are also discussed in detail below.

When control fluid is used to actuate this pump, dialysate may be drawn through the dialyzer in a way that is not balanced with respect to the flow of blood through the dialyzer. The independent action of the bypass pump 35 on the dialysate outlet side of the dialyzer causes an additional net ultrafiltration of fluid from the blood in the dialyzer. This may cause the net flow of liquid away from the patient, through the dialyzer, towards the drain. Such a bypass may be useful, for example, in reducing the amount of fluid a patient has, which is often increased due to the patient's inability to lose fluid (primarily water) through the kidneys. As shown in FIG. 5, bypass pump 35 may be controlled by a control fluid (e.g., air), irrespective of the operation of pod pumps 161 and 162. This configuration may allow for easier control of net fluid removal from a patient, without the need to operate the balancing pumps (inside and outside dialysate pumps) in a way that would allow for such fluid to be withdrawn from the patient. Using this configuration, it is not necessary to operate the inside dialysate pumps either out of balance or out of phase with the blood pumps in order to achieve a net withdrawal of fluid from the patient.

To achieve balanced flow across the dialyzer, the blood flow pump, the pumps of the balancing circuit, and the pumps of the directing circuit (discussed below) may be operated to work together to ensure that flow into the dialyzer is generally equal to flow out of the dialyzer. If ultrafiltration is required, the ultrafiltration pump (if one is present) may be run independently of some or all of the other blood and/or dialysate pumps to achieve the desired ultrafiltration rate.

To prevent outgassing of the dialysate, the pumps of the balancing circuit may be always kept at pressures above atmospheric pressure. In contrast, however, the blood flow pump and the directing circuit pumps use pressures below atmosphere to pull the diaphragm towards the chamber wall for a fill stroke. Because of the potential of fluid transfer across the dialyzer and because the pumps of the balancing circuit run at positive pressures, the balancing circuit pumps may be able to use information from the blood flow pump(s) in order to run in a balanced flow mode. The delivery strokes of the balancing circuit chambers to the dialyzer can thus be synchronized with the delivery strokes of the blood pumps.

In one set of embodiments, when running in such a balanced mode, if there is no delivery pressure from the blood flow pump, the balancing circuit pump diaphragm will push fluid across the dialyzer into the blood and the alternate pod of the balancing circuit will not completely fill. For this reason, the blood flow pump reports when it is actively delivering a stroke. When the blood flow pump is delivering a stroke the balancing pump operates. When the blood flow pump is not delivering blood, the valves that control the flow from the dialyzer to the balancing pumps (and other balancing valves ganged together with these valves, as previously discussed) may be closed to prevent any fluid transfer from the blood side to the dialysate side from occurring. During the time the blood flow pump is not delivering, the balancing pumps are effectively frozen, and the stroke continues once the blood flow pump starts delivering again. The balancing pump fill pressure can be set to a minimal positive value to ensure that the pump operates above atmosphere at minimal impedance. Also, the balancing pump delivery pressure can be set to the blood flow pump pressure to generally match pressures on either side of the dialyzer, minimizing flow across the dialyzer during delivery strokes of the inside pump.

In some cases, it may be advantageous to have the dialysate pump deliver dialysate to the dialyzer at a pressure higher than the delivery pressure of the blood pump to the dialyzer. This can help to ensure, for example, that a full chamber of clean dialysate can get delivered to the dialyzer. In an embodiment, the delivery pressure on the dialysate pump is set sufficiently high to allow the inside pump to finish its stroke, but not so high as to stop the flow of blood in the dialyzer. Conversely, when the dialysate pump is receiving spent dialysate from the dialyzer, in some cases it may also be advantageous to have the pressure in the dialysate pump set lower than the outlet pressure on the blood side of the dialyzer. This can help ensure that the receiving dialysate chamber can always fill, in turn ensuring that there is enough dialysate available to complete a full stroke at the balancing chamber. Flows across the semipermeable membrane caused by these differential pressures will tend to cancel each other; and the pumping algorithm otherwise attempts to match the average pressures on the dialysate and blood sides of the dialyzer.

Convective flow that does occur across the dialyzer membrane may be beneficial, because a constant and repeated shifting of fluid back and forth across the dialyzer in small increments—resulting in no net ultrafiltration—can nevertheless help to prevent clot formation within the blood tubing and dialyzer, which in turn may allow for a smaller heparin dosage, prolong the useful life of the dialyzer, and facilitate dialyzer cleaning and re-use. Backflushing has the additional benefit of promoting better solute removal through convection. In another embodiment, a form of continuous backflushing across the dialyzer membrane can also be achieved by making small adjustments to the synchronization of the delivery strokes of blood with the delivery strokes of dialysate through the dialyzer.

It is generally beneficial to keep the blood flow as continuous as possible during therapy, as stagnant blood flow can result in blood clots. In addition, when the delivery flow rate on the blood flow pump is discontinuous, the balancing pump must pause its stroke more frequently, which can result in discontinuous and/or low dialysate flow rates.

However, the flow through the blood flow pump can be discontinuous for various reasons. For instance, pressure may be limited within the blood flow pump, e.g., to +600 mmHg and/or −350 mmHg to provide safe pumping pressures for the patient. For instance, during dual needle flow, the two pod pumps of the blood flow pump can be programmed to run 180° out of phase with one another. If there were no limits on pressure, this phasing could always be achieved. However to provide safe blood flow for the patient these pressures are limited. If the impedance is high on the fill stroke (due to a small needle, very viscous blood, poor patient access, etc.), the negative pressure limit may be reached and the fill flow rate will be slower then the desired fill flow rate. Thus the delivery stroke must wait for the previous fill stroke to finish resulting in a pause in the delivery flow rate of the blood flow pump. Similarly, during single needle flow, the blood flow pump may be run at 0° phase, where the two blood flow pump pod pumps are simultaneously emptied and filled. When both pod pumps are filled, the volumes of the two pod pumps are delivered. In an embodiment, the sequence of activation causes a first pod pump and then a second pod pump to fill, followed by the first pod pump emptying and then the second pod pump emptying. Thus the flow in single needle or single lumen arrangement may be discontinuous.

One method to control the pressure saturation limits would be to limit the desired flow rate to the slowest of the fill and deliver strokes. Although this would result in slower blood delivery flow rates, the flow rate would still be known and would always be continuous, which would result in more accurate and continuous dialysate flow rates. Another method to make the blood flow rate more continuous in single needle operation would be to use maximum pressures to fill the pods so the fill time would be minimized. The desired deliver time could then be set to be the total desired stroke time minus the time that the fill stroke took. However, if blood flow rate cannot be made continuous, then dialysate flow rate may have to be adjusted so that when the blood flow rate is delivering the dialysate flow is higher then the programmed value to make up for the time that the dialysate pump is stopped when the blood flow pump is filling. The less continuous the blood flow, the more the dialysate flow rate may have to be adjusted upward during blood delivery to the dialyzer. If this is done with the correct timing, an average dialysate flow rate taken over several strokes can still match the desired dialysate flow rate.

A non-limiting example of a balancing cassette is shown in FIGS. 34-36. In one structure of the cassette shown in FIG. 34A, the valves are ganged such that they are actuated at the same time. In one embodiment, there are four gangs of valves 832, 834, 836, 838. In some cases, the ganged valves are actuated by the same air line. However, in other embodiments, each valve has its own air line. Ganging the valves as shown in the exemplary embodiment creates the fluid-flow described above. In some embodiments, ganging the valves also ensures the appropriate valves are opened and closed to dictate the fluid pathways as desired.

In this embodiment, the fluid valves are volcano valves, as described in more detail herein. Although the fluid flow-path schematic has been described with respect to a particular flow path, in various embodiments, the flow paths may change based on the actuation of the valves and the pumps. Additionally, the terms inlet and outlet as well as first fluid and second fluid are used for description purposes only (for this cassette, and other cassettes described herein as well). In other embodiments, an inlet can be an outlet, as well as, a first and second fluid may be different fluids or the same fluid types or composition.

Figure 35A:
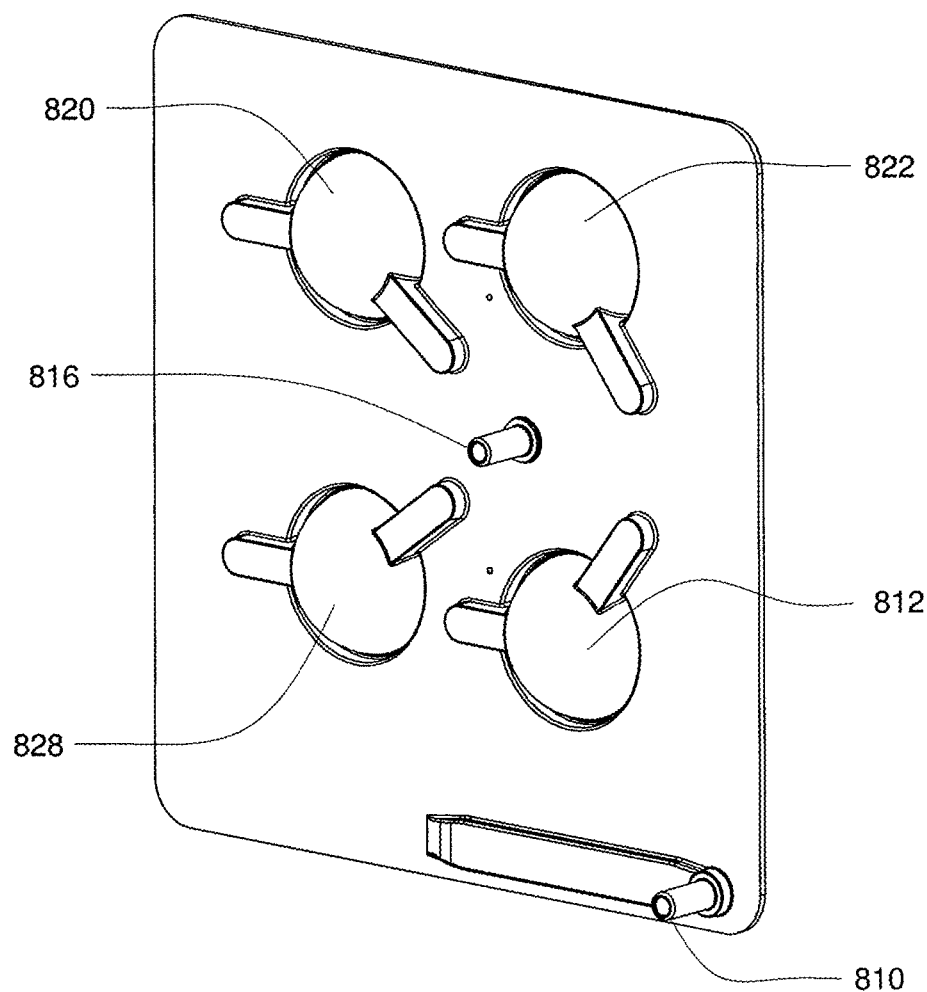
FIGS. 35A-35B are isometric and top views of an exemplary embodiment of the top plate of an exemplary embodiment of the cassette.
Figure 35B:
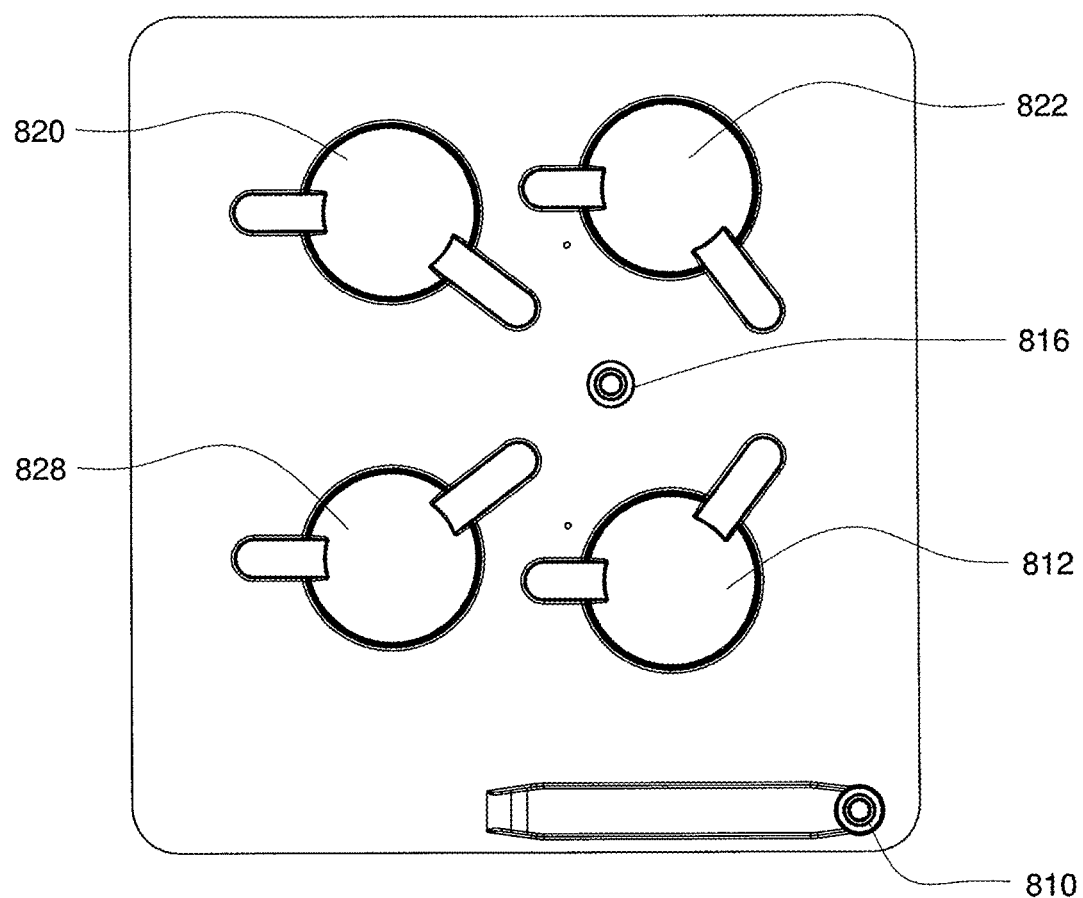

Referring now to FIGS. 35A-35E, the top plate 1000 of an exemplary embodiment of the cassette is shown. Referring first to FIGS. 35A and 35B, the top view of the top plate 1000 is shown. In this exemplary embodiment, the pod pumps 820, 828 and the balancing pods 812, 822 on the top plate, are formed in a similar fashion. In this embodiment, the pod pumps 820, 828 and balancing pods 812, 822, when assembled with the bottom plate, have a total volume of capacity of 38 ml. However, in various embodiments, the total volume capacity can be greater or less than in this embodiment. The first fluid inlet 810 and the second fluid outlet 816 are shown.

Figure 35C:
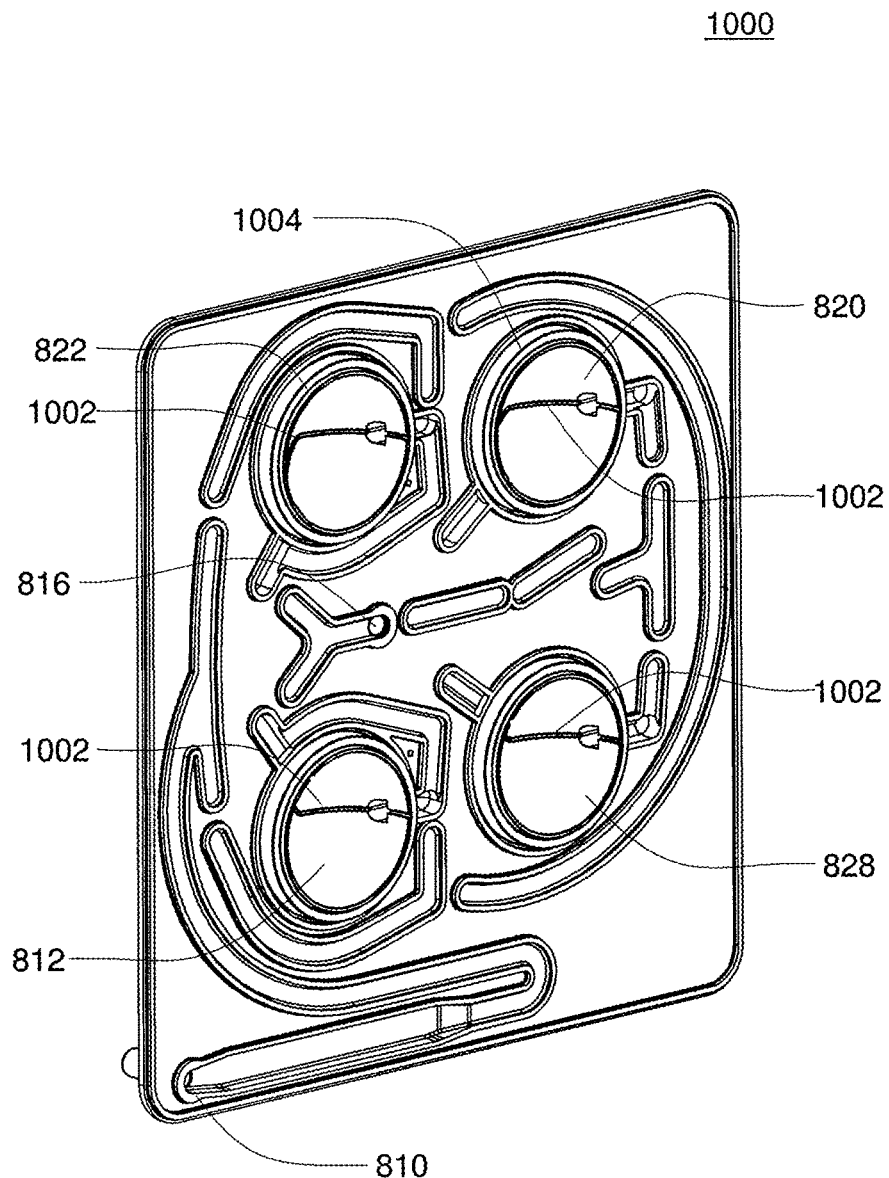
FIGS. 35C-35D are isometric views of an exemplary embodiment of the top plate of an exemplary embodiment of the cassette.
Figure 35D:
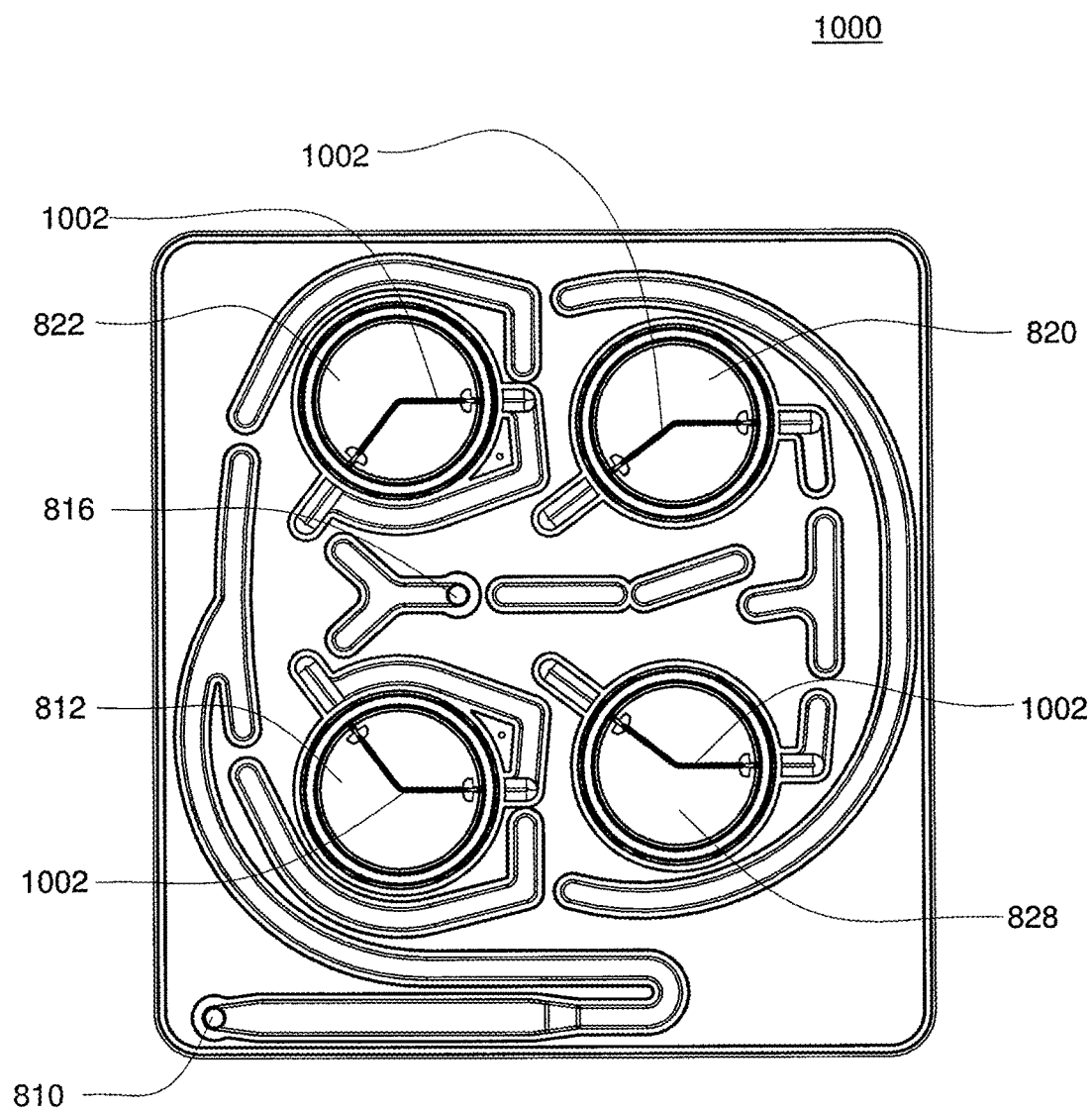

Referring now to FIGS. 35C and 35D, the bottom view of the top plate 1000 is shown. The fluid paths are shown in this view. These fluid paths correspond to the fluid paths shown in FIG. 34B in the midplate 900. The top plate 1000 and the top of the midplate form the liquid or fluid side of the cassette for the pod pumps 820, 828 and for one side of the balancing pods 812, 822. Thus, most of the liquid flow paths are on the top and midplates. The other side of the balancing pods' 812, 822 flow paths are located on the inner side of the bottom plate, not shown here, shown in FIGS. 36A-36B.

Still referring to FIGS. 35C and 35D, the pod pumps 820, 828 and balancing pods 812, 822 include a groove 1002. The groove 1002 is shown having a particular shape, however, in other embodiments, the shape of the groove 1002 can be any shape desirable. The shape shown in FIGS. 35C and 35D is an exemplary embodiment. In some embodiments of the groove 1002, the groove forms a path between the fluid inlet side and the fluid outlet side of the pod pumps 820, 828 and balancing pods 812, 822.

The groove 1002 provides a fluid path whereby when the diaphragm is at the end of stroke, there is still a fluid path between the inlet and outlet such that the pockets of fluid or air do not get trapped in the pod pump or balancing pod. The groove 1002 is included in both the liquid and air sides of the pod pumps 820, 828 and balancing pods 812, 822 (see FIGS. 36A-36B with respect to the air side of the pod pumps 820, 828 and the opposite side of the balancing pods 812, 822).

The liquid side of the pod pumps 820, 828 and balancing pods 812, 822, in one exemplary embodiment, include a feature whereby the inlet and outlet flow paths are continuous while the outer ring 1004 is also continuous. This feature allows for the seal, formed with the diaphragm (not shown) to be maintained.

Figure 35E:
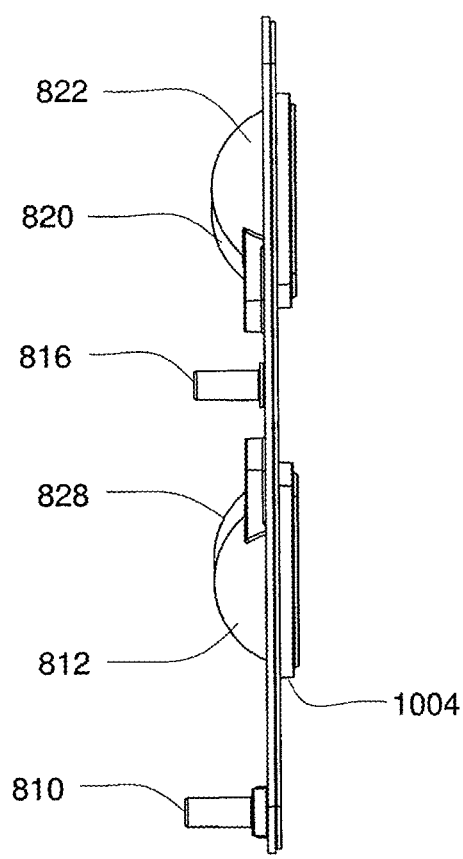
FIG. 35E is a side view of an exemplary embodiment of the top plate of a cassette.

Referring to FIG. 35E, the side view of an exemplary embodiment of the top plate 1000 is shown. The continuous outer ring 1004 of the pod pumps 820, 828 and balancing pods 812, 822 can be seen.

Figure 36A:
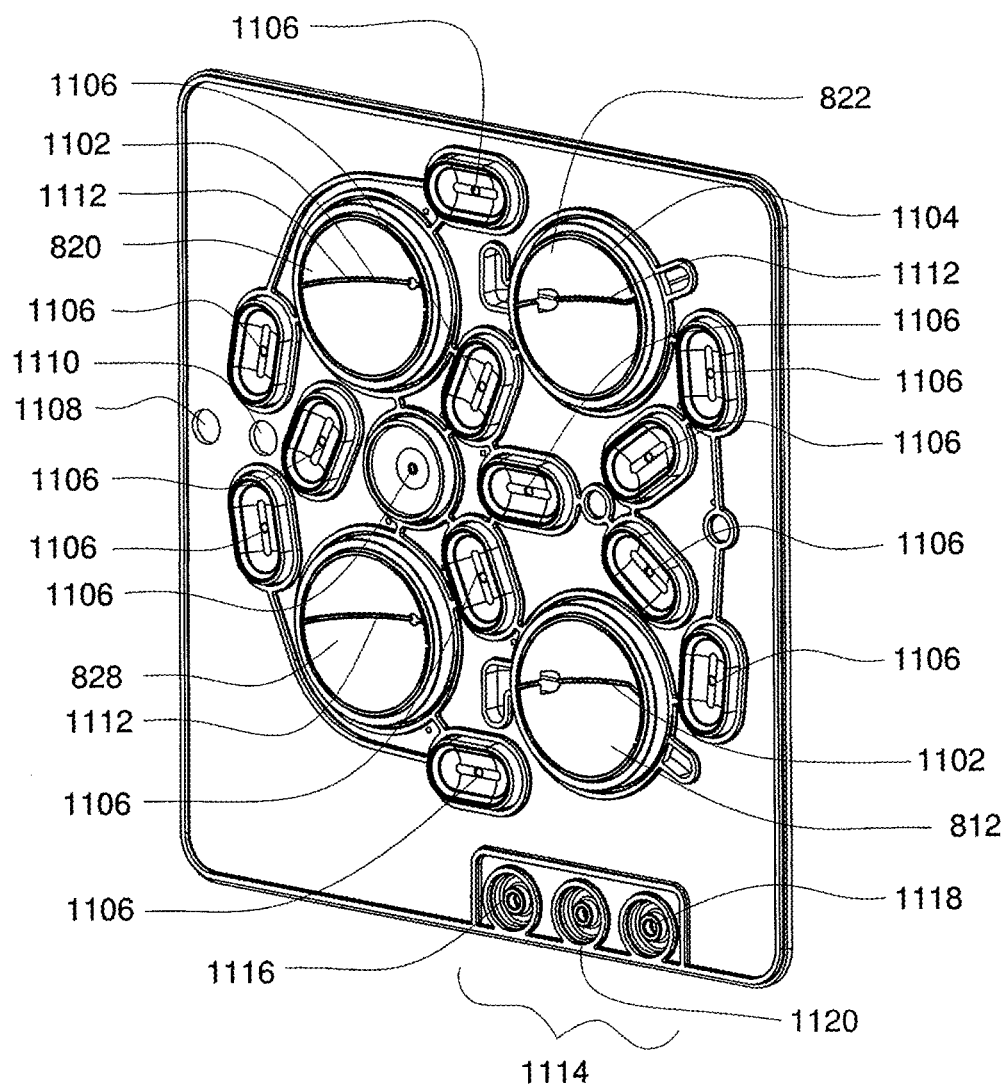
FIGS. 36A and 36B are isometric bottom views of an exemplary embodiment of the bottom plate of an exemplary embodiment of a cassette.
Figure 36B:
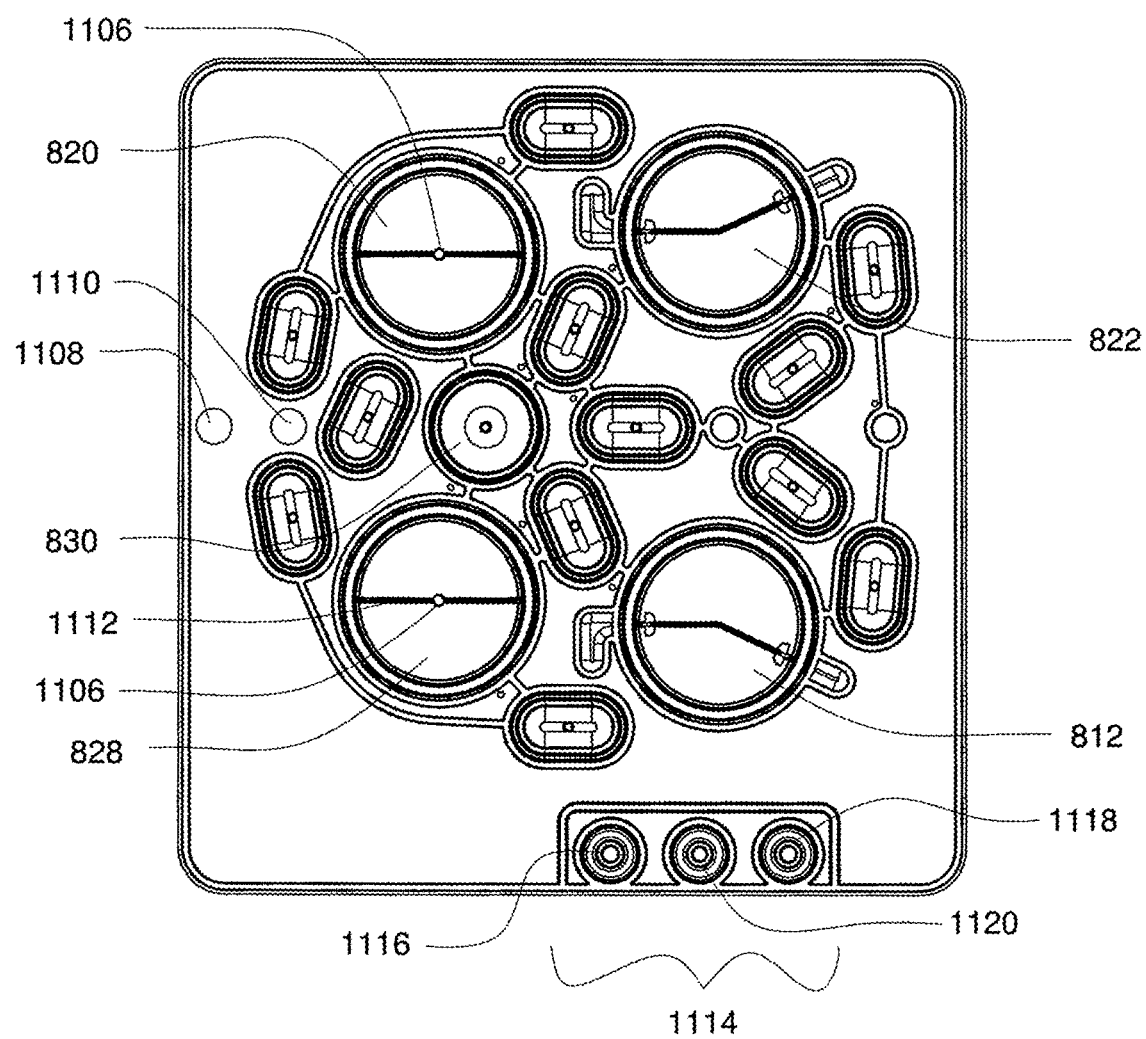

Referring now to FIGS. 36A-36E, the bottom plate 1100 is shown. Referring first to FIGS. 36A and 36B, the inside surface of the bottom plate 1100 is shown. The inside surface is the side that contacts the bottom surface of the midplate (not shown, see FIG. 34E). The bottom plate 1100 attaches to the air lines (not shown). The corresponding entrance holes for the air that actuates the pod pumps 820, 928 and valves (not shown, see FIG. 34E) in the midplate can be seen 1106. Holes 1108, 1110 correspond to the second fluid inlet and second fluid outlet shown in FIGS. 34C, 824, 826 respectively. The corresponding halves of the pod pumps 820, 828 and balancing pods 812, 822 are also shown, as are the grooves 1112 for the fluid paths. Unlike the top plate, the bottom plate corresponding halves of the pod pumps 820, 828 and balancing pods 812, 822 make apparent the difference between the pod pumps 820, 828 and balancing pods 812, 822. The pod pumps 820, 828 include an air path on the second half in the bottom plate, while the balancing pods 812, 822 have identical construction to the half in the top plate. Again, the balancing pods 812, 822 balance liquid, thus, both sides of the diaphragm, not shown, will include a liquid fluid path, while the pod pumps 820, 828 are pressure pumps that pump liquid, thus, one side includes a liquid fluid path and the other side, shown in the bottom plate 1100, includes an air actuation chamber or air fluid path.

In one exemplary embodiment of the cassette, sensor elements are incorporated into the cassette so as to discern various properties of the fluid being pumped. In one embodiment, the three sensor elements are included. In one embodiment, the sensor elements are located in the sensor cell 1114. The cell 1114 accommodates three sensor elements in the sensor element housings 1116, 1118, 1120. In an embodiment, two of the sensor housings 1116, 1118 accommodate a conductivity sensor element and the third sensor element housing 1120 accommodates a temperature sensor element. The conductivity sensor elements and temperature sensor elements can be any conductivity or temperature sensor elements in the art. In one embodiment, the conductivity sensor elements are graphite posts. In other embodiments, the conductivity sensor elements are posts made from stainless steel, titanium, platinum or any other metal coated to be corrosion resistant and still be electrically conductive. The conductivity sensor elements can include an electrical lead that transmits the probe information to a controller or other device. In one embodiment, the temperature sensor is a thermistor potted in a stainless steel probe. In alternate embodiments, there are either no sensors in the cassette or only a temperature sensor, only one or more conductivity sensors or one or more of another type of sensor. In some embodiments, the sensor elements are located outside of the cassette, in a separate cassette, and may be connected to the cassette via a fluid line.

Figure 36C:
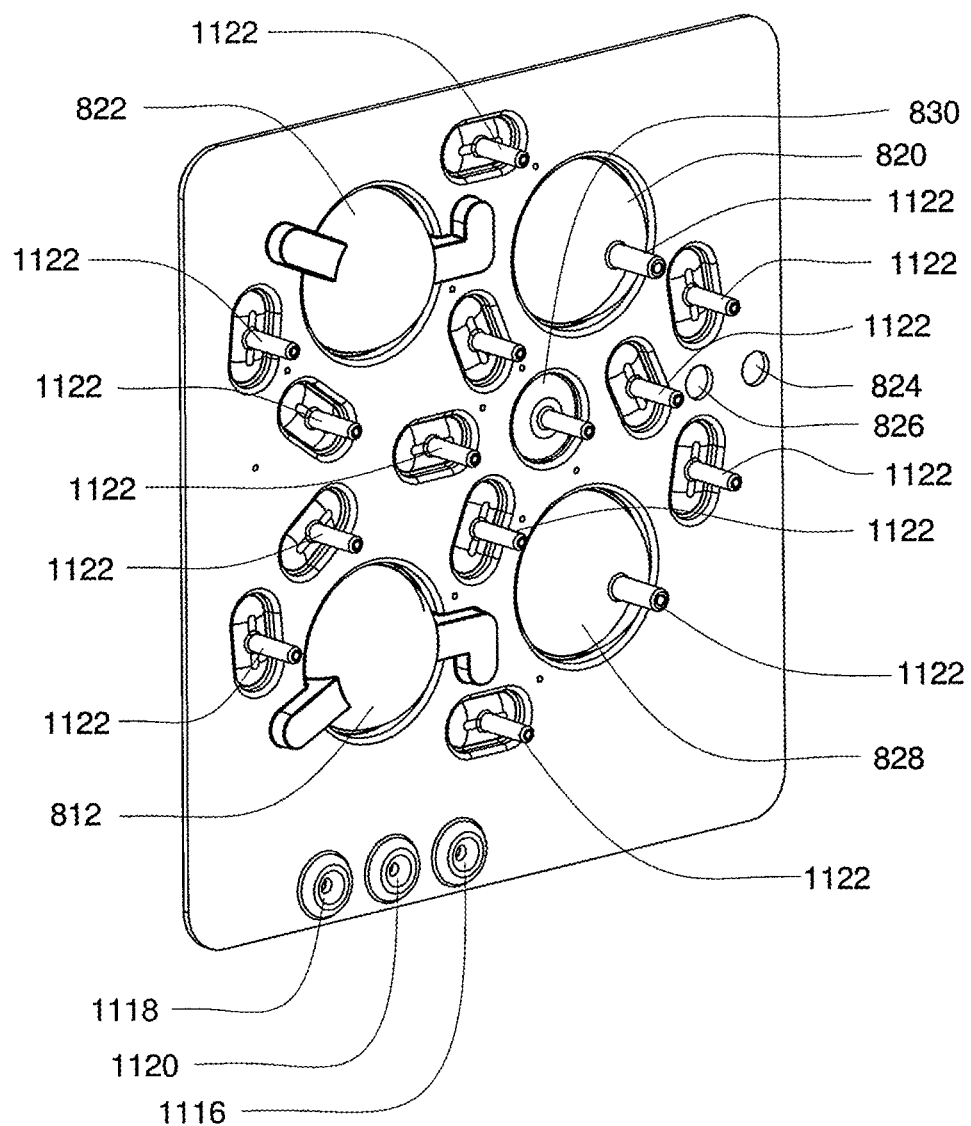
FIGS. 36C and 36D are isometric top views of an exemplary embodiment of the bottom plate of an exemplary embodiment of a cassette.
Figure 36D:
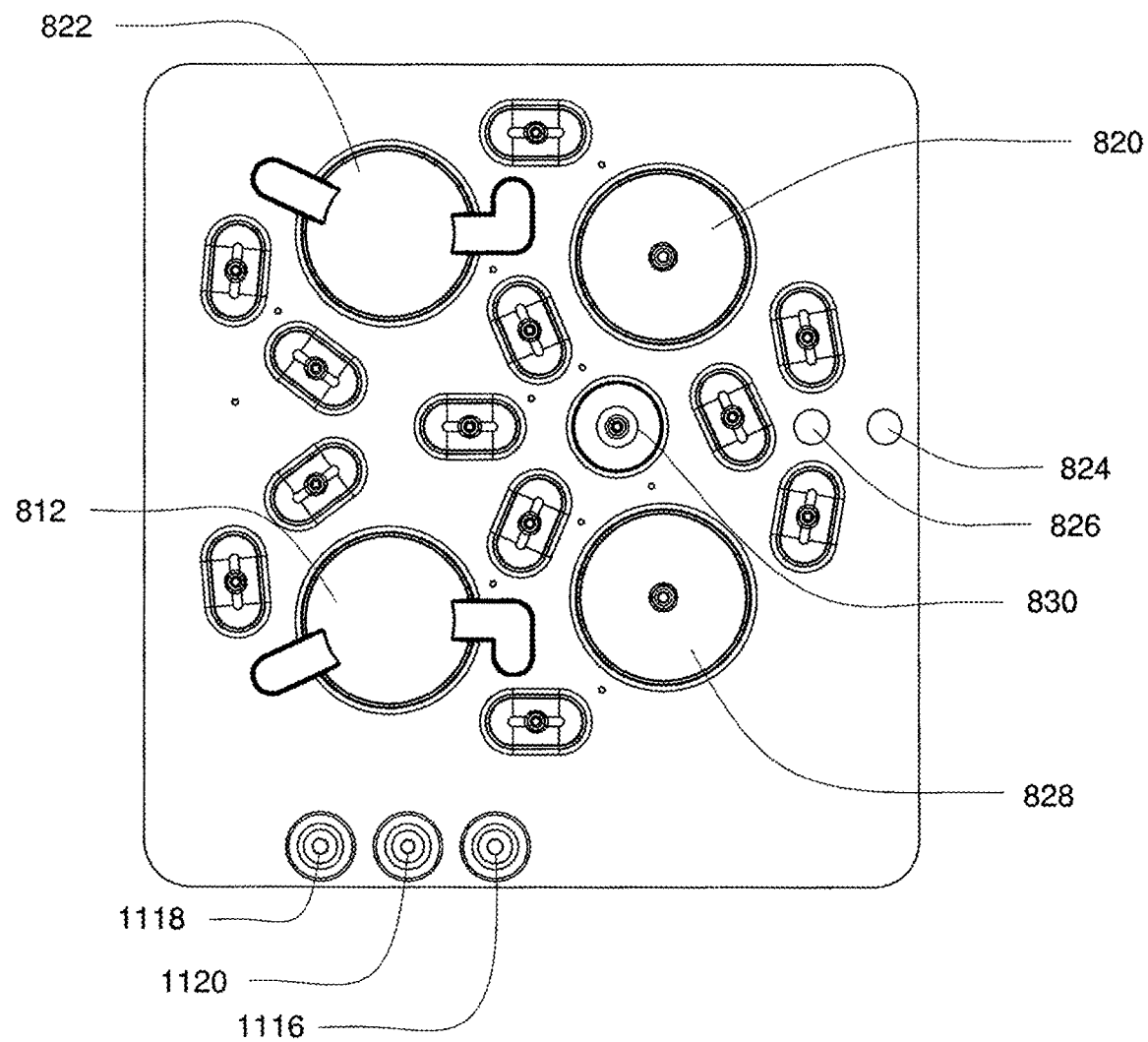

Still referring to FIGS. 36A and 36B, the actuation side of the metering pump 830 is also shown as well as the corresponding air entrance hole 1106 for the air that actuates the pump. Referring now to FIGS. 36C and 36D, the outer side of the bottom plate 1100 is shown. The valve, pod pumps 820, 828 and metering pump 830 air line connection points 1122 are shown. Again, the balancing pods 812, 822 do not have air line connection points as they are not actuated by air. As well, the corresponding openings in the bottom plate 1100 for the second fluid outlet 824 and second fluid inlet 826 are shown.

Figure 36E:
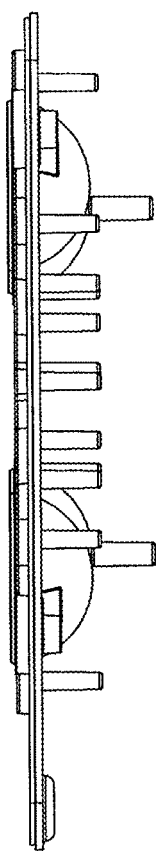
FIG. 36E is a side view of an exemplary embodiment of the bottom plate of an exemplary embodiment of a cassette.

Referring now to FIG. 36E, a side view of the bottom plate 1100 is shown. In the side view, the rim 1124 that surrounds the inner bottom plate 1100 can be seen. The rim 1124 is raised and continuous, providing for a connect point for the diaphragm (not shown). The diaphragm rests on this continuous and raised rim 1124 providing for a seal between the half of the pod pumps 820, 828 and balancing pods 812, 822 in the bottom plate 1100 and the half of the pod pumps 820, 828 and balancing pods 812, 822 in the top plate (not shown, see FIGS. 35A-35D).

As mentioned, dialysate flows from a directing circuit, optionally through a heater and/or through an ultrafilter, to the balancing circuit. In some cases, the directing circuit is implemented on a cassette, although it need not be. An example of a directing circuit can be seen in FIG. 3A as directing circuit 142. Directing circuit 142 is able to perform a number of different functions, in this example. For instance, dialysate flows from a dialysate supply (such as from a mixing circuit, as discussed below) through the directing circuit to a balancing circuit, while used dialysate flows from the balancing circuit to a drain. The dialysate may flow due to the operation of one or more pumps contained within the directing circuit. In some cases, the directing circuit may also contain a dialysate tank, which may contain dialysate prior to passing the dialysate to the balancing circuit. Such a dialysate tank, in certain instances, may allow the rate of production of dialysate to be different than the rate of use of dialysate in the dialyzer within the system. The directing circuit may also direct water from a water supply to the mixing circuit (if one is present). In addition, as previously discussed, the blood flow circuit may be fluidically connected to the directing circuit for some operations, e.g., disinfection.

Thus, in some cases, dialysate may be made as it is needed, so that large volumes of dialysate do not need to be stored. For instance, after the dialysate is prepared, it may be held in a dialysate tank 169. A dialysate valve 17 may control the flow of dialysate from tank 169 into the dialysate circuit 20. The dialysate may be filtered and/or heated before being sent into the dialyzer 14. A waste valve 18 may be used to control the flow of used dialysate out of the dialysate circuit 20.

Figure 6:
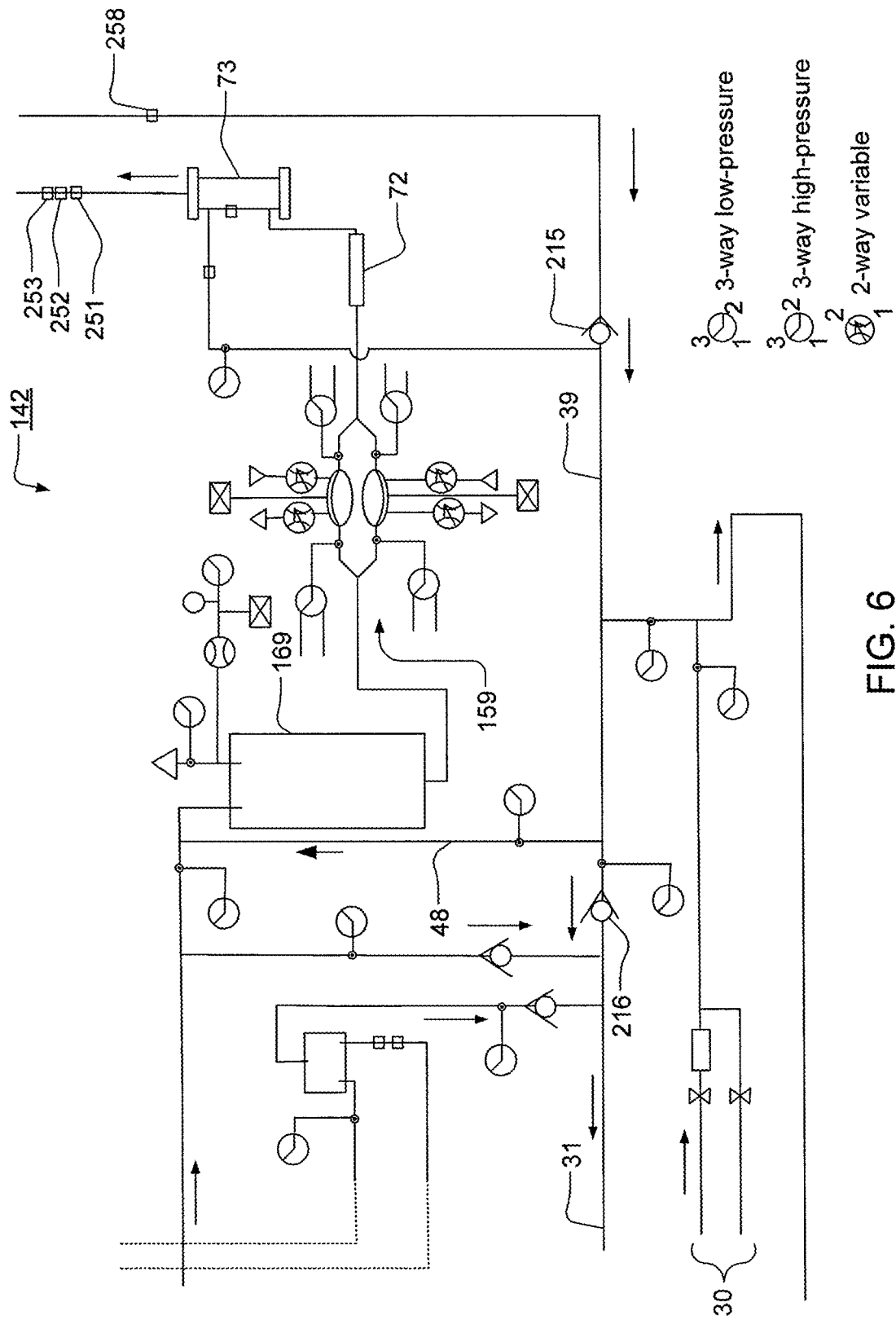
FIG. 6 is a schematic representation of a directing circuit that may be used in a hemodialysis system.

One non-limiting example of a directing circuit is shown in FIG. 6. In this figure, directing circuit 142 fluidically connects dialysate from a dialysate supply to a dialysate tank 169, then through dialysate pump 159, heater 72, and ultrafilter 73, before entering a balancing circuit, as previously discussed. It should be understood that although this figure shows that dialysate in the dialysate flow path flows from the dialysate supply to the dialysate tank, the pump, the heater, and the ultrafilter (in that order), other orderings are also possible in other embodiments. Heater 72 may be used to warm the dialysate to body temperature, and/or a temperature such that the blood in the blood flow circuit is heated by the dialysate, and the blood returning to the patient is at body temperature or higher. Ultrafilter 73 may be used to remove any pathogens, pyrogens, etc. which may be in the dialysate solution, as discussed below. The dialysate solution then flows into the balancing circuit to be directed to the dialyzer.

Dialysate tank 169 may comprise any suitable material and be of any suitable dimension for storing dialysate prior to use. For instance, dialysate tank 169 may comprise plastic, metal, etc. In some cases, dialysate tank may comprise materials similar to those used to form the pod pumps as discussed herein.

The flow of dialysate through directing circuit 142 may be controlled (at least in part) by operation of dialysate pump 159. In addition, dialysate pump 159 may control flow through the balancing circuit. For instance, as discussed above with reference to FIG. 5, fresh dialysate from the directing circuit flows into balancing chambers 341 and 342 on balancing circuit 143; pump 159 may be used as a driving force to cause the fresh dialysate to flow into these balancing chambers. In one set of embodiments, dialysate pump 159 includes a pod pump, similar to those described above. The pod pump may include a rigid chamber with a flexible diaphragm dividing each chamber into a fluid compartment and control compartment. The control compartment may be connected to a control fluid source, such as an air source. Non-limiting examples of pumps that may be used as pod pumps and/or balancing chambers are described in U.S. Provisional Patent Application Ser. No. 60/792,073, filed Apr. 14, 2006, entitled "Extracorporeal Thermal Therapy Systems and Methods"; or in U.S. patent application Ser. No. 11/787,212, filed Apr. 13, 2007, entitled "Fluid Pumping Systems, Devices and Methods," each incorporated herein by reference. Pod pumps are also discussed in detail below.

After passing through pump 159, the dialysate may flow to a heater, e.g., heater 72 in FIG. 6. The heater may be any heating device suitable for heating dialysate, for example, an electrically resistive heater as is known to those of ordinary skill in the art. The heater may be kept separated from the directing circuit (e.g., as is shown in FIG. 3A), or the heater may be incorporated into the directing circuit, or other circuits as well (e.g., the balancing circuit).

In some cases, the dialysate is heated to a temperature such that blood passing through the dialyzer is not significantly chilled. For instance, the temperature of the dialysate may be controlled such that the dialysate is at a temperature at or greater than the temperature of the blood passing through the dialyzer. In such an example, the blood may be heated somewhat, which may be useful in offsetting heat loss caused by the blood passing through the various components of the blood flow circuit, as discussed above. In addition, in some cases as discussed below, the heater may be connected to a control system such that dialysate that is incorrectly heated (i.e., the dialysate is too hot or too cold) may be recycled (e.g., back to the dialysate tank) or sent to drain instead of being passed to the dialyzer, for example, via line 731. The heater may be integrated as part of a fluid circuit, such as a directing circuit and/or a balancing circuit, or, as is shown in FIG. 3A, the heater may be a separate component within the dialysate flow path.

The heater may also be used, in some embodiments, for disinfection or sterilization purposes. For instance, water may be passed through the hemodialysis system and heated using the heater such that the water is heated to a temperature able to cause disinfection or sterilization to occur, e.g., temperatures of at least about 70° C., at least about 80° C., at least about 90° C., at least about 100° C., at least about 110° C., etc.

In some cases, as discussed below, the water may be recycled around the various components and/or heat loss within the system may be minimized (e.g., as discussed below) such that the heater is able to heat the water to such disinfection or sterilization temperatures.

The heater may include a control system that is able to control the heater as discussed above (e.g., to bring dialysate up to body temperature for dialyzing a patient, to bring the water temperature up to a disinfection temperatures in order to clean the system, etc.).

A non-limiting example of a heater controller follows. The controller may be selected to be capable of dealing with varying inlet fluid temperatures as well as for pulsatile or varying flow rates. In addition the heater control must function properly when flow is directed through each of the different flow paths (dialyze, disinfect, recirculate etc). In one embodiment, the heater controller is used on SIP1 boards with an IR (infrared) temperature sensor on the ultra filter and an IR temperature sensor on the tank. In other embodiments, the board is in a box with less heat losses and to uses conductivity sensors for the inlet temperature sensor. Another embodiment of the controller uses a simple proportional controller using both tank (heater inlet) and ultrafilter (heater outlet) temperatures, e.g.:

$$\text{powerHeater} = \text{massFlow} * ((\text{tank}P\text{Gain}*\text{errorTank}) + (\text{UFPGain}*\text{errorUF}),$$

where:
PowerHeater=heater duty cycle cmd (0-100%);
MassFlow=the fluid mass flow rate;
TankPGain=proportional gain for the tank or inlet temperature sensor;
ErrorTank=difference between the tank or inlet temperature sensor and the desired temperature;
UFPGain=proportional gain for the ultrafilter or outlet temperature sensor; and
ErrorUF=difference between the uf or outlet temperature sensor and the desired temperature.

From the heater duty cycle command (0-100%) a PWM command is generated. In some embodiments, this controller may reduce the mass flow rate if the given temperature is not maintained and the heater is saturated.

It should be understood that the above-described heater control is by way of example only, and that other heater control systems, and other heaters, are also possible in other embodiments of the invention.

The dialysate may also be filtered to remove contaminants, infectious organisms, pathogens, pyrogens, debris, and the like, for instance, using an ultrafilter. The filter may be positioned in any suitable location in the dialysate flow path, for instance, between the directing circuit and the balancing circuit, e.g., as is shown in FIG. 3A, and/or the ultrafilter may be incorporated into the directing circuit or the balancing circuit. If an ultrafilter is used, it may be chosen to have a mesh or pore size chosen to prevent species such as these from through the filter. For instance, the mesh or pore size may be less than about 0.3 micrometers, less than about 0.2 micrometers, less than about 0.1 micrometers, or less than about 0.05 micrometers, etc. Those of ordinary skill in the art will be aware of filters such as ultrafilters, and in many cases, such filters may be readily obtained commercially.

In some cases, the ultrafilter may be operated such that waste from the filter (e.g., the retentate stream) is passed to a waste stream, such as waste line 39 in FIG. 6. In some cases, the amount of dialysate flowing into the retentate stream may be controlled. For instance, if the retentate is too cold (i.e., heater 72 is not working, or heater 72 is not heating the dialysate to a sufficient temperature, the entire dialysate stream (or at least a portion of the dialysate) may be diverted to waste line 39, and optionally, recycled to dialysate tank 169 using line 48. Flow from the filter may also be monitored for several reasons, e.g., using temperature sensors (e.g., sensors 251 and 252), conductivity sensors (for confirming dialysate concentration, e.g., sensor 253), or the like. An example of such sensors is discussed below; further non-limiting examples can be seen in U.S. patent application Ser. No. 12/038,474 entitled "Sensor Apparatus Systems, Devices and Methods," filed on Feb. 27, 2008, and incorporated herein by reference.

It should be noted that the ultrafilter and the dialyzer provide redundant screening methods for the removal of contaminants, infectious organisms, pathogens, pyrogens, debris, and the like, in this particular example (although in other cases, the ultrafilter may be absent). Accordingly, for contaminants to reach the patient from the dialysate, the contaminants must pass through both the ultrafilter and the dialyzer. Even in the event that one fails, the other may still be able to provide sterility and prevent contaminants from reaching the patient's blood.

Directing circuit 142 may also be able to route used dialysate coming from a balancing circuit to a drain, e.g., through waste line 39 to drain 31 in FIG. 6. The drain may be, for example, a municipal drain or a separate container for containing the waste (e.g., used dialysate) to be properly disposed of. In some cases, one or more check or "one-way" valves (e.g., check valves 215 and 216) may be used to control flow of waste from the directing circuit and from the system. Also, in certain instances, a blood leak sensor (e.g., sensor 258) may be used to determine if blood is leaking through the dialyzer into the dialysate flow path. In addition, a liquid sensor can be positioned in a collection pan at the bottom of the hemodialysis unit to indicate leakage of either blood or dialysate, or both, from any of the fluid circuits.

In addition, directing circuit 142 may receive water from a water supply 30, e.g., from a container of water such as a bag, and/or from a device able to produce water, e.g., a reverse osmosis device such as those that are commercially available. In some cases, as is known to those of ordinary skill in the art, the water entering the system is set at a certain purity, e.g., having ion concentrations below certain values. The water entering directing circuit 142 may be passed on to various locations, e.g., to a mixing circuit for producing fresh dialysate and/or to waste line 39. In some cases, as discussed below, valves to drain 31, various recycle lines are opened, and conduits 67 may be connected between directing circuit 142 and blood flow circuit 141, such that water is able to flow continuously around the system. If heater 72 is also activated, the water passing through the system will be continuously heated, e.g., to a temperature sufficient to disinfect the system. Such disinfection methods will be discussed in detail below.

A non-limiting example of a directing cassette is shown in FIGS. 41-45. Referring now to FIGS. 41A and 41B, the outer side of the top plate 900 of one embodiment of the cassette is shown. The top plate 900 includes one half of the pod pumps 820, 828. This half is the fluid/liquid half where the source fluid will flow through. The inlet and outlet pod pump fluid paths are shown. These fluid paths lead to their respective pod pumps 820, 828.

Figure 41A:
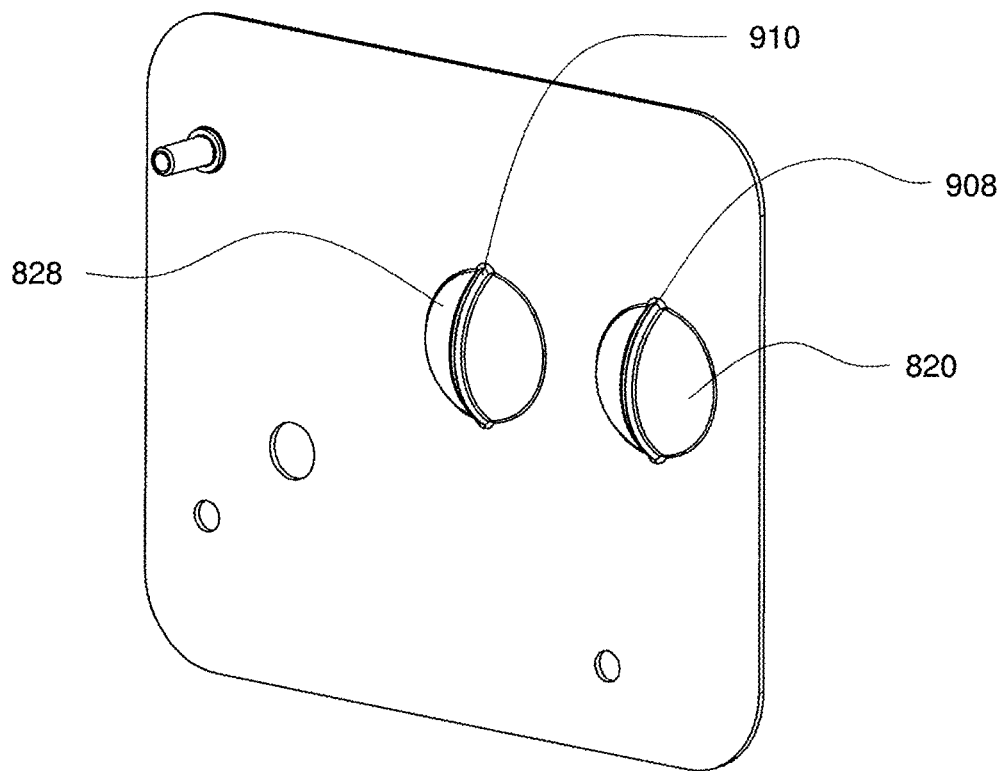
FIGS. 41A and 41B are isometric and front views of an exemplary embodiment of the outer top plate of an exemplary embodiment of a cassette.
Figure 41B:
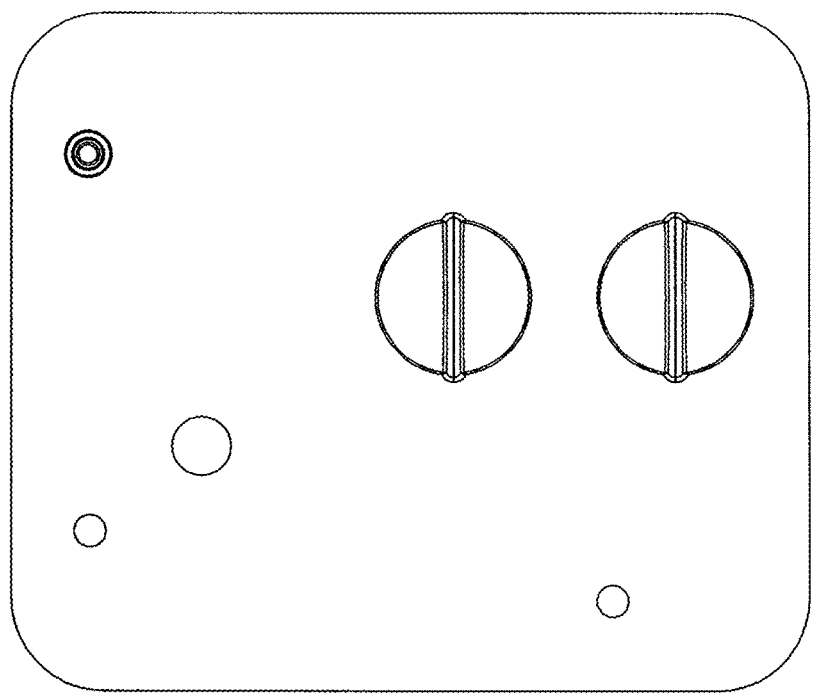
Figure 41C:
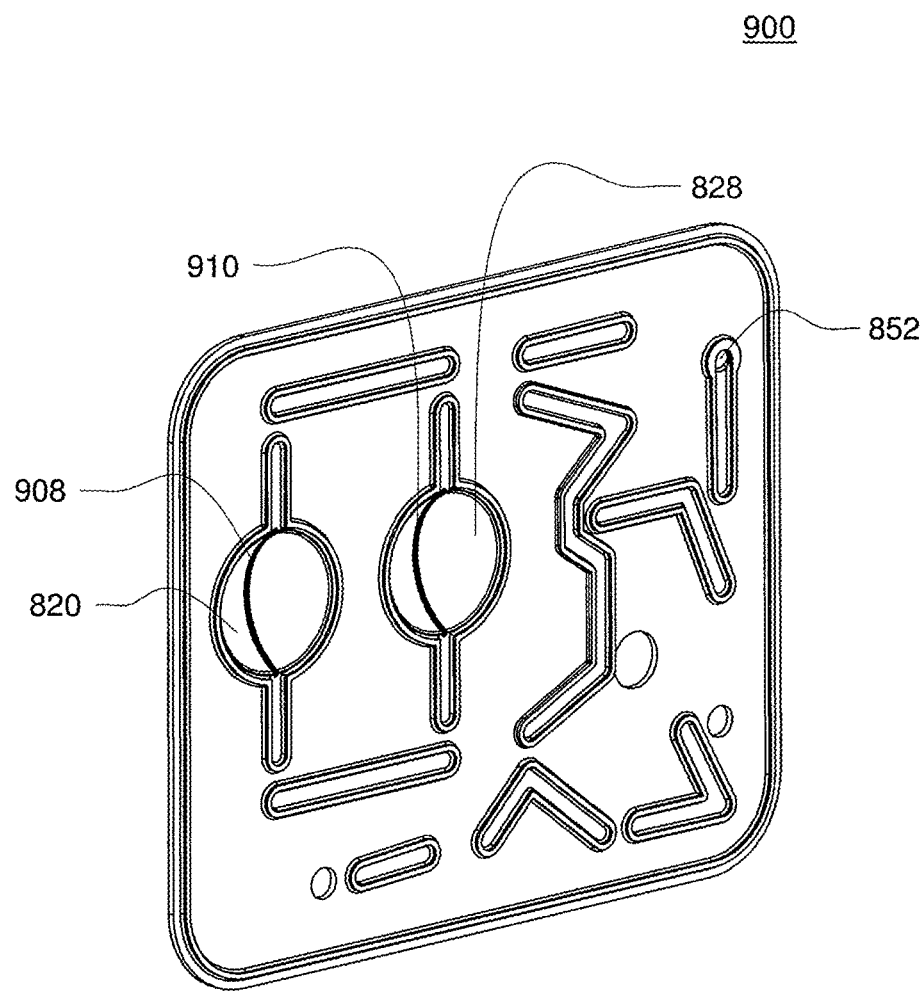
FIGS. 41C and 41D are isometric and front views of an exemplary embodiment of the inner top plate of a cassette.
Figure 41D:
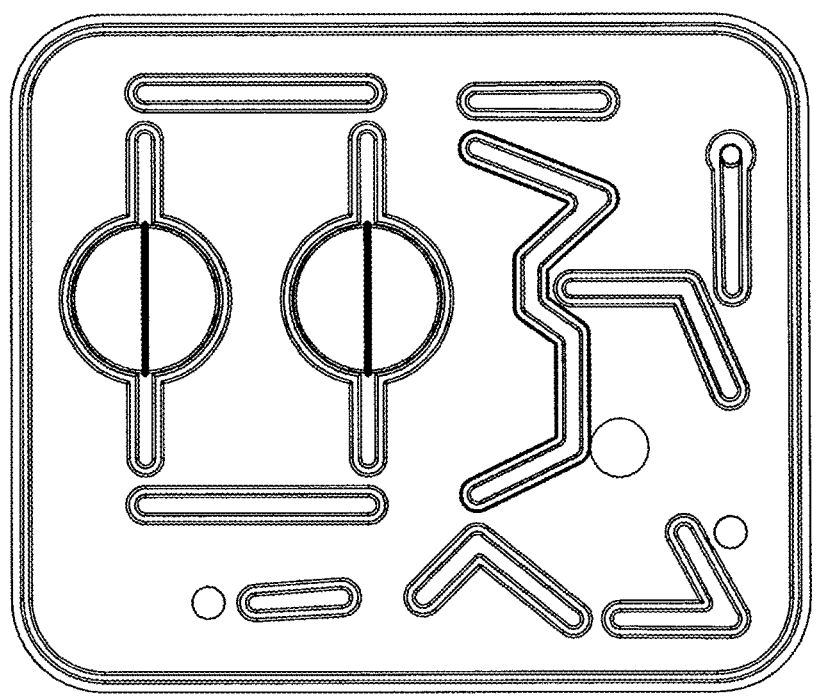
Figure 41E:
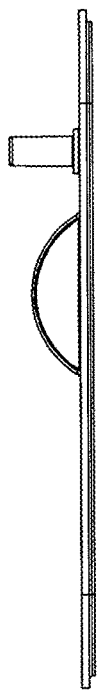
FIG. 41E is a side view of the top plate of an exemplary embodiment of a cassette.

The pod pumps 820, 828 can include a raised flow path 908, 910. The raised flow path 908, 910 allows for the fluid to continue to flow through the pod pumps 820, 828 after the diaphragm (not shown) reaches the end of stroke. Thus, the raised flow path 908, 910 minimizes the diaphragm causing air or fluid to be trapped in the pod pump 820, 828 or the diaphragm blocking the inlet or outlet of the pod pump 820, 828, which would inhibit flow. The raised flow path 908, 910 is shown in this embodiment having particular dimensions. In alternate embodiments, the raised flow path 908, 910 is larger or narrower, or in still other embodiments, the raised flow path 908, 910 can be any dimension as the purpose is to control fluid flow so as to achieve a desired flow rate or behavior of the fluid. Thus, the dimensions shown and described here with respect to the raised flow path, the pod pumps, the valves, or any other aspect are mere exemplary and alternate embodiments. Other embodiments are readily apparent. FIGS. 41C and 41D show the inner side of the top plate 900 of this embodiment of the cassette. FIG. 41E shows a side view of the top plate 900.

Figure 42A:
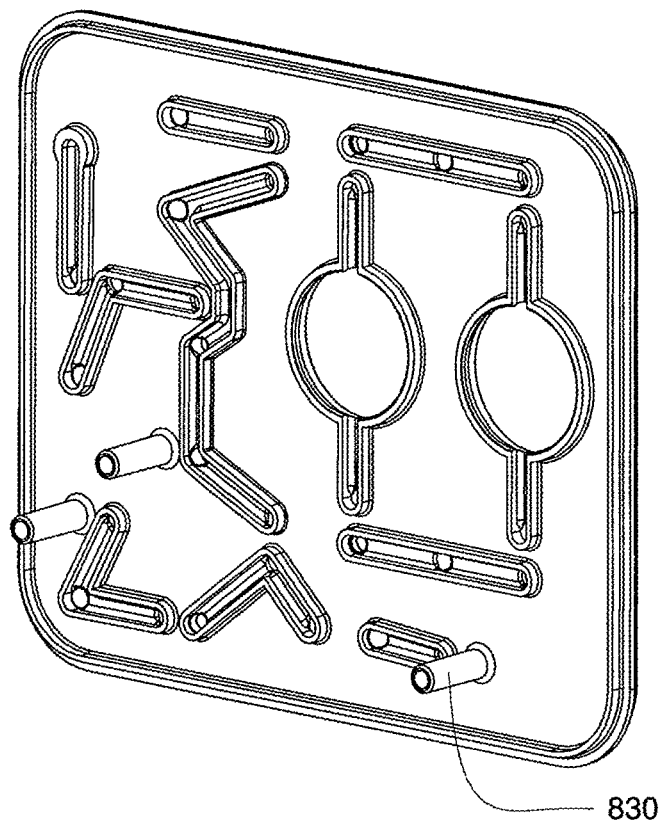
FIGS. 42A and 42B are isometric and front views of an exemplary embodiment of the liquid side of the midplate of a cassette.
Figure 42B:
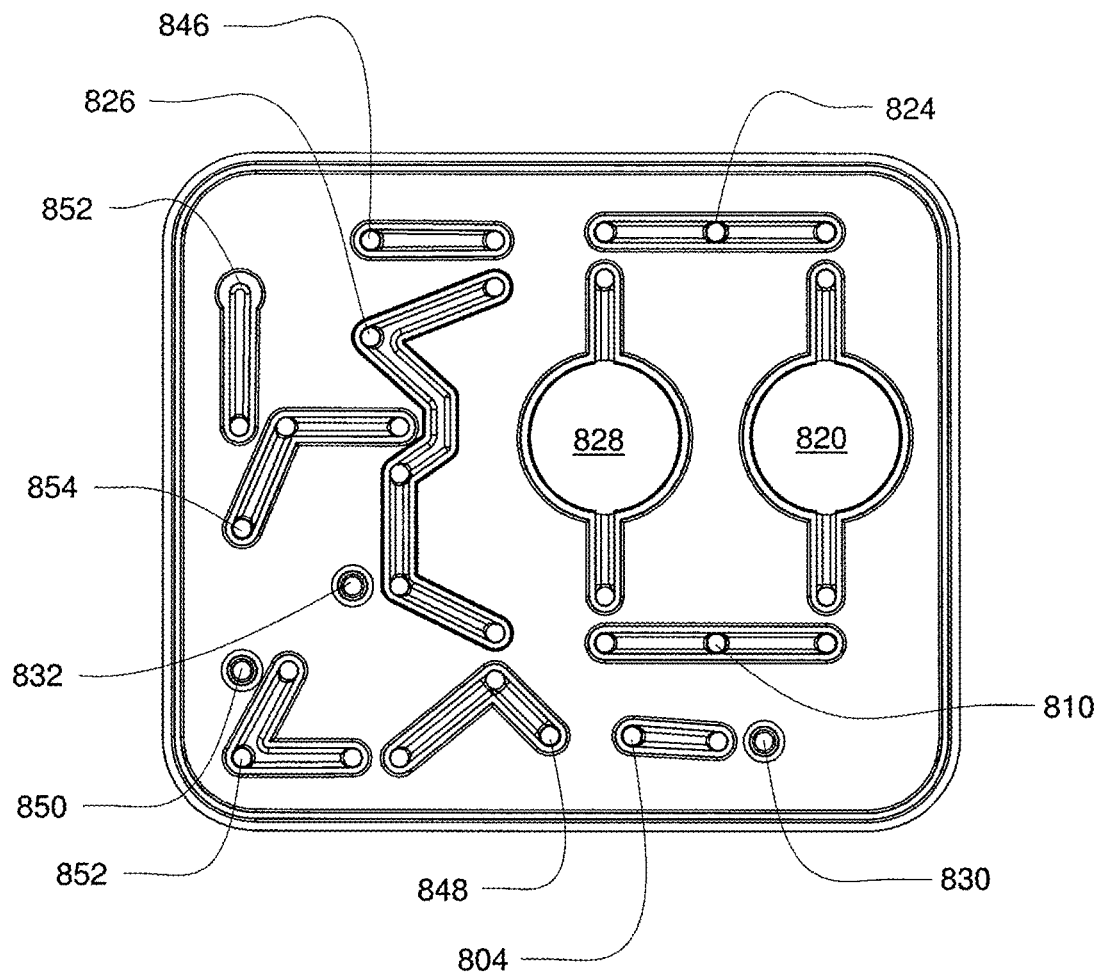

Referring now to FIGS. 42A and 42B, the fluid/liquid side of the midplate 1000 is shown. The areas complementary to the fluid paths on the inner top plate shown in FIGS. 41C and 41D are shown. These areas are slightly raised tracks that present a surface finish that is conducive to laser welding, which is one mode of manufacturing in this embodiment. Other modes of manufacturing the cassette are discussed above.

Figure 42C:
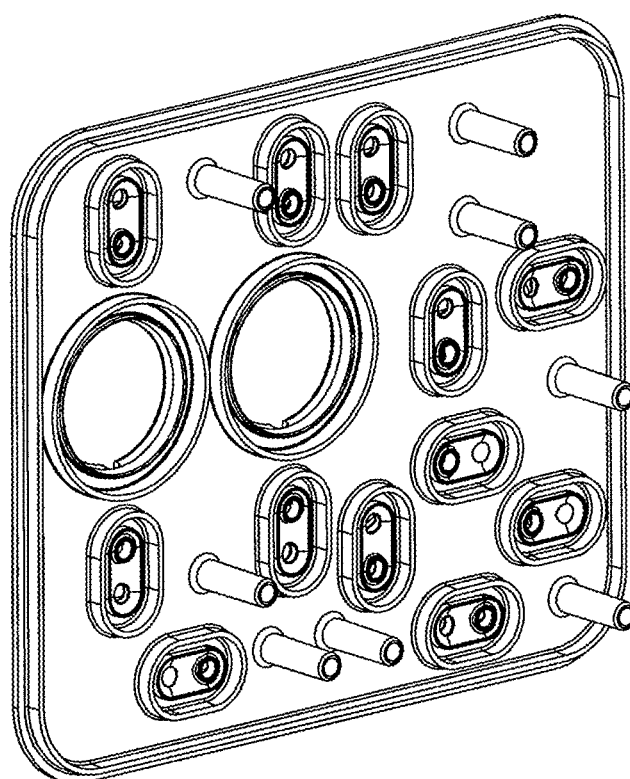
FIGS. 42C and 42D are isometric and front views of an exemplary embodiment of the air side of the midplate of a cassette.
Figure 42D:
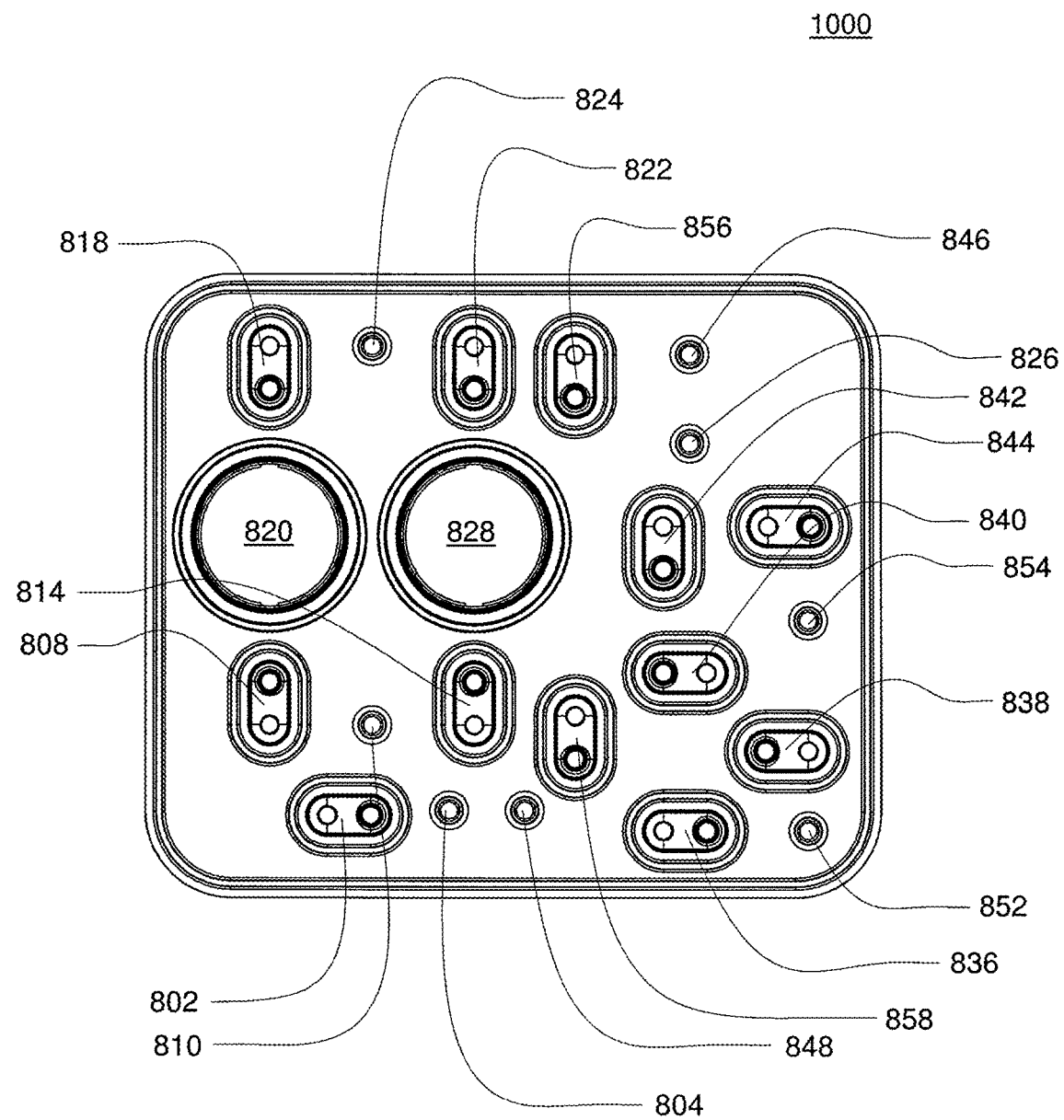
Figure 42E:
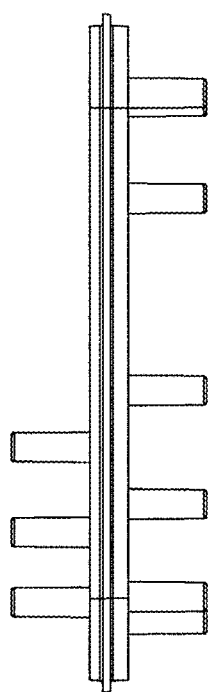
FIG. 42E is a side view of the midplate according to an exemplary embodiment of a cassette.
Figure 43A:
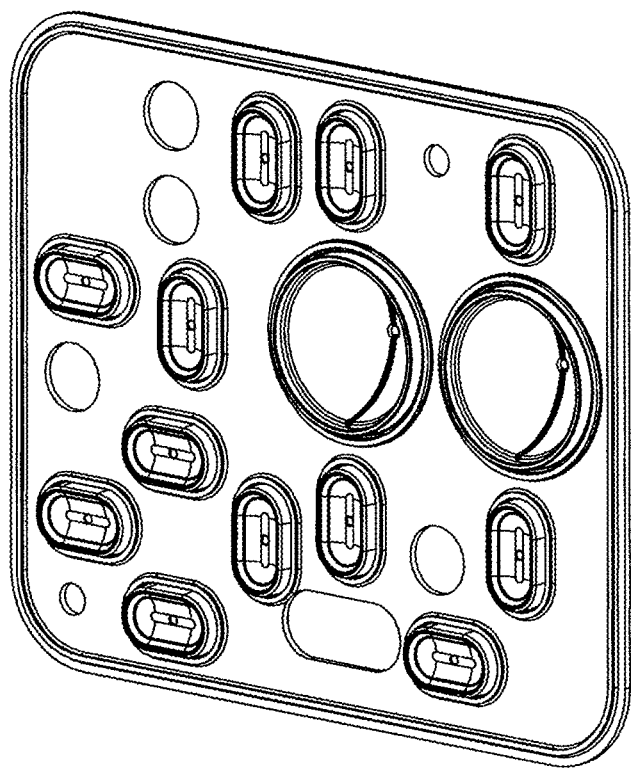
FIGS. 43A and 43B are isometric and front views of the inner side of a bottom plate according to an exemplary embodiment of a cassette.
Figure 43B:
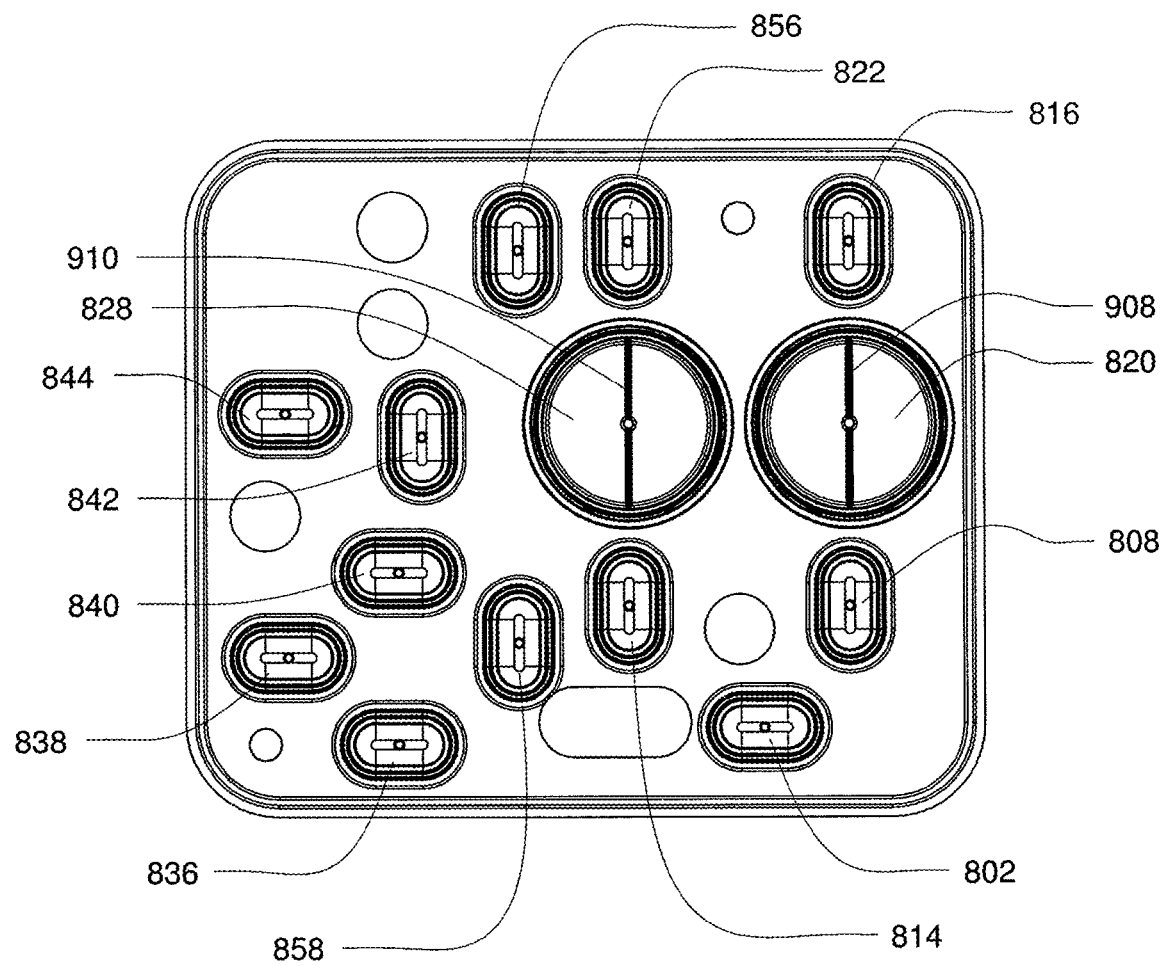
Figure 43C:
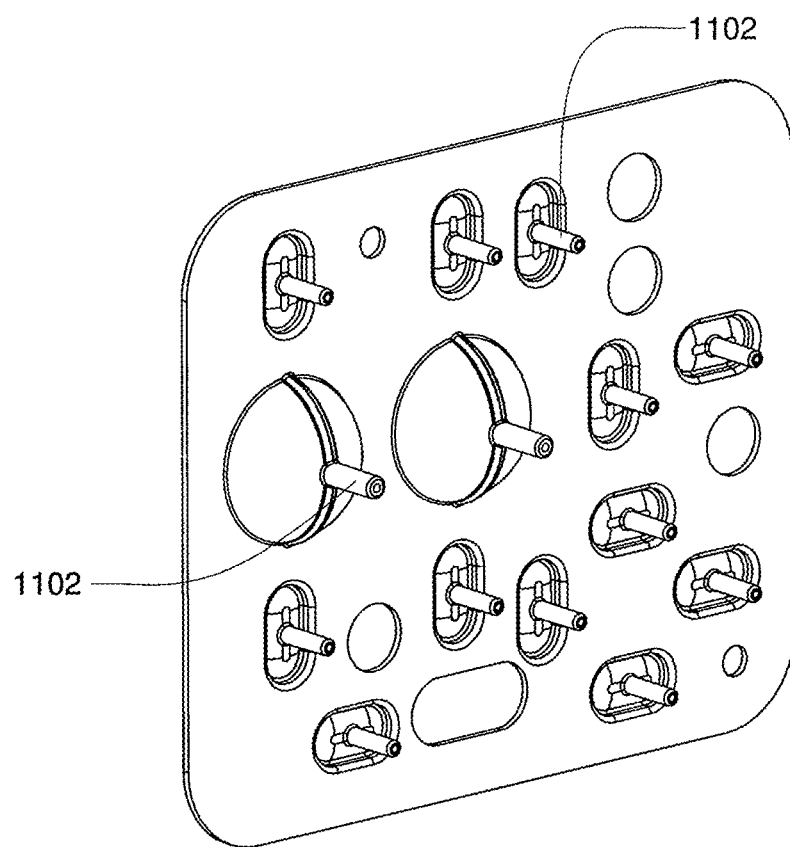
FIGS. 43C and 43D are isometric and front views of an exemplary embodiment of the outer side of the bottom plate of a cassette.
Figure 43D:
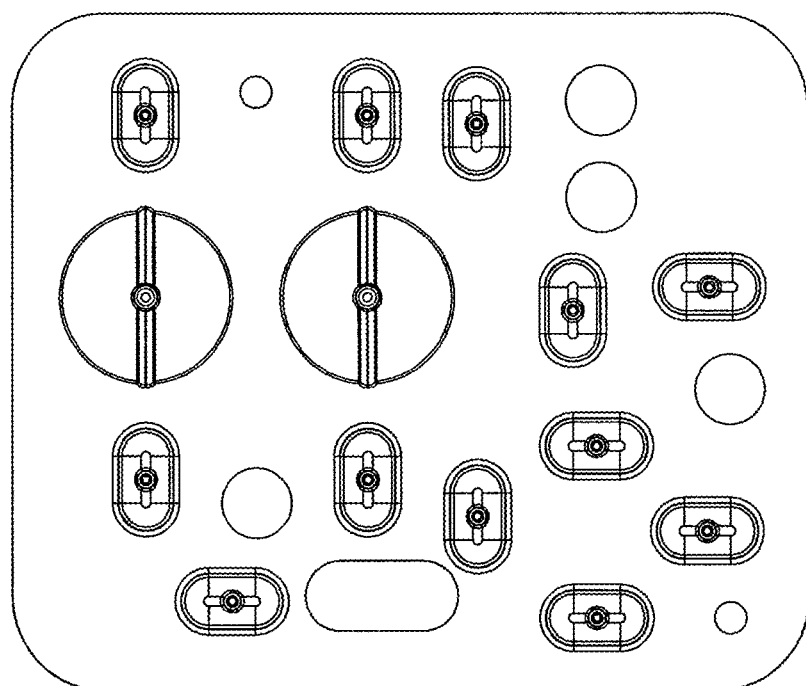
Figure 43E:
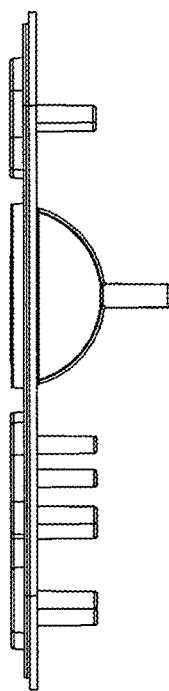
FIG. 43E is a side view of a bottom plate according to an exemplary embodiment of a cassette.

Referring next to FIGS. 42C and 42D, the air side, or side facing the bottom plate (not shown, shown in FIGS. 43A-43E) of the midplate 1000 is shown according to this embodiment. The air side of the valve holes 802, 808, 814, 816, 822, 836, 838, 840, 842, 844, 856 correspond to the holes in the fluid side of the midplate 1000 (shown in FIGS. 42A and 42B). As seen in FIGS. 44C and 44D, diaphragms 1220 complete pod pumps 820, 828 while diaphragms 1222 complete valves 802, 808, 814, 816, 822, 836, 838, 840, 842, 844, 856. The valves 802, 808, 814, 816, 822, 836, 838, 840, 842, 844, 856 are actuated pneumatically, and as the diaphragm is pulled away from the holes, liquid/fluid is allowed to flow. As the diaphragm is pushed toward the holes, fluid flow is inhibited. The fluid flow is directed by the opening and closing of the valves 802, 808, 814, 816, 822, 836, 838, 840, 842, 844, 856. Referring next to FIGS. 43A and 43B, the inner view of the bottom plate 1100 is shown. The inside view of the pod pumps 820, 828, and the valves 802, 808, 814, 816, 822, 836, 838, 840, 842, 844, 856 actuation/air chamber is shown. The pod pumps 820, 828, and the valves 802, 808, 814, 816, 822, 836, 838, 840, 842, 844, 856 are actuated by a pneumatic air source. Referring now to FIGS. 43C and 43D, the outer side of the bottom plate 1100 is shown. The source of air is attached to this side of the cassette. In one embodiment, tubes connect to the tubes on the valves and pumps 1102. In some embodiments, the valves are ganged, and more than one valve is actuated by the same air line.

Figure 44A:
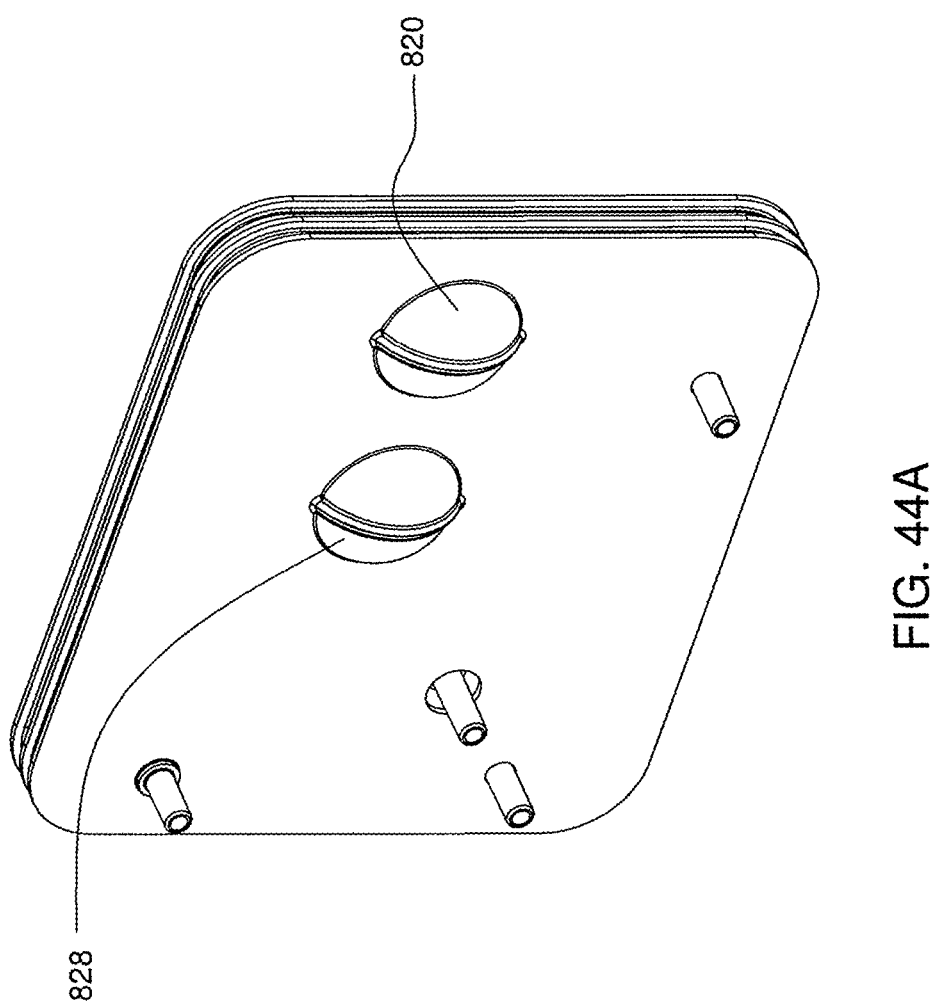
FIG. 44A is a top view of an assembled exemplary embodiment of a cassette.
Figure 44B:
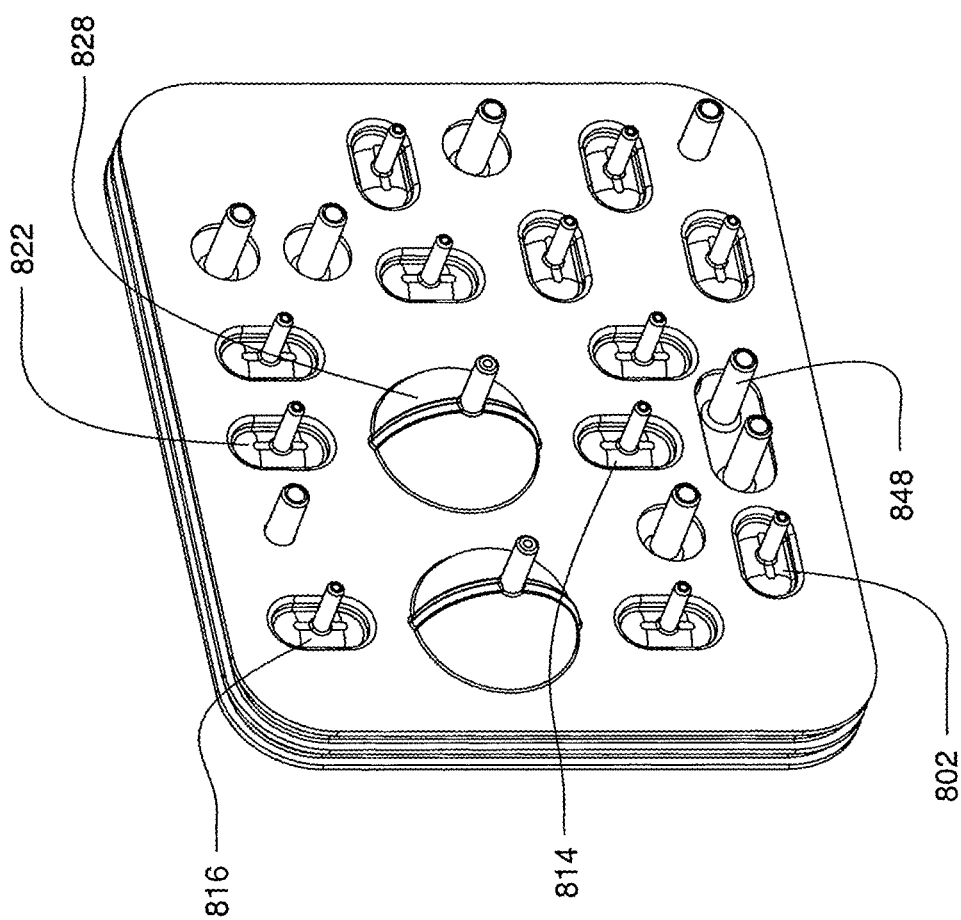
FIG. 44B is a bottom view of an assembled exemplary embodiment of a cassette.
Figure 44C:
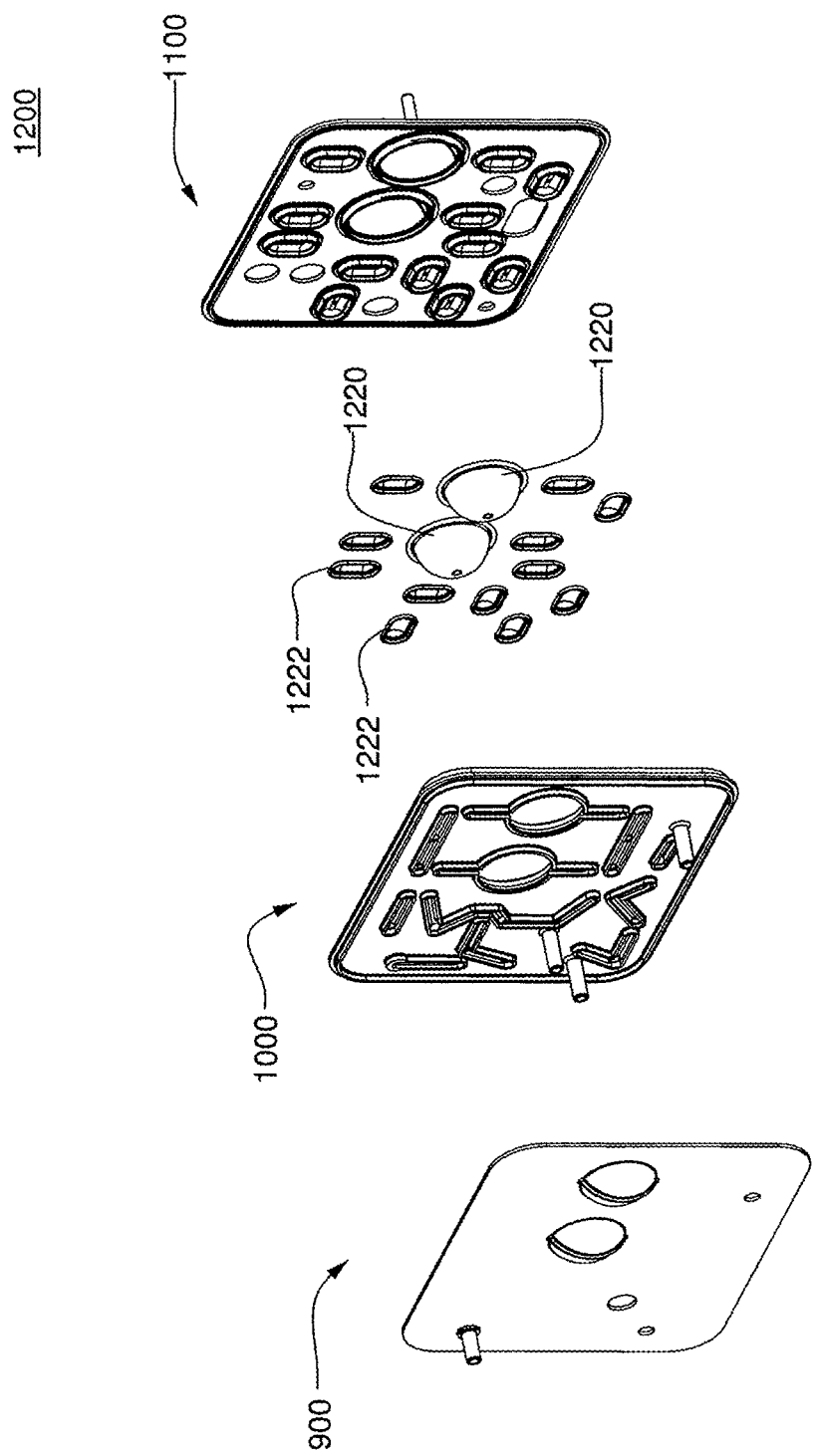
FIG. 44C is an exploded view of an assembled exemplary embodiment of a cassette.
Figure 44D:
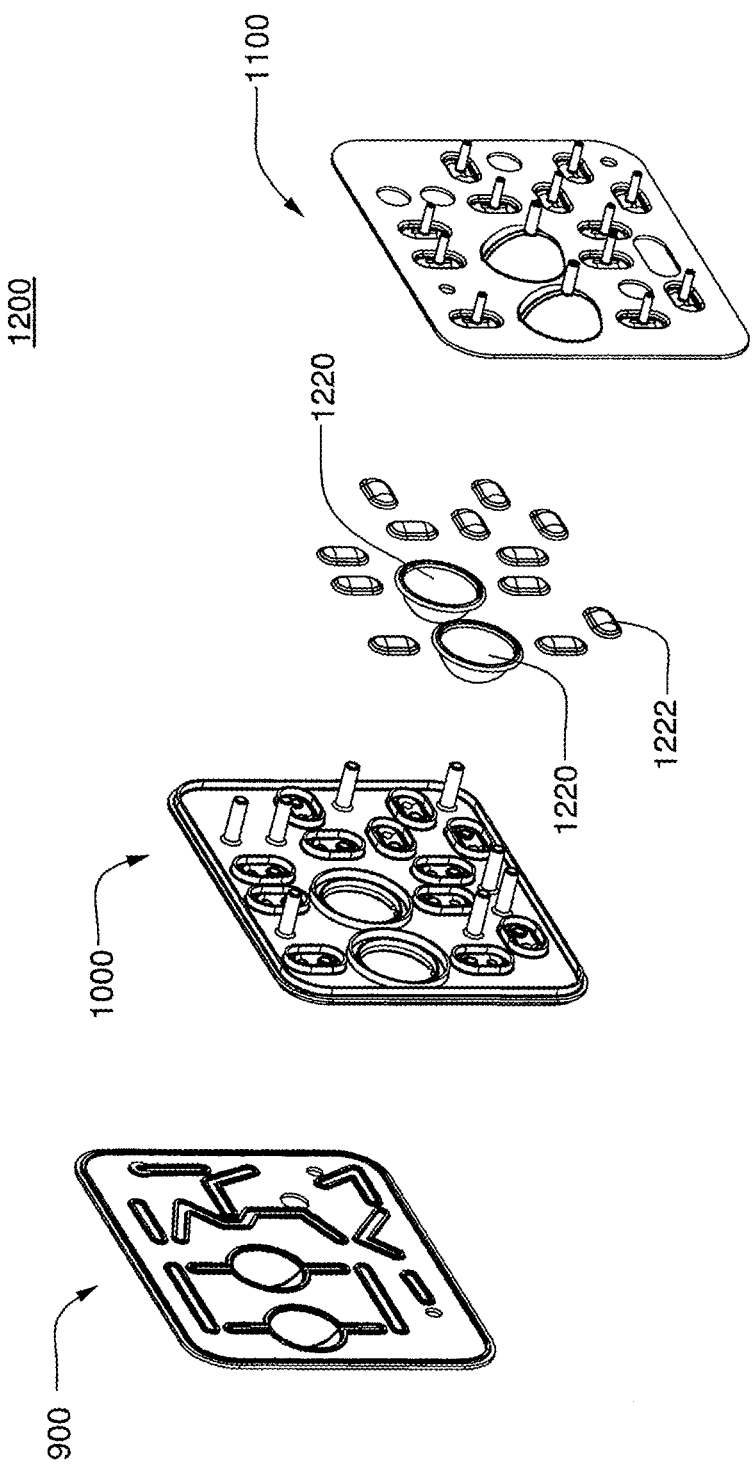
FIG. 44D is an exploded view of an assembled exemplary embodiment of a cassette.

Referring now to FIGS. 44A and 44B, an assembled cassette 1200 is shown. An exploded view of the assembled cassette 1200 shown in FIGS. 44A and 44B is shown in FIGS. 12C and 12D. In these views, the embodiment of the pod pump diaphragms 1220 is shown. The gasket of the diaphragm provides a seal between the liquid chamber (in the top plate 900) and the air/actuation chamber (in the bottom plate 1100). In some embodiment, texture on the dome of the diaphragms 1220 provide, amongst other features, additional space for air and liquid to escape the chamber at the end of stroke. In alternate embodiments of the cassette, the diaphragms may include a double gasket. The double gasket feature would be preferred in embodiments where both sides of the pod pump include liquid or in applications where sealing both chambers' sides is desired. In these embodiments, a rim complementary to the gasket or other feature (not shown) would be added to the inner bottom plate 1100 for the gasket to seal the pod pump chamber in the bottom plate 1100.

Figure 45:
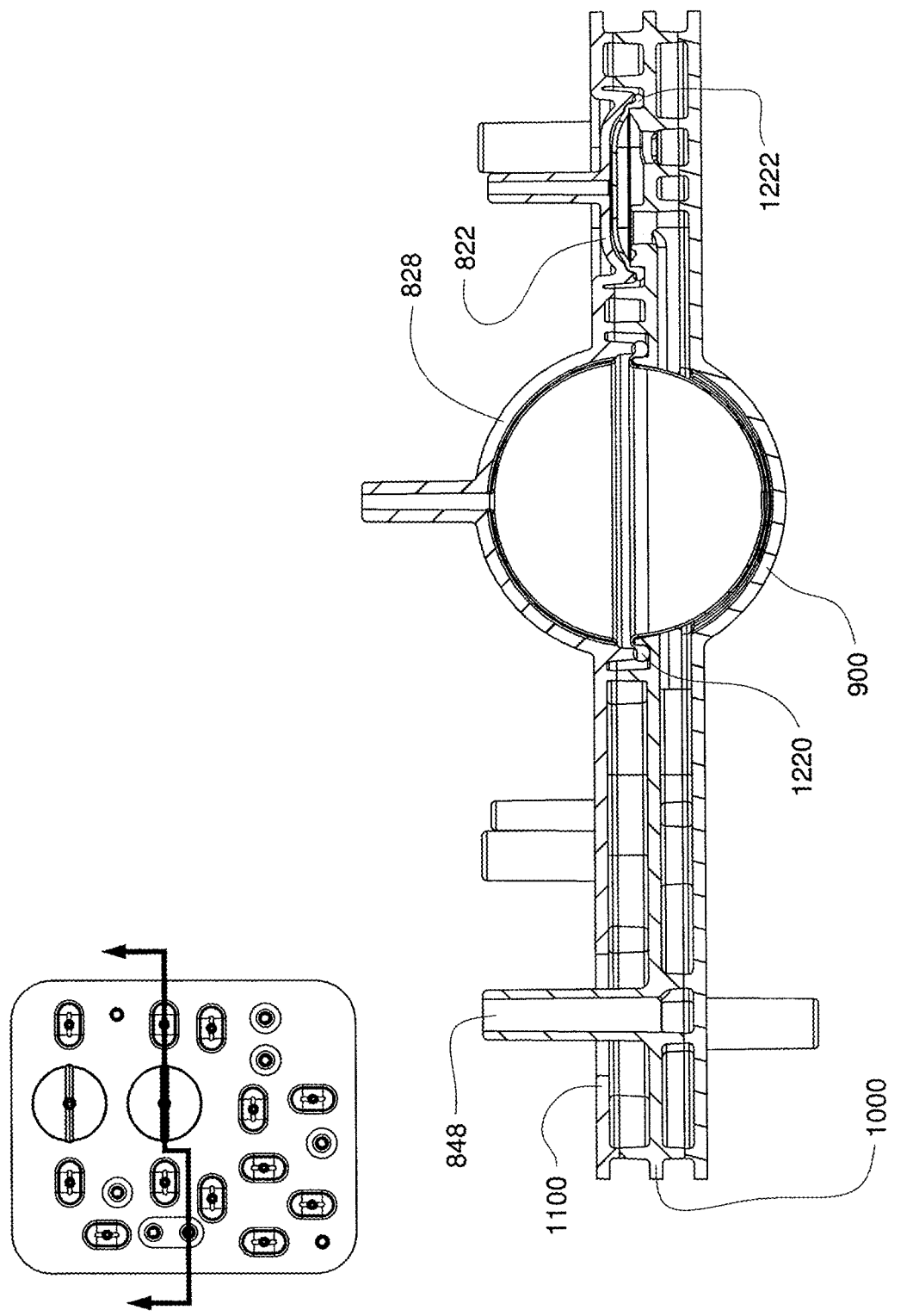
FIG. 45 shows a cross sectional view of an exemplary embodiment of an assembled cassette.

Referring now to FIG. 45, a cross sectional view of the pod pumps 828 in the cassette is shown. The details of the attachment of the diaphragm 1220 can be seen in this view. Again, in this embodiment, the diaphragm 1220 gasket is pinched by the midplate 1000 and the bottom plate 1100. A rim on the midplate 1000 provides a feature for the gasket to seal the pod pump 828 chamber located in the top plate 900.

Referring next to FIG. 45, this cross sectional view shows the valves 834, 836 in the assembled cassette. The diaphragms 1220 are shown assembled and are held in place, in this embodiment, by being sandwiched between the midplate 1000 and the bottom plate 1100. Still referring to FIG. 45, this cross sectional view also shows a valve 822 in the assembled cassette. The diaphragm 1222 is shown held in place by being sandwiched between the midplate 1000 and the bottom plate 1100.

In one set of embodiments, dialysate may be prepared separately and brought to the system for use in the directing circuit. However, in some cases, dialysate may be prepared in a mixing circuit. The mixing circuit may be run to produce dialysate at any suitable time. For instance, dialysate may be produced during dialysis of a patient, and/or prior to dialysis (the dialysate may be stored, for instance, in a dialysate tank. Within the mixing circuit, water (e.g., from a water supply, optionally delivered to the mixing circuit by a directing circuit) may be mixed with various dialysate ingredients to form the dialysate. Those of ordinary skill in the art will know of suitable dialysate ingredients, for instance, sodium bicarbonate, sodium chloride, and/or acid, as previously discussed. The dialysate may be constituted on an as-needed basis, so that large quantities do not need to be stored, although some may be stored within a dialysate tank, in certain cases.

Figure 7A:
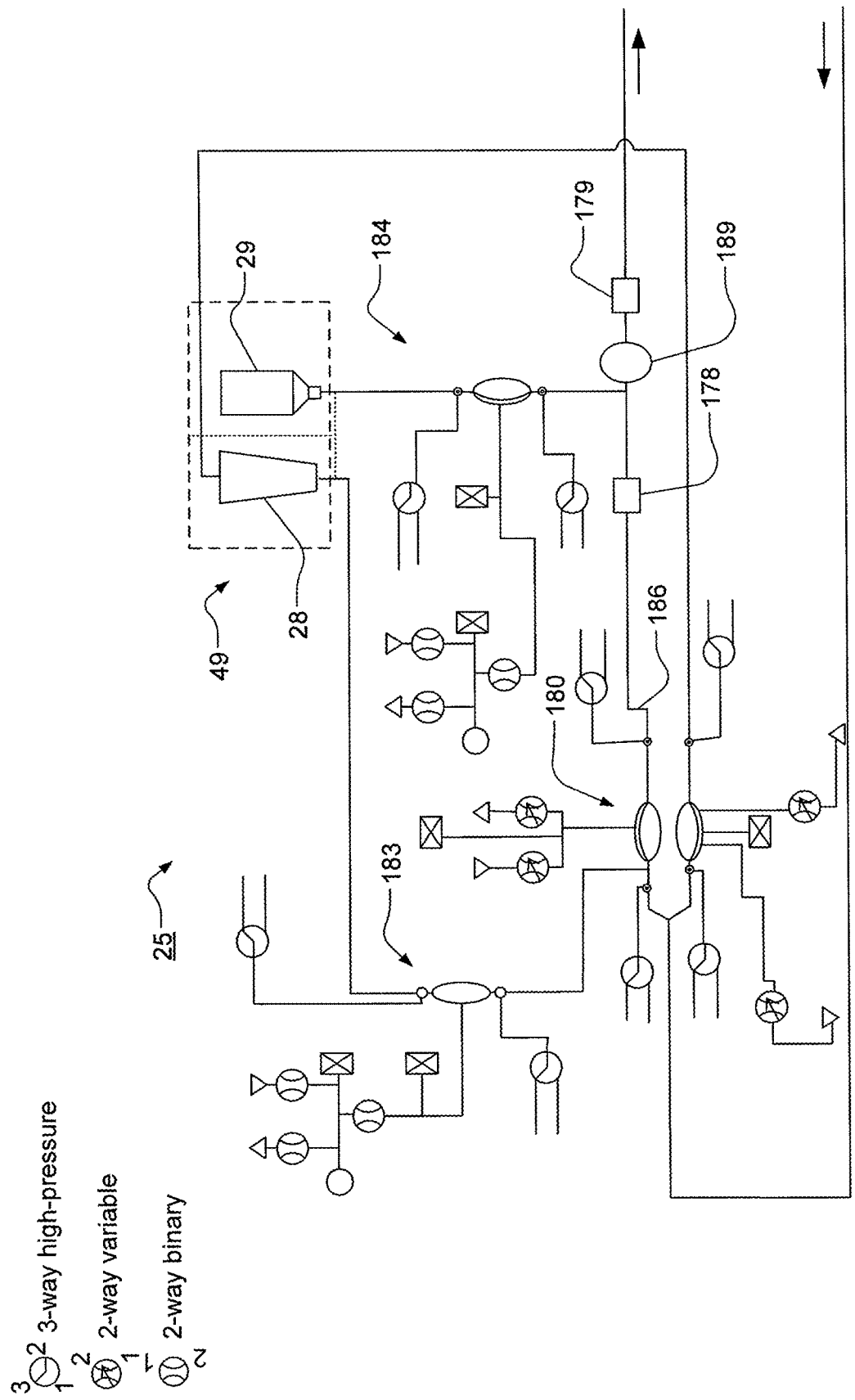
FIGS. 7A-7B are schematic representations of mixing circuits that may be used in a hemodialysis system.

FIG. 7A illustrates a non-limiting example of a mixing circuit, which may be implemented on a cassette in some cases. In FIG. 7A, water from a directing circuit flows into mixing circuit 25 due to action of pump 180. In some cases, a portion of the water is directed to ingredients 49, e.g., for use in transporting the ingredients through the mixing circuit. As shown in FIG. 7A, water is delivered to bicarbonate source 28 (which may also contain sodium chloride in some cases). The sodium chloride and/or the sodium bicarbonate may be provided, in some cases, in a powdered or granular form, which is moved through the action of water. Bicarbonate from bicarbonate source 28 is delivered via bicarbonate pump 183 to a mixing line 186, to which water from the directing circuit also flows. Acid from acid source 29 (which may be in a liquid form) is also pumped via acid pump 184 to mixing line 186. The ingredients (water, bicarbonate, acid, NaCl, etc.) are mixed in mixing chamber 189 to produce dialysate, which then flows out of mixing circuit 25. Conductivity sensors 178 and 179 are positioned along mixing line 186 to ensure that as each ingredient is added to the mixing line, it is added at proper concentrations.

In one set of embodiments, pump 180 comprises one or more pod pumps, similar to those described above. The pod pumps may include a rigid chamber with a flexible diaphragm dividing each chamber into a fluid compartment and control compartment. The control compartment may be connected to a control fluid source, such as an air source. Non-limiting examples of pumps that can be used as pod pumps are described in U.S. Provisional Patent Application Ser. No. 60/792,073, filed Apr. 14, 2006, entitled "Extracorporeal Thermal Therapy Systems and Methods"; or in U.S. patent application Ser. No. 11/787,212, filed Apr. 13, 2007, entitled "Fluid Pumping Systems, Devices and Methods," each incorporated herein by reference. Similarly, in some cases, pumps 183 and/or 184 may each be pod pumps. Additional details of pod pumps are discussed below.

In some cases, one or more of the pumps may have pressure sensors to monitor the pressure in the pump. This pressure sensor may be used to ensure that a pump compartment is filling and delivering completely. For example, ensuring that the pump delivers a full stroke of fluid may be accomplished by (i) filling the compartment, (ii) closing both fluid valves, (iii) applying pressure to the compartment by opening the valve between the positive pneumatic reservoir and the compartment, (iv) closing this positive pressure valve, leaving pressurized air in the path between the valve and the compartment, (v) opening the fluid valve so the fluid can leave the pump compartment, and (vi) monitoring the pressure drop in the compartment as the fluid leaves. The pressure drop corresponding to a full stroke may be consistent, and may depend on the initial pressure, the hold-up volume between the valve and the compartment, and/or the stroke volume. However, in other embodiments of any of the pod pumps described herein, a reference volume compartment may be used, where the volume is determined through pressure and volume data.

The volumes delivered by the water pump and/or the other pumps may be directly related to the conductivity measurements, so the volumetric measurements may be used as a cross-check on the composition of the dialysate that is produced. This may ensure that the dialysate composition remains safe even if a conductivity measurement becomes inaccurate during a therapy.

Figure 7B:
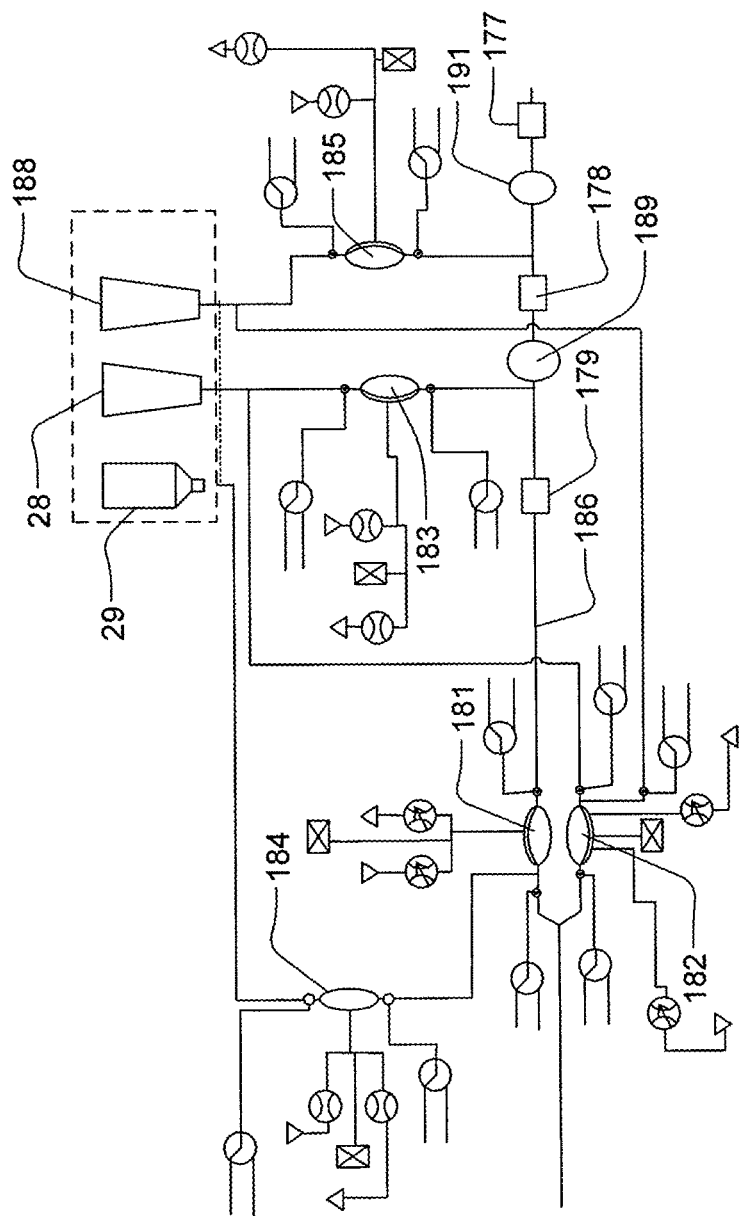

FIG. 7B is a schematic diagram showing another example of a mixing circuit, implementable on a cassette in certain cases. Mixing circuit 25 in this figure includes a pod pump 181 for pumping water from a supply along a line 186 into which the various ingredients for making the dialysate are introduced into the water. Another pump 182 pumps water from a water supply into source 28 holding the sodium bicarbonate (e.g., a container) and/or into source 188 holding the sodium chloride. A third pump 183 introduces the dissolved bicarbonate into mixing line 186 (mixed in mixing chamber 189), while a fourth pump 185 introduces dissolved sodium chloride into line 186 (mixed in mixing chamber 191). A fifth pump 184 introduces acid into the water before it passes through the first pump 181. Mixing is monitored using conductivity sensors 178, 179, and 177, which each measure the conductivity after a specific ingredient has been added to mixing line 186, to ensure that the proper amount and/or concentration of the ingredient has been added. An example of such sensors is discussed below; further non-limiting examples can be seen in U.S. patent application Ser. No. 12/038,474 entitled "Sensor Apparatus Systems, Devices and Methods," filed on Feb. 27, 2008, and incorporated herein by reference.

Figure 3B:
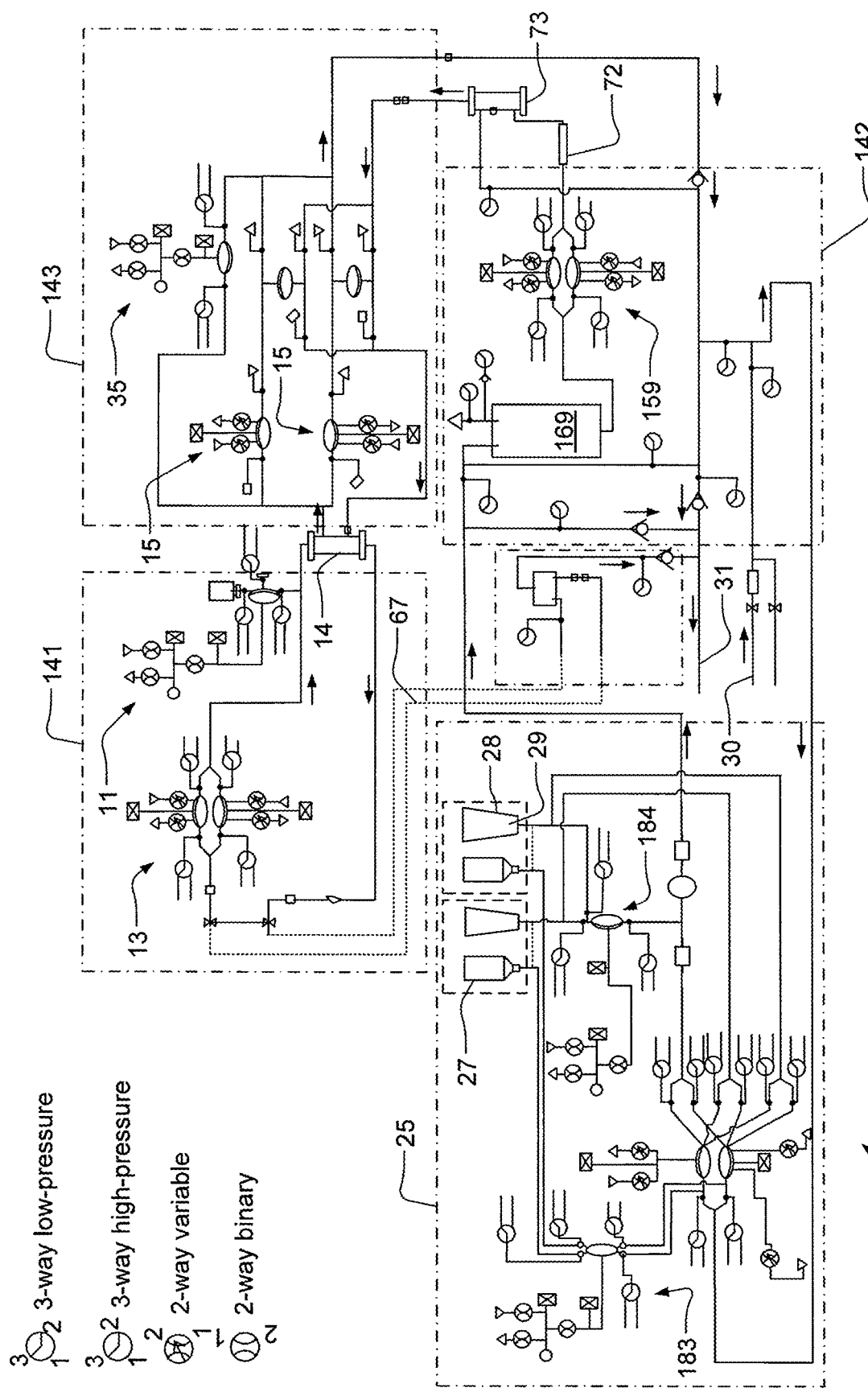

Referring now to FIG. 3B, in this embodiment, mixing circuit 25 constitutes dialysate using two sources: an acid concentrate source 27 and a combined sodium bicarbonate (NaHCO$_3$) and sodium chloride (NaCl) source. As shown in the embodiment shown in FIG. 3B, in some embodiments, the dialysate constituting system 25 may include multiples of each source. In embodiments of the method where the system is run continuously, the redundant dialysate sources allow for continuous function of the system, as one set of sources is depleted, the system uses the redundant source and the first set of sources is replaced. This process is repeated as necessary, e.g., until the system is shut down.

Figure 37:
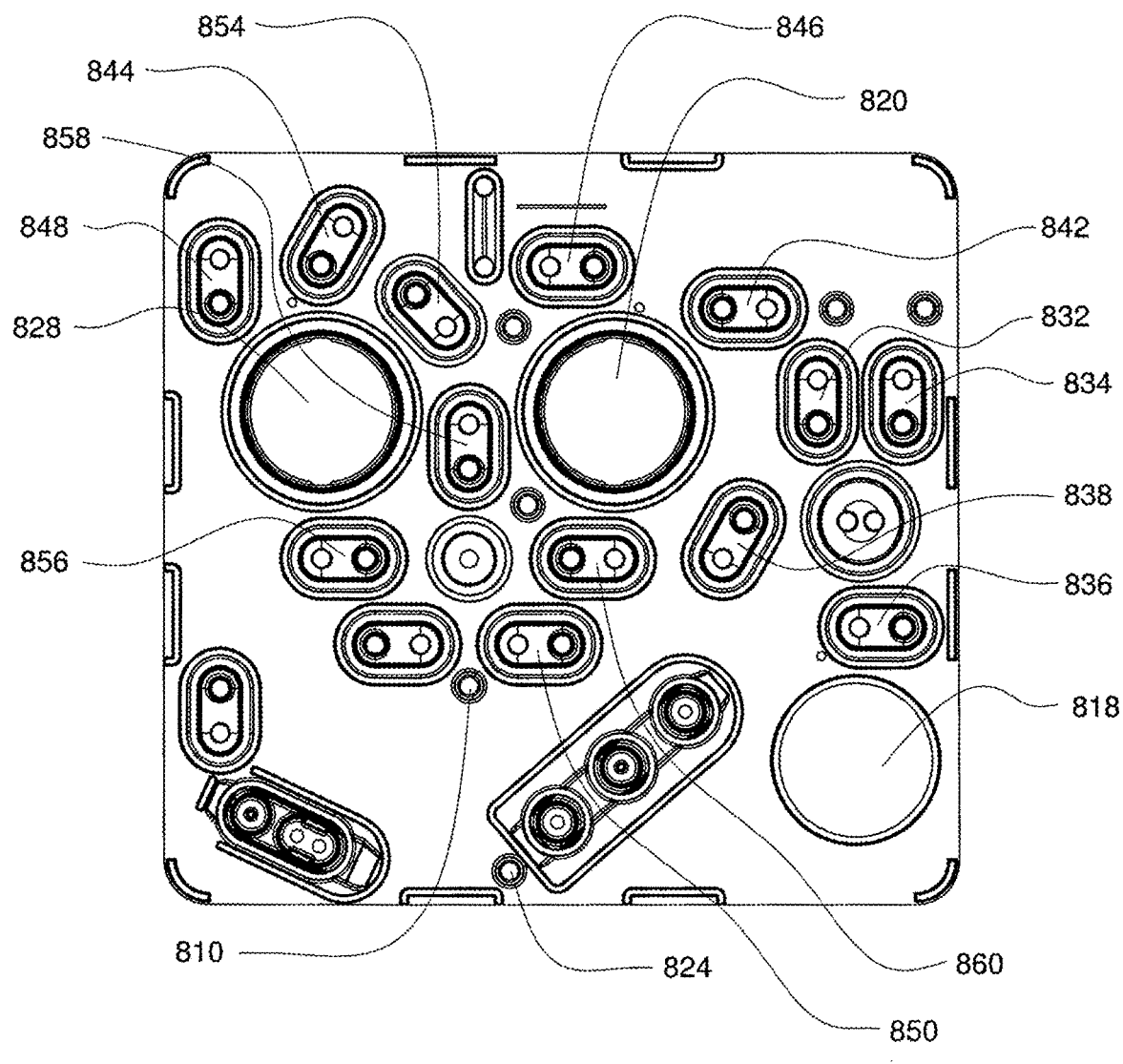
FIG. 37 is an isometric front view of an exemplary embodiment of the actuation side of the midplate of a cassette with the valves indicated corresponding to FIG. 36.

A non-limiting example of a balancing cassette is shown in FIGS. 34-36. In the exemplary fluid flow-path cassette shown in FIGS. 37, valves are open individually. In this exemplary embodiment, the valves are pneumatically open. Also, in this embodiment, the fluid valves are volcano valves, as described in more detail elsewhere in this specification.

Figure 38A:
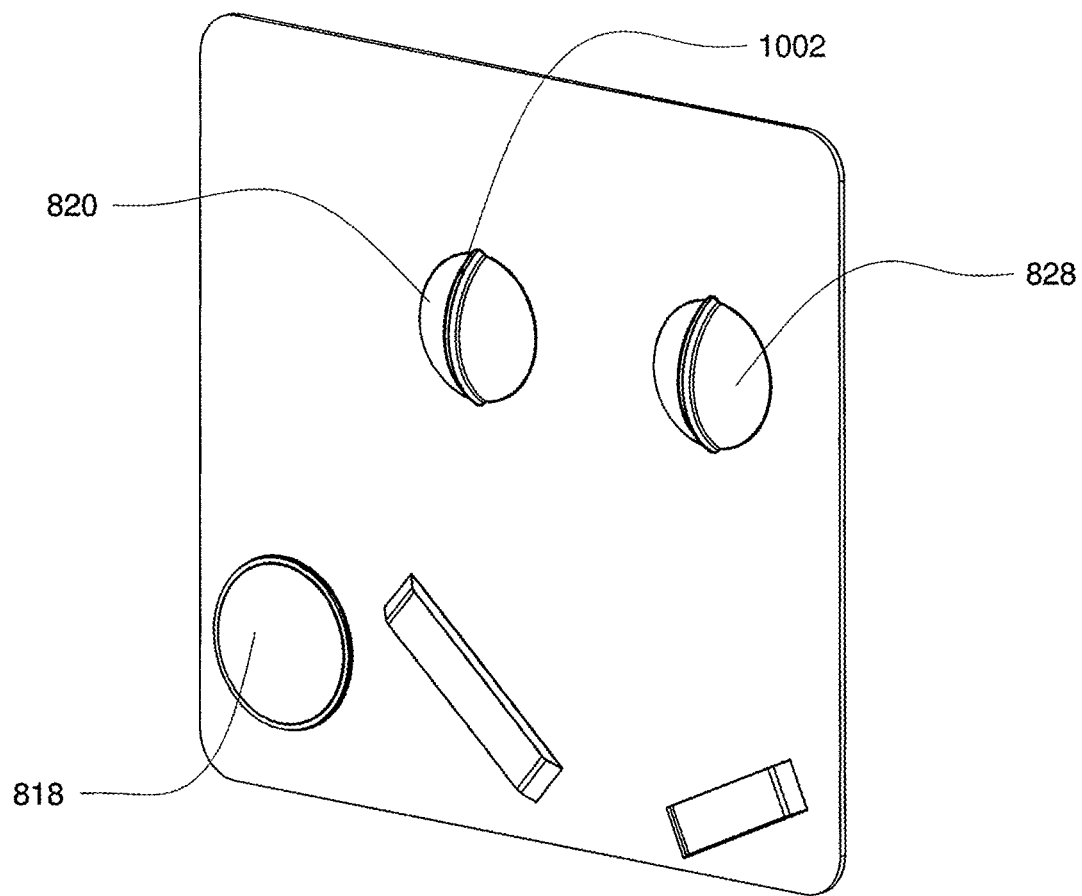
FIG. 38A is a view of an exemplary embodiment of the outer top plate of a cassette.
Figure 38B:
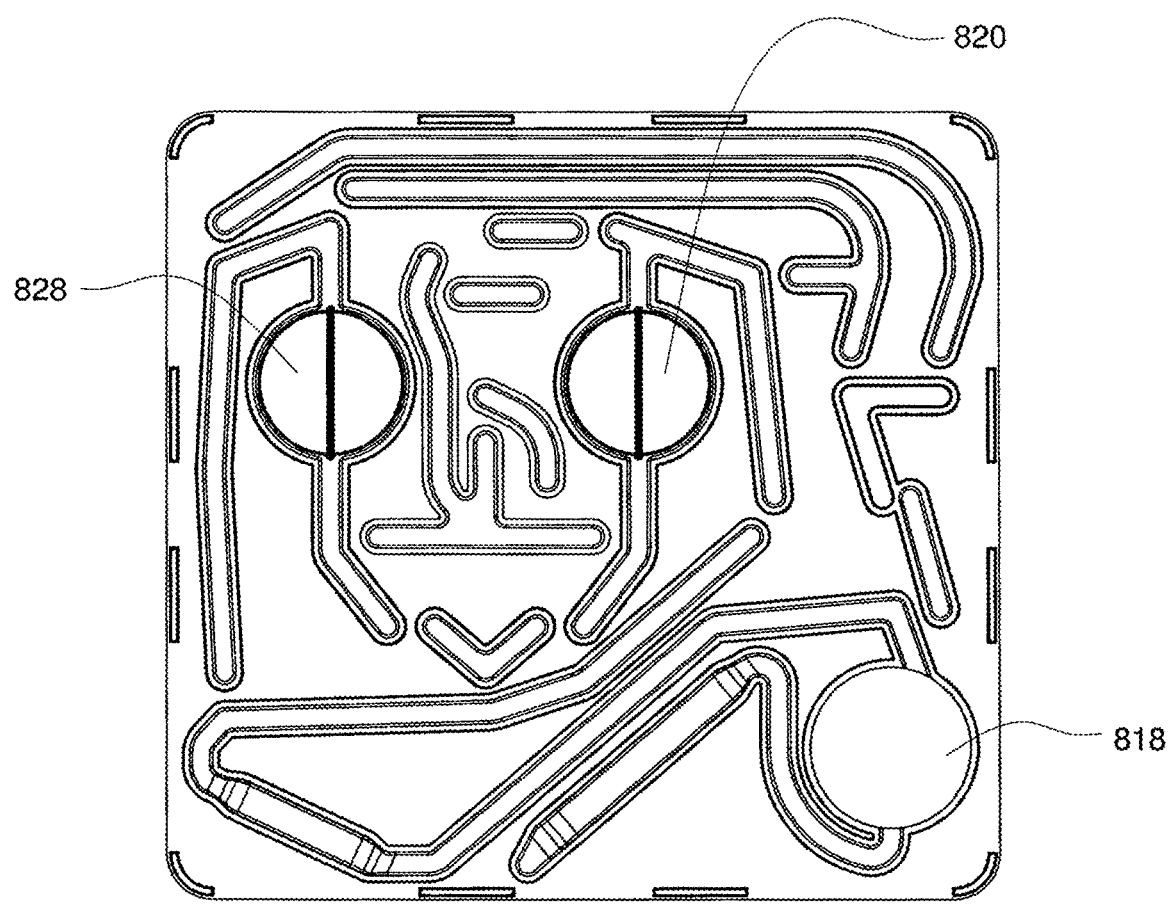
FIG. 38B is a view of an exemplary embodiment of the inner top plate of a cassette.
Figure 38C:
FIG. 38C is a side view of an exemplary embodiment of the top plate of a cassette.

Referring now to FIGS. 38A-38B, the top plate 1100 of one exemplary embodiment of the cassette is shown. In this exemplary embodiment, the pod pumps 820, 828 and the mixing chambers 818 on the top plate 1100, are formed in a similar fashion. In this exemplary embodiment, the pod pumps 820, 828 and mixing chamber 818, when assembled with the bottom plate, have a total volume of capacity of 38 ml. However, in other embodiments, the mixing chamber may have any size volume desired.

Referring now to FIGS. 38B, the bottom view of the top plate 1100 is shown. The fluid paths are shown in this view. These fluid paths correspond to the fluid paths shown in FIGS. 39A-39B in the midplate 1200. The top plate 1100 and the top of the midplate 1200 form the liquid or fluid side of the cassette for the pod pumps 820, 828 and for one side of the mixing chamber 818. Thus, most of the liquid flow paths are on the top 1100 and midplates 1200. Referring to FIG. 39B, the first fluid inlet 810 and the first fluid outlet 824 are shown.

Still referring to FIGS. 38A and 38B, the pod pumps 820, 828 include a groove 1002 (in alternate embodiments, this is a groove). The groove 1002 is shown having a particular size and shape, however, in other embodiments, the size and shape of the groove 1002 may be any size or shape desirable. The size and shape shown in FIGS. 38A and 38B is one exemplary embodiment. In all embodiments of the groove 1002, the groove 1002 forms a path between the fluid inlet side and the fluid outlet side of the pod pumps 820, 828. In alternate embodiments, the groove 1002 is a groove in the inner pumping chamber wall of the pod pump.

The groove 1002 provides a fluid path whereby when the diaphragm is at the end-of-stroke there is still a fluid path between the inlet and outlet such that the pockets of fluid or air do not get trapped in the pod pump. The groove 1002 is included in both the liquid/fluid and air/actuation sides of the pod pumps 820, 828. In some embodiments, the groove 1002 may also be included in the mixing chamber 818 (see FIGS. 40A-40B with respect to the actuation/air side of the pod pumps 820, 828 and the opposite side of the mixing chamber 818. In alternate embodiments, the groove 1002 is either not included or on only one side of the pod pumps 820, 828.

In an alternate embodiment of the cassette, the liquid/fluid side of the pod pumps 820, 828 may include a feature (not shown) whereby the inlet and outlet flow paths are continuous and a rigid outer ring (not shown) is molded about the circumference of the pumping chamber is also continuous. This feature allows for the seal, formed with the diaphragm (not shown) to be maintained. Referring to FIG. 38E, the side view of an exemplary embodiment of the top plate 1100 is shown.

Figure 39A:
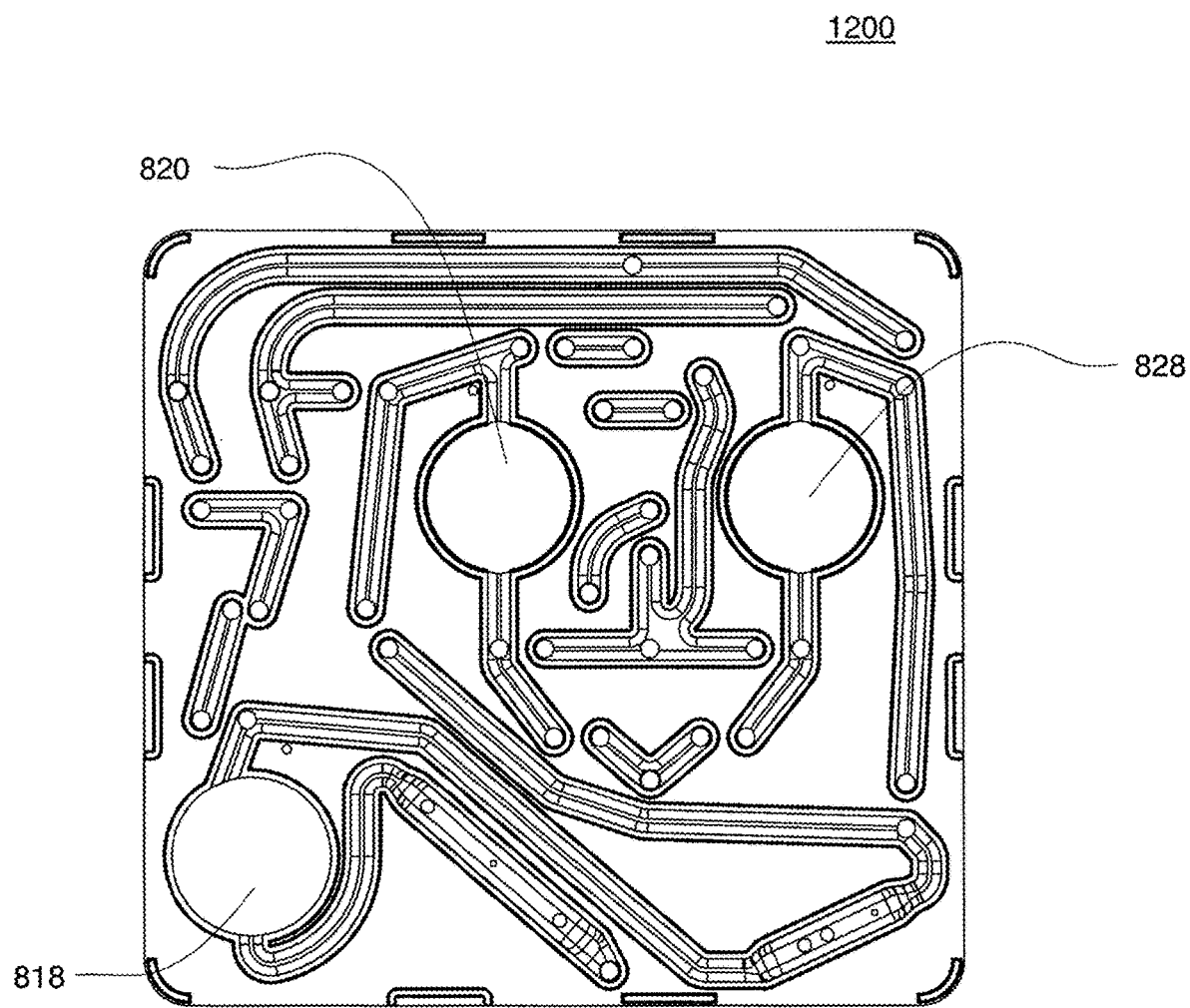
FIG. 39A is a view of an exemplary embodiment of the fluid side of the midplate of a cassette.
Figure 39B:
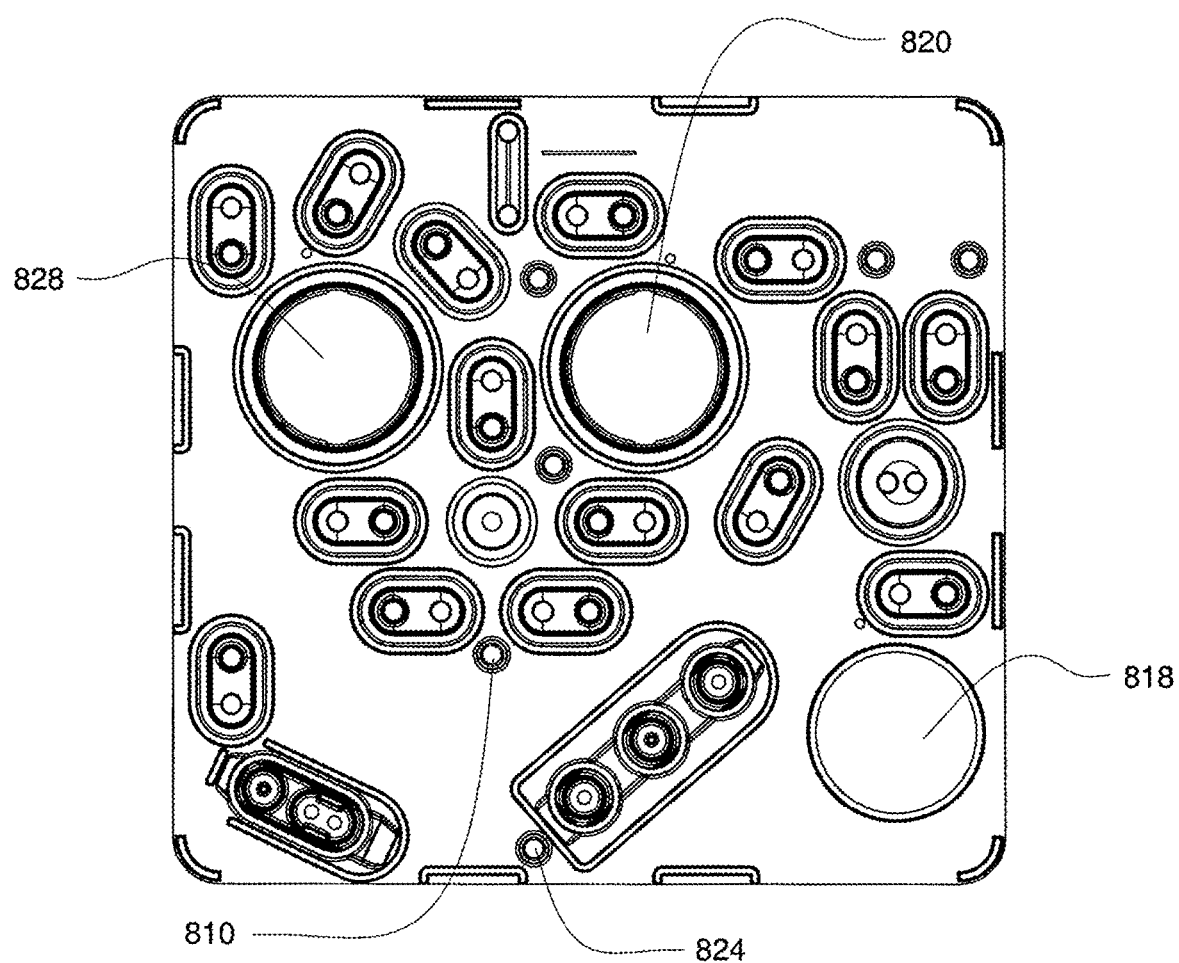
FIG. 39B is a front view of an exemplary embodiment of the air side of the midplate of a cassette.

Referring now to FIGS. 39A-39B, an exemplary embodiment of the midplate 1200 is shown. The midplate 1200 is also shown in FIGS. 37A-37F, where these Figs. correspond with FIGS. 39A-39B. Thus, FIGS. 37A-37F indicate the locations of the various valves and valving paths. The locations of the diaphragms (not shown) for the respective pod pumps 820, 828 as well as the location of the mixing chamber 818 are shown.

Referring now to FIGS. 39A, in one exemplary embodiment of the cassette, sensor elements are incorporated into the cassette so as to discern various properties of the fluid being pumped. In one embodiment, three sensor elements are included. However, in this embodiment, six sensor elements (two sets of three) are included. The sensor elements are located in the sensor cell 1314, 1316. In this embodiment, a sensor cell 1314, 1316 is included as an area on the cassette for sensor(s) elements. In one embodiment, the three sensor elements of the two sensor cells 1314, 1316 are housed in respective sensor elements housings 1308, 1310, 1312 and 1318, 1320, 1322. In one embodiment, two of the sensor elements housings 1308, 1312 and 1318, 1320 accommodate conductivity sensor elements and the third sensor elements housing 1310, 1322 accommodates a temperature sensor element. The conductivity sensor elements and temperature sensor elements may be any conductivity or temperature sensor elements in the art. In one embodiment, the conductivity sensors are graphite posts. In other embodiments, the conductivity sensor elements are posts made from stainless steel, titanium, platinum or any other metal coated to be corrosion resistant and still be electrically conductive. The conductivity sensor elements will include an electrical lead that transmits the probe information to a controller or other device. In one embodiment, the temperature sensor is a thermistor potted in a stainless steel probe. However, in alternate embodiments, a combination temperature and conductivity sensor elements is used similar to the one described in a U.S. Patent Application entitled "Sensor Apparatus Systems, Devices and Methods," filed Oct. 12, 2007 (U.S. Patent Publication No. US-2008-0240929-A1).

In alternate embodiments, there are either no sensors in the cassette or only a temperature sensor, only one or more conductivity sensors or one or more of another type of sensor.

Figure 39C:
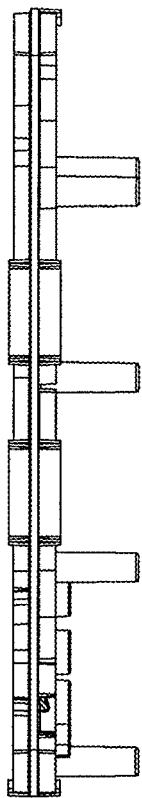
FIG. 39C is a side view of an exemplary embodiment of the midplate of a cassette.
Figure 40A:
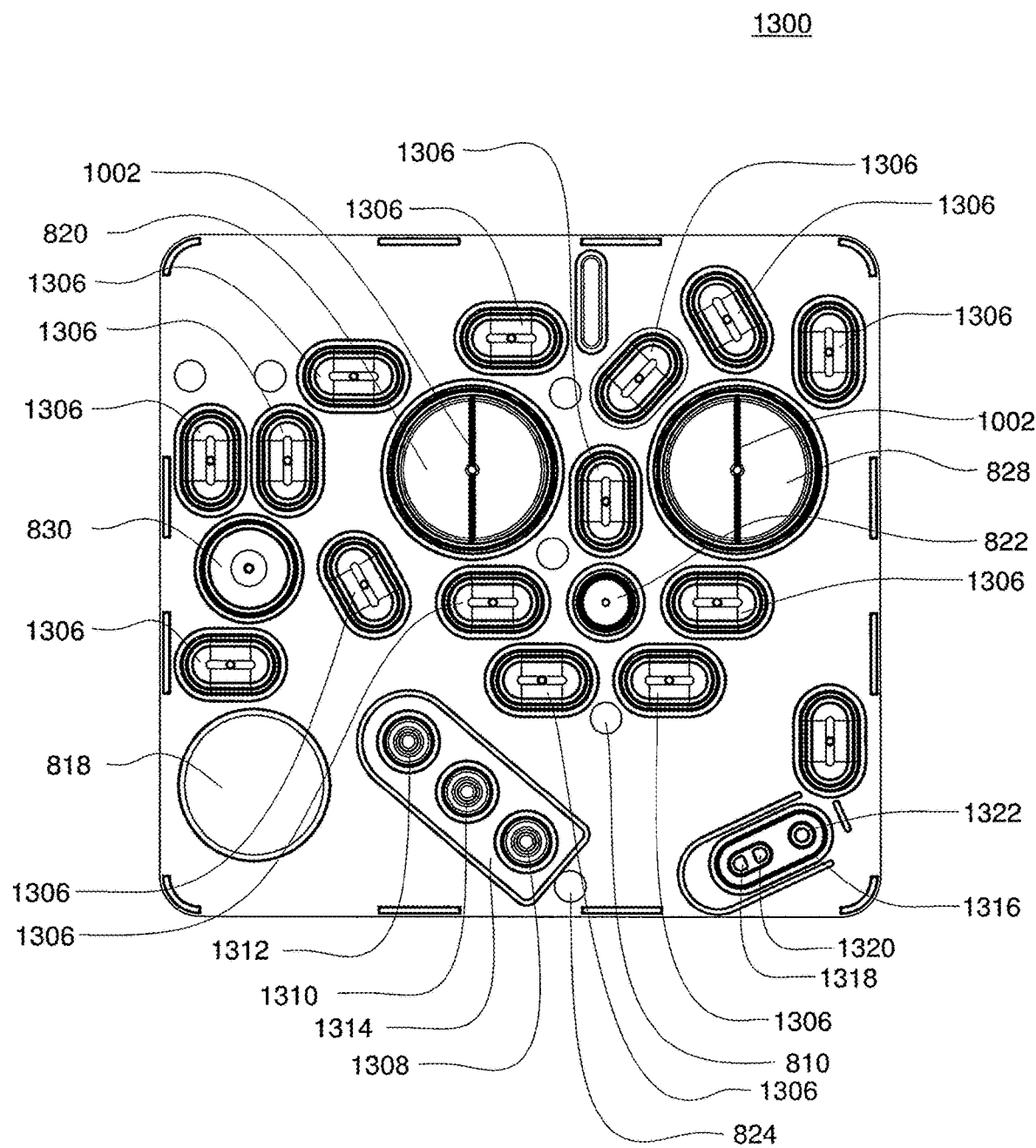
FIG. 40A is a view of an exemplary embodiment of the inner side of the bottom plate of a cassette.
Figure 40B:
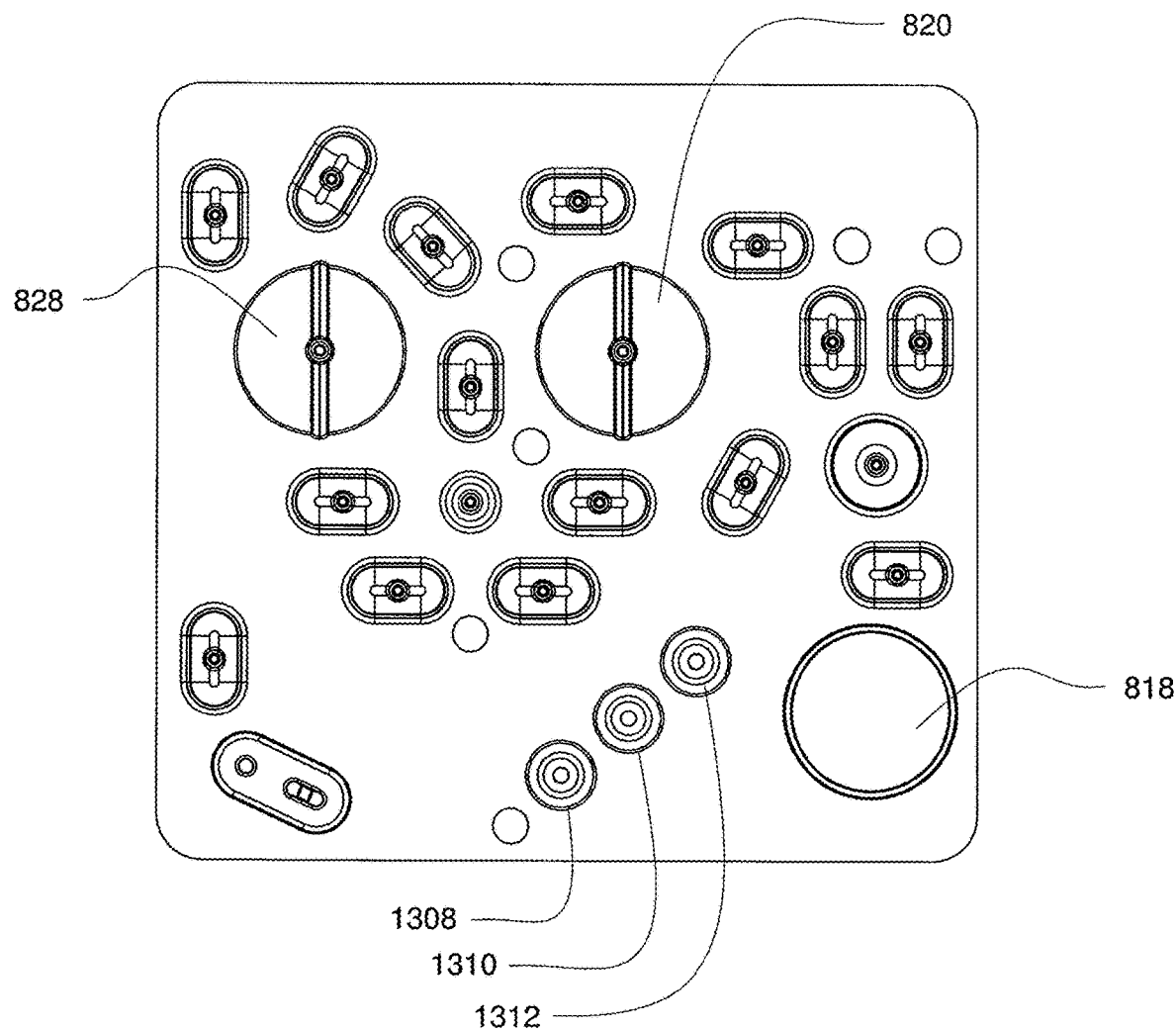
FIG. 40B is a view of an exemplary embodiment of the outer side of the bottom plate of a cassette.

Referring now to FIGS. 39C, the side view of an exemplary embodiment of the midplate 1200 is shown. Referring now to FIGS. 40A-40B, the bottom plate 1300 is shown. Referring first to FIGS. 40A, the inner or inside surface of the bottom plate 1300 is shown. The inner or inside surface is the side that contacts the bottom surface of the midplate (not shown). The bottom plate 1300 attaches to the air or actuation lines (not shown). The corresponding entrance holes for the air that actuates the pod pumps 820, 828 and valves (not shown, see FIGS. 37A-37F) in the midplate 1300 can be seen. Holes 810, 824 correspond to the first fluid inlet and first fluid outlet shown in FIGS. 39B, 810, 824 respectively. The corresponding halves of the pod pumps 820, 828 and mixing chamber 818 are also shown, as are the grooves 1002 for the fluid paths. The actuation holes in the pumps are also shown. Unlike the top plate, the bottom plate 1300 corresponding halves of the pod pumps 820, 828 and mixing chamber 818 make apparent the difference between the pod pumps 820, 828 and mixing chamber 818. The pod pumps 820, 828 include an air/actuation path on the bottom plate 1300, while the mixing chamber 818 has identical construction to the half in the top plate. The mixing chamber 818 mixes liquid and therefore, does not include a diaphragm (not shown) nor an air/actuation path. The sensor cell 1314, 1316 with the three sensor element housings 1308, 1310, 1312 and 1318, 1320, 1322 are also shown.

Figure 40C:
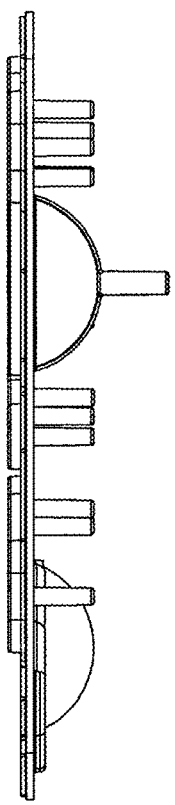
FIG. 40C is a side view of an exemplary embodiment of the midplate of a cassette.

Referring now to FIGS. 40B, the actuation ports 1306 are shown on the outside or outer bottom plate 1300. An actuation source is connected to these actuation ports 1306. Again, the mixing chamber 818 does not have an actuation port as it is not actuated by air. Referring to FIG. 40C, a side view of the exemplary embodiment of the bottom plate 1300 is shown.

As described above, in various aspects of the invention, one or more fluid circuits may be implemented on a cassette, such as the blood flow circuit, the balancing circuit, the directing circuit, and/or the mixing circuit, etc. Other cassettes may be present, e.g., a sensing cassette as is disclosed in U.S. patent application Ser. No. 12/038,474 entitled "Sensor Apparatus Systems, Devices and Methods," filed on Feb. 27, 2008, and incorporated herein by reference. In some embodiments, some or all of these circuits are combined in a single cassette. In alternate embodiments, these circuits are each defined in respective cassettes. In still other embodiments, two or more of the fluid circuits are included on one cassette. In some cases, two, three, or more cassettes may be immobilized relative to each other, optionally with fluidic connections between the cassettes. For instance, in one embodiment, two cassettes may be connected via a pump, such as a pod pump as previously described. The pod pump may include a rigid chamber with a flexible diaphragm dividing each chamber into a first side and a second side, and the sides may be used for various purposes as noted above.

Non-limiting examples of cassettes that may be used in the present invention include those described in U.S. patent application Ser. No. 11/871,680, filed Oct. 12, 2007, entitled "Pumping Cassette"; U.S. patent application Ser. No. 11/871,712, filed Oct. 12, 2007, entitled "Pumping Cassette"; U.S. patent application Ser. No. 11/871,787, filed Oct. 12, 2007, entitled "Pumping Cassette"; U.S. patent application Ser. No. 11/871,793, filed Oct. 12, 2007, entitled "Pumping Cassette"; U.S. patent application Ser. No. 11/871,803, filed Oct. 12, 2007, entitled "Cassette System Integrated Apparatus"; or in U.S. patent application Ser. No. 12/038,648 entitled "Cassette System Integrated Apparatus," filed on Feb. 27, 2008. Each of these is incorporated by reference herein in their entireties.

A cassette may also include various features, such as pod pumps, fluid lines, valves, or the like. The cassette embodiments shown and described in this description include exemplary and various alternate embodiments. However, any variety of cassettes is contemplated that include a similar functionality. Although the cassette embodiments described herein are implementations of the fluid schematics as shown in the figures, in other embodiments, the cassette may have varying fluid paths and/or valve placement and/or pod pump placements and numbers and thus, is still within the scope of the invention.

In one example embodiment, a cassette may includes a top plate, a midplate and a bottom plate. There are a variety of embodiments for each plate. In general, the top plate includes pump chambers and fluid lines, the midplate includes complementary fluid lines, metering pumps and valves and the bottom plate includes actuation chambers (and in some embodiments, the top plate and the bottom plate include complementary portions of a balancing chamber or a pod pump).

In general, the diaphragms are located between the midplate and the bottom plate, however, with respect to a balancing chamber or a pod pump, a portion of a diaphragm is located between the midplate and the top plate. Some embodiments include where the diaphragm is attached to the cassette, either overmolded, captured, bonded, press fit, welded in or any other process or method for attachment, however, in the exemplary embodiments, the diaphragms are separate from the top plate, midplate and bottom plate until the plates are assembled.

The cassettes may be constructed of a variety of materials. Generally, in the various embodiments, the materials used are solid and non-flexible. In one embodiment, the plates are constructed of polysulfone, but in other embodiments, the cassettes are constructed of any other solid material and in exemplary embodiment, of any thermoplastic or thermoset.

In one exemplary embodiment, the cassettes are formed by placing diaphragms in their correct locations (e.g., for one or more pod pumps, if such pod pumps are present), assembling the plates in order, and connecting the plates. In one embodiment, the plates are connected using a laser welding technique. However, in other embodiments, the plates may be glued, mechanically fastened, strapped together, ultrasonically welded or any other mode of attaching the plates together.

In practice, the cassette may be used to pump any type of fluid from any source to any location. The types of fluid include nutritive, nonnutritive, inorganic chemicals, organic chemicals, bodily fluids or any other type of fluid. Additionally, fluid in some embodiments include a gas, thus, in some embodiments, the cassette is used to pump a gas.

The cassette serves to pump and direct the fluid from and to the desired locations. In some embodiments, outside pumps pump the fluid into the cassette and the cassette pumps the fluid out. However, in some embodiments, the pod pumps serve to pull the fluid into the cassette and pump the fluid out of the cassette.

As discussed above, depending on the valve locations, control of the fluid paths is imparted. Thus, the valves being in different locations or additional valves are alternate embodiments of this cassette. Additionally, the fluid lines and paths shown in the figures described above are mere examples of fluid lines and paths. Other embodiments may have more, less and/or different fluid paths. In still other embodiments, valves are not present in the cassette.

The number of pod pumps (if pod pumps are present within the cassette) described above may also vary depending on the embodiment. For example, although the various embodiments shown and described above include two pod pumps, in other embodiments, the cassette includes one pod pump. In still other embodiments, the cassette includes more than two pod pumps, or there may be no pod pumps present. The pod pumps may be single pumps or multiple pod pumps may be present that can work in tandem, e.g., to provide a more continuous flow, as discussed above. Either or both may be used in various embodiments of the cassette. However, as noted above, in some cases, there may be pod pumps not present on a cassette, but contained between two or more cassettes. Non-limiting examples of such systems can be seen in U.S. patent application Ser. No. 12/038,648 entitled "Cassette System Integrated Apparatus," filed on Feb. 27, 2008, and incorporated by herein reference.

The various fluid inlets and fluid outlets disclosed herein may be fluid ports in some cases. In practice, depending on the valve arrangement and control, a fluid inlet may be a fluid outlet. Thus, the designation of the fluid port as a fluid inlet or a fluid outlet is only for description purposes. The various embodiments have interchangeable fluid ports. The fluid ports are provided to impart particular fluid paths onto the cassette. These fluid ports are not necessarily all used all of the time; instead, the variety of fluid ports provides flexibility of use of the cassette in practice.

Figure 50A:
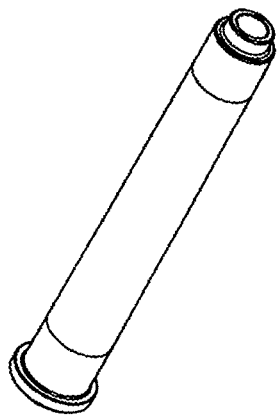
FIG. 50A is an exploded view of one embodiment of a check valve fluid line in the cassette system.
Figure 50A:
Figure 50A:
Figure 50B:
FIG. 50B is an exploded view of one embodiment of a check valve fluid line in the cassette system.
Figure 50B:
Figure 50B:
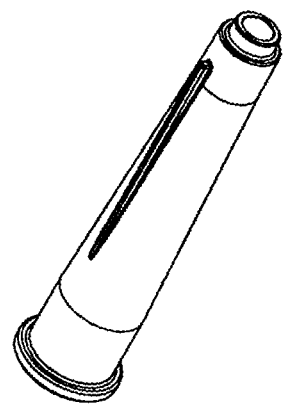
Figure 50C:
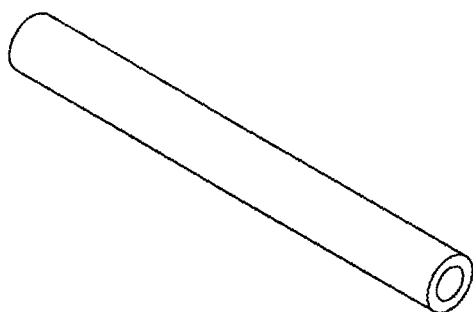
FIG. 50C is an isometric view of an exemplary embodiment of a fluid line in the cassette system.

Another non-limiting example of a cassette is shown with reference to FIG. 46. Referring now to FIG. 46A, the assembled cassette system integrated is shown. The mixing cassette 500, middle cassette 600 and balancing cassette 700 are linked by fluid lines or conduits. The pods are between the cassettes. Referring now to FIGS. 46B and 46C, the various views show the efficiency of the cassette system integrated. The fluid lines or conduits 1200, 1300, 1400 are shown in FIG. 50A, FIG. 50B and FIG. 50C respectively. The fluid flows between the cassettes through these fluid lines or conduits. Referring now to FIGS. 50A and 50B, these fluid lines or conduits represent larger 1300 and smaller 1200 check valve fluid lines. In the exemplary embodiment, the check valves are duck bill valves; however, in other embodiments, any check valve may be used. Referring to FIG. 50C, fluid line or conduit 1400 is a fluid line or conduit that does not contain a check valve. For purposes of this description, the terms "fluid line" and "conduit" are used with respect to 1200, 1300 and 1400 interchangeably.

Figure 46A:
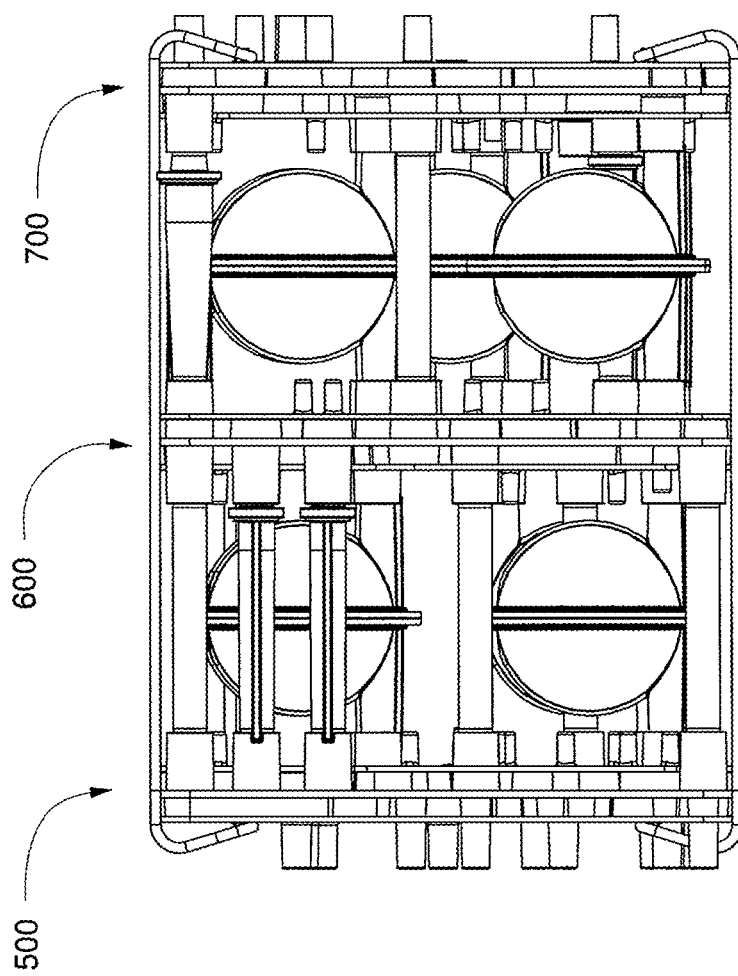
FIG. 46A is a front view of the assembled exemplary embodiment of the cassette system.
Figure 46B:
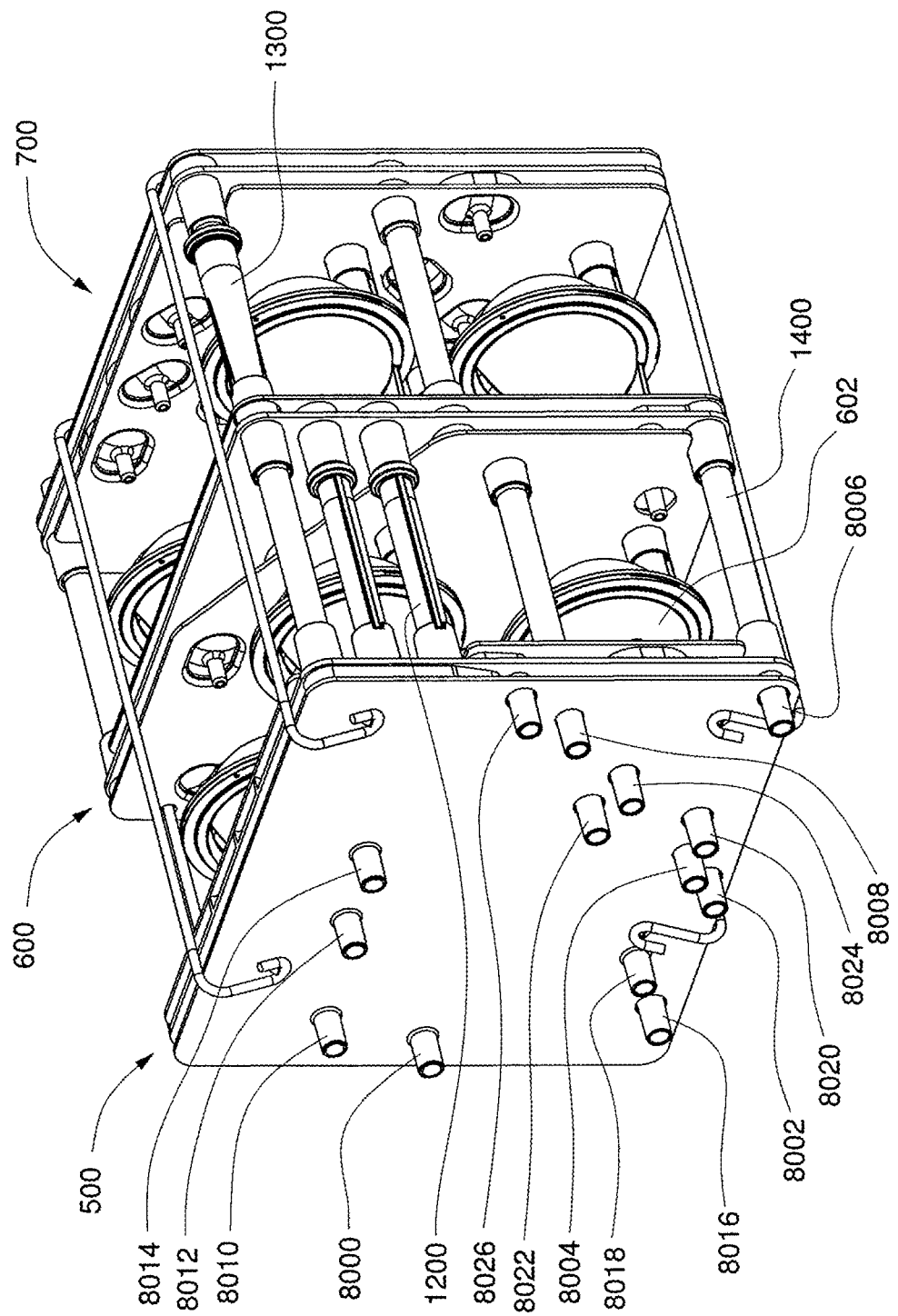
FIG. 46B is an isometric view of the assembled exemplary embodiment of the cassette system.
Figure 46C:
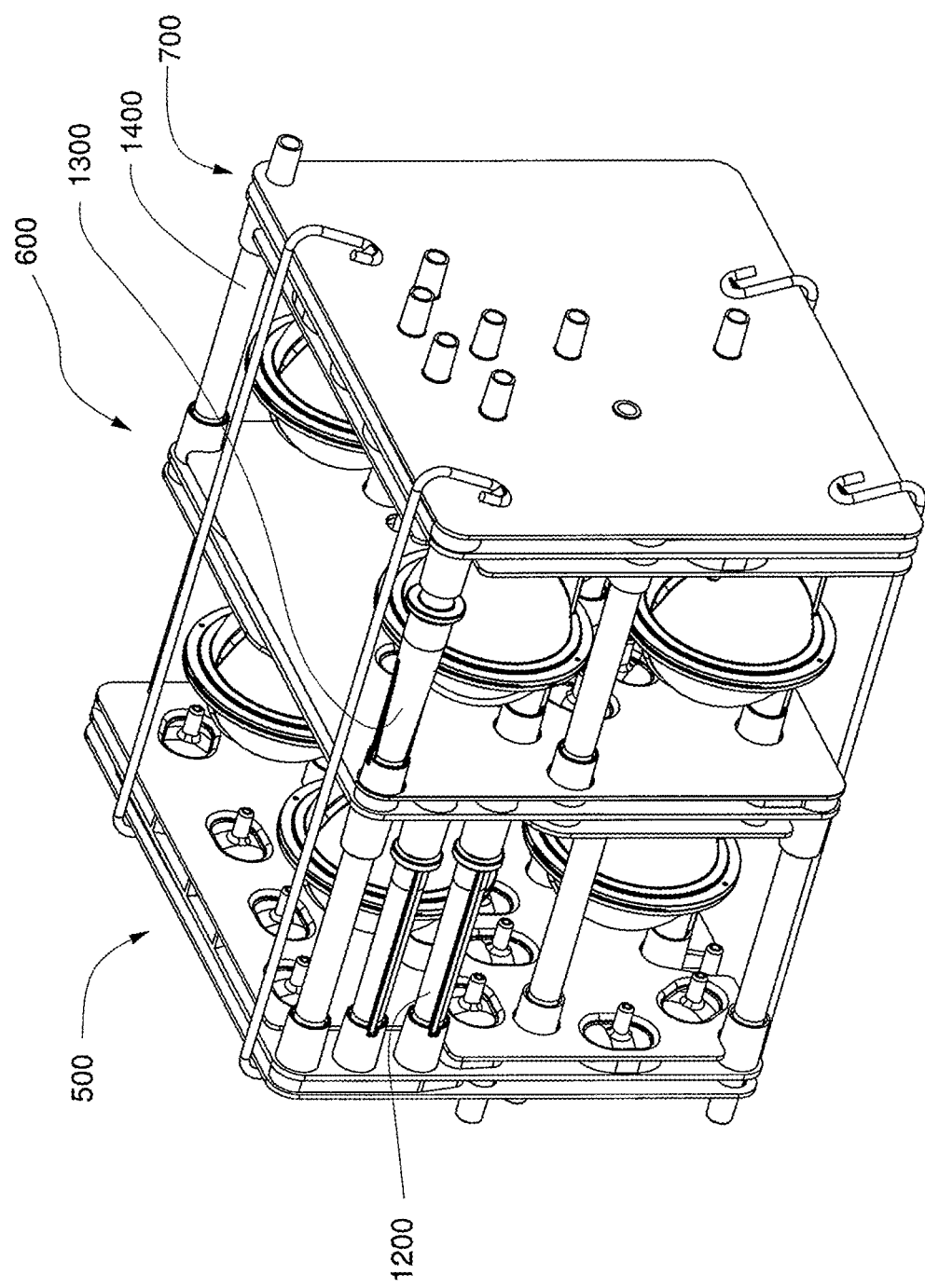
FIG. 46C is an isometric view of the assembled exemplary embodiment of the cassette system.
Figure 51A:
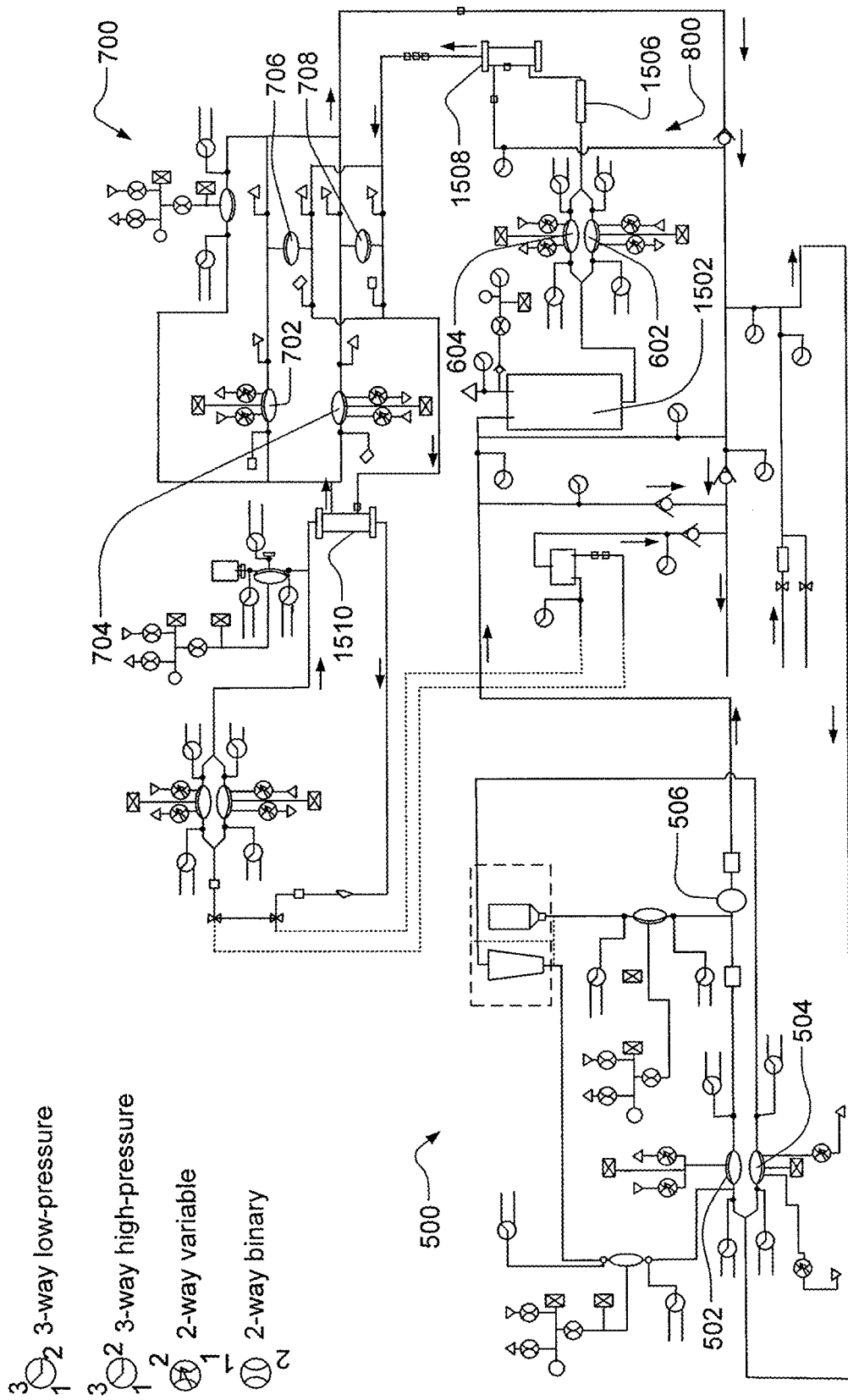
FIG. 51A is one embodiment of the fluid flow-path schematic of the cassette system integrated.

Referring now to FIGS. 46B and 46C, and FIG. 51A, the following is a description of one embodiment of the fluid flow through the various cassettes. For ease of description, the fluid flow will begin with the mixing cassette 500. Referring now to FIG. 46B and FIG. 51A, the fluid side of the mixing cassette 500 is shown. The fluid side includes a plurality of ports 8000, 8002, 8004, 8006, 8008 and 8010-8026 that are either fluid inlets or fluid outlets. In the various embodiments, the fluid inlets and outlets may include one or more fluid inlets for reverse osmosis ("RO") water 8004, bicarbonate, an acid, and a dialysate 8006. Also, one or more fluid outlets, including a drain, acid 8002 and at least one air vent outlet as the vent for the dialysate tank. In one embodiment, a tube (not shown) hangs off the outlet and is the vent (to prevent contamination). Additional outlets for water, bicarbonate and water mixture, dialysate mixture (bicarbonate with acid and water added) are also included.

Figure 46D:
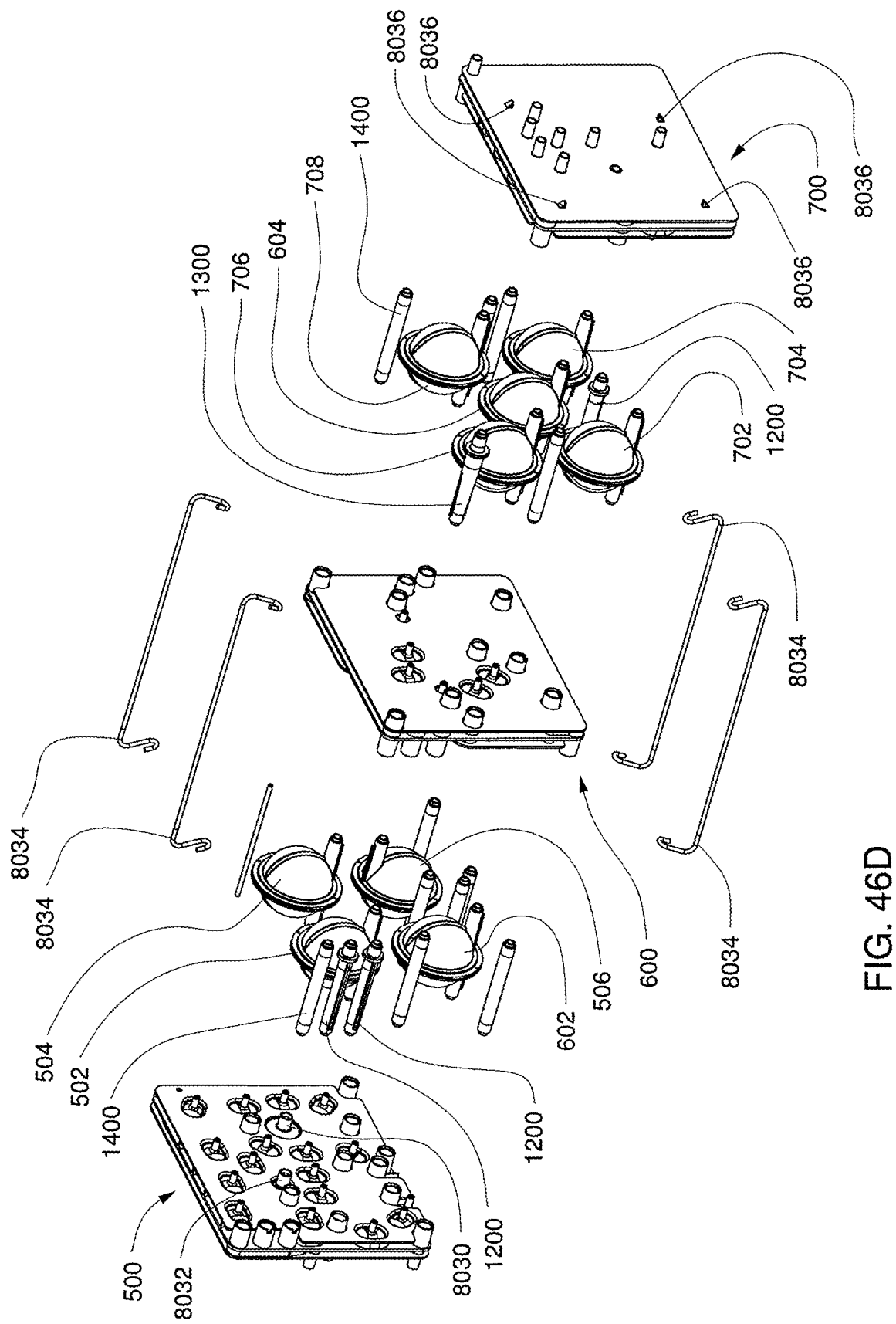
FIG. 46D is an exploded view of the assembled exemplary embodiment of the cassette system.
Figure 46E:
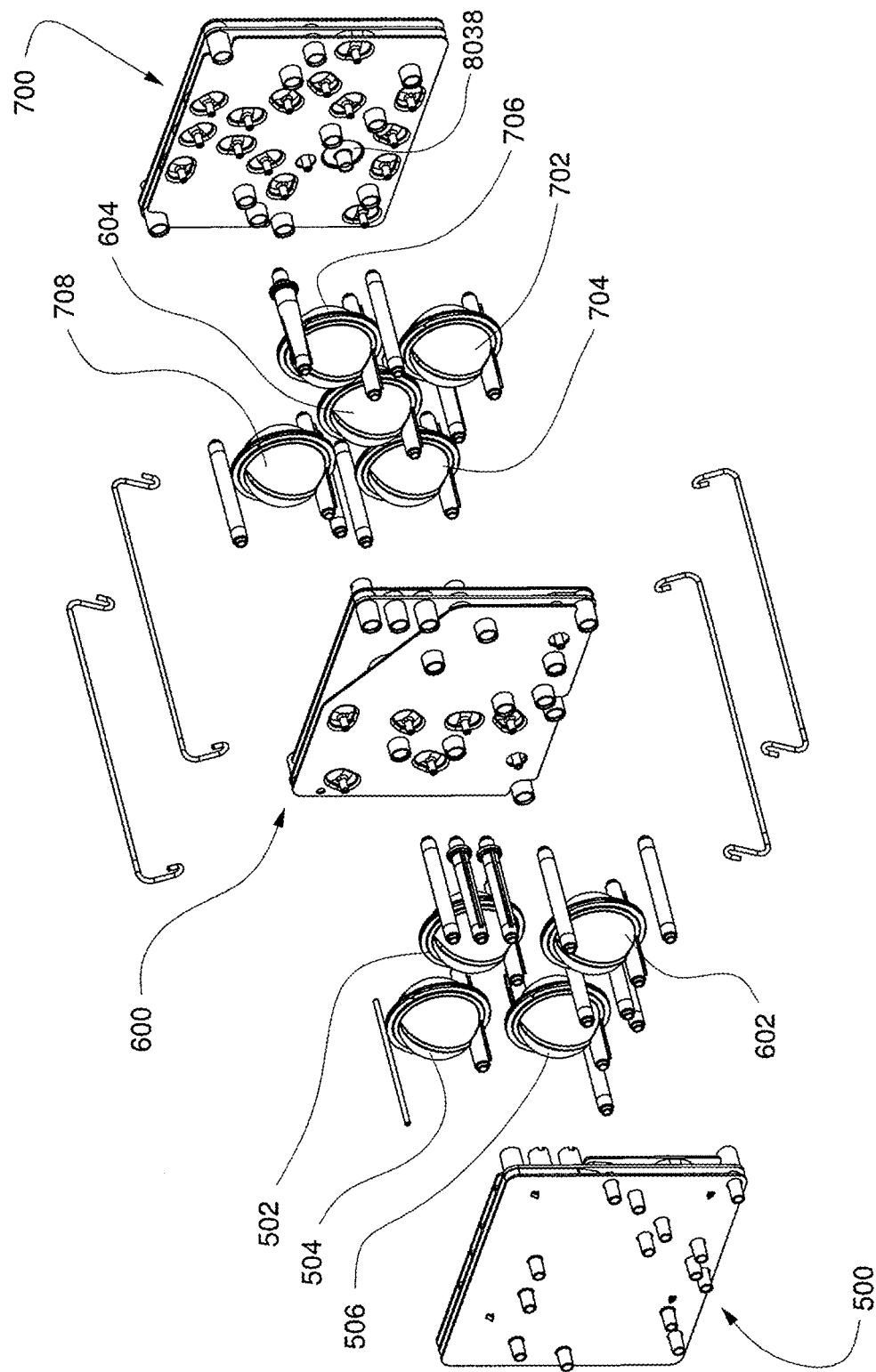
FIG. 46E is an exploded view of the assembled exemplary embodiment of the cassette system.

The dialysate flows out of the mixing cassette 500, to a dialysate tank (not shown, shown as 1502 in FIG. 51A) and then through a conduit to the inner dialysate cassette 700 (pumped by the outer dialysate cassette 600 pod pumps 602 and 604 (604 not shown, shown in FIGS. 46D and 46E). The fluid paths within the cassettes may vary. Thus, the location of the various inlet and outlets may vary with various cassette fluid paths.

Figure 51B:
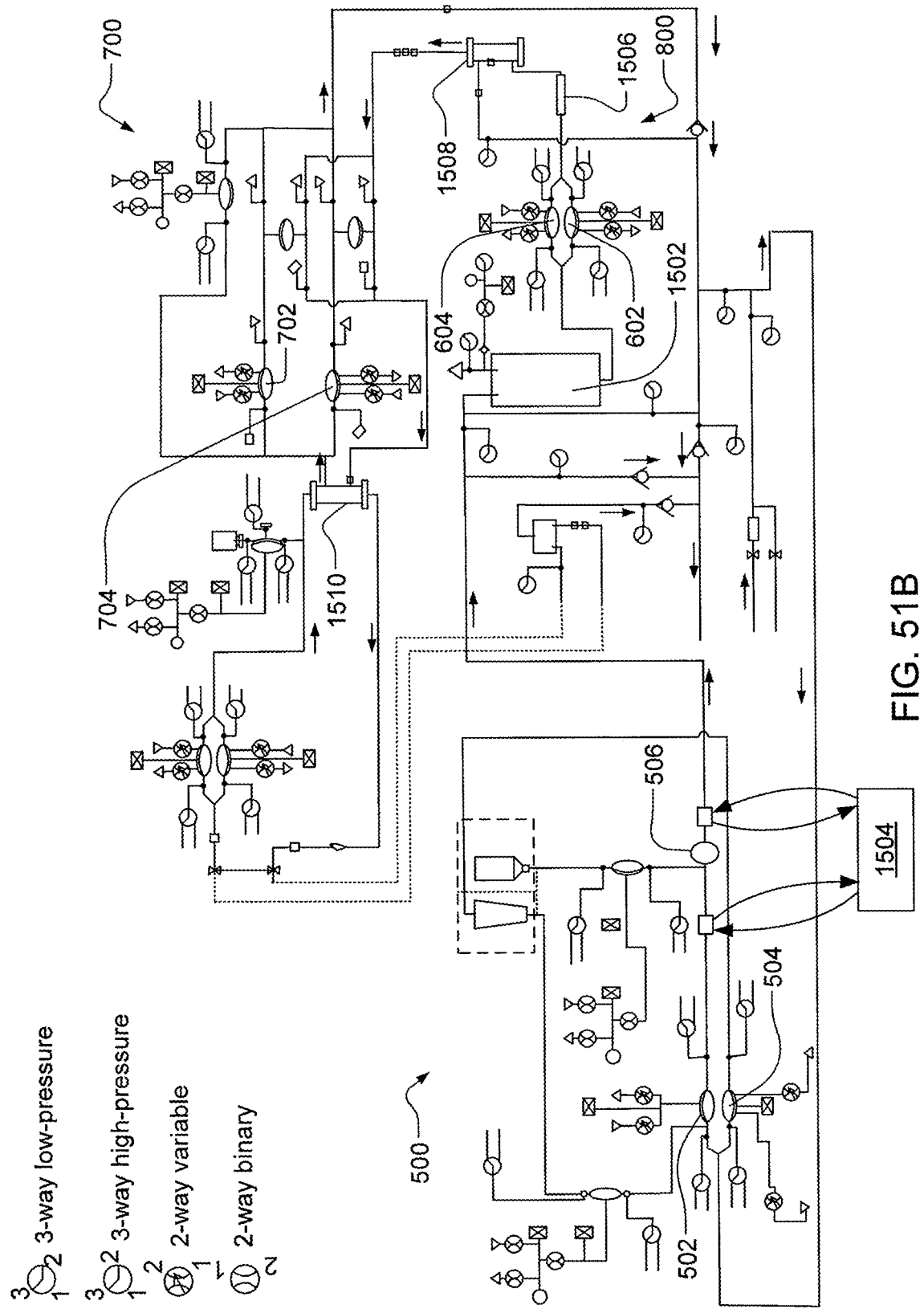
FIG. 51B is one embodiment of the fluid flow-path schematic of the cassette system integrated.
Figure 52F:
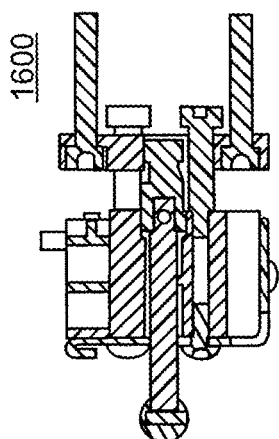
FIGS. 52A-52F are various views of one embodiment of the block for connecting the pneumatic tubes to the manifold according to one embodiment of the present system.
Figure 52E:
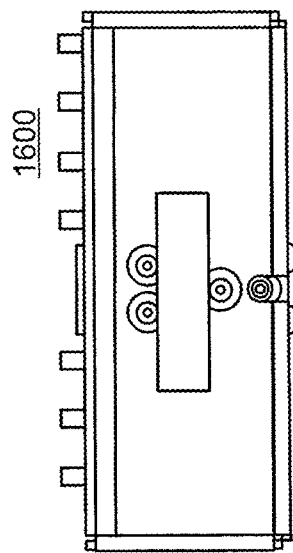
Figure 52B:
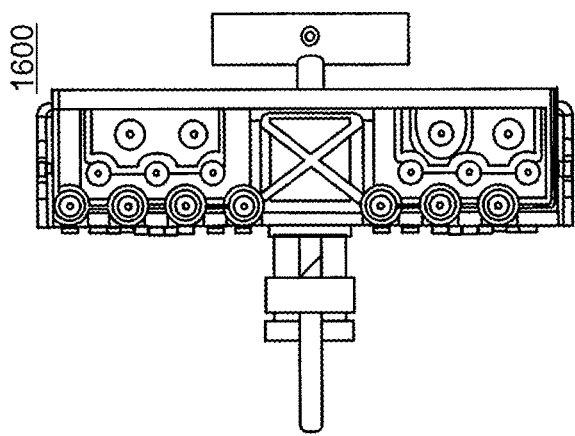
Figure 52D:
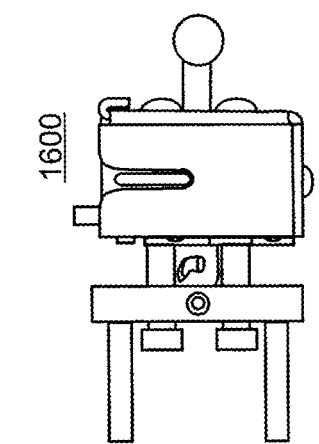
Figure 52A:
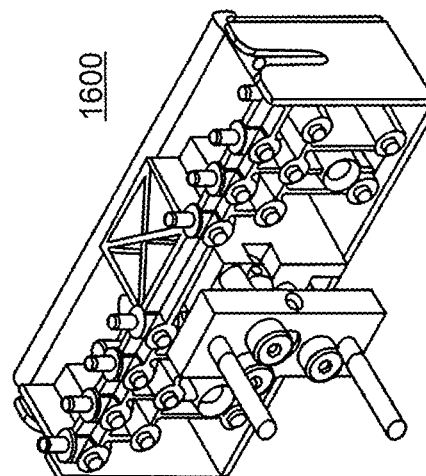
Figure 52C:
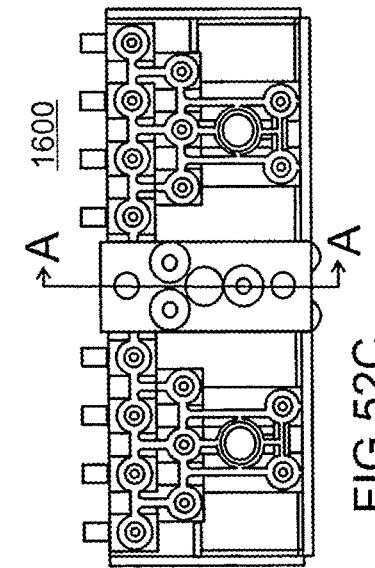

Referring now to FIG. 51B, in one embodiment of the cassette system, the condo cells, conductivity and temperature sensors, are included in a separate cassette 1504 outside of the cassette system shown in FIGS. 46A-46 C. This outside sensor cassette 1504 may be one of those described in U.S. patent application Ser. No. 12/038,474 entitled "Sensor Apparatus Systems, Devices and Methods," filed on Feb. 27, 2008, and incorporated herein by reference.

The fluid flow-path for this embodiment is shown in FIG. 51B. In this embodiment, during the mixing process for the dialysate, the bicarbonate mixture leaves the mixing cassette 500 and flows to an outside sensor cassette, and then flows back into the mixing cassette 500. If the bicarbonate mixture meets pre-established thresholds, acid is then added to the bicarbonate mixture. Next, once the bicarbonate and acid are mixed in the mixing chamber 506, the dialysate flows out of the cassette into the sensor cassette and then back to the mixing cassette 500.

Referring now to FIG. 46D, the mixing cassette 500 include a pneumatic actuation side. In the block shown as 500, there are a plurality of valves and two pumping chambers 8030, 8032 build into the cassette 500 for pumping or metering the acid or bicarbonate. In some embodiments, additional metering pumps, or less metering pumps, are included. The metering pumps 8030, 8032 can be any size desired. In some embodiments, the pumps are different sizes with respect to one another, however, in other embodiments, the pumps are the same size with respect to one another. For example, in one embodiment, the acid pump is smaller than the bicarbonate pump. This may be more efficient and effective when using a higher concentration acid, as it may be desirable to use a smaller pump for accuracy and also, it may be desirable for control schemes to have a smaller pump so as to use full strokes in the control rather than partial strokes.

The conduits 1200, 1300 include a check-valve. These conduits 1200,1300 allow for one-way flow. In the exemplary embodiment, these conduits 1200, 1300 all lead to drain. Referring to the flow-path schematic FIG. 51A, the locations of these check-valve conduits are apparent. In the embodiment shown, any fluid that is meant for drain flows through the mixing cassette 500. Referring again to FIG. 46B, a fluid drain port 8006 is located on the fluid side of the cassette 500.

Once the dialysate is mixed, and after the dialysate flows to the sensor cassette (1504 in FIG. 51B) and it is determined that the dialysate is not within set parameters/thresholds, then the dialysate will be pumped back into the mixing cassette 500, through a plain conduit 1400 then to the outer dialysate cassette 600, then back through conduit a check valve conduit 1200 and then through the mixing cassette 500 to the drain fluid outlet.

Referring now to FIGS. 46D and 46E, the various pods 502, 504, 506, 602, 604, 702, 704, 706, 708 are shown. Each of the pod housings are constructed identically, however, the inside of the pod housing is different depending on whether the pod is a pod pump 502, 504 602, 604, 702, 704 a balancing chamber pods 706, 708 or a mixing chamber pod 504.

Referring now to FIGS. 46D and 46E, together with FIGS. 51A and 51B, the various pods are shown both in the fluid flow-path and on the cassette system. Pod 502 is the water pod pump and 504 is the bicarbonate water pod pump (sends water to the bicarbonate) of the mixing cassette 500. Pod 506 is the mixing chamber. Once the dialysate is mixed in the mixing chamber 506, and then flows from the mixing cassette 500 to the sensor cassette 1504, and it is determined that the dialysate qualifies as acceptable, then the dialysate flows to the dialysate tank 1502 through the mixing cassette dialysate tank outlet. However, if the dialysate is rendered unacceptable, then the fluid is pumped back into the cassette 500, then through a 1400 conduit, to the outer dialysate cassette 600 and then pumped through a 1200 check valve conduit, through the mixing cassette 500 and out the drain outlet.

Referring to FIGS. 46A-46C, together with FIGS. 51A-B, the outer dialysate cassette is shown 600 between the mixing cassette 500 and the inner dialysate cassette 700. Pod pumps 602, 604, pump the dialysate from the dialysate tank 1502 and send it to the balancing chambers 706,708 in the inner dialysate cassette 700 (driving force for the dialysate solution). The outer dialysate cassette 600 pushes the dialysate into the inner dialysate cassette (i.e., the pumps in the inner dialysate cassette 700 do not draw the dialysate in). Thus, from the outer dialysate cassette 600, the dialysate is pumped from the dialysate tank 1502, through a heater 1506 and through an ultrafilter 1508, and then into the inner dialysate cassette 700.

Still referring now to FIGS. 46D and 46E, together with FIGS. 51A-B, the inner dialysate cassette 700 includes a metering pod 8038 (i.e., an ultra filtration metering pod) and includes balancing pods 706, 708 and pod pumps 702, 704. The inner dialysate cassette 700 also includes fluid outlets and inlets. These inlets and outlets include the outlet to the dialyzer 1510, the inlet from the dialyzer 1510, and a dialysate inlet (the ultrafilter 1508 connects to a port of the inner dialysate cassette). Fluid inlets and outlets are also included for the DCA and DCV connections during priming and disinfection. Various conduits (1200,1300,1400) serve as fluid connections between the cassettes 500, 600, 700 and are used for dialysate fluid flow as well as fluid to pass through in order to drain through the mixing cassette 500. The largest check valve 1300 (also shown in FIG. 50B) is the largest check-valve, and is used during disinfection. This tube is larger in order to accommodate, in the preferred embodiment, blood clots and other contaminants that flow through the conduits during disinfection.

The valves and pumps of the cassette system are pneumatically actuated in the exemplary embodiment. The pneumatics attach to the cassettes via individual tubes. Thus, each pump, balancing pod, or valve includes an individual tube connection to a pneumatic actuation manifold (not shown). Referring now to FIGS. 52A-F, the tubes are connected, in the exemplary embodiment, to at least one block, 1600. In some embodiments, more than one block is used to connect the various tubes. The block 1600 is dropped into the manifold and then connected to the pneumatics actuators appropriately. This allows for easy connection of the pneumatic tubes to the manifold.

Referring again to FIG. 46D, the cassette system includes springs 8034, in one embodiment, to aid in holding the system together. The springs 8034 hook onto the mixing cassette 500 and inner dialysate cassette 700 via catches 8036. However, in other embodiments, any other means or apparatus to assist in maintaining the system in appropriate orientation may be used including, but not limited to, latching means or elastic means, for example.

Figure 47A:
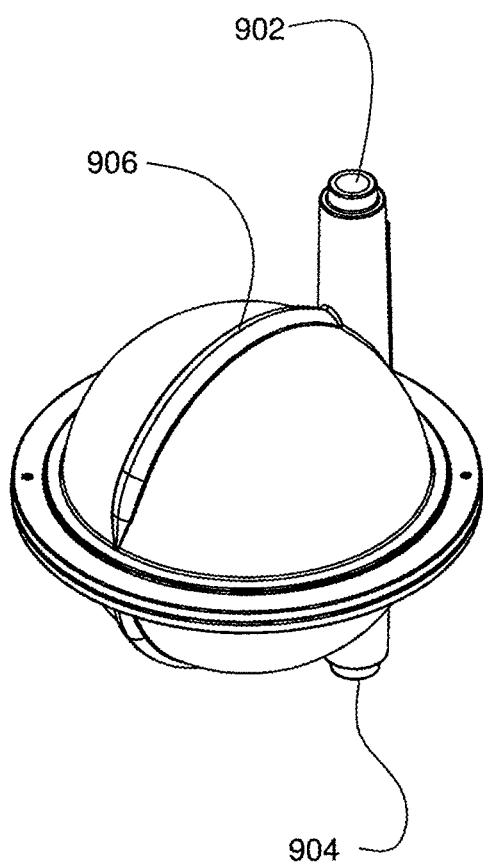
FIG. 47A is an isometric view of an exemplary embodiment of the pod of the cassette system.
Figure 47B:
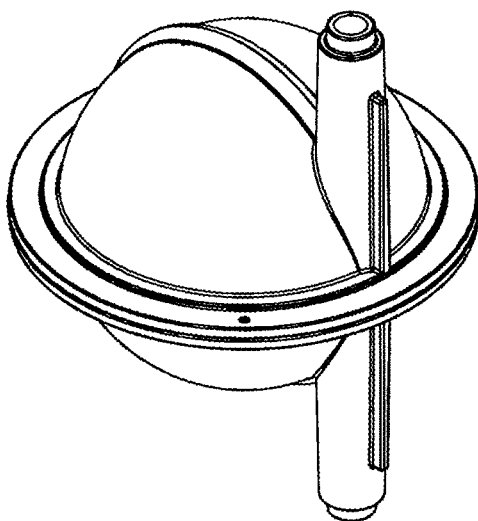
FIG. 47B is an isometric view of an exemplary embodiment of the pod of the cassette system.
Figure 47C:
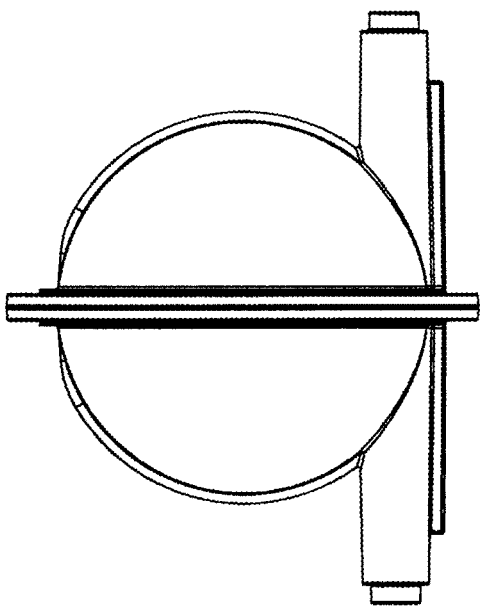
FIG. 47C is a side view of an exemplary embodiment of the pod of the cassette system.

Referring now to FIGS. 47A-47C, the exemplary embodiment of the pod is shown. The pod includes two fluid ports 902, 904 (an inlet and an outlet) and the pod may be constructed differently in the various embodiments. A variety of embodiments of construction are described in U.S. patent application Ser. No. 11/787,212, filed Apr. 13, 2007, and entitled "Fluid Pumping Systems, Devices and Methods," which is hereby incorporated herein by reference in its entirety.

Figure 47D:
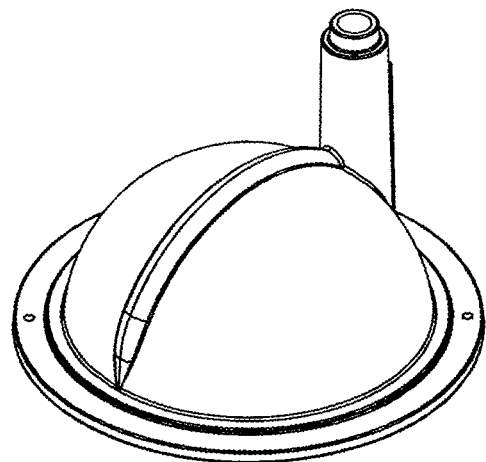
FIG. 47D is an isometric view of an exemplary embodiment of one half of the pod of the cassette system.
Figure 47E:
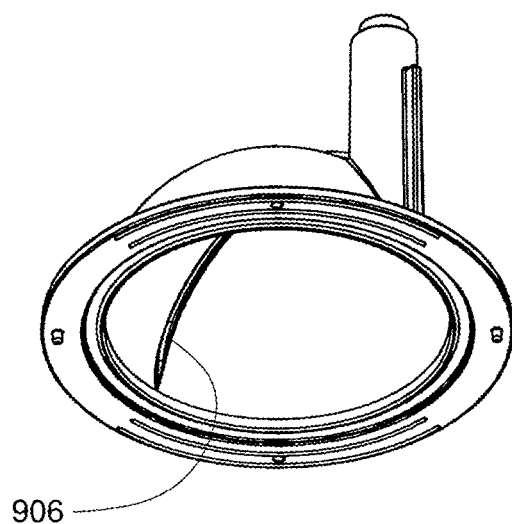
FIG. 47E is an isometric view of an exemplary embodiment of one half of the pod of the cassette system.

Referring now to FIGS. 47A, 47D and 47E the groove 906 in the chamber is shown. A groove 906 is included on each half of the pod housing. In other embodiments, a groove is not included and in some embodiments, a groove is only included on one half of the pod.

Figure 48A:
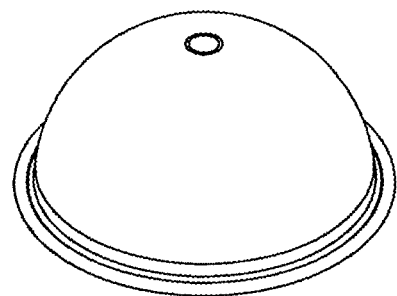
FIG. 48A is a pictorial view of the exemplary embodiment of the pod membrane of the cassette system.
Figure 48B:
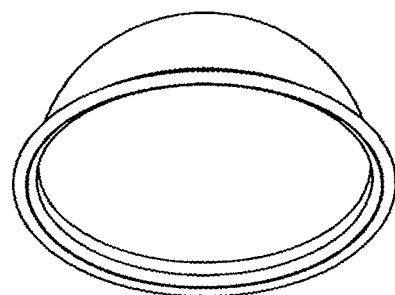
FIG. 48B is a pictorial view of the exemplary embodiment of the pod membrane of the cassette system.
Figure 49:
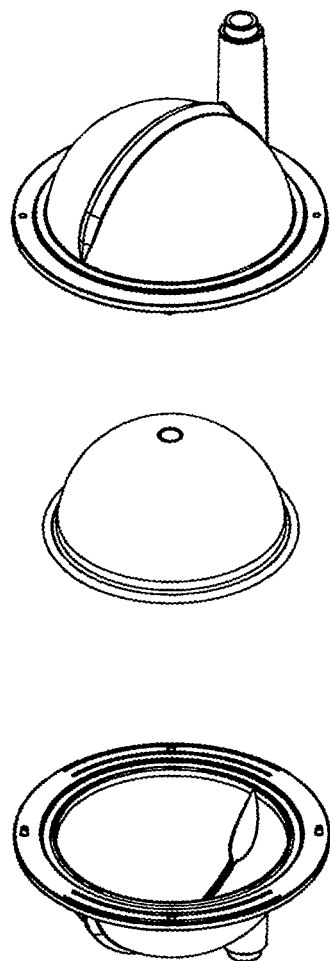
FIG. 49 is an exploded view of an exemplary embodiment of the pod of the cassette system.

Referring now to FIGS. 48A and 48B, the exemplary embodiment of the membrane used in the pod pumps 502, 504 602, 604, 702, 704 is shown. This membrane is shown and described above with respect to FIG. 5A. In other embodiments, any of the membranes shown in FIGS. 5B-5D may be used. An exploded view of a pod pump according to the exemplary embodiment is shown FIG. 49.

Various aspects of the invention include one or more "pod pumps," used for various purposes. The structure of a general pod pump will now be described, although, as noted above, this structure may be modified for various uses, e.g., as a pump, a balancing chamber, a mixing chamber, or the like. In addition, a pod pump may be positioned anywhere in the system, for instance, on a cassette or between two or more cassettes, etc.

Generally, a pod pump includes a rigid chamber (which may have any suitable shape, e.g., spherical, ellipsoid, etc.), and the pod pump may include a flexible diaphragm dividing each chamber into a first half and a second half. In some cases, the rigid chamber is a spheroid. As used herein, "spheroid" means any three-dimensional shape that generally corresponds to a oval rotated about one of its principal axes, major or minor, and includes three-dimensional egg shapes, oblate and prolate spheroids, spheres, and substantially equivalent shapes.

Each half of the pod pump may have at least one entry valve, and often (but not always) has at least one exit valve (in some cases, the same port may be used for both entry and exit). The valves may be, for instance, open/closing valves or two-way proportional valves. For instance, valves on one side of a chamber may be two-way proportional valves, one connected to a high pressure source, the other connected to a low pressure (or vacuum) sink, while the valves on the other half may be opened and closed to direct fluid flow.

In some embodiments, the diaphragm has a variable cross-sectional thickness. Thinner, thicker or variable thickness diaphragms may be used to accommodate the strength, flexural and other properties of the chosen diaphragm materials. Thinner, thicker or variable diaphragm wall thickness may also be used to manage the diaphragm thereby encouraging it to flex more easily in some areas than in other areas, thereby aiding in the management of pumping action and flow of subject fluid in the pump chamber. In this embodiment, the diaphragm is shown having its thickest cross-sectional area closest to its center. However in other embodiments having a diaphragm with a varying cross-sectional, the thickest and thinnest areas may be in any location on the diaphragm. Thus, for example, the thinner cross-section may be located near the center and the thicker cross-sections located closer to the perimeter of the diaphragm. In one embodiment of the diaphragm, the diaphragm has a tangential slope in at least one section, but in other embodiments, the diaphragm is completely smooth or substantially smooth.

The diaphragm may be made of any flexible material having a desired durability and compatibility with the subject fluid. The diaphragm may be made from any material that may flex in response to fluid, liquid or gas pressure or vacuum applied to the actuation chamber. The diaphragm material may also be chosen for particular bio-compatibility, temperature compatibility or compatibility with various subject fluids that may be pumped by the diaphragm or introduced to the chambers to facilitate movement of the diaphragm. In the exemplary embodiment, the diaphragm is made from high elongation silicone. However, in other embodiments, the diaphragm is made from any elastomer or rubber, including, but not limited to, silicone, urethane, nitrile, EPDM or any other rubber, elastomer or flexible material.

The shape of the diaphragm is dependent on multiple variables. These variables include, but are not limited to: the shape of the chamber; the size of the chamber; the subject fluid characteristics; the volume of subject fluid pumped per stroke; and the means or mode of attachment of the diaphragm to the housing. The size of the diaphragm is dependent on multiple variables. These variables include, but are not limited to: the shape of the chamber; the size of the chamber; the subject fluid characteristics; the volume of subject fluid pumped per stroke; and the means or mode of attachment of the diaphragm to the housing. Thus, depending on these or other variables, the shape and size of the diaphragm may vary in various embodiments.

The diaphragm may have any thickness. However, in some embodiments, the range of thickness is between 0.002 inches to 0.125 inches (1 inch=2.54 cm). Depending on the material used for the diaphragm, the desired thickness may vary. In one embodiment, high elongation silicone is used in a thickness ranging from 0.015 inches to 0.050 inches. However in other embodiments, the thickness may vary.

In the exemplary embodiment, the diaphragm is pre-formed to include a substantially dome-shape in at least part of the area of the diaphragm. Again, the dimensions of the dome may vary based on some or more of the variables described above. However, in other embodiments, the diaphragm may not include a pre-formed dome shape.

In the exemplary embodiment, the diaphragm dome is formed using liquid injection molding. However, in other embodiments, the dome may be formed by using compression molding. In alternate embodiments, the diaphragm is substantially flat. In other embodiments, the dome size, width or height may vary.

In various embodiments, the diaphragm may be held in place by various means and methods. In one embodiment, the diaphragm is clamped between the portions of the cassette, and in some of these embodiments, the rim of the cassette may include features to grab the diaphragm. In others of this embodiment, the diaphragm is clamped to the cassette using at least one bolt or another device. In another embodiment, the diaphragm is over-molded with a piece of plastic and then the plastic is welded or otherwise attached to the cassette. In another embodiment, the diaphragm is pinched between a mid plate and a bottom plate. Although some embodiments for attachment of the diaphragm to the cassette are described, any method or means for attaching the diaphragm to the cassette may be used. The diaphragm, in one alternate embodiment, is attached directly to one portion of the cassette. In some embodiments, the diaphragm is thicker at the edge, where the diaphragm is pinched by the plates, than in other areas of the diaphragm. In some embodiments, this thicker area is a gasket, in some embodiments an O-ring, ring or any other shaped gasket.

In some embodiments of the gasket, the gasket is contiguous with the diaphragm. However, in other embodiments, the gasket is a separate part of the diaphragm. In some embodiments, the gasket is made from the same material as the diaphragm. However, in other embodiments, the gasket is made of a material different from the diaphragm. In some embodiments, the gasket is formed by over-molding a ring around the diaphragm. The gasket may be any shape ring or seal desired so as to complement the pod pump housing embodiment. In some embodiments, the gasket is a compression type gasket.

Due to the rigid chamber, the pod pump has a generally constant volume. However, within the pod pump, the first and second compartments may have differing volumes depending on the position of the flexible diaphragm dividing the chamber. Forcing fluid into one compartment may thus cause the fluid within the other compartment of the chamber to be expelled. However, the fluids are typically not able to come into direct contact with each other within the pod pump due to the presence of the flexible diaphragm.

Accordingly, in one embodiment, a pod pump used for pumping is constructed to receive a control fluid in a first compartment and a fluid to be pumped in a second compartment. The control fluid may be any fluid, and may be a liquid or a gas. In one embodiment, the control fluid is air. Drawing control fluid away from the pod pump (e.g., through a vacuum, or at least a pressure lower than the pressure within the pod pump) causes the pod pump to draw in fluid (e.g., blood, dialysate, etc.) into the other compartment of the pod pump. Similarly, forcing control fluid into the pod pump (e.g., from a high pressure source) causes the pod pump to expel fluid. By also controlling the valves of the second compartment, fluid may be brought in through a first valve and then expelled through a second valve due to action of the control fluid.

As another example, a pod pump may be used for fluid balancing, e.g., of dialysate as discussed above. In such cases, instead of a control fluid, a fluid may be directed to each compartment of the pod pump. As mentioned, the volume of the pod pump remains generally constant due to the rigid chamber. Accordingly, when a first volume of fluid is drawn into a first compartment of a balancing pod, an equal volume of fluid is expelled from the second compartment of the balancing pod (assuming the fluids to be generally incompressible under conditions in which the pod is operated). Thus, using such balancing pods, equal volumes of fluid can be moved. For instance, in FIG. 5, a balancing pod may allow fresh dialysate to enter a first compartment and used dialysate to enter a second compartment; the volumetric flows of fresh dialysate and used dialysate can be balanced against each other.

In some cases, a pod pump is used that does not contain a flexible diaphragm dividing the chamber. In such instances, the pod pump can be used as a mixing chamber. For instance, mixing chamber 189 in FIG. 7A may be such a pod pump.

Figure 9:
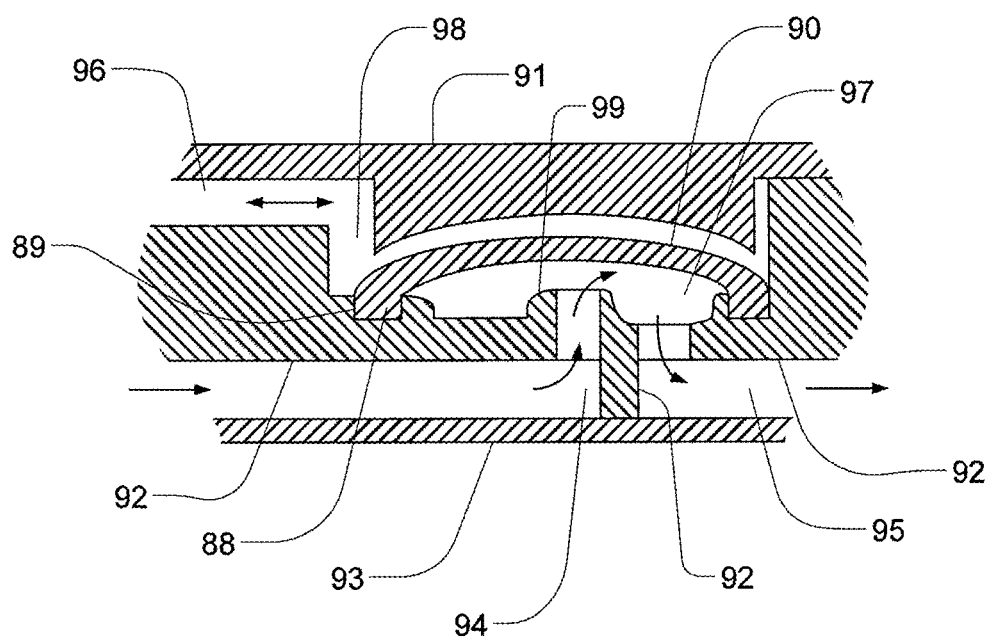
FIG. 9 is a sectional view of a valve that may be incorporated into embodiments of the fluid-control cassettes.

A non-limiting example of a pod pump is shown in FIG. 9. This figure is a sectional view of a pneumatically controlled valve that may be used in embodiments of the cassettes. "Pneumatic," as used herein, means using air or other gas to move a flexible diaphragm or other member. (It should be noted that air is used by way of example only, and in other embodiments, other control fluids, such as nitrogen ($N_2$), $CO_2$, water, an oil, etc. may be used). Three rigid pieces are used, a "top" plate 91, a middle plate 92, and a "bottom" plate. (The terms "top" and "bottom" only refer to the orientation shown in FIG. 9. The valve may be oriented in any direction in actual use.) The top and bottom plates 91, 93 may be flat on both sides, while the middle plate 92 is provided with channels, indentations and holes to define the various fluid paths, chamber and ports. A diaphragm 90, along with the middle plate 92, defines a valving chamber 97. Pneumatic pressure is provided through a pneumatic port 96 to either force, with positive gas pressure, the diaphragm 90 against a valve seat 99 to close the valve, or to draw, with negative gas pressure, the diaphragm away from the valve seat to open the valve. A control gas chamber 98 is defined by the diaphragm 90, the top plate 91, and the middle plate 92. The middle plate 92 has an indentation formed on it, into which the diaphragm 90 is placed so as to form the control gas chamber 98 on one side of the diaphragm and the valving chamber 97 on the other side.

The pneumatic port 96 is defined by a channel formed on the "top" surface of the middle plate 92, along with the top plate 91. By providing fluid communication between several valving chambers in a cassette, valves may be ganged together so that all the valves ganged together may be opened or closed at the same time by a single source of pneumatic pressure. Channels formed on the "bottom" surface of the middle plate 92, along with the bottom plate, define the valve inlet 94 and the valve outlet 95. Holes formed through the middle plate 92 provide communication between the inlet 94 and the valving chamber 97 (through the valve seat 99) and between the valving chamber and the outlet 95.

The diaphragm 90 is provided with a thickened rim 88, which fits tightly in a groove 89 in the middle plate 92. Thus, the diaphragm 90 may be placed in and held by the groove 88 before the top plate 91 is ultrasonically welded to the middle plate 92, so the diaphragm will not interfere with the ultrasonic welding of the two plates together, and so that the diaphragm does not depend on the two plates being ultrasonically welded together in just the right way to be held in place. Thus, this valve may be manufactured easily without relying on ultrasonic welding to be done to very tight tolerances. As shown in FIG. 9, the top plate 91 may include additional material extending into control gas chamber 98 so as to prevent the diaphragm 90 from being urged too much in a direction away from the groove 89, so as to prevent the diaphragm's thickened rim 88 from popping out of the groove 89.

Pressure sensors may be used to monitor pressure in the pods. For instance by alternating applied air pressure to the pneumatic side of the chamber, the diaphragm is cycled back and forth across the total chamber volume. With each cycle, fluid is drawn through the upstream valve of the inlet fluid port when the pneumatics pull a vacuum on the pods. The fluid is then subsequently expelled through the outlet port and the downstream valve when the pneumatics deliver positive pressure to the pods.

Figure 10:
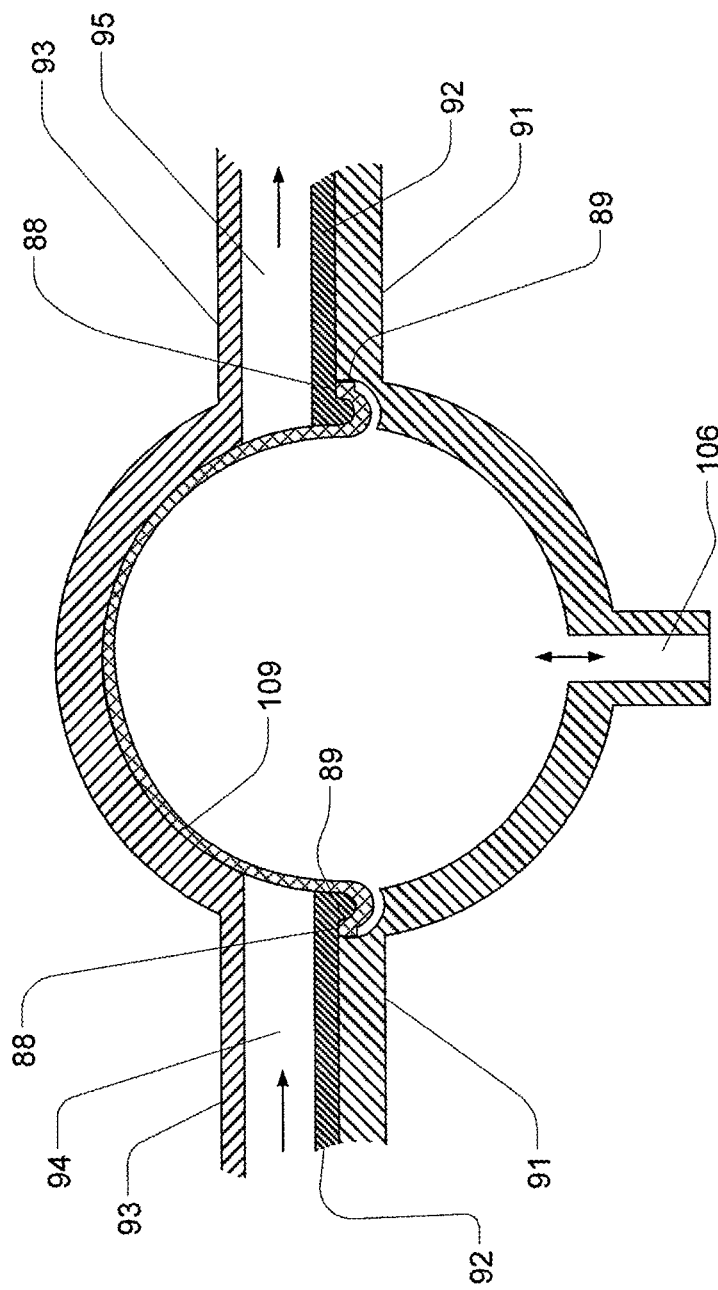
FIG. 10 is a sectional view of a pod-pump that may be incorporated into embodiments of the fluid-control cassettes.

FIG. 10 is a sectional view of one embodiment of a pod pump that may be incorporated into embodiments of the fluid-control cassettes. In some embodiments, the cassette would incorporate several pod pumps and several valves made in accordance with the construction techniques shown in FIGS. 9 and 10. In such embodiments, the pod pump of FIG. 10 is made from different portions of the same three rigid pieces used to make the valve of FIG. 9. These rigid pieces are the "top" plate 91, the middle plate 92, and the "bottom" plate. (As noted above, the terms "top" and "bottom" only refer to the orientation shown in FIG. 9.) To form the pod pump, the top and bottom plates 91, 93 may include generally hemispheroid portions that together define a hemispheroid pod pump.

A diaphragm 109 separates the central cavity of the pod pump into a chamber (the pumping chamber) that receives the fluid to be pumped and another chamber (the actuation chamber) for receiving the control gas that pneumatically actuates the pump. An inlet 94 allows fluid to enter the pumping chamber, and an outlet allows fluid to exit the pumping chamber. The inlet 94 and the outlet 95 may be formed between middle plate 92 and the bottom plate 93. Pneumatic pressure is provided through a pneumatic port 106 to either force, with positive gas pressure, the diaphragm 109 against one wall of pod pump's cavity to minimize the pumping chamber's volume (as shown in FIG. 10), or to draw, with negative gas pressure, the diaphragm towards the other wall of the pod pump's cavity to maximize the pumping chamber's volume.

In some embodiments of the pod pump, various configurations, including grooving on one or more plates exposed to the cavity of the pod pump, are used. Amongst other benefits, grooving can prevent the diaphragm from blocking the inlet or outlet (or both) flow path for fluid or air (or both).

The diaphragm 109 may be provided with a thickened rim 88, which is held tightly in a groove 89 in the middle plate 92. Thus, like in the valving chamber of FIG. 9, the diaphragm 109 may be placed in and held by the groove 89 before the top plate 91 is ultrasonically welded to the middle plate 92, so the diaphragm will not interfere with the ultrasonic welding of the two plates together, and so that the diaphragm does not depend on the two plates being ultrasonically welded together in just the right way to be held in place. Thus, this pod pump can be manufactured easily without relying on ultrasonic welding to be done to very tight tolerances.

Figure 11A:
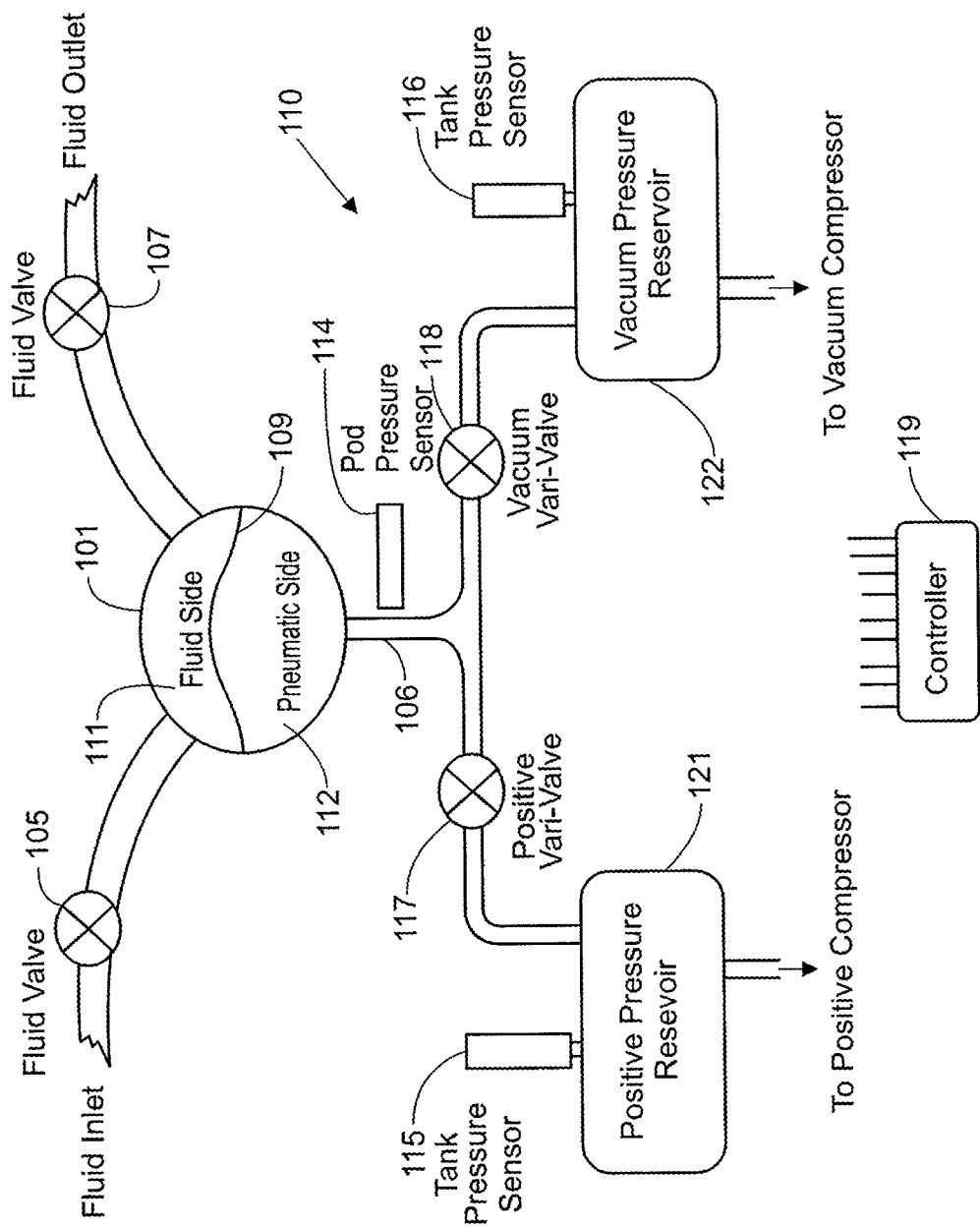
FIGS. 11A-11B are schematic views of various pneumatic control system for a pod pump.

FIG. 11A is a schematic view showing an embodiment of a pressure actuation system 110 for a pod pump, such as that shown in FIG. 10. In this example, air is used as a control fluid (e.g., such that the pump is pneumatically driven). As mentioned, other fluids (e.g., water) may also be used as control fluids in other embodiments.

In FIG. 11A, pressure actuation system 110 alternately provides positive and negative pressurizations to the gas in the actuation chamber 112 of the pod pump 101. The pneumatic actuation system 110 includes an actuation-chamber pressure transducer 114, a variable positive-supply valve 117, a variable negative-supply valve 118, a positive-pressure gas reservoir 121, a negative-pressure gas reservoir 122, a positive-pressure-reservoir pressure transducer 115, a negative-pressure-reservoir pressure transducer 116, as well as an electronic controller 119.

The positive-pressure reservoir 121 provides to the actuation chamber 112 the positive pressurization of a control gas to urge the diaphragm 109 towards a position where the pumping chamber 111 is at its minimum volume (i.e., the position where the diaphragm is against the rigid pumping-chamber wall). The negative-pressure reservoir 122 provides to the actuation chamber 112 the negative pressurization of the control gas to urge the diaphragm 109 in the opposite direction, towards a position where the pumping chamber 111 is at its maximum volume (i.e., the position where the diaphragm is against the rigid actuation-chamber wall).

A valving mechanism is used in this example to control fluid communication between each of these reservoirs 121, 122 and the actuation chamber 112. In FIG. 11A, a separate valve is used for each of the reservoirs; a positive-supply valve 117 controls fluid communication between the positive-pressure reservoir 121 and the actuation chamber 112, and a negative-supply valve 118 controls fluid communication between the negative-pressure reservoir 122 and the actuation chamber 112. These two valves are controlled by an electronic controller 119. (Alternatively, a single three-way valve may be used in lieu of the two separate valves 117, 118.) In some cases, the positive-supply valve 117 and the negative-supply valve 118 are variable-restriction valves, as opposed to binary on-off valves. An advantage of using variable valves is discussed below.

The controller 119 also receives pressure information from the three pressure transducers shown in FIG. 11A: an actuation-chamber pressure transducer 114, a positive-pressure-reservoir pressure transducer 115, and a negative-pressure-reservoir pressure transducer 116. As their names suggest, these transducers respectively measure the pressure in the actuation chamber 112, the positive-pressure reservoir 121, and the negative-pressure reservoir 122. The controller 119 monitors the pressure in the two reservoirs 121, 122 to ensure they are properly pressurized (either positively or negatively). A compressor-type pump or pumps may be used to attain the desired pressures in these reservoirs 121, 122.

In one embodiment, the pressure provided by the positive-pressure reservoir 121 is strong enough, under normal conditions, to urge the diaphragm 109 all the way against the rigid pumping-chamber wall. Similarly, the negative pressure (i.e., the vacuum) provided by the negative-pressure reservoir 122 is preferably strong enough, under normal conditions, to urge the diaphragm all the way against the rigid actuation-chamber wall. In some embodiments, however, these positive and negative pressures provided by the reservoirs 121, 122 are within safe enough limits that even with either the positive-supply valve 117 or the negative-supply valve 118 open all the way the positive or negative pressure applied against the diaphragm 109 is not so strong as to harm the patient.

In one embodiment, the controller 119 monitors the pressure information from the actuation-chamber-pressure transducer 114 and, based on this information, controls the valving mechanism (valves 117, 118) to urge the diaphragm 109 all the way to its minimum-pumping-chamber-volume position and then after this position is reached to pull the diaphragm 109 all the way back to its maximum-pumping-chamber-volume position.

The pressure actuation system (including the actuation-chamber pressure transducer 114, the positive-pressure-reservoir pressure transducer 115, the negative-pressure-reservoir pressure transducer 116, the variable positive-supply valve 117, the variable negative-supply valve 118, the controller 119, the positive-pressure gas reservoir 121, and the negative-pressure gas reservoir 122) is located entirely or mostly outside the insulated volume (item 61 of FIG. 6). The components that come into contact with blood or dialysate (namely, pod pump 101, the inlet valve 105 and the outlet valve 107) may be located, in some cases, in the insulated volume so that they can be more easily disinfected.

Figure 11B:
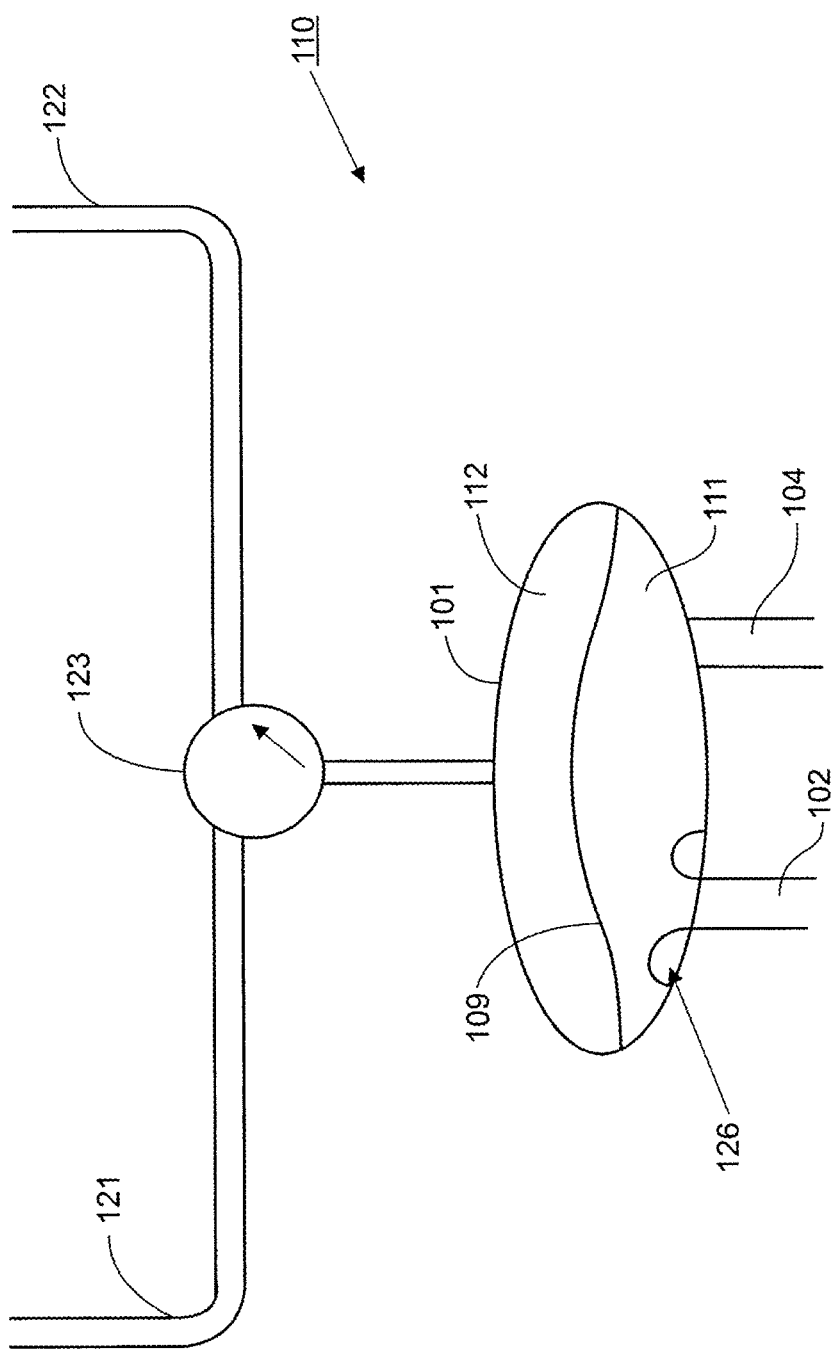

Another example of a pressure actuation system 110 for a pod pump is illustrated in FIG. 11B. In this example, pod pump 101 includes a pumping chamber 111, an actuation chamber 112, and a diaphragm 109 separating the two sides. Fluid ports 102 and 104 allow access of fluid in and out of pumping chamber 111, e.g., through the use of fluid valves (not shown). Within pod pump 101, however, fluid ports 102 and 104 include a "volcano" port 126, generally having a raised shape, such that when diaphragm 109 contacts the port, the diaphragm is able to form a tight seal against the port. Also shown in FIG. 11B is a 3-way valve connecting pressure reservoirs 121, 122. The 3-way valve 123 is in fluid communication with actuation chamber 112 by a single port in this example.

It will be appreciated that other types of actuation systems may be used to move the diaphragm back and forth instead of the two-reservoir pneumatic actuation system shown in FIGS. 11A-11B.

As noted above, the positive-supply valve 117 and the negative-supply valve 118 in the pneumatic actuation system 110 of FIG. 11A are preferably variable-restriction valves, as opposed to binary on-off valves. By using variable valves, the pressure applied to the actuation chamber 112 and the diaphragm 109 can be more easily controlled to be just a fraction of the pressure in reservoir 121, 122, instead of applying the full reservoir pressure to the diaphragm. Thus, the same reservoir or set of reservoirs may be used for different pod pumps, even though the pressures for operating the pod pumps may differ from pod pump to pod pump. Of course, the reservoir pressure needs to be greater than the desired pressures to be applied to various pod pump's diaphragms, but one pod pump may be operated at, say, half of the reservoir pressure, and another pod pump may be actuated with the same reservoir but at, say, a quarter of the reservoir pressure. Thus, even though different pod pumps in the dialysis system are designed to operate at different pressures, these pod pumps may all share the same reservoir or set of reservoirs but still be actuated at different pressures, through the use of variable valves. The pressures used in a pod pump may be changed to address conditions that may arise or change during a dialysis procedure. For example, if flow through the system's tubing becomes constricted because the tubes get twisted, one or both of the positive or negative pressures used in the pod pump may be increased in order to over compensate for the increased restriction.

Figure 12:
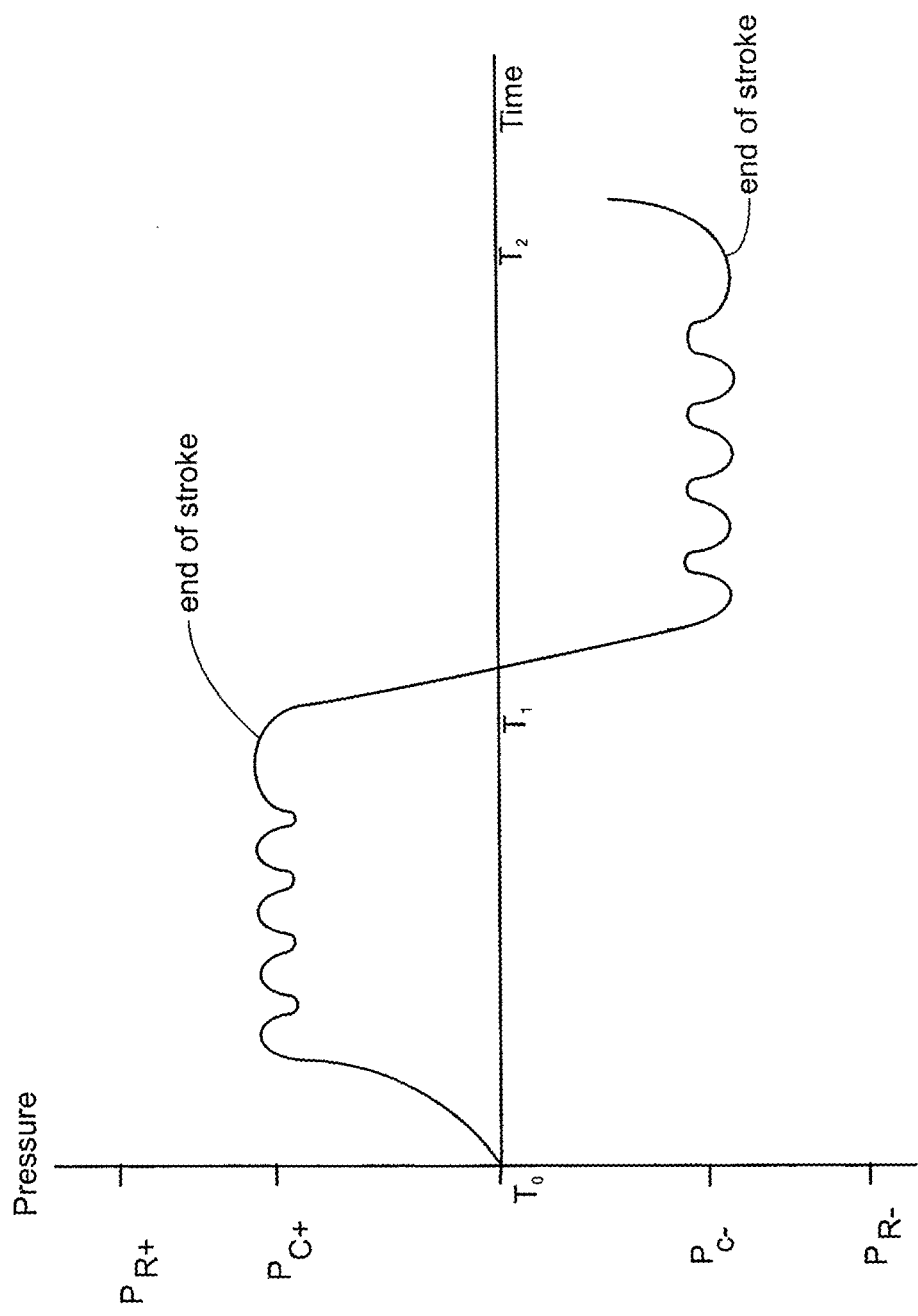
FIG. 12 is a graph showing how pressures applied to a pod pump may be controlled.

FIG. 12 is a graph showing how pressures applied to a pod pump may be controlled using variable valves. The vertical axis represents pressure with $P_{R+}$ and $P_{R-}$ representing respectively the pressures in the positive and negative reservoirs (items 121 and 122 in FIG. 11A), and $P_{C+}$ and $P_{C-}$ representing respectively the positive and negative control pressures acting on the pod pump's diaphragm. As can be seen in FIG. 12, from time $T_0$ to about time $T_1$, a positive pressure is applied to the actuation chamber (so as to force fluid out of the pumping chamber). By repeatedly reducing and increasing the flow restriction caused by the positive variable valve (item 117 in FIG. 11A), the pressure being applied to the actuation chamber can be held at about the desired positive control pressure, $P_{C+}$. The pressure varies, in a sinusoidal manner, around the desired control pressure. An actuation-chamber pressure transducer (item 114 in FIG. 11A) in communication with the actuation chamber measures the pressure in the actuation chamber and passes the pressure-measurement information to the controller (item 119 in FIG. 11A), which in turn controls the variable valve so as to cause the actuation chamber's pressure to vary around the desired control pressure, $P_{C+}$. If there are no fault conditions, the diaphragm is pushed against a rigid wall of the pumping chamber, thereby ending the stroke. The controller determines that the end of stroke has been reached when the pressure measured in the actuation chamber no longer drops off even though the restriction created by the variable valve is reduced. In FIG. 12, the end of the expelling stroke occurs around time $T_1$. When the end of stroke is sensed, the controller causes the variable valve to close completely so that the actuation chamber's pressure does not increase much beyond the desired control pressure, $P_{C+}$.

After the positive variable valve is closed, the negative variable valve (item 118 in FIG. 11A) is partially opened to allow the negative pressure reservoir to draw gas from the actuation chamber, and thus draw fluid into the pumping chamber. As can be seen in FIG. 12, from a time shortly after $T_1$ to about time $T_2$, a negative pressure is applied to the actuation chamber). As with the expelling (positive pressure), stroke described above, repeatedly reducing and increasing the flow restriction caused by the negative variable valve can cause the pressure being applied to the actuation chamber can be held at about the desired negative control pressure, $P_{C-}$ (which is weaker than the pressure in the negative pressure reservoir). The pressure varies, in a sinusoidal manner, around the desired control pressure. The actuation-chamber pressure transducer passes pressure-measurement information to the controller, which in turn controls the variable valve so as to cause the actuation chamber's pressure to vary around the desired control pressure, $P_{C-}$. If there are no fault conditions, the diaphragm is pulled against a rigid wall of the actuation chamber, thereby ending the draw (negative pressure) stroke. As described above, the controller determines that the end of stroke has been reached when the partial vacuum measured in the actuation chamber no longer drops off even though the restriction created by the variable valve is reduced. In FIG. 12, the end of the draw stroke occurs around time $T_2$. When the end of stroke is sensed, the controller causes the variable valve to close completely so that the actuation chamber's vacuum does not increase much beyond the desired negative control pressure, $P_{C-}$. Once the draw stroke has ended, the positive variable valve can be partially opened to begin a new expelling stroke with positive pressure.

Thus, each pod pump in this example uses the two variable-orifice valves to throttle the flow from the positive-pressure source and into the negative-pressure. The pressure in the actuation chamber is monitored and a controller uses this pressure measurement to determine the appropriate commands to both valves to achieve the desired pressure in the actuation chamber. Some advantages of this arrangement are that the filling and delivering pressure may be precisely controlled to achieve the desired flow rate while respecting pressure limits, and that the pressure may be varied with a small sinusoidal signature command. This signature may be monitored to determine when the pump reaches the end of a stroke.

Another advantage of using variable valves in this way, instead of binary valves, is that by only partially opening and closing the variable valves the valves are subject to less wear and tear. The repeated "banging" of binary valves all the way opened and all the way closed can reduce the life of the valve.

Figure 13A:
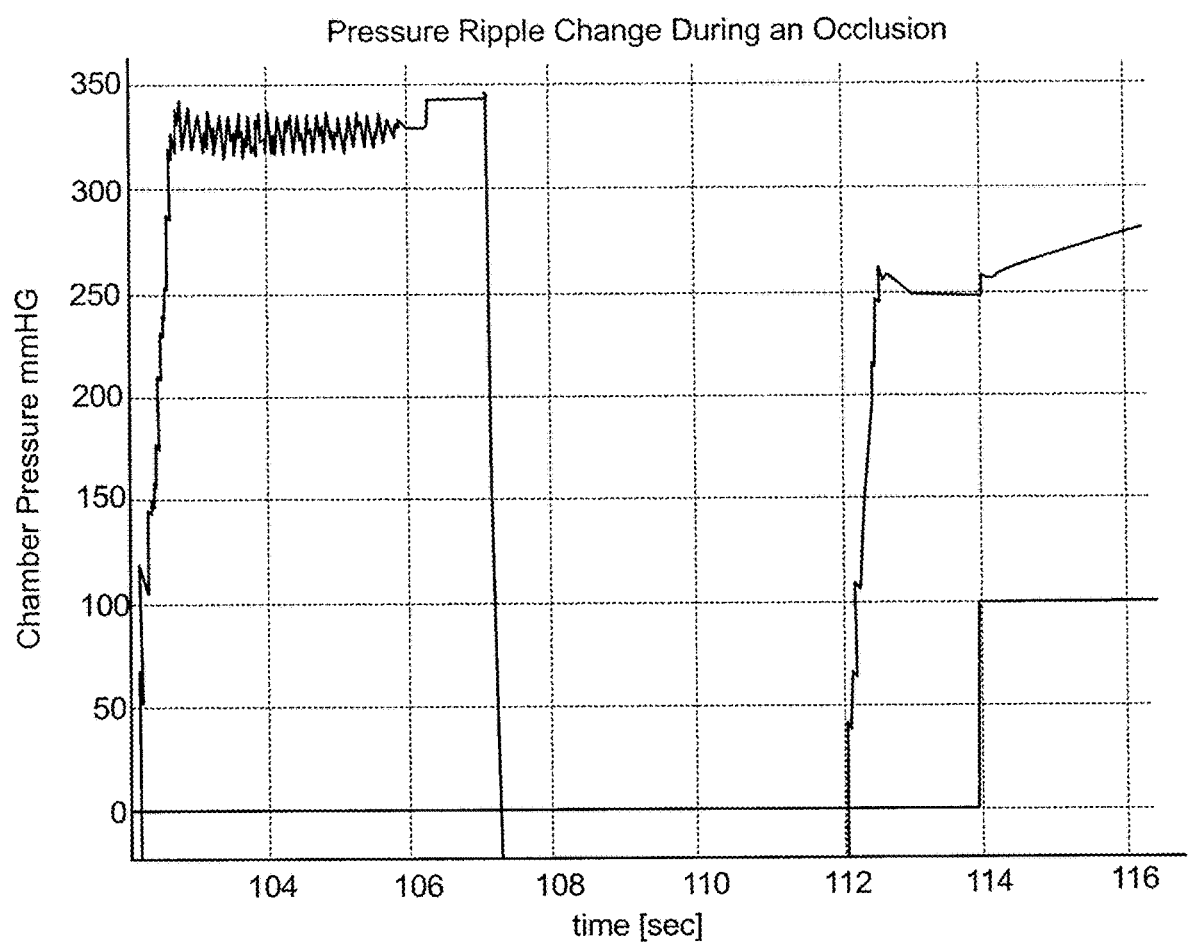
FIGS. 13A-13B are graphical representations of occlusion detection.
Figure 13B:
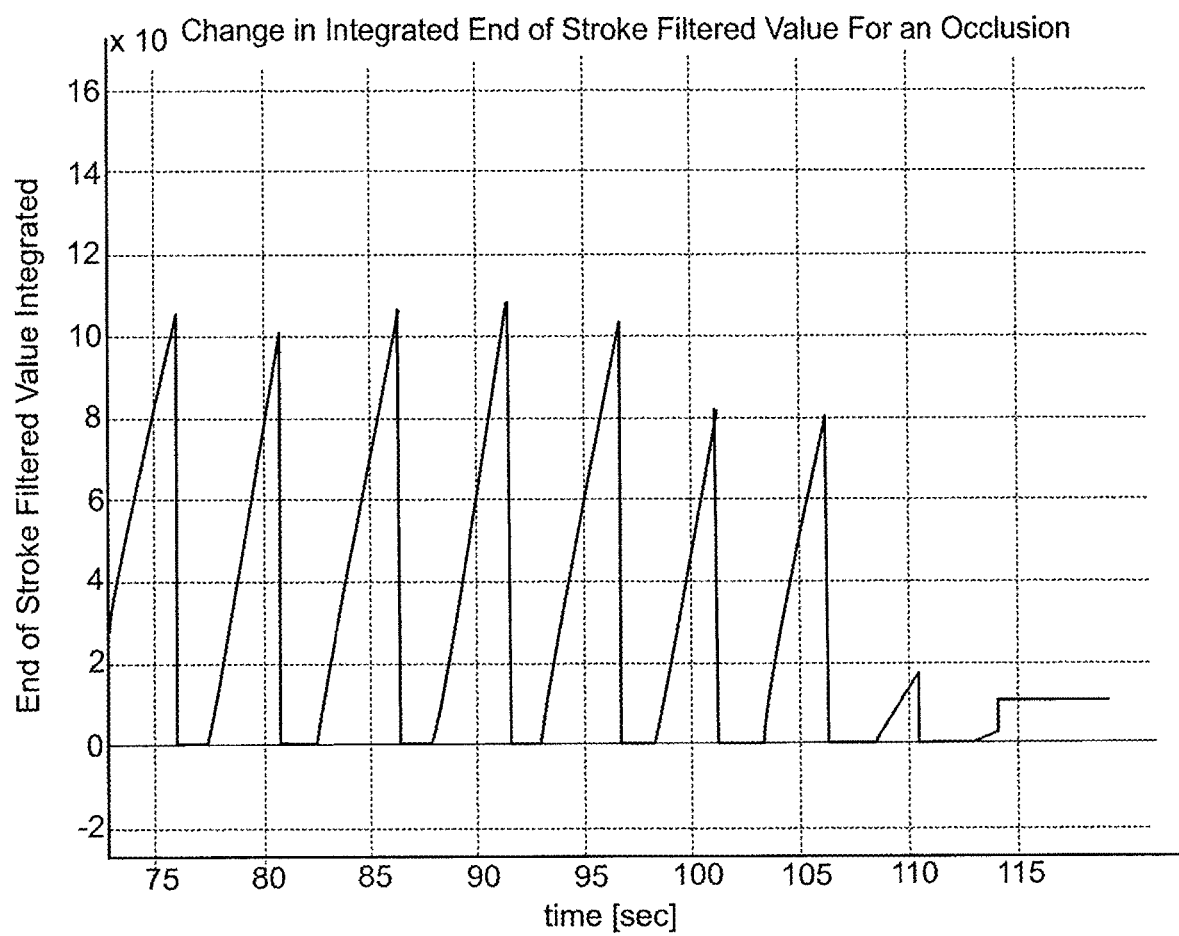

If the end of stroke is detected and the integrated value of the correlation function is very small, this may be an indication that the stroke occluded and did not complete properly. It may be possible to distinguish upstream occlusions from downstream occlusions by looking at whether the occlusion occurred on a fill or a delivery stroke (this may be difficult for occlusions that occur close to the end of a stroke when the diaphragm is near the chamber wall). FIGS. 13A-13B depict occlusion detection (the chamber pressure drops to 0 when an occlusion is detected).

Under normal operation, the integrated value of the correlation function increases as the stroke progresses. If this value remains small or does not increase the stroke is either very short (as in the case of a very low impedance flow or an occlusion) or the actual pressure may not be tracking the desired sinusoidal pressure due to a bad valve or pressure signals. Lack of correlation can be detected and used for error handling in these cases.

Under normal circumstances when the flow controller is running, the control loop will adjust the pressure for any changes in flow rate. If the impedance in the circuit increases dramatically and the pressure limits are saturated before the flow has a chance to reach the target rate, the flow controller will not be capable of adjusting the pressures higher to reach the desired flow rate. These situations may arise if a line is partially occluded, such as when a blood clot has formed in the circuit. Pressure saturation when the flow has not reached the target flow rate can be detected and used in error handling.

If there are problems with the valves or the pneumatics such as a leaking fluid valve or a noisy pressure signal, ripple may continue on the stroke indefinitely and the end of stroke algorithm may not see enough of a change in the pressure ripple to detect end of stroke. For this reason a safety check is added to detect if the time to complete a stroke is excessive. This information can be used for error handling.

In a dual pump, such as pump 13 in FIG. 3A, the two pump chambers may be cycled in opposite directions to affect the pumping cycle. A phase relationship from 0° (both chambers act in the same direction) to 180° (chambers act in opposite directions) can be selected. Phase movement may be modified somewhat in certain cases because it may not be possible to move both chambers in the same direction simultaneously; doing so could have both input or output valves open and end of stroke will not be detected properly.

Selecting a phase relationship of 180° yields continuous flow into and out of the pod. This is the nominal pumping mode when continuous flow is desired. Setting a phase relationship of 0° is useful for single needle flow. The pods will first fill from the needle and then deliver to the same needle. Running at phases between 0 and 180 degrees can be used to achieve a push/pull relationship (hemodiafiltration/continuous back flush) across the dialyzer. FIGS. 8A-8C are graphical representations of such phase relationships.

The pod pumps may control flow of fluid through the various subsystems. For instance, a sinusoidal pressure waveform may be added to a DC pressure command to make up the commanded pressure signal for the pod pumps. When the diaphragm is moving, the pressure in the pods tracks the sinusoidal command. When the diaphragm comes in contact with the chamber wall and is no longer moving, the pressure in the pod remains constant and does not track the sinusoidal input command. This difference in the pressure signal command following of the pods is used to detect the end of a stroke. From the end of stroke information, the time for each stroke is calculated. Knowing the volume of the pods and the time to complete a stroke, a flow rate for each pod can be determined. The flow rate is fed back in a PI loop in order to calculate the required DC pressure for the next stroke.

The amplitude of the sinusoidal input may be selected such it is large enough for the actual pressure to reasonably track the command and small enough such that when it is subtracted from the minimum DC pump pressure and applied to the pod, the pressure is sufficient to cause the diaphragm to move under expected operating conditions of fluid viscosity, head height and fluid circuit resistance. The frequency of the sinusoidal input was selected empirically such that it is possible to reliably detect end of stroke. The more cycles of the sine wave per stroke, the more accurate the end of stroke detection algorithm.

To detect the change in the command following of the pod pressure, the pressure signal in the pods is sent through a cross correlation filter. The size of the sampling window for the cross correlation filter is equivalent to the period of the input sine wave. For every sample in the window the commanded pressure signal is multiplied by the previous sample of the actual pressure and added to the previous correlation value. The window is then shifted by one frame and the process is repeated. The resulting product is then differentiated and passed through a second order filter with a corner frequency the same as the input sine wave frequency and a damping ratio of one. The effect of this filter is to act as a band pass filter, isolating correlated signals at the input sinusoidal frequency. The absolute value of the output of this filter is then passed through a second order low pass filter with the same frequency of the sinusoidal frequency and a damping ratio of 3.0. This second filter is used integrate the differentiated signal to and to reduce noise in the resulting signal. If the two signals are correlated, the resulting filtered value will be large. If the two signals are not correlated (for example at end of stroke), the resulting filtered value will be small. The end of stroke can be detected when the filtered cross correlation signal drops below a particular threshold, or when the signal drops off a by a percentage of its maximum value through out the stroke. To tune performance for a particular pumping scenario, this threshold or percent drop can be varied as a function of pressure or flow rate.

Since the end of stroke algorithm typically takes about one cycle of the sinusoidal ripple to detect end of stroke, minimizing this cycle time (maximizing the sine wave frequency) reduces the delay at the end of stroke. Low pressure, high frequency flows are not well tracked by the controller. Lower pressure strokes tend to have lower flow rates and thus the delay at the end of stroke is a lesser percentage of the total stroke time. For this reason, the frequency can be lower for low pressure strokes. Frequency of the sine wave can be adjusted as a linear function of the delivery pressures. This insures minimum delays when the strokes are the shortest. When the frequency of the sine wave for the desired pressure is changed, the filters for the cross correlation function must also be adjusted. Filters are set up to continuously calculate the filter coefficients based on this changing frequency.

Pressure in the pod chambers may also be controlled using two variable solenoid valves; one connecting the plenum to a higher pressure source, the second connecting the plenum to lower pressure (or vacuum) sink. Solenoid valves tend to have a large dead band region so a non-linear offset term is added to the controller to compensate.

A diagram of an example control algorithm is shown in FIG. 14. The controller in this example is a standard discrete PI controller. The output of the PI controller is split into two paths; one for the source valve, one to the sink valve. An offset term is added to each of these paths to compensate for the valve dead band. The resulting command is then limited to valves greater than zero (after being inverted in the case of the sink valve).

The offset term is positive in the case of the source valve, and negative in the case of the sink valve. As a result, both valves will be active even as the error goes to zero. These offsets do improve the trajectory following and disturbance rejection ability of the controller, but can also result in leakage from both valves at steady state if the command offsets are slightly larger than the actual valve dead band. If this is the case, the valves will have equal and opposite leakage mass flows at steady state.

To eliminate this leakage mass flow when the control system is idle, a "power save" block can be added to turn off the valves if the absolute value of the error term remains small for a period of time. This is analogous to using mechanical brakes on a servomotor.

Figure 15:
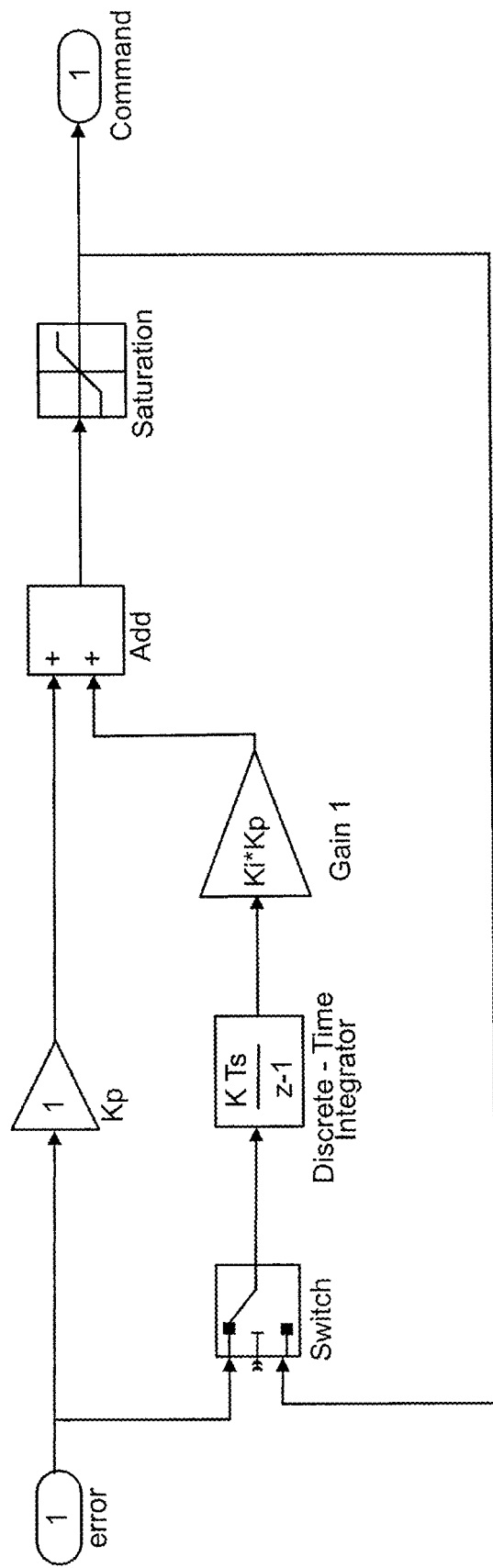
FIG. 15 is a diagram of one embodiment of the controller's standard discrete PI regulator.

Referring now to FIG. 15, the controller in this example uses a standard discrete PI regulator; a diagram of the PI regulator is shown. The integrator can be limited to prevent wind up when the commands are saturated. The integrator will always be capable of unwinding. Because there are different amounts of air in the pod for a fill and a deliver stroke, the response of the pod can be very different for a fill and deliver stroke. The proportional gain is adjusted differently for a fill and deliver stroke to better tune for the different pod responses.

The saturation limits chosen for the PI regulator should take into account the offset that will be added to the result. For example, if the valve saturates at 12V and a 5V fixed offset will be added after the PI loop, the saturation limit in the PI loop should be set to 7V. This positive and negative saturation limits will likely be different due to the different dead band in the source and sink valves.

During a fill stroke, the upstream fluid valve is closed and the down stream fluid valve is opened to allow fluid flow into the chamber. During a delivery stroke the upstream fluid valve is opened and the downstream fluid valve is closed to allow fluid flow out of the chamber. At the end of stroke, and until the next stroke starts, both fluid valves are closed.

As discussed, in certain aspects, a pod pump may be operated through action of a control fluid, for example, air, nitrogen, water, an oil, etc. The control fluid may be chosen to be relatively incompressible, and in some cases, chosen to be relatively inexpensive and/or non-toxic. The control fluid may be directed into the system towards the pumps using a series of tubes or other suitable conduits. A controller may control flow of control fluid through each of the tubes or conduits. In some cases, the control fluid may be held at different pressures within the various tubes or conduits. For instance, some of the control fluid may be held at positive pressure (i.e., greater than atmospheric pressure), while some of the control fluid may be held at negative pressures (less than atmospheric pressure) or even zero pressure (i.e., vacuum). As a specific, non-limiting example, a pod pump such as the one illustrated in FIG. 11A may be controlled through operation of the control fluid by the controller. As previously discussed, the controller (119) may open and close valves (e.g., valves 117 and 118) to expose the pneumatic side of the pod pump to a positive pressure (121) or a vacuum pressure (122) at different points during a pumping cycle.

In addition, in certain embodiments, the controller (typically electronic) may also be kept separate from the various fluid circuits, such that there is no electronic contact between the controller and the various fluid circuits, although the control fluid (e.g., air) is able to pass between the controller and the various pumps. This configuration has a number of advantages, including ease of maintenance (the controller and the various circuits can be repaired independently of each other). In one embodiment, the fluid circuits may be heated to disinfection temperatures and/or exposed to relatively high temperatures or other harsh conditions (e.g., radiation) to effect disinfection, while the electronic controller (which is typically more delicate) is not exposed to such harsh conditions, and may even be kept separate by an insulating wall (e.g., a "firewall") or the like.

Thus, in some embodiments, the system may include a "cold" section (which is not heated), and a "hot" section, portions of which may be heated, e.g., for disinfection purposes. The cold section may be insulated from the hot section through insulation. In one embodiment, the insulation may be molded foam insulation, but in other embodiments can be any type of insulation, including but not limited to a spray insulation or an insulation cut from sheets.

In some cases, the "hot" section may be heated to relatively high temperatures, e.g., the "hot" section may be heated to temperatures sufficient to sterilize components within the "hot" section. As many electronics can not go above 50° C. without failing or other adverse consequences, it may be advantageous in some embodiments to separate the electronics from other components that may be disinfected. Thus, in some cases, the components that may need to be disinfected are kept in the "hot" section, while components that cannot be heated to such temperatures are kept in the "cold" section. In one embodiment, the cold section includes a circulation system, e.g., a fan and/or a grid to allow air to flow in and out of the cold box.

All, or a portion of, the "hot" section may be encased in insulation. In some cases, the insulation may be extended to cover access points to the "hot" section, e.g., doors, ports, gaskets, and the like. For instance, when the "hot" section is sealed, the insulation may completely surround the "hot" section in some cases.

Non-limiting examples of components that may be present within the "cold" section include power supplies, electronics, power cables, pneumatic controls, or the like. In some cases, at least some of the fluids going to and from the "hot" section may pass through the "cold" section; however, in other cases, the fluids may pass to the "hot" section without passing through the "cold" section.

Non-limiting examples of components that may be present within the "hot" section include cassettes (if present), fluid lines, or the like. In some cases, some electrical components may also be included in the "hot" section. These include, but are not limited to, a heater. In one embodiment, the heater can be used to heat the hot box itself, in addition to fluid (see, e.g., heater 72 of FIG. 3A). In some embodiments, the heater heats the entire "hot" section to reach a desired temperature.

In one embodiment, the "hot" section includes some or all of the fluidic lines. In addition, in some cases, the "hot" section may include, but is not limited to, temperature and conductivity sensors, blood leak sensors, heaters, other sensors, switches, emergency lights, or the like.

In some cases, a manifold may transition from the "cold" section to the "hot" section, e.g., a manifold for air or another control fluid.

Separating the components into "hot" and "cold" sections may offer several advantages; those include, but are not limited to: longevity of electrical components, reliability, or efficiency. For example, by separating the components into hot and cold, the entire hot box may be heated. This may allows for more efficient use of heat which leads to a more energy efficient system. This also may allow for the use of standard, off the shelf electronics which leads to lower cost.

In some embodiments, the control fluid used for controlling the pumps, valves, etc. is air, and the air may be brought into the system through the operation of one or more air compressors. In some cases, the air compressor may be kept separate from the blood flow path and the dialysate flow path systems within the system, and air from the air compressor may be brought to the various pumps through various tubes, conduits, pipes, or the like. For example, in one embodiment, a pneumatic interface is used to direct air from the air compressor to a series of tubes or conduits fluidically connected with the various pumps or chambers.

Figure 16:
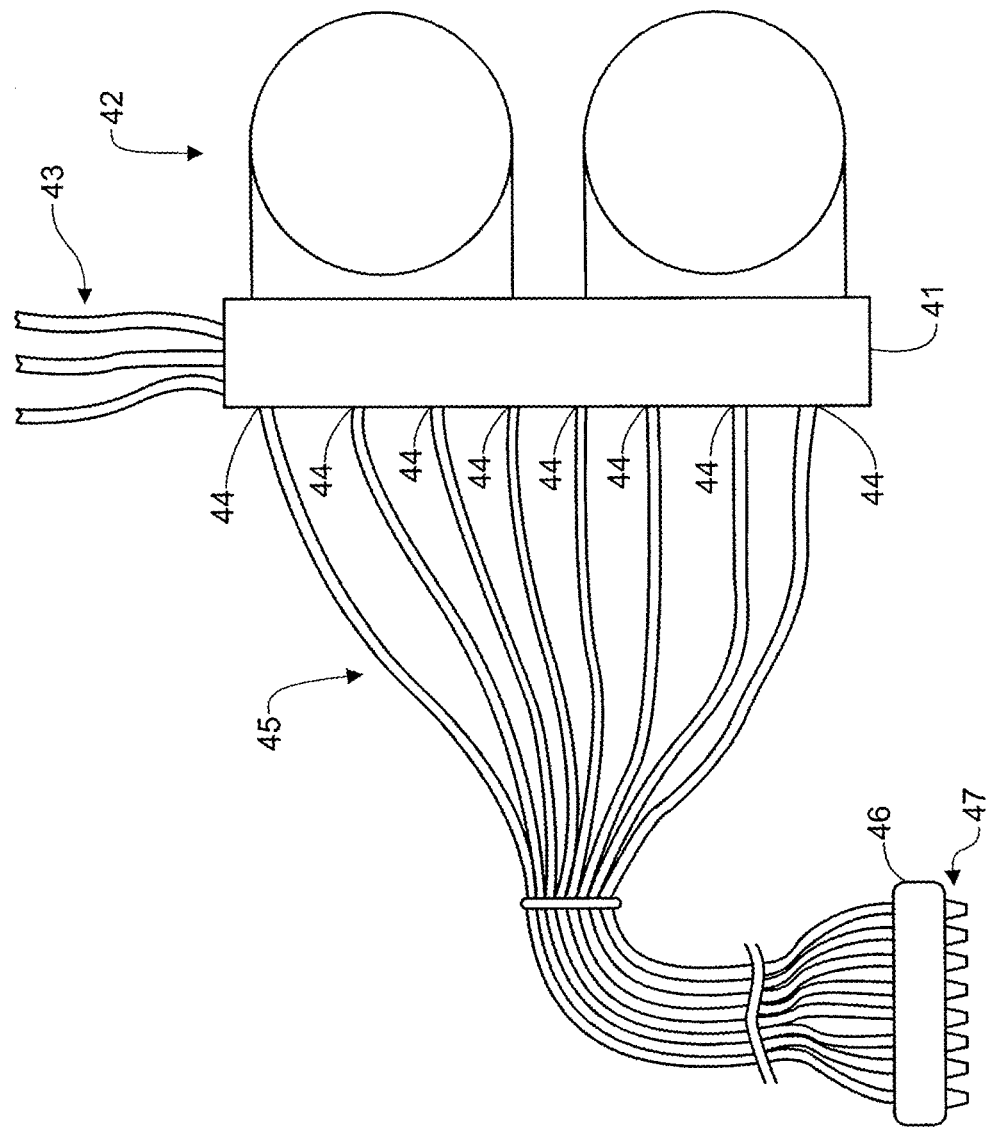
FIG. 16 is a schematic representation of a dual-housing cassette arrangement according to one embodiment.

A non-limiting example can be seen in FIG. 16, which shows a schematic representation of a dual-housing arrangement according to one embodiment. This arrangement may be advantageously used with cassettes that include many pneumatically actuated pumps and/or valves. If the number of pneumatically actuated pumps and/or valves in a cassette is large enough, the cassette containing these pumps and valves can become so large, and the pressures involved can become so great, that it may become difficult to properly seal and position all of the pumps and valves. This difficulty may be alleviated by using two or more different housings. The valves and pumps (such as pod pumps 42) are placed in a main housing 41, from which connecting tubes 45 lead from pneumatic ports 44. The main housing 41 also has inlet and outlet tubes 43, which allow liquid to flow into and out of the main housing. The connecting tubes 45 provide pneumatic communication between valves and pumps in the main housing 41 and a smaller, secondary tube-support housing 46, which is provided with a pneumatic interface 47 for each of the tubes. The proper positioning and sealing of all the pneumatic interfaces 47 against receptacles in the base unit can be accomplished more easily with the smaller tube-support housing 46 than it would be if the pneumatic actuation was applied to the larger main housing directly.

The control fluid (e.g., air) may be supplied to the system with one or more supply tanks or other pressure sources, in one set of embodiments. For instance, if two tanks are used, one supply tank may be a positive pressure reservoir, and in one embodiment, has a set point of 750 mmHg (gauge pressure) (1 mmHg is about 133.3 pascals). The other supply tank can be a vacuum or negative pressure reservoir, and in one embodiment, has a set point of −450 mmHg (gauge pressure). This pressure difference may be used, for instance, between the supply tanks and the required pod pressure to allow for accurate control of the variable valves to the pod pumps. The supply pressure limits can be set based on maximum pressures that can be set for the patient blood flow pump plus some margin to provide enough of a pressure difference for control of the variable valves. Thus, in some cases, the two tanks may be used to supply pressures and control fluids for the entire system.

In one embodiment, two independent compressors service the supply tanks. Pressure in the tanks can be controlled using any suitable technique, for instance, with a simple bang-bang controller (a controller that exists in two states, i.e., in an on or open state, and an off or closed state), or with more sophisticated control mechanisms, depending on the embodiment. As an example of a bang-bang controller, for the positive tank, if the actual pressure is less then the desired pressure minus a hysteresis, the compressor servicing the positive tank is turned on. If the actual pressure is greater then the desired pressure plus a hysteresis, the compressor servicing the positive tank is turned off. The same logic may be applied to the vacuum tank and control of the vacuum compressor with the exception that the sign of the hysteresis term is reversed. If the pressure tanks are not being regulated, the compressor is turned off and the valves are closed.

Tighter control of the pressure tanks can be achieved by reducing the size of the hysteresis band, however this will result in higher cycling frequencies of the compressor. If very tight control of these reservoirs is required, the bang-bang controller could be replaced with a PID controller and using PWM signals on the compressors. Other methods of control are also possible.

However, other pressure sources may be used in other embodiments, and in some cases, more than one positive pressure source and/or more than one negative pressure source may be used. For instance, more than one positive pressure source may be used that provides different positive pressures (e.g., 1000 mmHg and 700 mmHg), which may be used to minimize leakage. For example, high positive pressure can be used to control valves, whereas lower positive pressures can be used to control pumps. This limits the amount of pressure that can potentially be sent to the dialyzer or to the patient, and helps to keep actuation of the pumps from overcoming the pressures applied to adjacent valves. A non-limiting example of a negative pressure is −400 mmHg. In some cases, the negative pressure source may be a vacuum pump, while the positive pressure pump may be an air compressor.

Certain aspects of the invention include various sensors; for instance, in various embodiments of the inventions described herein, systems and methods for fluid handling may be utilized that comprise sensor apparatus systems comprising a sensor manifold. Examples of such embodiments may include systems and methods for the diagnosis, treatment, or amelioration of various medical conditions, including embodiments of systems and methods involving the pumping, metering, measuring, controlling, and/or analysis of various biological fluids and/or therapeutic agents, such as various forms of dialysis, cardiac bypass, and other types of extracorporeal treatments and therapies. Further examples include fluid treatment and preparation systems, including water treatment systems, water distillation systems, and systems for the preparation of fluids, including fluids utilized diagnosis, treatment, or amelioration of various medical conditions, such as dialysate.

Examples of embodiments of the inventions described herein may include dialysis systems and methods. More specifically, examples of embodiments of the inventions described herein may include hemodialysis systems and methods of the types described in U.S. patent application Ser. No. 11/871,680, filed Oct. 12, 2007 entitled "Pumping Cassette"; or U.S. patent application Ser. No. 12/038,648 entitled "Cassette System Integrated Apparatus," filed on Feb. 27, 2008, each of which is incorporated herein by reference.

In such systems and methods, the utilization of one or more sensor manifolds may allow subject media to be moved from one environment to another environment that is more conducive to obtaining sensor readings. For example, the cassette manifold may be contained in an area that is less subject to various types of environment conditions, such as temperature and/or humidity, which would not be preferable for sensor apparatus such as a sensing probe. Alternatively, sensing apparatus and sensing apparatus system may be delicate and may be more prone to malfunctions than other components of a system. Separating the sensor apparatus and the sensor apparatus systems from other components of the system by use of a sensor manifold may allow the sensing apparatus and sensing apparatus systems to be checked, calibrated, repaired or replaced with minimal impact to other components in the system. The ability to check, calibrate, repair or replace the sensor manifold with minimal impact to the remainder of the system may be advantageous when utilized in connection with the integrated cassette systems and methods described in U.S. patent application Ser. No. 12/038,648 entitled "Cassette System Integrated Apparatus," filed on Feb. 27, 2008. Alternatively, the sensor manifold may be replaced either more or less frequently than other components of the system.

With reference to FIGS. 53-58, various embodiments of an exemplary sensor manifold are shown. One or more subject media, e.g., a liquid in these exemplary embodiments, may be contained in or flow through cassette manifold 4100. For example, one subject media may enter cassette manifold 4100 via pre-molded tube connector 4101 and exit the cassette manifold via pre-molded tube connector 4102. Between tube connector 4101 and 4102, there is a fluid path though the cassette (best shown as fluid path 4225 in FIG. 54). Likewise, fluid paths (shown as fluid paths 4223, 4220, 4222, 4224, and 4221 respectively in FIG. 54) extend between sets of tube connectors 4103 and 4104; 4105 and 4106; 4107, 4108, and 4109; 4110 and 4111; and 4112 and 4113. In certain embodiments, each fluid path may contain subject media of different composition or characteristics. In other embodiments, one or more fluid paths may contain the same or similar subject media. In certain embodiments, the same subject media may be flowed through more than one flow path at the same time to check and/or calibrate the sensor apparatus systems associated with such fluid paths.

Figure 54:
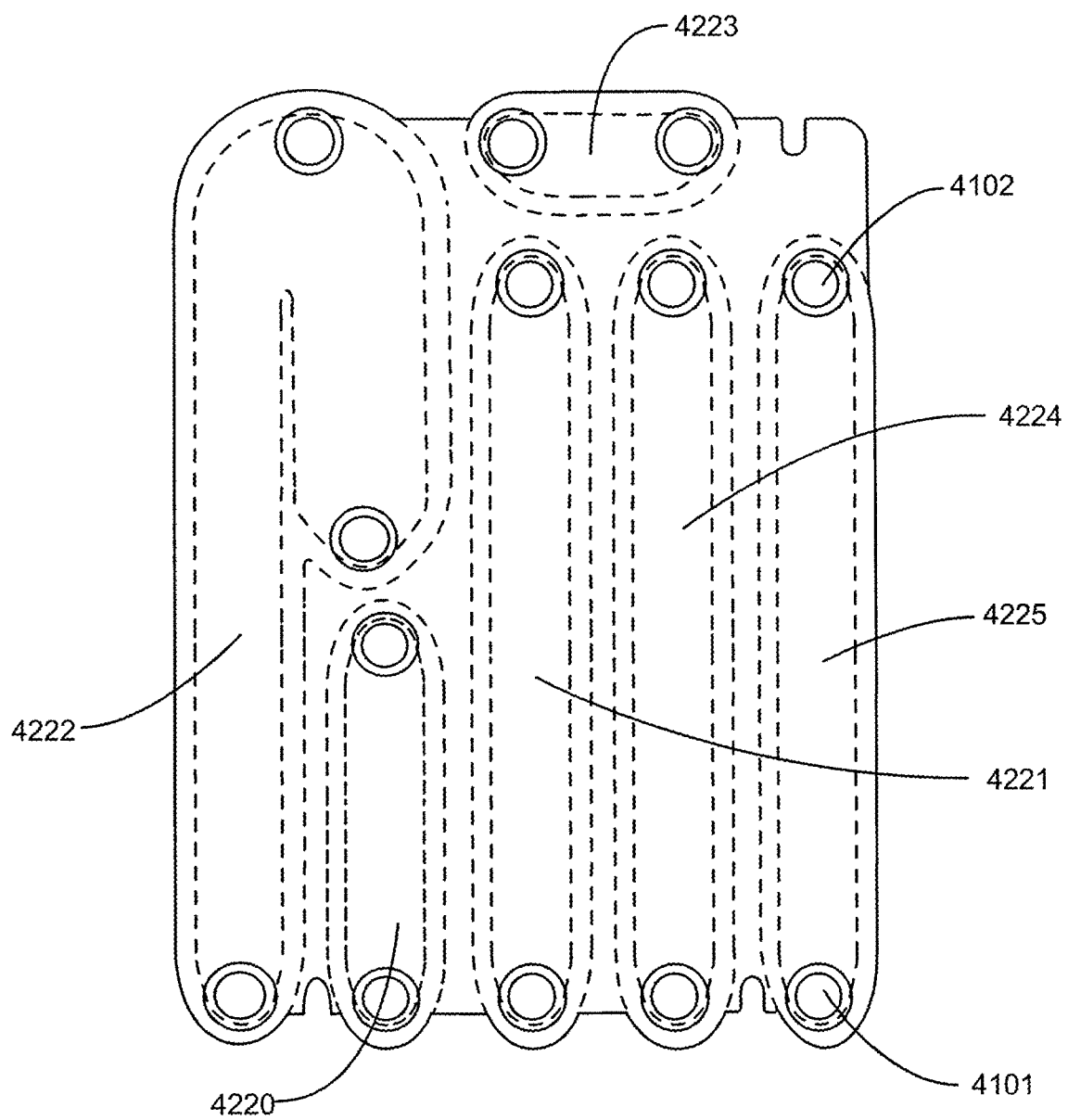
FIG. 54 is a view of the fluid paths within the exemplary sensor manifold shown in FIG. 53.
Figure 55:
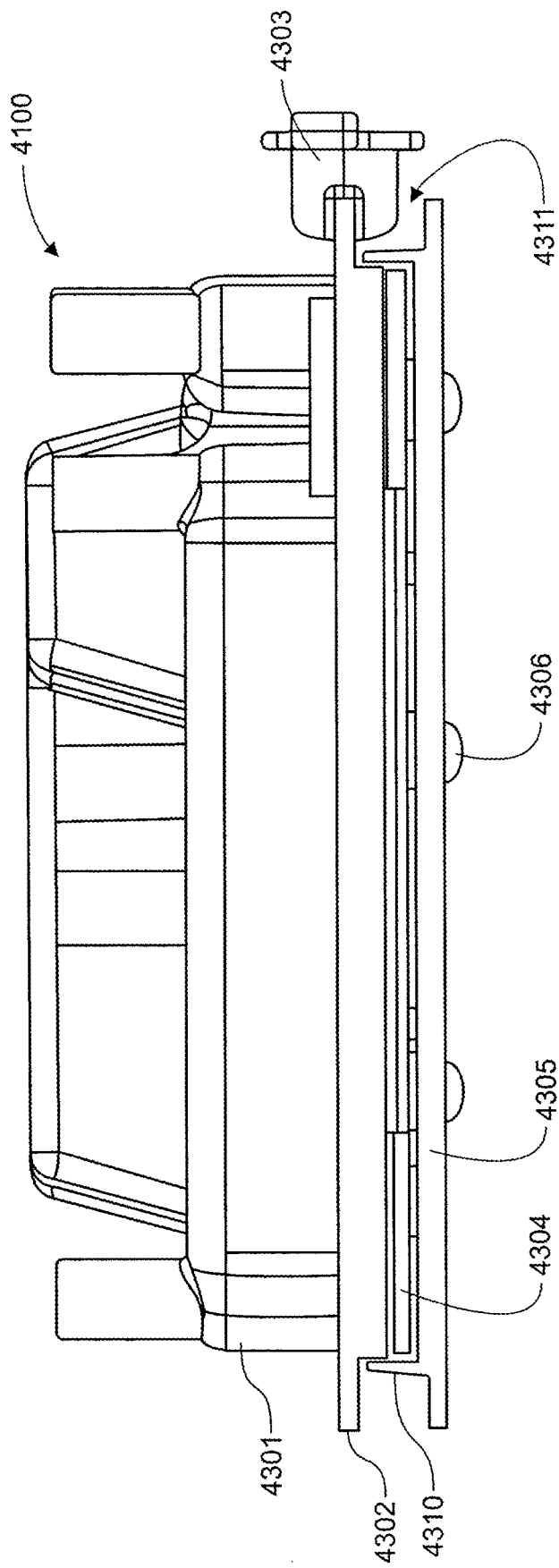
FIG. 55 is a side view of the exemplary sensor manifold shown in FIG. 53.

Referring now to FIG. 55, in these exemplary embodiments of sensor manifold 4100 that may be used in conjunction with the sensor apparatus and sensor apparatus systems described herein, the cassette includes a top plate 4302 and a base 4301. Fluid paths, such as the fluid path 4225 (as shown in FIG. 54) extending between tube connectors 4101 and 4102 extend between the base and top plate. The cassettes may be constructed from a variety of materials. Generally, in the various exemplary embodiment, the materials used are solid and non flexible. In the preferred embodiment, the plates are constructed of polysulfone, but in other embodiments, the cassettes are constructed of any other solid material and in exemplary embodiments, of any thermoplastic. Some embodiments of sensor manifold 4100 may be fabricated utilizing the systems and methods described in U.S. patent application Ser. No. 12/038,648, entitled "Cassette System Integrated Apparatus," filed on Feb. 27, 2008.

Referring again to FIG. 55, in these exemplary embodiments of sensor manifolds that may be used in conjunction with the sensor apparatus and sensor apparatus systems described herein, the sensor manifold 4100 may also include printed circuit board (PCB) 4304 and a PCB cover 4305. Various embodiments may also include connector 4303 (also shown in FIGS. 53 and 56B) which may be utilized to mechanically connect the cassette manifold 4100 to the system, such as a hemodialysis system. Cassette manifold 4100 may also utilize various methods to hold the layers of sensor manifold 4100 together as a unit. In various embodiments, as shown in FIG. 43, connectors 4306 (also shown in FIG. 56B), which in one embodiment is a screw, but in other embodiments may be any means for connection, are utilized, but any means known to one of skill in the art, such as other types of screws, welds, clips, clamps, and other types of chemical and mechanical bonds may be utilized.

Figure 56A:
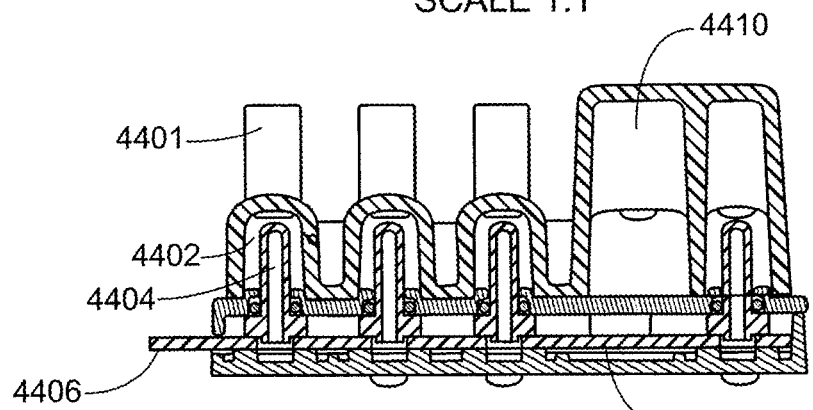
FIG. 56A is a cross sectional view of the exemplary sensor manifold shown in FIG. 53 at cross section A-A of FIG. 56B.

Referring now to FIG. 56A, in exemplary embodiments of the sensor manifold 4100, tube connectors, such as tube connector 4401, is utilized to bring subject media into or remove subject media from fluid path 4402. Sensing probes, such as sensing probe 4404 extending into fluid path 4402, are incorporated into sensor manifold 4100 so as to determine various properties of the subject media contained in or flowing through the particular fluid path in the sensor manifold. In various embodiments one sensing probe may be utilized to sense temperature and/or other properties of the subject media. In another embodiment, two sensing probes may be utilized to sense temperature and/or conductivity and/or other properties of the subject media. In yet further embodiments, three or more sensing probes may be included. In some embodiments, one or more combination temperature and conductivity sensing probes of the types generally described herein may be utilized. In other embodiments, the conductivity sensors and temperature sensor can be any conductivity or temperature sensor in the art. In one embodiment, the conductivity sensor elements (or sensor leads) are graphite posts. In other embodiments, the conductivity sensors elements are posts made from stainless steel, titanium, or any other material of the type typically used for (or capable of being used for) conductivity measurements. In certain embodiments, the conductivity sensors will include an electrical connection that transmits signals from the sensor lead to a sensor mechanism, controller or other device. In various embodiments, the temperature sensor can be any of the temperature sensors commonly used (or capable of being used) to sense temperature.

Figure 53:
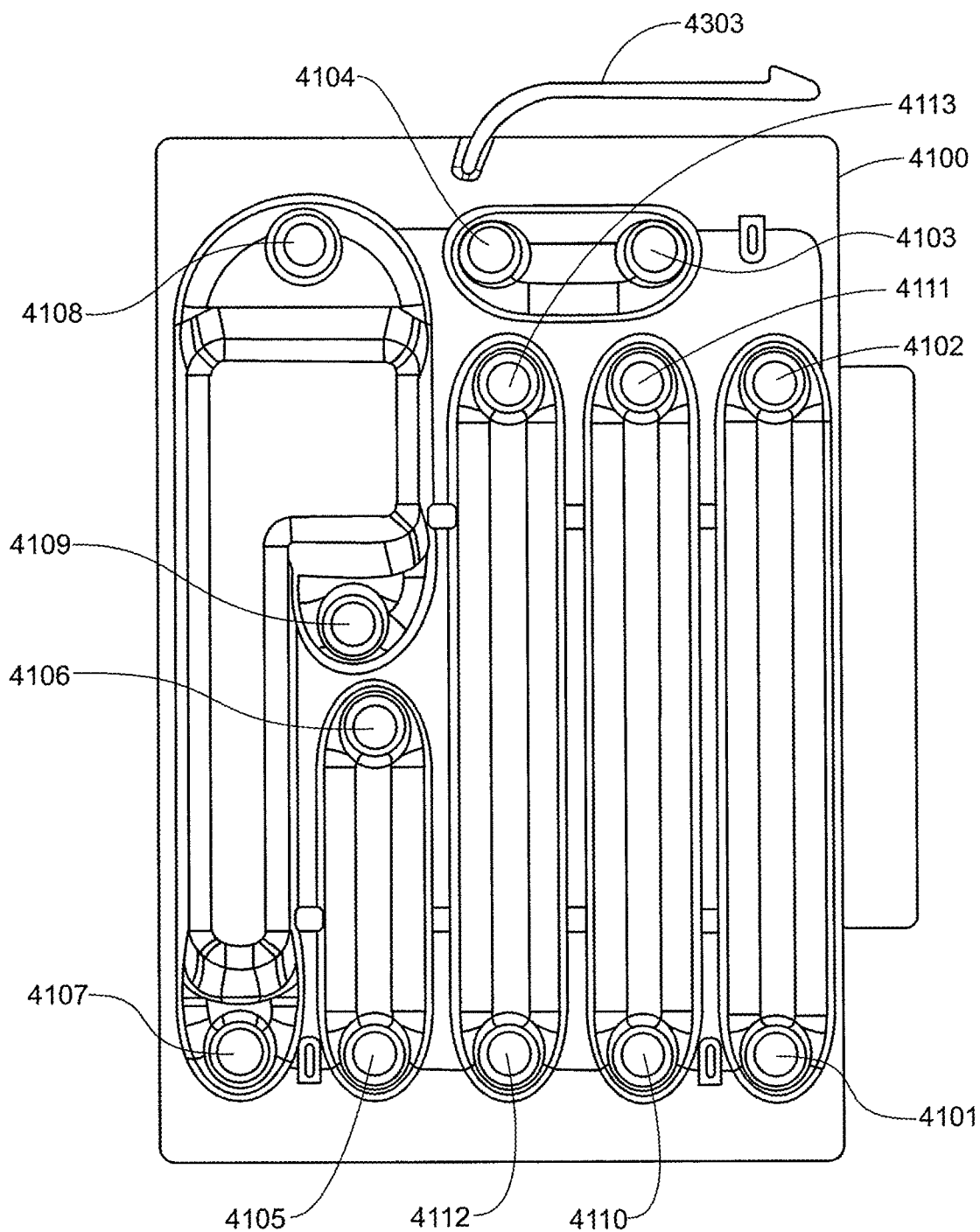
FIG. 53 is a view of another exemplary sensor manifold.

Referring again to FIG. 56A, sensing probe 4404 is electrically connected to PCB 4405. In certain embodiments, an electrically conductive epoxy is utilized between sensor element 4404 and PCB 4405 to ensure appropriate electrical connection, although other methods known to those of skill in the art may be used to obtain an appropriate electrical connection between sensor element 4404 and PCB 4405. PCB 4405 is shown with edge connector 4406. In various embodiments, edge connector 4406 may be used to transmit sensor information from cassette manifold 4100 to the main system. Edge connector 4406 may be connected to a media edge connector (such as media edge connector 4601 shown in FIG. 58). In various embodiments, media edge connector 4601 may be installed in a hemodialysis machine (not shown). In such embodiments, guide tracks 4310 and 4311 (as shown in FIG. 55) may be utilized to assist in the connection of edge connector 4406 and media edge connector 4601. Various embodiments may also include connector 4303 (as shown in FIGS. 53, 55 and 56B) which may be utilized to mechanically connect the cassette manifold 4100 to the system, such as a hemodialysis system.

Referring again to FIG. 56A, air trap 4410 is shown. In certain embodiments, an air trap, such as air trap 4410, may be utilized to trap and purge air in the system. As may be best shown in FIG. 54, subject media may flow through fluid path 4222 between tube connectors 4107 and 4109 in sensor manifold 4100. As the flow of the subject media is slowed around the turn in fluid path 4222 (near tube connector 4108), air may be removed from the subject media through connector 4108.

Figure 56B:
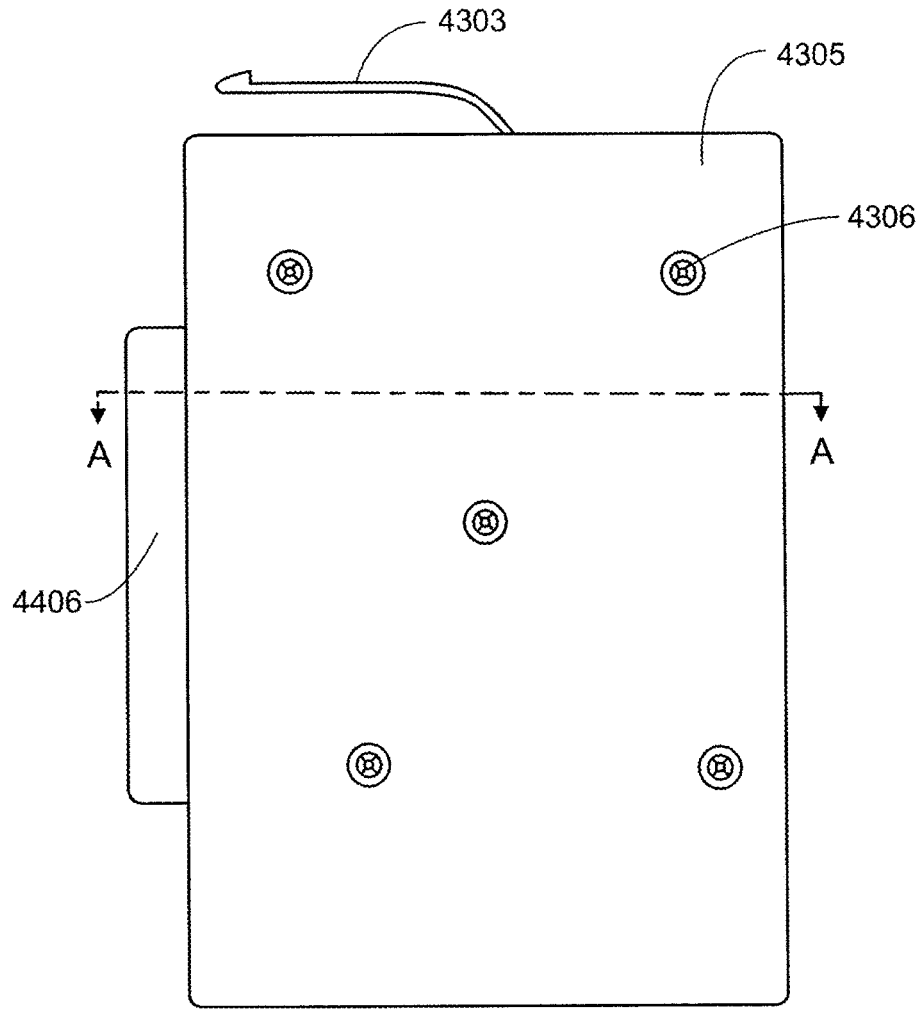
FIG. 56B is a front view of the exemplary sensor manifold shown in FIG. 53.

Referring now to FIG. 56B, PCB cover 4305 is shown. PCB cover 4305 may be connected to sensor manifold 4100 by connectors 4306. Edge connector 4406 is also shown.

In accordance with certain embodiments, sensor manifold 4100 is passive with respect to control of the fluid flow. In such embodiments, sensor manifold 4100 does not contain valves or pumping mechanisms to control the flow of the subject media. In such embodiments, the flow of the subject media may be controlled by fluid control apparatus external to sensor manifold 4100. In other embodiments, the sensor manifold may include one or more mechanical valves, pneumatic valves or other type of valve generally used by those of skill in the art. In such embodiments, the sensor manifold may include one or more pumping mechanisms, including pneumatic pumping mechanisms, mechanical pumping mechanisms, or other type of pumping mechanisms generally used by those of skill in the art. Examples of such valves and pumping mechanisms may include the valves and pumping mechanisms described in U.S. patent application Ser. No. 11/871,680, filed Oct. 12, 2007 entitled "Pumping Cassette"; or U.S. patent application Ser. No. 12/038,648, entitled "Cassette System Integrated Apparatus," filed on Feb. 27, 2008.

Figure 57:
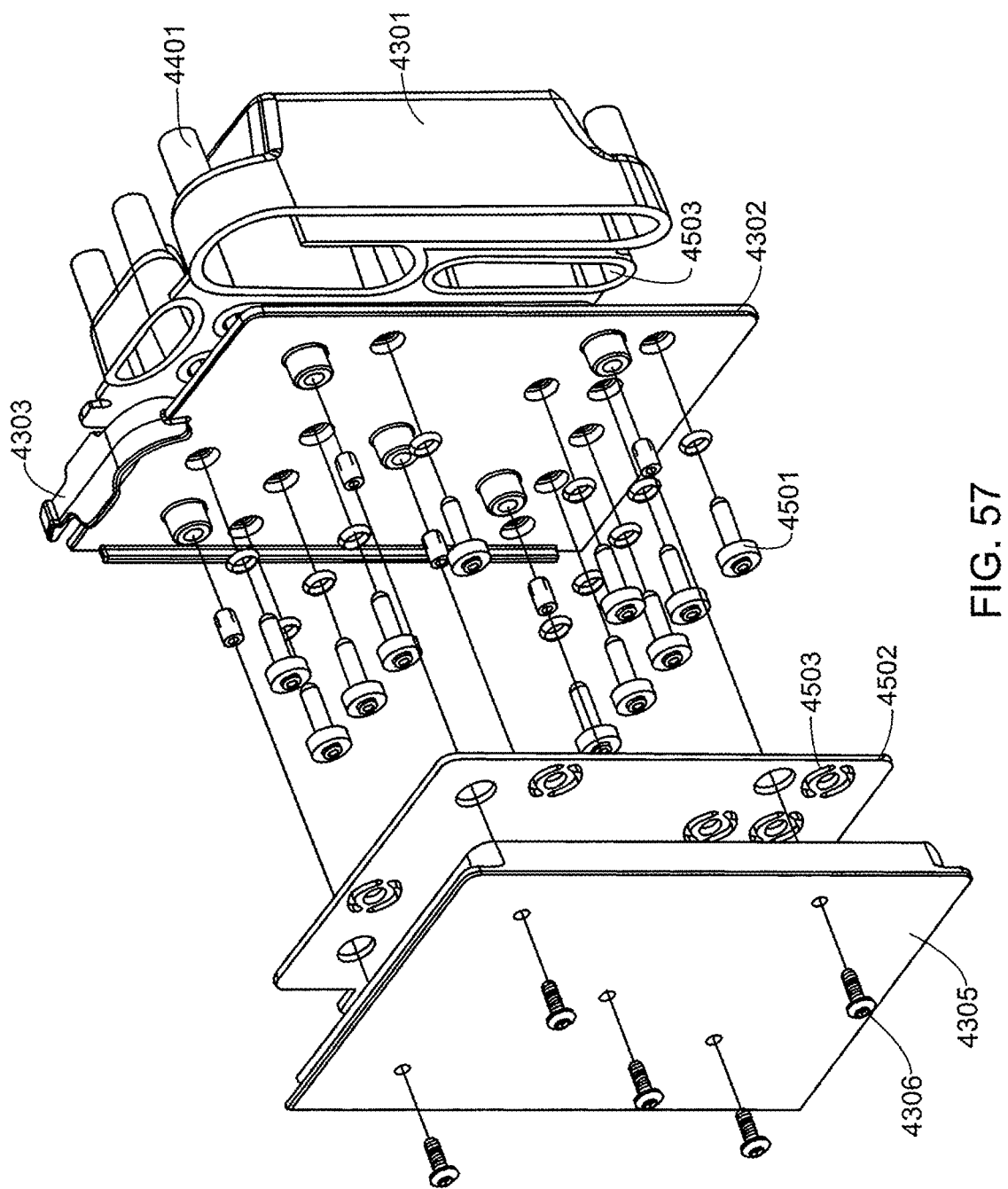
FIG. 57 is an exploded view of the exemplary sensor manifold shown in FIG. 53.
Figure 58:
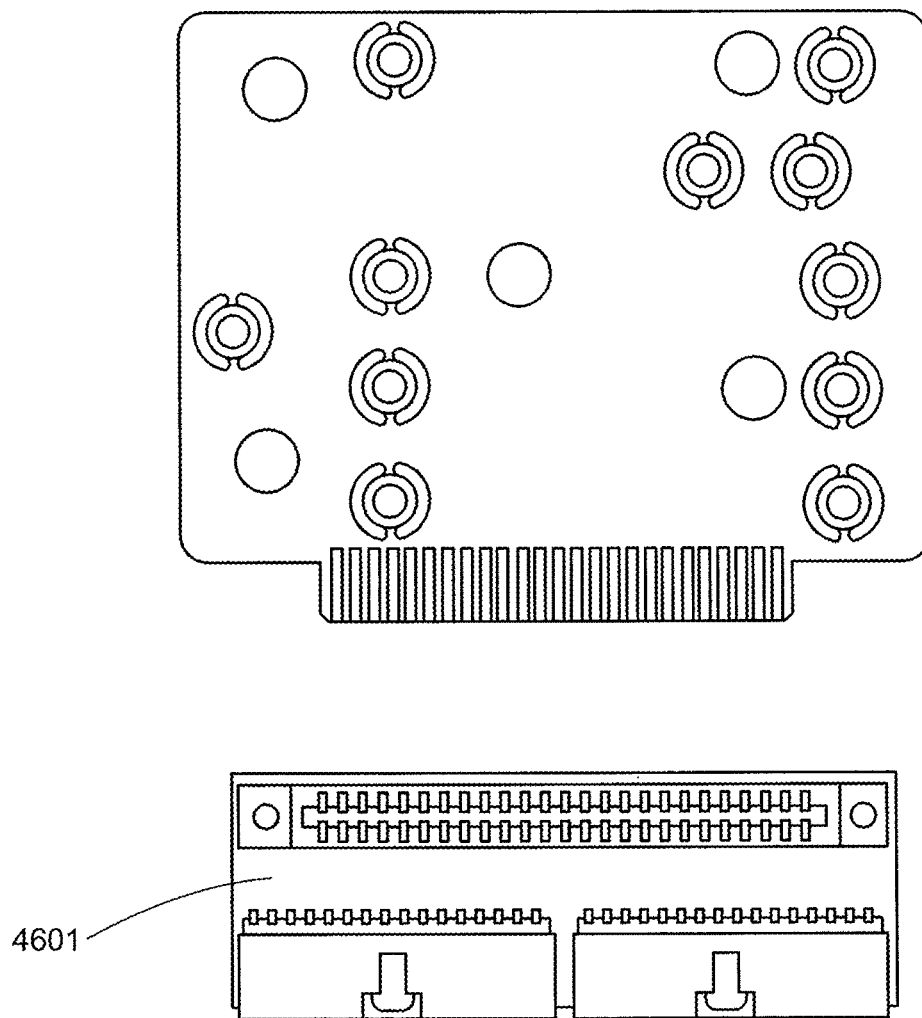
FIG. 58 is a view of a printed circuit board and media edge connector in accordance with the exemplary sensor manifold shown in FIG. 53.

Referring now to FIG. 57, tube connector 4401 is shown in base 4301. Top plate 4302 is shown, along with connector 4303. Sensing probes, such as sensing probe 4501, extend through top plate 4302 into fluid path 4503. Sensing probe 4501 may be various types of sensors, including the embodiments of sensing probes generally discussed herein.

The sensing probes, such as sensing probe 4501, may be all the same, may be individually selected from various sensors based on the type of function to be performed, or the same probe may be individually modified based on the type of function to be performed. Similarly, the configuration of the fluid paths, such as the length of the fluid path and the shape of the fluid path, may be selected based on the function to be performed. By way of example, to detect the temperature of the subject media in a fluid path, a temperature sensor, such as a thermistor, may be used. Again, by way of example, to measure the conductivity of the subject media, one sensing probe configured to measure temperature and conductivity, and one sensing probe configured only to measure conductivity may be utilized. In other embodiments, two or more sensing probes configured to measure both temperature and conductivity may be utilized. In various embodiments of such configurations, by way of example, the second temperature sensor may be present but not utilized in normal operation, or the second temperature may be utilized for redundant temperature measurements, or the or the second temperature may be utilized for redundant temperature measurements.

Referring again to FIG. 57, PCB 4502 is shown with electrical connection 4503. As further shown in FIG. 58, PCB 4602 is shown with electrical connection 4603 for connection to a sensing probe (shown as 4501 in FIG. 45). PCB 4602 also contains opening 4604 for attachment to top plate (shown as 4305 in FIG. 57). In certain embodiments, electrical connection 4603 is mounted onto, or manufactured with, PCB 4602 with air gap 4606. In such embodiments, air gap 4606 may be utilized to provide protection to the electrical connection between sensing probe 4501 and PCB 4602 by allowing shrinking and expansion of the various components of sensor manifold 4100 with lesser impact to PCB 4602.

Referring again to FIG. 58, PCB 4602 is also shown with edge connector 4605. As described herein, edge connector 4605 may interface with edge connector receiver 4601, which may be connected to the system, such as the hemodialysis system, to which sensor manifold 4100 interfaces.

Figure 59:
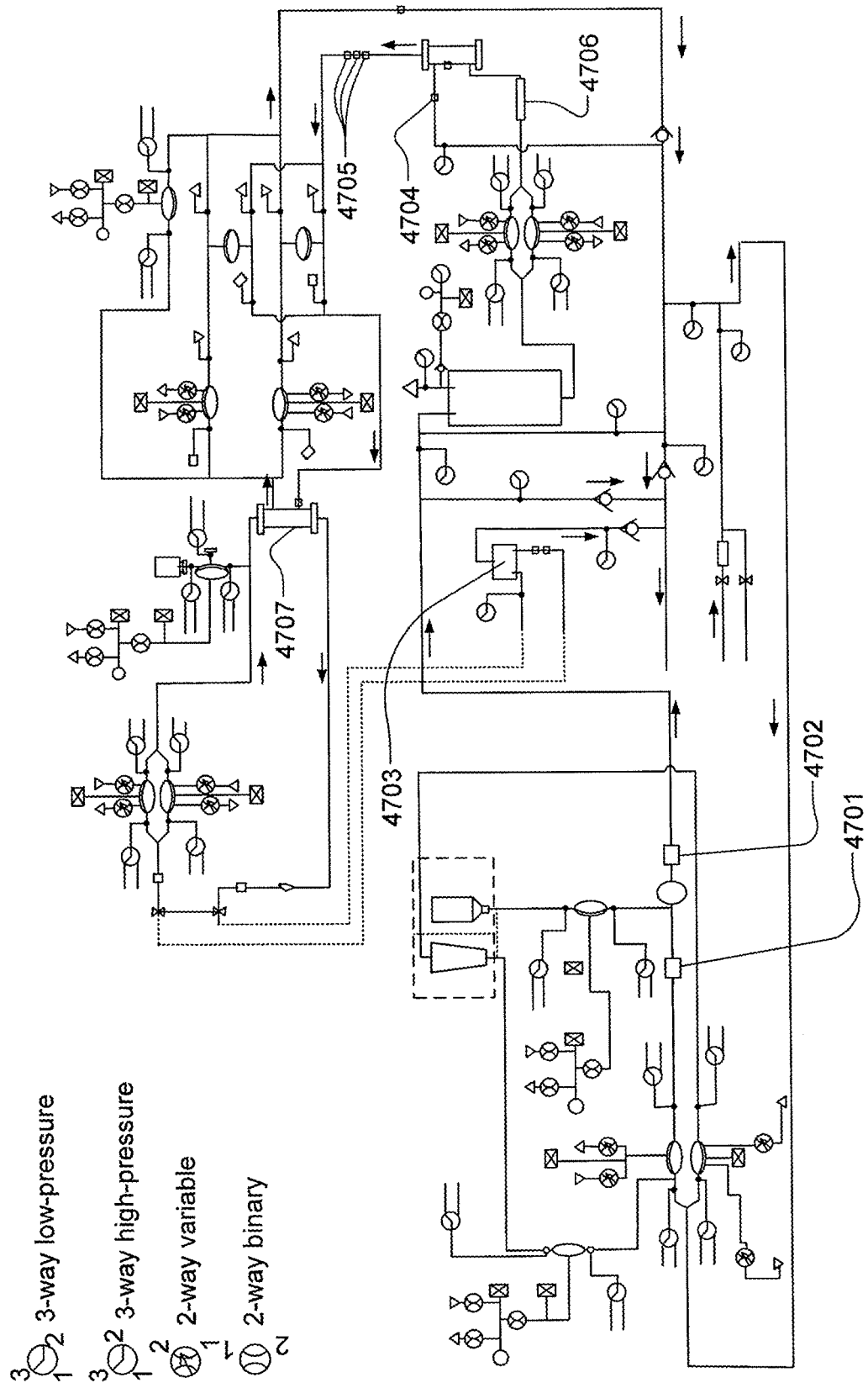
FIG. 59 is an exemplary fluid schematic of a hemodialysis system.

Various embodiments of exemplary sensor manifold 4100 shown in FIG. 53-58 may be utilized in conjunction with hemodialysis systems and methods described in U.S. patent application Ser. No. 11/871,680, filed Oct. 12, 2007 entitled "Pumping Cassette"; or U.S. patent application Ser. No. 12/038,648, entitled "Cassette System Integrated Apparatus," filed on Feb. 27, 2008. In certain embodiments, sensor manifold 4100 contains all of the temperature and conductivity sensors shown in FIG. 59. FIG. 59 depicts a fluid schematic in accordance with one embodiment of the inventions described in the patent applications reference above.

By way of example, in various embodiments, the temperature and conductivity of the subject media at position 4701 as shown in FIG. 59 may be determined utilizing sensor manifold 4100. In such embodiments, subject media flows into tube connector 4105 (as shown in FIG. 53) through fluid path 4220 (as shown in FIG. 54) and exits at tube connector 4106 (as shown in FIG. 53). The conductivity of the subject media is measured by two sensing probes (not shown) extending into fluid path 4220, at least one of which has been configured to include a temperature sensing element, such as a thermistor. The conductivity measurement or the temperature measurement of the subject media may be utilized to determine and/or correlate a variety of information of utility to the hemodialysis system. For example, in various embodiments at position 4701 in FIG. 59, the subject media may be comprised of water to which a bicarbonate-based solution has been added. Conductivity of the subject media at position 4701 may be utilized to determine if the appropriate amount of the bicarbonate based solution has been added prior to position 4701. In certain embodiments, if the conductivity measurement deviates from a predetermined range or deviates from a predetermined measurement by more than a predetermined amount, then the subject media may not contain the appropriate concentration of the bicarbonate based solution. In such instances, in certain embodiments, the hemodialysis system may be alerted.

Again, by way of example, in various embodiments, the conductivity of the subject media at position 4702 as shown in FIG. 59 may be determined utilizing sensor manifold 4100. In such embodiments, subject media flows into tube connector 4112 (as shown in FIG. 41) through fluid path 4221 (as shown in FIG. 54) and exits at tube connector 4113 (as shown in FIG. 53). The conductivity of the subject media is measured by two sensing probes (not shown) extending into fluid path 4221, at least one of which has been configured to include a temperature sensing element, such as a thermistor. The conductivity measurement or the temperature measurement of the subject media may be utilized to determine and/or correlate a variety of information of utility to the hemodialysis system. For example, in various embodiments at position 4702 in FIG. 59, the subject media may be comprised of water to which a bicarbonate-based solution and then an acid based solution has been added. Conductivity of the subject media at position 4702 may be utilized to determine if the appropriate amount of the acid based solution (and the bicarbonate based solution in a previous step) has been added prior to position 4702. In certain embodiments, if the conductivity measurement deviates from a predetermined range or deviates from a predetermined measurement by more than a predetermined amount, then the subject media may not contain the appropriate concentration of the acid based solution and the bicarbonate based solution. In such instances, in certain embodiments, the hemodialysis system may be alerted.

By way of further example, in various embodiments, the temperature and conductivity of the subject media at position 4703 as shown in FIG. 59 may be determined utilizing sensor manifold 4100. In such embodiments, subject media may flow into or out of tube connector 4107 (as shown in FIG. 53) through fluid path 4222 (as shown in FIG. 54) and may flow into or out of tube connector 4109 (as shown in FIG. 53). As described herein, air may be removed from the subject media as it moves past the turn in fluid path 4222. In such instances, a portion of the subject media may be removed through tube connector 4108 to the drain, bringing with it air from the air trap. The conductivity of the subject media is measured by two sensing probes (not shown) extending into fluid path 4222, at least one of which has been configured to include a temperature sensing element, such as a thermistor. The conductivity measurement or the temperature measurement of the subject media may be utilized to determine and/or correlate a variety of information of utility to the hemodialysis system. For example, in various embodiments, the conductivity measurement at position 4703 in FIG. 59 may be utilized to correlate to the clearance of the dialyzer. In such instances, in certain embodiments, this information may then be sent to the hemodialysis system.

Again, by way of further example, in various embodiments, the temperature of the subject media at position 4704 as shown in FIG. 59 may be determined utilizing sensor manifold 4100. In such embodiments, subject media flows into tube connector 4103 (as shown in FIG. 53) through fluid path 4223 (as shown in FIG. 54) and exits at tube connector 4104 (as shown in FIG. 53). The temperature of the subject media is measured by one or more sensing probes (not shown) extending into fluid path 4223. The temperature measurement of the subject media at position 4704 may be utilized to determine and/or correlate a variety of information of utility to the hemodialysis system. For example, in various embodiments at position 4704 in FIG. 59, the temperature of the subject media is determined down stream of a heating apparatus 4706. If the temperature deviates from a predetermined range or deviates from a predetermined measurement by more than a predetermined amount, then the hemodialysis system may be alerted. For example in certain embodiments, the subject media may be re-circulated through the heating apparatus 4706 until the temperature of the subject media is within a predetermined range.

Again, by way of further example, in various embodiments, the temperature and conductivity of the subject media at position 4705 as shown in FIG. 59 may be determined utilizing sensor manifold 4100. In such embodiments, subject media flows into tube connector 4110 (as shown in FIG. 53) through fluid path 4224 (as shown in FIG. 54) and exits at tube connector 4111 (as shown in FIG. 53). The conductivity of the subject media is measured by two sensing probes (not shown) extending into fluid path 4224, at least one of which has been configured to include a temperature sensing element, such as a thermistor. The conductivity measurement or the temperature measurement of the subject media may be utilized to determine and/or correlate a variety of information of utility to the hemodialysis system. For example, the temperature and conductivity measurement at position 4705 may be used as a further safety check to determine if the temperature, conductivity, and, by correlation, the composition of, the subject media is within acceptable ranges prior to the subject media reaching the dialyzer 4707 and, thus, the patient. In certain embodiments, if the temperature and/or conductivity measurement deviates from a predetermined range or deviates from a predetermined measurement by more than a predetermined amount, then the hemodialysis system may be alerted.

For the various embodiments described herein, the cassette may be made of any material, including plastic and metal. The plastic may be flexible plastic, rigid plastic, semi-flexible plastic, semi-rigid plastic, or a combination of any of these. In some of these embodiments the cassette includes one or more thermal wells. In some embodiments one or more sensing probes and/or one or more other devices for transferring information regarding one or more characteristics of such subject media are in direct contact with the subject media. In some embodiments, the cassette is designed to hold fluid having a flow rate or pressure. In other embodiments, one or more compartments of the cassette is designed to hold mostly stagnant media or media held in the conduit even if the media has flow.

In some embodiments, the sensor apparatus may be used based on a need to separate the subject media from the sensing probe. However, in other embodiments, the sensing probe is used for temperature, conductivity, and/or other sensing directly with subject media.

Another aspect of the invention is generally directed to methods and operations of the systems as discussed herein. For instance, a hemodialysis system may be primed, flow-balanced, emptied, purged with air, disinfected, or the like.

Figure 17A:
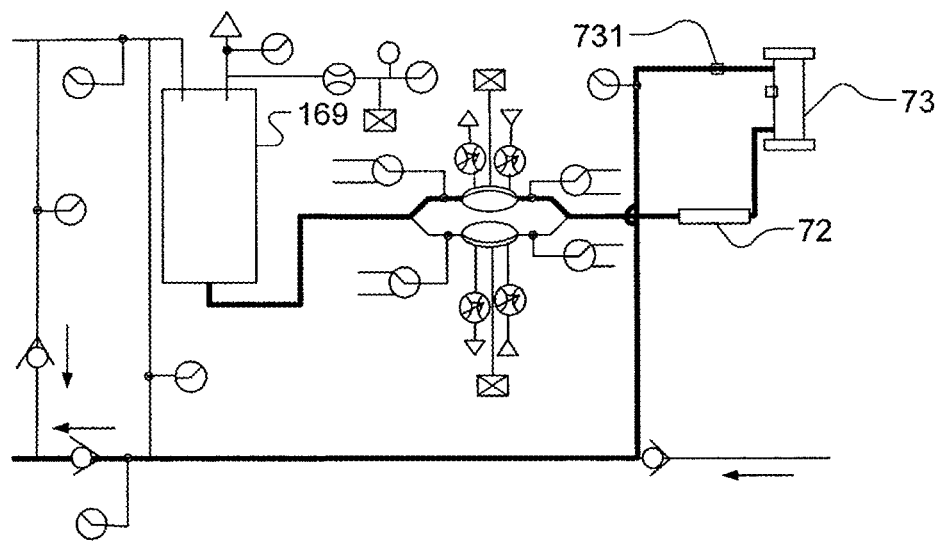
FIGS. 17A-17C are schematics relating to the priming of a portion of a system, in one embodiment of the invention.

One set of embodiments is generally directed to priming of the system with a fluid. The fluid to be primed is first directed to a dialysate tank (e.g. dialysate tank 169). Ultrafilter 73 is then first primed by pushing fluid from dialysate tank 169 to ultrafilter 73, and caused to exit line 731 through waste line 39 to the drain, as is shown by the heavy black lines in FIG. 17A. Any air present in ultrafilter 73 naturally rises to the priming port and is flushed to the drain.

Figure 17B:
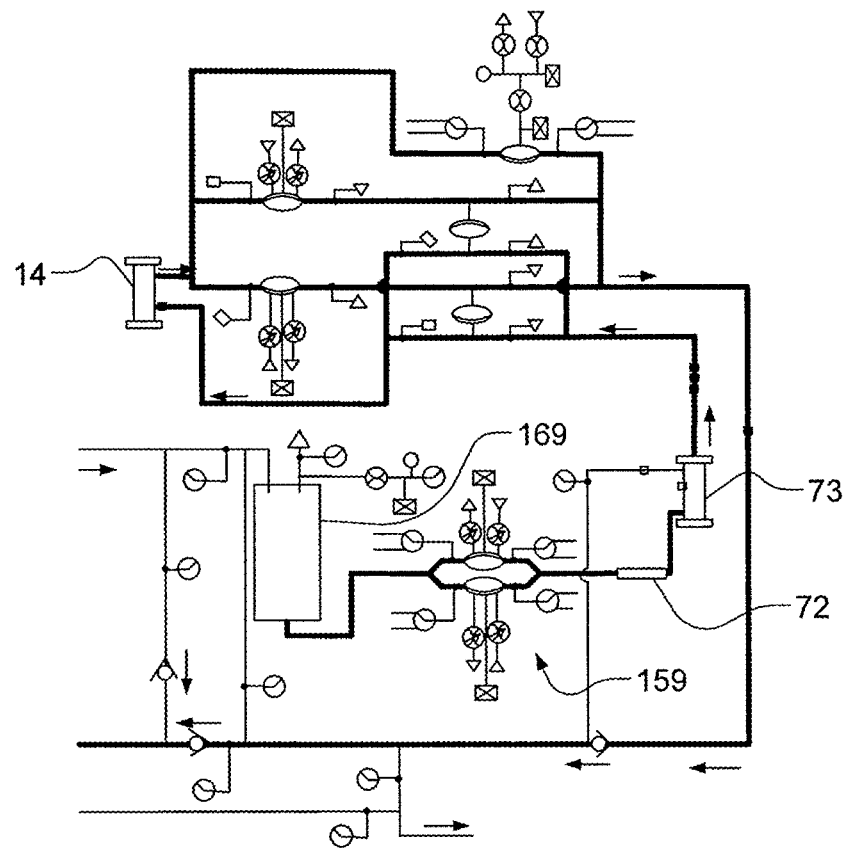

Next, as is shown in FIG. 17B, the balancing circuit and pump 159 of the directing circuit are primed by pushing fluid through the ultrafilter 73, through the balancing circuit, and out to the drain. Pump 159 is primed by running fluid forwards (through the ultrafilter to the drain). Air entering dialyzer 14 bubbles to the top of the dialyzer and leaves through the dialyzer exit to the drain.

Figure 17C:
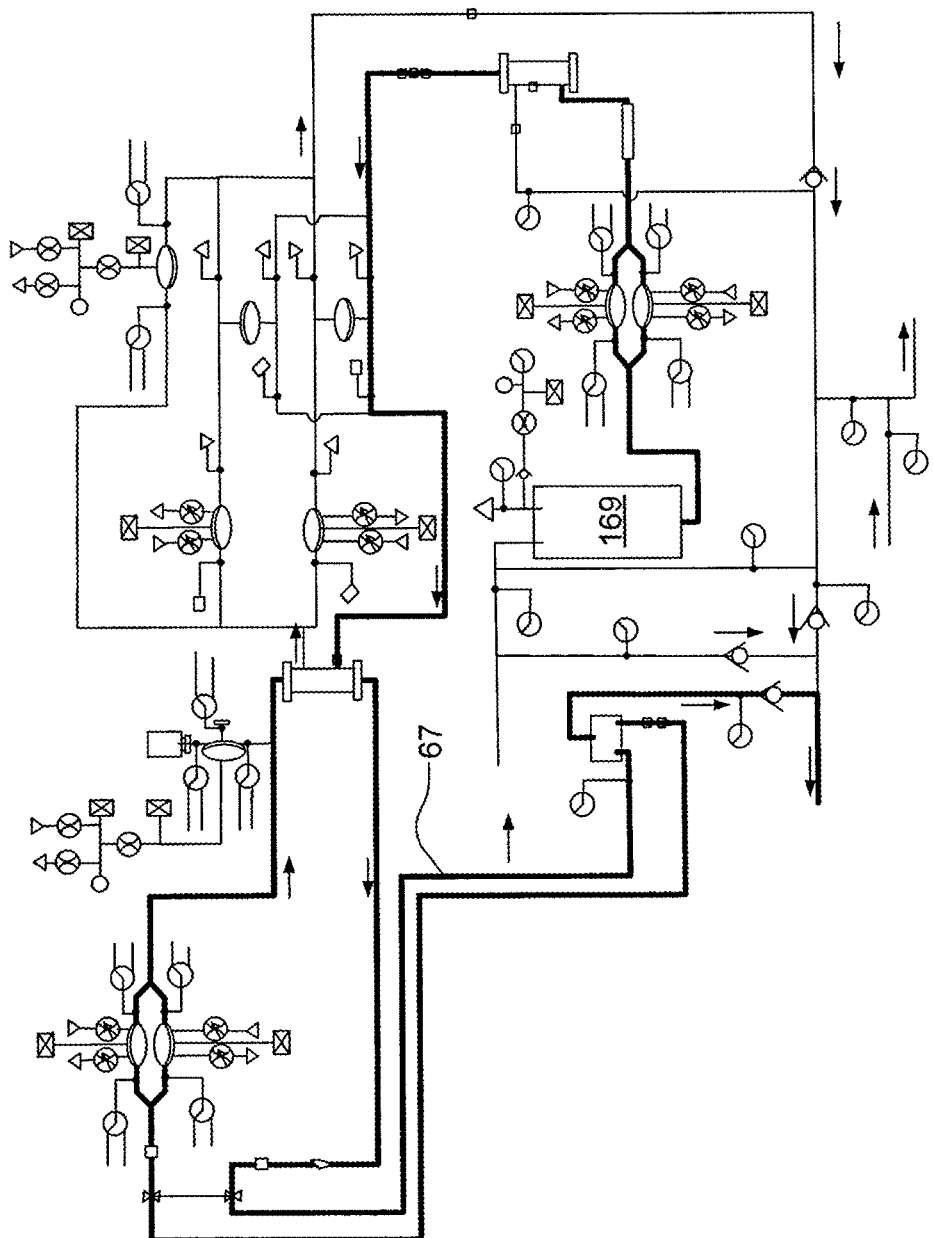

Next, the blood flow pump and tubing are primed by circulating fluid through the blood flow circuit and the air trap back to the directing circuit via conduit 67. As can be seen in FIG. 17C, fluid passes through the ultrafilter and dialyzer, forcing flow through the air trap and down the drain. The air trap traps air circulating in the blood flow circuit and sends it to the drain. Priming can be stopped when the air sensors stop detecting air (and some additional fluid has been passed through the system, as a safety margin).

Figure 19:
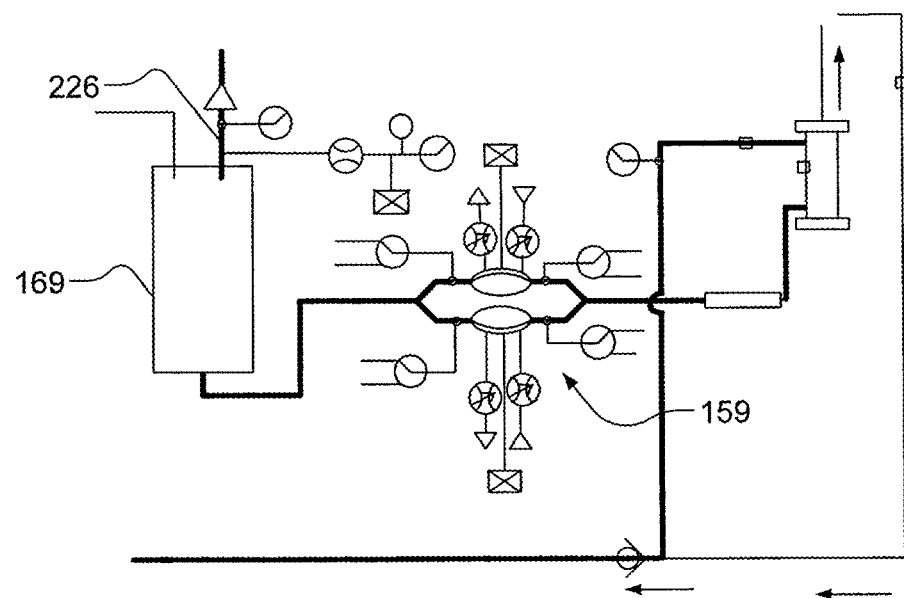
FIG. 19 illustrates emptying of a dialysate tank, in another embodiment of the invention.

Another set of embodiments is directed to adding air to the system, e.g., to empty the system of various fluids. For example, in one operation the dialysate tank is emptied. Vent 226 on dialysate tank 169 is opened, and pump 159 is used to pump fluid from the dialysate tank to the drain until air is detected in pump 159 (discussed below). This is shown in FIG. 19.

Figure 20:
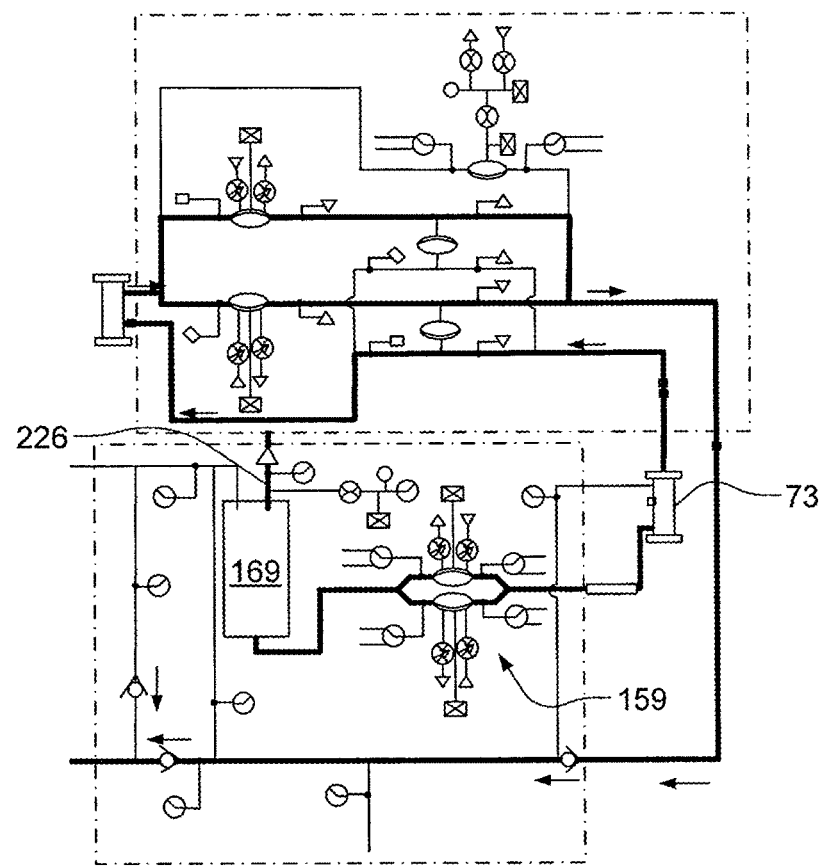
FIG. 20 illustrates the purging of the system with air at the end of treatment according to one embodiment of the invention.

Air may also be pumped into the balancing circuit in certain embodiments. This is shown in FIG. 20. Vent 226 on dialysate 16 is opened so that air may enter the dialysate tank. Pump 159 is used to pump air through the outside of ultrafilter 73. This air pressure displaces fluid outside the ultrafilter to the inside, then it flows through the dialyzer and down the drain. During this operation, pump 159 and the outside of the ultrafilter will fill with air.

Figure 21A:
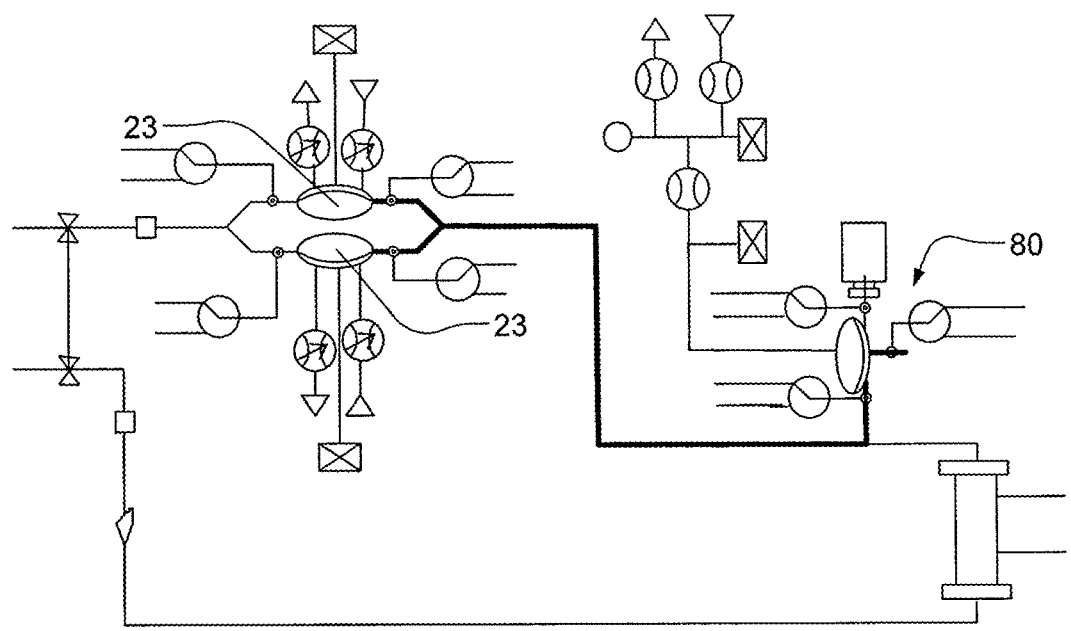
FIGS. 21A-21C illustrate the drawing of air in an anticoagulant pump, in still another embodiment of the invention.
Figure 21B:
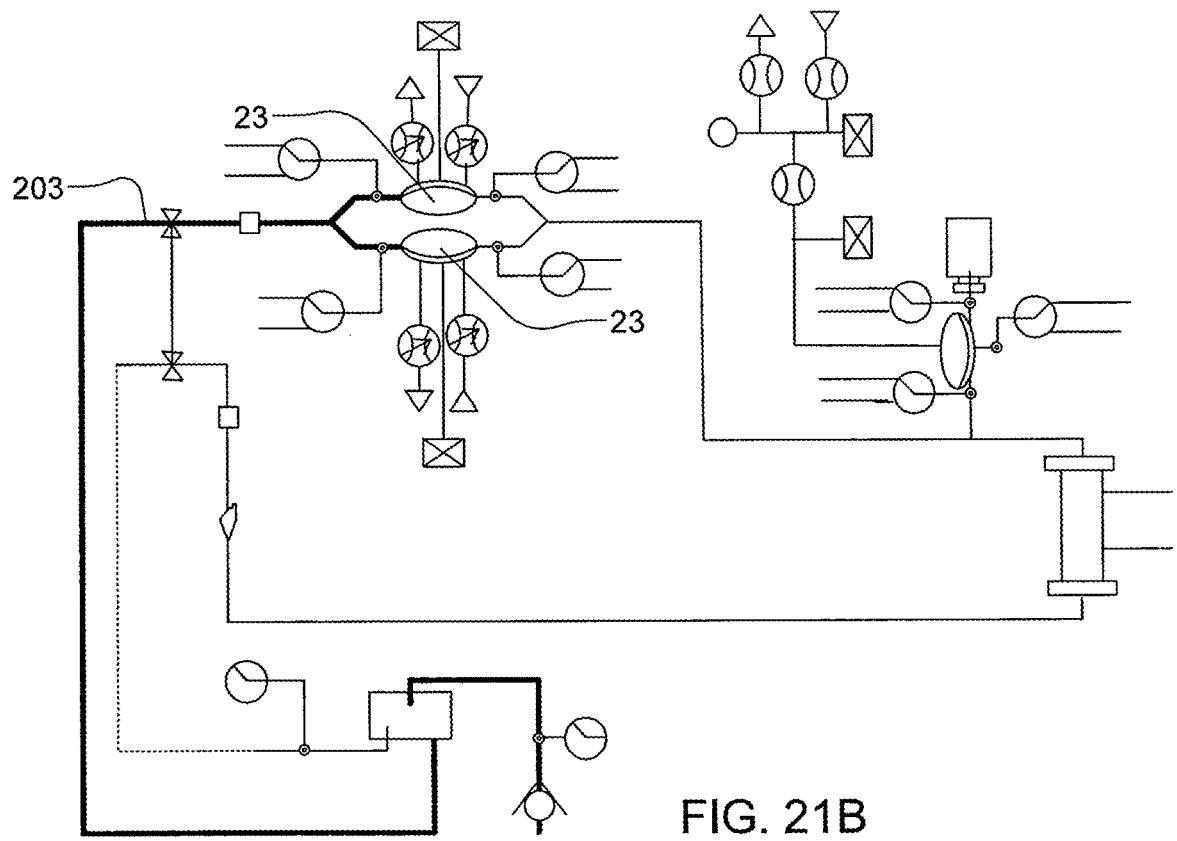
Figure 21C:
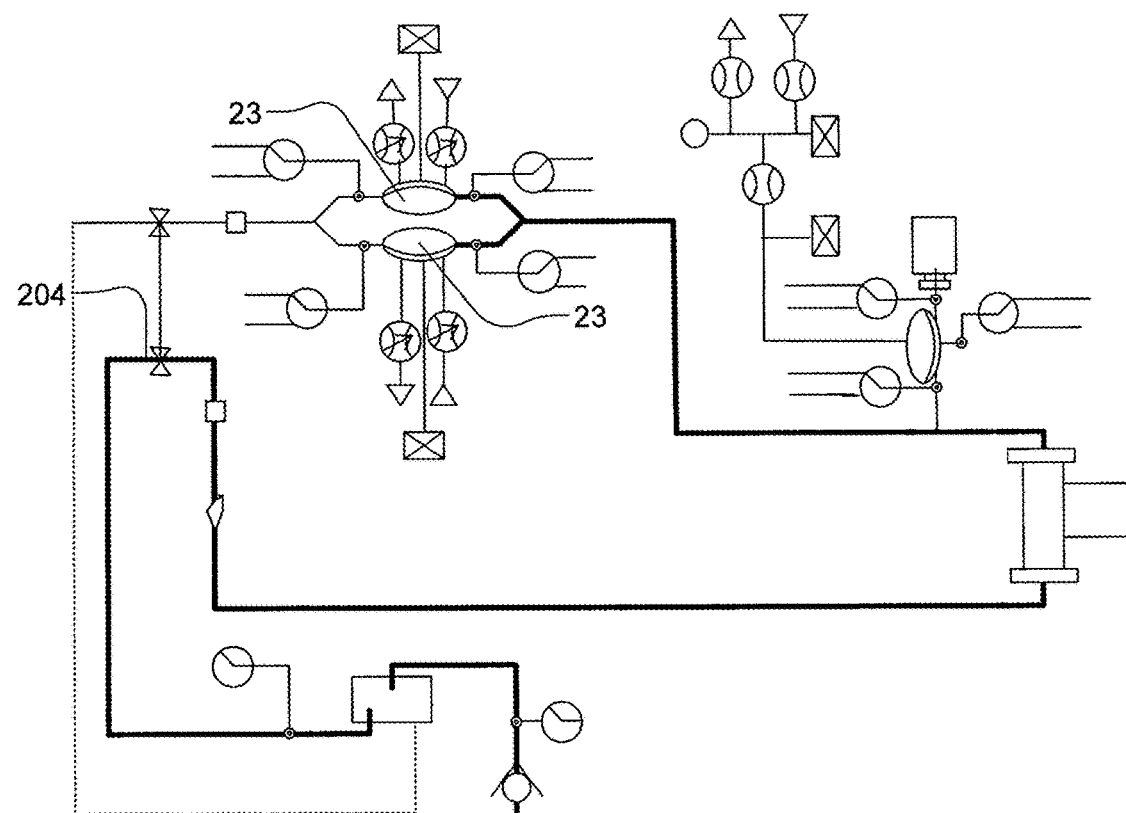

In addition, air can be drawn in through the anticoagulant pump 80 into the blood flow circuit, as is shown in FIG. 21A. The air is first brought into pod pumps 23 (FIG. 21A), then may be directed from the pod pumps to the arterial line 203 and down the drain (FIG. 21B), or to the venous line 204 (through dialyzer 14) and down the drain (FIG. 21C).

In one set of embodiments, integrity tests are conducted. As the ultrafilter and the dialyzer may be constructed with membrane material that will not readily pass air when wet, an integrity test may be conducted by priming the filter with water, then applying pressurized air to one side of the filter. In one embodiment, an air outlet is included on one of the blood flow pumps and thus, the pumping chamber may be used to pump air for use in the integrity test. This embodiment uses the advantage of a larger pump. The air pressure pushes all of the water through the filter, and the air flow stops once the water has been displaced. However, if the air flow continues, the membrane is ruptured and must be replaced. Accordingly, the system is primed with water. First, the mixing circuit is primed first to eliminate air prior to the dialysate tank. Then the outside of the ultrafilter is primed next, as the ultrafilter will not pass water to the balancing circuit until the outside is primed. The balancing circuit and the dialyzer are primed next. Finally, water is pushed across the dialyzer to prime the blood flow circuit.

Figure 22A:
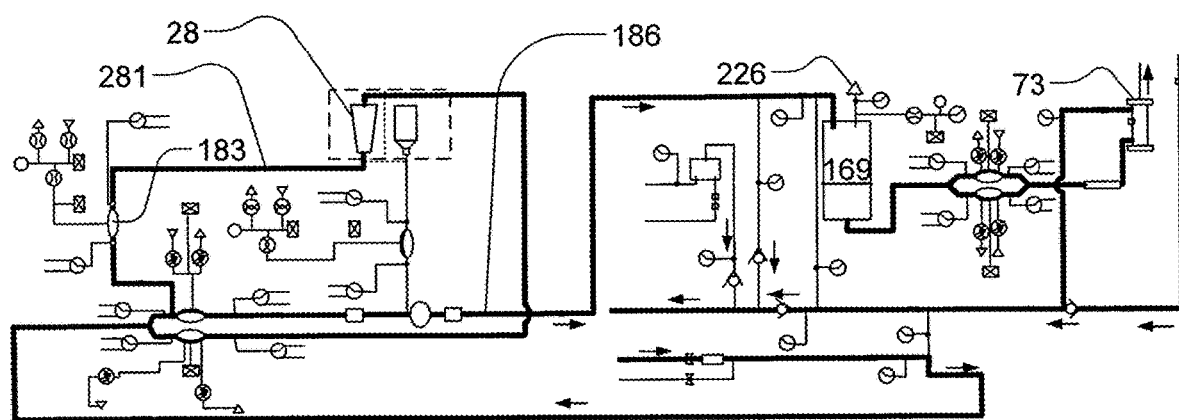
FIGS. 22A-22D illustrate integrity tests according to certain embodiments of the invention.
Figure 22B:
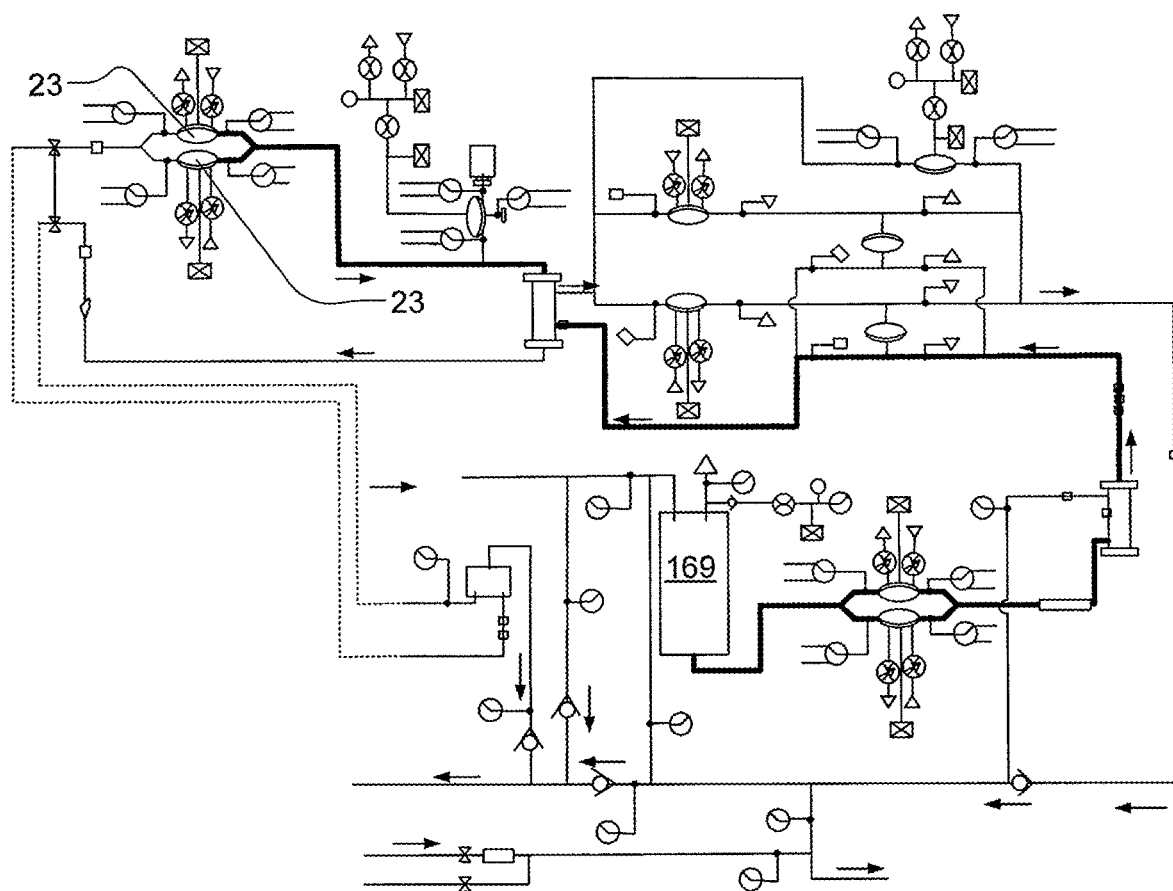
Figure 22C:
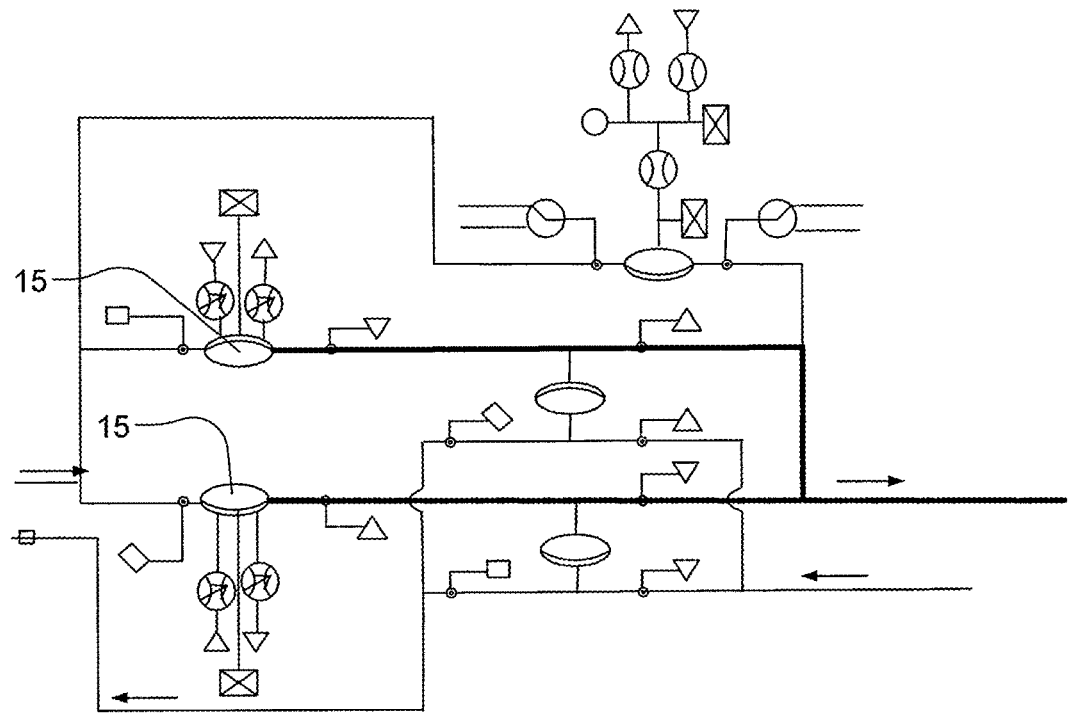

The mixing circuit is primed by first pushing water with pump 183, through line 281 and bicarbonate source 28, then through each of the pumps and through line 186 to dialysate tank 169. Dialysate tank 169 is vented so air that is pushed through bubbles to the top and leaves through vent 226. Once air has been primed out of dialysate tank 169, the tank is filled with water, then the priming flow continues from the dialysate tank through ultrafilter 73 to the drain. This can be seen in FIG. 22A. Water is then primed as previously discussed (see FIG. 17). Next, the blood flow pod pumps 23 are filled with water from dialysate tank 169, as is shown in FIG. 22B, while balancing pumps 15 are emptied, as is shown in FIG. 22C.

Figure 22D:
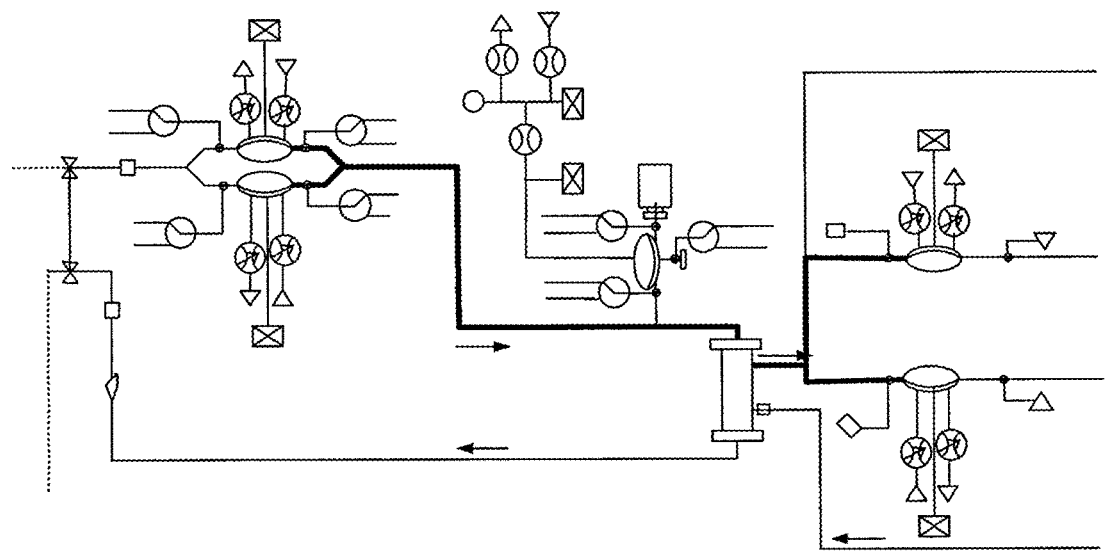

The test is conducted by using the blood flow pump to push each chamber of water across dialyzer 14 to balancing pump chambers 15, which start empty (FIG. 22C) and are vented to the atmosphere so that they are present at atmospheric pressure on the dialysate side of dialyzer 14. See FIG. 22D. Each of the blood flow circuit chambers delivers using a specific pressure and the end-of-stroke is determined to determine the flow rate.

Another integrity test is the ultrafilter flow test. In this test, the dialysate tank is filled with water, the ultrafilter is primed by pumping water from the dialysate tank through the ultrafilter and out line 731, and water is pumped through the ultrafilter, controlling flow rate, monitoring the delivery pressure required to maintain flow.

Another set of embodiments are directed to disinfection and rinsing of the system. This process removes any material which may have accumulated during therapy, and kills any active pathogens. Typically, heat is used, although in some cases, a disinfectant may be added. Water is maintained using the dialysate tank and replenished as necessary as water is discharged.

Figure 23:
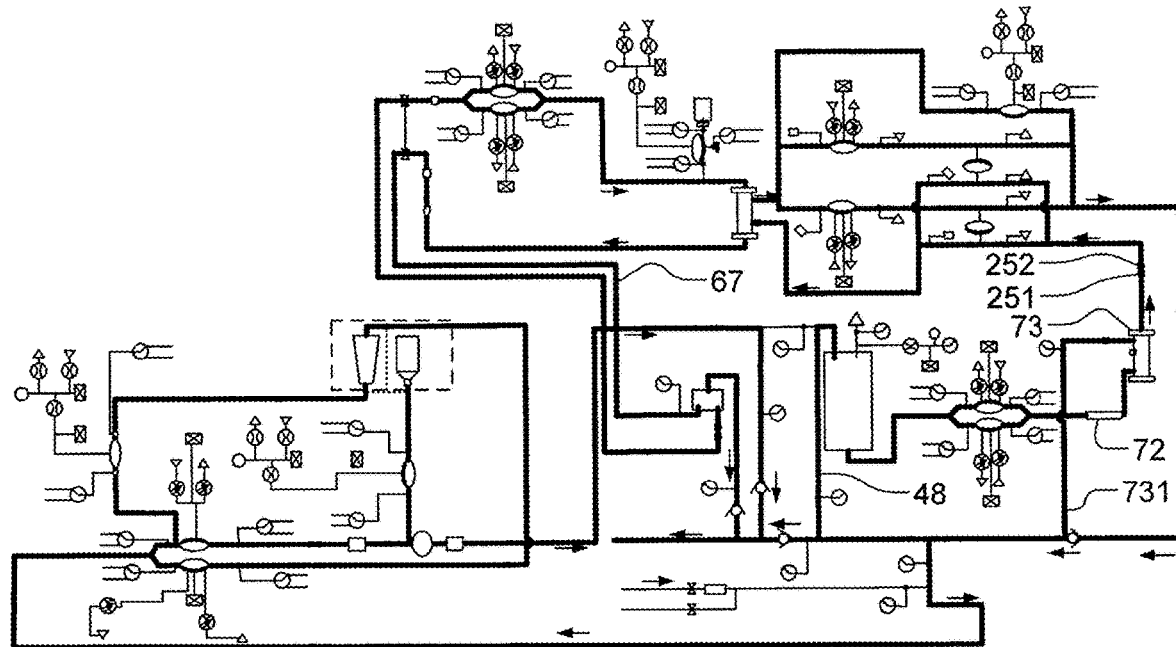
FIG. 23 illustrates a recirculating flow path, in another embodiment of the invention.

A recirculating flow path is shown in FIG. 23. The flow along this path is essentially continuous, and uses conduits 67 to connect the blood flow circuit with the directing circuit. The main flow path is heated using heater 72, which is used to increase the water temperature within the recirculating flow path, e.g., to a temperature that can kill any active pathogens that may be present. Most of the water is recirculated, although some is diverted to drain. Note that lines 48 and 731 are kept open in this example to ensure that these lines are properly disinfected. In addition, the flow paths through ultrafilter 73 can be periodically selected to purge air from the ultrafilter, and/or to provide recirculating flow through this path. Temperature sensors (e.g., sensors 251 and 252) can be used to ensure that proper temperatures are met. Non-limiting examples of such sensors can be seen in U.S. patent application Ser. No. 12/038,474, entitled "Sensor Apparatus Systems, Devices and Methods," filed on Feb. 27, 2008, and incorporated herein by reference.

Figure 24A:
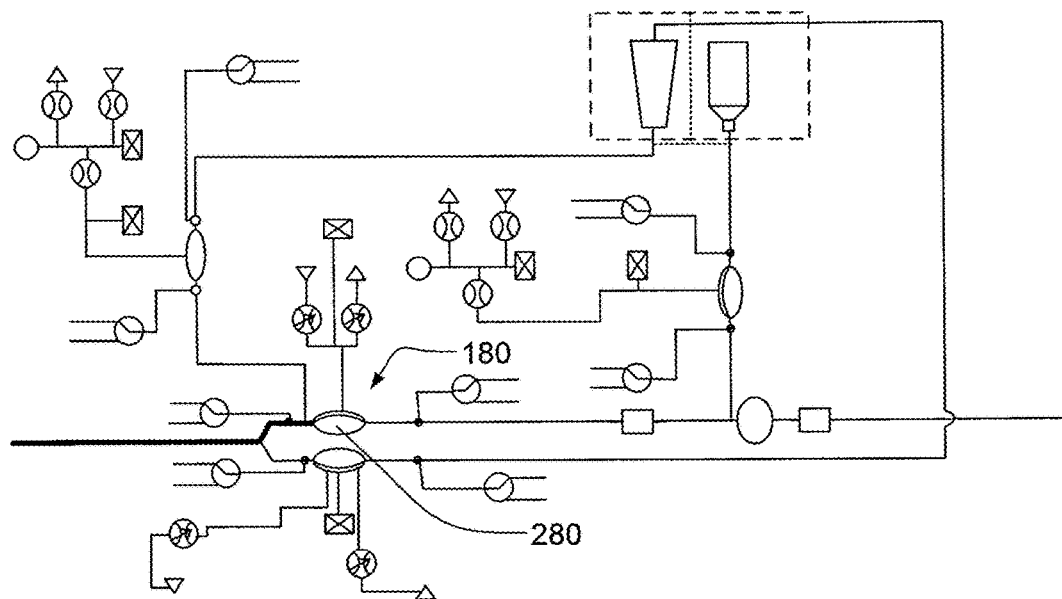
FIGS. 24A-24D illustrate the priming of a system with dialysate, in yet another embodiment of the invention.
Figure 24B:
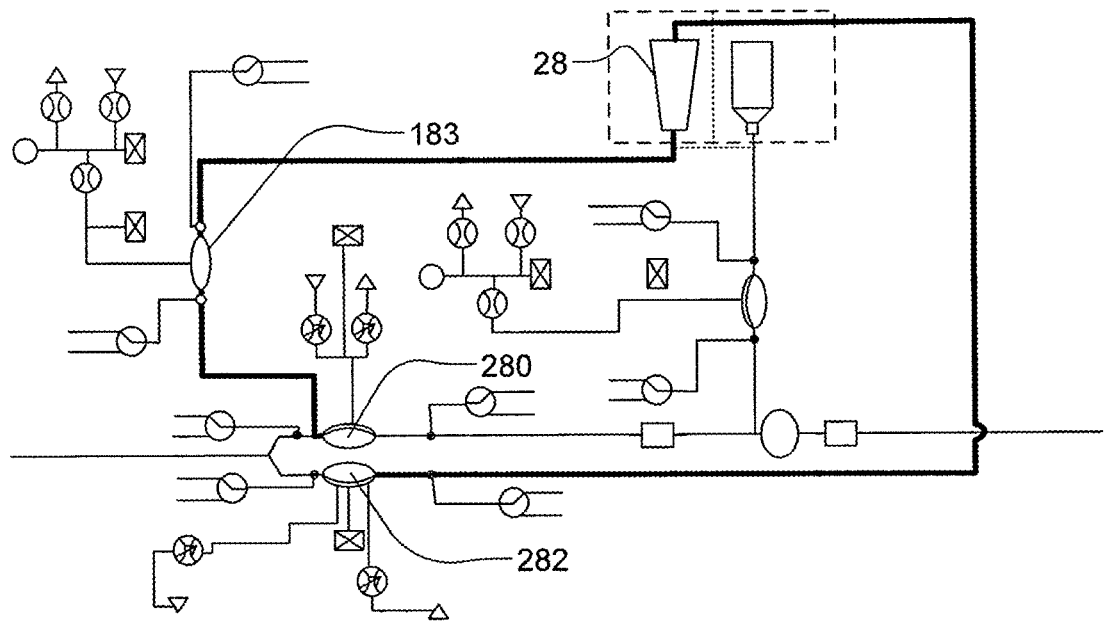
Figure 24D:
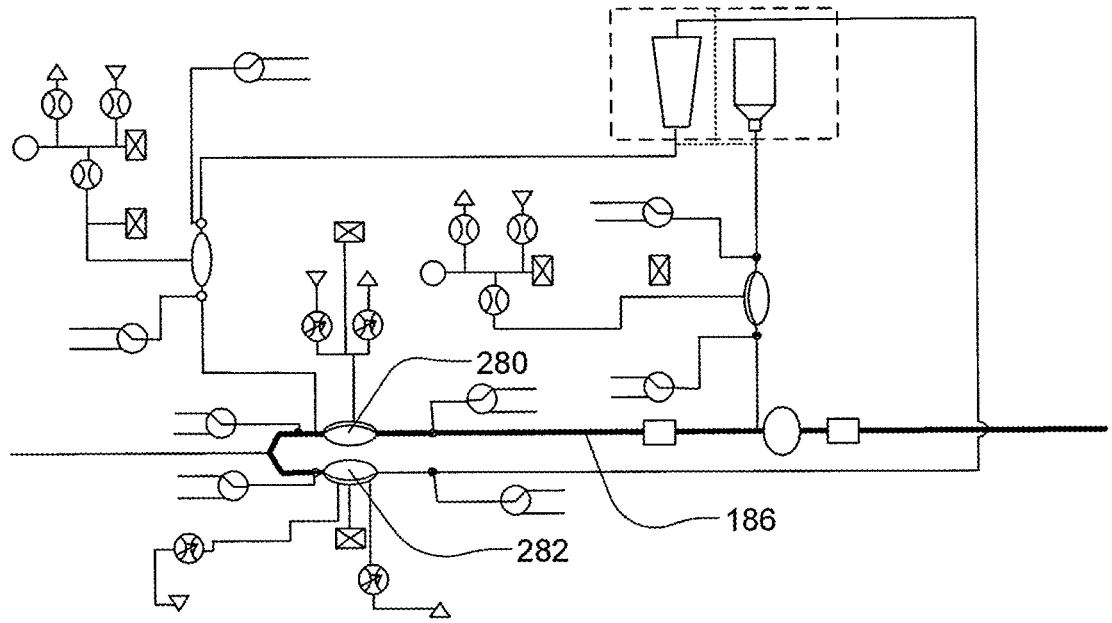
Figure 24C:
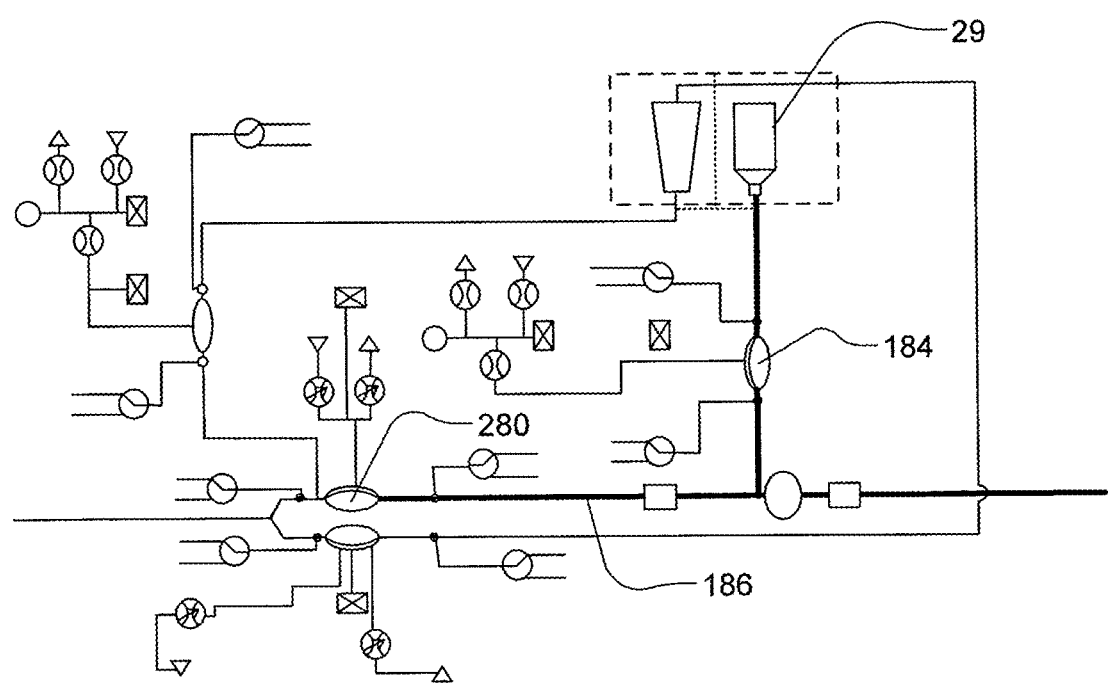

In one set of embodiments, the system is primed with dialysate as follows. In this operation, pod pump 280 is filled with water (FIG. 24A), and then water is pushed backwards through pump 183 to expel air from the top of bicarbonate source 28. The air is collected in pod pump 282. See FIG. 24B. Next, the air in pod pump 282 is expelled through pod pump 280 and line 186 to dialysate tank 169. Vent 226 in dialysate tank 169 is opened so that the air can leave the system (FIG. 24C). In addition, acid may be pumped in from acid source 29. Bicarbonate concentrate from bicarbonate source 28 and water are then mixed. Pump 183 is used to provide water pressure sufficient to fill bicarbonate source 28 with water, as is shown in FIG. 24D.

The acid and bicarbonate solutions (and sodium chloride solution, if a separate sodium chloride source is present) are then metered with incoming water to prepare the dialysate. Sensors 178 and 179 are used to ensure that the partial mixtures of each ingredient with water is correct. Dialysate that does not meet specification is emptied to the drain, while good dialysate is pumped into dialysate tank 14.

In another set of embodiments, the anticoagulant pump is primed. Priming the pump removes air from the heparin pump and the flow path, and ensures that the pressure in the anticoagulant vial is acceptable. The anticoagulant pump can be designed such that air in the pump chamber flows up into the vial. The test is performed by closing all of the anticoagulant pump fluid valves, measuring the external volume, charging the FMS chamber with vacuum, opening valves to draw from the vial into the pumping chamber, measuring the external volume (again), charging the FMS chamber with pressure, opening the valves to push fluid back into the vial, and then measuring the external volume (again). Changes in external volume that result from fluid flow should correspond to the known volume of the pumping chamber. If the pumping chamber cannot fill from the vial, then the pressure in the vial is too low and air must be pumped in. Conversely, if the pumping chamber cannot empty into the vial, then the pressure in the vial is too high and some of the anticoagulant must be pumped out of the vial. Anticoagulant pumped out of the vial during these tests can be discarded, e.g., through the drain.

In yet another set of embodiments, the system is rinsed with dialysate while the patient is not connected. This can be performed before or after treatment. Prior to treatment, dialysate may be moved and a portion sent to the drain to avoid accumulating sterilant in the dialysate. After treatment, this operation rinses the blood path with dialysate to push any residual blood to the drain. The flow paths used in this operation are similar to the flow paths used with water, as discussed above.

Figure 25:
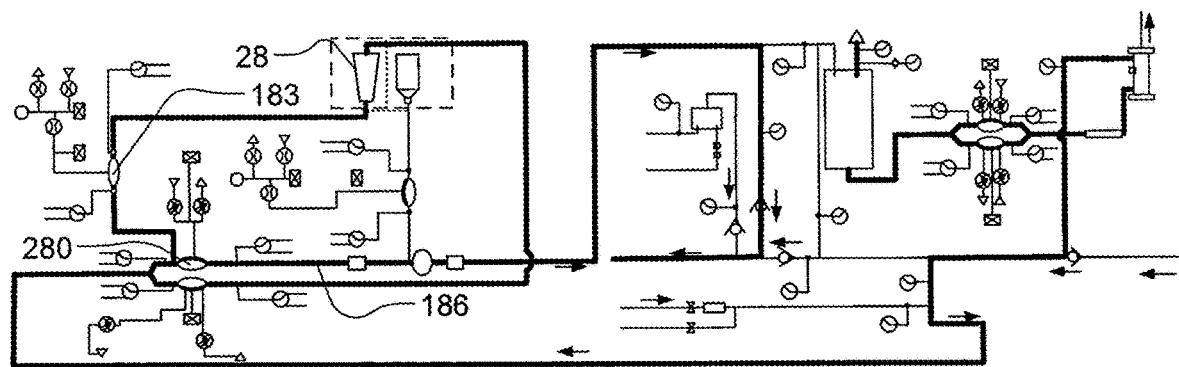
FIG. 25 illustrates the priming of an anticoagulant pump, in still another embodiment of the invention.

Acid concentrate may be pumped out of the mixing chamber. Pump 184 is activated so that pod pump 280 can draw out acid from pump 184 and acid source 29, to be mixed in line 186 and sent to the drain. Similarly, bicarbonate may be pumped out of the mixing chamber as is shown in FIG. 25. Pump 183 is used to draw water from bicarbonate source 28, then pod pump 280 is used to pass the water into line 186 to the drain.

Figure 26A:
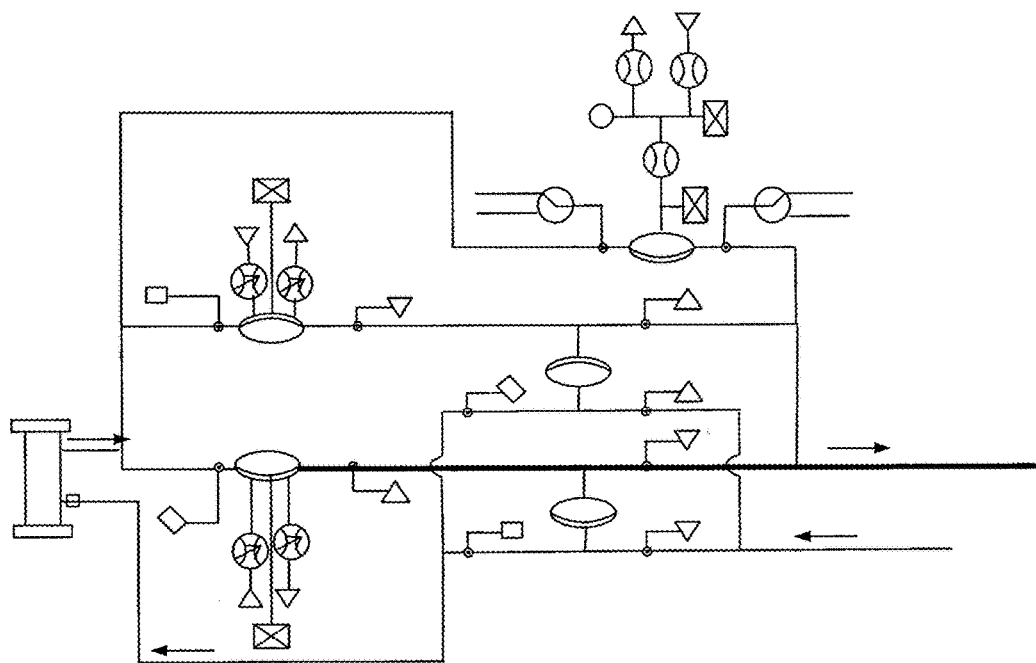
FIGS. 26A-26F illustrate the removal of dialysate from a blood flow circuit, in one embodiment of the invention.
Figure 26B:
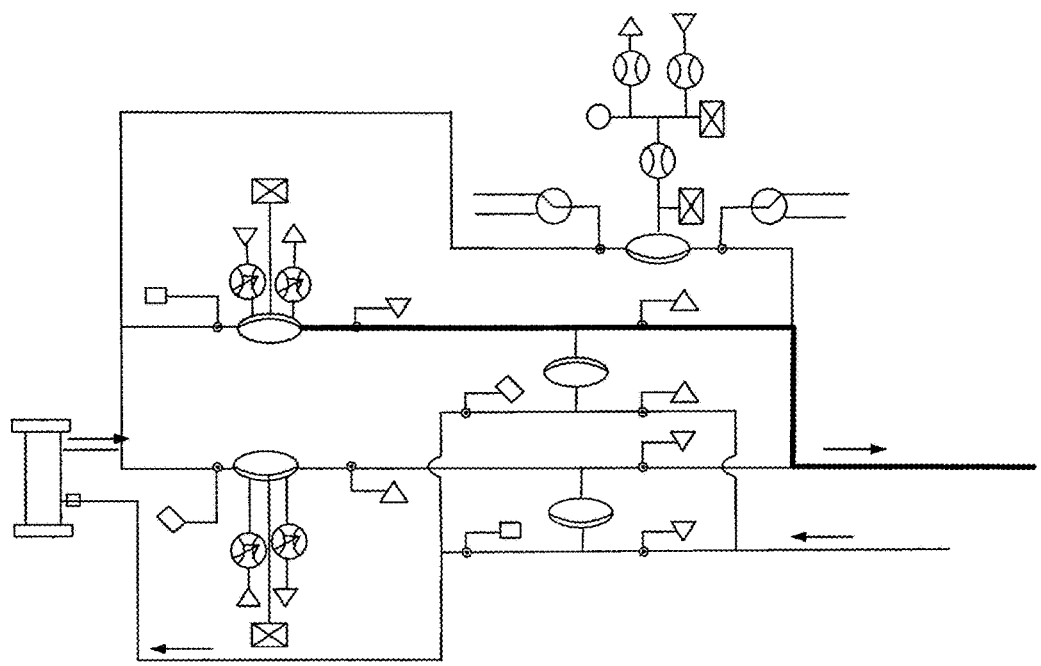
Figure 26C:
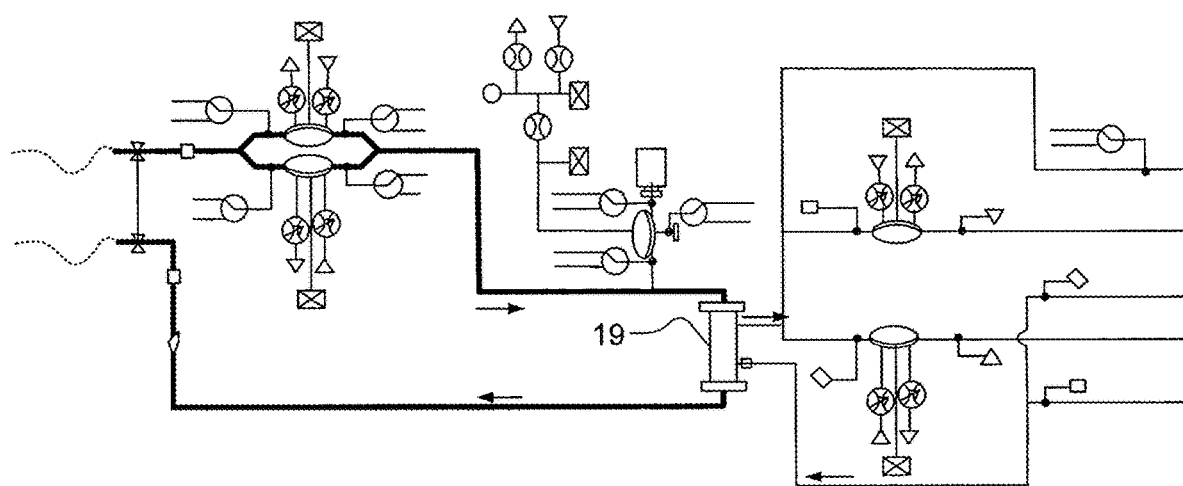
Figure 26D:
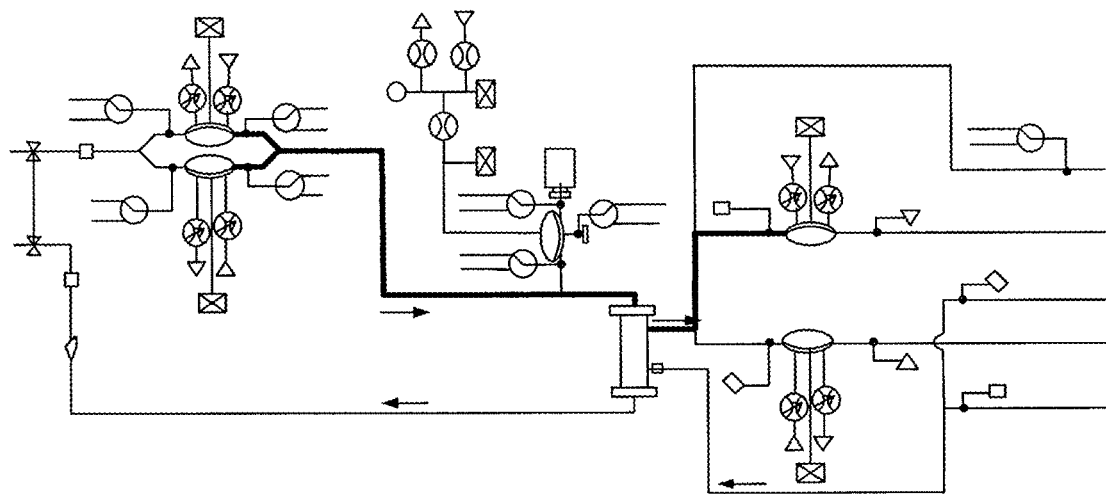
Figure 26E:
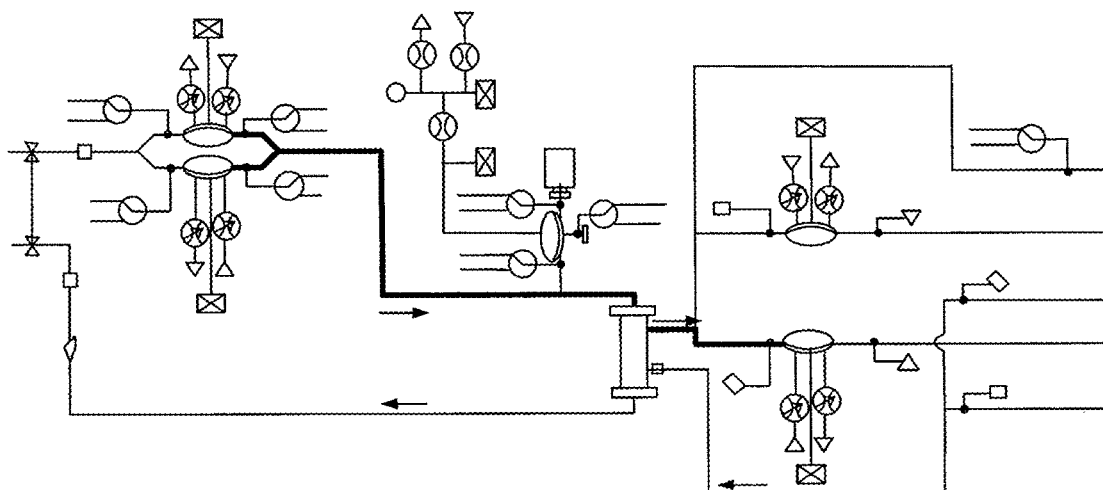
Figure 26F:
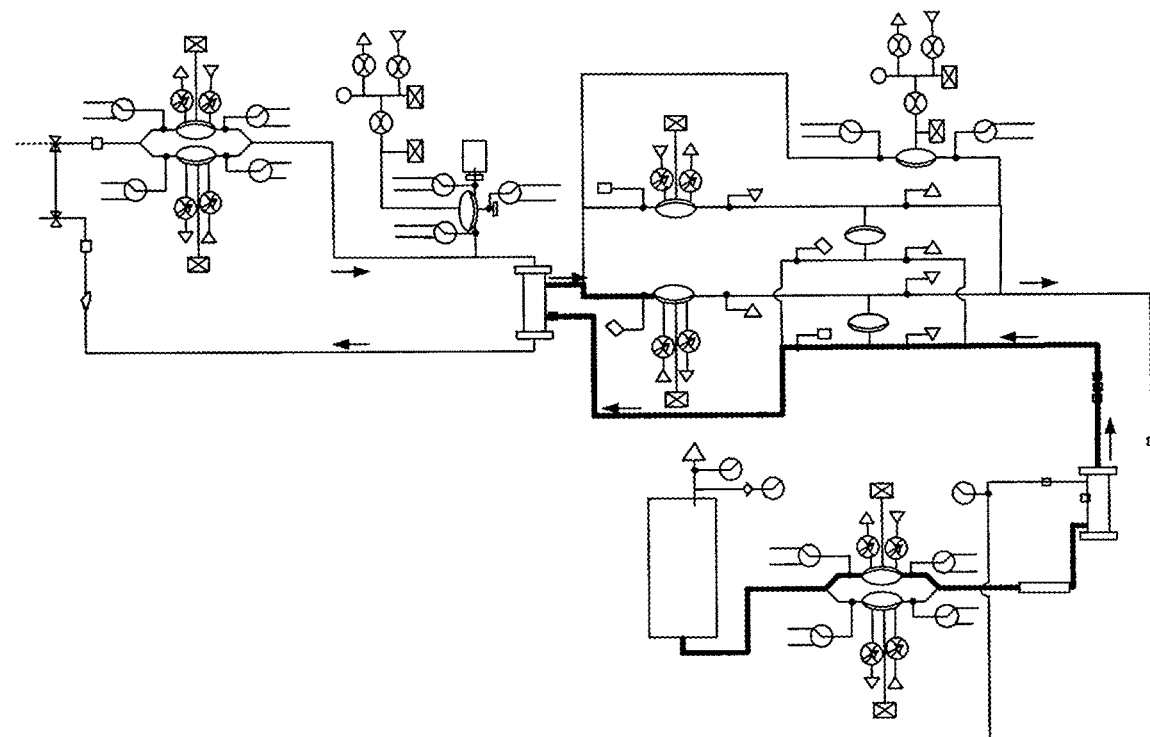

In still another set of embodiments, dialysate prime is removed from the blood flow circuit, to avoid giving the patient the priming fluid. FIGS. 26A and 26B show fluid leaving each of the balancing pump chambers and being expelled to the drain. Next, the dialysate side of dialyzer 14 is closed, while blood is drawn into the blood flow path from the patient (FIG. 26C). The patient connections are then occluded while the blood flow pump chambers 23 push the priming fluid across the dialyzer to the balancing circuit (FIGS. 26D and 26E). This fluid is then pushed to drain, as previously discussed. This operation can be repeated as necessary until sufficient priming fluid has been removed. Afterwards, the balancing pumps are then refilled with fresh dialysate, keeping the patient connections occluded, as is shown in FIG. 26F.

Figure 27A:
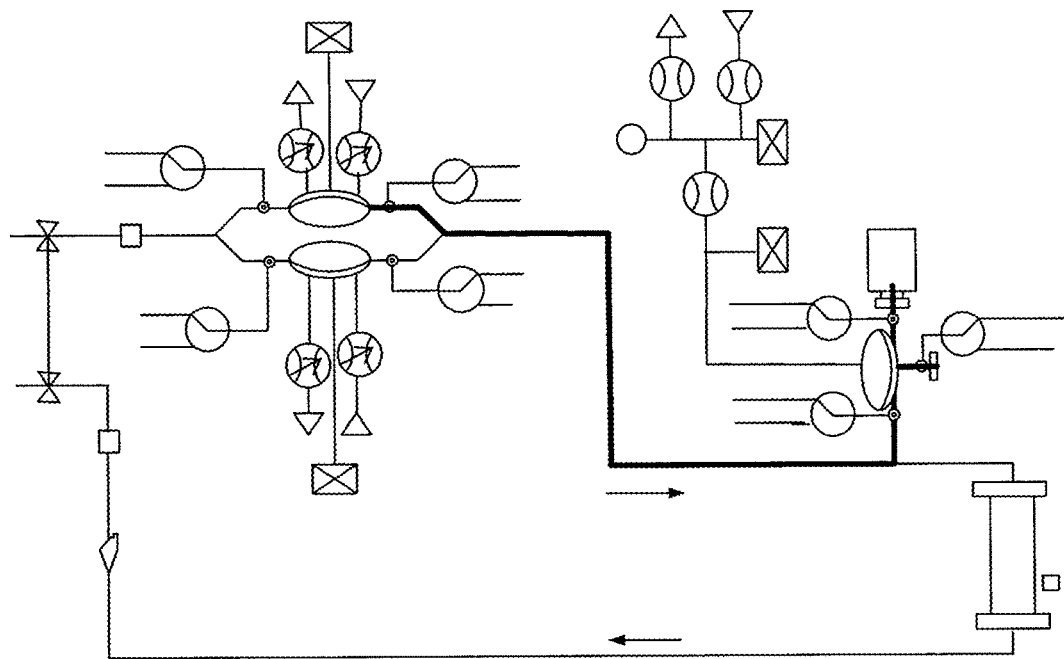
FIGS. 27A-27C illustrate the delivery of a bolus of anticoagulant to a patient, in another embodiment of the invention.
Figure 27B:
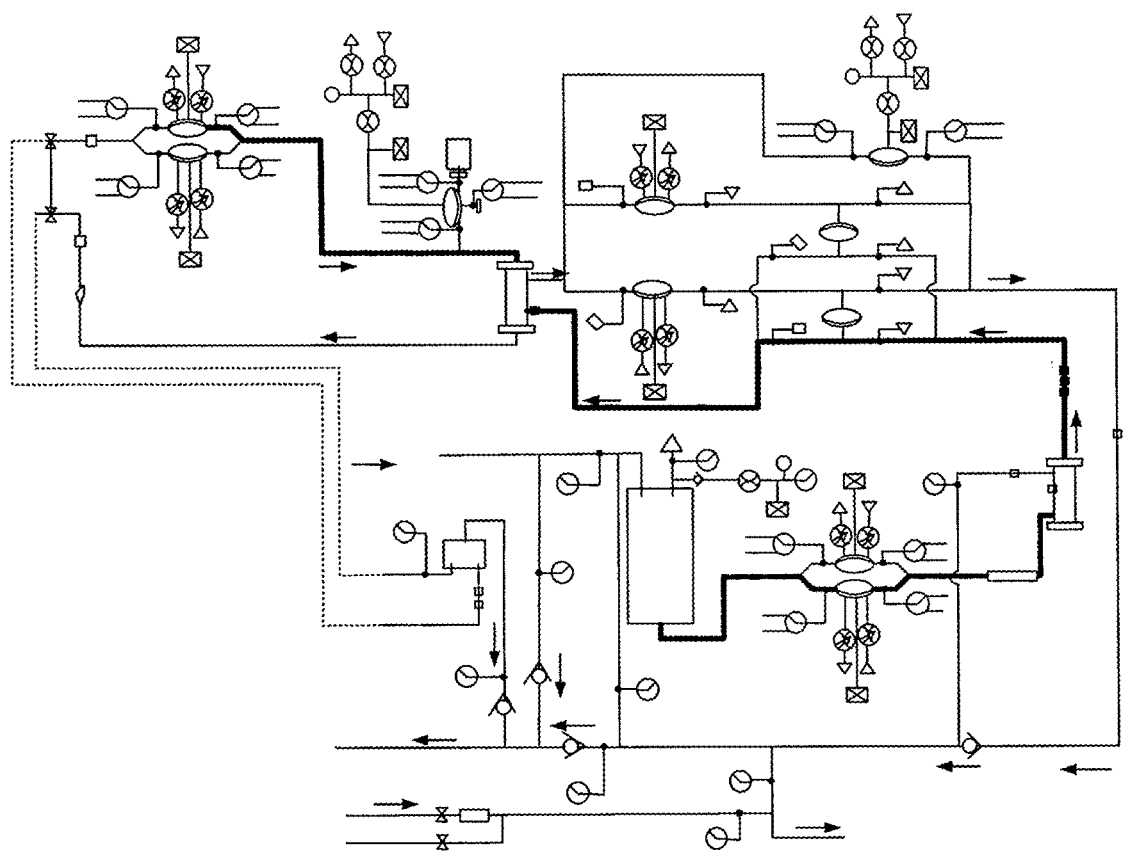
Figure 27C:
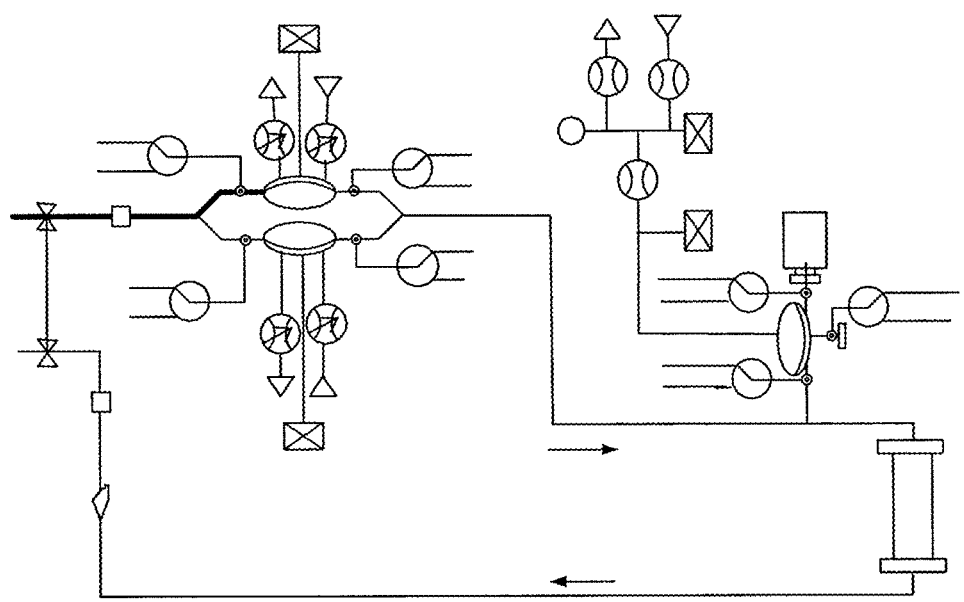

In yet another set of embodiments, a bolus of anticoagulant may be delivered to the patient. Initially, a bolus of anticoagulant is pumped from the vial (or other anticoagulant supply) to one chamber of pump 13, as is shown in FIG. 27A. The anticoagulant pump alternates between pumping air into the vial and pumping anticoagulant out of the vial, thereby keeping the pressure relatively constant. The remaining volume is then filled with dialysate (FIG. 27B). The combined fluids are then delivered to the patient down arterial line 203, as shown in FIG. 27B. In some cases, the same pump chamber may be refilled with dialysate again (see FIG. 27B), and that volume delivered to the patient also, to ensure that all of the anticoagulant has been properly delivered.

In still another set of embodiments, the system may perform push-pull hemodiafiltration. In such cases, blood flow pump 13 and balancing pumps 15 can be synchronized to pass fluid back and forth across the dialyzer. In hemodiafiltration, hydrostatic pressure is used to drive water and solute across the membrane of the dialyzer from the blood flow circuit to the balancing circuit, where it is drained. Without wishing to be bound by any theory, it is believed that larger solutes are more readily transported to the used dialysate due to the convective forces in hemodiafiltration.

Figure 28:
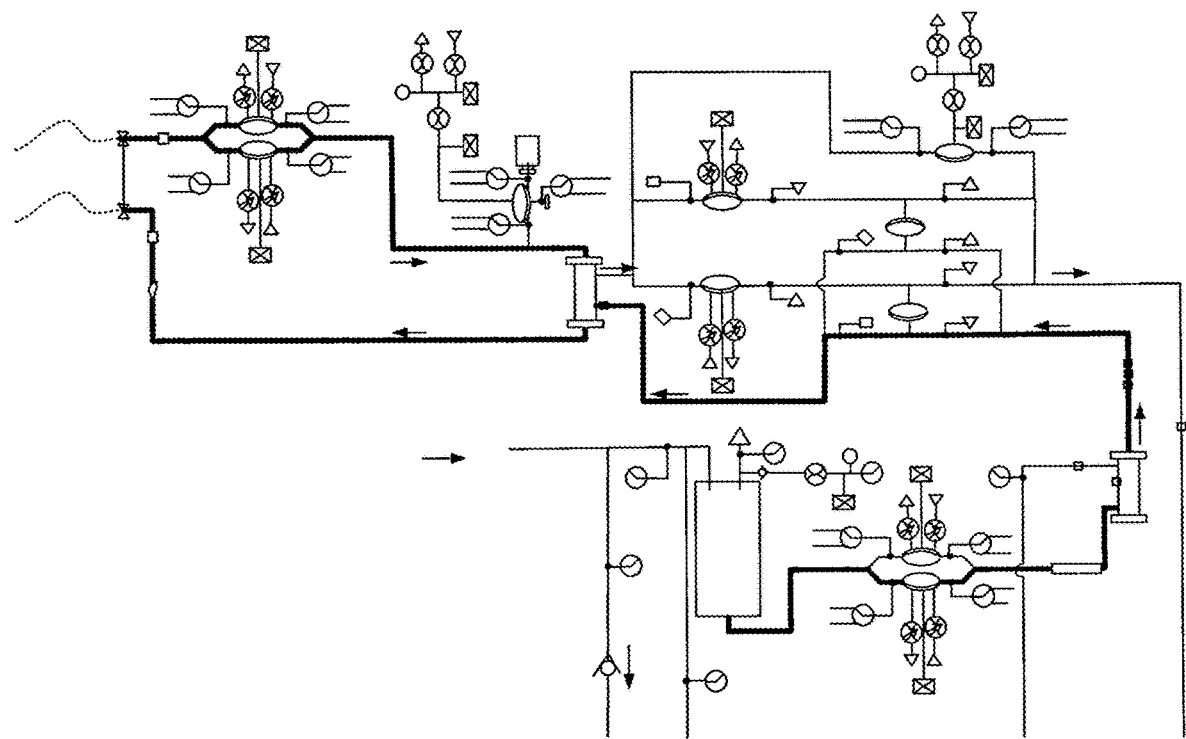
FIG. 28 illustrates solution infusion, in one embodiment of the invention.

In one set of embodiments, solution infusion may be used to delivery fluid to the patient. As is shown in FIG. 28, pump 159 in the directing circuit is used to push fluid across dialyzer 14 into the blood flow circuit, which thus causes delivery of fluid (e.g., dialysate) to the patient.

According to another set of embodiments, after repeated use, the dialyzer can lose its efficiency or even the ability to function at all as a result of compounds adhering to and building up on the membrane walls in the dialyzer. Any standard measure of dialyzer clearance determination may be used. However, one method of measuring how much build-up has accumulated in the dialyzer, i.e., how much the dialyzer's clearance has deteriorated, a gas is urged into the blood side of the dialyzer, while a liquid is held on the dialysate side of the dialyzer. By measuring the volume of gas in the dialyzer, the clearance of the dialyzer may be calculated based on the volume of gas measured in the dialyzer.

Alternatively, in other embodiments, because of the pneumatic aspects of the present system, clearance may be determined as follows. By applying a pressure differential along the dialyzer and measuring the flow rate of the dialyzer, the clearance of the dialyzer may then be correlated/determined or calculated, based on the pressure differential and the flow rate. For example, based on a known set of correlations or pre-programmed standards including a correlation table or mathematical relationship. For example, although a look-up table may be used, or a determined mathematical relationship may also be used.

The dialyzer's clearance can also be measured using a conductivity probe in the blood tube plug-back recirculation path. After treatment the patient connects the blood tubes back into the disinfection ports. The fluid in the blood tubes and dialyzer may be recirculated through these disinfection port connections, and the conductivity of this solution may be measured as it passes through the conductivity measurement cell in this recirculation path.

To measure the dialyzer clearance, pure water may be circulated through the dialysate path and the conductivity of the fluid flowing through the blood recirculation path is continuously monitored. The pure water takes ions from the solution in the blood flow circuit recirculation path at a rate which is proportional to the clearance of the dialyzer. The clearance of the dialyzer may be determined by measuring the rate at which the conductivity of the solution in the blood flow circuit recirculation path changes.

The dialyzer's clearance can be measured by circulating pure water on one side and dialysate on the other, and measuring the amount of fluid passing through the dialyzer using conductivity.

In one set of embodiments, in case of a power failure, it may be desirable to return as much blood to the patient as possible. Since one embodiment of the hemodialysis system uses compressed gas to actuate various pumps and valves used in the system, a further embodiment takes advantage of this compressed gas to use it in case of power failure to return blood in the system to the patient. In accordance with this procedure and referring to FIG. 29A, dialysate is pushed across the dialyzer 14, rinsing blood residing in the blood flow circuit 10 back to the patient. Compressed gas (which in a preferred embodiment is compressed air) can be used to push dialysate across the dialyzer 14. A valve 77 releases the compressed air to initiate this function. This method may be used in situations where electrical power loss or some other failure prevents the dialysis machine from rinsing back the patient's blood using the method normally employed at the end of treatment.

As compressed air is used to increase the pressure on the dialysate side of the dialyzer 14 and force dialysate through the dialyzer to the blood side, thereby pushing the patient's blood back to the patient, the patient, or an assistant, monitors the process and clamps the tubes between the blood flow circuit and the patient once adequate rinse back has been achieved.

In one embodiment, a reservoir 70 is incorporated into the hemodialysis system and is filled with compressed air prior to initiating treatment. This reservoir 70 is connected to the dialysate circuit 20 through a manually actuated valve 77. When the treatment is finished or aborted, this valve 77 is opened by the patient or an assistant to initiate the rinse-back process. The membrane of the dialyzer 14 allows dialysate to pass through, but not air. The compressed air displaces dialysate until the patient tubes are clamped, or the dialysate side of the dialyzer is filled with air.

In another embodiment, a reservoir containing compressed air is provided as an accessory to the dialysis machine. If the treatment is terminated early due to a power failure or system failure of the dialysis machine, this reservoir may be attached to the dialysate circuit on the machine to initiate the rinse-back process. As in the previous embodiment, the rinse-back process is terminated when the patient tubes are clamped, or the dialysate side of the dialyzer is filled with air.

Figure 29A:
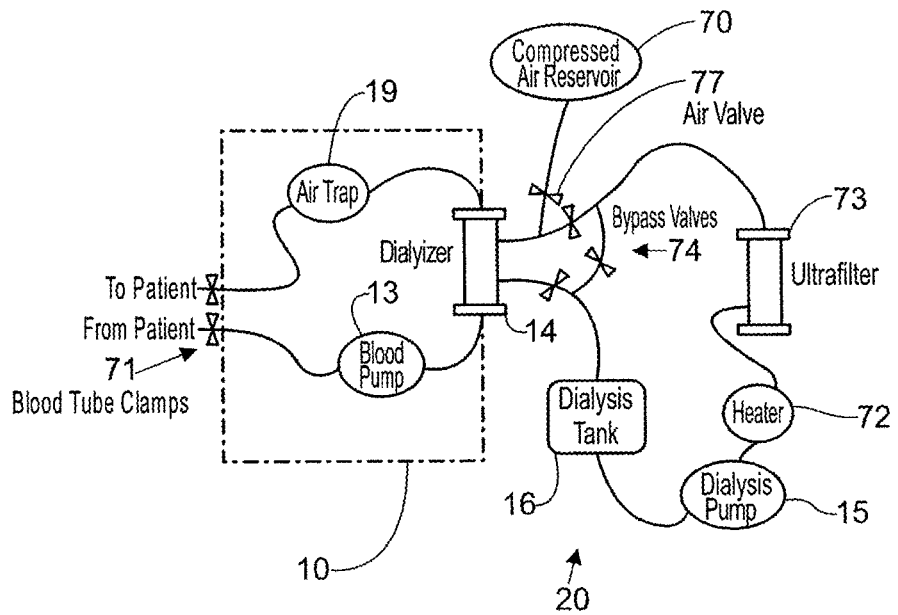
FIGS. 29A-29B are schematic representations showing how an emergency rinse-back procedure can be implemented.
Figure 29B:
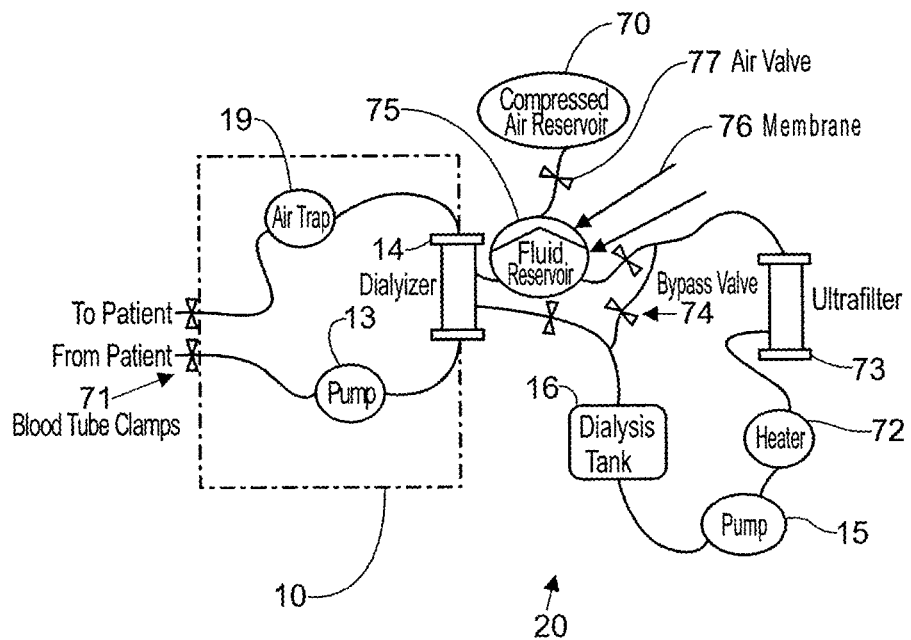

In yet another embodiment shown in FIG. 29B, an air reservoir 70 is incorporated into the system and attached to a fluid reservoir 75 with a flexible diaphragm 76 separating the air from the dialysate fluid. In this case, the compressed air pushes the diaphragm 76 to increase the pressure in the dialysate circuit 20 rather than having the compressed air enter the dialysate circuit. The volume of the dialysate that is available to be displaced is determined by the volume of the fluid chamber 75. The rinse-back process is terminated when the patient tubes are clamped, or when all of the fluid is expelled and the diaphragm 76 bottoms out against the wall of the fluid chamber 75.

In any of these embodiments, the operation of the systems or methods may be tested periodically between treatments by running a program on the dialysate machine. During the test the user interface prompts the user to actuate the rinse-back process, and the machine monitors the pressure in the dialysate circuit to ensure successful operation.

In the systems depicted in FIGS. 29A and 29B, blood is drawn from the patient by the blood flow pump 13, pushed through the dialyzer 14 and returned to the patient. These components and the tubing that connects them together make up the blood flow circuit 10. The blood contained in the blood flow circuit 10 should be returned to the patient when the treatment is finished or aborted.

The dialysate solution is drawn from the dialysate tank 169 by the dialysate pump 159, and passed through the heater 72 to warm the solution to body temperature. The dialysate then flows through the ultrafilter 73 which removes any pathogens and pyrogens which may be in the dialysate solution. The dialysate solution then flows through the dialyzer to perform the therapy and back to the dialysate tank.

The bypass valves 74 may be used to isolate the dialyzer 14 from the rest of the dialysate circuit 20. To isolate the dialyzer 14, the two valves connecting the dialysate circuit 20 to the dialyzer are closed, and the one shunting dialysate around the dialyzer is opened.

This rinse-back procedure may be used whether or not the dialyzer 14 is isolated and is used when the treatment is ended or aborted. The dialysate machine is turned off or deactivated so the pumps are not running. When the patient is ready for rinse-back, air valve 77 is opened by the patient or an assistant. The air in the compressed air reservoir 70 flows toward the dialysate circuit 20, increasing the pressure on the dialysate side of the dialyzer 14. This increase in pressure may be achieved by allowing the air to enter the dialysate circuit directly, as shown in FIG. 29A or indirectly by pushing on the diaphragm 76 shown in FIG. 29B.

The air pressure on the dialysate side of the dialyzer forces some dialysate solution through the dialyzer 14 into the blood flow circuit. This dialysate solution displaces the blood, rinsing the blood back to the patient. The patient or an assistant can observe the rinse process by looking at the dialyzer 14 and the blood tubes. The dialysate solution starts in the dialyzer, displacing the blood and making it appear much clearer. This clearer solution progresses from the dialyzer toward the patient. When it reaches the patient the blood tube clamps 71 are used to pinch the tubing to terminate the rinse-back process. If one line rinses back sooner than the other the quicker line may be clamped first and the slower line may be clamped later.

Once the rinse-back is completed and the blood lines are clamped the patient may be disconnected from the dialysis machine.

The implementation of one embodiment of the system and method is shown in FIG. 29A takes advantage of the hydrophilic nature of the material used to make the tiny tubes in the dialyzer 14. When this material is wet, the dialysate solution can pass through but air cannot. Where the embodiment shown in FIG. 29A is implemented, air may enter the dialyzer 14 but it will not pass across to the blood flow circuit 10.

In either implementation, the volume of dialysate that may be passed through the dialyzer 14 is limited. This limitation is imposed by the size of the compressed air reservoir 70, the volume of dialysate solution contained in the dialyzer 14 and in the case of the implementation shown in FIG. 7B the size of fluid reservoir 75. It is advantageous to limit the volume of dialysate that may be pushed across the dialyzer because giving too much extra fluid to the patient counteracts the therapeutic benefit of removing fluid during the therapy.

In another embodiment, in a loss of power, the air pressure to move dialysate from the dialysate circuit through the dialyzer can be derived from a pressurized air reservoir that normally powers the membrane pumps and also provides a pressure source for FMS measurements. As shown in FIG. 80, for example, this source of air pressure can be accessed via the FMS pathway 170 used to monitor the dialysate tank 169. In an embodiment, the manifold valves that direct air pressure or vacuum to the various pumps and valves in the liquid flow paths of the hemodialysis machine are electrically operated. In some embodiments, the valves in the liquid flow paths of the hemodialysis machine can themselves be electrically actuated. In the absence of electrical power, they can be chosen or pre-set to have default open or closed positions. If the default position of a manifold valve is closed, for example, then no air pressure (or vacuum) can be transmitted to its target. Similarly, if the default position of a manifold valve is open, then the pressure or vacuum source to which it is connected can pressurize the downstream device (such as a membrane-based pump, a membrane-based valve, or another type of valve). If a valve that directly controls flow in a liquid flow path is itself electrically actuated, the valve can be chosen to have a default position either to close off or to open its respective flow path. In the example illustrated in FIG. 80, by configuring the manifold valve 170a and the FMS valve 170b to have a default open position, for example, pressure from a pressurized air tank can be transmitted to the dialysate tank 169. By configuring various other manifold valves to the appropriate default positions, the corresponding flow path valves controlled by the manifold valves can be made to open a pathway from the dialysate tank 169, through the outer dialysate pump circuit 159, the ultrafilter 73, a portion of the balancing circuit 143, and ultimately to the dialyzer 14. Thus, in the absence of electrical power, and if the blood flow side of the dialyzer 14 offers no impedance, dialysate from the dialysate tank 169 can be made to flow to the dialyzer 14, allowing for rinseback of blood. During normal dialysis, the control software can ensure that there is a sufficient supply of dialysate in the dialysate tank 169 to allow for the rinseback of all of the blood residing in the blood tubing set.

In alternative embodiments, if the valves that directly control flow in the dialysate flow paths between the dialysate tank and the dialyzer are themselves electrically actuated, they can be chosen to have an open default position. Conversely, other valves that control flow in pathways that divert flow away from the dialyzer can be selected to have a default closed position.

For example, in FIG. 80, the default configuration for the appropriate manifold valves can cause the inlet and outlet valves 171 of the outer dialysate pump circuit 159, and the balancing circuit valves 172 to remain in an 'open' position, providing a flow path to the dialyzer 14. Conversely, the inlet feed valve 173a and the recirculation valve 173b of the dialysate tank 169, and the drain valve 174 of the ultrafilter 73 can be made to have 'closed' default positions in an unpowered state, to prevent the dialysate from being pushed to drain. In addition, the inlet valves 175 of the inner dialysate pump circuit 15 and the inlet valve 176 of the bypass or ultrafiltration pump circuit 35 can be made to have 'closed' default positions to prevent dialysate flow into those pathways from the dialyzer 14 in an unpowered state.

In order to avoid uncontrolled rinseback, the arterial supply and venous return lines of the blood tubing set can be compressed by an occluder mechanism that maintains a default 'occluded' position in the absence of power, and that is moved to an 'unoccluded' position during normal dialysis. The occluder can be positioned to simultaneously occlude both the arterial line before it reaches the blood pump cassette, and the venous line after exiting from the dialyzer or an air bubble trap. In a preferred embodiment, before rinseback is allowed, a patient, operator or assistant withdraws the arterial line from the patient's vascular access site when a rinseback is planned or a power-loss related rinseback is initiated. A suitable connector (such as a needle or needle-less spike, or Luer lock connector) is placed on the end of the arterial line, and is then connected to an air trap (such as air trap 19) in the venous return line. This helps to prevent any air caught in the blood flow path at the top of the blood pump cassette or the top of the dialyzer from being inadvertently rinsed back toward the patient's vascular access. Once the arterial line is connected to the air trap, the patient, operator or assistant may then manually move the occluder to an 'unoccluded' position, decompressing the venous return line and allowing the pressurized dialysate from the dialysate circuit to push the blood in the blood tubing set toward the patient's vascular access. If the patient observes air in the venous line downstream from the air trap, he or she may simply re-engage the occluder and stop the rinseback process.

Although the above rinseback procedures are described with dialysate as the solution that ultimately moves the blood in the blood flow path toward the patient's vascular access, any electrolyte solution that is physiologically compatible and can safely be mixed with blood can be used in a rinseback procedure. Furthermore, rinseback technology need not be limited to a dialysis system. Any system that circulates a patient's blood extracorporeally could potentially benefit from an emergency rinseback system and method. It would therefore be possible to introduce a filter having a semipermeable membrane (such as a dialyzer or ultrafilter) into the blood flow path of the extracorporeal system. The other side of the semipermeable membrane would then be exposed to an electrolyte solution in a flow path that can be pressurized by a compressed gas source with which it is in valved communication.

Another aspect of the invention is generally directed to a user interface for the system. The user interface may be operated by an individual, such as the patient, a family member, assistant, professional care provider, or service technician, to input options, such as treatment options, and to receive information, such as information about the treatment protocol, treatment status, machine status/condition, and/or the patient condition. The user interface may be mounted on the treatment device and controlled by one or more processors in the treatment device. In another embodiment, the user interface may be a remote device that may receive, transmit, or transmit and receive data or commands related to the treatment protocol, treatment status, and/or patient condition, etc. The remote device may be connected to the treatment device by any suitable technique, including optical and/or electronic wires, wireless communication utilizing Bluetooth©, RF frequencies, optical frequencies, IR frequencies, ultrasonic frequencies, magnetic effects, or the like, to transmit and/or receive data and/or commands from or to the treatment device. In some cases, an indication device may be used, which can indicate when data and/or a command has been received by the treatment device or the remote device. The remote device may include input devices such as a keyboard, touch screen, capacitive input device, or the like to input data and/or commands to the treatment device.

In some embodiments, one or more processors of the treatment device may have a unique identification code, and the remote device may include the capability to read and learn the unique identification code of the treatment. Alternatively, the user can program in the unique identification code. The treatment device and the remote device may use a unique identification code to substantially avoid interference with other receivers, including other treatment device.

In one set of embodiments, the treatment device may have one or more processors that are connected to a web-enabled server and the user interface device may be run on this web-enabled server. In one embodiment, the device uses an external CPU (e.g., a GUI, graphical user interface) to communicate via Internet protocol to the embedded web server in or connected to the treatment device. The web page may be served up inside the device and the GUI may communication directly via 802.11b or other such wired or wireless Ethernet equivalent. The GUI may be operated by an individual, such as the patient, a family member, assistant, professional care provider, or service technician, to input options, such as treatment options, and to receive information, such as information about the treatment protocol, treatment status, machine status/condition, and/or the patient condition.

In another embodiment, the embedded web server in or connected to the treatment device may communicate to an appropriate site on the Internet. The Internet site may require a password or other user identification to access the site. In another embodiment, the user may have access to different information depending on the type of user and the access provider. For example, a patient or professional caregiver may have full access to patient treatment options and patient information, while a family member may be given access to certain patient information, such as the status and duration remaining for a given treatment or frequency of treatments. The service technician, dialysis center, or treatment device provider may access other information for troubleshooting, preventive maintenance, clinical trials, and the like. Use of the web-enabled server may allow more than one individual to access patient information at the same time for a variety of purposes.

The use of a remote device, e.g., via wired or wireless communication, Internet protocol, or through an Internet site utilizing a web enabled server, could allow a dialysis center to more effectively monitor each patient and/or more efficiently monitor a larger number of patients simultaneously. In some embodiments, the remote device can serve as a nocturnal monitor or nocturnal remote alert to monitor the patient during nocturnal dialysis treatment and to provide an alarm if the patient's condition does not meet certain parameters. In some cases, the remote device may be used to provide alarms to the patient, a family member, assistant, professional care provider, or service technician. These alarms could alert an individual to certain conditions such as, but not limited to, a fluid leak, an occlusion, temperature outside normal parameters, and the like. These alarms may be audible alarms, visual alarms, and/or vibratory alarms.

Figure 60:
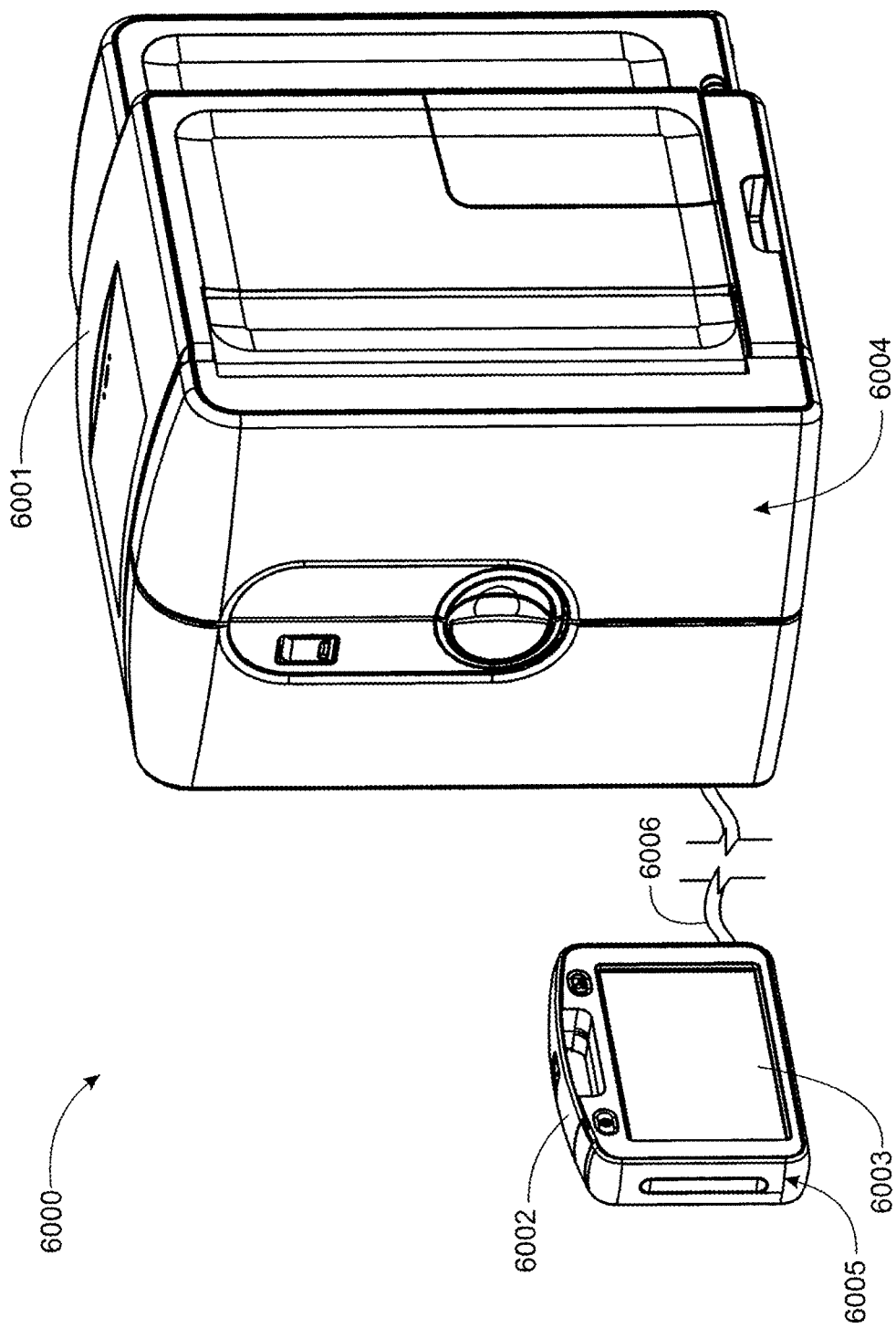
FIG. 60 is a perspective view of an exemplary embodiment of a user interface/treatment device combination.

An exemplary embodiment of a user interface/treatment device combination is shown in FIG. 60. In particular, FIG. 60 shows a perspective view of an exemplary hemodialysis system 6000 comprising a dialysis unit 6001 and a user interface unit 6002. In this embodiment, the dialysis unit 6001 comprises a housing 6004 that contains suitable components for performing hemodialysis. For example, the dialysis unit 6001 may include the mixing circuit 25, blood flow circuit 10, balancing circuit 143 and external or outer dialysate circuit 142 described, for example, in connection with FIG. 2A. The dialysis unit 6001 may also include all patient access connections and dialysate fluidic connections needed for operation of the system 6000.

The user interface unit 6002 comprises a user interface 6003 that a user, such as a hemodialysis patient, may use to control operation of the dialysis unit 6001 via a connection 6006. The connection 6006 may comprise any suitable data connection such as a bus, a wireless connection, a connection over a local area network (e.g., an Ethernet local area network), and/or a connection over a wide area network (e.g., the Internet). The user interface unit 6002 further comprises a housing 6005 that contains components for enabling operation of the user interface. In the example of FIG. 60, the user interface 6003 comprises a display screen with a touch sensitive overlay to allow touch control and interaction with a graphical user interface presented on the screen. However, many other types of user interfaces are possible, such as a screen with a separate input mechanism, such as a keyboard and/or pointing device. The user interface 6002 may also include other features, such as push buttons, a speaker, a microphone for receiving voice commands, and so on.

While the hemodialysis system 6000 of FIG. 60 comprises a user interface unit 6002 remote from and physically coupled to a dialysis unit 6001, many alternative arrangements are possible. For example, the user interface unit 6002 may be mounted to or within dialysis unit 6001. For convenience, a user interface unit 6002 so mounted may be moveable from its mount for use in different locations and positions.

Figure 61:
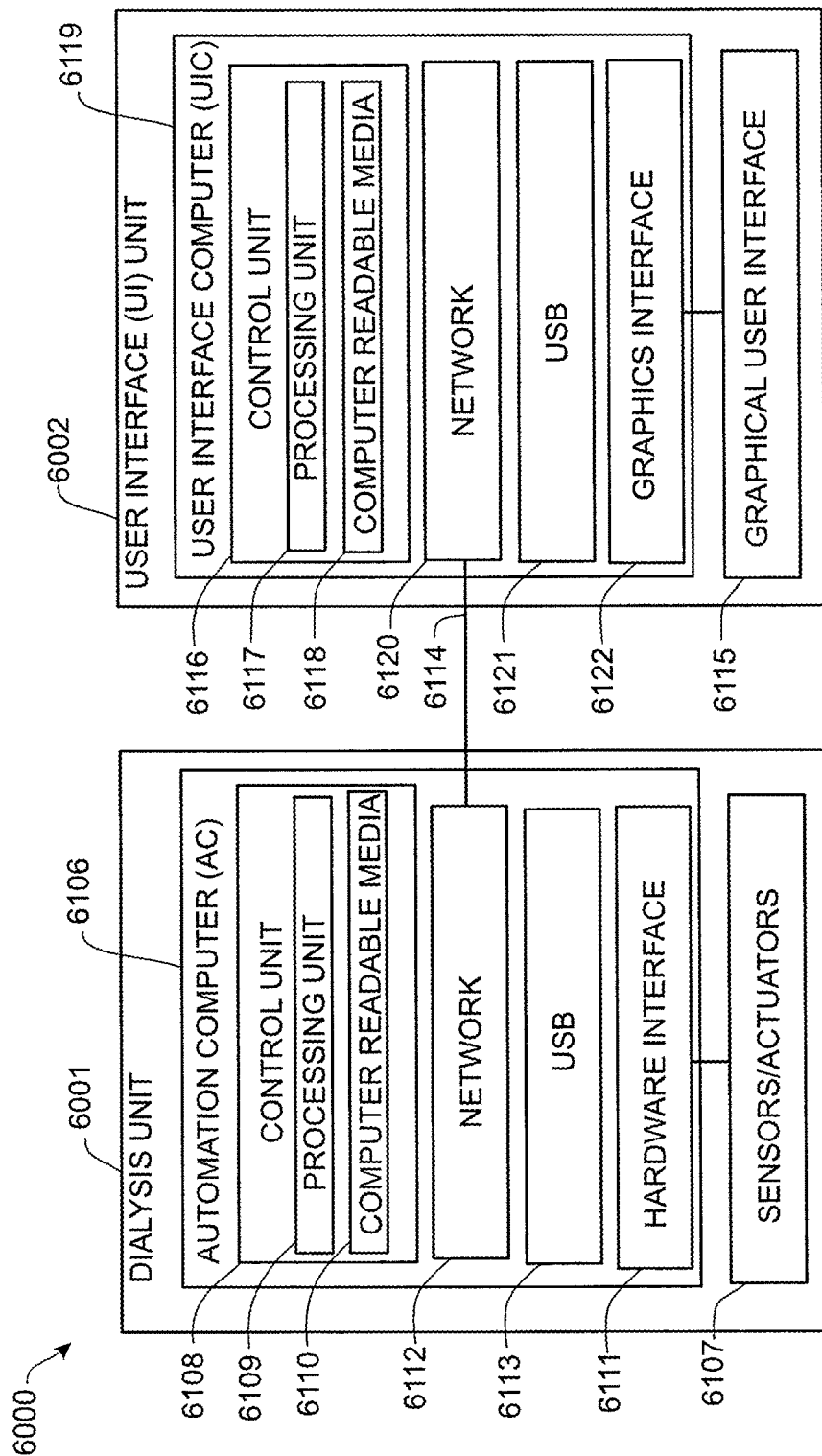
FIG. 61 is a schematic view of an exemplary hardware configuration for each of the dialysis unit and the user interface unit shown in FIG. 60.

FIG. 61 shows an exemplary hardware configuration for each of the dialysis unit 6001 and the user interface unit 6002. Each of these is controlled by a separate CPU, allowing for the separation of time and safety critical software from the user experience software. Once a therapy has begun, it can be completed even if the user interface computer fails or is disconnected. This can be supported by having some physical control buttons and indicator lights redundant to those implemented by the user interface unit 6002 and connected to the control processor of the dialysis unit 6001. The dialysis unit 6001 comprises an automation computer (AC) 6106 that controls hardware actuators and sensors 6107 that deliver and monitor hemodialysis-related therapy. The automation computer 6106 comprises a control unit 6108 that includes a processing unit 6109 and computer readable media 6110. The processing unit 6109 comprises one or more processors that may execute instructions and operate on data stored on the computer readable media 6110. The data may, for example, relate to hemodialysis processes that have been or may be performed on a patient. The system architecture provides the automation computer 6106 with software accessible safety sensors 6107 and the ability to command a fail-safe state (allowing for suspension or discontinuation of therapy in a safe manner). A parallel independent semiconductor device-based system can perform checks similar to those controlled by the software in order to provide a redundant safety system. This cam be implemented, for example in a field-programmable gate array ("FPGA"), and it can also command a fail-safe state independently of the software system if one or more safety checks is not satisfied. The integrity of the pneumatic, hydraulic and electrical systems can be checked both during and between treatment sessions. The instructions may comprise, for example, an operating system (e.g., Linux), application programs, program modules, and/or other encoded instructions that perform particular processes.

The computer readable media 6110 may comprise any available media that can be accessed by the processing unit 6109. For example, computer readable media 6110 may comprise computer storage media and/or communication media. Computer storage media may include any one or more of volatile and/or nonvolatile memory and removable and/or non-removable media implemented in any method or technology for storage of information, such as computer readable instructions, data structures, program modules or other data. Examples of such computer storage media includes, but is not limited to, RAM, ROM, solid state disks, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by the processing unit 6109. Communication media typically embodies computer readable instructions, data structures, program modules or other data in a modulated data signal, such as a carrier wave or other transport mechanism, and includes any information delivery media. The term "modulated data signal" means a signal that has one or more of its characteristics set or changed in such a manner as to encode information in the signal. By way of example, communication media may include wired media, such as a wired network or direct-wired connection, and/or wireless media, such as acoustic, RF, infrared and other wireless media.

The various components of the automation computer 6106, including the computer readable media 6110 and the processing unit 6109, may be electrically coupled via a system bus. The system bus may comprise any of several types of bus structures including a memory bus or memory controller, a peripheral bus, and a local bus using any of a variety of bus architectures. By way of example, such architectures may include Industry Standard Architecture (ISA), Micro Channel Architecture (MCA), Enhanced ISA (EISA), Video Electronics Standards Associate (VESA), and Peripheral Component Interconnect (PCI).

The automation computer 6106 may further include a universal serial bus (USB) interface 6113 so that various input and/or output devices may be coupled to the control unit 6108. Examples of such input and/or output devices include a monitor, speakers, a printer, a keyboard, a pointing device (e.g., a mouse), a scanner, personal digital assistants, a microphone and other peripheral devices. USB is merely one exemplary type of interface that may be used to connect peripheral devices. Other interfaces may alternatively be used.

As discussed above, dialysis unit 6001 includes components for performing and monitoring hemodialysis processes. Such components include sensors and actuators 6107. To couple the control unit 6108 to the sensors and actuators 6107, the automation computer may include a hardware interface 6111. The hardware interface 6111 may provide inputs to and receive outputs from the sensors and actuators 6107.

Automation computer 6106 may further comprise a network interface 6112 to allow the computer to connect with networked devices, such as those within a local area network (LAN) and/or a wide area network (WAN). For example, the network interface 6112 may allow the dialysis unit 6001 to exchange data with the user interface unit 6002 over a network 6114, which may comprise a LAN, such an Ethernet LAN, and/or a WAN, such as the Internet, and may be wired or wireless. Of course, the dialysis unit 6001 may alternatively or additionally exchange data with the user interface unit 6002 over a bus or other data connection.

The user interface unit 6002 comprises a user interface computer 6119 that controls a user interface, such as graphical user interface 6115 that displays information to and receives inputs from the user. Like the automation computer 6106, the user interface computer 6119 comprises a control unit 6116 having a processing unit 6117 and computer readable media 6118, a USB interface 6121 and a network interface 6120, each of which may be the same as or similar to their counterparts in the automation computer 6119. In addition, the user interface computer 6119 may include a graphics interface 6122 to couple the control unit 6116 to the graphical user interface 6115. In a preferred implementation, the user interface computer 6119 software is not tasked to interpret data received from the automation computer 6106, but rather is tasked to display the data in a user-friendly manner.

Figure 62:
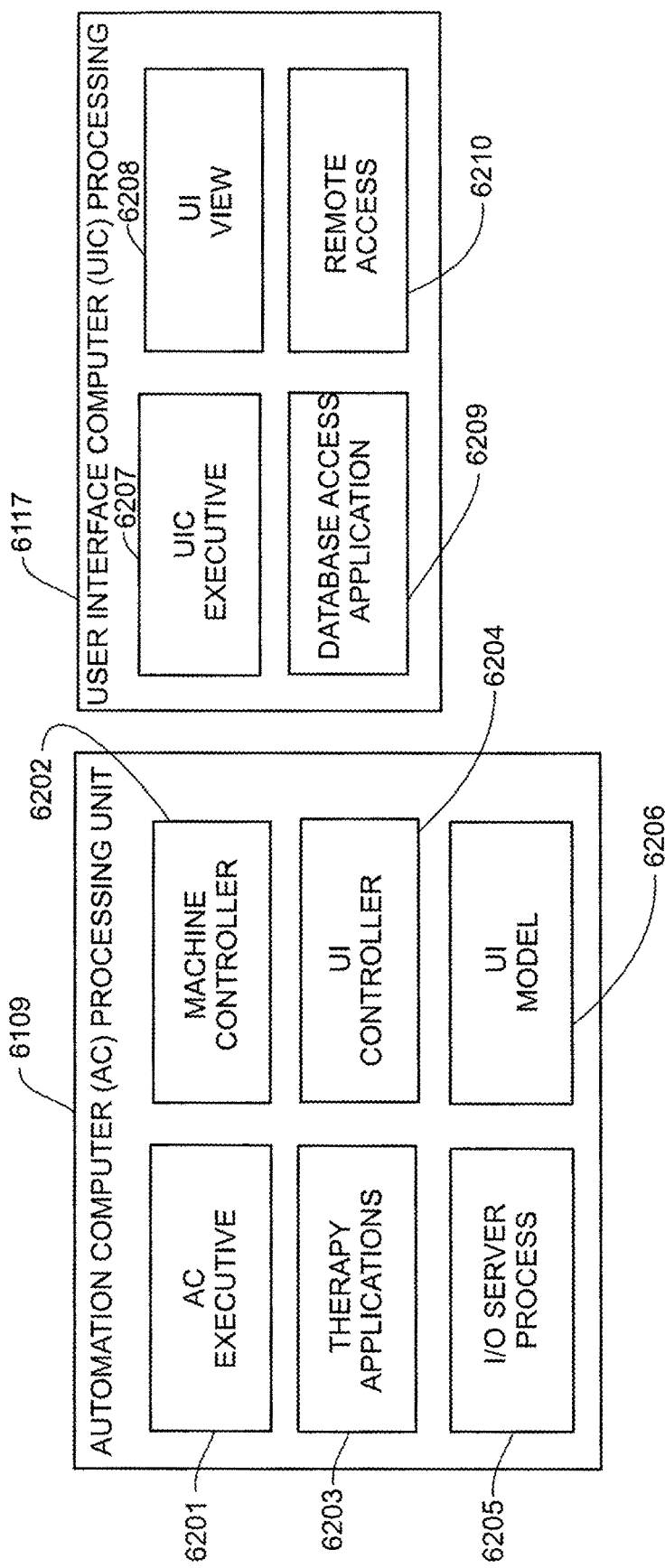
FIG. 62 is a schematic view showing exemplary software processes that may execute on the automation computer and user interface computer shown in FIG. 61.

FIG. 62 schematically shows various exemplary software processes that may execute on the processing units 6109 and 6117 of automation computer 6106 and user interface computer 6119, respectively. The processes shown may be launched and monitored by an executive process. For example, the AC processing unit 6109 and UIC processing unit 6117 may respectively include AC Executive 6201 and the UIC Executive 6207 to launch the processes within the given processing unit and provide a communications mechanism to determine the running status of the child processes. The executives monitor each child process to ensure that each starts as expected and continues to run. In particular, the AC Executive 6201 and the UIC Executive 6207 may detect hung processes. When a child process terminates or fails, each executive process may take appropriate action to ensure that the system continues to operate in a safe manner. This may involve terminating processes and informing the UIC executive 6207, leading to system shutdown, or restarting processes that are not safety-critical. On the UIC processor, this may entail informing the operator and allowing the treatment to be completed using the hard-keys. The AC Executive 6201 and the UIC Executive 6207 may use a Linux parent-child process relationship to receive notifications from the operating system about the termination of child processes. This allows handling of anomalous process terminations as well as expected terminations during a power-off sequence. The automation computer 6106 and the UIC Executives 6201 and 6207 may have a message interface between them to share information about their running processes. The status information may be shared on a periodic basis to allow a coherent view of state of all system processes on both processor units 6109 and 6117. The AC executive 6201 controls a watchdog signal to the electronics, allowing it to place the machine in a fail-safe state when any child process becomes unresponsive or requests a fail-safe state. Preferably, this control does not require an Input/Output server, but can occur directly via a hardware register.

As shown in the example of FIG. 62, the AC processing unit 6109 includes an I/O Server Process 6205. The I/O Server Process 6205 directly accesses hardware, such as sensors and actuators, of the dialysis unit, and provides an interface to allow other processes to request read and write operations. For example, the I/O Server Process 6205 may provide an interface for the Machine Controller 6202 to read from and write to the sensors and actuators, thereby isolating the Machine Controller from the details of the hardware. In the embodiment described, only the Machine Controller 6202 may communicate with the I/O Server Process 6205. The interface may be a synchronous message queue.

The Machine Controller 6202, mentioned above, serves as an interface for controlling machine operations and reporting machine operational status. In particular, the Machine Controller 6202 implements controllers that read sensors and set actuators via the I/O Server Process 6205. These controllers are designed to allow functions (e.g., pumping and heating) to be programmed with a variety of parameters (e.g., flow rates, phases, pressures, and temperatures) in order to support the various hemodialysis therapies that may be performed. The configuration of the controllers may be established by state machines that implement high-level machine functions, such as priming and disinfection. The state machines configure flow paths and controller set points based on the capabilities of the machine and the high level commands received from the Therapy Applications 6203, described below. The Machine Controller 6202 may also perform safety cross checks on various sensors to maintain a safe, effective therapy. Machine status and health information may be recorded by the Machine Controller 6202 to a database.

The Therapy Applications 6203 drive the patient's therapy by commanding the Machine Controller 6202 to perform individual operations relating to hemodialysis processes. In particular, the Therapy Applications 6203 may run state machines that implement therapies and control the modes of the system. The state machines may, for example, control priming the system with dialysate, connecting the patient to the machine, dialyzing the patient, rinsing the patient's blood back to their body, cleaning the machine, disinfecting the machine, running tests on the machine components, replacing old or worn out components, and waiting for the patient to return for their next treatment. The Therapy Applications 6203 issue commands to and request status information from the Machine Controller 6202 in order to implement the therapy operations. In order to obtain patient, therapy and machine information the Therapy Applications 6203 may interface with a database to access information and store treatment status information. The Therapy Applications 6203 may be used as an interface by the User Interface Model 6206 process, discussed below, to forward user selections and report therapy status back to the user interface. The Therapy Applications 6203 implements state machines that include treatment preparation, patient connection, dialysis, solution infusion, patient disconnect, recycle preparation, disinfect, rinse, and disposable replacement. The Therapy Applications 6203 process also contains a master control module responsible for sequencing the activity of all other therapy applications that prepare for and deliver daily treatment.

Like the Therapy Applications 6203, the User Interface (UI) Model 6206 runs on the AC processing unit 6109. The UI Model 6206 aggregates information describing the current state of the system and patient, and supports changes to the state of the system via operator input. The UI Model 6206 separates the content of the user interface display from non-content related aspects (e.g., presentation) by allowing the content of the user interface to change without affecting the underlying software that controls the user interface display. Thus, changes to the UI Model 6206 may be made without affecting the visual experience provided by the user interface. The UI Model 6206 does not have a display directly associated with it; rather, it commands the GUI 6115 of the user interface unit 6002 (FIG. 61) to display screens and return information. For example, when a user navigates to a new screen, the UI Model 6206 may send information to the user interface unit 6002 to be used in generating the new screen. The UI Model 6206 may also validate user data received from the user interface unit 6002 and, once validated, and forward the user data or commands based thereon to the Therapy Applications 6203.

To create the interactive displays for the GUI 6115 of the user interface unit 6002 (FIG. 61), the UI View Process 6208 runs on the UI processor 6117 of the user interface computer. The UI View Process 6208 need not keep track of screen flow or therapy state. Instead the UI View Process 6208 may receive from the UI Model 6206 running on the AC processing unit 6109 information specifying what and how to display the current state of a treatment to the user, as well as what may be input. As a result, the GUI 6115 may terminate and restart without impacting the system's operation. In addition, the GUI 6115 need not be responsible for validating user inputs. All inputs and commands received by the UI View 6208 may be sent to and validated by the UI Model 6206. Thus, all safety-critical aspects of the user interface may be handled by the UI Model 6206. Certain processes, such as those not safety-related, do not require the participation of the UI Model 6206. For example, allowing access to information stored in a database on the user interface computer may not require any functions to be performed by the UI Model 6206.

Also running on the UI processor 6117, a Remote Access Application 6210 provides an interface for external equipment. For example, the Remote Access Application 6210 may provide an interface for therapy monitoring, remote service, online assistance, and other external services, when authorized by a user. The Remote Access Application 6210 may be responsible for initiating a remote connection, validating the access, and supporting the communication from the remote site to the UI Model 6206.

A Database Access Application 6209 stores data to and retrieves data from one or more databases which may, for example, be located on the user interface computer 6119 (FIG. 61). The Database Access Application 6209 allows for record storage and retrieval, and provides a common access point for information required by the system, such as prescription, schedule, and history information. The Database Access Application 6209 may also manage database files to ensure they are backed up periodically.

As discussed in connection with FIG. 62, the functionality of the user interface software may be divided between the AC processing unit 6109 and the UIC processing unit 6117. The UI Model 6206 and UI Controller 6204 may cooperate to isolate the control of the UI data and state information on the automation computer 6106 so that software and screen design changes to the UI View 6208 will only affect the non-safety-critical software on the user interface computer 6119. Thus, while the UI Model 6206 may be tested and run at a safety-critical level, the UI View 6208 may run as a non-safety-critical process.

In general, therapy and machine state information displayed on the user interface computer 6119 originates only from the UI Model 6206. According to one exemplary embodiment, all data displayed on the user interface computer 6119 originates from the UI Model 6206, is taken directly from a database layer, or is temporary editing data entered by a user. The only local state information displayed or stored in the UI View 6208 may be this temporary editing data and details that allow for the local rendering of the information. In this manner, the UI Model 6208 may maintain and control the display of all validated data. Non-safety related data may be handled solely by the UI View 6208, if desired. For example, changes in the display language, or other display changes that do not impact safety-related content, may be performed using the UI View 6208 without any effect on the UI Model 6206.

It should be appreciated that the software processes shown in FIG. 62 and their association with processing units 6109 and 6117 represents just one example of a software configuration for performing the functions described above. The processes may be distributed in various alternative manners among processing units 6109 and 6117 and/or other local or remote processors. Further, not all processes may be required in the hemodialysis system. Certain processes may be omitted or modified while maintaining the functionality of a hemodialysis system.

Figure 63:
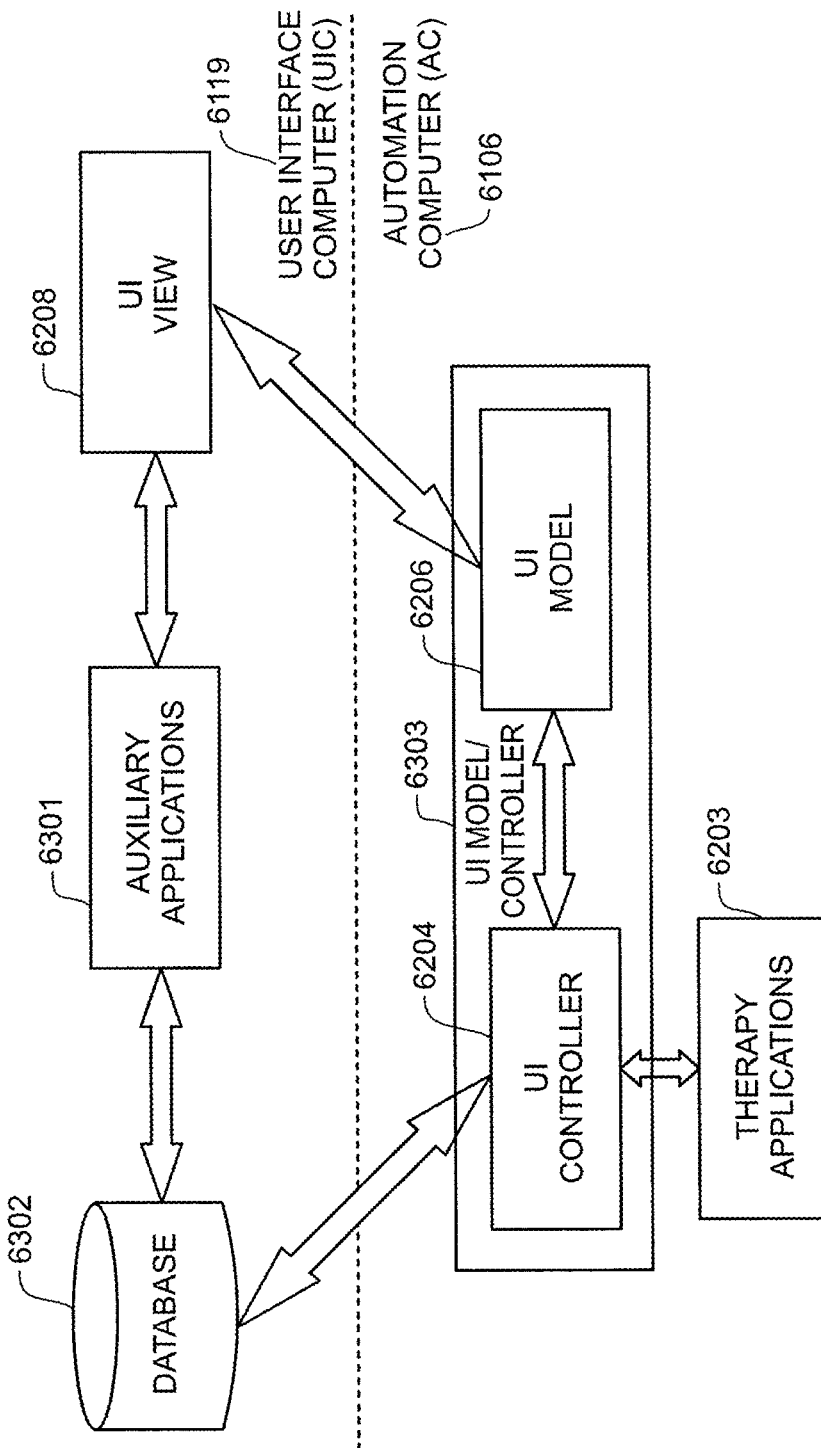
FIG. 63 is a schematic view showing an exemplary flow of information between and among the hardware and software components of the user interface computer and automation computer.

FIG. 63 shows an example of how information relating to the user interface may flow between and among the hardware and software components of the user interface computer 6119 and automation computer 6106. Information may flow and be handled so that safety-critical information is processed only at or below the UI Model layer. Safety-critical information relates to operations of the hemodialysis system. For example, safety-critical information may comprise a state of a dialysis process, a screen state of the graphical user interface, and/or the algorithms for implementing or monitoring therapies. In some cases, safety-critical information may be displayed by the graphical user interface. In such cases, the safety-critical information may comprise content that is material to the operations of the hemodialysis system. Non safety-critical information displayed by the user interface may comprise aspects of the display that relate to visual presentation and are not material to the operations of the hemodialysis system.

As shown in FIG. 63, the UI Model 6206, UI Controller 6204 and Therapy Applications 620, discussed in the connection with FIG. 62, run on the automation computer 6106. The UI View 6208 runs on the user interface computer 6119, along with Auxiliary Applications 6301. A database 6302, or an interface thereto (e.g., a database server) may also reside on the user interface computer 6119. The UI Model 6206 aggregates the information describing the current state of the system and patient, and commands the graphical user interface to display screens and return information. It validates and forwards user data and commands to the therapy applications in order to give the user control over the system. The UI Model 6206 keeps the content of the user interface independent from the display. The graphical user interface preferably does not maintain machine state information, allowing the user interface to be changed or temporarily disconnected without affecting the underlying software. Although the graphical user interface is not responsible for validating user inputs, it may constrain ranges of various inputs, the validation being the responsibility of the UI Model 6206.

Considering first the flow of information between the UI View 6208 and UI Model 6206, the UI View operates as a client of the UI Model, as explained below. The UI View 6208 requests the current screen state from the UI Model 6206, and the UI Model answers the request. The answer dictates the major screen state of the UI View 6208. The UI Model 6206 may publish data and state information in sufficient detail so that the UI View 6208 can present various subsets of display information according to a level of detail requested by a user. For example, the UI View 6208 could present the same therapy state as either a summary or a step-by-step guide using the same information from the UI Model 6206. The presentation of the information may be based, for example, on a mode selected by a user (e.g., "expert" or "novice"). The UT Model 6206 may provide the ability for the UI View 6208 to record sub-state information, such as a current presentation mode, in the UI Model. This allows the GUI to resume operation in its prior state in the event of a user interface computer 6119 reset.

The UI Model 6206 may accept user-input data and requests, such as a request to start a therapy, from the UI View 6208. Data integrity of any information submitted via the UI View 6208 may be enhanced or ensured in several ways, such as by sending data submitted via the UI View 6208 through the UI Model 6206 for verification. That is, while data may be edited locally in the UI View 6208, the accepted data may be transferred to the UI Model 6206 to be verified and recorded into database 6302 and/or sent to the Therapy Applications 6203. Verification may comprise, for example, verifying that entered data is within an expected range. Any entered information may be then read back from the database 6302 by the UI Model 6206, and sent to the UI View 6208 for display to the user. This process may be used to ensure that data stored in the database 6302 is correct or as a user intended. Data integrity may also be enhanced by requesting verification, by the user or another party, of entered data.

As shown in FIG. 63, direct authority to control the Therapy Applications 6203 in response to inputs received from the user interface, and thereby affect machine state, may be limited to the UI Model/UI Controller 6303 running on the automation computer 6106. In addition, direct authority to change information in the database 6302 may be limited to the UI Model/UI Controller 6303. In this case, the UI View 6208 and Auxiliary Applications 6301 may have read access to the database for actions such a viewing a log, but may not have write access to the database 6302, at least under most circumstances. In this way, actions that could have safety-critical implications may be isolated on the automation computer 6106. Of course, in some situations, it may be desirable to allow the UI View 6208 and Auxiliary Applications 6301 to have limited write access to the database 6302, such as to write to a particular portion of the database or to write non safety-related data to the database. In addition, in some embodiments, it may be desirable to allow the UI View 6208 to directly control aspects of the Therapy Applications 6203.

The Auxiliary Applications 6301, discussed above, may comprise log or documentation viewers, for example. These Applications 6301 may run on the user interface computer 6119 and operate in their own process space. However, to enable the UI View 6208 to control these applications, the Auxiliary Applications 6301 may be clients of the UI View 6208. This allows the UI View 6208 to communicate with the applications in a standard manner and allows the UI View to monitor these processes.

The UI Controller 6204 may comprise a table-based hierarchical state machine (HSM) that determines the state of the screens displayed by the UI View 6208 based on data polled from the Therapy Applications 6203, local timeouts, and command requests or data received from the UI View 6208. As represented in FIG. 63, the UI Controller 6204 may access and write data to the database 6302 as required. The state of the HSM in the UI Controller 6204 may determine the major state of the set of screens displayed by the UI View 6208.

Figure 64:
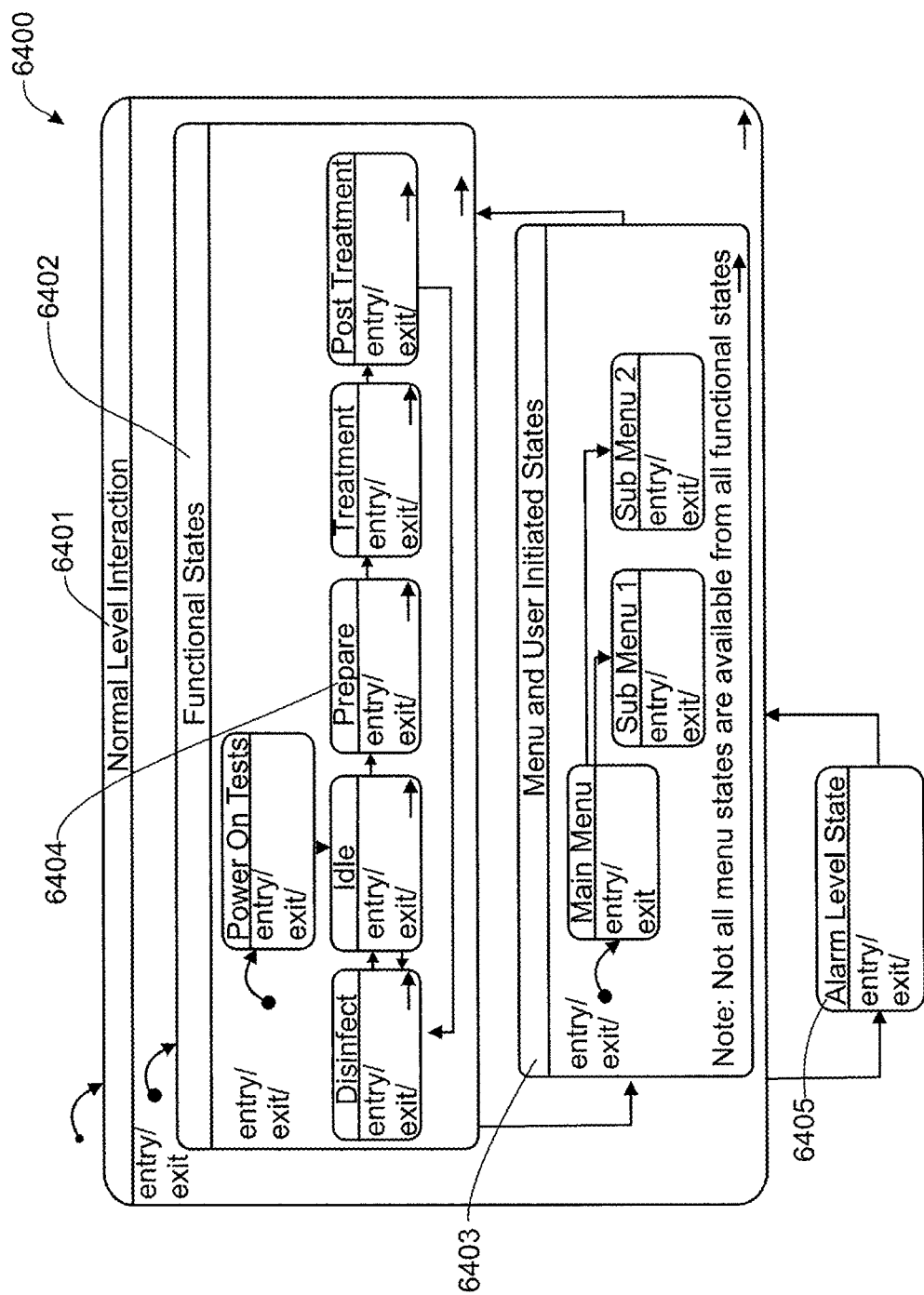
FIG. 64 is a schematic view of an exemplary hierarchical state machine (HSM) that may be used by the UI Controller shown in FIG. 63.

An exemplary HSM that may be used by the UI Controller 6204 to determine the state of the screens displayed by the UI View 6208 is schematically shown in FIG. 64. As shown, the HSM 6400 determines the state of "normal" (i.e., non-alarm) level interactions 6401, including the current functional state 6402 of the user interface and the current menu state 6403. The HSM 6400 shown in FIG. 64 is merely exemplary, and may be implemented in a much more detailed manner. For example, the state designated "Prepare" 6404 may involve several states relating to preparation for treatment, including a "gather supplies" state, an "install chemicals" state, the entering of patient information, and a validation screen. The validation screen gives the user the opportunity to return to any of the prior data entry screens so that inaccurate information can be corrected before the "Prepare" state is exited. The HSM 6400 also shows an alarm state 6405 that may be triggered. The alarm state is described in connection with FIG. 65.

Figure 65:
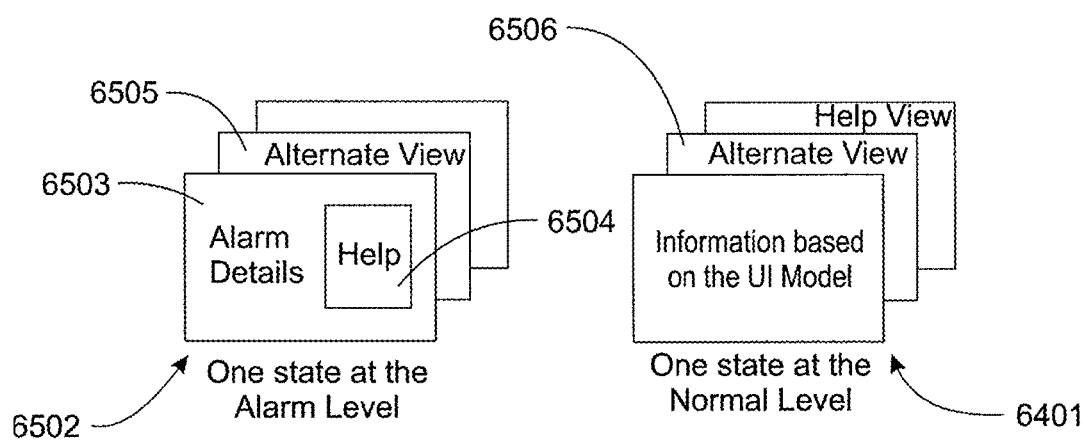
FIG. 65 is a schematic view of normal screen displays and alarm screen displays that may be displayed by the user interface shown in FIG. 61.

The UI View 6208 may have the ability to take over the screen display at any time in order to display alarms. An alarm condition may be triggered in certain circumstances to notify a user or other individual of an abnormal or otherwise noteworthy condition, such as a fluid leak, an occlusion, or an out-of-range temperature. When an alarm condition occurs, the state of the UI Controller 6204 may change. As shown in FIG. 65, when the UI View 6208 polls the UI Model 6206 for the current state, the UI View will change the display view from a normal state 6501 to an alarm state 6502 displaying alarm information 6503. When in an alarm condition, the UI View 6208 may prevent other information from blocking the display of the alarm. However, even during an alarm condition, the display may be configured such that a user may activate a "help" button to access additional information. In this case, help information 6504 may be laid out so that the help information covers only a portion of the view. Safety-critical logic of the alarm display, such as silencing logic, may be controlled in the automation computer 6106. For example, if a user would like an alarm to be silenced, an indication of the silencing request may be relayed back to the UI Model/UI Controller 6303, which can allow the audible alert to be silenced temporarily. In each of the alarm state and the normal state, alternate views 6505 and 6506, respectively, may be possible.

As explained above, when an alarm occurs, the normal UI View state is terminated so that the alarm state information can be displayed. Any local screen selection and/or editing data may be lost when the screen is changed. Since it may be desirable to preserve this information, the UI View 6208 may request that the UI Model/UI Controller 6303 stores information related to the screen displayed just prior to the alarm condition (i.e., the screen related to the normal state). At the conclusion of the alarm, if the normal state has not changed, the UI View 6208 may retrieve the stored information and restore the screen display. As an additional benefit, this feature may be used to restore the prior view in the event that the user interface computer 6119 is inadvertently reset.

Figure 66:
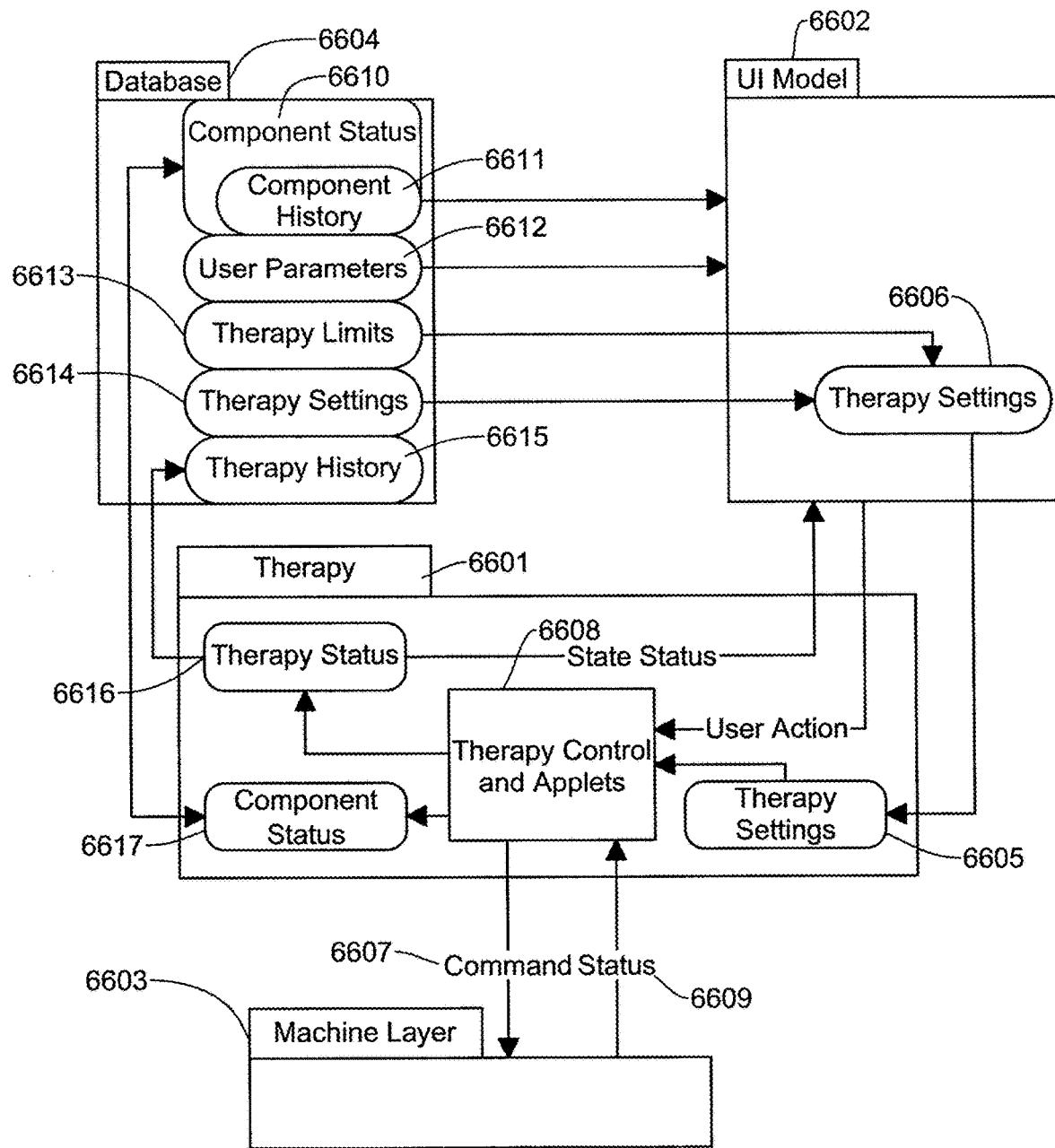
FIG. 66 is a schematic view showing how the Therapy Layer interfaces with other layers, such as the Machine Layer and User Interface Model Layer.

Therapy behavior is modeled and implemented as hierarchical state machines that define each activity and user interaction as discrete states. As shown in FIG. 66, the Therapy Layer 6601 is between the User Interface Model Layer 6602 and the Machine Layer 6603. The Therapy Layer both generates data and uses data stored in the Database 6604, which also shares data with the User Interface Model Layer.

The Therapy Layer 6601 controls the state of the system as a whole, and dictates available user interface interactions. The Therapy Layer 6601 is polled for state/status information by the User Interface Model Layer 6602. The Therapy Layer 6601 accepts user state change requests and changes to the Therapy Settings 6605 from the therapy settings 6606 on the User Interface Model Layer 6602. The Therapy Layer 6601 directs the Machine Layer 6603 in controlling the fluid path flows by issuing commands 6607 from Therapy Control and Applets 6608. The Therapy Layer 6601 polls status information 6609 from the Machine Layer 6603 to determine the state of processes.

Information read from and written to the Database 6604 may include Component Status 6610, Component History 6611, User Parameters 6612, Therapy Limits 6613, Therapy Settings 6614, and Therapy History 6615. For example, replaceable component information may be read from and updated to the Database 6604, and required fluid use and disinfect information may be read from the Database 6604. The Therapy Layer 6601 periodically writes Therapy Status 6616 information to the Database 6604 for logging purposes and to facilitate recovery in the event of a temporary power loss. The Therapy Layer 6601 also updates the Database 6604 with Component Status information 6617.

All inter-processor communications may be performed via server-defined client application programming interfaces (APIs) as remote process calls. The Therapy Layer 6601 may block when making Machine Layer and Database interface calls via their respective Client APIs. However, during critical functions, such as while performing patient therapy, the Therapy Layer generally will not perform any blocking database accesses. Generally, only non-critical updates to the database are performed using asynchronous (one-way) writes.

The User Interface Model Layer 6602 may block when making Therapy Layer calls via the Therapy Client API. The processes of the Therapy Layer may be considered higher-priority than those of its clients, such as the User Interface Model Layer 6602.

The system may handle exception conditions or errors generally in one of at least three ways. A system error detected in the software or associated with the CPU (such as, for example, a memory failure) call the reliability of the system into question, and trigger a failsafe state. A therapy error or condition may occur if a therapy variable approaches or exceeds permissible bounds. At least an alert or alarm (an event requiring user action) are triggered, and the condition is logged. Finally, system operation conditions can be triggered and logged to the database for later retrieval and analysis if problems are reported by an operator or service technician.

Generally, the Machine Layer 6603 will not change state unless explicitly requested by the Therapy Layer 6601. Thus, the Machine Layer 6603 generally should not generate an error in response to a change requested by the Therapy Layer 6601, assuming that the Therapy Layer 6601 makes change requests that are valid for the current operating state. As a result, Machine Layer 6603 command errors may not be tolerated. An exception is when a "Pause-Freeze-Stop" button is acted upon directly by the Machine Layer 6603 prior to Therapy Layer 6601 interaction. In this case, the Machine Layer 6603 will ignore any subsequent Therapy Layer 6601 commands until the Therapy Layer confirms the "Pause-Stop-Freeze" action.

Exception cases (e.g. in the event of a blood leak, or air in a line) and orthogonal states may be prioritized such that the state presented to the external User Interface Model Layer 6602 can be resolved to a unique current state. If multiple orthogonals attempt to set the user interface state, generally only the last orthogonal processed will be presented. Unexpected exceptions may be handled by commanding a Fail Safe state.

As explained above, the Therapy Layer 6601 software is a state-based control layer between the Machine Layer 6603, and the User Interface Model Layer 6602. The interface and access methodology that the Therapy Layer 6601 presents to the User Interface Model Layer 6602 are discussed below.

The Therapy Layer 6601 is a state-based layer that receives command requests from the User Interface Model Layer 6602. Some commands are valid from any state. Others are state specific, and the Therapy Layer 6601 will decide if the current command request will be acted upon or not. If the current state is not valid for the command request, the request from the User Interface Model Layer 6602 will be rejected and an appropriate reason for the rejection will be returned to the client. In this way, safety-critical operations will be protected from commands that are inappropriate in the current state. Only safe and validated operator command activities may be processed. The Therapy Layer 6601 interface to the User Interface Model Layer 6602 may be a server, and the User Interface Model Layer 6602 may access it as a client process using standard IPC client/server connection methods.

Synchronization between the Therapy Layer 6601 and the User Interface Model Layer 6602 may be based on two state-based enumerated types: the "Master State" and the "Sub-State." The Master State indicates the currently active Therapy Layer 6601 state machine. The Sub-State provides a unique state indication that can identify all of the alarms, user interaction, or the therapy sub-states that have duration. These state variables are updated in Therapy Status messages. This allows the Therapy Layer 6601 to verify what the active user operation is in a response to and provides the context to commands like "continue."

Figure 67:
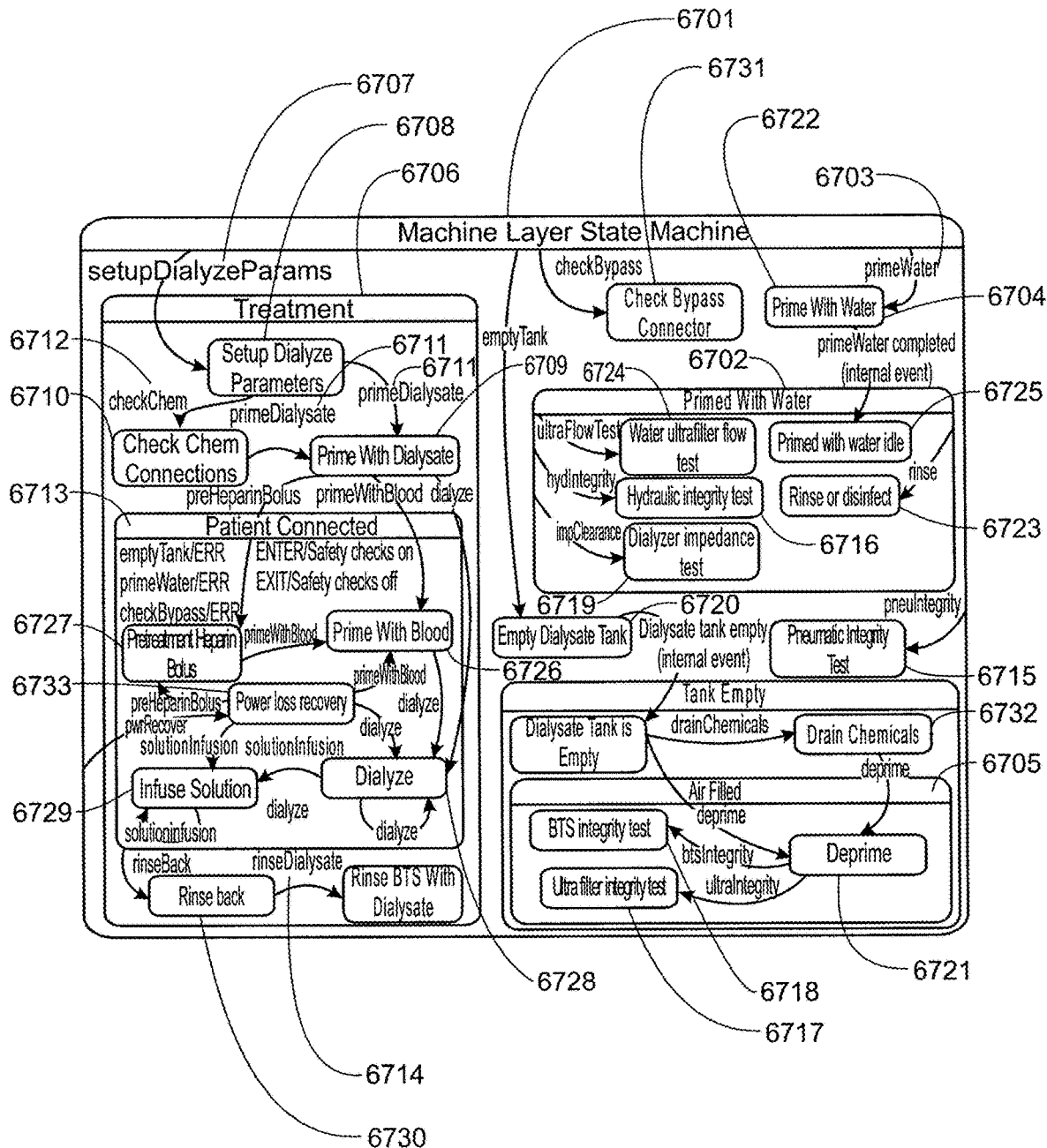
FIG. 67 is a schematic view showing an exemplary implementation of the Machine Layer shown in FIG. 66.

Turning now to the Machine Layer 6603 shown in FIG. 66, an exemplary implementation of the Machine Layer is shown in FIG. 67. The machine software is a layer of abstraction that provides the ability to implement a specific set of operations. These operations include priming the system, performing dialysis, disinfecting, draining and self testing. The machine software operates specific valves, runs pumps, controls flow paths and takes measurements. During the operations of the Machine Layer, status information can be requested at any time without interfering with operations.

With reference to FIG. 67, one state of the Machine Layer State Machine 6701 is the Primed With Water state 6702. This state is reached by sending the primeWater command 6703 and allowing the operation Prime with Water 6704 to complete. In the Primed With Water state 6702, the fluid paths are filled with reverse osmosis (RO) water and purged of air. In addition, this state is used to rinse, disinfect and perform various tests including flow tests and hydraulic integrity tests.

The Air Filled state 6705 is used to run the dialyzer and ultra filter integrity tests and for replacing components. In this state, the system may have had as much of the fluids removed as practically possible.

Dialysis treatment is performed in the Treatment state 6706. This state is entered by sending a command 6707 to set up the parameters of the dialyzer and the ultrafilter. For example, the setupDialyzeParams command 6707 may communicate the parameters of the installed disposable filters and the size of the needle/catheter. The initial state of the Treatment state 6706 is the Setup Dialyze Parameters state 6708.

The command issued by the Setup Dialyze Parameters state 6708 depends on the dialysate source. If the source is bagged dialysate, the primeDialysate command 6711 is issued and the process proceeds directly to Prime with Dialysate 6709. If the system is making dialysate from a bicarbonate cartridge and acid, the connections have to be verified. In this case, the CheckChem command 6712 is issued and the process proceeds to the Check Chem Connections state 6710. A dry test can be used to verify that an empty chemical container is connected. A wet test can be used to verify that a primed chemical container is connected by detecting the presence of no or minimal air in the container. Positive or negative pressure can be applied to the chemical container to detect the presence of loose connections or leaks. Conversely, a "CheckBypass" test can be performed to verify that the bypass connector is in place. Positive or negative pressure in the flow path can be measured to determine whether the chemical concentrate containers and tubing or the bypass connector are present. Positive or negative pressure can also be applied to determine the presence of any leaks associated with the connector. When this state is complete, the primeDialysate command 6711 is issued and the process proceeds to Prime with Dialysate 6709.

When using bagged dialysate, the priming process begins immediately. When making dialysate from reverse osmosis water, the system should prime the bicarbonate cartridge and cause the conductivity of the dialysate to stabilize at the requested level. Then, the dialysate tank should be filled to a minimum level. The system primes itself by running the pumps in the dialysate circuit forward and backward to drive air out of the cassette. The conductivity sensors can be checked during priming to ensure that their readings remain consistent. The system finishes priming by driving dialysate through the dialyzer and into the blood loop. Priming here can also involve forward and backward flow to help purge any air from the blood loop. The arterial and venous lines can also be isolated at times to purge the air more efficiently. Priming of the blood loop also serves to meet the minimum rinse volume required for the dialyzer before treatment. When this process is complete, the patient can be connected.

Before the start of a treatment, a Set Fluid Production Parameters command may be sent to the machine layer 6701. This command communicates the necessary information to either make dialysate or use pre-made dialysate. For example, the following dialysate information may be provided: bicarbonate cartridge priming volume (ml), bicarbonate volumetric ratio (mg/ml), target dialysate conductivity (mS/cm @ 25° C.) after addition of acid and salt (final dialysate composition), and acid volumetric mixture (ml acid/ml water). The following dialysate source information may be provided: reverse osmosis (RO) water or premade dialysate (RO/Bagged), and pre-made dialysate volume (ml).

The Pneumatic Integrity Test operation 6715 verifies the pneumatic devices in the system. This operation may check for leaks and verify sensors. This operation may comprise the following individual tests, which may be run individually or all in sequence: a cassette leak test, a pressure pump test, a meter pump test, and a dialysate tank leak test. The cassette leak test tests for air leaks in the valve manifold, the pressure pump chambers and the plumbing. The fluid valves are closed on all pressure pumps, and then positive varivalves are opened. Next, the compressors are activated and the pneumatics are pressurized. After a target pressure is reached, the compressors are turned off and the system pressures are monitored, e.g., for 10 seconds. At the end of that time, if the pressures are above a threshold, the test passes. Then the test is repeated with negative varivalves. The meter pump test charges FMS chambers with positive pressure, and verifies that the FMS chambers reach the pressure. The positive pressure valves are closed, and the system verifies that they do not leak more than the test threshold. The process is repeated with negative pressure. In some cases, the pressure decay rate is used to determine whether a leak test passes.

The Hydraulic Integrity Test operation 6716 verifies the fluid valves in the system. In this test, pump chambers are filled with water and the chamber is driven, and valve leaks are detected by measuring the pressure drop in the pump chamber. The operation is divided up into sets of valves based on which pressure pump drives fluid through the valve.

The Ultrafilter Integrity Test operation 6717 is a pressure test of the ultrafilter membrane to check for leakage. Air pressure is applied to the inlet side of the ultrafilter. Air pressure is maintained, since air generally will not pass through a wet intact filter. This test is performed in the "Air Filled" state, and verifies the ultrafilter by pressurizing the outer dialysate side and measuring the pressure drop over time.

The BTS/Dialyzer Integrity Test operation 6718 is a pressure test of the blood loop including the dialyzer. In this test, the blood loop is pressurized and the pressure is monitored over time. If the measured pressure drop is less than the input decay threshold, the test passes. As the blood tubing, pump and dialyzer are replaced as a unit, this test need not determine where the leak is.

The Impedance-Based Clearance Test operation 6719 verifies that the blood path through the dialyzer has low enough resistance to provide efficient dialysis therapy. Before starting the impedance test, the system is primed with water. During the test, flow is forced across the dialyzer. As water flows across the dialyzer, the pumping pressures will be monitored, which provides a measure of the dialyzer impedance. Alternatively, a constant pressure can be applied, and the time taken for a fixed volume to cross the filter membrane can be measured. The dialysate circuit is set to provide a constant low impedance destination of the fluid being pushed through the membrane. If the dialyzer impedance is too high, a failure will be reported and the dialyzer will need to be replaced. An Ultrafilter Flow Test operation 6724 may be also performed to ensure that the ultrafilter impedance is low enough to support the flow rate required for therapy. This test has the benefit of ensuring that the result of the integrity test will be valid.

The Empty Dialysate Tank state 6720 may stop fluid production and run the dialysate pump at the fastest reasonable rate to pump the contents of the dialysate tank to drain until some amount (e.g., 3000 ml) has been transferred, or air is detected in the drain. The Deprime operation 6721 is used to purge the system of fluid, filling the blood tube set and the dialysate circuit outside of the ultrafilter with air. This condition is used to perform pressure-decay tests to verify the integrity of the dialyzer and ultrafilter, as well as to change the fluid components and to prepare the unit for transport. The inner dialysate circuit generally cannot be deprimed because it may not be possible to pump air through an intact dialyzer or ultrafilter, and there may be no air vent in the inner circuit.

The Prime with Water operation 6722 fills the system with water and purges the air. It may fill the system in stages, starting with the fluid production section, and moving to the outer dialysate, inner dialysate, and then the blood loop. The bicarbonate cartridge and acid bag should be removed, and a bypass connector should be in place before this operation is performed. According to one exemplary implementation, the bypass connector comprises three connection points respectively corresponding to a bicarbonate charge line, an acid flow line and a bicarbonate return line of the mixing circuit 25. The bypass connector has three parallel prongs respectively corresponding to the three connection points. Channels in the prongs of the bypass connector terminate within a common chamber within the bypass connector. Thus, during a disinfect procedure, the bicarbonate charge line, acid flow line and bicarbonate return line are all interconnected, permitting disinfection of each of these flow lines during the disinfect procedure. An exemplary embodiment of such a bypass connector is the "disinfect connector" described in U.S. patent application Ser. No. 12/199,055 filed on Aug. 27, 2008 and issued as U.S. Pat. No. 8,393,690.

The Disinfect/Rinse state 6723 is used to run reverse osmosis water through all fluid paths at a specified temperature. Before this operation, the system should be in the "Primed With Water" state 6725. Disinfection occurs when this operation is performed at an elevated temperature. The tank is filled with reverse osmosis ("RO") water at the start of the operation. The water in the dialysate tank is recirculated from the Dialysate Circuit disinfect path through all Fluid Production fluid paths and blood tubing set paths, and back into the dialysate tank. As recirculated water is lost (sent to drain), reverse osmosis water may be added to maintain a minimum level in the dialysate tank. Alternatively, in a preferred embodiment, no further water is introduced in order to avoid the possibility of contamination. The chemical cartridge is not attached during this operation.

The Prime with Dialysate operation 6709, described above, is used to flush dialysate through all fluid paths and remove any air or water in the system. This operation must be completed before the system can move on to the Patient Connected state 6713. This operation activates the fluid production sub-system, which is responsible for mixing the RO water with the chemicals, and for maintaining the dialysate tank level. If the tank is less than 75% full, priming may be delayed until that level is reached. The tank level is preferably maintained at more than 1.1 liters; otherwise, a signal may be generated to stop therapy. This amount allows for a sufficient rinseback volume and a sufficiently large averaging volume needed for mixing control accuracy. During prime, the air-in-line sensors, the blood-leak sensor and the safety system are tested.

In the Patient Connected state 6713, a dialysis treatment can be performed. Prior to issuing the RinseDialysate command 6714, the blood tubes are returned to drain connections. For safety purposes, while in the Patient Connected state 6713, the dialysate temperature may be constrained, and the dialysate conductivity and flow rates may be monitored.

The Prime With Blood operation 6726 removes dialysate from the blood circuit and replaces it with patient blood. Dialysate is pulled across the dialyzer membrane into the dialyze circuit and is discarded to drain. Blood is pulled into the blood circuit from the patient to replace the dialysate pulled across the membrane. Thus most of the priming fluid occupying the BTS need not be administered to the patient at the start of dialysis. Optionally, the patient can choose to be administered the priming fluid by canceling this operation. This may be desirable, for example, if the patient is in need of additional fluid at the start of dialysis. This operation transitions the machine software into the Patient Connected state 6713, activating safety constraints such as temperature limiting.

The Heparin Bolus operation 6727 delivers a bolus of heparin before treatment without requiring patient interaction. Before normal dialysis operation, and to minimize the amount of fluid administered to the patient, the bolus can be delivered down the arterial line, which is a shorter route to the patient's vascular access. In the event of the detection or presence of an air-in-line condition, the heparin bolus can optionally be delivered down the venous line, which incorporates air-trapping mechanisms or devices.

The Dialyze operation 6728 is used to administer dialysis treatment to the patient. The rate of the blood circuit and the dialysate circuit may be specified independently. This operation can have a time limit or be terminated with a stop command. By way of example, the following parameters may be specified: the temperature at which the dialysate flowing through the system is heated and maintained, the rate at which dialysate is circulated through the blood circuit, the rate at which basal or maintenance heparin is added to the blood circuit, the rate at which dialysate is circulated through the dialysate circuit, and the rate at which dialysate is pumped through the ultrafiltration pump, among other parameters. During dialysis, the ultrafilter is periodically 'burped' to remove any gas that has accumulated within it during treatment. This can be accomplished by opening the pathway from the top of the ultrafilter to drain while closing the pathway fro the top of the ultrafilter to the dialysate circuit. Any air trapped in the top of the dialyzer can then be flushed to drain. After two or more pump strokes to divert the air and fluid to drain, the valves are reset and dialysis operations can continue.

The Power Loss Recovery 6733 command may be sent to tell the machine software that there was loss of power while it was in the Patient Connected state 6713. This forces the machine software into a Patient Disconnected state so that the dialysis machine can recover properly and prepare itself for the next treatment (e.g., Recycle Preparation).

The Solution Infusion operation 6729 delivers dialysate into the patient. Dialysate is pushed across the dialyzer by the outer dialysate pump and delivered to the patient by the blood pump. This command causes the system to prepare for the infusion by stopping dialyzing, freezing the inner pump, and filling the outer pump with dialysate to deliver to the patient. After receiving this command, the machine software expects one of the following commands: Solution Infusion Confirm (proceed with solution infusion), Dialyze (do not perform solution infusion, resume dialyzing instead), or StopCmd (return the system to an idle state). Preferably, the blood pump continues to run during solution infusion.

A Backflush operation can be programmed during dialysis to periodically flush dialysate backwards across the dialyzer membranes in order to help prevent clotting of the membranes. The Rinse Back operation 6730 pushes dialysate into the patient to return their blood in preparation for disconnection. Dialysate is pushed across the dialyzer by the outer dialysate pump and delivered to the patient. This is automated for both venous and arterial paths.

The Check Bypass operation 6731 checks for the presence of the bypass connector for the acid container and the bicarbonate cartridge or container. In a preferred embodiment, the operation causes a vacuum to pull on the bypass connector to detect leaks. The Drain Chemicals operation 6732 empties the contents of the chemical containers to the drain. In a preferred embodiment, the contents of the chemical containers are discarded after each treatment, making cleanup easier for the patient and discouraging potential problems in trying to reuse chemicals.

A CheckDoors operation verifies that the doors of the hemodialysis machine are closed, helping to ensure that the patient is disconnected. A CheckDCA operation can then verify that the patient has plugged the vascular access connectors of the blood tubing set back into the DCA/DCV ports of the machine for rinsing and disinfecting after a treatment session.

In addition, a Clean Blood Path operation may be performed to push the contents of the dialysate tank through the blood circuit and out the drain. Rinsing is used to flush residual blood from the blood circuit and dialyzer after the dialysis treatment. In an embodiment, air is introduced into the fluid to enhance the mechanical action of loosening debris from the dialyzer and tubing components. During this operation, fluid production may deliver water, which will dilute the dialysate in the tank.

A Recirculate operation may be used to maintain the temperature and dialysate freshness in the system after it has been primed when the patient is not yet connected. This is accomplished by running dialysate through the heater, ultrafilter into the inner pump, and passing it through the dialyzer, while also running the blood pump. A small amount of the dialysate can be constantly sent to drain.

The Machine Layer 6701 may also respond to stop, freeze, resume, and shut down commands. The stop command terminates the operation being performed by machine. When the stop command is issued, the current pump cycle is completed, then the valves are all closed. Because the stroke is completed, all fluid accounting will be accurate. After all valves are closed, the state machine returns to the "idle" condition where it waits for the next command. This command does not affect the getStatusCmd, setupDialyzeParams or setupFluidParams commands because they do not start operations.

The freeze command causes the system to close all valves on its current cycle. This includes the fluid production valves. The heater is turned off to prevent overheating of the fluid within it. Fluid volume accounting will be correct if the resume command is issued after the freeze command. If the freeze command is followed by a command to enter an operation other than the one that was frozen, fluid volumes are assigned to the new operation regardless of the fact that there may be partial fluid delivery in the original state. State history of the current operation is retained so the "resume"

command can be used to continue the operation. The resume command causes the machine to continue processing the command that was frozen. The shut down command is used to terminate the machine software process.

The Therapy Applications 6203 shown and described in connection with FIGS. 62 and 63 run state machines that implement therapies implemented by the Machine Controller and I/O Server Process. The state machines may perform such functions as treatment preparation, patient connection, dialysis, solution infusion, patient disconnect, recycle preparation, disinfect, rinse, and disposable replacement. The Therapy Applications 6203 also comprise a master control module responsible for sequencing the activity of all other therapy applications that prepare for and deliver daily treatment.

Referring to FIGS. 62 and 63, the Therapy Applications 6203 provide an interface that allows the UI Model 6206 to start, stop and configure therapies, as well as report therapy status. The Therapy Applications 6203 also interface with the Machine Controller. In particular, the Therapy Applications 6203 issue commands to and request status from the Machine Controller in order to implement the therapy operations. In order to access patient, therapy and machine information, the Therapy Applications 6203 interface with the database 6302. It also uses this interface to store treatment status information.

Described below are individual applications of the Therapy Applications 6203. These applications are (1) Recycle Preparation, (2) Clean Blood Path, (3) Disinfect, (4) Rinse Endotoxins, (5) Treatment Preparation, (6) Patient Connect, (7) Dialyze, (8) Solution Infusion, (9) Rinseback, (10) Take Samples, (11) Replace Components, and (12) Install Chemicals.

(1) Recycle Preparation

Figure 68:
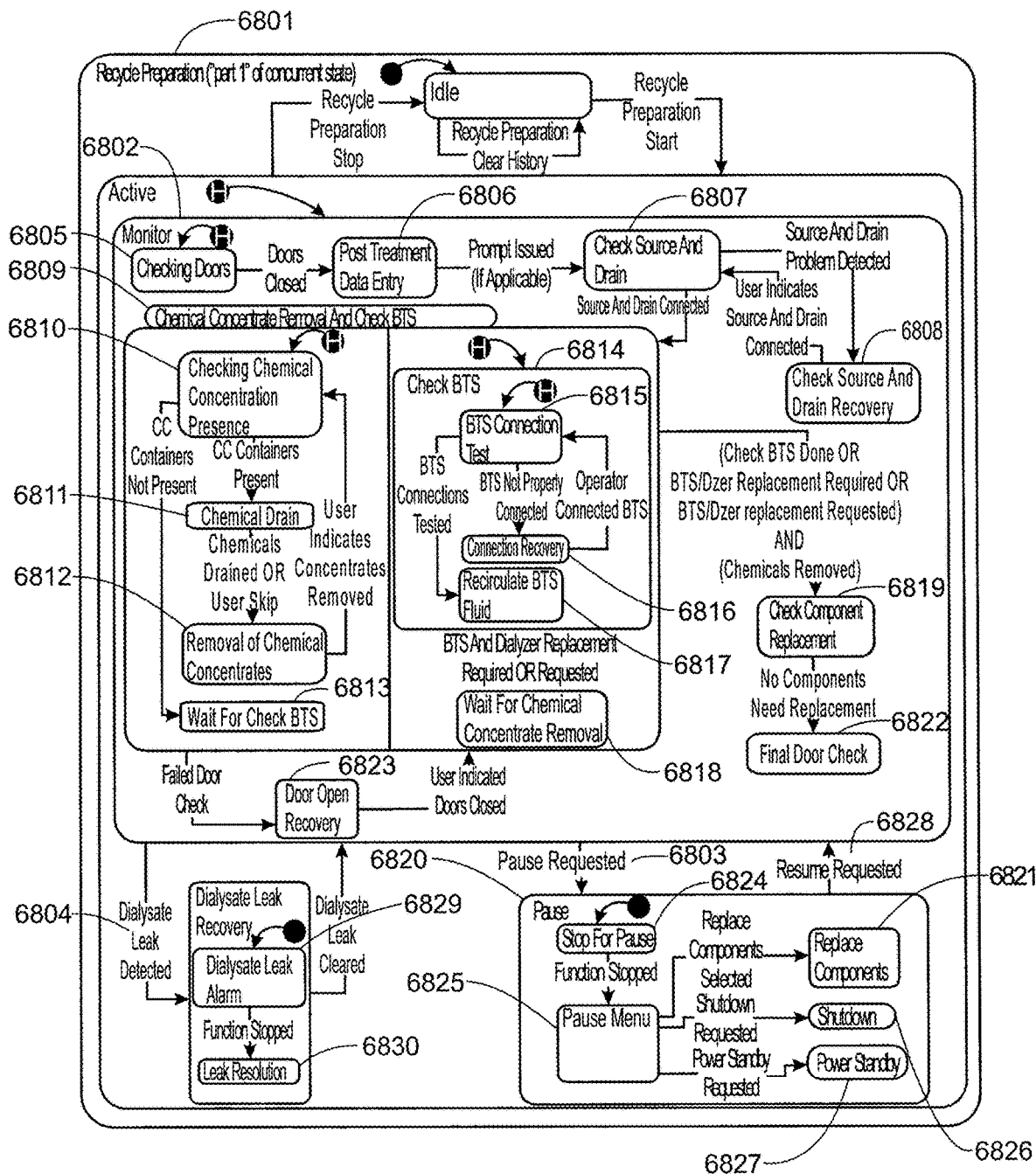
FIG. 68 is a schematic view showing shows an exemplary implementation of the Recycle Preparation application.

FIG. 68 shows an exemplary implementation of the Recycle Preparation application. The Recycle Preparation application prepares the system for recycling. Prior to initiating recycling, the system confirms that the doors are closed. This will allow the system to clean and disinfect successfully, but also ensures that the patient has not inadvertently failed to disconnect.

Next, the system prompts the user to remove and discard the chemical concentrate cartridge. The system first drains any remaining chemicals to minimize any spillage upon removal. The user may elect to bypass this draining step if they wish to remove their cartridge immediately. Once the cartridge is removed and discarded, the user prepares the system for recycling by installing the chemical bypass connector.

During chemical cartridge drain and removal, the system simultaneously performs pressure tests to ensure that the operator has connected the blood tubing set (BTS) properly, including installing a vial on the heparin connector. In this way, the operator can be notified of and correct any problems while they are present. Then, the system can successfully navigate through the remainder of recycling unattended. Testing is achieved by sequentially pressurizing the various sections of the BTS to ensure there are no kinks, clamps closed, or clots. BTS integrity can also be checked by pressurizing the entire BTS and dialyzer with air after the dialyzer has been wet, and monitoring for a threshold pressure decay value that would indicate a leak in the blood tubing, blood tubing connections, dialyzer or dialyzer connections. The disinfection ports are also checked to confirm that the venous and arterial lines are securely locked into their ports. If any of these tests fail, the user may be notified of the specific failure and instructed on how to correct it. The tests are repeated until all have passed.

If the dialyzer and blood tubing set have reached the treatment or disinfection usage limits or the operator chooses to replace them, then they may be replaced prior to recycling. If the ultrafilter has exceeded the ultrafilter transmembrane pressure (TMP) or impedance test limit, reached its disinfection usage limit, or the operator chooses to replace it, then the ultrafilter may be replaced prior to recycling. To replace these components, the user may invoke the Replace Components application described in connection with FIG. 78.

With reference to FIG. 68, Recycle Preparation application 6801 is shown. The Monitor state 6802 monitors for a Pause request 6803 or a dialysate leak 6804. Further during this state 6802, the system will confirm that the doors are closed. The fact that the doors are closed implies that the patient is not currently connected to the machine. This check will be performed in the Checking Doors state 6805. If the doors are closed, the process proceeds to the Post Treatment Data Entry state 6806.

The Post Treatment Data Entry state 6806 may prompt the patient/operator to enter miscellaneous post treatment data. If system indicates that pre treatment data was entered, the system will prompt the operator/patient to enter the post treatment data. The following post treatment data may be requested: Post Treatment Weight, Blood Pressure, and Pulse Rate. The information from these entries may be included in a systems log of treatment report information. In addition, the system will not require this information to be entered in order to continue on with the recycling process. If the system indicates that pre treatment data was not entered, the system will not prompt the operator/patient to enter the post treatment data.

The Check Source And Drain state 6807 confirms that the inlet water source and drain are properly connected. This ensures that the system can successfully perform recycling. The Check Source And Drain Recovery state 6808 provides the operator with information pertaining to a source/drain failure detected as well and required corrective actions. For example, the user may be notified that the inlet water source or drain is not installed properly and may be instructed on how to correct the problem.

The Chemical Concentrate Removal & Check BTS state 6809 will run two operations concurrently. Completion of both operations will allow the system to continue on with the recycling operations. The operations that take place during this state are: disposal and removal of the chemical concentrates and checking the BTS connections. The BTS and Dialyzer replacement is also evaluated at this time. In the first operation, the Checking Chemical Concentration Presence state 6810 detects whether chemicals are present or not to determine the next step. In particular, through the use of an air integrity test, the system will be able to detect the presence of the chemical concentrate container. In the Chemical Drain state 6811, the system will perform the necessary operations to drain any residual chemical concentrates from the containers. The purpose is to make removal and disposal of the containers cleaner and easier, producing as little waste as possible. The user may be prompted that they can choose to bypass draining. The Removal of Chemical Concentrates state 6812 provides instructions to the user to remove the chemical concentrates and close the chemical bypass doors, and may provide instructions. Included in the instructions may be how to configure the machine so that it will be able to effectively disinfect the chemical concentrate ports. The Wait for Check BTS state 6813 is an end point for the Chemical Disposal and Removal operations. The system will remain in this state until other concurrently performed operations are complete.

Turning to the second operation that is run by the Chemical Concentrate Removal & Check BTS state 6809, during the Check BTS state 6814 the system evaluates whether BTS and Dialyzer replacement is required. An option may also be displayed allowing the operator to choose dialyzer and BTS replacement. This option may include data entry as to the clotting status of the dialyzer, and may remain available to the user until the Chemical Concentrate Removal & Check BTS state 6809 is complete. If no replacement of the BTS and Dialyzer is required or requested, the system ensures that the BTS is properly connected for recycling and then recirculates the BTS fluid to prevent clotting. The BTS Connection Test 6815 confirms that the BTS has been connected properly for recycling. This may include ensuring that the patient connectors have been properly installed into their disinfection ports, that the clamps have been opened and the BTS is not kinked, and that the BTS is properly installed in the air detectors and occluders. The Connection Recovery state 6816 provides the user with information that pertains to the failure detected, as well as corrective actions that are required. For example, the user may be notified that the BTS is not installed properly, and indicate the specific problem. The notification may include corrective actions that should be performed based upon a failure code from the BTS Connection test 6815. A DC Connection test may be performed to verify that the patient has plugged the vascular access connectors of the blood tubing set back into the DCA/DCV ports of the machine for rinsing and disinfecting after a treatment session. A Heparin Vial Connection test may also be performed to verify that a vial is attached to the heparin/medication infusion spike on the blood pump cassette. This ensures that disinfection fluid can enter and exit the vial and clean the vial spike and heparin fluid path in the process.

The Recirculate BTS Fluid state 6817 will start recirculating the fluid in the BTS to prevent the residual patient blood from becoming stagnant and developing clots. The system may be configured such that this process can only be performed once the system has detected that the BTS connections are properly inserted into the disinfection ports. The Wait for Chemical Concentrate Removal state 6818 acts as a wait state that will allow the other operations that are concurrently taking place to complete. Once the system indicates that chemical concentrate removal is complete, the system will continue.

Regardless of which components are being replaced, the Check Component Replacement state 6819 may act as a transition point for the component replacements. It also evaluates whether ultrafilter replacement is required. If the ultrafilter has exceeded its TMP test limit or reached its disinfection usage limit, then ultrafilter replacement may be required. If BTS and dialyzer replacement was previously determined to be required or was requested by the user, then the BTS and dialyzer should be replaced. If any replacement is required, this data is transferred to the Pause state 6820 where Replace Components 6821 executes the activity. Once the replacement process has been completed by the system and the operator, the Recycle Preparation application will resume.

The Final Door Check state 6822 will perform a final check of the doors to confirm that the doors are still closed. This is intended to prevent any unnecessary alarms that might prevent the machine from recycling. The Doors Open Recovery state 6823 notifies the patient the doors are open, and prompts the user to close the door.

The Pause state 6820 will halt operation and may allow the patient to choose to perform additional activities. The Stop for Pause state 6824 halts all machine operations. For example, the state may stop all flows. The Pause Menu state 6825 allows the patient to choose to perform additional activities, and may display the following options: Replace Components 6821, Shutdown 6826, Power Standby 6827, and Resume Recycling Prep 6828.

The Dialysate Leak Alarm state 6829 will stop operation and notify the user that a dialysate leak has been detected. The Leak Resolution state 6830 waits for the user to clear the leak, and for an indication from the user of the same.

(2) Clean Blood Path

Next, a method may be performed to clean blood and dialysate from pathways prior to disinfection. Residual blood and dialysate, left over from treatment, is rinsed from the dialysis unit prior to performing disinfection. It is desirable to remove these substances because the disinfect process makes subsequent removal more difficult. Further, is desirable to remove residual blood and dialysate, as they are sources of bacteria. Special care may be taken to clean the dialyzer effectively so that its performance degrades as little as possible over multiple reuses.

Cleaning the blood and dialysate pathways may be accomplished by flushing a certain amount of fluid through those pathways and directing that fluid to a drain. Cleaning the blood pathways may take more effort and require more thoroughness than cleaning the dialysate pathways due to the blood and blood clots that reside in the blood pathways. Clots typically attach themselves to the venous and arterial headers of the dialyzer, which may reduce dialyzer efficiency by obstructing its fibers. Cleaning the arterial and venous headers may be difficult because their large volumes provide spaces of low flow where clots can migrate. In order to remove these residual clots from the dialyzer headers, it is desirable to first loosen or dislodge them. This may be accomplished by pushing fluid both through the dialyzer and across it, while increasing or maximizing flow rates, thereby creating or maximizing turbulence. Blood clots may also be loosened by moving fluid inside the BTS back and forth by controlling each blood pump chamber individually. The inner dialysate pumps and the BTS drain are closed, and blood chamber 1 is made to deliver fluid as blood chamber 2 fills. Once both are idle, blood chamber 1 fills as blood chamber 2 delivers. This cycle may be repeated a number of times (e.g., approximately 20 cycles). Air may also be injected into the BTS, and mixed with the water to increase the mechanical action to loosen debris. In one embodiment, air is drawn through the heparin air filter into a blood pump chamber, and is then delivered to the BTS. The displaced fluid in the BTS may be discharged to drain. The blood pump can then be run for a number of cycles (e.g. 40 cycles) at a specified rate and direction (e.g., 500 ml/min in a backwards direction).

Figure 69A:
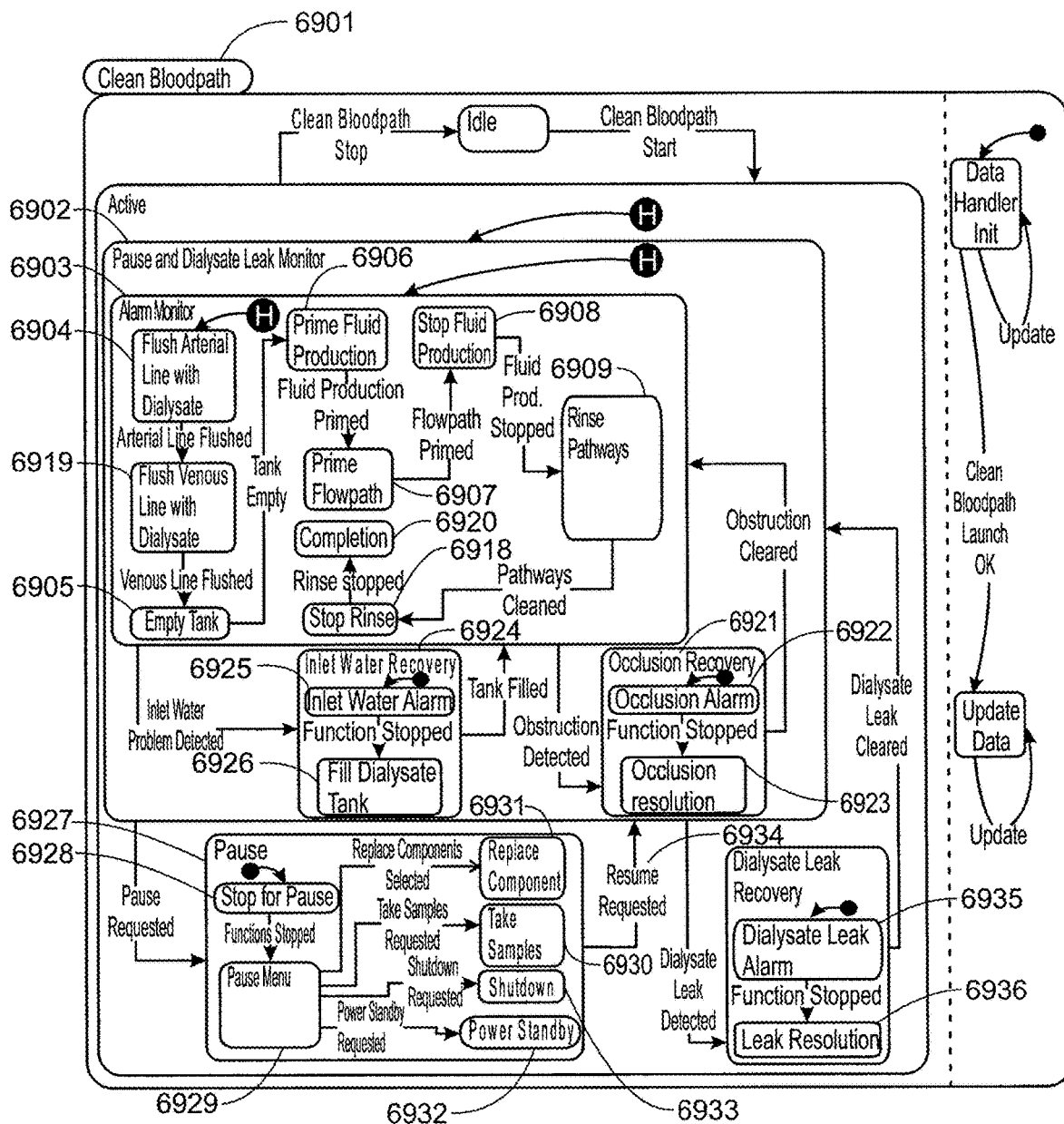
FIGS. 69a-b are schematic views showing shows an exemplary implementation of the Clean Blood Path application.
Figure 69B:
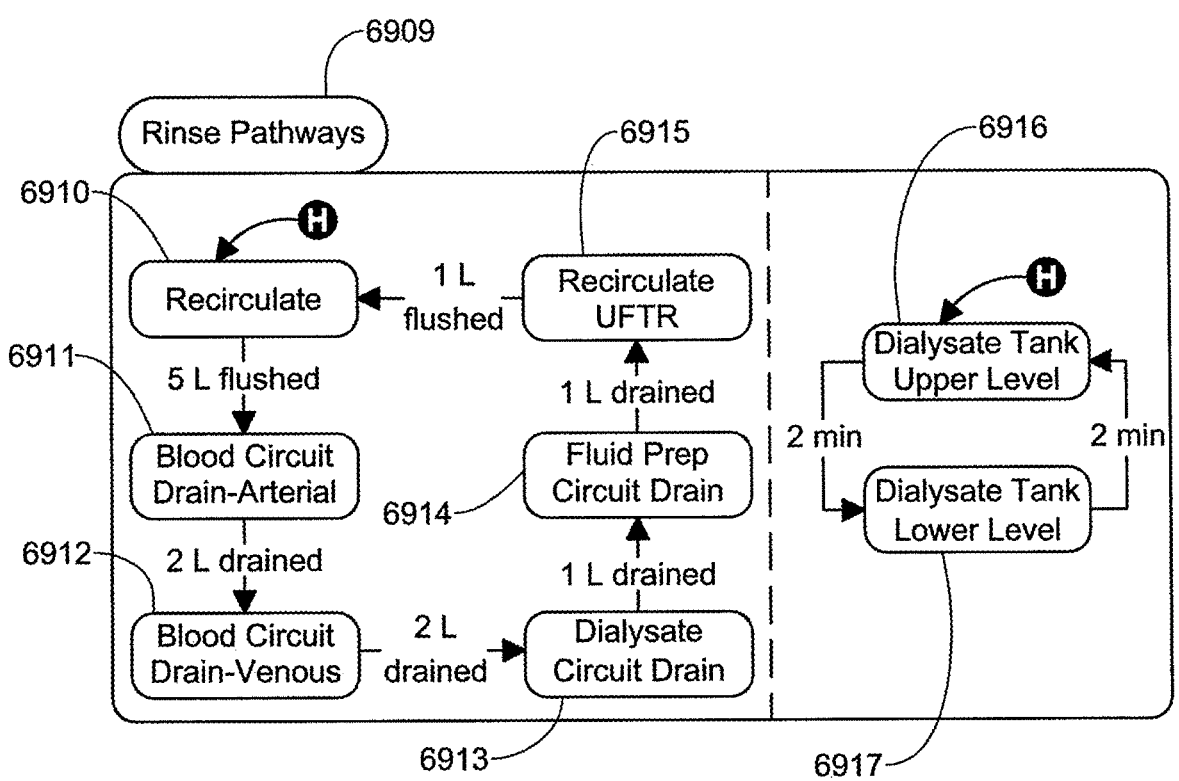

FIGS. 69*a* and 69*b* show an exemplary implementation of the Clean Blood Path application. With reference to FIG. 69*a*, Clean Blood Path 6901 is the top level state which coordinates the actions of the overall process. This state runs concurrently with the data handling elements of the state machine. During this state, residual blood and dialysate, left over from treatment, are rinsed from the machine. Updates to data of interest to the application will be processed by the data handling elements of the state machine. The Pause and Dialysate Leak Monitor state 6902 watches for certain failures and pause requests. Dialysate leak monitoring may be requested. The Alarm Monitor state 6903 watches for certain failures. Complete blood-side occlusion monitoring is requested, and inlet water monitoring is enabled. The Flush Arterial Line with Dialysate state 6904 takes a portion of the residual dialysate left over from treatment and flushes it through the arterial line and out to a drain. Flushing blood out with physiological fluid, such as dialysate, prior to sending water to the blood tubing set (BTS) may be done in order to minimize the hemolysis and foaming that occurs when blood is exposed to water. When blood foams, it typically makes cleaning more difficult. Similarly, the venous line may be flushed with dialysate in state 6919. The Empty Tank state 6905 removes any residual dialysate from the dialysate tank by sending it to a drain. The Prime Fluid Production state 6906 primes the fluid production module with water in preparation for rinsing. The Prime Flowpath state 6907 primes the entire flowpath with water in preparation for rinsing. The Stop Fluid Production state 6908 primes the entire flow path with water in preparation for rinsing, and stops fluid production.

The Rinse Pathways state 6909, shown in FIG. 69b, rinses all fluid pathways in order to flush residual blood and dialysate out of the system. This state will also start fluid production. With reference to FIG. 69b, the Recirculate state 6910 recirculates fluid in both the blood circuit and the dialysate circuit. The Blood Circuit Drain-Arterial state 6911 flushes fluid out through the arterial blood circuit line to a drain. The Blood Circuit Drain-Venous state 6912 flushes fluid out through the venous blood circuit line to drain. Flushing blood out with physiological fluid such as dialysate prior to sending water to the BTS is done in order to minimize the hemolysis and foaming that occurs when blood is exposed to water. The Dialysate Circuit Drain state 6913 flushes fluid out to drain from the dialysate circuit, while recirculating fluid in the blood tubing set. The Fluid Prep Circuit Drain state 6914 flushes fluid out to drain from the fluid preparation circuit, while reverse recirculating fluid in the blood tubing set. The Recirculate UFTR state 6915 recirculates fluid through the ultrafilter flush port, while recirculating fluid in the blood tubing set. The Dialysate Tank Upper Level state 6916 maintains the dialysate tank at a full level. Cycling the fluid level in the tank up and down acts to rinse the tank. The Dialysate Tank Lower Level state 6917 maintains the dialysate tank at a near empty level.

Either at this stage or near the beginning Disinfect, the metering pump (e.g. heparin pump) on the blood pump cassette may be directed to empty the medication (e.g. heparin) container. The medication may be replaced with either dialysate or water, but preferably the container is filled with air in preparation for the instillation and withdrawal of disinfection fluid during Disinfect. If the medication is heparin, any residual heparin remaining in the container or vial after a treatment session can be emptied into the BTS at this stage. Circulating the residual heparin through the BTS during Clean Blood Path or Disinfect may help to reduce clot formation and thus increase the efficiency of the cleaning process. Alternatively, the heparin may be discarded to drain.

Referring again to FIG. 69a, the Stop Rinse state 6918 stops the rinsing process. The Completion state 6920 finishes the application by emptying the dialysate tank. The Occlusion Recovery state 6921 handles the correction of any occlusions that have been detected by the system. The Occlusion Alarm state 6922 will stop Clean Blood Path 6901 and notify the patient there is an occlusion. The Occlusion Resolution state 6923 waits for the patient to clear the occlusion.

The Inlet Water Recovery state 6924 may handle the correction of any inlet water occlusion that has been detected by the system. The Inlet Water Alarm state 6925 will stop Clean Blood Path 6901 and notify the patient there is a problem with the incoming water. The Fill Dialysate Tank state 6926 attempts to fill the dialysate tank. The Pause state 6927 will halt operation. Additionally, the patient can choose to perform additional activities. The Stop for Pause state 6928 will halt all machine operation. The Pause Menu state 6929 allows the patient to choose to perform additional activities. The following options may be displayed: Take Samples (RO Sample) 6930, Replace Component 6931, Power Standby 6932, Shutdown 6933 and Continue Operation 6934.

The Dialysate Leak Alarm state 6935 will stop operation and notify the patient a dialysate leak has been detected. The Leak Resolution state 6936 waits for the patient to clear the leak, and may allow the continue button to be displayed on the GUI.

(3) Disinfect

Following the recycle preparation and the cleaning of the blood path, the Disinfection Application may implement the disinfection of fluid pathways. Disinfection is performed to provide fluid that is of infusible quality. To achieve this goal, the disinfection process may kill all vegetative bacterial cells, fungi, and all small or non-lipid viruses. Because the machine is generally dedicated to one patient, it is not imperative that the disinfection process eliminate viral contamination. Switching the machine between patients may require steps beyond this process. Disinfection may be achieved by bringing all fluid pathways to a certain temperature and holding that temperature for a minimum amount of time. For example, water circulated through the dialyzer, blood treatment set, ultrafilter, and dialysate set may be heated to a temperature of 85° C., ±5° C. for approximately one hour. Hot water pasteurization may be suitable for high-level disinfection. Exemplary conditions for hot water pasteurization may comprise a temperature of approximately 68° C. for a minimum of about 30 minutes. The Disinfect state is able to monitor the temperature at various points in the system and delays disinfection until the sensors are at least about 1° C. above the target temperature. The state monitors the temperature at various points and takes action to increase fluid heating if any sensor falls below the target temperature, for example, for more than 10 consecutive seconds.

Figure 70A:
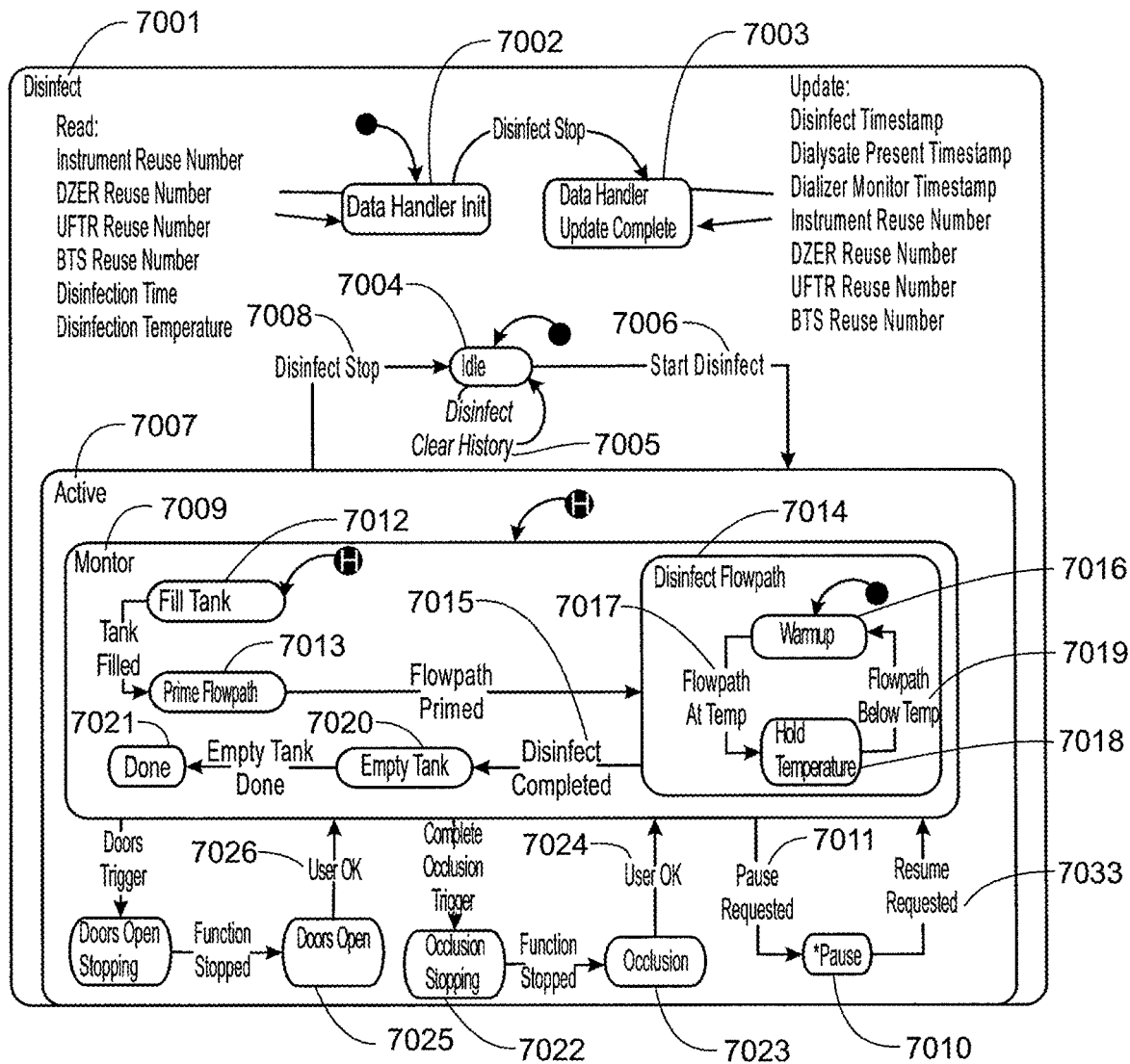
FIGS. 70a-b are schematic views showing shows an exemplary implementation of the Disinfect application.
Figure 70B:
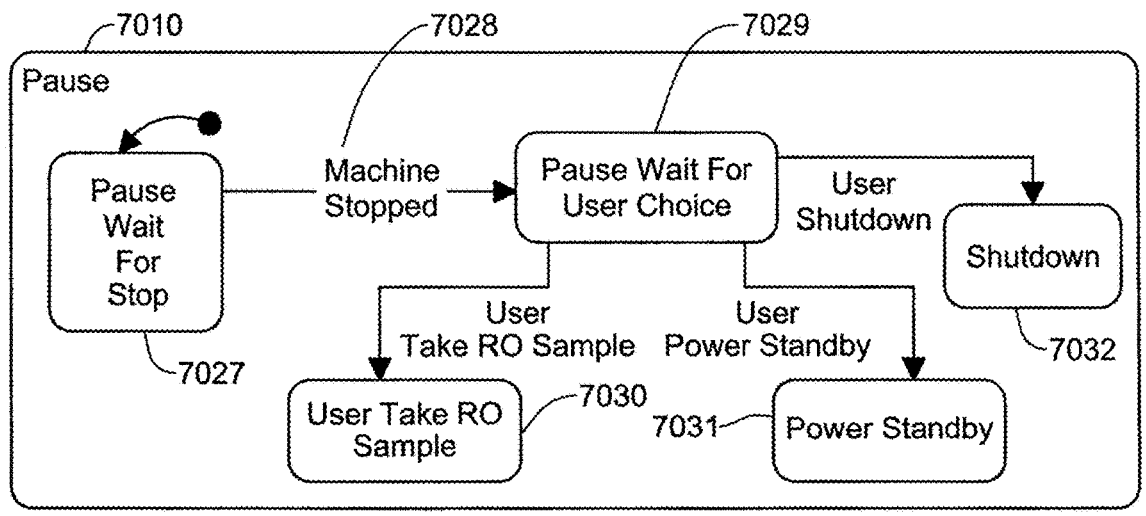

FIGS. 70a and 70b show an exemplary implementation of the Disinfect application. FIG. 70a shows the Disinfect state 7001, which enables the dialysis unit to disinfect itself. The Data Handler Init state 7002 handles reading data values from the database. The values may be in the following tables: Instrument, Dialyzer Use and Reuse, Ultrafilter Use and Reuse, Blood Tubing Set Use and Reuse, Disinfection, Expirations, and Treatment Flow sheet. The Data Handler Update Complete state 7003 handles updating data values in the Database once Disinfect has been completed. During the Idle state 7004, the history of the Disinfect state 7001 is cleared upon performance of Clear Disinfect History 7005. Start Disinfect 7006 transitions the process to the Active state 7007. The Active state 7007 watches for Disinfect Stop 7008. Disinfect Stop 7008 transitions the process back to the Idle state 7004. The Monitor state 7009 watches for the doors of the dialysis unit being opened, occlusions, and requests to Pause 7011 dialysis unit operations. If the user requests Pause 7011, the application proceeds to the Pause state 7010.

In the Monitor state 7009, the Fill Tank state 7012 starts reverse osmosis (RO) water production and fills the tank prior to priming the flow path. The Prime Flow path state 7013 primes the entire flow path with water in preparation for disinfection. The Disinfect Flow path state 7014 oversees disinfection of the machine and determines when it is complete. It starts flows and recirculates fluid in both the blood circuit as well as the dialysate circuit. Disinfection may be deemed complete when all temperature sensors remain at least 1° C. above the target temperature for a selected number of consecutive minutes. Of course, alternative parameters may be used to deem the disinfection complete. When such a determination is made, the event Disinfect Complete 7015 is generated. The Warm Up state 7016 monitors the temperature at various points and waits for portions of the dialysis unit to heat up. When all temperature sensors are at least 1° C. above the target temperature, the event Flowpath At Temp 7017 may be is generated. The Hold Temperature state 7018 monitors the temperature at various points and takes action if the monitored temperatures drop too low. For example, the event Flowpath Below Temp 7019 may be generated when the temperature at any sensor falls below the target temperature for more than 10 consecutive seconds. Other parameters may alternatively be used. The Empty Tank state 7020 empties the dialysate tank. In this way, the drain line receives a final round of disinfection. Further, an empty tank end condition allows for future applications to start with a known tank level. The Done state 7021 is the completion state for Disinfect.

The Occlusion Stopping state 7022 stops all flows and notifies the user that an occlusion has been detected. The Occlusion state 7023 waits for the user to indicate that the obstruction has been cleared. Once the User indicates that the problems have been corrected, the event User OK 7024 is accepted. The Doors Open Stopping state 7034 stops all flows. The Doors Open state 7025 prompts the user to close the doors of the dialysis unit. Once the user indicates the doors have been closed, the event User OK 7026 is accepted.

Referring now to FIG. 70*b*, the pause behavior will be discussed. The Pause Wait for Stop state 7027 waits for all operations to stop. When the machine is stopped, the event 7028 is generated. The Pause Wait For User Choice state 7029 prompts the user to choose the next step and waits for the user to choose what they want to do. The patient will have the following options: Take RO Sample 7030, Power Standby 7031, and Shutdown 7032. The User Take RO Sample state 7030 waits while the user takes an RO Sample, the Power Standby state 7031 waits for Power Standby, and the Shutdown state 7032 waits for Shutdown. The user may also select a Resume operations option to generate a Resume Requested event 7033 (FIG. 70*a*).

(4) Rinse Endotoxins

Following disinfection of the fluid pathways, endotoxins and dead biofilm may be rinsed from the pathways via the Rise Endotoxins Application. Endotoxins are part of the outer cell wall of bacteria and are released when bacteria are killed. Biofilm is a complex collection of microorganisms that attach to available surfaces. While the disinfection process kills viable biofilm bacteria, it may not remove all the biomass components, including endotoxins.

To remove dead biofilm and endotoxins, a certain amount of fluid is flushed throughout the flow path at a certain flow rate. This application is designed to rinse each tubing segment with at least three times the holding volume of that segment, although other implementations are possible. According to one exemplary implementation, the dead biofilm may be removed to achieve a Reynolds number of at least 100. According to another exemplary implementation, the Rinse Endotoxins application may be designed to achieve a Reynolds number of 200 or more.

Figure 71:
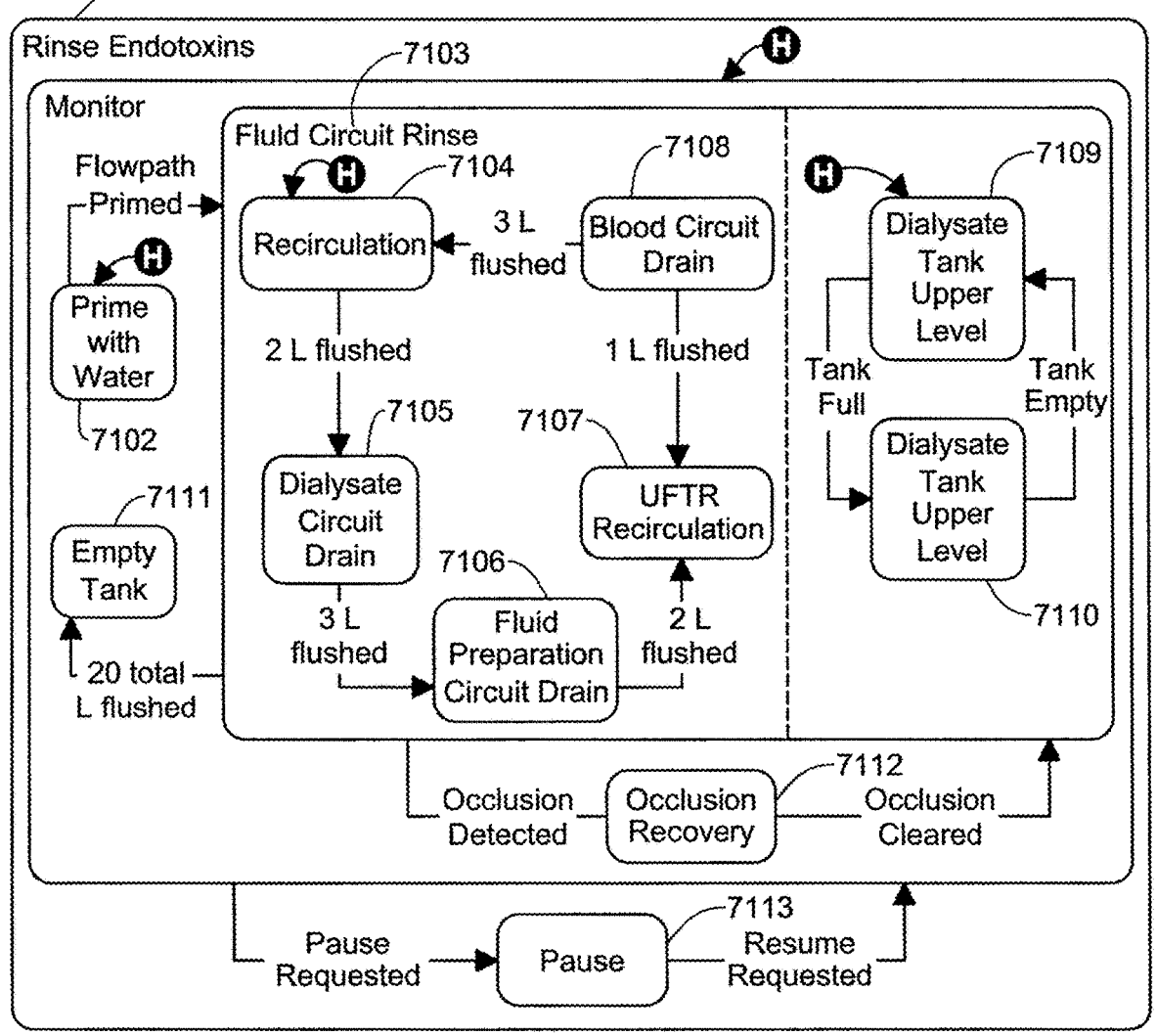
FIG. 71 is a schematic view showing shows an exemplary implementation of the Rinse Endotoxins application.

FIG. 71 shows an exemplary implementation of the Rinse Endotoxins application. In the Rinse Endotoxins application 7101, the Prime With Water state 7102 introduces fresh cool reverse osmosis water into the system that has just completed disinfect. Fluid Circuit Rinse 7103 is designed to rinse every fluid line of the system. The Recirculation state 7104 flushes the Fluid Production, Fluid Preparation, Recirculator, Dialyzer, Blood Circuit and access lines with reverse osmosis water. The flushing of these circuits rinses the system of endotoxins and biofilm that remain in the system after disinfect is complete.

Each of the remaining states are alternative pathways of the flow path that allow certain segments to be drained. The subsequent states will be performed for a percentage of the time or a percentage of fluid delivered. The Dialysate Circuit Drain 7105 state flushes fluid out to drain from the dialysate circuit, while recirculating fluid in the blood tubing set. The Fluid Prep Circuit Drain state 7106 flushes fluid out to drain from the fluid preparation circuit, while reverse recirculating fluid in the blood tubing set. The Ultrafilter Recirculation state 7107 recirculates fluid through the ultrafilter flush port, while recirculating fluid in the blood tubing set. The Blood Circuit Drain state 7108 flushes fluid out through the blood circuit to drain. The Dialysate Tank Upper Level state 7109 maintains the dialysate tank at a full level. Cycling the fluid level in the tank up and down acts to rinse the tank. The Dialysate Tank Lower Level state 7110 maintains the dialysate tank at a near empty level.

The Empty Tank state 7111 removes any residual dialysate from the dialysate tank by sending it to drain. The Occlusion Recovery state 7112 notifies the user that an occlusion has been detected, but does not stop any flows. The Pause state 7113 will halt operation. Additionally, the patient can choose to perform additional activities. The patient will have the following options: Replace Components (ultrafilter or Dialyzer/blood tubing set), Take Samples (RO Sample), Restart Recycling, Power Standby, and Shutdown.

(5) Treatment Preparation

The Treatment Preparation application performs a series of actions that prepare the system to perform a dialysis session. During this application, the chemical concentrates are installed, dissolved, and mixed to produce the prescribed dialysate composition. The system also tests the integrity of the ultrafilter, the dialyzer and blood tubing set, as well as key valves, pumps, and pneumatics. Fresh dialysate is used to fully prime the system, and then flush the blood tubing set and dialyzer. Further during this application, the clearance of the dialyzer and the transmembrane pressure of the ultrafilter are tested, and the protective systems are self-tested by simulating trigger conditions through electrical offsets.

When the user requests that a dialysis session be initiated, the system will allow the user to collect any scheduled samples. The user is also prompted to install their prescribed chemical concentrate cartridge. To mitigate possible user errors, the system prompts the user to verify that their chemical concentrate cartridge matches their prescription. Furthermore, the system checks to ensure that the cartridge is present and installed properly once the user indicates it to be so.

Reverse osmosis water is added to the powder chemicals and they are agitated to uniformly dissolve them. Once the powder chemicals are dissolved, they are mixed with the acid concentrate and the conductivity of the finished dialysate solution is checked against the expected conductivity. Acceptable dialysate is routed to the dialysate tank while unacceptable dialysate is routed to drain.

While the dialysate is being mixed, a series of integrity tests are performed. In each case, the component under test is pressurized and then isolated, while the pressure decay is measured over time. If pressure escapes too quickly, the component fails the test and should be replaced. The dialyzer, blood tubing set, and ultrafilter are generally replaced by the user, while other items are generally replaced by service personnel. The functionality of the blood line clamps is verified to ensure that the system can successfully isolate the patient from the machine in the event of a hazard detection. Daily integrity testing of the ultrafilter is desirable because repeated heat disinfection and high pressure flow may damage the filter fibers. If the ultrafilter fails integrity testing, endotoxins may be present downstream, including the dialyzer and blood tubing set. Therefore, all three components should be replaced in this case. Next, daily integrity testing of the dialyzer and blood tubing set is desirable because repeated treatments and heat disinfections may damage these disposables. A broken dialyzer fiber could cause a blood leak out of the blood side of the dialyzer and into the system and/or compromise its ability to prevent endotoxins from crossing from the dialysate side of the dialyzer and into the blood.

Key valves, pumps, pneumatics, and various replaceable cartridges are tested using pressure and vacuum tests. Either a pressure or a vacuum may be delivered to the component in test and then isolated while the pressure decay is measured over time. If pressure escapes too quickly, the component fails the test, indicating that it should be replaced.

The system is primed with the fresh dialysate. The dialyzer clearance is measured to determine whether its solute removal performance is acceptable. As the dialyzer is reused, the fibers can become clogged with blood clots and biofilm, reducing the effective surface area available for solute transfer (diffusion and convection). As this happens, the dialyzer's ability to "clear" the blood of toxins is reduced, hence the term clearance. If the clearance value has declined more than the allowable prescribed percentage, the operator may be notified and replacement may be performed following the completion of treatment.

The ultrafilter transmembrane pressure (TMP) may be tested daily to ensure that it does not exceed the maximum operating limit. The TMP limit is typically a manufacturer's specification used to prevent damage to the ultrafilter fibers or housing, which could lead to an external leak or endotoxins crossing the ultrafilter. Over time, the ultrafilter gradually becomes clogged with biofilm and other debris which causes the pressure drop across its fibers to increase. The TMP test sends the maximum system flow rate used through the ultrafilter and measures the pressure drop. If the pressure drop exceeds the maximum operating limit, the ultrafilter should be replaced following the completion of treatment.

The reverse osmosis water in the dialyzer and blood tubing set should be replaced with physiological fluid prior to treatment in order to prevent hemolysis. Further, any residual ethylene oxide (ETO) that may be present in the dialyzer prior to treatment should be flushed out in order to prevent First Use Syndrome-1 (FUS-1). Since dialysate is a microbial growth medium, the blood tubing prime is late in the application process to reduce stagnant time in the set.

Protective system self tests may be performed. This is accomplished by creating offsets in safety sensors to simulate unsafe conditions and then confirming that each protective system reacts as intended.

Figure 72:
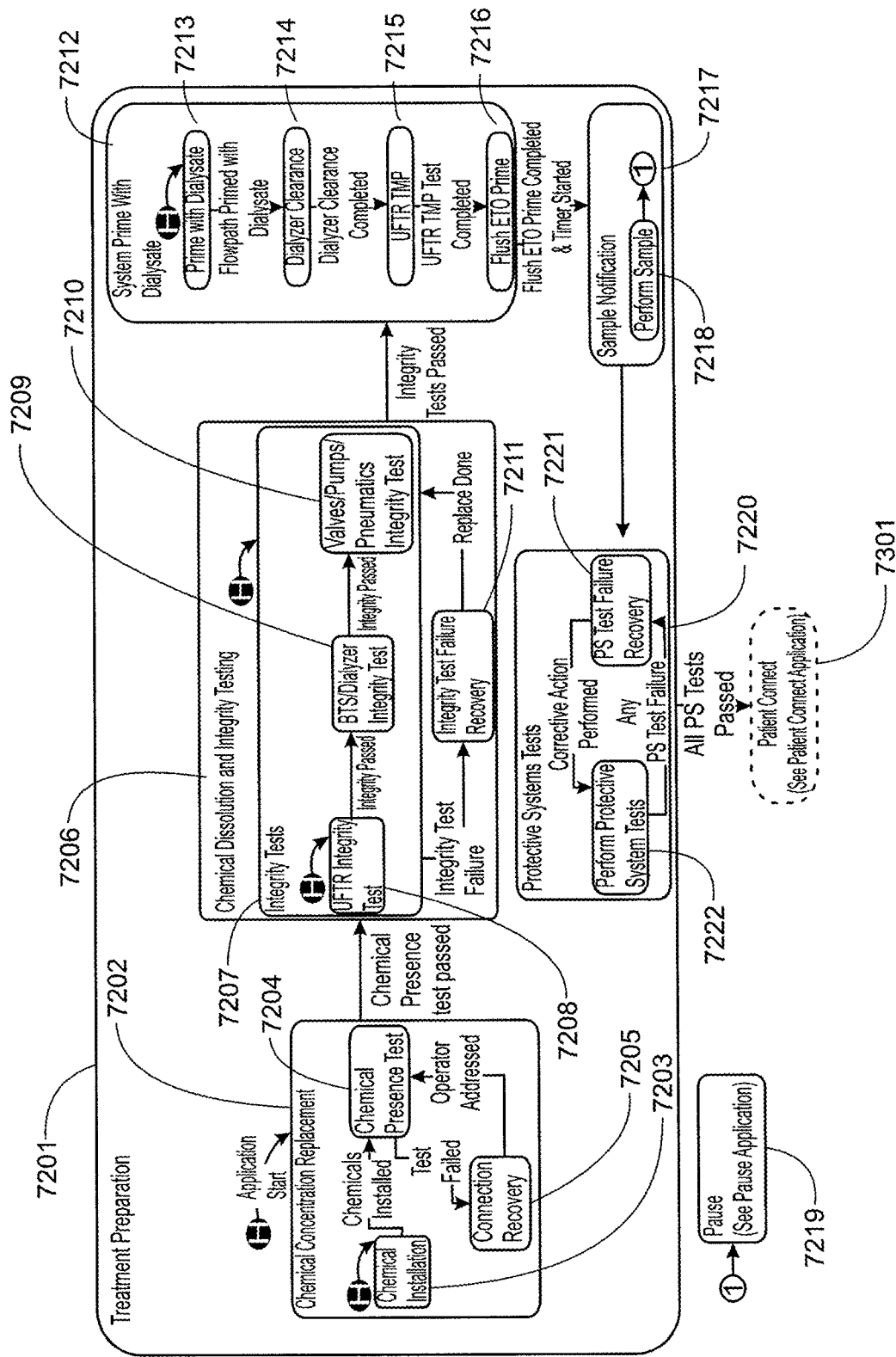
FIG. 72 is a schematic view showing shows an exemplary implementation of the Treatment Preparation application.

FIG. 72 shows an exemplary implementation of the Treatment Preparation application. Referring to FIG. 72, states of the Treatment Preparation application 7201 are described. The Chemical Concentration Replacement state 7202 will perform the necessary operations to allow the user to connect the chemical concentrates to begin the process for preparing the dialysate. This state will indicate when the machine is ready to receive the chemical concentrates. Also during this time, the system will verify that the chemical concentrate containers are present and connected properly. During the Chemical Installation state 7203, the system will prompt the user to install the chemical concentrates when it indicates it is ready. Included in the prompt may be instructions on how to perform the installation. The system may display an instructional prompt to install the chemical concentrates whether they are in a cartridge or bottle form. The operator may confirm installation by indicating their prescription using the user interface. The Chemical Presence Test 7204 detects whether the chemicals have been installed properly in the system. The system may verify that the chemicals have been installed by using a presence sensor to detect whether the chemicals have been installed or not. If the system indicates that the cartridges are not present, the system will transition to Connection Recovery 7205. In addition, the system monitors whether the chemical bypass door is opened, which implies that the chemical tubing is connected. The connections may also be verified by drawing a vacuum on the chemical container to confirm that the chemical addition ports are not open to atmosphere. Connection Recovery 7205 will handle the user interaction in the event that the system detects that the chemical concentrates are not installed properly. This recovery need only be performed in the event that the system is unable to detect the presence of the chemical concentrates or the vacuum integrity test fails. When the system indicates that the chemical concentrates are not installed properly, the system will instruct the user to verify that the chemicals are properly installed and that all connections are securely fastened. The system will then wait for the user to indicate that the connections have been checked and allow the system to perform the Chemical Presence Test 7204 again.

Upon successful completion of the Chemical Presence Test 7204, the system will transition to Chemical Dissolution and Integrity Tests 7206. During the Chemical Dissolution and Integrity Tests state 7206, the system will start the process of dissolving and combining the chemical concentrates to achieve the prescribed dialysate prescription. In addition, this state will perform routine daily integrity tests of the particular components. The actions of Dialysate Preparation and performing the Integrity Tests will be performed by the system concurrently to use time more efficiently.

The Integrity Tests state 7207 will handle the integrity testing of the Ultrafilter, Blood Tubing Set and Dialyzer, and the dialysate circuit. The Ultrafilter (UFTR) Integrity Test 7208 verifies the integrity of the Ultrafilter. The water in the housing is forced out, and then the air is pressurized and held against the fibers from the outside. If the allowable decay limit is exceeded, the filter should be replaced. During this state, in the event that the UFTR integrity test returns an indication that the test has failed, the system will relay this information to the user. The user will be instructed to Replace the UFTR via the transition to Replace Components. Upon completion of the installation of the new ultrafilter, the system will re-perform the integrity test and resume normal operation. The Blood Tubing Set (BTS)/Dialyzer Integrity Test sub-state 7209 is intended to test the integrity of the Blood Tubing Set and Dialyzer. This is accomplished by generating a pressure, and then measuring the decay. If the dialyzer/blood tubing set fails the integrity test, the user is notified to replace the dialyzer and blood tubing set. During this state, if the system returns a Failed status for the BTS and/or Dialyzer Integrity, the system will notify the operator that the BTS and/or Dialyzer Integrity test failed. The user will be provided with information and the ability to replace these components through the Replace Components option. Once the component(s) have been replaced, the system will re-perform the integrity test. If desired, a general system integrity test may be performed during a Valves/Pumps/Pneumatics Integrity state 7210.

The Integrity Test Failure Recovery state 7211 provides instructions to handle any integrity test failures identified during the integrity tests. If the system indicates that there was an integrity test failure, the user will be notified by the system of the failure, as well which component failed. The user may then perform the necessary actions to perform the replacement. Upon the user's indication that the new component has been installed, the system will resume normal operation.

The System Prime with Dialysate state 7212 will perform the necessary actions to prime the system with dialysate. This state includes a Prime with Dialysate state 7213, a Dialyzer Clearance state 7214, an Ultrafilter Transmembrane Pressure (UFTR TMP) state 7215, and a Flush ETO Prime state 7216. The Prime with Dialysate state 7213 begins chemical production and primes the system with dialysate. The Dialyzer Clearance state 7214 quantifies the amount of sodium clearance, used as a surrogate for urea clearance, that can pass across the dialyzer membrane under given flow rate and temperature conditions. The UFTR TMP state 7215 measures the transmembrane pressure (TMP) across the ultrafilter at the maximum system flow rate, to ensure that is does not exceed the specified maximum ultrafilter TMP. In the event that the UFTR TMP exceeds the acceptable limit, the system may continue with its normal operation. The user will be notified that the ultrafilter (UFTR) requires replacement due to a failed TMP test and that the replacement will be performed during Recycle Preparation. The Flush ETO Prime state 7216 flushes the dialyzer of ethylene oxide (ETO) that may have leached out.

During the Sample Notification state 7217, the system will identify if any samples have been previously scheduled by the patient or clinical representative. This state also notifies the operator of the samples scheduled. The following are samples that the operator may be notified to collect: Blood Samples, Chlorine Sample/Test, Chloramines Sample/Test, and RO Water Sample. During the Perform Sample state 7218, the system will notify the user that there are samples scheduled to be taken. During this state, the user will have the opportunity to accept or decline taking these samples. The system will evaluate whether there are samples scheduled or not. If the system indicates that there are sample(s) scheduled and the user elects to perform the sample, the system will transfer responsibility to Pause 7219, where each of the samples will be handled.

The system will create conditions that allow self-testing of the protective systems before a patient is connected to the machine. Upon the detection of a protective systems test failure, the Protective Systems Tests state 7220 will initiate corrective action if applicable. The following protective systems may be tested prior to patient connection: Air Detection (Venous and Arterial), Dialysate Conductivity, Dialysate Temperature, Blood Leak Test, Fluid Leak Test, and Doors Open. This may be accomplished by offsetting each of the sensors to simulate a condition where the protective system will trigger. The system will confirm that the proper protective system was initiated.

The Protective Systems Test Failure Recovery 7221 is triggered in the event that one of self tests returns a failed status. This state is entered upon the completion of all of the Protective System Tests 7222. In the event that any of the Dialysate Conductivity Protective System Test, Dialysate Temperature Protective System Test, Blood Leak Protective System Test, and Fluid Leak Protective System Test return the failed status, the operator may be instructed that operation cannot continue. In the event that either of the Air Detection Protective System Test or the Door Protective System Test return the failed status, the operator may be instructed to perform the corrective actions related to the failure.

(6) Patient Connect

Following the treatment preparation, the patient connection to the system is made and the extracorporeal blood tubing circuit is primed with blood. There are at least two priming prescription options: the first method is "Prime Discarded" (or Prime Not Returned) where the dialysate priming solution is drawn into the machine as blood is introduced into the extracorporeal circuit. The second method is "Prime Returned" where the dialysate priming solution is given to the patient as blood is introduced into the extracorporeal circuit. Choice of these two methods depends on how much volume the patient wants to remove during the priming process and whether their venous access can tolerate fluid being drawn from it.

For Prime Discarded, blood is drawn from the patient's arterial and venous access sites simultaneously into the machine as the priming solution is discarded to drain. This priming method is often preferred, because patients typically begin dialysis treatment volume overloaded and therefore wish to accomplish priming without taking on additional fluid. The user may chose to switch priming methods to Prime Returned if their access cannot tolerate the reverse flow up the venous line. The arterial and venous flow rates may be matched as closely as possible such that the blood fronts just meet inside the dialyzer fibers. The extracorporeal circuit may be purposefully slightly "underprimed" in order to avoid localized hemoconcentration that could occur if the blood is ultrafiltrated during the priming process.

For Prime Returned, blood is drawn up the arterial line and the priming solution is displaced down the venous line to the patient. This priming method may be prescribed for those patients whose accesses cannot tolerate the reverse flow up the venous line used during Prime Discarded, or who are sensitive to hypovolemia. If the patient cannot tolerate losing volume quickly, this method allows them to keep their volume during prime.

Additionally, if the patient still needs extra volume, they can initiate a solution infusion any time they are connected. Especially for patients who are sensitive to hypovolemia, they may choose to start treatment with a slight excess of fluid.

For either priming method, the operator may choose to change the priming blood flow rate at any time. However, any changes do not affect the prescribed setting for the subsequent treatment. Access site compromise and pressure/flow problems are common at the initiation of treatment, and therefore the operator may wish to slow down the blood flow rate during priming.

While the dialyzer and blood tubing set have already been flushed to match the dialyzer manufacturer's instructions sheet, there is an industry concern about further leaching of sterilant out of dialyzers when they sit with fluid stagnate in them. Therefore, if the dialyzer sits stagnant for too long, it may be re-flushed.

Figure 73A:
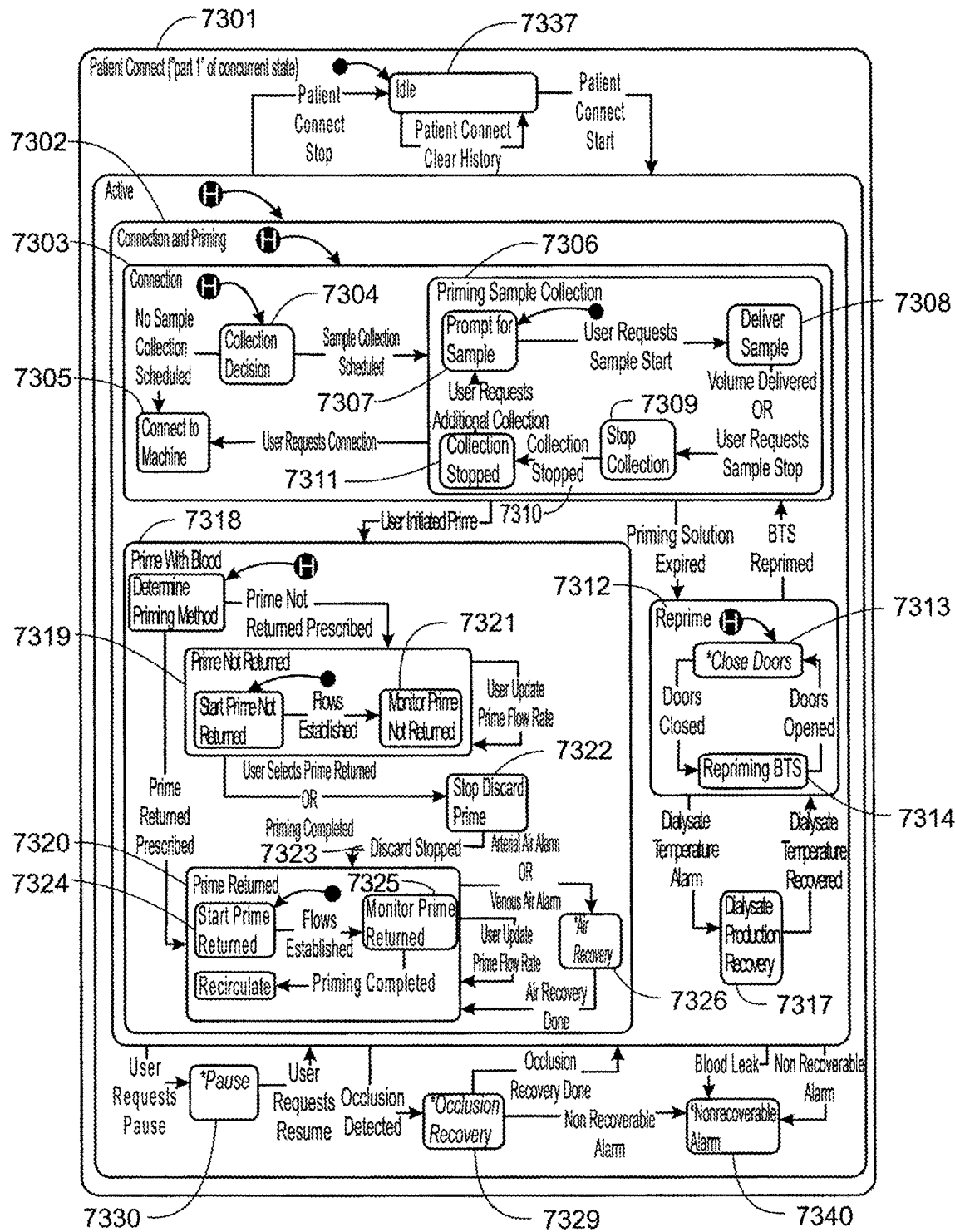
FIGS. 73a-d are schematic views showing shows an exemplary implementation of the Patient Connect application.

FIGS. 73a-d show an exemplary implementation of the Patient Connect application. With reference to FIG. 73a, the Connection and Priming state 7302 of the Patient Connection application 7301 allows the patient to take a priming sample if scheduled, connect to the machine, and prime the blood tubing set with blood. Within the Connection and Priming state 7302, the Connection state 7303 encompasses taking a priming sample and connecting to the machine. During this state, the system may determine whether the priming solution has expired. For brand new dialyzer, priming solution expires approximately 15 minutes after the last flush of dialyzer and blood tubing set. For a dialyzer that has at least one heat disinfect, priming solution may expire approximately 30 minutes after the last flush of dialyzer and blood tubing set.

There is an industry concern about leaching of sterilant out of dialyzers when they sit with fluid stagnant in them. Therefore, if the previous flush of the dialyzer occurred 15 minutes ago for a new dialyzer, or 30 minutes ago for a dialyzer that has one or more disinfects, the dialyzer may be re-flushed. This flush will remove any residual ethylene oxide (ETO) that may be present in the BTS in order to prevent First Use Syndrome-1 (FUS-1). The rationale for differing times between a brand new dialyzer and a dialyzer with one or more heat disinfects is that a brand new dialyzer will likely have more ETO that can leach out. A used dialyzer will have little or no residual ETO.

The Collection Decision state 7304 determines whether a priming sample is scheduled or not, based on certain database items. The Connect to Machine state 7305 prompts the patient to enter their weight and connect to the machine. It waits until they indicate they are connected. The state will post a message indicating the connection procedure and the means for entering patient weight. If heparin is prescribed, it will also prompt the patient to load a heparin vial into the pump.

The Priming Sample Collection state 7306 allows the patient to collect a priming sample. The priming solution sample is used to perform a microbiological evaluation of the dialysate fluid used to prime the dialyzer and blood tubing set. Within the Priming Sample Collection state 7306, the Prompt for Sample state 7307 prompts the patient to collect a priming sample. The Deliver Sample state 7308 pushes fluid across the dialyzer and out the venous line, providing the patient with a sample of the priming solution. A notice may be provided to the patient allowing them to terminate sample collection at any time.

The allowable volume for a priming solution sample may be 500 ml, for example. Typically, a sample of 150 ml is needed for microbiological evaluation. Sterile sample collection generally requires that some fluid flow into a waste container prior to taking the sample. A maximum volume of 500 ml also allows the user to take an additional sample if the first sample gets contaminated. The request for sample collection duration may be approximately 30 seconds or less. To obtain a 150-ml sample, the desired flow rate from the venous line may be 300 ml/min. The dialysate may be heated to the prescribed temperature in preparation for priming with blood. Should the patient elect to receive the dialysate prime in the blood tubing set, it will be a comfortable temperature.

The Stop Collection state 7309 stops fluid flow and waits for the machine stop to be completed. This state is entered either due to a sample volume limit being reached, or due to patient request. When the machine has stopped, a Collection Stopped event 7310 is triggered, causing a transition to the Collection Stopped state 7311. The Collection Stopped state 7311 waits for the patient to indicate they are ready to move on to connection. Alternatively, the patient may request additional sample collection.

Figure 73B:
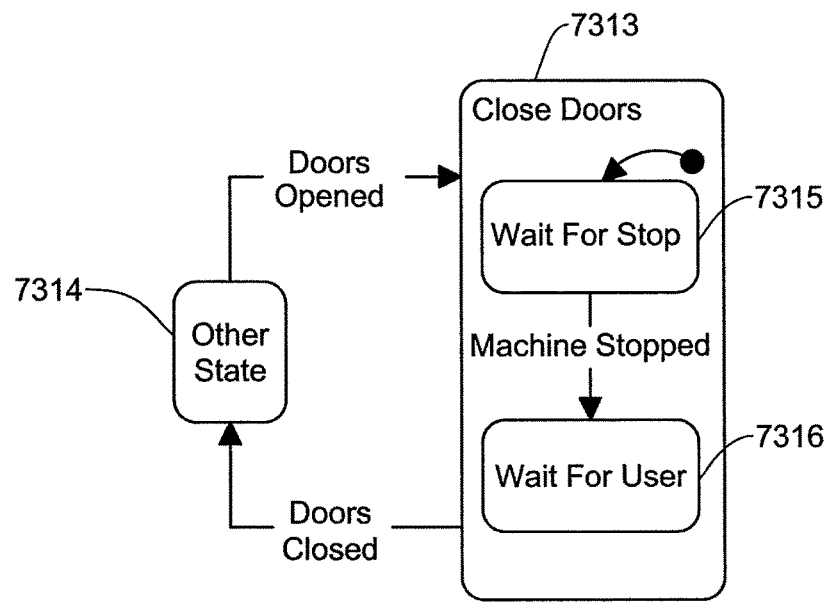

The Reprime state 7312 ensures the patient reconnects the blood tubing set and closes the doors. The dialysate and blood tubing set are then re-flushed. The Close Doors state 7313 prompts the user to close the doors. Referring to FIG. 73b, The Doors Wait For Stop state 7315 issues a stop command and waits for the machine to stop. The Doors Wait For User state 7316 waits for the common monitoring application to indicate that the doors are closed, either because the user or a detector indicated that the doors are closed. The Repriming blood tubing set state 7314 re-flushes any residual ETO that may have leached out during a period of inactivity.

Referring again to FIG. 73a, the Dialysate Production Recovery state 7317 allows the machine to recover from a scenario where the dialysate temperature is out of specification. Once the temperature of the dialysate is within 1° C. of the prescription temperature, for example, the process may transition to the Reprime state 7312.

The Prime With Blood state 7318 primes the blood tubing set and dialyzer using either the Prime Returned 7319 or Prime Not Returned 7320 method. If a blood leak is detected, an alarm event is generated. The Prime Not Returned state 7319 primes the blood tubing set by pulling blood up both the arterial and venous lines, and displacing the dialysate through the dialyzer and down to drain. The system may notify the patient that at any time during the state they can select Prime Returned 7320 or modify the priming blood flow rate. The arterial priming rate is a prescription item and may be modified by the patient. The blood tubing set and dialyzer volume may be slightly less than nominal in order to reflect dialyzer bundle volume decreases over time and also to avoid hemoconcentration. The Monitor Prime Not Returned state 7321 monitors priming of the blood tubing set by checking the status of the priming process.

The Stop Discard Prime 7322 state stops fluid and waits for the machine stop to be completed. When the machine has stopped, the Discard Stopped event 7323 is triggered, causing a transition to Prime Returned 7320. The Prime Returned state 7320 primes the blood tubing set by pulling blood up the arterial line and displacing dialysate down the venous line to the patient. Arterial air may be monitored. The patient may be notified of the ability to modify the priming blood flow rate at any time during the state. The Start Prime Returned state 7324 starts priming the blood tubing. While blood is being drawn up the arterial line, the priming solution will be given to the patient through the venous line. Rate is a prescription item and may be modified by the patient. The Monitor Prime Returned state 7325 monitors priming of the blood tubing set by accumulating the total volume pumped and comparing it to the total volume in the dialyzer and blood tubing set. When the volume pumped is greater than total dialyzer and blood circuit volume, priming is complete. If the patient started Prime Not Returned 7319, the amount primed during that state will be carried forward to this state. The patient is notified when they can begin treatment. If the patient indicates they are ready to begin treatment, the Patient Connection application is stopped and the Dialyze Application will be started.

Figure 73C:
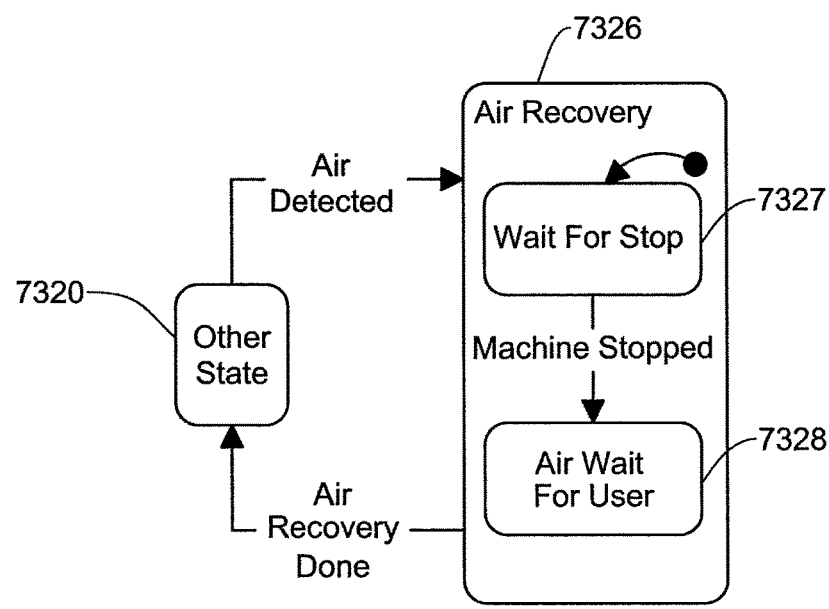

The Air Recovery state 7326, shown in FIG. 73c, allows the user to recover from air intrusion into the blood tubing set. The Air Wait for Stop state 7327 waits for the flow to stop. The Air Wait For User state 7328 waits for the common monitoring application to indicate that the alarm is cleared.

The Occlusion Recovery state 7329 notifies the user that an occlusion has been detected, but does not stop any flows. Within the Occlusion Recovery state 7329, an Occlusion Wait For Stop state issues a stop command and waits for the machine to stop. An Occlusion Wait For User state waits for the common monitoring application to indicate that the occlusion is cleared.

Figure 73D:
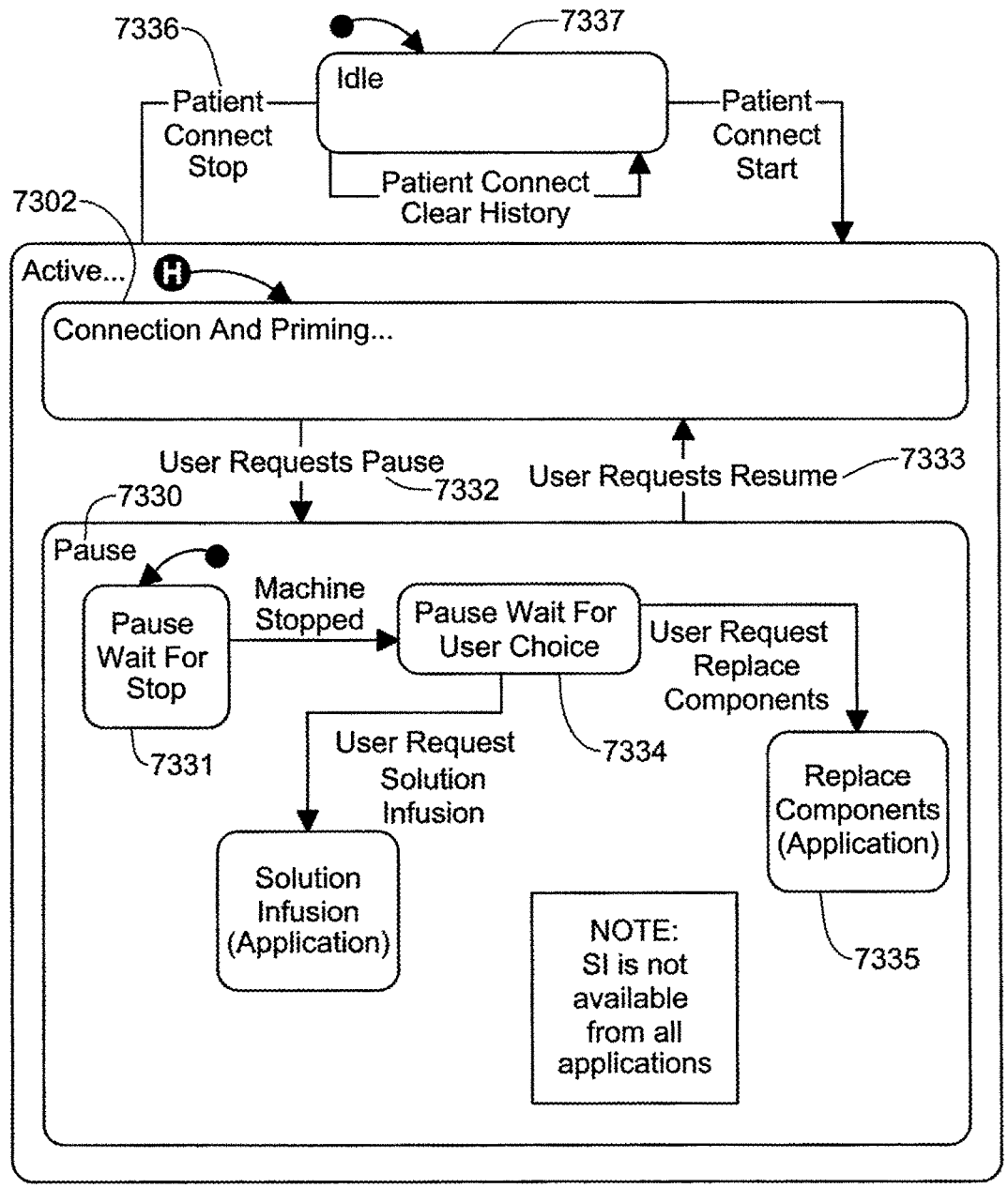

Referring to FIG. 73d, the Pause state 7330 is shown in detail. The Pause state 7330 will halt operation. Additionally, the patient can choose to perform additional activities. In particular, the patient may have the following options: Take RO Sample, Resume Active, Rinseback, Disconnect, Power Standby, and Shutdown. Since the Pause state 7330, does not have history, the state machine transitions to Pause Wait For Stop 7331, which issues the stop functions. Again, if the patient selects to resume operation, the process returns to the Connection And Priming state 7302, which dispatches to the prior sub-state(s) via a history mechanism. When the user selects a Pause button, the User Requests Pause event 7332 may be sent, causing the Patient Connect state machine to transition into Pause and then into the initial state Pause Wait For Stop. The entry action on Pause Wait For Stop calls the machine stop functions. Once the machine has stopped, the state machine transitions to Pause Wait For User Choice 7334. If the user selects Resume, the event User Requests Resume 7333 is accepted.

If the patient chooses to run another application, such as the Replace Components Application 7335, the Master Control triggers the Patient Connect Stop event 7336, causing the Patient Connect state machine to transition to the Idle state 7337. Once the machine has stopped, the state machine transitions to Pause Wait For User Choice 7334. When the User Requests Resume event 7333 is triggered, e.g., by the user pressing the resume button, the state machine transitions back to Connection And Priming 7302, and will resume according to the history within that state and its sub-states.

Referring again to FIG. 73a, the Nonrecoverable Alarm 7340 state notifies the patient that there is an unrecoverable alarm. The current application stops, and the patient may be instructed to disconnect from the system after acknowledging the alarm.

(7) Dialyze

Following connection to the dialysis unit, dialysis therapy may be delivered to a patient. Dialysis therapy removes toxins and excess fluid from a patient's blood, using diffusion, forward ultrafiltration and backward filtration (convection). In addition, heparin may be administered to the blood to prevent coagulation during treatment.

Diffusion is accomplished by exposing the patient's blood to a dialysate solution through a semi-permeable membrane. Blood may be drawn from the patient's arterial access and returned to their venous access. Simultaneously, fresh dialysate may be produced from reverse osmosis water and chemical concentrates, heated to the prescribed temperature, and delivered to the dialysate side of the dialyzer while spent dialysate is routed to drain. The concentration gradient at the dialyzer membrane causes toxins of various molecular sizes to equilibrate, by moving from the blood into the dialysate. The prescribed blood and dialysate flow rate settings and their accuracy is important in achieving the desired amount and rate of toxin removal. The flow of the blood and dialysate is countercurrent in order to maximize the concentration gradient at all points, increasing the amount of diffusion that will occur. Diffusion is also enhanced by the fact that dialysate delivered to the dialyzer is fresh rather than recirculated. Further factors that may affect dialysis therapy dose delivered include patient size, prescribed treatment duration, dialyzer effective surface area and dialyzer clearance.

Forward ultrafiltration removes excess fluid from the patient's blood. The prescribed fluid volume is removed by generating a lower pressure on the dialysate side of the dialyzer, thereby pulling fluid from the blood. The ultrafiltration rate is calculated using the prescribed fluid volume to be removed and also takes into account any dialysate volumes delivered to the patient during the priming, backflushing, and rinseback processes.

Backward filtration, or backflushing, is the inverse of forward ultrafiltration. Instead of pulling fluid from the blood side of the dialyzer to the dialysate side, fluid is pushed from the dialysate side to the blood side. This process helps to prevent clot formation within the blood tubing and dialyzer, which in turn may allow for a smaller heparin dosage, prolong the useful life of the dialyzer, and facilitate dialyzer cleaning and re-use. Backflushing has the additional benefit of promoting better solute removal through convection. Like diffusion, convection removes toxins from the blood. But unlike diffusion, which relies on a concentration gradient, convection relies on the active movement of fluid across the dialyzer to carry solutes. Backflushing is controlled by the synchronization of the blood and dialysate portions of the flow path. By changing the phase between blood and dialysate sides, there is constant and repeated shifting of fluid across the dialyzer in small increments. This shifting of fluid pushes dialysate into the blood circuit and then pulls it back, but results in no net ultrafiltration.

While dialysis is occurring, heparin may be administered. This administration can be handled either as a series of one or more boluses of fluid, or on a continuous basis. The patient may also choose to receive an additional bolus or boluses of heparin in the event that unexpected coagulation occurs.

Figure 74A:
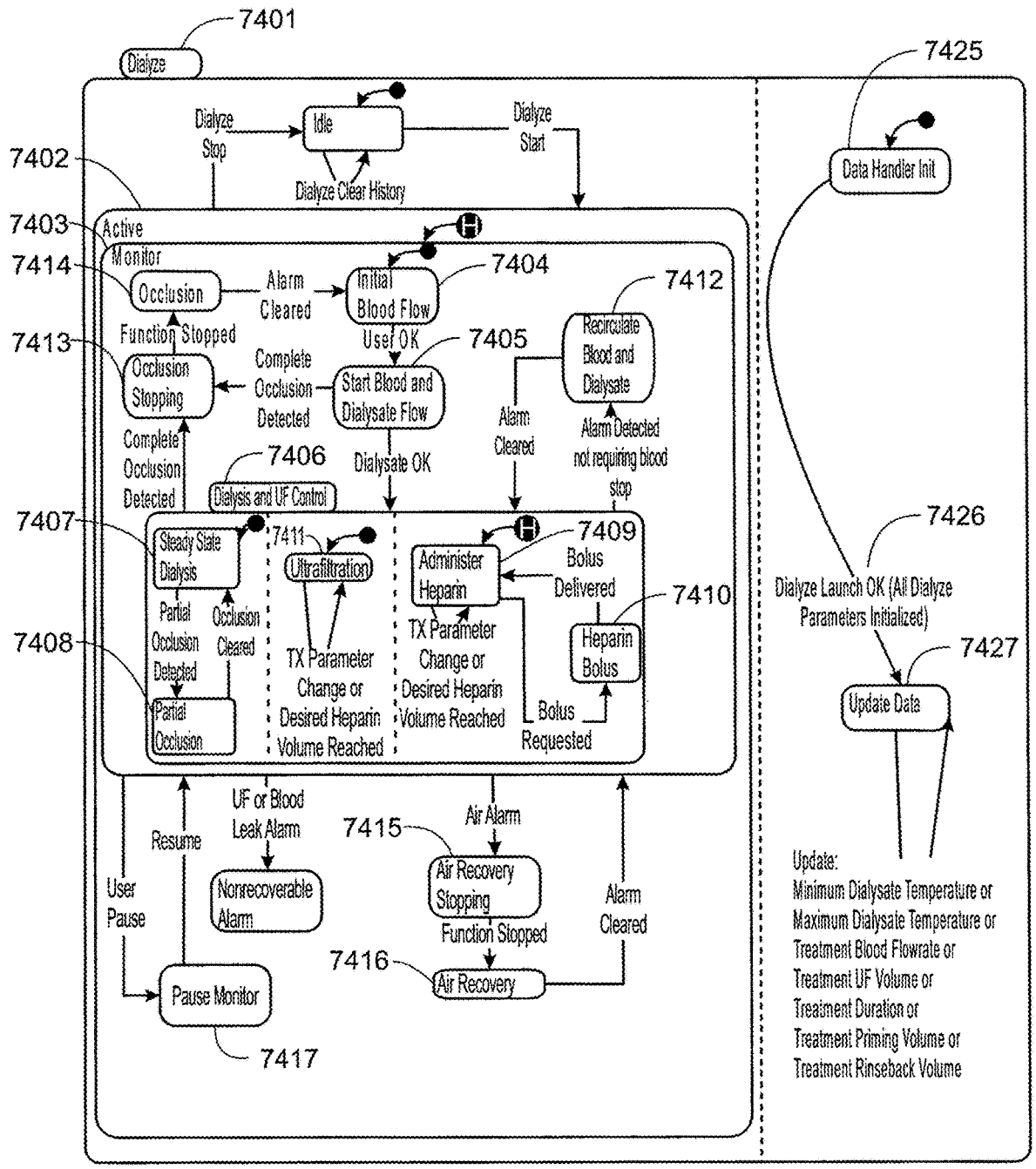
FIGS. 74a-b are schematic views showing shows an exemplary implementation of the Dialyze application.
Figure 74B:
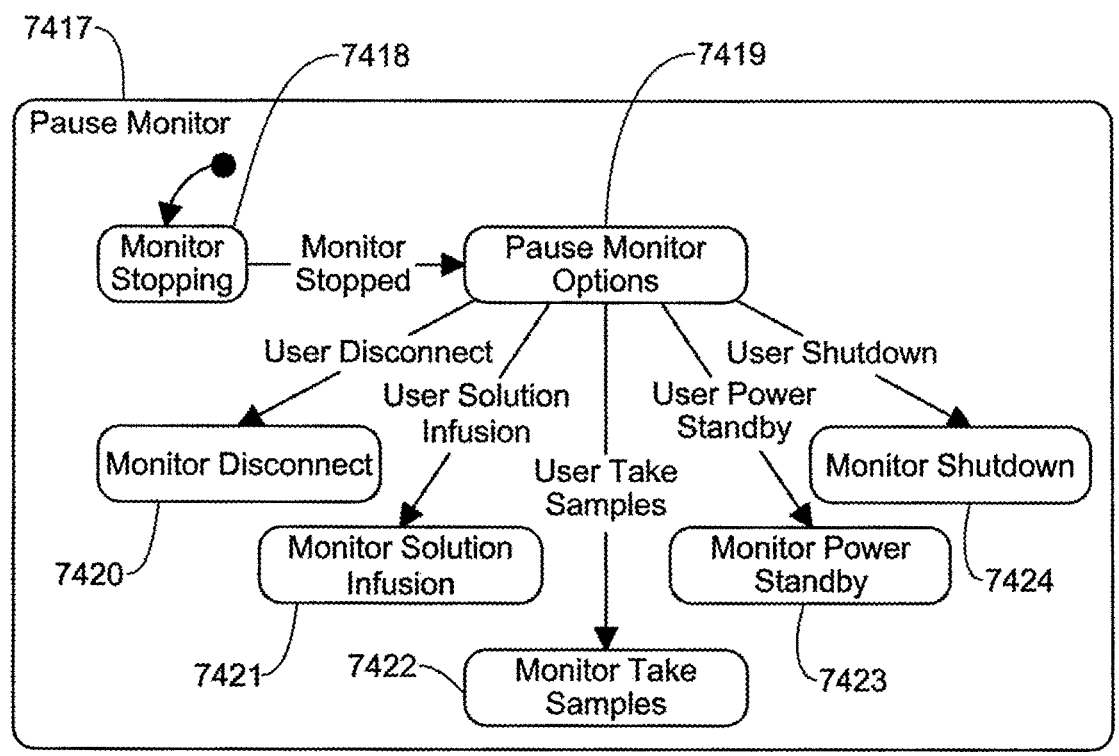

FIGS. 74a and 74b show an exemplary implementation of the Dialyze application. Referring to FIG. 74a, the Dialyze state 7401 is the top level state that coordinates the actions that lead to the overall dialysis therapy. This state runs concurrently with the data handling elements of the state machine. During this state, dialysate will be produced and an adequate buffer will be maintained in the dialysate tank. Updates to data of interest to the dialyze application will be processed by the data handling elements of the state machine.

The Active state 7402 of the dialyze application is where all dialysis related processing occurs. Dialysis is complete when the dialysis time remaining expires. The Monitor state 7403 is responsible for initiating the blood and dialysate flow rates so that treatment can be performed. Blood leak monitoring and air monitoring may be requested, and ultrafiltration monitoring may be enabled. The Initial Blood Flow state 7404 starts the blood pump at a low rate in order for the patient to check their access before starting treatment. The Start Blood and Dialysate Flow state 7405 increases the blood flow rate to the prescribed flow rate. It also starts dialysate flow by heating the fluid from the dialysate tank and diverting it around the dialyzer.

The Dialysis and UF Control state 7406 is responsible performing hemodialysis. Dialysis will occur with ultrafiltration and heparin administration. A dialysate temperature alarm may be generated if the temperature is not within acceptable limits. Complete blood side occlusion monitoring may be is requested, and partial blood side occlusion monitoring may be requested to stop. The Steady State Dialysis state 7407 performs dialysis by circulating blood and dialysate through the dialyzer. It also collects certain treatment related information. The Partial Occlusion state 7408 notifies the user that an occlusion has been detected, but does not stop any flows. The Administer Heparin state 7409 will administer heparin at a prescribed rate. Heparin will be stopped if the amount of heparin delivered is equal to the prescribed amount or the patient requests that heparin delivery be stopped. The Heparin Bolus state 7410 will deliver a bolus of heparin.

The Ultrafiltration state 7411 performs ultrafiltration. The ultrafiltration rate is determined by taking the amount of fluid needed to be removed divided by the time remaining in the treatment. If the target ultrafiltration volume differs by more than 500 ml from the current ultrafiltration volume, an ultrafiltration alarm may result. If either of the following is true, ultrafiltration may be stopped: (1) the amount of ultrafiltration is greater then or equal to Prescribed volume needed to be removed+Rinseback Volume+Priming Volume, or (2) the patient requests ultrafiltration to stop and the amount of ultrafiltration is greater then or equal to the Rinseback Volume+Priming Volume.

A counting algorithm may be used to compare the actual strokes of the ultrafiltration ("UF") pump with the predicted number of strokes to achieve the target volume of ultrafiltrate. The expected number of strokes can be synthesized based on the requested volume and rate of ultrafiltration. The actual strokes of the pump can be counted by having the controller monitor the valve states of the ultrafiltration pump. In one implementation, if the actual strokes exceed the expected strokes by greater than a safety threshold, the machine can be placed in a safe state. If the actual strokes fall behind the expected strokes by a threshold amount, the pumping rate or duration can be extended to avoid having the treatment session undershoot the desired ultrafiltration amount.

The Recirculate Blood and Dialysate state 7412 recirculates blood and dialysate, with dialysate bypassing the dialyzer, in order to bring the temperature of the dialysate into treatment limits.

The Occlusion Stopping state 7413 stops blood flow if the blood flow rate drops too far notifies the user that a problem exists. When no occlusion is detected in the Occlusion state 7414, the machine will continue to the Initial Blood Flow state 7404.

The Air Recovery Stopping state 7415 notifies the user that air intrusion into the blood tubing set has occurred and waits for the function to stop. The Air Recovery state 7416 allows the user to recover from air intrusion into the blood tubing set.

The Pause Monitor state 7417 is responsible for pausing the device and displaying pause menu options. Referring to FIG. 74b, the Monitor Stopping state 7418 will stop the device and give visual feedback to the user that the pause button was processed. The Pause Monitor Options state 7419 will display all the Pause menu options. The Monitor Disconnect application 7420 will wait in the state to be stopped by master control. The Monitor Solution Infusion application 7421 will wait in the state to be stopped by master control. The Monitor Take Samples application 7422 will wait in the state to be stopped by master control. The Monitor Power Standby application 7423 will wait in the state to be stopped by master control. The Monitor Shutdown application 7424 will wait in the state to be stopped my master control.

Referring again to FIG. 74a, the Data Handler Init state 7425 is responsible for initializing all the data of interest for the Dialyze application. Upon completion of this initialization it will generate a Dialyze Launch Ok event 7426 to indicate to Master Control the application is ready to be started. The Update Data state 7427 is responsible for maintaining up to date values or all the data of interest for the Dialyze application.

(8) Solution Infusion

To counteract a hypotensive event, the system may deliver a bolus of fluid volume to a patient. As the system removes fluid volume from the patient during treatment, it is possible that an unexpected drop in patient systemic blood pressure may occur. This hypotensive event can lead to patient lightheadedness, fainting, or even more serious complications. To prevent these outcomes, the user need only request a solution infusion. The system may then deliver a prescribed bolus of ultrapure dialysate.

Once the user has requested a solution infusion, the blood pump may be left running to prevent clotting. The Solution Infusion application will assess whether there is enough dialysate volume available to deliver the infusion and still have enough reserve volume to rinse back the patient's blood. If not, the user may be notified that infusion is not possible, and may be instructed to either select rinseback or resume treatment. If there is enough dialysate, a short countdown be displayed to the user prior to starting the infusion. Since solution infusion is available via a single button press, it is possible that the user may have pressed the button in error. This delay gives them the opportunity to cancel the infusion before it begins.

Following the delay, fresh, heated dialysate fluid is sent across the dialyzer and down the venous line to the patient. At the same time, the blood pump is slowly run forward to continue circulating blood and prevent clotting. In order to deliver relief as quickly as possible, the flow rate used for the infusion is as fast as reasonably tolerable by most patients' accesses and vasculature. A flow rate that is too high may create high pressures in the blood tubing set and lead to nuisance interruptions of the infusion delivery. Further, the infusion flow rate approximates the flow from a saline bag that a nurse might hang to counteract a hypotensive episode on other devices.

After the prescribed solution infusion volume has been delivered, if the patient continues to experience hypotensiveness, they may choose to infuse smaller additional boluses as long as enough dialysate volume is available. Once the patient leaves this application and returns back to the previous activity (e.g., Patient Connect or Dialyze), subsequent requests for a solution infusion may be for the full prescribed solution infusion volumes.

Figure 75A:
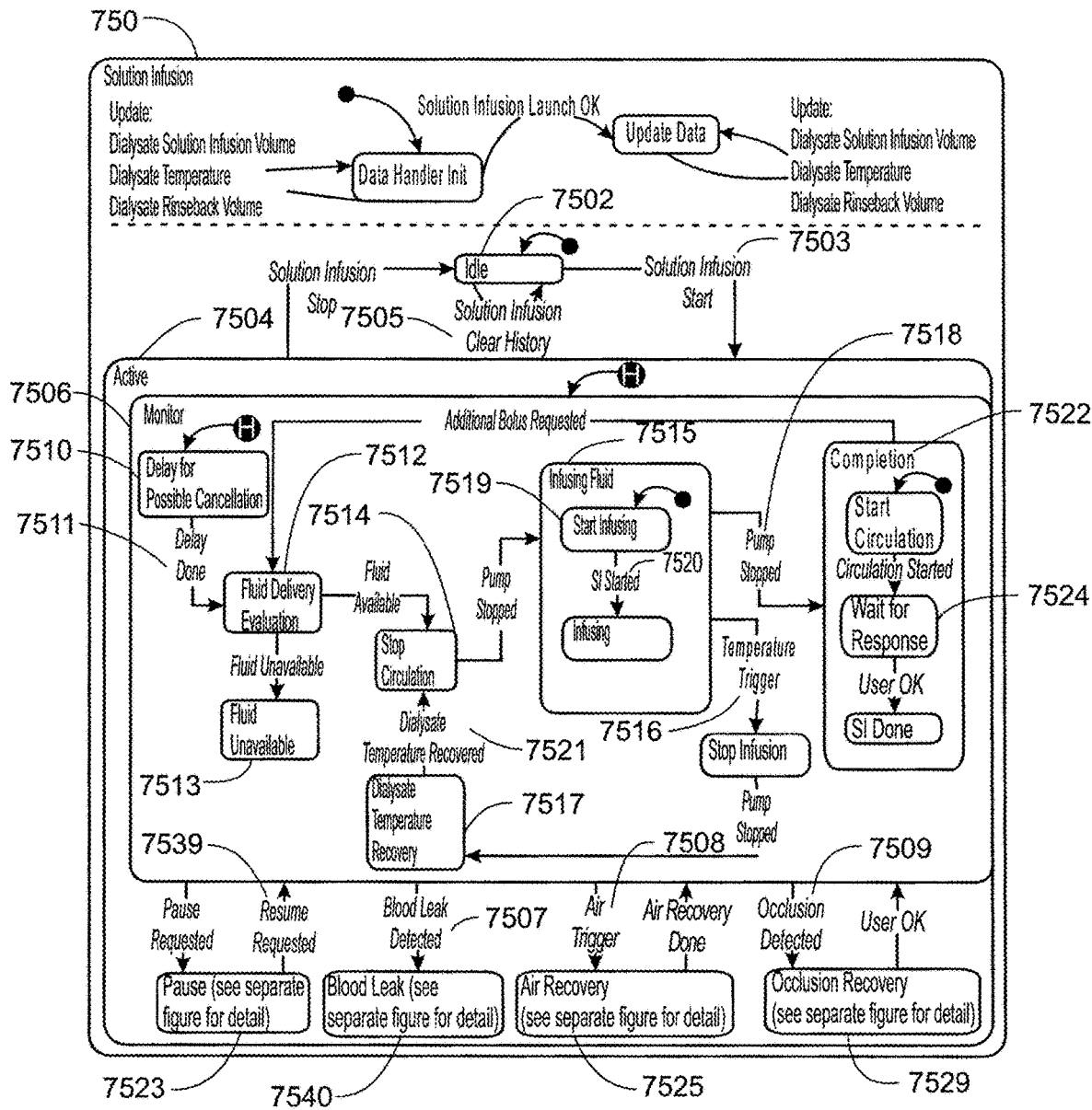

FIGS. 75a-e show an exemplary implementation of the Solution Infusion application. With reference to FIG. 75a, Solution Infusion 7501 is the top level state which coordinates the actions that lead to the delivery of a solution infusion. This state runs concurrently with the data handling elements of the state machine. Updates to data of interest to the Solution Infusion application will be processed by the data handling elements of the state machine. The Idle state 7502 is the state of the Solution Infusion application during all other system processing. Upon receiving a Solution Infusion Start event 7503 the Solution Infusion application will transition to the Active state 7504. The Solution Infusion application will indicate it has started when transitioning to the Active state. Upon receiving a Solution Infusion Clear History event 7505, the Solution Infusion application will clear the history and remain in the Idle State 7502. During the Active state 7504 of the Solution Infusion application, the solution infusion volume to be delivered is set.

The Monitor state 7506 watches for common hazards, such as Blood Leak 7507, Arterial and Venous Air 7508, and Occlusion 7509. The Monitor state 7506 starts the monitors by sending events to the monitoring process, and Starts dialysate production in case it has been stopped by a Pause or other interruption.

The Delay for Possible Cancellation state 7510 allows the patient to cancel the Solution Infusion if they choose. During the delay (e.g., 3 seconds), the user interface may give the user an updating visual indication of the time until the infusion will start and the ability to cancel the infusion. If the delay elapses without cancellation, the Delay Done 7511 event will occur.

The Fluid Delivery Evaluation state 7512 evaluates whether there is sufficient dialysate available to deliver the requested infusion. It also calculates the solution infusion volume to be given in the Infusing Fluid state. The Fluid Unavailable state 7513 will notify the patient that there is not enough fluid to perform the requested infusion. The blood pump will continue to circulate while the patient responds. If there is sufficient fluid, the Stop Circulation state 7514 will stop the circulation of blood so that the solution infusion may begin.

The Infusing Fluid super-state 7515 encapsulates the behavior of the application while the solution infusion machine layer command is running. The solution infusion operation pushes ultrapure dialysate across the dialyzer and down the venous line to the patient. Dialysate is heated before it is pushed across the dialyzer. At the same time, the blood pump is slowly run forward to minimize blood clotting. The volume of fluid left to be infused may be updated during this state. A static variable representing this volume may be initially set in the Fluid Delivery Evaluation state 7512 and then updated in this state as volume is accumulated in the machine layer status variable, Dialysate Circuit Volume. The volume to be infused should be decremented by the delivered volume. If the Dialysate Temperature Out of Spec 7516 event occurs, the transition will be to the Dialysate Temperature Recovery state 7517. If the volume to be infused is less than 25 ml due to interruption and re-entrance, the Pump Stopped event 7518 may be immediately issued and no infusion should be given.

In the Start Infusing state 7519, the solution infusion machine layer command is started. The volume to be infused is being continually updated as volume is delivered so that the correct volume is entered whenever the infusion is started or restarted. When the machine layer status indicates that the command has been started, the SI Started event 7520 is issued to cause the transition to the next state.

The Dialysate Temperature Recovery state 7517 allows the machine to recover from a situation in which the dialysate temperature is out of specification. Dialysate is routed directly to the drain, while the temperature is monitored for a return to its acceptable range. If the temperature of the dialysate is within the target range for five consecutive readings, for example, the recovery is complete and the Dialysate Temperature Recovered event 7521 is issued.

The Completion super-state 7522 starts blood circulation to prevent clotting, and waits for the patient to either indicate they would like an additional infusion, or that they are done with infusions. If a Pause occurs during any state within this super-state, the Pause state 7523 will stop the circulation. Upon returning from Pause, circulation will be restarted and the user will again be asked whether an additional bolus is required. The Wait for Response state 7524 waits for the patient to either indicate they would like an additional infusion, or that they are done with infusions. If no further infusions are desired, this application is ended. The patient will be notified by the user interface that Solution Infusion is complete and they have the option of performing additional bolus infusions. If the user indicates that an additional infusion is needed, the local variable solution infusion volume may be set to deliver equal to 100 ml and transition to the Fluid Delivery Evaluation state 7512.

Figure 75B:
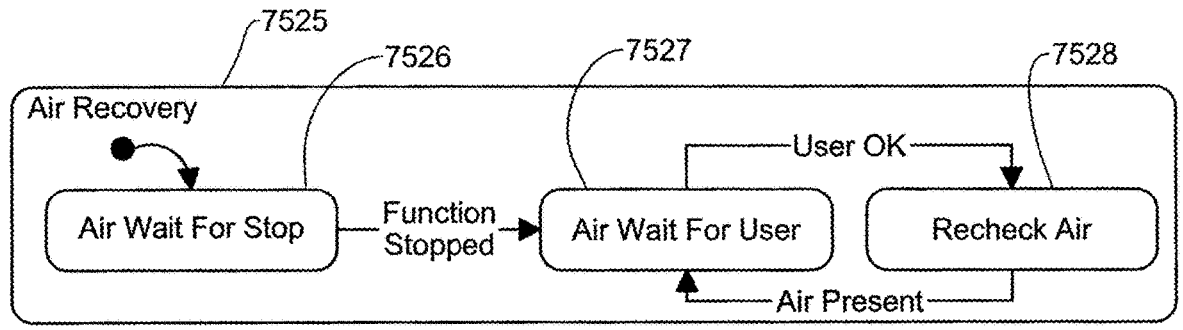

Referring to FIG. 75b, the Air Recovery state 7525 allows the user to recover from air intrusion into the blood tubing set. The machine layer fluid delivery function will be stopped, the user will be notified that air is present, and the application will remain in this state until the user indicates that the air has been cleared and the sensors do not detect air. The state machine history will return the application to the state that was interrupted. Following the Air Wait for Stop state 7526, the Air Wait for User state 7527 notifies the user that air is present in the blood tubing and provides instruction for removing the air, then waits for the user to indicate that the air is no longer present. When the user indicates that the air has been removed, the application will transition to the Recheck Air state 7528.

Figure 75C:
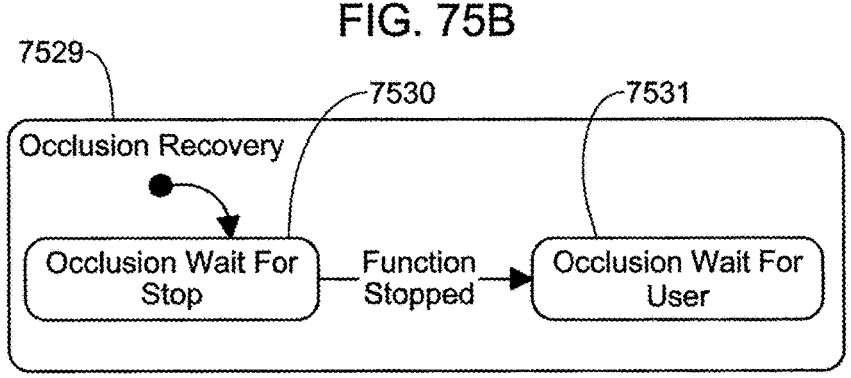

Referring to FIG. 75c, The Occlusion Recovery state 7529 notifies the user that an occlusion has been detected and waits for the user to respond. Following the Occlusion Wait for Stop 7530, the Occlusion Wait for User state 7531 notifies the user that an occlusion is present in the blood tubing and provides instruction for removing the occlusion, then waits for the user to indicate that the occlusion is no longer present.

Figure 75D:
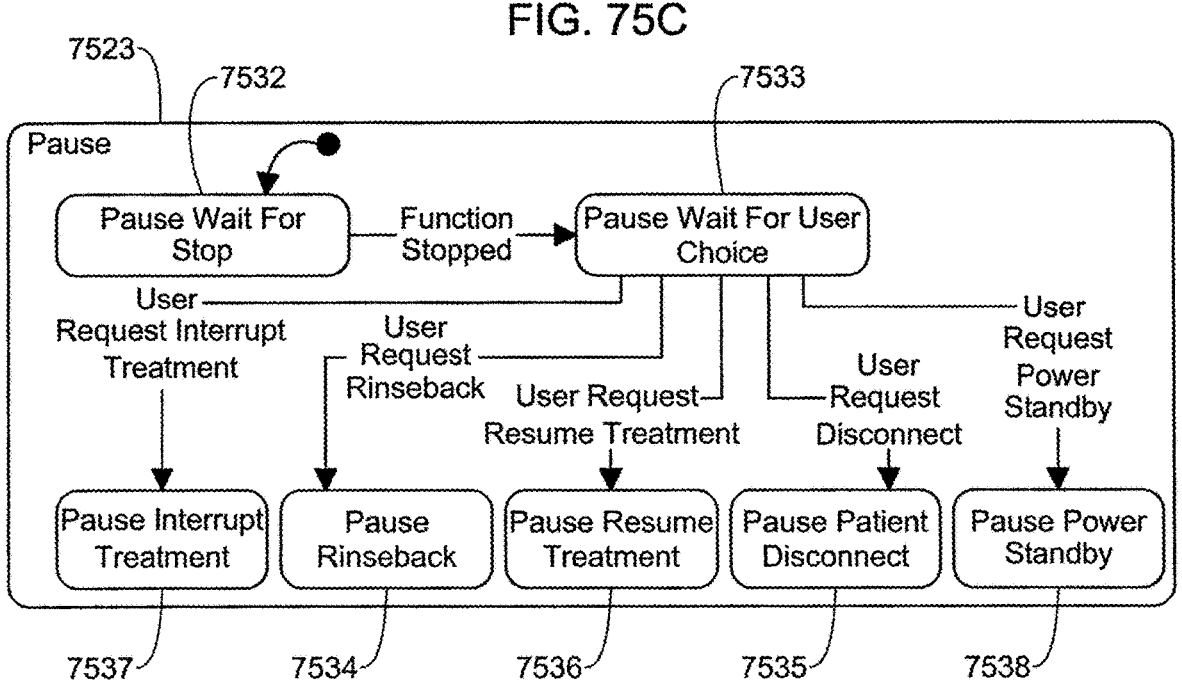

Referring to FIG. 75d, the Pause state 7523 will halt operation. Additionally, the patient can choose to perform additional activities. When the Pause operation has finished and the user chooses to resume this application, the history mechanism will return this application to the interrupted state. Following the Pause Wait for Stop state 7532, the Pause Wait for User Choice state 7533 presents options for the user and waits for the user to choose an option. In particular, the following options may be presented: Rinseback 7534, Patient Disconnect 7535, Resume Treatment 7536, Interrupt Treatment 7537, Power Standby 7538, and Resume Solution Infusion 7539.

Figure 75E:
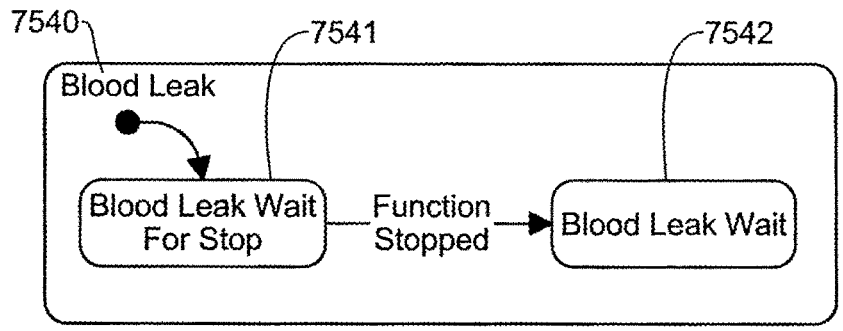

Referring to FIG. 75e, the Blood Leak state 7540 stops the current operation in state 7541 and notifies the patient that there is a nonrecoverable alarm in state 7542.

(9) Rinseback

The Rinseback application implements the process of returning the patient's blood and guiding the patient through disconnection from the extracorporeal circuit. This process occurs at the end of treatment. Treatment may end once the prescribed dialysis duration has elapsed, at any time as requested by the user, or due to a hazard detection by the system.

When the patient has requested that their blood be rinsed back, the system begins sending fresh, heated, ultrapure dialysate across the dialyzer to send the blood back to the patient. At the same time, the blood pump is run slowly in reverse such that both the arterial and venous lines clear simultaneously. The prescribed rinseback volume includes the total volume of the blood tubing set and dialyzer plus additional dialysate volume to flush the patient access and rinse the tubing lines clear of nearly all blood traces.

After this volume has been delivered, the user may choose to infuse an additional smaller rinseback bolus. This may be done to counteract patient hypotensive sensations and/or return visible blood traces remaining in the tubing. The user can request additional rinseback boluses in 50 mL increments until, for example, the total additional bolus volume delivered reaches 500 mL. The limit may be selected to prevent operator misuse, leading to fluid overload. Furthermore, rinseback fluid delivery may be limited by fresh dialysate availability.

In order to complete rinseback as quickly as possible, the flow rate used may be as fast as reasonably tolerable by most patients' accesses and vasculature. A flow rate that is too high may create high pressures in the blood tubing set and lead to nuisance interruptions of the rinseback process. Further, the flow rate may approximate the flow from a saline bag that a nurse might hang to rinseback blood on other devices.

Throughout rinseback, potential air embolism hazards exist, since blood is flowing down the arterial and venous lines towards the patient. If air is detected in the arterial line, the operator will be notified, and rinseback will continue down the venous line only.

FIGS. 76a and 76b show an exemplary implementation of the Rinseback application. With reference to FIG. 76a, the Active state 7602 of the Rinseback application 7601 is the state in which Rinseback processing occurs. The state 7602 generates the event Rinseback Stopped 7603 on transitioning to Idle 7604.

With reference to FIG. 76b, the Monitor state 7605 monitors for Pause requests 7606, venous air in the blood tubing set 7607, dialysate leaks 7608, and dialysate production problems 7609.

The Administer Fluid state 7610 administers the infusion and monitors for occlusions, dialysate temperature out of limits, conditions of unavailable fluid and inlet water out of limits. The Arterial and Venous Infusion state 7611 pushes ultrapure dialysate across the dialyzer. Dialysate may be heated as it is pushed across the dialyzer. Arterial air and venous air may be monitored. The Arterial Air Recovery state 7612 handles a recovery from an arterial air alarm. The Stop A&V Infusion state 7613 stops the infusion and posts an alarm to the GUI. The Arterial Air Resolution state 7614 waits for the user to indicate they are ready to continue with Venous-only Rinseback. The Venous Infusion state 7615 pushes ultrapure dialysate across the dialyzer. Again, dialysate may be heated as it is pushed across the dialyzer.

The Dialysate Tank Empty Alarm state 7616 will stop Rinseback and notify the patient there is not enough dialysate to continue with Rinseback. A dialysate tank low alarm may be posted to the GUI. Fluid production may be restarted, if stopped. The Wait for Fluid state 7617 waits for fluid to become available. Once the dialysate tank volume reaches a certain level, e.g., 300 ml, a Dialysate Tank Filled event 7618 may be generated. If the tank has not reached the given level in a selected period of time, e.g., 2 minutes, an error event may be generated.

It may be possible to improve the accuracy of liquid volume determinations in the dialysate tank by using at least two independent methods of measurement. One method, for example, counts the number of pump chamber strokes that deliver liquid to the tank, and subtracts the number of pump chamber strokes that withdraw fluid from the tank. Assuming that each pump stroke moves a fixed quantity of liquid, a cumulative net liquid volume in the tank can be tracked.

A second exemplary method involves taking an FMS measurement by charging a reference chamber to a predetermined pressure, and then venting the reference chamber to the tank. The volume of air in the tank can then be calculated from the equalized pressure between the tank and the reference chamber. Although an FMS-based method may yield more accurate results, it may also be more time-consuming. Thus it may be desirable to have the computer keep track of the tank volume continuously by pump stroke accounting, and have it perform an FMS measurement periodically to verify the ongoing accuracy of the pump stroke accounting. A controller applying one or both of these methods can use this data to determine whether fluid should be added to or removed from the tank, and whether the fluid level is below the minimum deemed necessary to safely continue therapy.

Pump stroke accounting operates by polling the pumps that can deliver fluid into and out of the tank, continuously accounting for completed strokes and discounting incomplete strokes due to occlusions. New fluid can be supplied to the dialysate tank by the mixing pump and the bicarbonate and acid pumps, and pump strokes can be tallied only when the outflow valve to the tank is registered as being open and the drain valve is registered as being closed. The state of the valves can be monitored by reading the valve state via the I/O subsystem; or in a simpler arrangement, the valve state can be assumed according to the particular operation being performed at the machine level. Fluid can be removed from the dialysate tank by the outer dialysate pump when the tank drain valve is open and the tank recirculation valves are closed. The outer pump can be polled for completed strokes, and strokes can be discounted if a chamber fill occlusion is detected. Should an occlusion be detected with any of the pumps, the pump stroke accounting value can be flagged as suspect or invalid, and a tank volume measurement can be taken using an independent method, for example the FMS method.

The FMS method of measuring the air (and therefore the liquid) volume in the dialysate tank is based on Boyle's law. A reference volume is pressurized and then vented into the closed dialysate tank, the volume then being calculated from the final pressure reached by the combined reference and tank air volumes. This method may be prone to some error because of delays in or incomplete closures of the valves that communicate with the tank, or because of physical distortion of the tank under pressure. The measurement may also take a substantial amount of time, which could reduce the efficiency of dialysate delivery for dialysis. Thus some of the physical characteristics of the dialysate tank and valves may introduce measurement error if the classical FMS equation $P_1V_1 = P_2V_2$ is used.

The FMS measurement method may be improved by using a third order equation, which may increase the accuracy of the volume determination at the target tank fluid level of 50-75%. Such an equation can take several forms, and is based on fitting experimentally derived pressure-volume data to a curve defined by the third-order equation. The measurement of the volume in the dialysate tank can be calibrated, for example, by incrementally filling the tank and performing FMS measurements on the tank at each increment. Data points are collected and a mathematical model correlating the FMS data to the actual fluid volume within the tank can then be generated. For example, the controller can perform an "AutoCal" function that empties the tank, and then fills it incrementally with seven 300 ml volumes of liquid, making an FMS volume measurement with each incremental fill. These measurements can then be inputted in the form of a vector into a function that calculates the coefficients for the third order equation using a least squares algorithm, for example, to minimize the error between the observed and predicted volumes. The function may then update the coefficients used in the third order FMS equation that are stored in a calibration data file on a hard drive or in the system memory.

The Occlusion Alarm state 7619 will stop Rinseback and notify the patient there is an occlusion, e.g., by posting an occlusion alarm to the GUI. The Occlusion Resolution state 7620 waits for the patient to clear the occlusion.

The Dialysate Temperature Alarm state 7621 will stop Rinseback and notify the patient the dialysate temperature is out of range, e.g., by posting a temperature alarm to the GUI. The Recirculate Dialysate state 7622 allows the machine to recover from a scenario where the dialysate temperature is out of specification. At the same time, blood may continue to circulate to prevent clotting. In this state, dialysate may be routed directly to drain as the machine attempts to bring the limits within range.

The High Inlet Water Temp Alarm state 7623 will stop Rinseback and notify the patient the water entering the machine is too hot, e.g., by posting an inlet water temperature high alarm to the GUI. This state diverts hot water to drain and waits for the water to reach nominal temperature.

The Wait state 7624 is intended to handle the transitions between Rinseback and Disconnection. This state will essentially put the system into an idle state. Besides handling the transitions between Rinseback and Disconnection, this state will also control the ability to perform additional bolus infusions. The Wait for User state 7625 waits for the user to either request an additional Rinseback or to indicate they are done with this process. If the patient indicates they are done with Rinseback, an event may be generated to terminate Rinseback.

The Venous Air Alarm state 7626 will stop Rinseback and notify the patient venous air has been detected. The Venous Air Resolution state 7627 waits for the patient to clear the air bubble and for an indication of the same from the patient.

The Dialysate Leak Alarm state 7628 will stop operation and notify the patient a dialysate leak has been detected. A dialysate leak alarm may be posted to the GUI. The Leak Resolution state 7629 waits for the patient to clear the leak and for an indication of the same from the patient.

The Dialysate Production Alarm state 7630 will stop operation and notify the patient a dialysate leak has been detected. A dialysate production alarm may be posted to the GUI. The End Rinseback state 7631 waits for the patient to acknowledge the alarm. Upon acknowledgement of the alarm, an event may be generated to end Rinseback.

The Pause Menu state 7632 allows the patient to choose to perform additional activities. The following options may be displayed and selected by a user: Patient Disconnect, Power Standby, and Shutdown.

(10) Take Samples

The Take Samples application gives the operator the ability to take certain fluid samples. In order to safely and effectively administer dialysis treatment, it may be necessary to periodically collect samples of dialysate and reverse osmosis water for laboratory analysis. This application allows the user to more easily collect these samples by presenting the fluid for sampling at a convenient location for collection.

For dialysate sample collection, dialysate is circulated through the dialyzer. For reverse osmosis (RO) sample collection, the reverse osmosis system is turned on and flushed for a predetermined amount of time to initiate production of reverse osmosis water. Then the user is prompted to collect the sample by tapping into this flow.

FIG. 77 shows an exemplary implementation of the Take Samples application. The Evaluate Dialysate Sample state 7702 of the Take Samples application 7701 determines whether a dialysate sample is scheduled. The Start Dialysate Sample state 7703 starts dialysate flow, allowing the patient to take a sample. The Evaluate RO Sample state 7704 determines whether a reverse osmosis sample is scheduled. The Start RO Production state 7705 starts RO production in preparation for an RO sample. A timer may allow the reverse osmosis membrane to be adequately flushed such that water quality is acceptable. The Collect RO Sample state 7706 allows the patient to collect an RO Sample.

(11) Replace Components

The Replace Components application gives the user the ability to replace certain components when they have reached the end of their life. FIG. 78 shows an exemplary implementation of the Replace Components application.

The Requesting Component Replacement state 7802 of the application 7801 shows which components should be replaced and allows the user to request additional replacements. The Deprime Flow path state 7803 decides which, if any, part of the machine needs to be deprimed. The Evaluating Blood Side Drain state 7804 determines if the blood side needs to be drained. It evaluates the different ways in which the dialyzer and blood tubing set could require replacement. If the dialyzer and blood tubing set need to be changed, but are not clotted off, then the state may request that they be drained of fluid. The Evaluating Dialysate Side Drain state 7805 determines if the dialysate side needs to be drained. It evaluates the different ways in which the dialysate-side components could require replacement; if so, then the state will request they be drained of fluid. The Empty Dialysate Tank state 7806 removes any residual dialysate or reverse osmosis water from the dialysate tank by sending it to drain. When the Empty Tanks command has completed, the event Tank Empty 7807 is emitted. The Draining Dialysate Side state 7808 removes fluid from the ultrafilter.

The Evaluating Dialyzer Replacement state 7809 determines whether the dialyzer and blood tubing set require replacement. The Replacing Dialyzer state 7810 steps the patient through dialyzer (and blood tubing set) replacement. For example, directions for replacing the dialyzer may be displayed. When the user indicates the dialyzer has been replaced, the Dialyzer Replaced event may be emitted. The Evaluating Ultrafilter Replacement state 7811 determines if the ultrafilter requires replacement. The Replacing Ultrafilter state 7812 steps the patient through ultrafilter replacement. The Replacing Drain Cassette state 7813 steps the patient through ultrafilter replacement. For example, directions for replacing the drain cassette may be displayed. When the user indicates the drain cassette has been replaced, a Drain Cassette Replaced event 7814 may be emitted. The Evaluating Dialysate Cartridge Replacement state 7815 determines if the Dialysate Cartridge requires replacement. For example, directions for replacing the dialysate cartridge may be displayed. When the user has indicated they have completed replacement, the Components Replaced event 7816 may be emitted.

The Evaluating Dialyzer Connections state 7817 determines whether the dialyzer and blood tubing set connections require testing. The Checking Dialyzer state 7818 may ensure that the dialyzer has been replaced correctly and that there are no leaking connections. If the dialyzer check is okay, the Dialyzer Check Okay event 7819 may be emitted.

The Fixing Dialyzer Connections state 7820 allows the patient to correct a misplaced connection. For example, instructions for fixing the dialyzer connection may be displayed. The Evaluating Ultrafilter Connections state 7821 determines whether the dialyzer and blood tubing set connections require testing. The Fixing Ultrafilter Connections state 7822 allows the patient to correct a misplaced connection. For example, instructions for fixing the ultrafilter connection may be displayed. If the ultrafilter check 7823 is okay, the Ultrafilter Check Okay event 7824 is emitted. The Evaluating Drain Cassette Connections state 7825 determines whether the drain cassette connections require testing. The Fixing Drain Connections 7826 state allows the patient to correct a misplaced connection. Instructions for fixing the drain cassette connections may be displayed. The Checking Dialysate Cartridge state 7827 ensures the dialysate cartridge has been replaced correctly and that there are no leaking connections. If the dialysate cartridge check is okay, the Connections Checked event 7828 may be emitted. The Fixing Dialysate Cartridge Connections state 7829 allows the patient to correct a misplaced connection.

(12) Install Chemicals

The Install Chemicals application allows the user to install chemical concentrates in preparation for dialysate production. Dialysate is made from chemical concentrates that are diluted with reverse osmosis water. The chemical concentrates are connected to the machine prior to dialysate production, but not during recycling. The machine checks the connection of the chemical concentrates following their installation. In the case that the chemical concentrates are not properly connected to the machine, the user will have the opportunity to correct the situation.

FIGS. 79a and 79b show an exemplary implementation of the Install Chemicals application. The Active state 7902 of the application 7901 is the state in which Install Chemicals processing occurs. The state generates the event Install Chemicals Stopped 7903 on transitioning to the Idle state 7904.

Referring to FIG. 79b, the Install new Concentrates state 7905 prompts the user to replace the chemical concentrate container. The Ensure Connection test 7906 detects whether the chemicals have been installed properly in the system. The Connection Recovery state 7907 handles the user interaction in the event that the system detects that the chemical concentrates are not installed properly. The system may notify the user to verify that the chemicals are properly installed and all connection are securely fastened. The Dilute Chemicals state 7908 fills the chemical bags with water to dilute the chemicals. The Start Dialysate Production state 7909 is responsible for starting Dialysate production.

The Dialysate Leak Alarm state 7910 will stop Operation and notify the user a dialysate leak has been detected. The Leak Resolution state 7911 waits for the user to clear the leak, and for an indication from the user of the same.

Referring again to FIG. 79a, the Data Handler Init state 7912 is responsible for initializing the data items for Install Chemicals. On completing this initialization, it will generate a Install Chemicals Launch OK event 7913 to indicate that Install Chemicals is ready for activation. The Update Data state 7914 is responsible for maintaining up to date values for the data items for Install Chemicals, such as the treatment prescription and mix.

A number of features or attributes may be desirable in the hemodialysis system embodiments described herein. These features or attributes may relate, for example, to automation, safety, usability, the user interface, therapy programming, prescription data, patient entry data, summary data, and/or therapy display data. Exemplary features or attributes of the hemodialysis system embodiments are described below. Various features or attributes or combinations of such features or attributes may be incorporated in embodiments of the hemodialysis systems described herein. However, such features and attributes may not be required by the system. Thus, while the features or attributes described may be advantageously incorporated into one or more hemodialysis system embodiments in some circumstances, the hemodialysis system need not include any of the described features or attributes, and the system is not limited to the inclusion of any such features or attributes.

Exemplary features or attributes of the automation of the system will be described first. Embodiments of the hemodialysis system described herein may be designed to permit the patient to operate the system and/or be treated from a standing, sitting and/or reclining position. As described herein, the hemodialysis system may automatically perform a number of functions, including: priming the blood set and dialysate pathways prior to treatment; rinsing and disinfecting; testing the integrity of ultrafilters and dialyzers; priming blood into the blood set, either through a prime returned or prime discarded operation; and rinsing back blood at the conclusion of a treatment. The hemodialysis system may minimize the residual red blood cells in the blood set at the completion of rinseback, and may ensure that the per-treatment red cell loss is less than or equal to the per-treatment red cell loss for traditional thrice weekly hemodialysis treatments. The hemodialysis system may automatically perform a solution infusion, upon request, at any time from the moment priming has started until rinseback is completed. The treatment device may automatically deliver heparin during treatment. The hemodialysis system may automatically record patient blood pressure and weight. This may be accomplished through the use of wireless communications with external, stand-alone sensor modules. The hemodialysis system may confirm that components have been loaded correctly and that the correct and sufficient supplies (i.e. solutions, concentrates, etc.) have been connected. The hemodialysis system may verify that the blood treatment set has been loaded correctly.

The hemodialysis system may comply with the FDA and AAMI guidelines on dialyzer reuse in testing and monitoring of the dialyzer's performance. The hemodialysis system may allow the patient to schedule their next treatment to reduce preparation time at the time of treatment. The hemodialysis system may provide a feature to allow the user to safely disconnect temporarily with a rinse back during treatment for 30 minutes or less. The hemodialysis system may provide the ability for the Healthcare Professional to disable the temporary disconnect feature. The hemodialysis system may minimize therapy interruptions by preventing or attempting to self-resolve conditions that may lead to an interruption (i.e. an alarm).

Next, exemplary safety features and attributes will be described. The hemodialysis may be designed to meet certain safety standards. For example, the hemodialysis system may meet all relevant AAMI and IEC safety requirements for hemodialysis machines, and may be designed such that exterior exposed surfaces stay below the levels indicated in the IEC-60601-1 standard during operation. Further, the user interface for the dialysis system may certain safety control features. For example, the hemodialysis system may provide a mechanism for the patient to terminate a therapy and rinseback at any point during treatment. Further, a method for the patient to rinse back their blood even if a nonrecoverable alarm occurs or power is lost may be provided. The user may also be able to bring the instrument to a safe state (i.e. pause all instrument activities) at any time during operation with a single button press.

As described herein, air bubbles may be dangerous to a patient. Thus, the hemodialysis system may be constructed to prevent air bubbles sized 20 microliters or larger from reaching the patient. The hemodialysis system may trigger an alarm when streams of bubbles greater than or equal to 1 microliter accumulate to exceed 20 microliters total within 30 sec. Further, the hemodialysis system may trigger an alarm when streams of bubbles greater than or equal to 3 microliters accumulate to exceed 20 microliters total within 30 sec.

The hemodialysis system may include a number of safety detection features. For example, the hemodialysis system may include, or interface to, a feature to detect venous needle dislodgement. The hemodialysis system may detect the passage of blood across the dialyzer membrane. The hemodialysis system may also detect and alert the user to dripping leaks from the portions of the blood circuit contained within the confines of the device. In addition, fluid in the blood circuit that the patient is exposed to may be of "dialysate for injection" quality.

The hemodialysis system may be designed to be usable to patients of varying physical and mental abilities. For example, the hemodialysis system user interface may be compatible with dialysis operators suffering from retinopathy and neuropathy and readable by someone who is color blind. In particular, critical information displayed by the user interface may be viewable from a distance of 3 feet by a user with 20/70 vision, and non-critical information displayed by the user interface may be viewable from a distance of 2 feet by a user with 20/70 vision. The hemodialysis system user interface may be designed to be intuitive, so that it may be understood by an operator with a 5th grade reading level. In addition, the hemodialysis system may be designed to be operated one-handed, including during therapy. This assists patients who have one arm immobilized due to needles being present in the access site.

The user interface may also be designed to be flexible and functional. For example, the hemodialysis system user interface may be splash/spill resistant and cleanable with the following cleaning solutions without degradation of operation: wiped 5.25% sodium hypochlorite bleach diluted 1:10, wiped accelerated hydrogen peroxide (made by Virox Tech Inc), and wiped PDI Sani-Cloth Plus.

Illumination may be controllable by the user or based on certain factors. For example, the hemodialysis system may be provided with a mechanism to dim the user interface and minimize all other light emissions either by request or automatically. In addition, it may be possible to turn off all light emitting sources except those necessary to locate safety-critical controls such as the stop button. In the event of a power outage, illumination of the blood set and dialyzer may be provided to support the patient managing their blood lines and access. The hemodialysis system may provide illumination to the appropriate controls when user interaction with the controls is necessary. This assists the user in finding necessary controls when performing therapy in a dark environment.

As discussed herein, alarms may be triggered during use of the dialysis system. The hemodialysis system may provide audible and visual indication of alarm conditions. Further, the hemodialysis system may distinguish the importance of an alarm condition. The audio abilities of the hemodialysis system may allow for a range of frequencies and sound levels, e.g., for alarm and alert situations, which may be adjustable by a user. The hemodialysis system may provide the ability for the user to mute an alarm. The hemodialysis system may have a visual indicator, in addition to the GUI, to call attention to alarms and alerts. For example, the hemodialysis system may generate a "light pole" or other such visual alarm indicator that can be viewed from a significant distance in all directions (e.g., 20 feet).

The hemodialysis system GUI may explain possible causes of an alarm and whether the alarm is correctable or not correctable. If an alarm is correctable, the hemodialysis system user interface may guide the user through resolving the alarm. The hemodialysis system may also provide instructions on when to call service or a Healthcare Professional.

The user interface and labeling may support a number of different languages and alternative character sets. Further, the hemodialysis system may provide voice guidance in the supported languages. Where possible, connections may be keyed and color-coded to facilitate correct connections.

The hemodialysis system user interface may provide the user with an option to receive a notification at the end of treatment, and may allow the user to review relevant treatment data at the end of the treatment.

It may be desirable that the hemodialysis system be easy to operate and user friendly for non-professionals. The user interface and industrial design of the hemodialysis system may allow the device to look and feel like a home product, and have a simple interface. Operations to be performed by a patient may be graphically simulated on-screen. A properly trained patient may be able to initiate treatment within 10 minutes of requesting a therapy. The hemodialysis system user interface may be configurable into "novice" and "advanced" modes that help encourage and guide novice users, while providing quick navigation for advanced users.

The hemodialysis system may allow the user to recover from missteps and mistakes, for example through use of back navigation in the user interface or an undo function. Further, the hemodialysis system user interface may minimize the user time and effort required to obtain help. The hemodialysis system may provide Healthcare Professional-specific training manuals, patient-specific training manuals, and an operator's manual.

The hemodialysis system may support Healthcare Professional localization of the device consisting of setting the language for display of text elements, setting the time, and setting units for parameters (i.e. lbs or kgs). The hemodialysis system may support Healthcare Professional configuration of the patient prescription, including setting the patient's target weight, the allowable therapy configurations (i.e. short daily, extended treatment) and the associated blood flow rate, the flexibility to set either dialysate flow rate and time or the dialysate volume and time for each therapy configuration (i.e. short daily, extended treatment), the prescribed heparin protocol, the maximum ultrafiltration rate, the dialysate composition, the dialyzer identification, solution infusion bolus size and limits, arterial and venous pressure limits, rinseback volume, and prime method (prime return or prime dump). The hemodialysis system may provide the option to prevent the patient adjustment of each prescription parameter and provide maximum/minimum limits on patient adjustment of the prescription parameters.

The hemodialysis system may support manual and electronic input of the patient prescription. The hemodialysis system may be designed to minimize the amount of information that is required to be manually entered for each therapy.

The device may require the patient to provide the following inputs at the start of therapy: therapy type (e.g. short daily, extended duration) and pre-dialysis weight. Prior to and during therapy, the hemodialysis system may allow the user to adjust the therapy end time. The hemodialysis system may provide the ability for input of the sitting and/or standing patient blood pressure both prior to therapy and after therapy completion.

The device may display, for confirmation, the following calculated parameters, at a minimum, on the summary screen prior to the start of treatment: therapy duration/end time and the patient's end weight. The hemodialysis system may allow the user to adjust the end weight for the therapy prior to and during therapy. in addition, prior to and during therapy, the hemodialysis system may allow the user to adjust the therapy end time/duration for the therapy.

Unless superseded by an alarm or user request, the hemodialysis system may always display the following information: current system state (i.e. priming, therapy, etc.), current blood flow rate, current patient weight and target patient weight, cumulative therapy time and therapy end time, and volume of heparin delivered. When using an associated blood pressure monitor (cuff), the hemodialysis system may display a new blood pressure measurement for 5 minutes after that measurement was taken. The hemodialysis system may display, on demand, real-time feedback on actual blood flow. This facilitates needle adjustment for optimal blood flow. On demand, the hemodialysis system may provide a means for the user to view the following information: dialysate conductivity and flow rate, the most recent blood pressure measurement, current ultrafiltration removal rate, cumulative bolus volume infused, dialysate temperature, current arterial and venous pump pressures, and the blood volume processed.

The following are each incorporated herein by reference in their entireties: U.S. Provisional Patent Application Ser. No. 60/903,582, filed Feb. 27, 2007, entitled "Hemodialysis System and Methods"; U.S. Provisional Patent Application Ser. No. 60/904,024, filed Feb. 27, 2007, entitled "Hemodialysis System and Methods"; U.S. patent application Ser. No. 11/787,213, filed Apr. 13, 2007, entitled "Heat Exchange Systems, Devices and Methods"; U.S. patent application Ser. No. 11/787,212, filed Apr. 13, 2007, entitled "Fluid Pumping Systems, Devices and Methods"; U.S. patent application Ser. No. 11/787,112, filed Apr. 13, 2007, entitled "Thermal and Conductivity Sensing Systems, Devices and Methods"; U.S. patent application Ser. No. 11/871,680, filed Oct. 12, 2007, entitled "Pumping Cassette"; U.S. patent application Ser. No. 11/871,712, filed Oct. 12, 2007, entitled "Pumping Cassette"; U.S. patent application Ser. No. 11/871,787, filed Oct. 12, 2007, entitled "Pumping Cassette"; U.S. patent application Ser. No. 11/871,793, filed Oct. 12, 2007, entitled "Pumping Cassette"; and U.S. patent application Ser. No. 11/871,803, filed Oct. 12, 2007, entitled "Cassette System Integrated Apparatus." In addition, the following are incorporated by reference in their entireties: U.S. Pat. No. 4,808,161, issued Feb. 28, 1989, entitled "Pressure-Measurement Flow Control System"; U.S. Pat. No. 4,826,482, issued May 2, 1989, entitled "Enhanced Pressure Measurement Flow Control System"; U.S. Pat. No. 4,976,162, issued Dec. 11, 1990, entitled "Enhanced Pressure Measurement Flow Control System"; U.S. Pat. No. 5,088,515, issued Feb. 18, 1992, entitled "Valve System with Removable Fluid Interface"; and U.S. Pat. No. 5,350,357, issued Sep. 27, 1994, entitled "Peritoneal Dialysis Systems Employing a Liquid Distribution and Pumping Cassette that Emulates Gravity Flow."

Also incorporated herein by reference are U.S. patent application Ser. No. 12/038,474, entitled "Sensor Apparatus Systems, Devices and Methods," filed on Feb. 27, 2008; U.S. patent application Ser. No. 12/038,648, entitled "Cassette System Integrated Apparatus," filed on Feb. 27, 2008; and U.S. patent application Ser. No. 12/072,908, filed Feb. 27, 2008, entitled "Hemodialysis Systems and Methods."

In addition, incorporated herein by reference in their entireties, and filed on an even date herewith, are the following: U.S. patent application Ser. No. 12/198,947, entitled "Occluder for a Medical Infusion System"; U.S. patent application Ser. No. 12/199,055, entitled "Enclosure for a Portable Hemodialysis System"; U.S. patent application Ser. No. 12/199,062, entitled "Dialyzer Cartridge Mounting Arrangement for a Hemodialysis System"; U.S. patent application Ser. No. 12/199,068, entitled "Modular Assembly for a Portable Hemodialysis System"; U.S. patent application Ser. No. 12/199,077, entitled "Blood Circuit Assembly for a Hemodialysis System"; U.S. patent application Ser. No. 12/199,166, entitled "Air Trap for a Medical Infusion Device"; U.S. patent application Ser. No. 12/199,176, entitled "Blood Line Connector for a Medical Infusion Device"; U.S. patent application Ser. No. 12/199,196, entitled "Reagent Supply for a Hemodialysis System"; and U.S. patent application Ser. No. 12/199,452, filed Aug. 27, 2008, and entitled "Hemodialysis System and Methods."

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more"

of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A controller for a hemodialysis system, the hemodialysis system comprising actuators that cooperate to perform dialysis functions and sensors that cooperate to monitor dialysis functions, the controller comprising:
   a user interface model layer configured to manage state of a graphical user interface and receive inputs from a graphical user interface;
   a therapy layer, below the user interface model layer, configured to run state machines that generate therapy commands based at least in part on the inputs from the graphical user interface; and
   a machine layer, below the therapy layer, configured to provide commands for actuators based on the therapy commands,
   wherein the therapy layer is configured to receive command requests from the user interface model layer, wherein some commands are state specific and other commands are valid in any state,
   wherein the therapy layer is configured to decide if current command request will be acted upon or not,
   and wherein the therapy layer is configured to reject the command request and to return to a user an appropriate reason for rejection, if current state is not valid for the command.

2. The controller of claim 1, further comprising a user interface views layer, above the user interface model layer, configured to control visual appearance of the graphical user interface.

3. The controller of claim 2, wherein the user interface model layer is configured to provide to the user interface views layer a current screen state.

4. The controller of claim 1, wherein the therapy layer is further configured to verify the inputs from the graphical user interface relative to information relating to expected inputs.

5. The controller of claim 1, wherein the therapy layer is configured to provide to the user interface model layer a status of therapy.

6. The controller of claim 1, wherein the machine layer is configured to provide to the therapy layer an indication of integrity of the actuators.

7. The controller of claim 1, wherein the machine layer is configured to provide to the therapy layer data sensed by sensors.

* * * * *